US011857616B2

(12) United States Patent
Tangy et al.

(10) Patent No.: US 11,857,616 B2
(45) Date of Patent: Jan. 2, 2024

(54) RECOMBINANT MEASLES VIRUS EXPRESSING ZIKA VIRUS PRM AND E PROTEINS

(71) Applicants: INSTITUT PASTEUR, Paris (FR); CENTRE NATIONAL DE LA RECHERCHE SCIENTIFIQUE, Paris (FR)

(72) Inventors: Frederic Tangy, Les Lilas (FR); Etienne Simon-Loriere, Paris (FR)

(73) Assignees: INSTITUT PASTEUR, Paris (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 92 days.

(21) Appl. No.: 16/618,823

(22) PCT Filed: Jun. 6, 2018

(86) PCT No.: PCT/EP2018/064943
§ 371 (c)(1),
(2) Date: Dec. 3, 2019

(87) PCT Pub. No.: WO2018/224573
PCT Pub. Date: Dec. 13, 2018

(65) Prior Publication Data

US 2020/0237893 A1 Jul. 30, 2020

(30) Foreign Application Priority Data

Jun. 7, 2017 (EP) .................................... 17305676

(51) Int. Cl.
*A61K 39/12* (2006.01)
*C07K 14/005* (2006.01)
*C12N 7/00* (2006.01)
*A61K 39/00* (2006.01)

(52) U.S. Cl.
CPC ............ *A61K 39/12* (2013.01); *C07K 14/005* (2013.01); *C12N 7/00* (2013.01); *A61K 2039/5254* (2013.01); *A61K 2039/53* (2013.01); *C12N 2760/18421* (2013.01); *C12N 2760/18423* (2013.01); *C12N 2770/24122* (2013.01); *C12N 2770/24123* (2013.01); *C12N 2770/24134* (2013.01)

(58) Field of Classification Search
CPC .... A61K 39/12; A61K 39/165; C07K 14/005; C12N 2760/18421; C12N 2760/18423; C12N 2770/24122; C12N 2770/24123; C12N 2770/24134
See application file for complete search history.

(56) References Cited

U.S. PATENT DOCUMENTS 9,655,961 B2 * 5/2017 Tangy ...................... C12N 7/00
11,110,162 B2 * 9/2021 Tauber .................. A61K 39/12

OTHER PUBLICATIONS

Higuchi, A., et al., Mar. 2016, Recombinant measles AIK-C vaccine strain expressing the prM-E antigen of Japanese encephalitis virus, PloS One 11(3):e0150213, pp. 1-9.*
Richner, J. M., et al., Mar. 2017, Modified mRNA vaccines protect against Zika virus infection, Cell 168:1114-1125.*
Naim, H. Y., Jan. 2015, Measles Virus: A pathogen, vaccine, and a vector, Human Vaccines and Immunotherapeutics, 11(1):21-26.*
Bardina, S. V., et al., Apr. 2017, Enhancement of Zika virus pathogenesis by preexisting antiflavivirus immunity, Science 356:175-180.*
Scherwitzl, I., et al., May 2017, Recent advances in human flavivirus vaccines, Curr. Opin. Virol. 23:95-101.*
Britto, C., et al., 2018, Rapid travel to a Zika vaccine: are we heading towards success or more questions? Exp. Opin. Biol. Ther. 18(11):1171-1179.*
European Search Report, U.S. Appl. No. 17/305,676, filed Nov. 8, 2017.
International Search Report and Written Opinion, PCT/EP2018/0649, dated Aug. 2, 2018.
Anna Durbin, et al., "Role of a ZIKV CHIM in vaccine evaluation," Jun. 2, 2017 (Jun. 2, 2017), XP055419451, Retrieved from the Internet: URL:https://www.google.de/url?sa=t&rct=j&q=&esrc=s&source=web&cd=I&ved=DahUKEwiruOOVpo7XAhWDbFAKHYyVChoQFggn1'1AA&url=http://www.who.int/entity/blueprint/what/norms-standards/1 Durbin CHIM.pdf?ua=l&usg=AOvVaw3sraJTiT8oBPIV6yWhMhVq [retrieved on Oct. 26, 2017].
Penelope Koraka, et al., "Bioinformatics in New Generation Flavivirus Vaccines," Journal of Biomedicine and Biotechnology, vol. 9, No. 5, Jan. 1, 2010 (Jan. 1, 2010), Article ID 864029, 17 pages.

(Continued)

*Primary Examiner* — Jeffrey S Parkin
(74) *Attorney, Agent, or Firm* — Arrigo, Lee, Guttman & Mouta-Bellum LLP

(57) ABSTRACT

The present invention relates to recombinant measles virus expressing Zika virus proteins and their applications, in particular in inducing preventive protection against Zika virus. The present invention is directed to recombinant measles virus (MV) expressing at least (i) the precursor of membrane (prM) protein of a Zika virus (ZIKV), and the envelope (E) protein of a ZIKV or a truncated version thereof, or (ii) the E protein of a ZIKV or a truncated version thereof, and concerns recombinant infectious particles of said MV-ZIKV able to replicate in a host after an administration, and also Virus Like Particles (VLPs) that contain these ZIKV proteins at their surface. The present invention provides means, in particular nucleic acids, vectors, cells and rescue systems to produce these recombinant infectious particles and VLPs. The present invention also relates to the use of these recombinant infectious particles and/or VLPs, in particular under the form of a composition, more particularly in a vaccine formulation, for the prevention of an infection by ZIKV or for the preventive protection against clinical outcomes of ZIKV infection.

24 Claims, 17 Drawing Sheets

Specification includes a Sequence Listing.

(56) References Cited

OTHER PUBLICATIONS

PRESENTATION 1, Usp/institut Pasteur/fiocruz: "Workshop—Beyond Zika—A tripartite Initiative," Aug. 29, 2016 (Aug. 29, 2016), Retrieved from the Internet: URL:http://www.usp.br/aucani/zika/archive/Presentations Afternoon Aug. 30.pdf [retrieved on-Oct. 26, 2017].

PRESENTATION 2, Usp/institut Pasteur/fiocruz: "Workshop—Beyond Zika—A tripartite Initiative," Aug. 29, 2016 (Aug. 29, 2016), Retrieved from the Internet: URL:http://www.usp.br/aucani/zika/archive/Presentations Afternoon Aug. 30.pdf [retrieved on-Oct. 26, 2017].

PRESENTATION 3, Usp/institut Pasteur/fiocruz: "Workshop—Beyond Zika—A tripartite Initiative," Aug. 29, 2016 (Aug. 29, 2016), Retrieved from the Internet: URL:http://www.usp.br/aucani/zika/archive/Presentations Afternoon Aug. 30.pdf [retrieved on-Oct. 26, 2017].

Shen Zhang-zhou, Research progress on Zika virus, Chin J Viral Dis, 2016, vol. 6, no. 5, pp. 391-397.

* cited by examiner

|                          | prM | E |
|---|---|---|
| | MVsp'   sp' | stem  anchor |

D1. MVsp'_ZikaprME

D2. MVsp'_Zika_prMEd456

D3. MVsp'_Zika_Ed445

D4. MVsp'_Zika_Ed404

D5. MVsp'_ZikaE

D6. MVsp'_ZikaEd456

D7. MVsp'_ZikaEd445

D8. MVsp'_ZikaEd404

D9. MVsp'_ZikaprME
    _MVTMintracyto

D10. MVsp'_Zika
    _MVTMintracytoE

6 CD46-IFNAR mice per group

Immunization: MV vectors $10^6$ $TCID_{50}$/mouse

Challenge: ZIKV African strain $10^6$ pfu/mouse

Prime — Boost — challenge

0 — 1 — 2 months

6 CD46-IFNAR mice per group
Immunization: MV vectors $10^6$ TCID$_{50}$/mouse
Challenge: ZIKV African strain $10^3$ pfu/mouse

ZIKA 2

$\log_{10}$ ZIKV EDIII ELISA titer

Days

☐ MV-Sch
● MV-prMEd404 native
▲ MV-ssEd445 native

RECOMBINANT MEASLES VIRUS EXPRESSING ZIKA VIRUS PRM AND E PROTEINS

CROSS REFERENCE TO RELATED APPLICATIONS

This application is a U.S. National Stage Application of PCT Application No. PCT/EP2018/064943 under 37 C.F.R. § 371, with an international filing date of Jun. 6, 2018, which claims priority to European Patent Application No. EP17305676.3, which has a filing date of Jun. 7, 2017, of which both applications are herein incorporated by reference in their entirety.

SEQUENCE LISTING

The instant application contains a Sequence Listing which has been submitted in ASCII format via EFS-Web and is hereby incorporated by reference in its entirety. Said ASCII copy, created on Apr. 3, 2020, is named 16618823_ST25.txt and is 580,273 bytes in size The present invention relates to recombinant measles virus expressing Zika virus proteins and their applications, in particular in inducing preventive protection against Zika virus. The present invention is directed to recombinant measles virus (MV) expressing at least (i) the precursor of membrane (prM) protein of a Zika virus (ZIKV), and the envelope (E) protein of a ZIKV or a truncated version thereof, or (ii) the E protein of a ZIKV or a truncated version thereof, and concerns recombinant infectious particles of said MV-ZIKV able to replicate in a host after an administration, and also Virus Like Particles (VLPs) that contain these ZIKV proteins at their surface. The present invention provides means, in particular nucleic acids, vectors, cells and rescue systems to produce these recombinant infectious particles and VLPs. The present invention also relates to the use of these recombinant infectious particles and/or VLPs, in particular under the form of a composition, more particularly in a vaccine formulation, for the prevention of an infection by ZIKV or for the preventive protection against clinical outcomes of ZIKV infection.

ZIKV is an emerging mosquito-borne flavivirus. Although it was initially isolated in 1947, to date there are no specific treatments or any vaccines available against ZIKV disease, making it a truly neglected and emerging disease. The recent rapid spread of ZIKV in previously unaffected regions such as South Pacific islands and Latin America has provided strong epidemiological evidence that infection with this virus might be associated with neurological complications in adults and with an increase in severe congenital brain malformations of new-borns. Consequently, the World Health Organization (WHO) has declared the recent outbreak of the ZIKV a public health emergency.

ZIKV was initially isolated from a rhesus monkey in the Zika forest in Uganda in 1947 (Gubler D J, et al., eds. *Fields Virology, 5th edn. Philadelphia, PA: Lippincott Williams & Wilkins Publishers,* 2007: 1155-227; Dick G W A, et al. *Trans R Soc Trop Med Hyg* 1952; 46: 509-20). The first human infection was reported in Nigeria in 1954 (Macnamara F N. *Trans R Soc Trop Med Hyg* 1954; 48: 139-45). Like dengue and chikungunya viruses, ZIKV adapted from an ancestral transmission cycle involving non-human primates and a broad spectrum of forest mosquito species as vectors to an urban cycle involving humans as reservoirs and the widely distributed Aedes mosquitoes as vectors (Musso D, et al. *Lancet* 2015; 386: 243-44). Since the 1950s, ZIKV had only been reported as circulating sporadically in Africa and Southeast Asia. *In* 2007, ZIKV was isolated for the first time in the Pacific, on the Micronesian island of Yap (Duffy M R, et al. *N Engl J Med* 2009; 360: 2536-43). Between October 2013 and April 2014, French Polynesia experienced the largest Zika outbreak ever reported at that time (Cao-Lormeau V M, et al. *Emerg Infect Dis* 2013; 20: 1085-86). More than 32,000 patients were suspected of ZIKV infection. Between 2014 and 2015, ZIKV spread to other Pacific islands, notably the Cook Islands and Easter Island (Chile). *In March* 2015, Brazil reported the autochthonous transmission of ZIKV (Zanluca C, et al. *Mem Inst Oswaldo Cruz* 2015; 110: 569-72) and declared an unprecedented outbreak 6 months later (Dyer O. *BMJ* 2015; 351: h6983) with preliminary estimates of 440,000 to 1.3 million cases of infection through December 2015 (*European Centre for Disease Prevention and Control, Dec.* 10, 2015). As of March 2016, ZIKV infection has been reported from 43 countries and territories worldwide.

The current Zika epidemic is the largest epidemic ever recorded for this virus (Abushouk et al. An updated review of Zika virus, *J. Clin. Virol.* 2016, 84, 53-58). Although infection with ZIKV was usually associated with mild disease, its emergence in the Americas has coincided with a steep increase in patients developing Guillain-Barré syndrome. Moreover, infection with ZIKV has been linked to the birth of babies with neurological complications, in particular congenital microcephaly (WHO. *Guillain-Barré syndrome—El Salvador. Jan.* 21, 2016*; ECDC. Rapid risk assessment. Zika virus epidemic in the Americas: potential association with microcephaly and Guillain-Barré syndrome. Dec.* 10, 2015; Soares de AraCijo J, et al. *Microcephaly in northeast Brazil: a review of* 16 208 births between 2012 and 2015), and it was shown that when pregnant women are exposed to ZIKV during the first trimester of pregnancy, the risk of microcephaly for the newborn is increased 50 times from 2/10 000 to 1/100 (Cauchemez S, et al. *Association between Zika virus and microcephaly in French Polynesia,* 2013-15*: a retrospective study. The Lancet* 2016). In February 2016, the WHO declared the suspected link between ZIKV and neurological disorders and neonatal malformations a Public Health Emergency of International Concern.

In this context, in March 2016, experts gathered at WHO agreed that the development of a preventive vaccine is a major priority to respond to Zika epidemics in the future. Pragmatic strategies were asked to fast track the development of a safe and effective vaccine. Due to the established link between ZIKV infection and the appearance of congenital microcephaly in babies born to infected mothers, one could argue that a Zika vaccine has to be suitable for use in pregnant women. However, no licensed vaccine is currently recommended for use during pregnancy. Moreover, with the demonstrated association of Zika infection with Guillain-Barré syndrome, the observation of possible sexual transmission, and the appearance of developmental defects probably appearing very early in pregnancy, it is very likely that the vaccine should be addressed to the general population. In any case a Zika vaccine will have to demonstrate an excellent safety profile, particularly concerning the risk of neurotropism.

To allow fast track development of a Zika vaccine, the inventors used one of the safest and most efficacious vaccines available, the live-attenuated measles vaccine, as a delivery vector for ZIKV protective antigens to ensure the timely availability of a preventive vaccine whenever a new epidemic occurs. This delivery platform technology has demonstrated proof of principle in humans and a preclinical track record of rapid adaptability and effectiveness for a variety of pathogens. Moreover, the manufacturing process for these measles vector-based vaccines has been optimized to give higher yields and purity than the standard manufacturing measles vaccine process. It uses standard equipment and thus lends itself to further scale up as well as technology transfer to low and middle-income countries.

Measles vaccination has been used for more than 40 years in over 1 billion children and is approximately 93% efficacious after one administration and 97% after 2 administrations. Attenuated measles vaccine strains have been shown to be genetically stable. Reversion to pathogenicity or integration into the host cell genome is virtually impossible and has never been observed. Taking advantage of these characteristics, the inventors previously cloned the attenuated measles Schwarz vaccine virus and developed a method to genetically manipulate this negative strand RNA virus into a versatile chimeric or recombinant vector (Combredet, C. et al., 2003*, J Virol,* 77(21): 11546-11554).

A prophylactic vaccine against ZIKV, as for any other target, has to be safe and efficacious. In addition, the special epidemiology of a rapidly emerging virus, affecting both industrialized and developing countries, and the threat of infections during pregnancy causing serious birth defects, calls for a number of additional features for an ideal ZIKV vaccine.

ZIKV infection during pregnancy is strongly suspected to cause birth defects. Although live vaccines are generally contraindicated during pregnancy, measles infections have not been connected to birth defects (Rasmussen S A, et al. *Obstet Gynecol.* 2015 July; 126 (1):163-70), and accidental application of the MMR vaccine during pregnancy was not connected to congenital birth defects (Swamy G K, et al. *Obstet Gynecol.* 2015 January; 125(1):212-26). In contrast to measles-based vaccine according to the invention, a live-attenuated Zika vaccine approach would raise very significant safety concerns if accidentally applied during pregnancy. It has to be seriously questioned, if a vaccine against Zika intended for use during pregnancy could be developed and licensed in any acceptable time frame to stop the current epidemic. Instead, a vaccine for adolescents with minimal safety concerns for accidental use during pregnancy seems the most practical and realistic intervention to eliminate Zika-induced disease. A measles-based vaccine would exactly meet that target profile.

The measles-based approach of the invention can meet all of the relevant criteria of a future ZIKV vaccine at least equally well or better than alternative approaches. In particular a non-adjuvanted measles-based ZIKV vaccine for children, adolescents and travelers represents one of the most likely candidates to be developed in a short time frame, has an excellent safety and efficacy profile, and has production and cost characteristics that are compatible with its use also in countries of limited economic strength.

To this end, a sequential development path was defined by the inventors. The first stage was the construction and characterisation of recombinant MV expressing at least ZIKV prM-E or E proteins as soluble secreted antigens. The characterisation included demonstration of Zika antigen expression, established growth characteristics in a production cell line, and analysis of genetic stability. Preclinical immunogenicity and protective efficacy of selected recombinant MV-Zika vaccine was evaluated in CD46-IFNAR mice susceptible to MV infection. The currently best candidate selected was evaluated for immunogenicity and protective efficacy in non-human primate model of ZIKV infection.

The inventors achieved the production of vaccines based on recombinant infectious replicative MV recombined with polynucleotides encoding at least ZIKV prM-E or E antigens, which are recovered when the recombinant virus replicates in particular in the host after administration. The invention thus relates to a live ZIKV vaccine active ingredient based on the widely used measles, in particular measles from the Schwarz strain, pediatric vaccine. In a preferred embodiment, this recombinant live MV-ZIKV vaccine yields ZIKV VLPs by replicating in infected cells.

MV is a non-segmented single-stranded, negative-sense enveloped RNA virus of the genus Morbillivirus within the family of Paramyxoviridae. This virus has been isolated in 1954 (Enders, J. F., and T. C. Peebles. 1954. *Propagation in tissue cultures of cytopathogenic agents from patients with measles. Proc. Soc. Exp. Biol. Med.* 86:277-286), and live-attenuated vaccines have been derived from this virus since then to provide vaccine strains, in particular from the Schwarz strain. Measles vaccines have been administered to hundreds of millions of children over the last 30 years and have proved its efficiency and safety. It is produced on a large scale in many countries and is distributed at low cost. For all these reasons, the inventors used attenuated MVs to generate recombinant MV particles stably expressing prM-E or E antigens of ZIKV, and possibly capable of expressing also VLPs.

The invention thus relates to a nucleic acid construct which comprises:

(1) a polynucleotide encoding at least (i) the precursor of membrane (prM) protein of a Zika virus (ZIKV), and the envelope (E) protein of a ZIKV or a truncated version thereof, or (ii) the E protein of a ZIKV or a truncated version thereof; and (2) a cDNA molecule encoding a full-length, infectious antigenomic (+) RNA strand of a measles virus (MV);

wherein the polynucleotide encoding at least (i) the prM protein of the ZIKV, and the E protein of the ZIKV or the truncated version thereof, or (ii) the E protein of the ZIKV or the truncated version thereof is operatively linked, in particular cloned into the cDNA molecule.

A nucleic acid construct according to the invention is in particular a purified DNA molecule, obtained or obtainable by recombination of various polynucleotides of different origins, operably linked together.

The expression "operably linked" refers to the functional link existing between the different polynucleotides of the nucleic acid construct of the invention such that said different polynucleotides and nucleic acid construct are efficiently transcribed and if appropriate translated, in particular in cells or cell lines, especially in cells or cell lines used as part of a rescue system for the production of chimeric infectious MV particles of the invention or in host cells, especially in human cells.

In a particular embodiment of the invention, the construct is prepared by cloning a polynucleotide encoding at least (i) the prM protein of a ZIKV, and the E protein of a ZIKV or a truncated version thereof, or (ii) the E protein of a ZIKV or a truncated version thereof, in the cDNA encoding a full-length, infectious antigenomic (+) RNA strand of a MV. Alternatively, a nucleic acid construct of the invention may be prepared using steps of synthesis of nucleic acid fragments or polymerization from a template, including by PCR.

In a particular embodiment of the invention, the polynucleotide encoding at least (i) the prM protein of the ZIKV, and the E protein of the ZIKV or the truncated version thereof, or (ii) the E protein of the ZIKV or the truncated version thereof, is cloned into an ATU (Additional Transcription Unit) inserted in the cDNA of the MV. ATU sequences are known from the skilled person and comprise, for use in steps of cloning into cDNA of MV, cis-acting sequences necessary for MV-dependent expression of a transgene, such as a promoter of the gene preceding, in MV cDNA, the insert represented by the polynucleotide encoding at least (i) the prM protein of the ZIKV, and the E protein of the ZIKV or the truncated version thereof, or (ii) the E protein of the ZIKV or the truncated version thereof, and a multiple cloning sites cassette for insertion of said polynucleotide.

When used to carry out the invention, the ATU is advantageously located in the N-terminal sequence of the cDNA molecule encoding the full-length (+)RNA strand of the antigenome of the MV and is especially located between the P and M genes of this virus or between the H and L genes. It has been observed that the transcription of the viral RNA of MV follows a gradient from the 5' to the 3' end. This explains that, when inserted in the 5' end of the coding sequence of the cDNA, the ATU will enable a more efficient expression of the heterologous DNA sequence (e.g. the polynucleotide encoding at least (i) the prM protein of the ZIKV, and the E protein of the ZIKV or the truncated version thereof, or (ii) the E protein of the ZIKV or the truncated version thereof) that it contains.

The polynucleotide encoding at least (i) the prM protein of the ZIKV, and the E protein of the ZIKV or the truncated version thereof, or (ii) the E protein of the ZIKV or the truncated version thereof, may thus be inserted in any intergenic region of the cDNA molecule of the MV in particular in an ATU. Particular constructs of the invention are those illustrated in the examples.

In a preferred embodiment of the invention, the polynucleotide encoding at least (i) the prM protein of the ZIKV, and the E protein of the ZIKV or the truncated version thereof, or (ii) the E protein of the ZIKV or the truncated version thereof, is inserted in the intergenic region of the P and M genes of the MV cDNA molecule, in particular in an ATU.

As used herein, the expression "encoding" defines the ability of the nucleic acid molecules to be transcribed and where appropriate translated for product expression into selected cells or cell lines. Accordingly, the nucleic acid construct may comprise regulatory elements controlling the transcription of the coding sequences, in particular promoters and termination sequences for the transcription and possibly enhancer and other cis-acting elements. These regulatory elements may be heterologous with respect to the ZIKV polynucleotide sequences.

The term "protein" is used interchangeably with the terms "antigen" or "polypeptide" and defines a molecule resulting from a concatenation of amino acid residues. In particular, the proteins disclosed in the application originate from the ZIKV and are structural proteins that may be identical to native proteins or alternatively that may be derived thereof by mutation, including by substitution (in particular by conservative amino acid residues) or by addition of amino acid residues or by secondary modification after translation or by deletion of portions of the native proteins(s) resulting in fragments having a shortened size with respect to the native protein of reference. Fragments are encompassed within the present invention to the extent that they bear epitopes of the native protein suitable for the elicitation of an immune response in a host in particular in a human host, preferably a response that enables the protection against ZIKV infection or against ZIKV associated disease. Epitopes are in particular of the type of B epitopes involved in the elicitation of a humoral immune response through the activation of the production of antibodies in a host to whom the protein has been administered or in whom it is expressed following administration of the infectious replicative particles of the invention. Epitopes may alternatively be of the type of T epitopes involved in elicitation of Cell Mediated Immune response (CMI response). Fragments may have a size representing more than 50% of the amino-acid sequence size of the native protein of ZIKV, preferably at least 90% or 95%. Alternatively, fragments may be short polypeptides with at least 10 amino acid residues, which harbor epitope(s) of the native protein. Fragments in this respect also include polyepitopes as defined herein.

In a particular embodiment of the invention, said nucleic acid construct complies with the rule of six (6) of the MV genome, i.e. the polynucleotide encoding at least (i) the prM protein of the ZIKV, and the E protein of the ZIKV or the truncated version thereof, or (ii) the E protein of the ZIKV or the truncated version thereof, taken together with the cDNA molecule encoding the full-length, infectious antigenomic (+) RNA strand of the MV consist of a number of nucleotides that is a multiple of six.

The organization of the genome of MVs and their replication and transcription process have been fully identified in the prior art and are especially disclosed in Horikami S. M. and Moyer S. A. (*Curr. Top. Microbiol. Immunol.* (1995) 191, 35-50) or in Combredet C. et al (*Journal of Virology*, November 2003, p 11546-11554) for the Schwarz vaccination strain of the virus or for broadly considered negative-sense RNA viruses, in Neumann G. et al (*Journal of General Virology* (2002) 83, 2635-2662).

The "rule of six" is expressed in the fact that the total number of nucleotides present in a nucleic acid representing the MV(+) strand RNA genome or in nucleic acid constructs comprising same is a multiple of six. The "rule of six" has been acknowledged in the state of the art as a requirement regarding the total number of nucleotides in the genome of the MV, which enables efficient or optimized replication of the MV genomic RNA. In the embodiments of the present invention defining a nucleic acid construct that meets the rule of six, said rule applies to the nucleic acid construct specifying the cDNA encoding the full-length MV (+) strand RNA genome and all inserted sequences, when taken individually or collectively. In this regard the rule of six applies to the cDNA encoding the full-length infectious antigenomic (+) RNA strand of the MV possibly and to the polynucleotide cloned into said cDNA and encoding at least (i) the prM protein of the ZIKV, and the E protein of the ZIKV or the truncated version thereof, or (ii) the E protein of the ZIKV or the truncated version thereof.

In a particular embodiment of the invention, the nucleic acid construct comprises the following polynucleotides from 5' to 3':

(a) a polynucleotide encoding the N protein of the MV;
(b) a polynucleotide encoding the P protein of the MV;
(c) the polynucleotide encoding at least (i) the prM protein of the ZIKV, and the E protein of the ZIKV or the truncated version thereof, or (ii) the E protein of the ZIKV or the truncated version thereof;
(d) a polynucleotide encoding the M protein of the MV;
(e) a polynucleotide encoding the F protein of the MV;
(f) a polynucleotide encoding the H protein of the MV; and
(g) a polynucleotide encoding the L protein of the MV;

wherein said polynucleotides are operably linked in the nucleic acid construct and under a control of viral replication and transcription regulatory sequences such as MV leader and trailer sequences.

The expressions "N protein", "P protein", "M protein", "F protein", "H protein" and "L protein" refer respectively to the nucleoprotein (N), the phosphoprotein (P), the matrix protein (M), the fusion protein (F), the hemagglutinin protein (H) and the RNA polymerase large protein (L) of a MV. These components have been identified in the prior art and are especially disclosed in Fields, Virology (Knipe & Howley, 2001).

In a preferred embodiment of the invention, the measles virus is an attenuated virus strain.

An "attenuated strain" of measles virus is defined as a strain that is avirulent or less virulent than the parent strain in the same host, while maintaining immunogenicity and possibly adjuvanticity when administered in a host i.e., preserving immunodominant T and B cell epitopes and possibly the adjuvanticity such as the induction of T cell costimulatory proteins or the cytokine IL-12.

An attenuated strain of a MV accordingly refers to a strain which has been serially passaged on selected cells and, possibly, adapted to other cells to produce seed strains suitable for the preparation of vaccine strains, harboring a stable genome which would not allow reversion to pathogenicity nor integration in host chromosomes. As a particular "attenuated strain", an approved strain for a vaccine is an attenuated strain suitable for the invention when it meets the criteria defined by the FDA (US Food and Drug Administration) i.e., it meets safety, efficacy, quality and reproducibility criteria, after rigorous reviews of laboratory and clinical data (fda. Gov/cber/vaccine/vacappr. htm).

Particular attenuated strains that can be used to implement the present invention and especially to derive the MV cDNA of the nucleic acid construct are the Schwarz strain, the Zagreb strain, the AIK-C strain and the Moraten strain. All these strains have been described in the prior art and access to them is provided in particular as commercial vaccines.

In a particular embodiment of the invention, the cDNA molecule is placed under the control of heterologous expression control sequences. The insertion of such a control for the expression of the cDNA, is favorable when the expression of this cDNA is sought in cell types which do not enable full transcription of the cDNA with its native control sequences.

In a particular embodiment of the invention, the heterologous expression control sequence comprises the T7 promoter and T7 terminator sequences. These sequences are respectively located 5' and 3' of the coding sequence for the full length antigenomic (+)RNA strand of MV and from the adjacent sequences around this coding sequence.

In a particular embodiment of the invention, the cDNA molecule, which is defined hereabove is modified i.e., comprises additional nucleotide sequences or motifs.

In a preferred embodiment, the cDNA molecule of the invention further comprises, at its 5'-end, adjacent to the first nucleotide of the nucleotide sequence encoding the full-length antigenomic (+)RNA strand of the MV approved vaccine strain, a GGG motif followed by a hammerhead ribozyme sequence and which comprises, at its 3'-end, adjacent to the last nucleotide of said nucleotide sequence encoding the full length anti-genomic (+)RNA strand, the sequence of a ribozyme. The Hepatitis delta virus ribozyme (δ) is appropriate to carry out the invention.

The GGG motif placed at the 5' end, adjacent to the first nucleotide of the above coding sequence improves the efficiency of the transcription of said cDNA coding sequence. As a requirement for the proper assembly of measles virus particles is the fact that the cDNA encoding the antigenomic (+)RNA of the nucleic acid construct of the invention complies with the rule of six, when the GGG motif is added, a ribozyme is also added at the 5' end of the coding sequence of the cDNA, 3' from the GGG motif, in order to enable cleavage of the transcript at the first coding nucleotide of the full-length antigenomic (+)RNA strand of MV.

In a particular embodiment of the invention, in order to prepare the nucleic acid construct of the invention, the preparation of a cDNA molecule encoding the full-length antigenomic (+) RNA of a MV disclosed in the prior art is achieved by known methods. Said cDNA provides especially the genome vector when it is inserted in a vector such as a plasmid.

A particular cDNA molecule suitable for the preparation of the nucleic acid construct of the invention is the one obtained using the Schwarz strain of MV. Accordingly, the cDNA used within the present invention may be obtained as disclosed in WO2004/000876 or may be obtained from plasmid pTM-MVSchw deposited by Institut Pasteur at the Collection Nationale de Culture de Microorganismes (CNCM), 28 rue du Dr Roux, 75724 Paris Cedex 15, France, under No 1-2889 on Jun. 12, 2002, the sequence of which is disclosed in WO2004/000876 incorporated herein by reference. The plasmid pTM-MVSchw has been obtained from a Bluescript plasmid and comprises the polynucleotide coding for the full-length measles virus (+) RNA strand of the Schwarz strain placed under the control of the promoter of the T7 RNA polymerase. It has 18967 nucleotides and a sequence represented as SEQ ID NO: 1. cDNA molecules (also designated cDNA of the measles virus or MV cDNA for convenience) from other MV strains may be similarly obtained starting from the nucleic acid purified from viral particles of attenuated MV such as those described herein.

The cDNA used within the present invention may also be obtained from plasmid pTM2-MVSchw-gfp deposited by Institut Pasteur at the Collection Nationale de Culture de Microorganismes (CNCM), 28 rue du Dr Roux, 75724 Paris Cedex 15, France, under No 1-2890 on Jun. 12, 2002. It has 19795 nucleotides and a sequence represented as SEQ ID NO: 2. This plasmid contains the sequence encoding the eGFP marker that may be deleted.

The nucleic acid construct of the invention is suitable and intended for the preparation of recombinant infectious replicative measles—Zika virus (MV-ZIKV) and accordingly said nucleic acid construct is intended for insertion in a transfer genome vector that as a result comprises the cDNA molecule of the measles virus, especially of the Schwarz strain, for the production of said MV-ZIKV and yield of at least (i) the prM protein of the ZIKV, and the E protein of the ZIKV or the truncated version thereof, or (ii) the E protein of the ZIKV or the truncated version thereof, in particular ZIKV VLPs. The pTM-MVSchw plasmid or the pTM2-MVSchw plasmid is suitable to prepare the transfer vector, by insertion of the ZIKV polynucleotide(s) necessary for the expression of at least (i) the prM protein of the ZIKV, and the E protein of the ZIKV or the truncated version thereof, or (ii) the E protein of the ZIKV or the truncated version thereof. The recombinant infectious replicating MV-ZIKV particles may be recovered from rescue helper cells or in production cells and may optionally be recovered with VLP expressing the ZIKV antigens disclosed in accordance with the invention.

The invention thus relates to a transfer vector, which is used for the preparation of recombinant MV-ZIKV particles when rescued from helper cells. Advantageously, the transfer vector of the invention is a transfer vector plasmid suitable for transfection of said helper cells or of production cells, comprising the nucleic acid construct of the invention, in particular is a plasmid obtained from a Bluescript plasmid, such as pMV-ZIKV.

In a particular embodiment of the invention, the transfer vector plasmid has the sequence of SEQ ID NO: 165, SEQ ID NO: 166 or SEQ ID NO: 167, preferably has the sequence of SEQ ID NO: 165.

The invention also concerns the use of said transfer vector to transform cells suitable for rescue of viral MV-ZIKV particles, in particular to transfect or to transduce such cells respectively with plasmids or with viral vectors harboring the nucleic acid construct of the invention, said cells being selected for their capacity to express required MV proteins for appropriate replication, transcription and encapsidation of the recombinant genome of the virus corresponding to the nucleic acid construct of the invention in recombinant infectious replicating MV-ZIKV particles.

In a preferred embodiment, the invention relates to transformed cells comprising inserted in their genome the nucleic acid construct according to the invention or comprising the transfer vector plasmid according to the invention, wherein said cells are in particular eukaryotic cells, such as avian cells, in particular CEF cells, mammalian cells such as HEK293 cells or yeast cells.

Polynucleotides are thus present in said cells, which encode proteins that include in particular the N, P and L proteins of a MV (i.e., native MV proteins or functional variants thereof capable of forming ribonucleoprotein (RNP) complexes), preferably as stably expressed proteins at least for the N and P proteins functional in the transcription and replication of the recombinant viral MV-ZIKV particles. The N and P proteins may be expressed in the cells from a plasmid comprising their coding sequences or may be expressed from a DNA molecule inserted in the genome of the cell. The L protein may be expressed from a different plasmid. It may be expressed transitory. The helper cell is also capable of expressing a RNA polymerase suitable to enable the synthesis of the recombinant RNA derived from the nucleic acid construct of the invention, possibly as a stably expressed RNA polymerase. The RNA polymerase may be the T7 phage polymerase or its nuclear form (nlsT7).

In an embodiment of the invention, the cDNA clone of MV is from the same MV strain as the N protein and/or the P protein and/or the L protein. In another embodiment of the invention, the cDNA clone of a MV is from a different strain of virus than the N protein and/or the P protein and/or the L protein.

The invention also relates to a process for the preparation of recombinant infectious measles virus (MV) particles comprising:

1) transferring, in particular transfecting, the nucleic acid construct of the invention or the transfer vector containing such nucleic acid construct in a helper cell line which also expresses proteins necessary for transcription, replication and encapsidation of the antigenomic (+)RNA sequence of MV from its cDNA and under conditions enabling viral particles assembly; and 2) recovering the recombinant infectious MV-ZIKV particles expressing at least (i) the prM protein of a ZIKV, and the E protein of a ZIKV or a truncated version thereof, or (ii) the E protein of a ZIKV or a truncated version thereof.

In a particular embodiment of the invention, this process comprises:

1) transfecting helper cells with a nucleic acid construct according to the invention and with a transfer vector, wherein said helper cells are capable of expressing helper functions to express an RNA polymerase, and to express the N, P and L proteins of a MV virus;
2) co-cultivating said transfected helper cells of step 1) with passaged cells suitable for the passage of the MV attenuated strain from which the cDNA originates;
3) recovering the recombinant infectious MV-ZIKV particles expressing at least (i) the prM protein of the ZIKV, and the E protein of the ZIKV or the truncated version thereof, or (ii) the E protein of the ZIKV or the truncated version thereof.

In another particular embodiment of the invention, the method for the production of recombinant infectious MV-ZIKV particles comprises:

1) recombining a cell or a culture of cells stably producing a RNA polymerase, the N protein of a MV and the P protein of a MV, with a nucleic acid construct of the invention and with a vector comprising a nucleic acid encoding the L protein of a MV, and 2) recovering the recombinant infectious MV-ZIKV particles from said recombinant cell or culture of recombinant cells.

In a particular embodiment of said process, recombinant MV are produced, which express at least (i) the prM protein of the ZIKV, and the E protein of the ZIKV or the truncated version thereof, or (ii) the E protein of the ZIKV or the truncated version thereof, in particular ZIKV VLPs expressing the same ZIKV protein(s).

Preferably, the invention relates to a process to rescue recombinant infectious measles virus-Zika virus (MV-ZIKV) particles expressing at least (i) the precursor of membrane (prM) protein of a ZIKV, and the envelope (E) protein of a ZIKV or a truncated version thereof, or (ii) the E protein of a ZIKV or a truncated version thereof, and ZIKV VLPs expressing the same ZIKV protein(s), comprising:

1) co-transfecting helper cells, in particular HEK293 helper cells, that stably express T7 RNA polymerase, and measles N and P proteins with (i) the transfer vector plasmid according to the invention and with (ii) a vector, especially a plasmid, encoding the MV L polymerase;
2) cultivating said co-transfected helper cells in conditions enabling the production of recombinant MV-ZIKV particles;
3) propagating the thus produced recombinant MV-ZIKV particles by co-cultivating said helper cells of step 2) with cells enabling said propagation such as Vero cells;
4) recovering replicating infectious replicating MV-ZIKV particles expressing at least (i) the prM protein of the ZIKV, and the E protein of the ZIKV or the truncated version thereof, or (ii) the E protein of the ZIKV or the truncated version thereof, and ZIKV VLPs expressing the same ZIKV protein(s).

According to a particular embodiment of said process, the transfer vector plasmid has the sequence of SEQ ID NO: 165, SEQ ID NO: 166 or SEQ ID NO: 167, preferably has the sequence of SEQ ID NO: 165.

As used herein, the term "recombining" means introducing at least one polynucleotide into a cell, for example under the form of a vector, said polynucleotide integrating (entirely or partially) or not integrating into the cell genome (such as defined above).

According to a particular embodiment, recombination can be obtained with a first polynucleotide, which is the nucleic acid construct of the invention. Recombination can, also or alternatively, encompasses introducing a polynucleotide, which is a vector encoding a RNA polymerase large protein (L) of a MV, whose definition, nature and stability of expression has been described herein.

In accordance with the invention, the cell or cell lines or a culture of cells stably producing a RNA polymerase, a nucleoprotein (N) of a measles virus and a polymerase cofactor phosphoprotein (P) of a measles virus is a cell or cell line as defined in the present specification or a culture of cells as defined in the present specification, i.e., are also recombinant cells to the extent that they have been modified by the introduction of one or more polynucleotides as defined above. In a particular embodiment of the invention, the cell or cell line or culture of cells, stably producing the RNA polymerase, the N and P proteins, does not produce the L protein of a measles virus or does not stably produce the L protein of a measles virus, e.g., enabling its transitory expression or production.

The production of recombinant infectious replicating MV-ZIKV particles of the invention may involve a transfer of cells transformed as described herein. The term "transfer" as used herein refers to the plating of the recombinant cells onto a different type of cells, and particularly onto monolayers of a different type of cells. These latter cells are competent to sustain both the replication and the production of infectious MV-ZIKV particles, i.e., respectively the formation of infectious viruses inside the cell and possibly the release of these infectious viruses outside of the cells. This transfer results in the co-culture of the recombinant cells of the invention with competent cells as defined in the previous sentence. The above transfer may be an additional, i.e., optional, step when the recombinant cells are not efficient virus-producing culture, i.e., when infectious MV-ZIKV particles cannot be efficiently recovered from these recombinant cells. This step is introduced after further recombination of the recombinant cells of the invention with nucleic acid construct of the invention, and optionally a vector comprising a nucleic acid encoding a RNA polymerase large protein (L) of a measles virus.

In a particular embodiment of the invention, a transfer step is required since the recombinant cells, usually chosen for their capacity to be easily recombined are not efficient enough in the sustaining and production of recombinant infectious MV-ZIKV particles. In said embodiment, the cell or cell line or culture of cells of step 1) of the above-defined methods is a recombinant cell or cell line or culture of recombinant cells according to the invention.

Cells suitable for the preparation of the recombinant cells of the invention are prokaryotic or eukaryotic cells, particularly animal or plant cells, and more particularly mammalian cells such as human cells or non-human mammalian cells or avian cells or yeast cells. In a particular embodiment, cells, before recombination of its genome, are isolated from either a primary culture or a cell line. Cells of the invention may be dividing or non-dividing cells.

According to a preferred embodiment, helper cells are derived from human embryonic kidney cell line 293, which cell line 293 is deposited with the ATCC under No. CRL-1573. Particular cell line 293 is the cell line disclosed in the international application WO2008/078198 and referred to in the following examples.

According to another aspect of this process, the cells suitable for passage are CEF cells. CEF cells can be prepared from fertilized chicken eggs as obtained from EARL Morizeau, 8 rue Moulin, 28190 Dangers, France, or from any other producer of fertilized chicken eggs.

The process which is disclosed according to the present invention is used advantageously for the production of infectious replicative MV-ZIKV particles and optionally VLPs expressing ZIKV antigens appropriate for use as immunization compositions.

The invention thus relates to an immunogenic composition whose active principle comprises infectious replicative MV-ZIKV particles rescued from the nucleic acid construct of the invention and in particular obtained by the process disclosed.

The nucleic acid construct of the invention and the MV-CHIKV of the invention encode or express at least (i) the prM protein of a ZIKV, and the E protein of a ZIKV or a truncated version thereof, or (ii) the E protein of a ZIKV or a truncated version thereof.

By "protein of a ZIKV" is meant a "protein" as defined herein, the sequence of which is identical to a counterpart in a strain of ZIKV, including a polypeptide which is a native mature or precursor of a protein of ZIKV or is a fragment thereof or a mutant thereof as defined herein. In the present invention, a "protein of a ZIKV" is in particular an antigen (prM or E or their derivatives as disclosed herein) designed using a consensus sequence for the ZIKV. In particular, said antigen is designed using the consensus amino acid sequence of Zika viruses as observed circulating from 2015 and onward, notably to include the S139N change that generated a novel potential N glycosylation site in prM that was absent from the African lineage, and the V763M in E. Thus the inventors included this S139N mutation that was present in all Asian lineage sequences, but did not include single mutations in particular isolates. The inventors observed that the amino acid sequence of the Asian strain BeH818995 (GenBank: KU365777) corresponded to the consensus amino acid sequence of Zika viruses as observed circulating from 2015 and onward.

In particular a fragment or a mutant having at least 50%, at least 80%, in particular advantageously at least 90% or preferably at least 95% amino acid sequence identity to a naturally occurring ZIKV capsid or envelope protein. Amino acid sequence identity can be determined by alignment by one skilled in the art using manual alignments or using the numerous alignment programs available. Fragments or mutants of ZIKV proteins of the invention may be defined with respect to the particular amino acid sequences illustrated herein.

According to a preferred embodiment, the invention also concerns modifications and optimization of the polynucleotide to allow an efficient expression of the at least (i) prM of ZIKV, and E protein of ZIKV or truncated version thereof, or (ii) E protein of ZIKV or truncated version thereof, at the surface of chimeric infectious particles of MV-ZIKV in the host, in particular the human host.

According to this embodiment, optimization of the polynucleotide sequence can be operated avoiding cis-active domains of nucleic acid molecules: internal TATA-boxes, chi-sites and ribosomal entry sites; AT-rich or GC-rich sequence stretches; ARE, INS, CRS sequence elements; repeat sequences and RNA secondary structures; cryptic splice donor and acceptor sites, branch points.

The optimized polynucleotides may also be codon optimized for expression in a specific cell type. This optimization allows increasing the efficiency of chimeric infectious particles production in cells without impacting the expressed protein(s).

In a particular embodiment of the invention, the polynucleotide encoding at least (i) the prM protein of the ZIKV, and the E protein of the ZIKV or the truncated version thereof, or (ii) the E protein of the ZIKV or the truncated version thereof, has been optimized for a Macaca codon usage or has been optimized for a human codon usage.

The optimization of the polynucleotide encoding at least (i) the prM protein of the ZIKV, and the E protein of the ZIKV or the truncated version thereof, or (ii) the E protein of the ZIKV or the truncated version thereof may be performed by modification of the wobble position in codons without impacting the identity of the amino acid residue translated from said codon with respect to the original one.

Optimization is also performed to avoid editing-like sequences from Measles virus. The editing of transcript of Measles virus is a process which occurs in particular in the transcript encoded by the P gene of Measles virus. This editing, by the insertion of extra G residues at a specific site within the P transcript, gives rise to a new protein truncated compared to the P protein. Addition of only a single G residue results in the expression of the V protein, which contains a unique carboxyl terminus (Cattaneo R et al., *Cell.* 1989 Mar. 10; 56(5):759-64).

In a particular embodiment of the invention, measles editing-like sequences have been deleted from said polynucleotide encoding at least (i) the prM protein of the ZIKV, and the E protein of the ZIKV or the truncated version thereof, or (ii) the E protein of the ZIKV or the truncated version thereof. The following measles editing-like sequences can be mutated: AAAGGG, AAAAGG, GGGAAA, GGGGAA, TTAAA, AAAA, as well as their complementary sequence: TTCCCC, TTTCCC, CCTTTT, CCCCTT, TTTAA, TTTT. For example, AAAGGG can be mutated in AAAGGC, AAAAGG can be mutated in AGAAGG or in TAAAGG or in GAAAGG, and GGGAAA in GCGAAA.

In a particular embodiment of the invention, the native and codon-optimized nucleotide sequences of the polynucleotide encoding particular peptides/proteins/antigen as well as the amino acid sequences of these peptides/proteins/antigen of the invention are the sequences disclosed as SEQ ID Nos: 3-164 and mentioned in Table 1 below. These sequences are also represented in FIGS. 3A-3D.

In a particular embodiment of the invention, the transfer vector plasmid pTM2-MVSchw_A1_Zikasp_ZikaprME has the optimized sequence of SEQ ID NO: 165, the transfer vector plasmid pTM2-MVSchw_insert 4 has the native sequence of SEQ ID NO: 166 and the transfer vector plasmid pTM2-MVSchw_insert 5 has the native sequence of SEQ ID NO: 167, as mentioned in Table 1 below.

In another particular embodiment of the invention, the native nucleotide sequences of the polynucleotide encoding insert 4 or insert 5 as well as the amino acid sequences of said insert 4 or insert 5 of the invention are the sequences disclosed as SEQ ID Nos: 168-171 and mentioned in Table 1 below. Insert 4 (SEQ ID NO: 169) is similar to Zikasp_Zika_prMEd404 (SEQ ID NO: 54) but with a shorter sp in 5'. Insert 5 (SEQ ID NO: 171) is similar to Zikasp'_ZikaEd445 (SEQ ID NO: 75) with 2 minor differences in 5'.

TABLE 1

Native and codon-optimized nucleotide sequences of the polynucleotide encoding particular peptides/proteins as well as amino acid sequences of these peptides/proteins used in the invention.

| Name of the compound, i.e. peptide/protein/antigen (abbreviation) | SEQ ID NO of the native nucleotide sequence of the polynucleotide encoding the compound | SEQ ID NO of the codon-optimized nucleotide sequence of the polynucleotide encoding the compound | SEQ ID NO of the amino acid sequence of the compound |
|---|---|---|---|
| Signal peptide from the capsid of ZIKV (sp) | 3 | 4 | 5 |
| Signal peptide from the membrane protein of ZIKV (sp') | 6 | 7 | 8 |
| Signal peptide from the capsid of JEV (JEVsp) | 9 | 10 | 11 |
| Signal peptide from the fusion protein of MV (MVsp) | 12 | 13 | 14 |
| Modified signal peptide from the fusion protein of MV (MVsp') | 15 | 16 | 17 |
| Precursor of membrane (prM) protein of ZIKV | 18 | 19 | 20 |
| Full-length E protein of ZIKV | 21 | 22 | 23 |
| E protein of ZIKV truncated at amino acid position 456 (Ed456) | 24 | 25 | 26 |
| E protein of ZIKV truncated at amino acid position 445 (Ed445) | 27 | 28 | 29 |
| E protein of ZIKV truncated at amino acid position 404 (Ed404) | 30 | 31 | 32 |
| E stem region of ZIKV | 33 | 34 | 35 |
| Intermediate domain between E stem and E anchor regions of ZIKV | 36 | 37 | 38 |
| E anchor region of ZIKV | 39 | 40 | 41 |
| Transmembrane (TM) and intracytoplasmic tail of MV F protein | 42 | 43 | 44 |
| Zikasp_ZikaprME protein (A1) | 45 | 46 | 47 |
| Zikasp_Zika_prMEd456 protein (A2) | 48 | 49 | 50 |
| Zikasp_Zika_prMEd445 protein (A3) | 51 | 52 | 53 |

TABLE 1-continued

| Native and codon-optimized nucleotide sequences of the polynucleotide encoding particular peptides/proteins as well as amino acid sequences of these peptides/proteins used in the invention. | | | |
|---|---|---|---|
| Zikasp_Zika_prMEd404 protein (A4) | 54 | 55 | 56 |
| Zikasp_ZikaE protein (A5) | 57 | 58 | 59 |
| Zikasp_ZikaEd456 protein (A6) | 60 | 61 | 62 |
| Zikasp_ZikaEd445 protein (A7) | 63 | 64 | 65 |
| Zikasp_ZikaEd404 protein (A8) | 66 | 67 | 68 |
| Zikasp'_ZikaE protein (A9) | 69 | 70 | 71 |
| Zikasp'_ZikaEd456 protein (A10) | 72 | 73 | 74 |
| Zikasp'_ZikaEd445 protein (A11) | 75 | 76 | 77 |
| Zikasp'_ZikaEd404 protein (A12) | 78 | 79 | 80 |
| JEVsp_ZikaprME protein (B1) | 81 | 82 | 83 |
| JEVsp_Zika_prMEd456 protein (B2) | 84 | 85 | 86 |
| JEVsp_Zika_prMEd445 protein (B3) | 87 | 88 | 89 |
| JEVsp_Zika_prMEd404 protein (B4) | 90 | 91 | 92 |
| JEVsp_ZikaE protein (B5) | 93 | 94 | 95 |
| JEVsp_ZikaEd456 protein (B6) | 96 | 97 | 98 |
| JEVsp_ZikaEd445 protein (B7) | 99 | 100 | 101 |
| JEVsp_ZikaEd404 protein (B8) | 102 | 103 | 104 |
| MVsp_ZikaprME (C1) | 105 | 106 | 107 |
| MVsp_Zika_prMEd456 (C2) | 108 | 109 | 110 |
| MVsp_Zika_prMEd445 (C3) | 111 | 112 | 113 |
| MVsp_Zika_prMEd404 (C4) | 114 | 115 | 116 |
| MVsp_ZikaE (C5) | 117 | 118 | 119 |
| MVsp_ZikaEd456 (C6) | 120 | 121 | 122 |
| MVsp_ZikaEd445 (C7) | 123 | 124 | 125 |
| MVsp_ZikaEd404 (C8) | 126 | 127 | 128 |
| MVsp_ZikaprME_MVTMintracyto (C9) | 129 | 130 | 131 |
| MVsp_Zika_MVTMintracytoE (C10) | 132 | 133 | 134 |
| MVsp'_ZikaprME (D1) | 135 | 136 | 137 |
| MVsp'_Zika_prMEd456 (D2) | 138 | 139 | 140 |
| MVsp'_Zika_prMEd445 (D3) | 141 | 142 | 143 |
| MVsp'_Zika_prMEd404 (D4) | 144 | 145 | 146 |
| MVsp'_ZikaE (D5) | 147 | 148 | 149 |
| MVsp'_ZikaEd456 (D6) | 150 | 151 | 152 |
| MVsp'_ZikaEd445 (D7) | 153 | 154 | 155 |
| MVsp'_ZikaEd404 (D8) | 156 | 157 | 158 |
| MVsp'_ZikaprME_MVTMintracyto (D9) | 159 | 160 | 161 |
| MVsp'_Zika_MVTMintracytoE (D10) | 162 | 163 | 164 |

| Name of the transfer vector plasmid | SEQ ID NO |
|---|---|
| pTM2-MVSchw_A1_Zikasp_ZikaprME (optimized sequence) | 165 |
| pTM2-MVSchw_insert 4 (native sequence) | 166 |
| pTM2-MVSchw_insert 5 (native sequence) | 167 |

| Name of the compound, i.e. peptide/protein/antigen (abbreviation) | SEQ ID NO of the native nucleotide sequence of the polynucleotide encoding the compound | SEQ ID NO of the amino acid sequence of the compound |
|---|---|---|
| Insert 4 | 168 | 169 |
| Insert 5 | 170 | 171 |

In a particular embodiment of the invention, said ZIKV is from the African lineage, in particular from the African strain ArB1362 (GenBank: KF383115) or African isolate IbH_30656 (GenBank: HQ234500), or from the Asian lineage, in particular from the Asian strain BeH818995 (GenBank: KU365777), preferably is from ZIKV strains that circulated in the Pacific and Americas since 2013.

In another particular embodiment of the invention, said ZIKV corresponds to various lineages of ZIK viruses including strains that circulated in the Pacific and Americas since 2013.

In a preferred embodiment of the invention, the prM protein of the ZIKV has an amino acid sequence which is a consensus amino acid sequence representative of the prM sequences of a selection of various strains of ZIKV including from the Asian lineage, in particular is from the ZIKV strain BeH818995. The E protein of the ZIKV or the truncated version thereof has an amino acid sequence which is a consensus amino acid sequence representative of the E sequences of a selection of various strains of ZIKV including from the Asian lineage, in particular is from the ZIKV strain BeH818995.

In a particular embodiment of the invention, said polynucleotide encoding at least (i) the prM protein of the ZIKV, and the E protein of the ZIKV or the truncated version thereof, further encodes (iii) the signal peptide from the capsid of the ZIKV (sp) or the signal peptide from the capsid of a JEV (JEVsp) or the signal peptide from the fusion protein of MV (MVsp) or the modified signal peptide from the fusion protein of MV (MVsp') and the signal peptide from the membrane protein of the ZIKV (sp'), or said polynucleotide encoding at least (ii) the E protein of the ZIKV or the truncated version thereof, further encodes (iii) the signal peptide from the capsid of the ZIKV (sp) or the signal peptide from the membrane protein of the ZIKV (sp') or the signal peptide from the capsid of a JEV (JEVsp) or the signal peptide from the fusion protein of MV (MVsp) or the modified signal peptide from the fusion protein of MV (MVsp').

In a preferred embodiment of the invention, said polynucleotide encoding at least (i) the prM protein of the ZIKV, and the E protein of the ZIKV or the truncated version thereof, further encodes (iii) the signal peptide from the capsid of the ZIKV and the signal peptide from the membrane protein of the ZIKV, or said polynucleotide encoding at least (ii) the E protein of the ZIKV or the truncated version thereof, further encodes (iii) the signal peptide from the capsid of the ZIKV or the signal peptide from the membrane protein of the ZIKV.

In a particular embodiment of the invention, the polynucleotide encoding the E protein encodes either the full-length E protein or its soluble form lacking the two C-terminal transmembrane domains of the full-length E protein.

In a preferred embodiment of the invention, the polynucleotide encoding the truncated version of the E protein is selected from the group consisting of (i) the polynucleotide encoding the E protein truncated at amino acid position 456 of the full-length E protein of the ZIKV, i.e. the E protein lacking the anchor region and the intermediate domain between the stem and anchor regions, (ii) the polynucleotide encoding the E protein truncated at position 445 of the full-length E protein of the ZIKV, i.e. the E protein lacking the anchor region, the intermediate domain between the stem and anchor regions and a fragment of the second helix that composed the stem region, and (iii) the polynucleotide encoding the E protein truncated at position 404 of the full-length E protein of the ZIKV, i.e. the E protein lacking the stem region, the intermediate domain between the stem and anchor regions, and the anchor region.

In a preferred embodiment of the invention, the polynucleotide encodes the prM protein of the ZIKV whose sequence is SEQ ID NO: 20, and the polynucleotide encodes the E protein of the ZIKV or the truncated version thereof whose sequence is selected from the group consisting of SEQ ID NO: 23, SEQ ID NO: 26, SEQ ID NO: 29 and SEQ ID NO: 32.

In a preferred embodiment of the invention, the polynucleotide encoding the prM protein of the ZIKV has the sequence of SEQ ID NO: 19, and the polynucleotide encoding the E protein of the ZIKV or a truncated version thereof has a sequence selected from the group consisting of SEQ ID NO: 22, SEQ ID NO: 25, SEQ ID NO: 28 and SEQ ID NO: 31.

In a particular embodiment of the invention, said nucleic acid construct comprises a sequence selected from the group consisting of SEQ ID NOs: 45-164 and 168-171.

In a preferred embodiment of the invention, said nucleic acid construct comprises a sequence selected from the group consisting of SEQ ID NO: 46, SEQ ID NO: 52, SEQ ID NO: 55, SEQ ID NO: 70, SEQ ID NO: 76, SEQ ID NO: 79, SEQ ID NO: 168 and SEQ ID NO: 170, preferably has the sequence of SEQ ID NO: 46, SEQ ID NO: 55 or SEQ ID NO: 76, more preferably has the sequence of SEQ ID NO: 46.

In a preferred embodiment of the invention, the nucleic acid construct comprises the sequence from nucleotide at position 83 to nucleotide at position 18404 in the sequence of SEQ ID NO: 165, or the sequence from nucleotide at position 83 to nucleotide at position 18074 in the sequence of SEQ ID NO: 166, or the sequence from nucleotide at position 83 to nucleotide at position 17702 in the sequence of SEQ ID NO: 167.

The invention also concerns recombinant infectious replicating measles virus-Zika virus (MV-ZIKV) particles, which comprise as their genome a nucleic acid construct according to the invention.

In a particular embodiment of the invention, said recombinant infectious replicating MV-ZIKV particles are rescued from a helper cell line expressing an RNA polymerase recognized by said cell line, for example a T7 RNA polymerase, a nucleoprotein (N) of a MV, a phosphoprotein (P) of a MV, and optionally an RNA polymerase large protein (L) of a MV, and which is further transfected with the transfer vector plasmid according to the invention.

Said recombinant infectious replicating MV-ZIKV particles are thus produced by a method comprising expressing the nucleic acid construct according to the invention in a host cell comprising an RNA polymerase recognized by said host cell, for example a T7 RNA polymerase, a nucleoprotein (N) of a MV, a phosphoprotein (P) of a MV, and optionally an RNA polymerase large protein (L) of a MV.

According to a particular embodiment of the invention, said particles comprise in their genome a polynucleotide sequence comprising a sequence selected from the group consisting of SEQ ID NO: 46, SEQ ID NO: 52, SEQ ID NO: 55, SEQ ID NO: 70, SEQ ID NO: 76, SEQ ID NO: 79, SEQ ID NO: 168 and SEQ ID NO: 170, preferably has the sequence of SEQ ID NO: 46, SEQ ID NO: 55 or SEQ ID NO: 76, more preferably has the sequence of SEQ ID NO: 46.

The obtained at least (i) prM protein of the ZIKV, and E protein of the ZIKV or truncated version thereof, or (ii) E protein of the ZIKV or truncated version thereof, are also able to auto-assemble into ZIK virus-like-particles (VLPs), with the MV-ZIKV particles.

As used herein, the term "virus-like particle" (VLP) refers to a structure that in at least one attribute resembles a virus but which has not been demonstrated to be infectious as such. VLPs in accordance with the invention do not carry genetic information encoding the proteins of the VLPs, in general, VLPs lack a viral genome and, therefore, are non-infectious and non-replicative. In accordance with the present invention, VLPs can be produced in large quantities and are expressed together with recombinant infectious MV-ZIKV particles. Said VLPs are VLPs of ZIKV.

According to another aspect, the invention relates to recombinant infectious MV-ZIKV particles expressing at least (i) the prM protein of the ZIKV, and the E protein of the ZIKV or the truncated version thereof, or (ii) the E protein of the ZIKV or the truncated version thereof, in particular by reference to their nucleic acid and polypeptide sequences. The recombinant infectious MV-ZIKV advantageously expresses at least (i) the prM protein of the ZIKV, and the E protein of the ZIKV or the truncated version thereof, or (ii) the E protein of the ZIKV or the truncated version thereof, as VLPs.

The invention also relates to a composition or an assembly of active ingredients comprising the recombinant infectious replicating MV-ZIKV particles according to the invention, and a pharmaceutically acceptable vehicle.

The invention also concerns the association, in a composition, of VLPs comprising at least (i) the prM protein of the ZIKV, and the E protein of the ZIKV or the truncated version thereof, or (ii) the E protein of the ZIKV or the truncated version thereof, with recombinant infectious replicating MV-ZIKV-MV particles.

According to a preferred embodiment of the invention, the recombinant MV vector is designed in such a way and the production process involves cells such that the virus particles produced in helper cells transfected or transformed with said vector, originated from a MV strain adapted for vaccination, enable the production of recombinant infectious replicating MV and the production of ZIKV-VLPs for use in immunogenic compositions, preferably protective or even vaccine compositions.

Advantageously, the genome of the recombinant infectious MV-ZIKV particles of the invention is replication competent. By "replication competent', it is meant a nucleic acid, which when transduced into a helper cell line expressing the N, P and L proteins of a MV, is able to be transcribed and expressed in order to produce new viral particles.

Replication of the recombinant virus of the invention obtained using MV cDNA for the preparation of the recombinant genome of MV-ZIKV can also be achieved in vivo in the host, in particular the human host to which recombinant MV-ZIKV is administered.

The invention also concerns a composition or an assembly of active ingredients comprising the recombinant infectious replicating MV-ZIKV particles according to the invention, in association with ZIKV-VLPs expressing the same ZIKV protein(s) as said MV-ZIKV particles.

According to a preferred embodiment of the invention, said composition or assembly of active ingredients is used in the elicitation of an immune response, in particular a protective immune response, against ZIKV by the elicitation of antibodies directed against said ZIKV protein(s), and/or of a cellular immune response, in a host, in particular a human host in need thereof.

Said composition or assembly of active ingredients accordingly may comprise a suitable vehicle for administration e.g. a pharmaceutically acceptable vehicle to a host, especially a human host and may further comprise but not necessarily adjuvant to enhance immune response in a host. The inventors have indeed shown that the administration of the active ingredients of the invention may elicit an immune response without the need for adjuvantation.

According to a particular embodiment of the invention, said composition or assembly of active ingredients comprises a pharmaceutically acceptable vehicle.

The invention relates in particular to a composition, in particular an immunogenic composition, preferably a vaccine composition for administration to children, adolescents or travelers.

In a particular embodiment, said composition or vaccine is used for preventive protection against African and Asian strains of ZIKV.

Said composition or vaccine is used for protection against ZIKV infection or against clinical outcomes of infection by ZIKV (protection against ZIKV disease) in a prophylactic treatment. Such a vaccine composition has advantageously active principles (active ingredients) which comprise recombinant infectious replicating MV-ZIKV particles rescued from the vector as defined herein optionally associated with VLPs comprising the same ZIKV proteins.

In the context of the invention, the terms "associated" or "in association" refer to the presence, in a unique composition, of both recombinant infectious replicating MV-ZIKV particles and the above-mentioned ZIKV proteins, in particular as VLPs, usually as physically separate entities.

The invention also concerns the recombinant infectious replicating MV-ZIKV particles according to the invention in association with the above-mentioned ZIKV proteins, in particular in association with ZIKV-VLPs expressing the same ZIKV proteins, or the composition or the assembly of active ingredients according to the invention, for use in the prevention of an infection by ZIKV in a subject, or in the prevention of clinical outcomes of infection by ZIKV in a subject, in particular in a human.

The invention also concerns the recombinant infectious replicating MV-ZIKV particles according to the invention in association with the above-mentioned ZIKV proteins, in particular in association with ZIKV-VLPs expressing the same ZIKV proteins, for use in an administration scheme and according to a dosage regime that elicit an immune response, advantageously a protective immune response, against ZIKV infection or induced disease, in particular in a human host.

The administration scheme and dosage regime may require a unique administration of a selected dose of the recombinant infectious replicating MV-ZIKV particles according to the invention in association with the above-mentioned ZIKV proteins, in particular in association with ZIKV-VLPs expressing the same ZIKV proteins.

Alternatively it may require multiple administration doses in a prime-boost regimen. Priming and boosting may be achieved with identical active ingredients consisting of said recombinant infectious replicating MV-ZIKV particles in association with the above-mentioned ZIKV proteins, in particular in association with ZIKV-VLPs expressing the same ZIKV proteins.

Alternatively priming and boosting administration may be achieved with different active ingredients, involving said recombinant infectious replicating MV-ZIKV particles in association with the above-mentioned ZIKV proteins, in particular in association with ZIKV-VLPs expressing the same ZIKV proteins, in at least one of the administration steps and other active immunogens of ZIKV, such as the above-mentioned ZIKV proteins or ZIKV-VLPs expressing the same ZIKV proteins, in other administration steps.

Administration of recombinant infectious replicating MV-ZIKV particles according to the invention in association with ZIKV-VLPs expressing the same ZIKV proteins elicits an immune response and especially elicits antibodies that are cross-reactive for various ZIKV strains. Accordingly, it has been shown that administration of the active ingredients according to the invention, when prepared with the coding sequences of a particular strain of ZIKV, can elicit an immune response against a group of strains of ZIKV.

Considering available knowledge on doses of vaccines suitable for other pathogens (such as HBV or HPV) which involve the administration of VLPs and also for known human MV vaccines, the inventors have determined that the recovery of ZIKV-VLPs with the recombinant MV-ZIKV enables proposing administration of effective low doses of the active ingredients.

Indeed, considering that the recombinant MV-ZIKV enables production of around $10^4$ ZIKV-VLPs per recombinant infectious replicating MV-ZIKV particle, and considering that the currently known doses for human MV vaccines are in the range of $10^3$ to $10^5$ TCID50, a suitable dose of recombinant MV-ZIKV to be administered may be in the range of 0.1 to 10 ng, in particular 0.2 to 6 ng, and possibly as low as 0.2 to 2 ng. For comparison doses of VLPs administered in the case of HBV or HPV vaccines are in the range of 10 μg which means that a dose of recombinant MV-ZIKV vaccine could comprise around 2 000 or up to 5 000 to 10 000 times less VLPs.

According to a particular embodiment of the invention, the immunogenic or vaccine composition defined herein may also be used for protection against an infection by the measles virus.

Other features and advantages of the invention will be apparent from the examples which follow and will also be illustrated in the figures.

EXAMPLES

Generation of Vaccine Candidates

Figure 1:
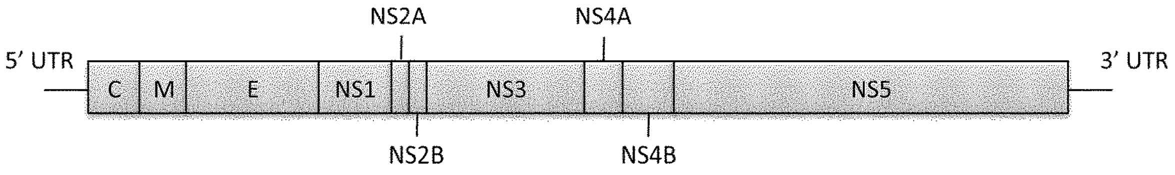
FIG. 1. Schematic representation of Zika virus genome.

Previous experiences with different flaviviruses (dengue, West Nile, Japanese encephalitis, tick-borne encephalitis) widely demonstrated that the flaviviral surface envelope (E) proteins are able to elicit protective neutralizing antibodies that allow reducing virus infectivity. The ZIKV genome consists of a single-stranded positive sense RNA molecule of ~10800 kb of length with 2 flanking non-coding regions (5' and 3' NCR) and a single long open reading frame encoding a polyprotein that is cleaved into three structural proteins (capsid (C), precursor of membrane (prM), envelope (E)) and seven non-structural proteins (NS) (FIG. 1). The E protein (53 kDa) is the major virion surface protein involved in various aspects of the viral cycle, mediating binding to target cells and membrane fusion.

The inventors therefore chose to express the Zika virus E protein. Several forms of E protein were selected in order to express either soluble secreted proteins or anchored proteins onto the surface of VLPs. The following Zika virus antigens were cloned and expressed from a mammalian expression plasmid in human cells: prM-E and different forms of E with or without the stem or anchor region. These proteins contain either the original signal peptide sequence of Zika virus E or a heterologous signal peptide sequence from JEV or MV fusion protein. These proteins contain the signalase cleavage site located between the prM and the E sequences (FIGS. 3A, 3B, 3C, 3D).

Antigens Selection and Design

Figure 2:
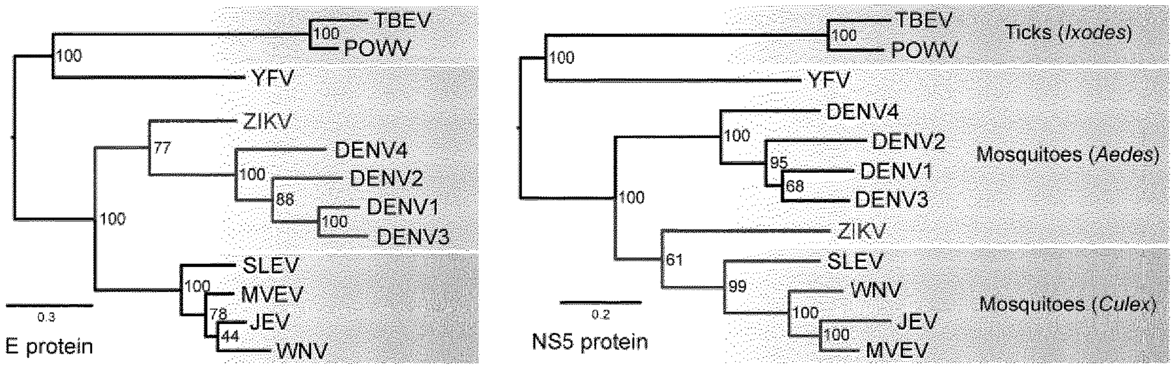
FIG. 2. Phylogenetic trees of the main human pathogenic flaviviruses based on the amino acid sequences of the E protein (left) and of the polymerase NS5 protein (right). JEV, Japanese encephalitis virus; MVEV, Murray Valley encephalitis virus; POWV, Powassan virus; SLEV, Saint Louis encephalitis virus; TBEV, tick-borne encephalitis virus; YFV, yellow fever virus; WNV, West Nile virus.
Figure 3A:
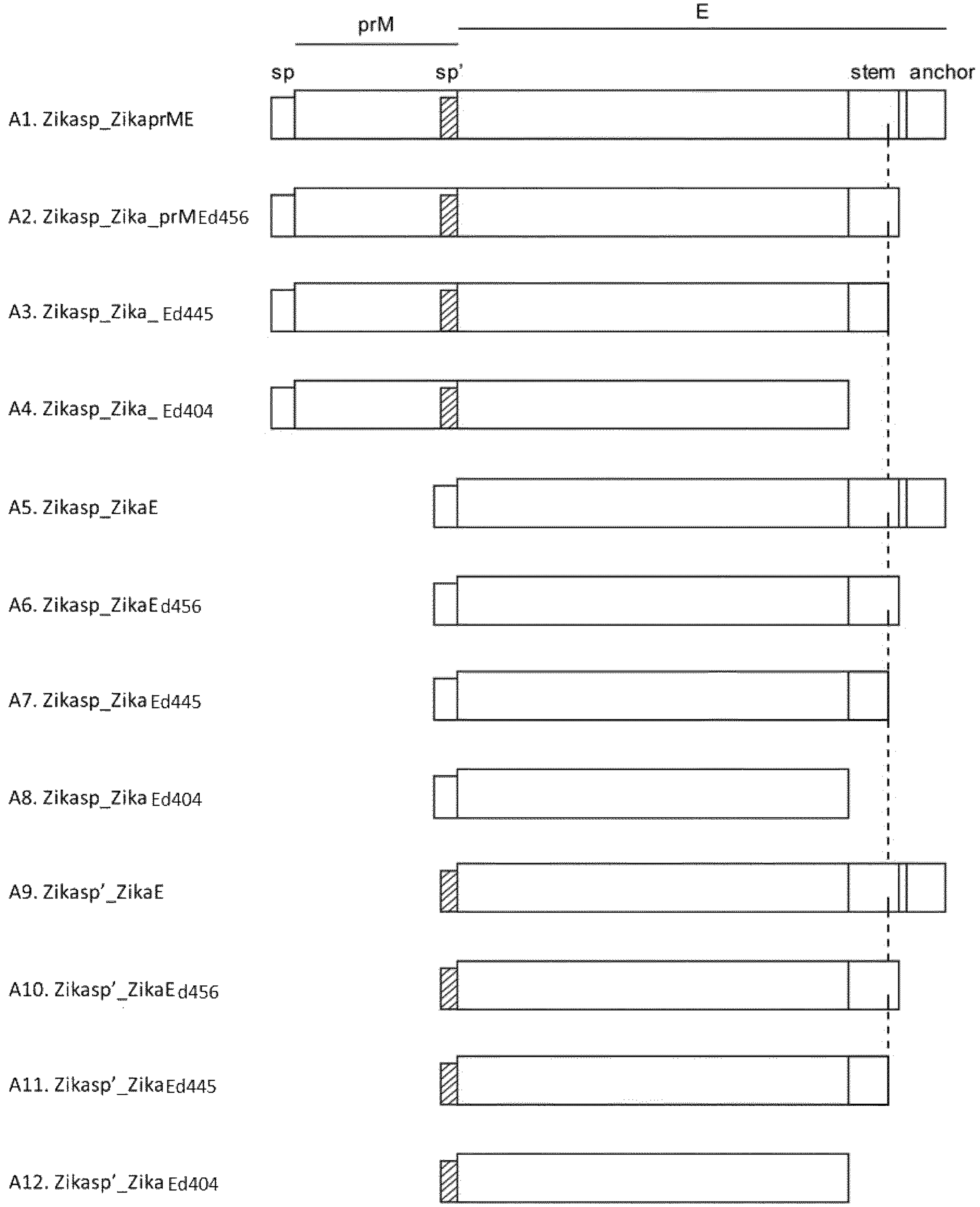
FIG. 3. Schematic representation of Zika virus antigens. Protein domains are drawn to scale. Zika, Zika virus; JEV, Japanese encephalitis virus; MV, Measles virus. A. 12 variants of the Zika antigen, where the native signal peptide from the capsid (sp) or from the membrane protein (sp') of Zika virus is used. B. 8 variants of the chimeric JEV-Zika antigen, where a signal peptide of the capside of JEV is used. C. 10 variants of the MV-Zika antigen, where the signal peptide of the fusion protein of MV (MVsp) is used. D. 10 variants of the MV Zika antigen, where a modified signal peptide of the fusion protein of MV (MVsp') is used.
Figure 3B:
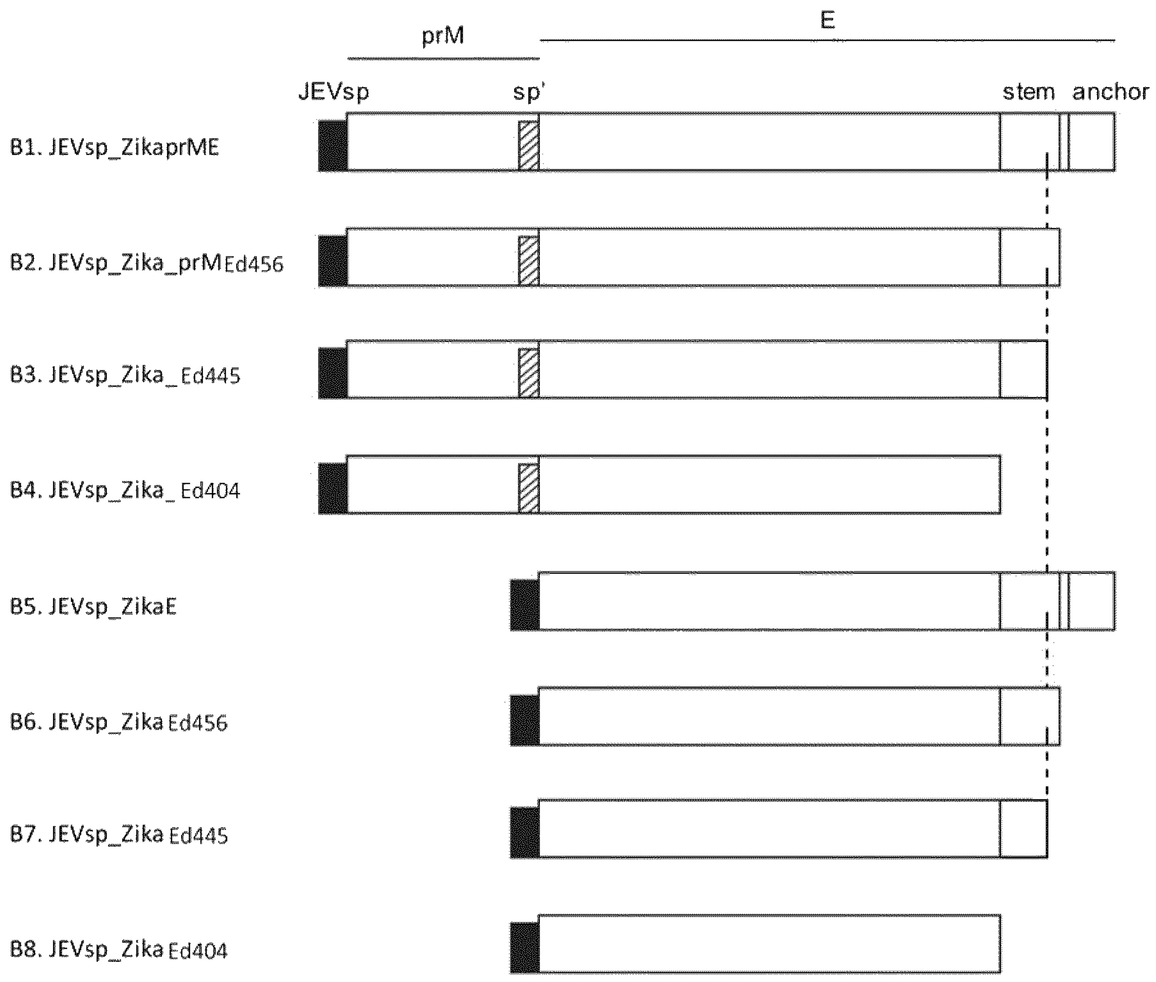

The Zika antigens were selected based on previous works concurring into suggesting that envelope antigens of flaviviruses may be able to elicit neutralizing antibodies and T cell responses. Selecting a suitable antigen should however take into consideration the evolution of the virus over time and the variety of existing virus strains. To this end, the inventors reconstructed the phylogeny of representative members of the flavivirus family, including Zika virus, using only the amino acid region of the flavivirus polyprotein corresponding to the envelope (E) gene. Unlike phylogenetic analyses based on the full genome, or the polymerase (NS5) of flaviviruses, where the closest relative of Zika virus are neurotropic viruses such as Saint-Louis Encephalitis virus, the inventors noticed that Zika E appeared closer to DENV E (FIG. 2) (Barba-Spaeth, et al. Nature 2016, 536, 48-53). The inventors then proceeded to identify the different domains of Zika membrane (M), its precursor (prM) and E proteins through structural homology modelling based on available data on DENV (Ekins et al. Illustrating and homology modeling the proteins of the Zika virus, F1000Research 2016, 5:275). The inventors also identified the signal peptides at the end of the Capsid (C) gene, just upstream of prM, using again homology modelling with dengue virus as a reference, as well as publicly available algorithms to predict signal peptide sequences (sigpep. services. came. sbg. ac. at/sidnalblast. html; cbs. dtu. dk/services/SignalP/; predisi. de/). The inventors chose to include the signal peptide sequence to induce the export and secretion of the candidate antigen, either the full-length prM-E, or the E only, outside the cells. For the E antigen, the inventors also predicted the signal peptide at the end of M, just upstream of E, and designed versions of the antigen using this native signal (FIG. 3A). In addition, the inventors also designed chimeric antigens where the native signal peptide of Zika virus was replaced with the signal peptide present at the end of JEV C (FIG. 3B), or the signal peptide present at the N-terminal of the fusion protein (F) of MV (FIG. 3C), hypothesizing that these sequences would provide enhanced export of the candidate antigens. The inventors designed an additional version of the chimeric antigen including the signal peptide of F from MV, where two amino acids corresponding to the junction between the end of the signal peptide of F and the beginning of F itself were removed (FIG. 3D).

Secondly, the inventors also designed shorter variations of the antigens by removing C terminal fragments of the E protein corresponding to the predicted stem and/or anchor domains, including the intermediate region between the stem and anchor (as predicted by comparison to DENV). The aim of these modifications that reduced antigens size was to generate antigens that were able to form VLPs. For a third variant, the inventors removed the anchor, the intermediate domain between the anchor and the stem, as well as a fragment of the second helix that composed the stem, this time in homology modelling with WNV (variant Ed445).

Figure 3C:
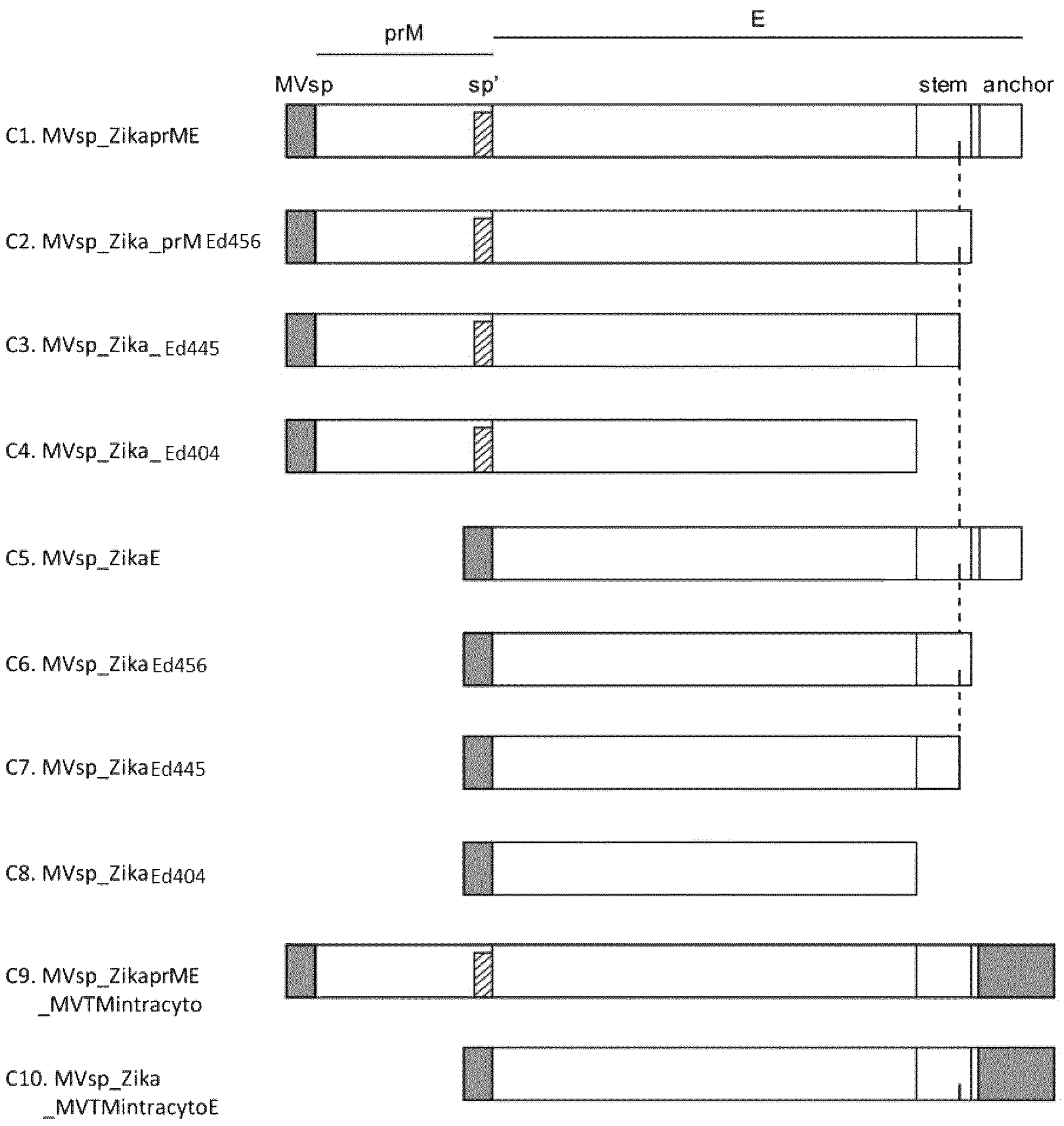
Figure 3D:
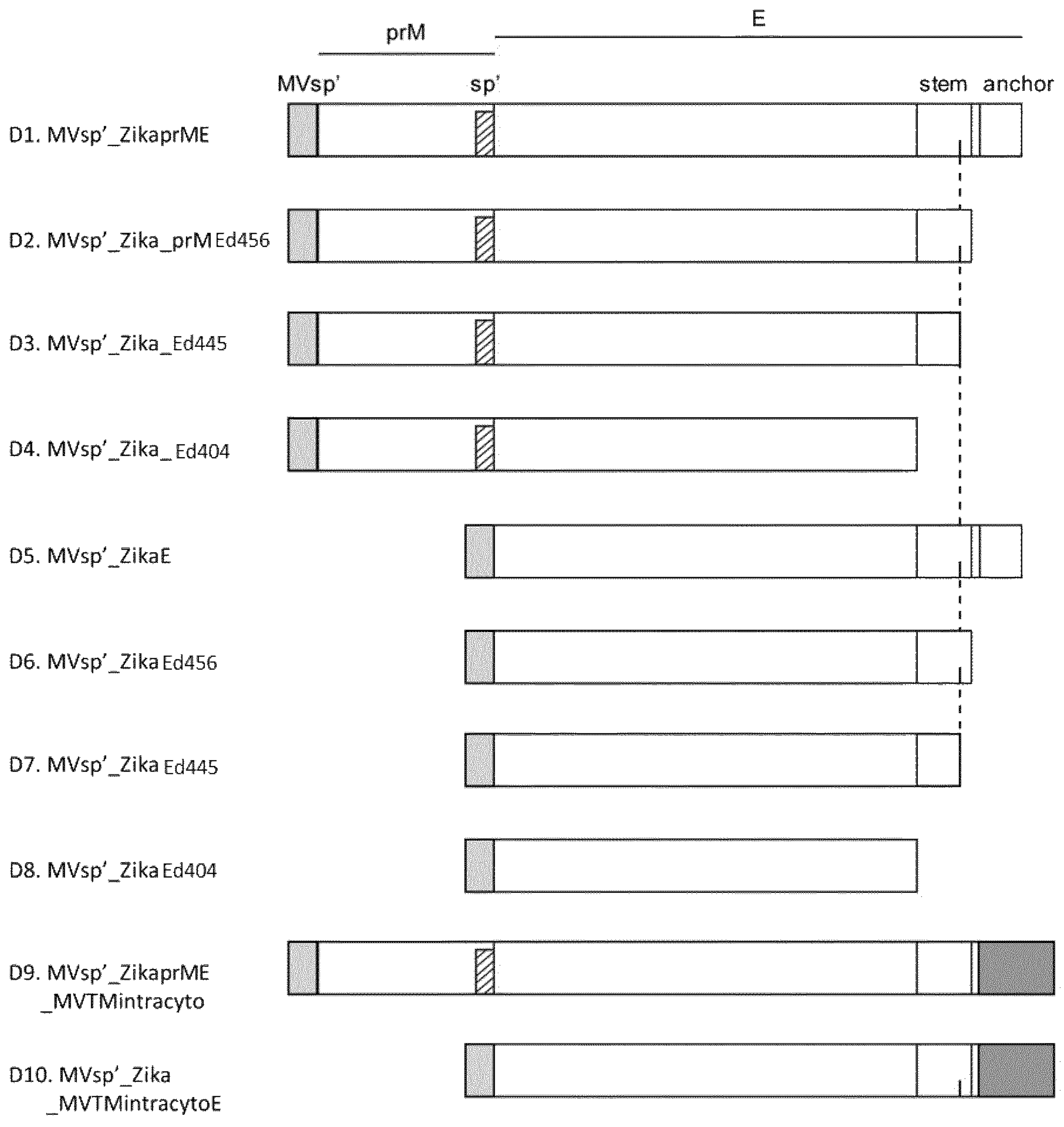
Figure 4:
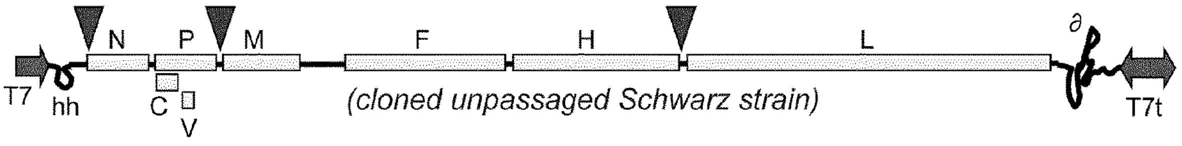
FIG. 4. Schematic representation of MV Vector. MV genes are indicated: N (nucleoprotein), PVC (phoshoprotein and V/C proteins), M (matrix), F (fusion), H (hemagglutinin), L (polymerase), T7 (T7 RNA polymerase promoter), hh (hammerhead ribozyme), T7t (T7 RNA polymerase terminator), a (hepatitis delta virus ribozyme), red arrows (additional transcription units).

Finally, the inventors designed chimeric prM-E and E antigens using the signal peptide from MV F protein, and replacing Zika E anchor by the transmembrane (TM) and intracytoplasmic tail of MV F protein (FIGS. 3C and 3D).

For the selection sequence of the antigen itself, the inventors analyzed all publicly available sequences of Zika virus (both Asian and African lineages), as well as unpublished sequences generated by the inventors, from the epidemic in South America and Pacific. Based on the epidemiological data reporting an association of congenital syndromes and neurological afflictions in adults with only the Asian lineage, the inventors designed an antigen using the consensus amino acid sequence of Zika viruses as observed circulating from 2015 and onward, notably to include the S139N change that generated a novel potential N glycosylation site in prM that was absent from the African lineage, and the V763M in E.

The sequences were codon-optimized for *Homo sapiens* expression and adapted to measles vector cloning and to the "rule of six" (total number of nucleotides divisible by 6). Regions very rich (>80%) or very poor (<30%) in GC were avoided to increase RNA stability, a high CAI value (0.97) was obtained to increase translation efficacy, the following CIS active sequences were avoided: internal TATA-boxes, chi-sites, ribosomal entry sites, AT- or GC-rich sequence stretches, ARE, INS, CRS elements, repeat sequences, RNA secondary structures, cryptic splice donor and acceptor sites, branch points. The following measles virus editing sequences were avoided where possible: AAAGGG, AAAAGG, GGGAAA, GGGGAA, TTAAA, AAAA, and also their complementary sequences on the same strand: TTCCCC, TTTCCC, CCTTTT, CCCTT, TTTAA, TTTT.

The enzyme restriction sites BssHII, BsiWI were avoided internally and inserted at both ends for cloning purpose.

Antigen Expression in Mammalian Cells

The optimized antigen sequences were cloned into pcDNA5 mammalian expression plasmid and transfected into HEK293 cells. The size and level of expression of each antigen were characterized after western blotting using appropriate antibodies for detection.

Antigen Expression in Measles Vector

Figure 7:
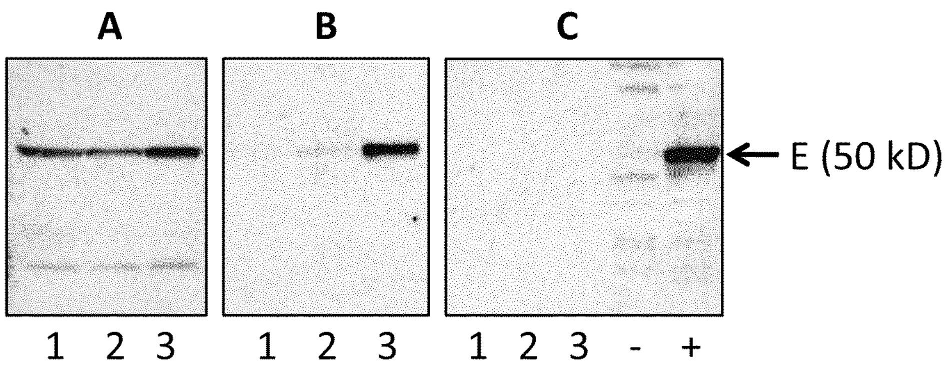
FIG. 7. Recombinant MV expressing the full-length prME Zika antigen (construct A1) produces Zika VLPs. Vero cells were infected with three different clones of rMV-Zika_A1 (1, 2, 3) for 48 hours. Cell lysates and medium were collected. Supernatant medium was clarified by low-speed centrifugation (1500 rpm) then concentrated by ultracentrifugation on a 20% sucrose cushion for 3 hours (36000 rpm). All material was analyzed by western blot to detect the Zika E protein (50 kD) with 4G2 panflavi monoclonal antibody. (A) Cell lysates, (B) Concentrated medium, (C) Non-concentrated medium and positive and negative controls. Positive control is a lysate of Vero cells transfected for 48 hours with pcDNA5 plasmid expressing the Zika A1 antigen. The positive E protein recovered in panel B after ultracentrifugation demonstrates that high density VLPs were produced in the supernatant of infected Vero cells.

The optimized Zika antigen sequences were inserted into the MV vector in different additional transcription units, according to the desired level of expression. After sequencing of the measles vector plasmids expressing the different Zika antigens, the replicating recombinant vectors were generated by reverse genetics using a cell-based system previously developed (Combredet, C. et al., 2003, *J Virol*, 77(21): 11546-11554), and the rescued viruses were amplified and titrated on Vero cells. The recombinant viruses were grown on Vero cells to document the expression of Zika proteins detected both in supernatants and in cells by using Western Blot and indirect immunofluorescence staining with appropriate antibodies. The presence of Zika virus VLPs (in prM/E expressing vectors) was identified after ultracentrifugation of culture medium and western blot (FIG. 7). The correct processing of antigens in infected cells was checked by Western Blot. The vectors with the best expression capacity of Zika antigens were isolated by serial dilution and single plaque cloning before amplification on Vero cells.

Growth Capacity of Recombinant Vaccine Virus

The growth capacity of selected vaccine viruses was compared with standard MV Schwarz. Growth curve analysis was performed in Vero cell culture by using different multiplicity of infection then titration.

Stability of Recombinant Vaccine Virus

The best vaccine vectors selected were tested for their genetic stability by serial passaging over 10 cell culture passages on Vero cell culture followed by western blot for antigen expression and full sequencing analysis.

Preclinical Evaluation of First MV-Zika Recombinant in Mice

Single Immunization

The two recombinant vectors MV-prMEd404 (native sequence, insert 4) and MV-ssEd445 (native sequence, insert 5) were evaluated in CD46/IFNAR mice susceptible to measles infection. Mice were immunized with one or two intraperitoneal injections with defined infectious units of vaccine virus and functional antibodies and cell-mediated immune responses were analysed using both standard and specifically developed assays. Binding antibodies to Zika virus were determined with ELISA and neutralizing antibodies with specific plaque reduction neutralization test (PRNT). The T cell responses were analysed by Elispot assay using Zika virus-specific peptides for ex vivo stimulation of splenic cells. The vaccine vectors were then tested for protective efficacy: immunized mice were challenged with a lethal dose of Zika virus. A dose-response challenge was previously established in CD46/IFNAR mice showing that doses between $10^2$ and $10^6$ focus forming unit (ffu) of Zika virus African strain HD78788 (adapted to mouse) efficiently kill these mice.

Figure 5A:
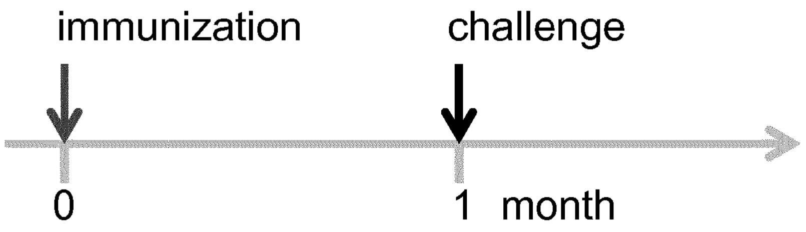
FIG. 5. Single immunization in mice. A) Zika antibody response measured in mice sera by ELISA at one month after a single immunization. MV-prMEd404 (native sequence, insert 4); MV-ssEd445 (native sequence, insert 5). B) Survival of immunized mice after challenge by Zika virus. C) Zika virus viremia in serums of immunized mice (determined by RT-qPCR) at different days after challenge. D) IFN-gamma Elispot detected in splenocytes of mice one week after immunization with MV-Zika or control MVSchw viruses. Elispots are detected against MV (Schwarz), Zika virus (Zika) and Concanavalin A as a control.
Figure 5A:
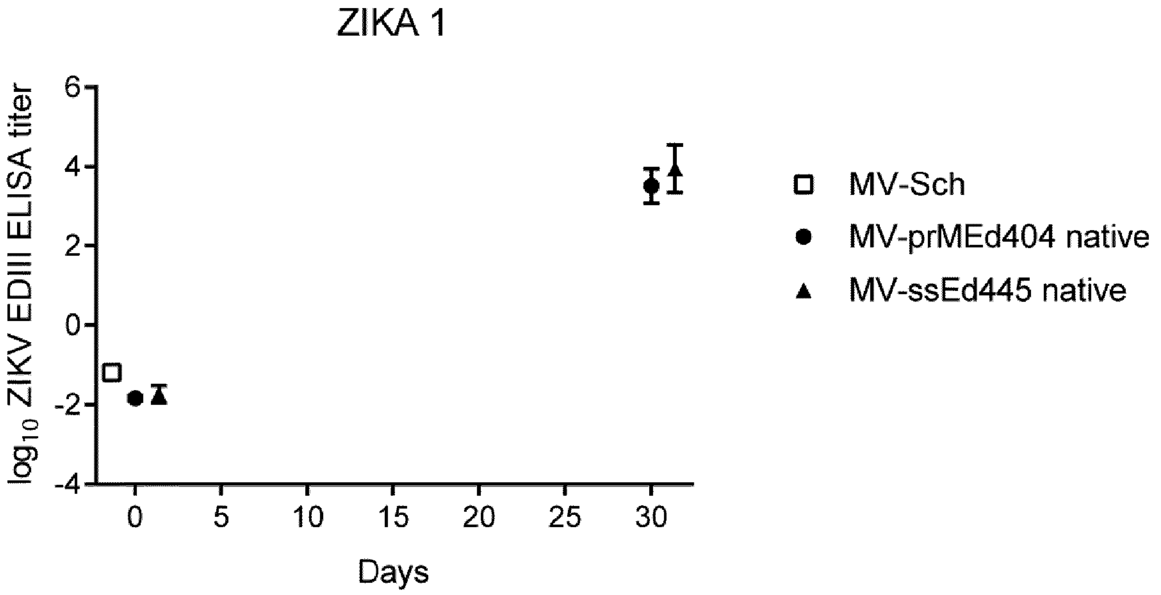

In a first experiment 6 mice per group were immunized with a single intraperitoneal injection of $10^6$ TCID50 of MV-prMEd404 (native sequence, insert 4), MV-ssEd445 (native sequence, insert 5) or empty MVSchw as a control. Blood was taken before immunization and at day 30 after immunization, and Zika virus ELISA titers were determined (FIG. 5A).

Figure 5B:
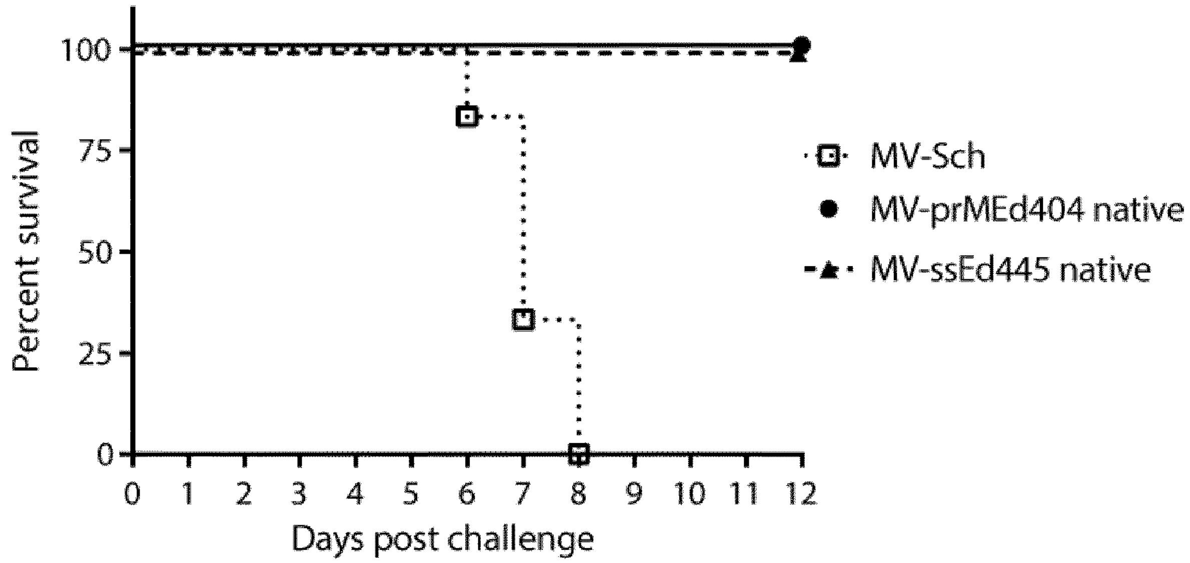
Figure 5C:
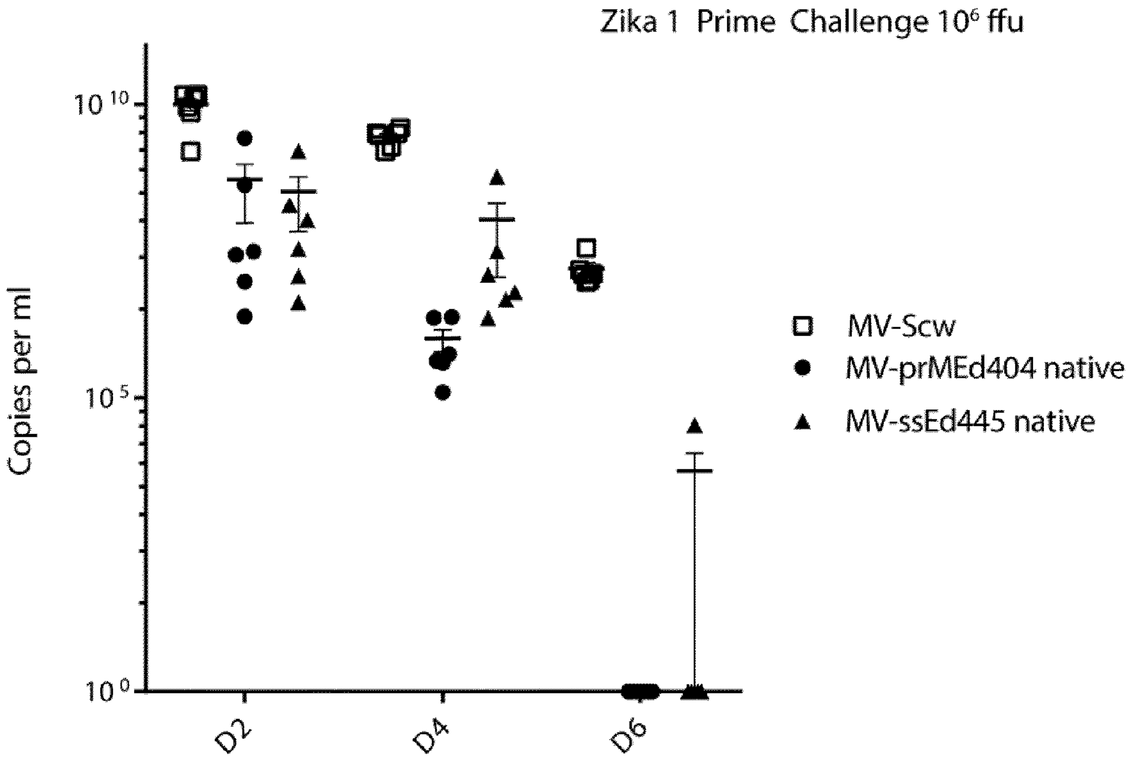

The immunized mice were then challenged at day 30 by intraperitoneal injection of $10^6$ ffu of Zika virus African strain HD78788 (mouse adapted). Morbidity and mortality were controlled during 12 days (FIG. 5B) and Zika virus viremia was determined in serum by qRT-PCR (FIG. 5C).

Figure 5D:
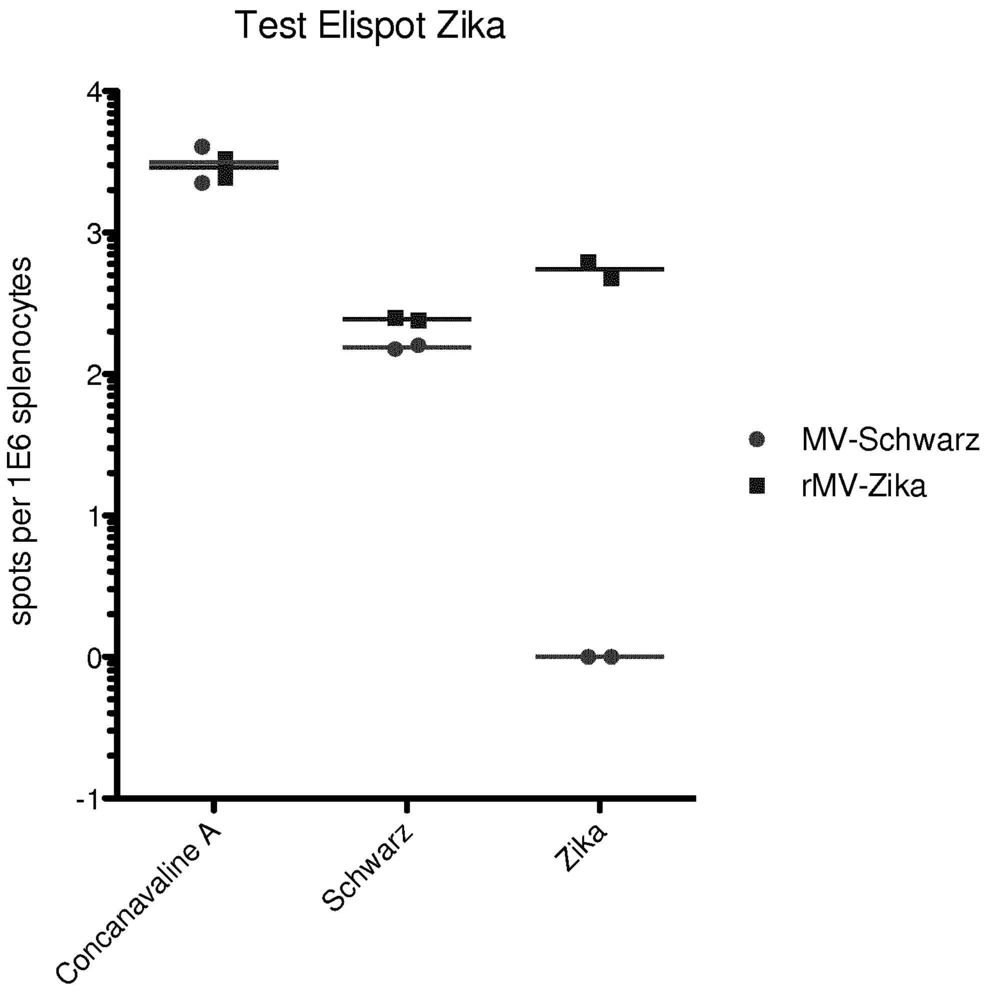

To determine T-cell response to the vaccine, another group of CD46/IFNAR mice were immunized by MV-prMEd404 (insert 4) or empty MVSchw and spleens were collected at 8 days after immunization. Elispot assay was performed on freshly extracted splenocytes using MVSchw or Zika virus to re-stimulate T-cells or concanavalin A as a control (FIG. 5D).

Prime-Boost Immunization

Figure 6A:
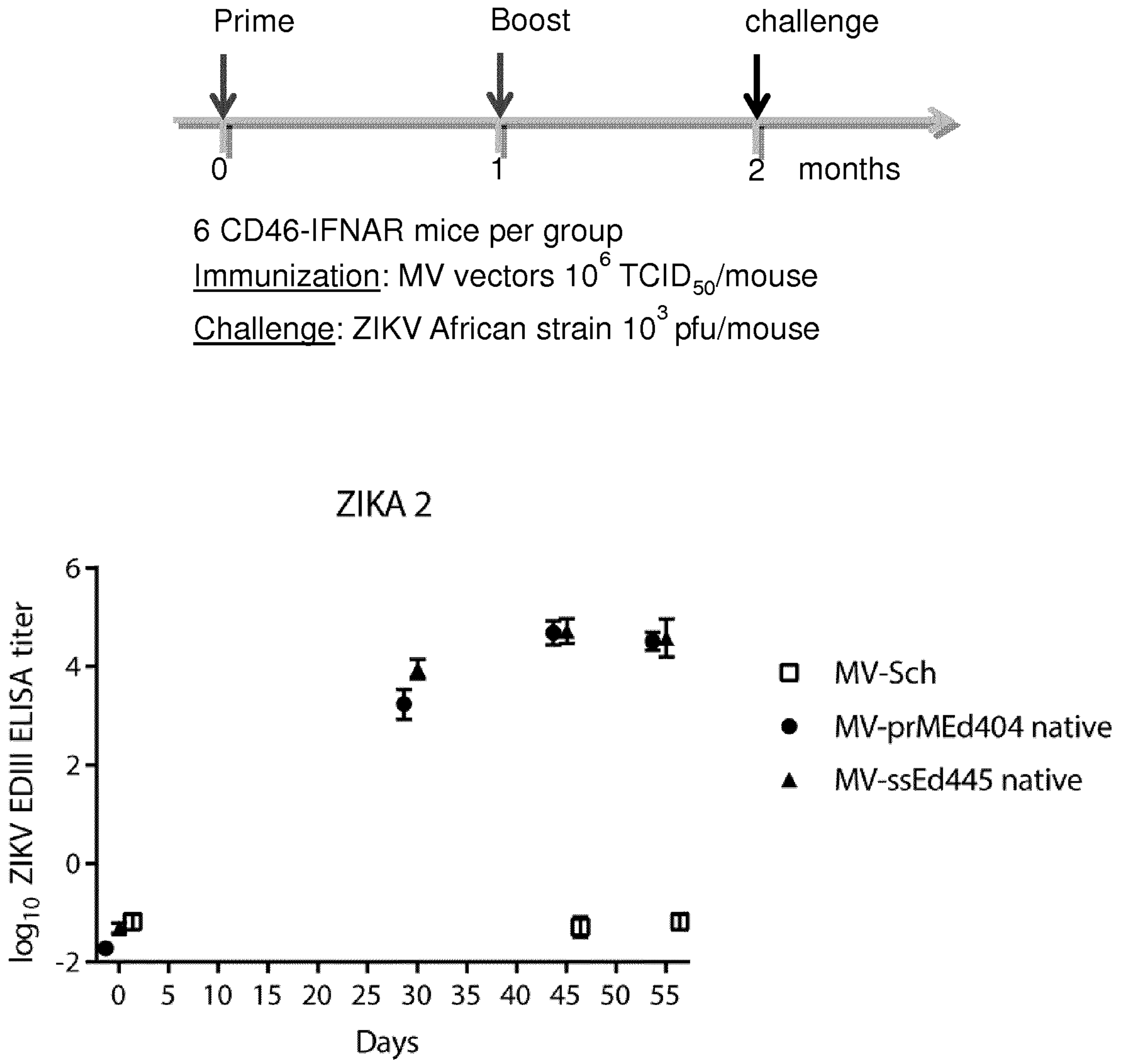
FIG. 6. Prime-boost immunization in mice. A) Zika antibody response measured in mice sera by ELISA at day 30, 45 and 55 after two immunizations. B) Detection of Zika virus neutralizing antibodies in the sera of mice immunized with two injections of MV-prMEd404 (native sequence, insert 4), MV-ssEd445 (native sequence, insert 5). C) Survival of immunized mice after challenge with low dose of Zika virus. D) Zika virus viremia in serums of immunized mice (determined by RT-qPCR) at different days after challenge.
Figure 6B:
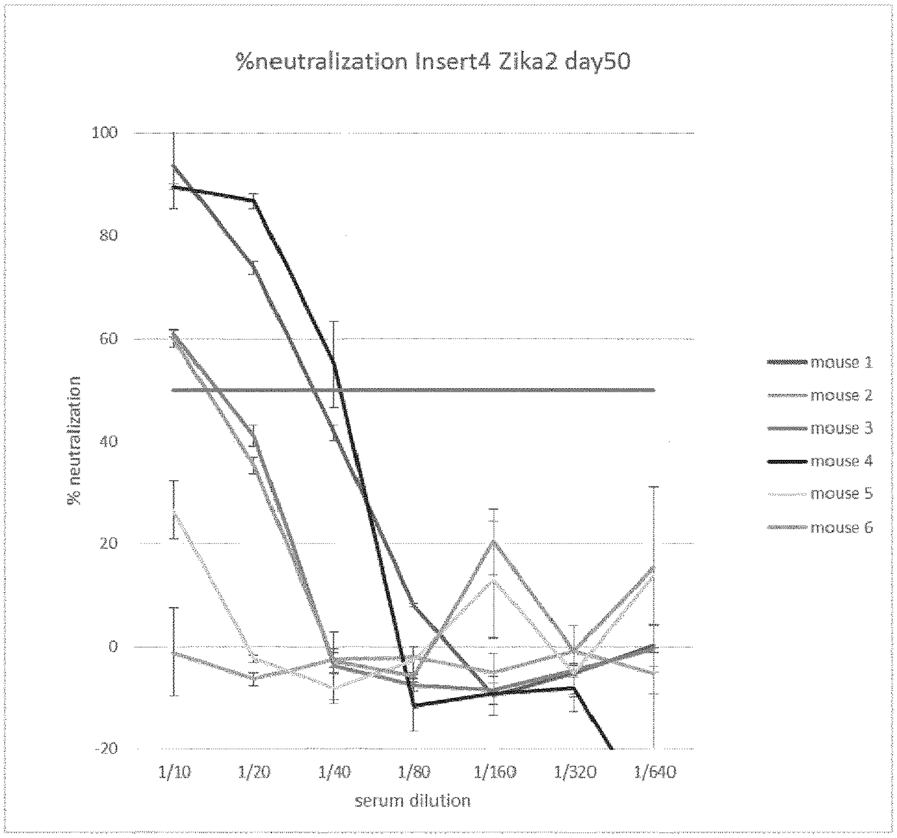
Figure 6B:
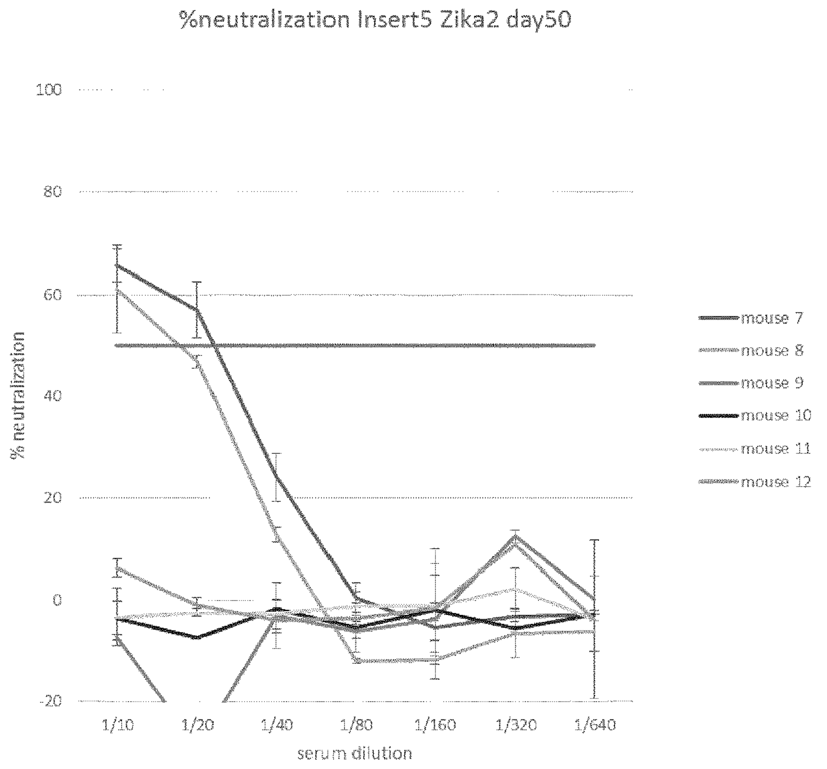
Figure 6C:
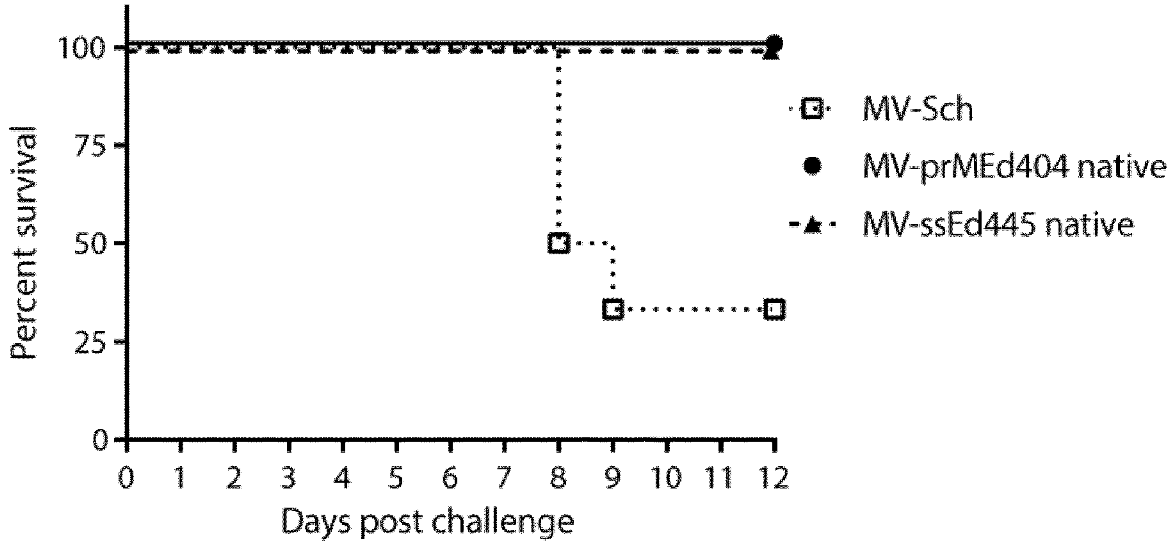
Figure 6D:
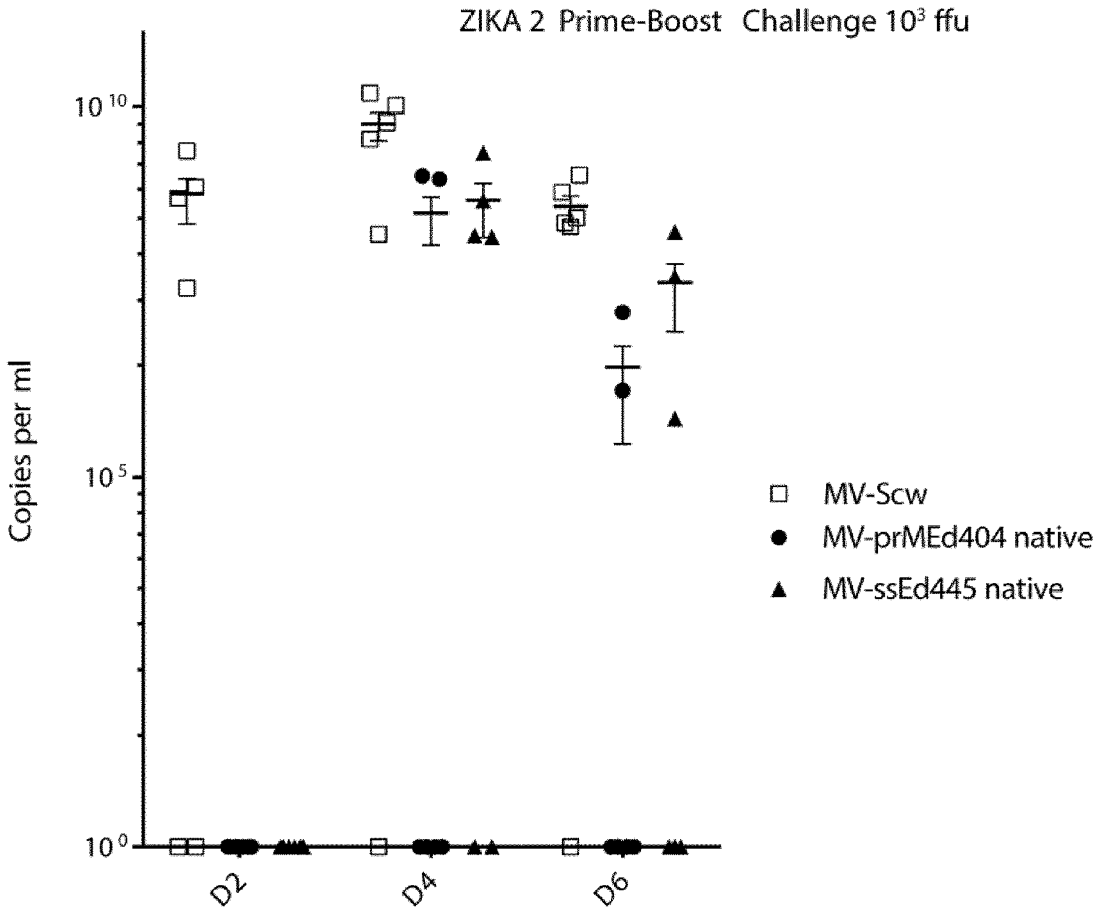

In a second set of experiments, groups of CD46/IFNAR mice were immunized with two successive intraperitoneal injections of $10^6$ TCID50 of MV-prMEd404 (native sequence, insert 4), MV-ssEd445 (native sequence, insert 5) or empty MVSchw as a control. Blood was taken before immunization and at day 30, 45 and 55 after immunizations and Zika virus ELISA titers were determined (FIG. 6A). Neutralizing antibodies were determined in sera collected at day 50 using a specific neutralization test of Zika virus (FIG. 6B). The immunized mice were then challenged at day 60 by intraperitoneal injection of $10^6$ ffu of Zika virus African strain HD78788 (mouse adapted). Morbidity and mortality were controlled during 12 days (FIG. 6C) and Zika virus viremia was determined in serum by qRT-PCR at days 2, 4 and 6 post infection (FIG. 6D).

Preclinical Evaluation in Non-Human Primates (NHP)

Validation of the ZIKV Strain Used in the NHP Challenge Study

Because little is known about the physiopathology of ZIKV in cynomolgus macaque (*Macaca fascicularis*), two animals were inoculated in a preliminary assay with three doses of Zika wild-type virus ($10^4$, $10^5$ and $10^6$ pfu) to assess the viral stock and associated clinics in macaques. These two animals were submitted to the same follow-up than vaccinated and challenged animals but for a 6-month period. The following points were addressed: Virology (qRT-PCR; clinics (Rash, Fever); Blood cell count (Lymphocytes, Monocytes, Granulocytes, platelettes); Biochemistry (ASAT, ALAT, CRP); Non-specific (innate and inflammatory) and specific immune response: Cytokines/chemokines by luminex, NK, B and T cell profile (14 colors flow cytometry), Antibodies (neutralizing, binding) on serial sera samples, T cells functional response and memory cells (ELISpot, ICS). Shedding of the virus in biological fluid (saliva, tears, genital fluids) was assessed by qRT-PCR and/or isolation methods at various time-points.

Vaccine Immunogenicity Study in NHP

Macaques were immunized with one or two subcutaneous injections at 3 months interval of defined infectious units of vaccine virus. Humoral and cell-mediated immune responses were determined at different times post immunization. Macaques were then challenged with infectious doses of ZIKV. Infectious viremia and clinical signs were determined. For this task, twenty-one adult cynomolgus macaques were selected to be negative for anti-flaviviruses and anti-measles antibodies; Two groups of 7 animals were vaccinated with a single dose or a prime boost regiment with the best MV-ZIKV recombinant virus (MV-prMEd404 native) selected. Immunity (Humoral and cell associated) was explored and virology was followed up to 1 month post vaccination. Clinics and biological parameters are assessed in parallel to a third group of 7 animals vaccinated with the control empty MVSchw strain following the prime boost schedule. Antibody neutralization titer was determined.

Vaccine Efficacy Study in NHP

Immunized NHP were challenged with ZIKV two months after immunization. ZIKV viremia level (qRT-PCR) was analyzed in blood, saliva and tears. Inflammation and immune response was assessed in plasma (neutralizing Ab, cytokines).

Expression Assays

Figure 8:
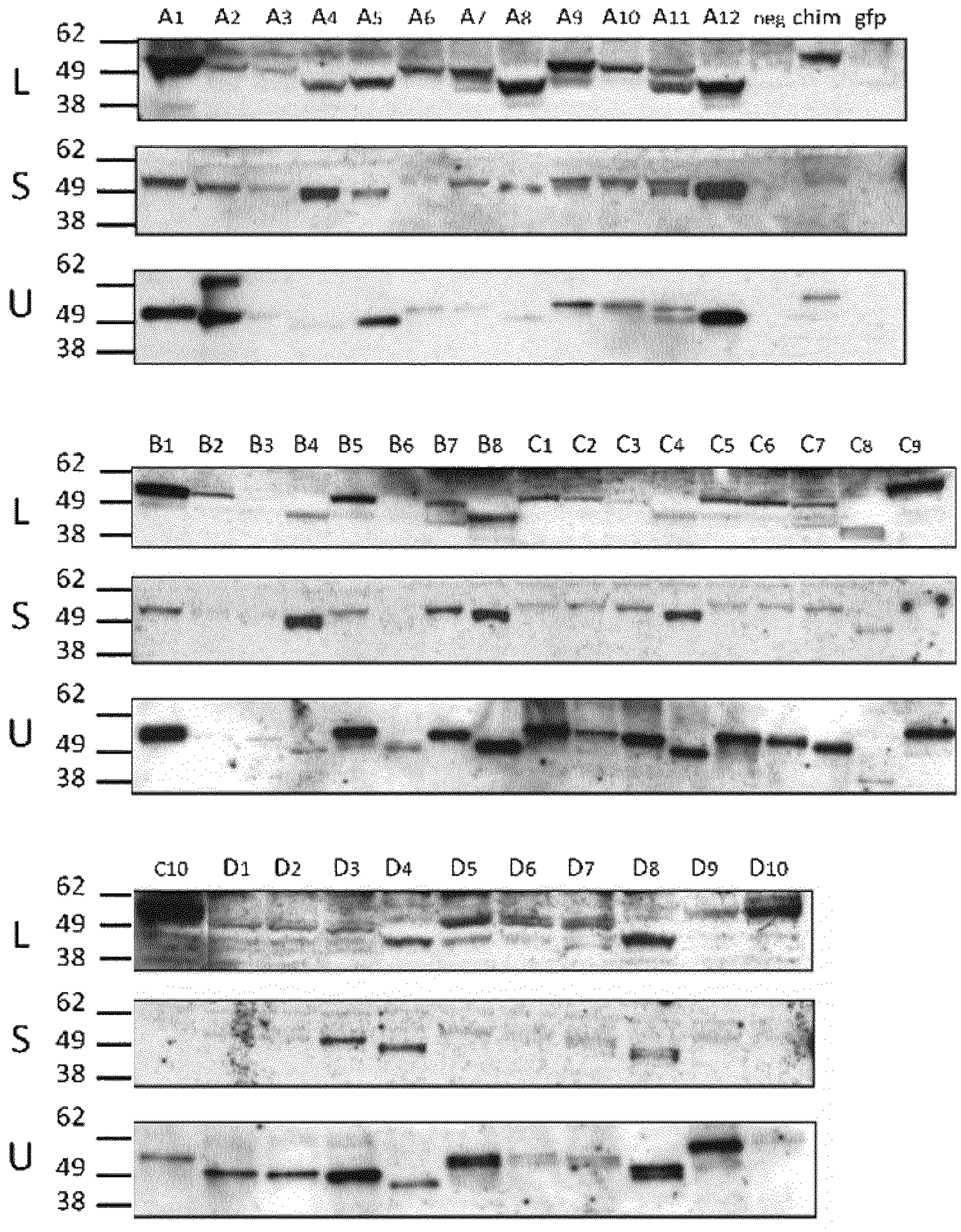
FIG. 8. Zika virus antigen expression assay. HEK293T cells were transfected with each codon-optimized construct, and cell lysates and medium were collected after 48 h. Supernatant medium was clarified by low-speed centrifugation (1500 rpm), and then a fraction was concentrated by ultracentrifugation on a 20% sucrose cushion for 3 hours (36000 rpm). All material was analyzed by western blot to detect the Zika virus E protein (~50 kD) with the 4G2 pan-flavivirus antibody. (L) Cell lysates, (S) non-concentrated medium, and (U) ultracentrifugated medium.
Figure 9:
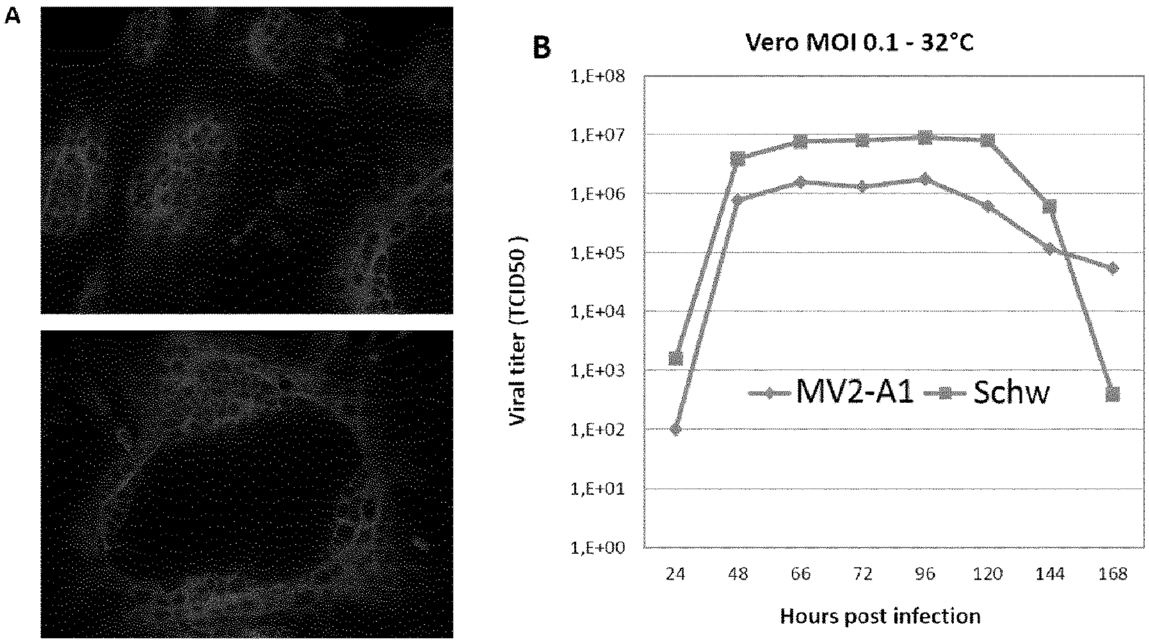
FIG. 9. Expression of Zika virus antigen A1 from measles vector and growth curve of recombinant MV-Zika-A1. (A) Immunofluorescence analysis showed large syncytia in Vero cells infected for 24 hours with MV-Zika-A1 (the Zika virus E protein was detected with the 4G2 pan-flavivirus antibody). (B) Replication of recombinant MV-Zika-A1 virus on Vero cells at 32° C. after infection with a multiplicity of infection of 0.01 (titers were determined by limiting dilution and the Karber method).

The expression assays performed for all constructs generated (FIG. 8) showed a strong expression for several of them. Signal was detected in the ultracentrifugated fraction, which was compatible with the generation of virus-like particles, in varying amounts for some candidate antigens, notably A1 and A12. These two antigens were thus further cloned into the measles vector and demonstrated high-level expression as shown by immunofluorescence (FIG. 9A). The recombinant MV-ZIKV-A1 vector replicated similarly to standard MV Schwarz virus, although with a lower final titer (FIG. 9B).

Figure 10:
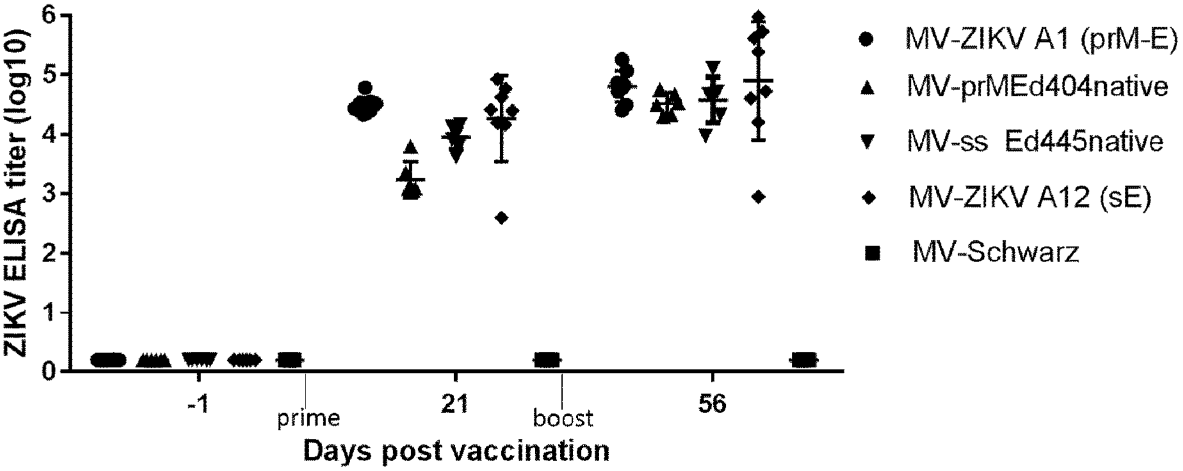
FIG. 10. Antibody response to ZIKV in immunized CD46-IFNAR$^{-/-}$ mice. The antibody titers against ZIKV EDIII were determined using indirect ELISA in mice sera collected after prime and boost with MV-ZIKV-A1, MV-prMEd404 (native sequence, insert 4), MV-ssEd445 (native sequence, insert 5), MV-ZIKV-A12 or control empty MV-Schwarz. Readings from wells coated with mock antigens were subtracted from wells with ZIKV-EDIII and the ZIKV specific IgG titers were calculated as the reciprocal of the highest dilution of an individual serum giving an absorbance of 0.5. A strong antibody response to ZIKV was induced in immunized mice with slightly higher values for A1 (highly reproducible) and A12 (more variability).
Figure 11:
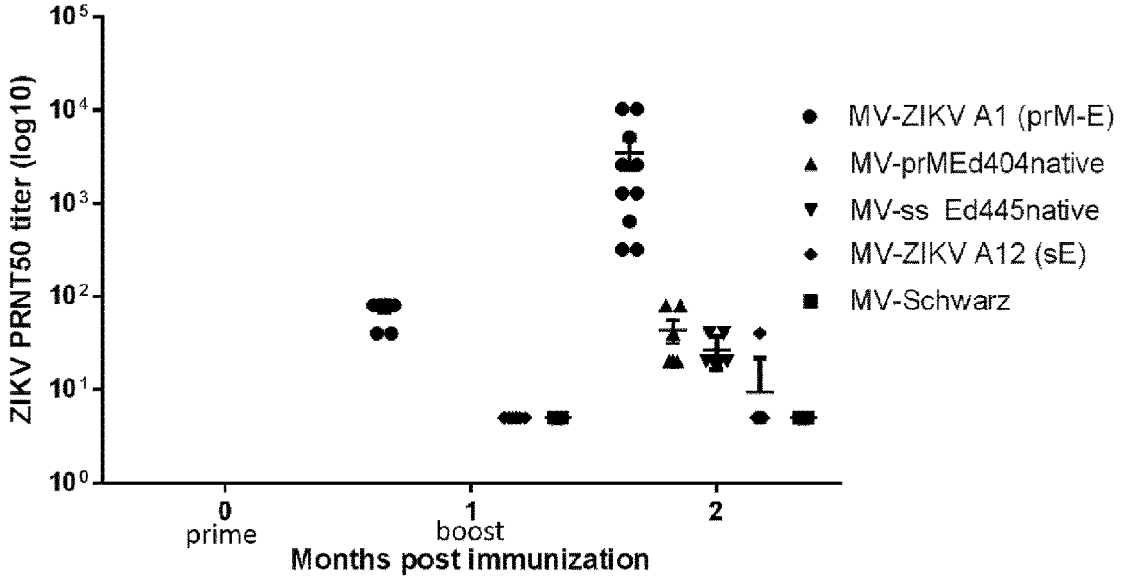
FIG. 11. ZIKV neutralizing antibody titers in immunized CD46-IFNAR$^{-/-}$ mice. Neutralizing antibody titers against ZIKV were determined by using plaque reduction neutralizing tests ($PRNT_{50}$) in mice sera collected after last boost with MV-ZIKV-A1, MV-prMEd404 (native sequence, insert 4), MV-ssEd445 (native sequence, insert 5), MV-ZIKV-A12 or control empty MV-Schwarz and before challenge. The strongest neutralizing titers were observed with the MV-ZIKV-A1 construct.
Figure 12:
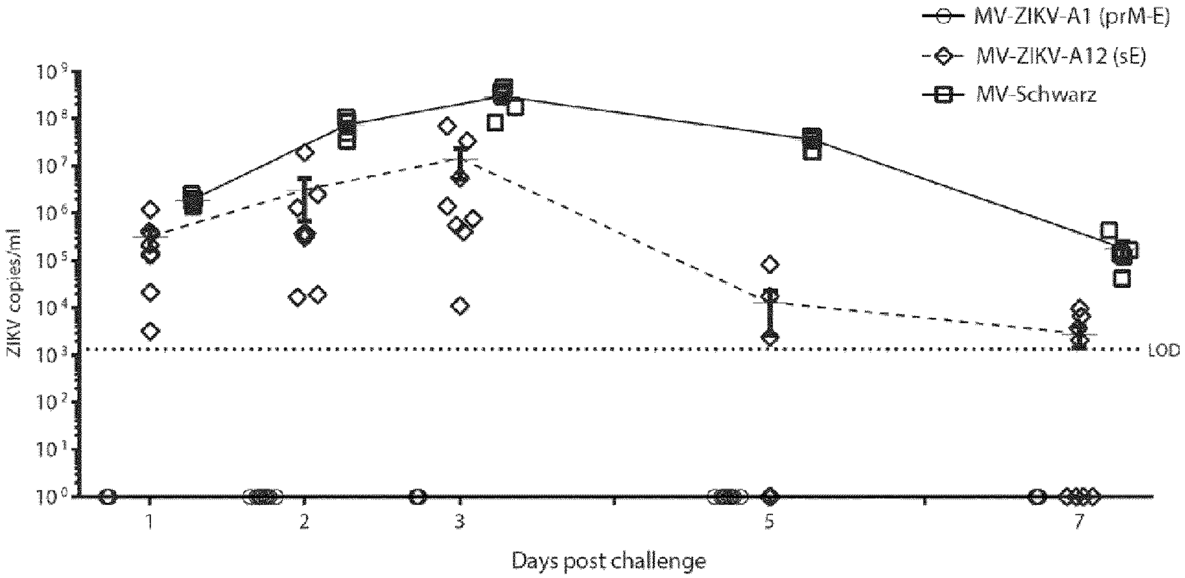
FIG. 12. Protection of immunized CD46-IFNAR$^{-/-}$ mice from ZIKV non-lethal challenge. Mice immunized twice with MV-ZIKV-A1, MV-ZIKV-A1 2 or control empty MV- Schwarz were challenged with $10^3$ ffu of ZIKV (Asian-South American lineage, isolated in December 2015) one month after the last immunization. Viral loads were determined by RT-qPCR. LOD indicates the limit of detection of the RT-qPCR. Mice immunized with construct MV-ZIKV-A1 were all protected from viremia while mice immunized with MV-ZIKV-A12 or empty MV Schwarz control were infected.
Figure 13:
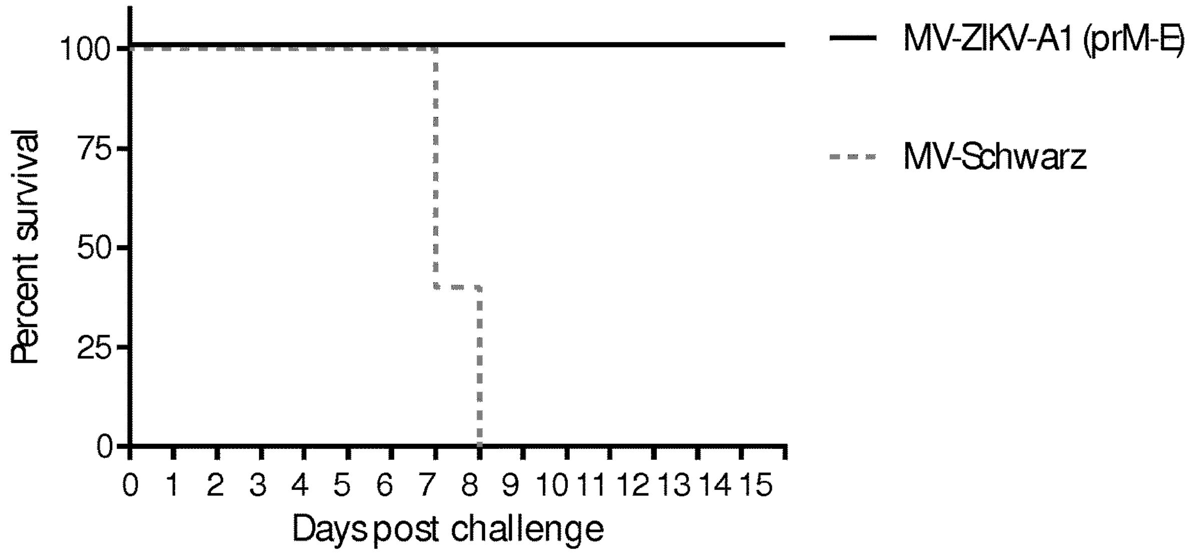
FIG. 13. Protection of immunized CD46-IFNAR$^{-/-}$ mice from ZIKV lethal challenge. Mice immunized twice with MV-ZIKV-A1, or control empty MV-Schwarz were challenged with $10^3$ ffu of ZIKV (Mouse adapted strain of the African lineage) one month after the last immunization. Animals were monitored for morbidity and mortality for 15 days. All animals immunized with MV-ZIKV-A1 survived without presenting signs of disease, while all control mice died by day 8.

Tested for their immunogenicity in CD46/IFNAR mice, MV-ZIKV-A1 and MV-ZIKV-A12 vectors elicited strong immune responses following a prime and boost regimen with 1-month interval, comparable to MV-prMEd404 and MV-ssEd445 vectors, as detected by ELISA (FIG. 10). However, different amounts of neutralizing antibodies were induced (FIG. 11). Only the candidate MV-ZIKV-A1 induced a strong neutralizing response (2 log stronger). This correlated with the complete protection conferred to mice by immunization with MV-ZIKV-A1 (FIG. 12) against viremia, as well as protection from a lethal challenge (FIG. 13).

In conclusion, this study demonstrated that the A1 full-length Zika antigen expressed in MV vector was able to provide sterile protection from infectious and lethal challenge of immunized animals, correlating with strong neutralizing antibody induction.

The invention claimed is:

1. A nucleic acid construct which comprises:
(1) a polynucleotide encoding at least (i) the precursor of membrane (prM) protein of a Zika virus (ZIKV), and the envelope (E) protein of a ZIKV or a truncated version thereof of SEQ ID NO: 26, SEQ ID NO: 29 and SEQ ID NO: 32, or (ii) the E protein of a ZIKV or the truncated version thereof of SEQ ID NO: 26, SEQ ID NO: 29 and SEQ ID NO: 32; and
(2) a cDNA molecule encoding a full-length, infectious antigenomic (+) RNA strand of a live-attenuated measles virus (MV) vaccine strain;
wherein the polynucleotide encoding at least (i) the prM protein of the ZIKV, and the E protein of the ZIKV or the truncated version thereof, or (ii) the E protein of the ZIKV or the truncated version thereof and the cDNA molecule are operatively linked;
the nucleic acid construct comprising the following polynucleotides from 5' to 3':
(a) a polynucleotide encoding the N protein of the MV;
(b) a polynucleotide encoding the P protein of the MV;
(c) the polynucleotide encoding at least (i) the prM protein of the ZIKV, and the E protein of the ZIKV or the truncated version thereof, or (ii) the E protein of the ZIKV or the truncated version thereof;
(d) a polynucleotide encoding the M protein of the MV;
(e) a polynucleotide encoding the F protein of the MV;
(f) a polynucleotide encoding the H protein of the MV; and
(g) a polynucleotide encoding the L protein of the MV;
wherein said polynucleotides are operably linked in the nucleic acid construct and under a control of viral replication and transcription regulatory sequences.

2. The nucleic acid construct according to claim 1, characterized in that the polynucleotide of (1) and the cDNA molecule of (2) together consist of a number of nucleotides that is a multiple of six.

3. The nucleic acid construct according to claim 1, wherein said live-attenuated MV vaccine strain is selected from the group consisting of the Schwarz strain, the Zagreb strain, the AIK-C strain and the Moraten strain.

4. The nucleic acid construct according to claim 1, wherein said polynucleotide encoding at least (i) the prM protein of the ZIKV, and the E protein of the ZIKV or the truncated version thereof, or (ii) the E protein of the ZIKV or the truncated version thereof, has been optimized for a Macaca codon usage or has been optimized for a human codon usage.

5. The nucleic acid construct according to claim 1, wherein measles editing-like sequences have been deleted from said polynucleotide encoding at least (i) the prM protein of the ZIKV, and the E protein of the ZIKV or the truncated version thereof, or (ii) the E protein of the ZIKV or the truncated version thereof.

6. The nucleic acid construct according to claim 1, wherein said ZIKV is from the African lineage, or from the Asian strain.

7. The nucleic acid construct according to claim 1, wherein said polynucleotide encoding at least (i) the prM protein of the ZIKV, and the E protein of the ZIKV or the truncated version thereof, further encodes (iii) the signal peptide from the capsid of the ZIKV and the signal peptide from the membrane protein of the ZIKV, or
wherein said polynucleotide encoding at least (ii) the E protein of the ZIKV or the truncated version thereof, further encodes (iii) the signal peptide from the capsid of the ZIKV or the signal peptide from the membrane protein of the ZIKV.

8. The nucleic acid construct according to claim 1, wherein the polynucleotide encoding the E protein encodes either the full-length E protein or its soluble form lacking the two C-terminal transmembrane domains of the full-length E protein.

9. The nucleic acid construct according to claim 1, wherein the polynucleotide encoding the truncated version of the E protein is selected from the group consisting of (i) the polynucleotide encoding the E protein truncated at amino acid position 456 of the full-length E protein of the ZIKV of SEQ ID NO: 23, (ii) the polynucleotide encoding the E protein truncated at amino acid position 445 of the full-length E protein of the ZIKV of SEQ ID NO: 23 and (iii) the polynucleotide encoding the E protein truncated at amino acid position 404 of the full-length E protein of the ZIKV of SEQ ID NO: 23.

10. The nucleic acid construct according to claim 1, wherein the polynucleotide encodes the prM protein of the ZIKV whose sequence is SEQ ID NO: 20, and the polynucleotide encodes the E protein of the ZIKV or the truncated version thereof whose sequence is selected from the group consisting of SEQ ID NO: 23, SEQ ID NO: 26, SEQ ID NO: 29 and SEQ ID NO: 32.

11. The nucleic acid construct according to claim 1, wherein the polynucleotide encoding the prM protein of the ZIKV has the sequence of SEQ ID NO: 19, and the polynucleotide encoding the E protein of the ZIKV or the truncated version thereof has a sequence selected from the group consisting of SEQ ID NO: 22, SEQ ID NO: 25, SEQ ID NO: 28 and SEQ ID NO: 31.

12. The nucleic acid construct according to claim 1, wherein said nucleic acid construct comprises a sequence selected from the group consisting of SEQ ID NO: 46, SEQ ID NO: 52, SEQ ID NO: 55, SEQ ID NO: 70, SEQ ID NO: 76, SEQ ID NO: 79, SEQ ID NO: 168 and SEQ ID NO: 170.

13. The nucleic acid construct according to claim 1, which comprises the sequence from nucleotide at position 83 to nucleotide at position 18404 in the sequence of SEQ ID NO: 165, or the sequence from nucleotide at position 83 to nucleotide at position 18074 in the sequence of SEQ ID NO: 166, or the sequence from nucleotide at position 83 to nucleotide at position 17702 in the sequence of SEQ ID NO: 167.

14. A transfer vector plasmid, comprising the nucleic acid construct according to claim 1.

15. The transfer vector plasmid according to claim 14, whose sequence is SEQ ID NO: 165, SEQ ID NO: 166 or SEQ ID NO: 167.

16. Isolated transformed eukaryotic cells comprising inserted in their genome the nucleic acid construct according to claim 1.

17. Isolated recombinant infectious replicating measles virus-Zika virus (MV-ZIKV) particles, which comprise as their genome a nucleic acid construct according to claim 1.

18. The isolated recombinant infectious replicating MV-ZIKV particles according to claim 17, which are rescued from a helper cell line expressing an RNA polymerase recognized by said cell line, a nucleoprotein (N) of a MV, a phosphoprotein (P) of a MV, and an RNA polymerase large protein (L) of a MV.

19. The isolated recombinant infectious replicating MV-ZIKV particles according to claim 17, wherein said particles comprise in their genome a polynucleotide sequence comprising a sequence selected from the group consisting of SEQ ID NO: 46, SEQ ID NO: 52, SEQ ID NO: 55, SEQ ID NO: 70, SEQ ID NO: 76, SEQ ID NO: 79, SEQ ID NO: 168 and SEQ ID NO: 170.

20. A pharmaceutical composition comprising the recombinant infectious replicating MV-ZIKV particles according to claim 17, in association with ZIKV-Virus Like Particles (VLPs) expressing the same ZIKV protein(s) as said MV-ZIKV particles, and a pharmaceutically acceptable vehicle.

21. A method of inducing a ZIKV-specific immune response in a host, comprising administering the pharmaceutical composition of claim 20 to the host.

22. A method of treating ZIKV infection or inhibiting ZIKV infection in a host, comprising administering the recombinant infectious replicating MV-ZIKV particles according to claim 17 in association with ZIKV-VLPs expressing the same ZIKV protein(s), or the pharmaceutical composition according to claim 20 to the host.

23. A process to rescue recombinant infectious measles virus-Zika virus (MV-ZIKV) particles expressing at least (i) the precursor of membrane (prM) protein of a ZIKV, and the envelope (E) protein of a ZIKV or a truncated version thereof, or (ii) the E protein of a ZIKV or a truncated version thereof, and ZIKV Virus Like Particles (VLPs) expressing the same ZIKV protein(s), comprising:

1) co-transfecting helper cells that stably express T7 RNA polymerase, and measles N and P proteins with (i) the transfer vector plasmid according to claim 14 and with (ii) a vector, encoding the MV L polymerase;
2) cultivating said co-transfected helper cells in conditions enabling the production of recombinant MV-ZIKV particles;
3) propagating the thus produced recombinant MV-ZIKV particles by co-cultivating said helper cells of step 2) with cells enabling said propagation;
4) recovering recombinant infectious replicating MV-ZIKV particles expressing at least (i) the prM protein of the ZIKV, and the E protein of the ZIKV or the truncated version thereof, or (ii) the E protein of the ZIKV or the truncated version thereof, and ZIKV VLPs expressing the same ZIKV protein(s).

24. The process according to claim 23, wherein the transfer vector plasmid has the sequence of SEQ ID NO: 165, SEQ ID NO: 166 or SEQ ID NO: 167, preferably has the sequence of SEQ ID NO: 165.

* * * * *

SEQUENCE LISTING

```
<160> NUMBER OF SEQ ID NOS: 171

<210> SEQ ID NO 1
<211> LENGTH: 18967
<212> TYPE: DNA
<213> ORGANISM: Artificial sequence
<220> FEATURE:
<223> OTHER INFORMATION: pTM-MVSchw

<400> SEQUENCE: 1

gcggccgcta atacgactca ctatagggcc aactttgttt ggtctgatga gtccgtgagg      60

acgaaacccg gagtcccggg tcaccaaaca aagttgggta aggatagttc aatcaatgat     120

catcttctag tgcacttagg attcaagatc ctattatcag ggacaagagc aggattaggg     180

atatccgaga tggccacact tttaaggagc ttagcattgt tcaaaagaaa caaggacaaa     240

ccacccatta catcaggatc cggtggagcc atcagaggaa tcaaacacat tattatagta     300

ccaatccctg gagattcctc aattaccact cgatccagac ttctggaccg gttggtgagg     360

ttaattggaa acccggatgt gagcgggccc aaactaacag gggcactaat aggtatatta     420

tccttatttg tggagtctcc aggtcaattg attcagagga tcaccgatga ccctgacgtt     480

agcataaggc tgttagaggt tgtccagagt gaccagtcac aatctggcct taccttcgca     540

tcaagaggta ccaacatgga ggatgaggcg gaccaatact tttcacatga tgatccaatt     600

agtagtgatc aatccaggtt cggatggttc gggaacaagg aaatctcaga tattgaagtg     660

caagaccctg agggattcaa catgattctg ggtaccatcc tagcccaaat ttgggtcttg     720

ctcgcaaagg cggttacggc cccagacacg gcagctgatt cggagctaag aaggtggata     780

aagtacaccc aacaaagaag ggtagttggt gaatttagat tggagagaaa atggttggat     840

gtggtgagga acaggattgc cgaggacctc tccttacgcc gattcatggt cgctctaatc     900

ctggatatca agagaacacc cggaaacaaa cccaggattg ctgaaatgat atgtgacatt     960

gatacatata tcgtagaggc aggattagcc agttttatcc tgactattaa gtttgggata    1020

gaaactatgt atcctgctct tggactgcat gaatttgctg gtgagttatc cacacttgag    1080

tccttgatga acctttacca gcaaatgggg gaaactgcac cctacatggt aatcctggag    1140

aactcaattc agaacaagtt cagtgcagga tcataccctc tgctctggag ctatgccatg    1200

ggagtaggag tggaacttga aaactccatg ggaggtttga actttggccg atcttacttt    1260

gatccagcat attttagatt agggcaagag atggtaagga ggtcagctgg aaaggtcagt    1320

tccacattgg catctgaact cggtatcact gccgaggatg caaggcttgt ttcagagatt    1380
```

-continued gcaatgcata ctactgagga caagatcagt agagcggttg gacccagaca agcccaagta 1440
tcatttctac acggtgatca aagtgagaat gagctaccga gattgggggg caaggaagat 1500
aggagggtca aacagagtcg aggagaagcc agggagagct acagagaaac cgggcccagc 1560
agagcaagtg atgcgagagc tgcccatctt ccaaccggca cacccctaga cattgacact 1620
gcaacggagt ccagccaaga tccgcaggac agtcgaaggt cagctgacgc cctgcttagg 1680
ctgcaagcca tggcaggaat ctcggaagaa caaggctcag acacggacac ccctatagtg 1740
tacaatgaca gaaatcttct agactaggtg cgagaggccg agggccagaa caacatccgc 1800
ctaccatcca tcattgttat aaaaaactta ggaaccaggt ccacacagcc gccagcccat 1860
caaccatcca ctcccacgat tggagccaat ggcagaagag caggcacgcc atgtcaaaaa 1920
cggactggaa tgcatccggg ctctcaaggc cgagcccatc ggctcactgg ccatcgagga 1980
agctatggca gcatggtcag aaatatcaga caacccagga caggagcgag ccacctgcag 2040
ggaagagaag gcaggcagtt cggtctcag caaaccatgc ctctcagcaa ttggatcaac 2100
tgaaggcggt gcacctcgca tccgcggtca gggacctgga gagagcgatg acgacgctga 2160
aactttggga atccccccaa gaaatctcca ggcatcaagc actgggttac agtgttatta 2220
cgtttatgat cacagcggtg aagcggttaa gggaatccaa gatgctgact ctatcatggt 2280
tcaatcaggc cttgatggtg atagcaccct ctcaggagga gacaatgaat ctgaaaacag 2340
cgatgtggat attggcgaac ctgataccga gggatatgct atcactgacc ggggatctgc 2400
tcccatctct atggggttca gggcttctga tgttgaaact gcagaaggag gggagatcca 2460
cgagctcctg agactccaat ccagaggcaa caactttccg aagcttggga aaactctcaa 2520
tgttcctccg cccccggacc ccggtagggc cagcacttcc gggacaccca ttaaaaaggg 2580
cacagacgcg agattagcct catttggaac ggagatcgcg tctttattga caggtggtgc 2640
aacccaatgt gctcgaaagt caccctcgga accatcaggg ccaggtgcac ctgcggggaa 2700
tgtccccgag tgtgtgagca atgccgcact gatacaggag tggacacccg aatctggtac 2760
cacaatctcc ccgagatccc agaataatga agaaggggga gactattatg atgatgagct 2820
gttctctgat gtccaagata ttaaaacagc cttggccaaa atacacgagg ataatcagaa 2880
gataatctcc aagctagaat cactgctgtt attgaaggga gaagttgagt caattaagaa 2940
gcagatcaac aggcaaaata tcagcatatc caccctggaa ggacacctct caagcatcat 3000
gatcgccatt cctggacttg ggaaggatcc caacgacccc actgcagatg tcgaaatcaa 3060
tcccgacttg aaacccatca taggcagaga ttcaggccga gcactggccg aagttctcaa 3120
gaaacccgtt gccagccgac aactccaagg aatgacaaat ggacggacca gttccagagg 3180
acagctgctg aaggaatttc agctaaagcc gatcgggaaa aagatgagct cagccgtcgg 3240
gtttgttcct gacaccggcc ctgcatcacg cagtgtaatc cgctccatta taaaatccag 3300
ccggctagag gaggatcgga agcgttacct gatgactctc cttgatgata tcaaaggagc 3360
caatgatctt gccaagttcc accagatgct gatgaagata ataatgaagt agctacagct 3420
caacttacct gccaacccca tgccagtcga cccaactagt acaacctaaa tccattataa 3480
aaaacttagg agcaaagtga ttgcctccca aggtccacaa tgacagagac ctacgacttc 3540
gacaagtcgg catgggacat caaagggtcg atcgctccga tacaacccac cacctacagt 3600
gatggcaggc tggtgcccca ggtcagagtc atagatcctg gtctaggcga caggaaggat 3660
gaatgcttta tgtacatgtt tctgctgggg gttgttgagg acagcgattc cctagggcct 3720

```
ccaatcgggc gagcatttgg gttcctgccc ttaggtgttg gcagatccac agcaaagccc   3780
gaaaaactcc tcaaagaggc cactgagctt gacatagttg ttagacgtac agcagggctc   3840
aatgaaaaac tggtgttcta caacaacacc ccactaactc tcctcacacc ttggagaaag   3900
gtcctaacaa cagggagtgt cttcaacgca aaccaagtgt gcaatgcggt taatctgata   3960
ccgctcgata ccccgcagag gttccgtgtt gtttatatga gcatcacccg tctttcggat   4020
aacgggtatt acaccgttcc tagaagaatg ctggaattca gatcggtcaa tgcagtggcc   4080
ttcaacctgc tggtgaccct taggattgac aaggcgatag gccctgggaa gatcatcgac   4140
aatacagagc aacttcctga ggcaacattt atggtccaca tcgggaactt caggagaaag   4200
aagagtgaag tctactctgc cgattattgc aaaatgaaaa tcgaaaagat gggcctggtt   4260
tttgcacttg gtgggatagg gggcaccagt cttcacatta gaagcacagg caaaatgagc   4320
aagactctcc atgcacaact cgggttcaag aagaccttat gttacccgct gatggatatc   4380
aatgaagacc ttaatcgatt actctggagg agcagatgca agatagtaag aatccaggca   4440
gttttgcagc catcagttcc tcaagaattc cgcatttacg acgacgtgat cataaatgat   4500
gaccaaggac tattcaaagt tctgtagacc gtagtgccca gcaatgcccg aaaacgaccc   4560
ccctcacaat gacagccaga aggcccggac aaaaaagccc cctccgaaag actccacgga   4620
ccaagcgaga ggccagccag cagccgacgg caagcgcgaa caccaggcgg ccccagcaca   4680
gaacagccct gacacaaggc caccaccagc caccccaatc tgcatcctcc tcgtgggacc   4740
cccgaggacc aacccccaag gctgccccg atccaaacca ccaaccgcat ccccaccacc   4800
cccgggaaag aaacccccag caattggaag gcccctcccc ctcttcctca acacaagaac   4860
tccacaaccg aaccgcacaa gcgaccgagg tgacccaacc gcaggcatcc gactccctag   4920
acagatcctc tctccccggc aaactaaaca aaacttaggg ccaaggaaca tacacaccca   4980
acagaaccca gaccccggcc cacggcgccg cgcccccaac ccccgacaac cagagggagc   5040
ccccaaccaa tcccgccggc tccccggtg cccacaggca gggacaccaa cccccgaaca   5100
gacccagcac ccaaccatcg acaatccaag acggggggc cccccaaaa aaaggccccc   5160
aggggccgac agccagcacc gcgaggaagc ccacccaccc cacacacgac cacggcaacc   5220
aaaccagaac ccagaccacc ctgggccacc agctcccaga ctcggccatc accccgcaga   5280
aaggaaaggc cacaacccgc gcaccccagc cccgatccgg cggggagcca cccaacccga   5340
accagcaccc aagagcgatc cccgaaggac ccccgaaccg caaaggacat cagtatccca   5400
cagcctctcc aagtccccg gtctcctcct cttctcgaag ggaccaaaag atcaatccac   5460
cacacccgac gacactcaac tccccacccc taaaggagac accgggaatc ccagaatcaa   5520
gactcatcca atgtccatca tgggtctcaa ggtgaacgtc tctgccatat tcatggcagt   5580
actgttaact ctccaaacac ccaccggtca aatccattgg ggcaatctct ctaagatagg   5640
ggtggtagga ataggaagtg caagctacaa agttatgact cgttccagcc atcaatcatt   5700
agtcataaaa ttaatgccca atataactct cctcaataac tgcacgaggg tagagattgc   5760
agaatacagg agactactga gaacagtttt ggaaccaatt agagatgcac ttaatgcaat   5820
gacccagaat ataagaccgg ttcagagtgt agcttcaagt aggagacaca agagatttgc   5880
gggagtagtc ctggcaggtg cggccctagg cgttgccaca gctgctcaga taacagccgg   5940
cattgcactt caccagtcca tgctgaactc tcaagccatc gacaatctga gagcgagcct   6000
ggaaactact aatcaggcaa ttgagacaat cagacaagca gggcaggaga tgatattggc   6060
tgttcagggt gtccaagact acatcaataa tgagctgata ccgtctatga accaactatc   6120
```

```
ttgtgattta atcggccaga agctcgggct caaattgctc agatactata cagaaatcct   6180
gtcattattt ggccccagtt tacgggaccc catatctgcg gagatatcta tccaggcttt   6240
gagctatgcg cttggaggag acatcaataa ggtgttagaa aagctcggat acagtggagg   6300
tgatttactg ggcatcttag agagcggagg aataaaggcc cggataactc acgtcgacac   6360
agagtcctac ttcattgtcc tcagtatagc ctatccgacg ctgtccgaga ttaagggggt   6420
gattgtccac cggctagagg gggtctcgta caacataggc tctcaagagt ggtataccac   6480
tgtgcccaag tatgttgcaa cccaagggta ccttatctcg aattttgatg agtcatcgtg   6540
tactttcatg ccagagggga ctgtgtgcag ccaaaatgcc ttgtacccga tgagtcctct   6600
gctccaagaa tgcctccggg ggtacaccaa gtcctgtgct cgtacactcg tatccgggtc   6660
ttttgggaac cggttcattt tatcacaagg gaacctaata gccaattgtg catcaatcct   6720
ttgcaagtgt tacacaacag gaacgatcat taatcaagac cctgacaaga tcctaacata   6780
cattgctgcc gatcactgcc cggtagtcga ggtgaacggc gtgaccatcc aagtcgggag   6840
caggaggtat ccagacgctg tgtacttgca cagaattgac ctcggtcctc ccatatcatt   6900
ggagaggttg gacgtaggga caaatctggg gaatgcaatt gctaagttgg aggatgccaa   6960
ggaattgttg gagtcatcgg accagatatt gaggagtatg aaaggtttat cgagcactag   7020
catagtctac atcctgattg cagtgtgtct tggagggttg atagggatcc ccgctttaat   7080
atgttgctgc agggggcgtt gtaacaaaaa gggagaacaa gttggtatgt caagaccagg   7140
cctaaagcct gatcttacgg gaacatcaaa atcctatgta aggtcgctct gatcctctac   7200
aactcttgaa acacaaatgt cccacaagtc tcctcttcgt catcaagcaa ccaccgcacc   7260
cagcatcaag cccacctgaa attatctccg gcttccctct ggccgaacaa tatcggtagt   7320
taatcaaaac ttagggtgca agatcatcca caatgtcacc acaacgagac cggataaatg   7380
ccttctacaa agataacccc catcccaagg gaagtaggat agtcattaac agagaacatc   7440
ttatgattga tagaccttat gttttgctgg ctgttctgtt tgtcatgttt ctgagcttga   7500
tcgggttgct agccattgca ggcattagac ttcatcgggc agccatctac accgcagaga   7560
tccataaaag cctcagcacc aatctagatg taactaactc aatcgagcat caggtcaagg   7620
acgtgctgac accactcttc aaaatcatcg gtgatgaagt gggcctgagg acacctcaga   7680
gattcactga cctagtgaaa ttaatctctg acaagattaa attccttaat ccggataggg   7740
agtacgactt cagagatctc acttggtgta tcaacccgcc agagagaatc aaattggatt   7800
atgatcaata ctgtgcagat gtggctgctg aagagctcat gaatgcattg gtgaactcaa   7860
ctctactgga gaccagaaca accaatcagt tcctagctgt ctcaaaggga aactgctcag   7920
ggcccactac aatcagaggt caattctcaa acatgtcgct gtccctgtta gacttgtatt   7980
taggtcgagg ttacaatgtg tcatctatag tcactatgac atcccaggga atgtatgggg   8040
gaacttacct agtggaaaag cctaatctga gcagcaaaag gtcagagttg tcacaactga   8100
gcatgtaccg agtgtttgaa gtaggtgtta tcagaaatcc gggtttgggg gctccggtgt   8160
tccatatgac aaactatctt gagcaaccag tcagtaatga tctcagcaac tgtatggtgg   8220
ctttggggga gctcaaactc gcagcccttt gtcacgggga agattctatc acaattccct   8280
atcagggatc agggaaaggt gtcagcttcc agctcgtcaa gctaggtgtc tggaaatccc   8340
caaccgacat gcaatcctgg gtccccttat caacggatga tccagtgata gacaggcttt   8400
acctctcatc tcacagaggt gttatcgctg acaatcaagc aaaatgggct gtcccgacaa   8460
```

-continued

```
cacgaacaga tgacaagttg cgaatggaga catgcttcca acaggcgtgt aagggtaaaa   8520
tccaagcact ctgcgagaat cccgagtggg caccattgaa ggataacagg attccttcat   8580
acggggtctt gtctgttgat ctgagtctga cagttgagct taaaatcaaa attgcttcgg   8640
gattcgggcc attgatcaca cacggttcag ggatggacct atacaaatcc aaccacaaca   8700
atgtgtattg gctgactatc ccgccaatga agaacctagc cttaggtgta atcaacacat   8760
tggagtggat accgagattc aaggttagtc cctacctctt cactgtccca attaaggaag   8820
caggcgaaga ctgccatgcc ccaacatacc tacctgcgga ggtggatggt gatgtcaaac   8880
tcagttccaa tctggtgatt ctacctggtc aagatctcca atatgttttg gcaacctacg   8940
atacttccag ggttgaacat gctgtggttt attacgttta cagcccaagc cgctcatttt   9000
cttactttta tccttttagg ttgcctataa agggggtccc catcgaatta caagtggaat   9060
gcttcacatg ggaccaaaaa ctctggtgcc gtcacttctg tgtgcttgcg gactcagaat   9120
ctggtggaca tatcactcac tctgggatgg tgggcatggg agtcagctgc acagtcaccc   9180
gggaagatgg aaccaatcgc agatagggct gctagtgaac caatcacatg atgtcaccca   9240
gacatcaggc atacccacta gtgtgaaata gacatcagaa ttaagaaaaa cgtagggtcc   9300
aagtggttcc ccgttatgga ctcgctatct gtcaaccaga tcttataccc tgaagttcac   9360
ctagatagcc cgatagttac caataagata gtagccatcc tggagtatgc tcgagtccct   9420
cacgcttaca gcctggagga ccctacactg tgtcagaaca tcaagcaccg cctaaaaaac   9480
ggattttcca accaaatgat tataaacaat gtggaagttg ggaatgtcat caagtccaag   9540
cttaggagtt atccggccca ctctcatatt ccatatccaa attgtaatca ggatttattt   9600
aacatagaag acaaagagtc aacgaggaag atccgtgaac tcctcaaaaa ggggaattcg   9660
ctgtactcca aagtcagtga taaggttttc caatgcttaa gggacactaa ctcacggctt   9720
ggcctaggct ccgaattgag ggaggacatc aaggagaaag ttattaactt gggagtttac   9780
atgcacagct cccagtggtt tgagcccttt ctgttttggt ttacagtcaa gactgagatg   9840
aggtcagtga ttaaatcaca aacccatact tgccatagga ggagacacac acctgtattc   9900
ttcactggta gttcagttga gttgctaatc tctcgtgacc ttgttgctat aatcagtaaa   9960
gagtctcaac atgtatatta cctgacattt gaactggttt tgatgtattg tgatgtcata  10020
gaggggaggt taatgacaga gaccgctatg actattgatg ctaggtatac agagcttcta  10080
ggaagagtca gatacatgtg gaaactgata gatggtttct tccctgcact cgggaatcca  10140
acttatcaaa ttgtagccat gctggagcct ctttcacttg cttacctgca gctgagggat  10200
ataacagtag aactcagagg tgctttcctt aaccactgct ttactgaaat acatgatgtt  10260
cttgaccaaa acgggttttc tgatgaaggt acttatcatg agttaactga agctctagat  10320
tacattttca taactgatga catacatctg acaggggaga ttttctcatt tttcagaagt  10380
ttcggccacc ccagacttga agcagtaacg gctgctgaaa atgttaggaa atacatgaat  10440
cagcctaaag tcattgtgta tgagactctg atgaaaggtc atgccatatt ttgtggaatc  10500
ataatcaacg gctatcgtga caggcacgga ggcagttggc caccgctgac cctcccccctg  10560
catgctgcag acacaatccg gaatgctcaa gcttcaggtg aagggttaac acatgagcag  10620
tgcgttgata actggaaatc ttttgctgga gtgaaatttg gctgctttat gcctcttagc  10680
ctggatagtg atctgacaat gtacctaaag gacaaggcac ttgctgctct ccaaagggaa  10740
tgggattcag tttacccgaa agagttcctg cgttacgacc ctcccaaggg aaccgggtca  10800
cggaggcttg tagatgtttt ccttaatgat tcgagctttg acccatatga tgtgataatg  10860
```

```
tatgttgtaa gtggagctta cctccatgac cctgagttca acctgtctta cagcctgaaa  10920
gaaaaggaga tcaaggaaac aggtagactt tttgctaaaa tgacttacaa aatgagggca  10980
tgccaagtga ttgctgaaaa tctaatctca aacgggattg gcaaatattt taaggacaat  11040
gggatggcca aggatgagca cgatttgact aaggcactcc acactctagc tgtctcagga  11100
gtccccaaag atctcaaaga aagtcacagg ggggggccag tcttaaaaac ctactcccga  11160
agcccagtcc acacaagtac caggaacgtg agagcagcaa aagggtttat agggttccct  11220
caagtaattc ggcaggacca agacactgat catccggaga atatggaagc ttacgagaca  11280
gtcagtgcat ttatcacgac tgatctcaag aagtactgcc ttaattggag atatgagacc  11340
atcagcttgt ttgcacagag gctaaatgag atttacggat tgccctcatt tttccagtgg  11400
ctgcataaga ggcttgagac ctctgtcctg tatgtaagtg accctcattg cccccccgac  11460
cttgacgccc atatcccgtt atataaagtc cccaatgatc aaatcttcat taagtaccct  11520
atgggaggta tagaagggta ttgtcagaag ctgtggacca tcagcaccat tccctatcta  11580
tacctggctg cttatgagag cggagtaagg attgcttcgt tagtgcaagg ggacaatcag  11640
accatagccg taacaaaaag ggtacccagc acatggccct acaaccttaa gaaacgggaa  11700
gctgctagag taactagaga ttactttgta attcttaggc aaaggctaca tgatattggc  11760
catcacctca aggcaaatga gacaattgtt tcatcacatt tttttgtcta ttcaaaagga  11820
atatattatg atgggctact tgtgtcccaa tcactcaaga gcatcgcaag atgtgtattc  11880
tggtcagaga ctatagttga tgaaacaagg gcagcatgca gtaatattgc tacaacaatg  11940
gctaaaagca tcgagagagg ttatgaccgt taccttgcat attccctgaa cgtcctaaaa  12000
gtgatacagc aaattctgat ctctcttggc ttcacaatca attcaaccat gacccgggat  12060
gtagtcatac ccctcctcac aaacaacgac ctcttaataa ggatggcact gttgcccgct  12120
cctattgggg ggatgaatta tctgaatatg agcaggctgt ttgtcagaaa catcggtgat  12180
ccagtaacat catcaattgc tgatctcaag agaatgattc tcgcctcact aatgcctgaa  12240
gagaccctcc atcaagtaat gacacaacaa ccggggggact cttcattcct agactgggct  12300
agcgaccctt actcagcaaa tcttgtatgt gtccagagca tcactagact cctcaagaac  12360
ataactgcaa ggtttgtcct gatccatagt ccaaacccaa tgttaaaagg attattccat  12420
gatgacagta aagaagagga cgagggactg gcggcattcc tcatggacag gcatattata  12480
gtacctaggg cagctcatga aatcctggat catagtgtca caggggcaag agagtctatt  12540
gcaggcatgc tggataccac aaaaggcttg attcgagcca gcatgaggaa ggggggggtta  12600
acctctcgag tgataaccag attgtccaat tatgactatg aacaattcag agcagggatg  12660
gtgctattga caggaagaaa gagaaatgtc ctcattgaca aagagtcatg ttcagtgcag  12720
ctggcgagag ctctaagaag ccatatgtgg gcgaggctag ctcgaggacg gcctatttac  12780
ggccttgagg tccctgatgt actagaatct atgcgaggcc accttattcg gcgtcatgag  12840
acatgtgtca tctgcgagtg tggatcagtc aactacggat ggtttttttgt cccctcgggt  12900
tgccaactgg atgatattga caaggaaaca tcatccttga gagtcccata tattggttct  12960
accactgatg agagaacaga catgaagctt gccttcgtaa gagccccaag tcgatccttg  13020
cgatctgctg ttagaatagc aacagtgtac tcatgggctt acggtgatga tgatagctct  13080
tggaacgaag cctggttgtt ggctaggcaa agggccaatg tgagcctgga ggagctaagg  13140
gtgatcactc ccatctcaac ttcgactaat ttagcgcata ggttgaggga tcgtagcact  13200
```

caagtgaaat actcaggtac atcccttgtc cgagtggcga ggtataccac aatctccaac 13260
gacaatctct catttgtcat atcagataag aaggttgata ctaactttat ataccaacaa 13320
ggaatgcttc tagggttggg tgttttagaa acattgtttc gactcgagaa agataccgga 13380
tcatctaaca cggtattaca tcttcacgtc gaaacagatt gttgcgtgat cccgatgata 13440
gatcatccca ggatacccag ctcccgcaag ctagagctga gggcagagct atgtaccaac 13500
ccattgatat atgataatgc acctttaatt gacagagatg caacaaggct atacacccag 13560
agccatagga ggcaccttgt ggaatttgtt acatggtcca caccccaact atatcacatt 13620
ttagctaagt ccacagcact atctatgatt gacctggtaa caaaatttga gaaggaccat 13680
atgaatgaaa tttcagctct catagggat gacgatatca atagtttcat aactgagttt 13740
ctgctcatag agccaagatt attcactatc tacttgggcc agtgtgcggc catcaattgg 13800
gcatttgatg tacattatca tagaccatca gggaaatatc agatgggtga gctgttgtca 13860
tcgttccttt ctagaatgag caaaggagtg tttaaggtgc ttgtcaatgc tctaagccac 13920
ccaaagatct acaagaaatt ctggcattgt ggtattatag agcctatcca tggtccttca 13980
cttgatgctc aaaacttgca cacaactgtg tgcaacatgg tttacacatg ctatatgacc 14040
tacctcgacc tgttgttgaa tgaagagtta gaagagttca catttctctt gtgtgaaagc 14100
gacgaggatg tagtaccgga cagattcgac aacatccagg caaaacactt atgtgttctg 14160
gcagatttgt actgtcaacc agggacctgc ccaccaattc gaggtctaag accggtagag 14220
aaatgtgcag ttctaaccga ccatatcaag gcagaggcta tgttatctcc agcaggatct 14280
tcgtggaaca taaatccaat tattgtagac cattactcat gctctctgac ttatctccgg 14340
cgaggatcga tcaaacagat aagattgaga gttgatccag gattcatttt cgacgccctc 14400
gctgaggtaa atgtcagtca gccaaagatc ggcagcaaca acatctcaaa tatgagcatc 14460
aaggctttca gacccccaca cgatgatgtt gcaaaattgc tcaaagatat caacacaagc 14520
aagcacaatc ttcccatttc agggggcaat ctcgccaatt atgaaatcca tgctttccgc 14580
agaatcgggt tgaactcatc tgcttgctac aaagctgttg agatatcaac attaattagg 14640
agatgccttg agccagggga ggacggcttg ttcttgggtg agggatcggg ttctatgttg 14700
atcacttata aagagatact taaactaaac aagtgcttct ataatagtgg ggtttccgcc 14760
aattctagat ctggtcaaag ggaattagca ccctatccct ccgaagttgg ccttgtcgaa 14820
cacagaatgg gagtaggtaa tattgtcaaa gtgctcttta acgggaggcc cgaagtcacg 14880
tgggtaggca gtgtagattg cttcaatttc atagttagta atatccctac ctctagtgtg 14940
gggtttatcc attcagatat agagaccttg cctgacaaag atactataga gaagctagag 15000
gaattggcag ccatcttatc gatggctctg ctcctgggca aaataggatc aatactggtg 15060
attaagctta tgcctttcag cggggatttt gttcagggat ttataagtta tgtagggtct 15120
cattatagag aagtgaacct tgtataccct agatacagca acttcatctc tactgaatct 15180
tatttggtta tgacagatct caaggctaac cggctaatga atcctgaaaa gattaagcag 15240
cagataattg aatcatctgt gaggacttca cctggactta taggtcacat cctatccatt 15300
aagcaactaa gctgcataca agcaattgtg ggagacgcag ttagtagagg tgatatcaat 15360
cctactctga aaaaacttac acctatagag caggtgctga tcaattgcgg gttggcaatt 15420
aacggaccta agctgtgcaa agaattgatc caccatgatg ttgcctcagg gcaagatgga 15480
ttgcttaatt ctatactcat cctctacagg gagttggcaa gattcaaaga caaccaaaga 15540
agtcaacaag ggatgttcca cgcttacccc gtattggtaa gtagcaggca acgagaactt 15600

```
atatctagga tcacccgcaa attctggggg cacattcttc tttactccgg gaacaaaaag    15660

ttgataaata agtttatcca gaatctcaag tccggctatc tgatactaga cttacaccag    15720

aatatcttcg ttaagaatct atccaagtca gagaaacaga ttattatgac ggggggtttg    15780

aaacgtgagt gggtttttaa ggtaacagtc aaggagacca agaatggta taagttagtc     15840

ggatacagtg ccctgattaa ggactaattg gttgaactcc ggaaccctaa tcctgcccta    15900

ggtggttagg cattatttgc aatatattaa agaaaacttt gaaaatacga agtttctatt    15960

cccagctttg tctggtggcc ggcatggtcc cagcctcctc gctggcgccg gctgggcaac    16020

attccgaggg gaccgtcccc tcggtaatgg cgaatgggac gcggccgatc cggctgctaa    16080

caaagcccga aaggaagctg agttggctgc tgccaccgct gagcaataac tagcataacc    16140

ccttggggcc tctaaacggg tcttgagggg ttttttgctg aaaggaggaa ctatatccgg    16200

atgcggccgc gggccctatg gtacccagct tttgttccct ttagtgaggg ttaattccga    16260

gcttggcgta atcatggtca tagctgtttc ctgtgtgaaa ttgttatccg ctcacaattc    16320

cacacaacat aggagccgga agcataaagt gtaaagcctg gggtgcctaa tgagtgaggt    16380

aactcacatt aattgcgttg cgctcactgc ccgctttcca gtcgggaaac ctgtcgtgcc    16440

agctgcatta atgaatcggc caacgcgcgg ggagaggcgg tttgcgtatt gggcgctctt    16500

ccgcttcctc gctcactgac tcgctgcgct cggtcgttcg gctgcggcga gcggtatcag    16560

ctcactcaaa ggcggtaata cggttatcca cagaatcagg ggataacgca ggaaagaaca    16620

tgtgagcaaa aggccagcaa aaggccagga accgtaaaaa ggccgcgttg ctggcgtttt    16680

tccataggct ccgcccccct gacgagcatc acaaaaatcg acgctcaagt cagaggtggc    16740

gaaacccgac aggactataa agataccagg cgttccccccc tggaagctcc ctcgtgcgct    16800

ctcctgttcc gaccctgccg cttaccggat acctgtccgc ctttctccct tcgggaagcg    16860

tggcgctttc tcaatgctca cgctgtaggt atctcagttc ggtgtaggtc gttcgctcca    16920

agctgggctg tgtgcacgaa ccccccgttc agcccgaccg ctgcgcctta tccggtaact    16980

atcgtcttga gtccaacccg gtaagacacg acttatcgcc actggcagca gccactggta    17040

acaggattag cagagcgagg tatgtaggcg gtgctacaga gttcttgaag tggtggccta    17100

actacggcta cactagaagg acagtatttg gtatctgcgc tctgctgaag ccagttacct    17160

tcggaaaaag agttggtagc tcttgatccg gcaaacaaac caccgctggt agcggtggtt    17220

tttttgtttg caagcagcag attacgcgca gaaaaaaagg atctcaagaa gatcctttga    17280

tcttttctac ggggtctgac gctcagtgga acgaaaactc acgttaaggg attttggtca    17340

tgagattatc aaaaaggatc ttcacctaga tccttttaaa ttaaaaatga agttttaaat    17400

caatctaaag tatatatgag taaacttggt ctgacagtta ccaatgctta atcagtgagg    17460

cacctatctc agcgatctgt ctatttcgtt catccatagt tgcctgactg cccgtcgtgt    17520

agataactac gatacgggag ggcttaccat ctggccccag tgctgcaatg ataccgcgag    17580

acccacgctc accggctcca gatttatcag caataaacca gccagccgga agggccgagc    17640

gcagaagtgg tcctgcaact ttatccgcct ccatccagtc tattaattgt tgccgggaag    17700

ctagagtaag tagttcgcca gttaatagtt tgcgcaacgt tgttgccatt gctacaggca    17760

tcgtggtgtc acgctcgtcg tttggtatgg cttcattcag ctccggttcc caacgatcaa    17820

ggcgagttac atgatccccc atgttgtgaa aaaaagcggt tagctccttc ggtcctccga    17880

tcgttgtcag aagtaagttg gccgcagtgt tatcactcat gcttatggca gcactgcata    17940
```

attctcttac tgtcatgcca tccgtaagat gcttttctgt gactggtgag tactcaacca 18000
agtcattctg agaatagtgt atgcggcgac cgagttgctc ttgcccggcg tcaatacggg 18060
ataataccgc gccacatagc agaactttaa aagtgctcat cattggaaaa cgttcttcgg 18120
ggcgaaaact ctcaaggatc ttaccgctgt tgagatccag ttcgatgtaa cccactcgtg 18180
cacccaactg atcttcagca tcttttactt tcaccagcgt ttctgggtga gcaaaaacag 18240
gaaggcaaaa tgccgcaaaa aagggaataa gggcgacacg gaaatgttga atactcatac 18300
tcttcctttt tcaatattat tgaagcattt atcagggtta ttgtctcatg agcggataca 18360
tatttgaatg tatttagaaa aataaacaaa taggggttcc gcgcacattt ccccgaaaag 18420
tgccacctga aattgtaaac gttaatattt tgttaaaatt cgcgttaaat ttttgttaaa 18480
tcagctcatt ttttaaccaa taggccgaaa tcggcaaaat cccttataaa tcaaaagaat 18540
agaccgagat agggttgagt gttgttccag tttggaacaa gagtccacta ttaaagaacg 18600
tggactccaa cgtcaaaggg cgaaaaaccg tctatcaggg cgatggccca ctacgtgaac 18660
catcacccta atcaagtttt ttggggtcga ggtgccgtaa agcactaaat cggaacccta 18720
aagggagccc ccgatttaga gcttgacggg gaaagccggc gaacgtggcg agaaaggaag 18780
ggaagaaagc gaaaggagcg ggcgctaggg cgctggcaag tgtagcggtc acgctgcgcg 18840
taaccaccac acccgccgcg cttaatgcgc cgctacaggg cgcgtcccat tcgccattca 18900
ggctgcgcaa ctgttgggaa gggcgatcgg tgcgggcctc ttcgctatta cgccagccac 18960
cgcggtg 18967

<210> SEQ ID NO 2
<211> LENGTH: 19795
<212> TYPE: DNA
<213> ORGANISM: Artificial sequence
<220> FEATURE:
<223> OTHER INFORMATION: pTM2-MVSchw-gfp

<400> SEQUENCE: 2
gcggccgcta atacgactca ctatagggcc aactttgttt ggtctgatga gtccgtgagg 60
acgaaacccg gagtcccggg tcaccaaaca aagttgggta aggatagttc aatcaatgat 120
catcttctag tgcacttagg attcaagatc ctattatcag ggacaagagc aggattaggg 180
atatccgaga tggccacact tttaaggagc ttagcattgt tcaaaagaaa caaggacaaa 240
ccacccatta catcaggatc cggtggagcc atcagaggaa tcaaacacat tattatagta 300
ccaatccctg gagattcctc aattaccact cgatccagac ttctggaccg gttggtgagg 360
ttaattggaa acccggatgt gagcgggccc aaactaacag ggcactaat aggtatatta 420 tccttatttg tggagtctcc aggtcaattg attcagagga tcaccgatga ccctgacgtt 480
agcataaggc tgttagaggt tgtccagagt gaccagtcac aatctggcct taccttcgca 540
tcaagaggta ccaacatgga ggatgaggcg gaccaatact tttcacatga tgatccaatt 600
agtagtgatc aatccaggtt cggatggttc gggaacaagg aaatctcaga tattgaagtg 660
caagaccctg agggattcaa catgattctg ggtaccatcc tagcccaaat ttgggtcttg 720
ctcgcaaagg cggttacggc cccagacacg gcagctgatt cggagctaag aaggtggata 780
aagtacaccc aacaaagaag ggtagttggt gaatttagat tggagagaaa atggttggat 840
gtggtgagga acaggattgc cgaggacctc tccttacgcc gattcatggt cgctctaatc 900
ctggatatca agagaacacc cggaaacaaa cccaggattg ctgaaatgat atgtgacatt 960
gatacatata tcgtagaggc aggattagcc agttttatcc tgactattaa gtttgggata 1020

-continued

```
gaaactatgt atcctgctct tggactgcat gaatttgctg gtgagttatc cacacttgag   1080
tccttgatga acctttacca gcaaatgggg gaaactgcac cctacatggt aatcctggag   1140
aactcaattc agaacaagtt cagtgcagga tcataccctc tgctctggag ctatgccatg   1200
ggagtaggag tggaacttga aaactccatg ggaggtttga actttggccg atcttacttt   1260
gatccagcat attttagatt agggcaagag atggtaagga ggtcagctgg aaaggtcagt   1320
tccacattgg catctgaact cggtatcact gccgaggatg caaggcttgt ttcagagatt   1380
gcaatgcata ctactgagga caagatcagt agagcggttg gacccagaca agcccaagta   1440
tcatttctac acggtgatca aagtgagaat gagctaccga gattgggggg caaggaagat   1500
aggagggtca aacagagtcg aggagaagcc agggagagct acagagaaac cgggcccagc   1560
agagcaagtg atgcgagagc tgcccatctt ccaaccggca caccccctaga cattgacact   1620
gcaacggagt ccagccaaga tccgcaggac agtcgaaggt cagctgacgc cctgcttagg   1680
ctgcaagcca tggcaggaat ctcggaagaa caaggctcag acacggacac ccctatagtg   1740
tacaatgaca gaaatcttct agactaggtg cgagaggccg agggccagaa caacatccgc   1800
ctaccatcca tcattgttat aaaaaactta ggaaccaggt ccacacagcc gccagcccat   1860
caaccatcca ctcccacgat tggagccaat ggcagaagag caggcacgcc atgtcaaaaa   1920
cggactggaa tgcatccggg ctctcaaggc cgagcccatc ggctcactgg ccatcgagga   1980
agctatggca gcatggtcag aaatatcaga caacccagga caggagcgag ccacctgcag   2040
ggaagagaag gcaggcagtt cgggtctcag caaaccatgc ctctcagcaa ttggatcaac   2100
tgaaggcggt gcacctcgca tccgcggtca gggacctgga gagagcgatg acgacgctga   2160
aactttggga atccccccaa gaaatctcca ggcatcaagc actgggttac agtgttatta   2220
cgtttatgat cacagcggtg aagcggttaa gggaatccaa gatgctgact ctatcatggt   2280
tcaatcaggc cttgatggtg atagcaccct ctcaggagga gacaatgaat ctgaaaacag   2340
cgatgtggat attggcgaac ctgataccga gggatatgct atcactgacc ggggatctgc   2400
tcccatctct atggggttca gggcttctga tgttgaaact gcagaaggag gggagatcca   2460
cgagctcctg agactccaat ccagaggcaa caactttccg aagcttggga aaactctcaa   2520
tgttcctccg cccccggacc ccggtagggc cagcacttcc gggacaccca ttaaaaaggg   2580
cacagacgcg agattagcct catttggaac ggagatcgcg tctttattga caggtggtgc   2640
aacccaatgt gctcgaaagt caccctcgga accatcaggg ccaggtgcac ctgcggggaa   2700
tgtccccgag tgtgtgagca atgccgcact gatacaggag tggacacccg aatctggtac   2760
cacaatctcc ccgagatccc agaataatga agaaggggga gactattatg atgatgagct   2820
gttctctgat gtccaagata ttaaaacagc cttggccaaa atacacgagg ataatcagaa   2880
gataatctcc aagctagaat cactgctgtt attgaaggga gaagttgagt caattaagaa   2940
gcagatcaac aggcaaaata tcagcatatc caccctggaa ggacacctct caagcatcat   3000
gatcgccatt cctggacttg ggaaggatcc caacgacccc actgcagatg tcgaaatcaa   3060
tcccgacttg aaacccatca taggcagaga ttcaggccga gcactggccg aagttctcaa   3120
gaaacccgtt gccagccgac aactccaagg aatgacaaat ggacggacca gttccagagg   3180
acagctgctg aaggaatttc agctaaagcc gatcgggaaa aagatgagct cagccgtcgg   3240
gtttgttcct gacaccggcc ctgcatcacg cagtgtaatc cgctccatta taaaatccag   3300
ccggctagag gaggatcgga agcgttacct gatgactctc cttgatgata tcaaaggagc   3360
```

-continued

```
caatgatctt gccaagttcc accagatgct gatgaagata ataatgaagt agctacagct   3420

caacttacct gccaacccca tgccagtcga cccaactagc ctaccctcca tcattgttat   3480

aaaaaactta ggaaccaggt ccacacagcc gccagcccat caacgcgtac gatggtgagc   3540

aagggcgagg agctgttcac cggggtggtg cccatcctgg tcgagctgga cggcgacgta   3600

aacggccaca agttcagcgt gtccggcgag ggcgagggcg atgccaccta cggcaagctg   3660

accctgaagt tcatctgcac caccggcaag ctgcccgtgc cctggcccac cctcgtgacc   3720

accctgacct acggcgtgca gtgcttcagc cgctaccccg accacatgaa gcagcacgac   3780

ttcttcaagt ccgccatgcc cgaaggctac gtccaggagc gcaccatctt cttcaaggac   3840

gacggcaact acaagacccg cgccgaggtg aagttcgagg gcgacaccct ggtgaaccgc   3900

atcgagctga agggcatcga cttcaaggag gacggcaaca tcctggggca caagctggag   3960

tacaactaca acagccacaa cgtctatatc atggccgaca agcagaagaa cggcatcaag   4020

gtgaacttca agatccgcca caacatcgag gacggcagcg tgcagctcgc cgaccactac   4080

cagcagaaca cccccatcgg cgacggcccc gtgctgctgc ccgacaacca ctacctgagc   4140

acccagtccg ccctgagcaa agaccccaac gagaagcgcg atcacatggt cctgctggag   4200

ttcgtgaccg ccgccgggat cactctcggc atggacgagc tgtacaagta ggcgcgcagc   4260

gcttagacgt ctcgcgatcg atactagtac aacctaaatc cattataaaa aacttaggag   4320

caaagtgatt gcctcccaag gtccacaatg acagagacct acgacttcga caagtcggca   4380

tgggacatca aagggtcgat cgctccgata caacccacca cctacagtga tggcaggctg   4440

gtgccccagg tcagagtcat agatcctggt ctaggcgaca ggaaggatga atgctttatg   4500

tacatgtttc tgctgggggt tgttgaggac agcgattccc tagggcctcc aatcgggcga   4560

gcatttgggt tcctgccctt aggtgttggc agatccacag caaagcccga aaaactcctc   4620

aaagaggcca ctgagcttga catagttgtt agacgtacag cagggctcaa tgaaaaactg   4680

gtgttctaca acaacacccc actaactctc ctcacacctt ggagaaaggt cctaacaaca   4740

gggagtgtct tcaacgcaaa ccaagtgtgc aatgcggtta atctgatacc gctcgatacc   4800

ccgcagaggt tccgtgttgt ttatatgagc atcacccgtc tttcggataa cgggtattac   4860

accgttccta gaagaatgct ggaattcaga tcggtcaatg cagtggcctt caacctgctg   4920

gtgaccctta ggattgacaa ggcgataggc cctgggaaga tcatcgacaa tacagagcaa   4980

cttcctgagg caacatttat ggtccacatc gggaacttca ggagaaagaa gagtgaagtc   5040

tactctgccg attattgcaa aatgaaaatc gaaaagatgg gcctggtttt tgcacttggt   5100

gggataggggg gcaccagtct tcacattaga agcacaggca aaatgagcaa gactctccat   5160

gcacaactcg ggttcaagaa gaccttatgt tacccgctga tggatatcaa tgaagacctt   5220

aatcgattac tctggaggag cagatgcaag atagtaagaa tccaggcagt tttgcagcca   5280

tcagttcctc aagaattccg catttacgac gacgtgatca taaatgatga ccaaggacta   5340

ttcaaagttc tgtagaccgt agtgcccagc aatgcccgaa aacgaccccc ctcacaatga   5400

cagccagaag gcccggacaa aaaagccccc tccgaaagac tccacggacc aagcgagagg   5460

ccagccagca gccgacggca agcgcgaaca ccaggcggcc ccagcacaga acagccctga   5520

cacaaggcca ccaccagcca ccccaatctg catcctcctc gtgggacccc cgaggaccaa   5580

cccccaaggc tgcccccgat ccaaaccacc aaccgcatcc ccaccacccc cgggaaagaa   5640

acccccagca attggaaggc ccctccccct cttcctcaac acaagaactc cacaaccgaa   5700

ccgcacaagc gaccgaggtg acccaaccgc aggcatccga ctccctagac agatcctctc   5760
```

-continued

```
tccccggcaa actaaacaaa acttagggcc aaggaacata cacacccaac agaacccaga   5820
ccccggccca cggcgccgcg cccccaaccc ccgacaacca gagggagccc ccaaccaatc   5880
ccgccggctc ccccggtgcc cacaggcagg gacaccaacc cccgaacaga cccagcaccc   5940
aaccatcgac aatccaagac ggggggggccc ccccaaaaaa aggcccccag gggccgacag   6000
ccagcaccgc gaggaagccc acccacccca cacacgacca cggcaaccaa accagaaccc   6060
agaccaccct gggccaccag ctcccagact cggccatcac cccgcagaaa ggaaaggcca   6120
caacccgcgc accccagccc cgatccggcg gggagccacc caacccgaac cagcacccaa   6180
gagcgatccc cgaaggaccc ccgaaccgca aaggacatca gtatcccaca gcctctccaa   6240
gtcccccggt ctcctcctct tctcgaaggg accaaaagat caatccacca cacccgacga   6300
cactcaactc cccaccccta aaggagacac cgggaatccc agaatcaaga ctcatccaat   6360
gtccatcatg ggtctcaagg tgaacgtctc tgccatattc atggcagtac tgttaactct   6420
ccaaacaccc accggtcaaa tccattgggg caatctctct aagatagggg tggtaggaat   6480
aggaagtgca agctacaaag ttatgactcg ttccagccat caatcattag tcataaaatt   6540
aatgcccaat ataactctcc tcaataactg cacgagggta gagattgcag aatacaggag   6600
actactgaga acagttttgg aaccaattag agatgcactt aatgcaatga cccagaatat   6660
aagaccggtt cagagtgtag cttcaagtag gagacacaag agatttgcgg gagtagtcct   6720
ggcaggtgcg gccctaggcg ttgccacagc tgctcagata acagccggca ttgcacttca   6780
ccagtccatg ctgaactctc aagccatcga caatctgaga gcgagcctgg aaactactaa   6840
tcaggcaatt gagacaatca gacaagcagg gcaggagatg atattggctg ttcagggtgt   6900
ccaagactac atcaataatg agctgatacc gtctatgaac caactatctt gtgatttaat   6960
cggccagaag ctcgggctca aattgctcag atactataca gaaatcctgt cattatttgg   7020
ccccagttta cgggacccca tatctgcgga gatatctatc caggctttga gctatgcgct   7080
tggaggagac atcaataagg tgttagaaaa gctcggatac agtggaggtg atttactggg   7140
catcttagag agcggaggaa taaaggcccg gataactcac gtcgacacag agtcctactt   7200
cattgtcctc agtatagcct atccgacgct gtccgagatt aagggggtga ttgtccaccg   7260
gctagagggg gtctcgtaca acataggctc tcaagagtgg tataccactg tgcccaagta   7320
tgttgcaacc caagggtacc ttatctcgaa ttttgatgag tcatcgtgta ctttcatgcc   7380
agaggggact gtgtgcagcc aaaatgcctt gtacccgatg agtcctctgc tccaagaatg   7440
cctccggggg tacaccaagt cctgtgctcg tacactcgta tccgggtctt ttgggaaccg   7500
gttcatttta tcacaaggga acctaatagc caattgtgca tcaatccttt gcaagtgtta   7560
cacaacagga acgatcatta atcaagaccc tgacaagatc ctaacataca ttgctgccga   7620
tcactgcccg gtagtcgagg tgaacggcgt gaccatccaa gtcgggagca ggaggtatcc   7680
agacgctgtg tacttgcaca gaattgacct cggtcctccc atatcattgg agaggttgga   7740
cgtagggaca aatctgggga atgcaattgc taagttggag gatgccaagg aattgttgga   7800
gtcatcggac cagatattga ggagtatgaa aggtttatcg agcactagca tagtctacat   7860
cctgattgca gtgtgtcttg gagggttgat agggatcccc gctttaatat gttgctgcag   7920
ggggcgttgt aacaaaaagg gagaacaagt tggtatgtca agaccaggcc taaagcctga   7980
tcttacggga acatcaaaat cctatgtaag gtcgctctga tcctctacaa ctcttgaaac   8040
acaaatgtcc cacaagtctc ctcttcgtca tcaagcaacc accgcaccca gcatcaagcc   8100
```

-continued

```
cacctgaaat tatctccggc ttccctctgg ccgaacaata tcggtagtta atcaaaactt   8160
agggtgcaag atcatccaca atgtcaccac aacgagaccg gataaatgcc ttctacaaag   8220
ataaccccca tcccaaggga agtaggatag tcattaacag agaacatctt atgattgata   8280
gaccttatgt tttgctggct gttctgtttg tcatgtttct gagcttgatc gggttgctag   8340
ccattgcagg cattagactt catcgggcag ccatctacac cgcagagatc cataaaagcc   8400
tcagcaccaa tctagatgta actaactcaa tcgagcatca ggtcaaggac gtgctgacac   8460
cactcttcaa aatcatcggt gatgaagtgg gcctgaggac acctcagaga ttcactgacc   8520
tagtgaaatt aatctctgac aagattaaat tccttaatcc ggatagggag tacgacttca   8580
gagatctcac ttggtgtatc aacccgccag agagaatcaa attggattat gatcaatact   8640
gtgcagatgt ggctgctgaa gagctcatga atgcattggt gaactcaact ctactggaga   8700
ccagaacaac caatcagttc ctagctgtct caaagggaaa ctgctcaggg cccactacaa   8760
tcagaggtca attctcaaac atgtcgctgt ccctgttaga cttgtattta ggtcgaggtt   8820
acaatgtgtc atctatagtc actatgacat cccagggaat gtatgggggga acttacctag   8880
tggaaaagcc taatctgagc agcaaaaggt cagagttgtc acaactgagc atgtaccgag   8940
tgtttgaagt aggtgttatc agaaatccgg gtttgggggc tccggtgttc catatgacaa   9000
actatcttga gcaaccagtc agtaatgatc tcagcaactg tatggtggct ttgggggagc   9060
tcaaactcgc agccctttgt cacggggaag attctatcac aattccctat cagggatcag   9120
ggaaaggtgt cagcttccag ctcgtcaagc taggtgtctg gaaatcccca accgacatgc   9180
aatcctgggt ccccttatca acggatgatc cagtgataga caggctttac ctctcatctc   9240
acagaggtgt tatcgctgac aatcaagcaa aatgggctgt cccgacaaca cgaacagatg   9300
acaagttgcg aatggagaca tgcttccaac aggcgtgtaa gggtaaaatc caagcactct   9360
gcgagaatcc cgagtgggca ccattgaagg ataacaggat tccttcatac ggggtcttgt   9420
ctgttgatct gagtctgaca gttgagctta aaatcaaaat tgcttcggga ttcgggccat   9480
tgatcacaca cggttcaggg atggacctat acaaatccaa ccacaacaat gtgtattggc   9540
tgactatccc gccaatgaag aacctagcct taggtgtaat caacacattg gagtggatac   9600
cgagattcaa ggttagtccc tacctcttca ctgtcccaat taaggaagca ggcgaagact   9660
gccatgcccc aacataccta cctgcggagg tggatggtga tgtcaaactc agttccaatc   9720
tggtgattct acctggtcaa gatctccaat atgttttggc aacctacgat acttccaggg   9780
ttgaacatgc tgtggtttat tacgtttaca gcccaagccg ctcattttct tacttttatc   9840
cttttaggtt gcctataaag ggggtcccca tcgaattaca agtggaatgc ttcacatggg   9900
accaaaaact ctggtgccgt cacttctgtg tgcttgcgga ctcagaatct ggtggacata   9960
tcactcactc tgggatggtg ggcatgggag tcagctgcac agtcacccgg gaagatggaa   10020
ccaatcgcag atagggctgc tagtgaacca atcacatgat gtcacccaga catcaggcat   10080
acccactagt gtgaaataga catcagaatt aagaaaaacg tagggtccaa gtggttcccc   10140
gttatggact cgctatctgt caaccagatc ttataccctg aagttcacct agatagcccg   10200
atagttacca ataagatagt agccatcctg gagtatgctc gagtccctca cgcttacagc   10260
ctggaggacc ctacactgtg tcagaacatc aagcaccgcc taaaaaacgg attttccaac   10320
caaatgatta taaacaatgt ggaagttggg aatgtcatca agtccaagct taggagttat   10380
ccggcccact ctcatattcc atatccaaat tgtaatcagg atttatttaa catagaagac   10440
aaagagtcaa cgaggaagat ccgtgaactc ctcaaaaagg ggaattcgct gtactccaaa   10500
```

gtcagtgata aggttttcca atgcttaagg gacactaact cacggcttgg cctaggctcc 10560
gaattgaggg aggacatcaa ggagaaagtt attaacttgg gagtttacat gcacagctcc 10620
cagtggtttg agccctttct gttttggttt acagtcaaga ctgagatgag gtcagtgatt 10680
aaatcacaaa cccatacttg ccataggagg agacacacac ctgtattctt cactggtagt 10740
tcagttgagt tgctaatctc tcgtgacctt gttgctataa tcagtaaaga gtctcaacat 10800
gtatattacc tgacatttga actggttttg atgtattgtg atgtcataga ggggaggtta 10860
atgacagaga ccgctatgac tattgatgct aggtatacag agcttctagg aagagtcaga 10920
tacatgtgga aactgataga tggtttcttc cctgcactcg ggaatccaac ttatcaaatt 10980
gtagccatgc tggagcctct ttcacttgct tacctgcagc tgagggatat aacagtagaa 11040
ctcagaggtg ctttccttaa ccactgcttt actgaaatac atgatgttct tgaccaaaac 11100
gggttttctg atgaaggtac ttatcatgag ttaactgaag ctctagatta cattttcata 11160
actgatgaca tacatctgac aggggagatt ttctcatttt tcagaagttt cggccacccc 11220
agacttgaag cagtaacggc tgctgaaaat gttaggaaat acatgaatca gcctaaagtc 11280
attgtgtatg agactctgat gaaaggtcat gccatatttt gtggaatcat aatcaacggc 11340
tatcgtgaca ggcacggagg cagttggcca ccgctgaccc tcccccctgca tgctgcagac 11400 acaatccgga atgctcaagc ttcaggtgaa gggttaacac atgagcagtg cgttgataac 11460
tggaaatctt ttgctggagt gaaatttggc tgctttatgc ctcttagcct ggatagtgat 11520
ctgacaatgt acctaaagga caaggcactt gctgctctcc aaagggaatg ggattcagtt 11580
tacccgaaag agttcctgcg ttacgaccct cccaagggaa ccgggtcacg gaggcttgta 11640
gatgttttcc ttaatgattc gagctttgac ccatatgatg tgataatgta tgttgtaagt 11700
ggagcttacc tccatgaccc tgagttcaac ctgtcttaca gcctgaaaga aaaggagatc 11760
aaggaaacag gtagactttt tgctaaaatg acttacaaaa tgagggcatg ccaagtgatt 11820
gctgaaaatc taatctcaaa cgggattggc aaatatttta aggacaatgg gatggccaag 11880
gatgagcacg atttgactaa ggcactccac actctagctg tctcaggagt ccccaaagat 11940
ctcaaagaaa gtcacagggg ggggccagtc ttaaaaacct actcccgaag cccagtccac 12000
acaagtacca ggaacgtgag agcagcaaaa gggtttatag ggttccctca agtaattcgg 12060
caggaccaag acactgatca tccggagaat atggaagctt acgagacagt cagtgcattt 12120
atcacgactg atctcaagaa gtactgcctt aattggagat atgagaccat cagcttgttt 12180
gcacagaggc taaatgagat ttacggattg ccctcatttt tccagtggct gcataagagg 12240
cttgagacct ctgtcctgta tgtaagtgac cctcattgcc cccccgacct tgacgcccat 12300
atcccgttat ataaagtccc caatgatcaa atcttcatta agtaccctat gggaggtata 12360
gaagggtatt gtcagaagct gtggaccatc agcaccattc cctatctata cctggctgct 12420
tatgagagcg gagtaaggat tgcttcgtta gtgcaagggg acaatcagac catagccgta 12480
acaaaaaggg tacccagcac atggccctac aaccttaaga aacgggaagc tgctagagta 12540
actagagatt actttgtaat tcttaggcaa aggctacatg atattggcca tcacctcaag 12600
gcaaatgaga caattgtttc atcacatttt tttgtctatt caaaaggaat atattatgat 12660
gggctacttg tgtcccaatc actcaagagc atcgcaagat gtgtattctg gtcagagact 12720
atagttgatg aaacaagggc agcatgcagt aatattgcta caacaatggc taaaagcatc 12780
gagagaggtt atgaccgtta ccttgcatat tccctgaacg tcctaaaagt gatacagcaa 12840
attctgatct ctcttggctt cacaatcaat tcaaccatga cccgggatgt agtcataccc 12900
ctcctcacaa acaacgacct cttaataagg atggcactgt tgcccgctcc tattgggggg 12960
atgaattatc tgaatatgag caggctgttt gtcagaaaca tcggtgatcc agtaacatca 13020
tcaattgctg atctcaagag aatgattctc gcctcactaa tgcctgaaga gaccctccat 13080
caagtaatga cacaacaacc gggggactct tcattcctag actgggctag cgacccttac 13140
tcagcaaatc ttgtatgtgt ccagagcatc actagactcc tcaagaacat aactgcaagg 13200
tttgtcctga tccatagtcc aaacccaatg ttaaaaggat tattccatga tgacagtaaa 13260
gaagaggacg agggactggc ggcattcctc atggacaggc atattatagt acctagggca 13320
gctcatgaaa tcctggatca tagtgtcaca ggggcaagag agtctattgc aggcatgctg 13380
gataccacaa aaggcttgat tcgagccagc atgaggaagg gggggttaac ctctcgagtg 13440
ataaccagat tgtccaatta tgactatgaa caattcagag cagggatggt gctattgaca 13500
ggaagaaaga gaaatgtcct cattgacaaa gagtcatgtt cagtgcagct ggcgagagct 13560
ctaagaagcc atatgtgggc gaggctagct cgaggacggc ctatttacgg ccttgaggtc 13620
cctgatgtac tagaatctat gcgaggccac cttattcggc gtcatgagac atgtgtcatc 13680
tgcgagtgtg gatcagtcaa ctacggatgg ttttttgtcc cctcgggttg ccaactggat 13740
gatattgaca aggaaacatc atccttgaga gtcccatata ttggttctac cactgatgag 13800
agaacagaca tgaagcttgc cttcgtaaga gccccaagtc gatccttgcg atctgctgtt 13860
agaatagcaa cagtgtactc atgggcttac ggtgatgatg atagctcttg gaacgaagcc 13920
tggttgttgg ctaggcaaag ggccaatgtg agcctggagg agctaagggt gatcactccc 13980
atctcaactt cgactaattt agcgcatagg ttgagggatc gtagcactca agtgaaatac 14040
tcaggtacat cccttgtccg agtggcgagg tataccacaa tctccaacga caatctctca 14100
tttgtcatat cagataagaa ggttgatact aactttatat accaacaagg aatgcttcta 14160
gggttgggtg ttttagaaac attgtttcga ctcgagaaag ataccggatc atctaacacg 14220
gtattacatc ttcacgtcga aacagattgt tgcgtgatcc cgatgataga tcatcccagg 14280
atacccagct cccgcaagct agagctgagg gcagagctat gtaccaaccc attgatatat 14340
gataatgcac ctttaattga cagagatgca acaaggctat acacccagag ccataggagg 14400
caccttgtgg aatttgttac atggtccaca ccccaactat atcacatttt agctaagtcc 14460
acagcactat ctatgattga cctggtaaca aaatttgaga aggaccatat gaatgaaatt 14520
tcagctctca taggggatga cgatatcaat agtttcataa ctgagtttct gctcatagag 14580
ccaagattat tcactatcta cttgggccag tgtgcggcca tcaattgggc atttgatgta 14640
cattatcata gaccatcagg gaaatatcag atgggtgagc tgttgtcatc gttcctttct 14700
agaatgagca aaggagtgtt taaggtgctt gtcaatgctc taagccaccc aaagatctac 14760
aagaaattct ggcattgtgg tattatagag cctatccatg gtccttcact tgatgctcaa 14820
aacttgcaca caactgtgtg caacatggtt tacacatgct atatgaccta cctcgacctg 14880
ttgttgaatg aagagttaga agagttcaca tttctcttgt gtgaaagcga cgaggatgta 14940
gtaccggaca gattcgacaa catccaggca aaacacttat gtgttctggc agatttgtac 15000
tgtcaaccag ggacctgccc accaattcga ggtctaagac cggtagagaa atgtgcagtt 15060
ctaaccgacc atatcaaggc agaggctatg ttatctccag caggatcttc gtggaacata 15120
aatccaatta ttgtagacca ttactcatgc tctctgactt atctccggcg aggatcgatc 15180
aaacagataa gattgagagt tgatccagga ttcattttcg acgccctcgc tgaggtaaat 15240

```
gtcagtcagc caaagatcgg cagcaacaac atctcaaata tgagcatcaa ggctttcaga  15300
cccccacacg atgatgttgc aaaattgctc aaagatatca acacaagcaa gcacaatctt  15360
cccatttcag gggcaatct cgccaattat gaaatccatg ctttccgcag aatcgggttg  15420
aactcatctg cttgctacaa agctgttgag atatcaacat taattaggag atgccttgag  15480
ccaggggagg acggcttgtt cttgggtgag ggatcgggtt ctatgttgat cacttataaa  15540
gagatactta aactaaacaa gtgcttctat aatagtgggg tttccgccaa ttctagatct  15600
ggtcaaaggg aattagcacc ctatccctcc gaagttggcc ttgtcgaaca cagaatggga  15660
gtaggtaata ttgtcaaagt gctctttaac gggaggcccg aagtcacgtg ggtaggcagt  15720
gtagattgct tcaatttcat agttagtaat atccctacct ctagtgtggg gtttatccat  15780
tcagatatag agaccttgcc tgacaaagat actatagaga agctagagga attggcagcc  15840
atcttatcga tggctctgct cctgggcaaa ataggatcaa tactggtgat taagcttatg  15900
cctttcagcg gggattttgt tcagggattt ataagttatg tagggtctca ttatagagaa  15960
gtgaaccttg tataccctag atacagcaac ttcatctcta ctgaatctta tttggttatg  16020
acagatctca aggctaaccg gctaatgaat cctgaaaaga ttaagcagca gataattgaa  16080
tcatctgtga ggacttcacc tggacttata ggtcacatcc tatccattaa gcaactaagc  16140
tgcatacaag caattgtggg agacgcagtt agtagaggtg atatcaatcc tactctgaaa  16200
aaacttacac ctatagagca ggtgctgatc aattgcgggt tggcaattaa cggacctaag  16260
ctgtgcaaag aattgatcca ccatgatgtt gcctcagggc aagatggatt gcttaattct  16320
atactcatcc tctacaggga gttggcaaga ttcaaagaca accaaagaag tcaacaaggg  16380
atgttccacg cttaccccgt attggtaagt agcaggcaac gagaacttat atctaggatc  16440
acccgcaaat tctgggggca cattcttctt tactccggga acaaaaagtt gataaataag  16500
tttatccaga atctcaagtc cggctatctg atactagact tacaccagaa tatcttcgtt  16560
aagaatctat ccaagtcaga gaaacagatt attatgacgg ggggtttgaa acgtgagtgg  16620
gtttttaagg taacagtcaa ggagaccaaa gaatggtata agttagtcgg atacagtgcc  16680
ctgattaagg actaattggt tgaactccgg aaccctaatc ctgccctagg tggttaggca  16740
ttatttgcaa tatattaaag aaaactttga aaatacgaag tttctattcc cagctttgtc  16800
tggtggccgg catggtccca gcctcctcgc tggcgccggc tgggcaacat tccgagggga  16860
ccgtcccctc ggtaatggcg aatgggacgc ggccgatccg gctgctaaca aagcccgaaa  16920
ggaagctgag ttggctgctg ccaccgctga gcaataacta gcataacccc ttggggcctc  16980
taaacgggtc ttgaggggtt ttttgctgaa aggaggaact atatccggat gcggccgcgg  17040
gccctatggt acccagcttt tgttcccttt agtgagggtt aattccgagc ttggcgtaat  17100
catggtcata gctgtttcct gtgtgaaatt gttatccgct cacaattcca cacaacatag  17160
gagccggaag cataaagtgt aaagcctggg gtgcctaatg agtgaggtaa ctcacattaa  17220
ttgcgttgcg ctcactgccc gctttccagt cgggaaacct gtcgtgccag ctgcattaat  17280
gaatcggcca acgcgcgggg agaggcggtt tgcgtattgg gcgctcttcc gcttcctcgc  17340
tcactgactc gctgcgctcg gtcgttcggc tgcggcgagc ggtatcagct cactcaaagg  17400
cggtaatacg gttatccaca gaatcagggg ataacgcagg aaagaacatg tgagcaaaag  17460
gccagcaaaa ggccaggaac cgtaaaaagg ccgcgttgct ggcgtttttc cataggctcg  17520
gcccccctga cgagcatcac aaaaatcgac gctcaagtca gaggtggcga aacccgacag  17580
```

```
gactataaag ataccaggcg tttccccctg gaagctccct cgtgcgctct cctgttccga  17640
ccctgccgct taccggatac ctgtccgcct ttctcccttc gggaagcgtg gcgctttctc  17700
aatgctcacg ctgtaggtat ctcagttcgg tgtaggtcgt tcgctccaag ctgggctgtg  17760
tgcacgaacc ccccgttcag cccgaccgct gcgccttatc cggtaactat cgtcttgagt  17820
ccaacccggt aagacacgac ttatcgccac tggcagcagc cactggtaac aggattagca  17880
gagcgaggta tgtaggcggt gctacagagt tcttgaagtg gtggcctaac tacggctaca  17940
ctagaaggac agtatttggt atctgcgctc tgctgaagcc agttaccttc ggaaaaagag  18000
ttggtagctc ttgatccggc aaacaaacca ccgctggtag cggtggtttt tttgtttgca  18060
agcagcagat tacgcgcaga aaaaaaggat ctcaagaaga tcctttgatc ttttctacgg  18120
ggtctgacgc tcagtggaac gaaaactcac gttaagggat tttggtcatg agattatcaa  18180
aaaggatctt cacctagatc cttttaaatt aaaaatgaag ttttaaatca atctaaagta  18240
tatatgagta aacttggtct gacagttacc aatgcttaat cagtgaggca cctatctcag  18300
cgatctgtct atttcgttca tccatagttg cctgactgcc cgtcgtgtag ataactacga  18360
tacgggaggg cttaccatct ggccccagtg ctgcaatgat accgcgagac ccacgctcac  18420
cggctccaga tttatcagca ataaaccagc cagccggaag ggccgagcgc agaagtggtc  18480
ctgcaacttt atccgcctcc atccagtcta ttaattgttg ccgggaagct agagtaagta  18540
gttcgccagt taatagtttg cgcaacgttg ttgccattgc tacaggcatc gtggtgtcac  18600
gctcgtcgtt tggtatggct tcattcagct ccggttccca acgatcaagg cgagttacat  18660
gatcccccat gttgtgaaaa aaagcggtta gctccttcgg tcctccgatc gttgtcagaa  18720
gtaagttggc cgcagtgtta tcactcatgc ttatggcagc actgcataat tctcttactg  18780
tcatgccatc cgtaagatgc ttttctgtga ctggtgagta ctcaaccaag tcattctgag  18840
aatagtgtat gcggcgaccg agttgctctt gcccggcgtc aatacgggat aataccgcgc  18900
cacatagcag aactttaaaa gtgctcatca ttggaaaacg ttcttcgggg cgaaaactct  18960
caaggatctt accgctgttg agatccagtt cgatgtaacc cactcgtgca cccaactgat  19020
cttcagcatc ttttactttc accagcgttt ctgggtgagc aaaaacagga aggcaaaatg  19080
ccgcaaaaaa gggaataagg gcgacacgga aatgttgaat actcatactc ttcctttttc  19140
aatattattg aagcatttat cagggttatt gtctcatgag cggatacata tttgaatgta  19200
tttagaaaaa taaacaaata ggggttccgc gcacatttcc ccgaaaagtg ccacctgaaa  19260
ttgtaaacgt taatattttg ttaaaattcg cgttaaattt ttgttaaatc agctcatttt  19320
ttaaccaata ggccgaaatc ggcaaaatcc cttataaatc aaaagaatag accgagatag  19380
ggttgagtgt tgttccagtt tggaacaaga gtccactatt aaagaacgtg gactccaacg  19440
tcaaagggcg aaaaaccgtc tatcagggcg atggcccact acgtgaacca tcaccctaat  19500
caagtttttt ggggtcgagg tgccgtaaag cactaaatcg gaaccctaaa gggagccccc  19560
gatttagagc ttgacgggga aagccggcga acgtggcgag aaaggaaggg aagaaagcga  19620
aaggagcggg cgctagggcg ctggcaagtg tagcggtcac gctgcgcgta accaccacac  19680
ccgccgcgct taatgcgccg ctacagggcg cgtcccattc gccattcagg ctgcgcaact  19740
gttgggaagg gcgatcggtg cgggcctctt cgctattacg ccagccaccg cggtg       19795
```

<210> SEQ ID NO 3
<211> LENGTH: 72
<212> TYPE: DNA
<213> ORGANISM: Artificial sequence

```
<220> FEATURE:
<223> OTHER INFORMATION: Native nucleotide sequence of signal peptide
      from the capsid of ZIKV (sp)

<400> SEQUENCE: 3

atggagaaga agagacgagg cgcagatact agtgtcggaa ttgttggcct cctgctgacc     60

acagctatgg ca                                                         72


<210> SEQ ID NO 4
<211> LENGTH: 72
<212> TYPE: DNA
<213> ORGANISM: Artificial sequence
<220> FEATURE:
<223> OTHER INFORMATION: Codon-optimized nucleotide sequence of signal
      peptide from the capsid of ZIKV (sp)

<400> SEQUENCE: 4

atggagaaga agcggagagg agcagacaca agcgtgggaa tcgtgggcct gctgctgacc     60

acagcaatgg ca                                                         72


<210> SEQ ID NO 5
<211> LENGTH: 24
<212> TYPE: PRT
<213> ORGANISM: Artificial sequence
<220> FEATURE:
<223> OTHER INFORMATION: Signal peptide from the capsid of ZIKV (sp)

<400> SEQUENCE: 5

Met Glu Lys Lys Arg Arg Gly Ala Asp Thr Ser Val Gly Ile Val Gly
1               5                   10                  15

Leu Leu Leu Thr Thr Ala Met Ala
            20


<210> SEQ ID NO 6
<211> LENGTH: 51
<212> TYPE: DNA
<213> ORGANISM: Artificial sequence
<220> FEATURE:
<223> OTHER INFORMATION: Native nucleotide sequence of signal peptide
      from the membrane protein of ZIKV (sp)

<400> SEQUENCE: 6

caaaaagtca tatacttggt catgatactg ctgattgccc cggcatacag c              51


<210> SEQ ID NO 7
<211> LENGTH: 52
<212> TYPE: DNA
<213> ORGANISM: Artificial sequence
<220> FEATURE:
<223> OTHER INFORMATION: Codon-optimized nucleotide sequence of signal
      peptide from the membrane protein of ZIKV (sp)

<400> SEQUENCE: 7

cagaaagtga tctacctggt catgatcctg ctgatcgctc ctgcctattc ta             52


<210> SEQ ID NO 8
<211> LENGTH: 17
<212> TYPE: PRT
<213> ORGANISM: Artificial sequence
<220> FEATURE:
<223> OTHER INFORMATION: Signal peptide from the membrane protein of
      ZIKV (sp)

<400> SEQUENCE: 8

Gln Lys Val Ile Tyr Leu Val Met Ile Leu Leu Ile Ala Pro Ala Tyr
```

-continued 1 5 10 15

Ser

<210> SEQ ID NO 9
<211> LENGTH: 72
<212> TYPE: DNA
<213> ORGANISM: Artificial sequence
<220> FEATURE:
<223> OTHER INFORMATION: Native nucleotide sequence of signal peptide from the capsid of JEV (JEVsp)

<400> SEQUENCE: 9
atgggcaaac gatcagccgg ctcaatcatg tggctcgcga gcttggcagt tgtcatagct 60
tgtgcaggag cc 72

<210> SEQ ID NO 10
<211> LENGTH: 72
<212> TYPE: DNA
<213> ORGANISM: Artificial sequence
<220> FEATURE:
<223> OTHER INFORMATION: Codon-optimized nucleotide sequence of signal peptide from the capsid of JEV (JEVsp)

<400> SEQUENCE: 10
atgggcaaga ggtccgcagg gagcattatg tggctggcat ctctggcagt cgtcatcgct 60
tgtgcaggag ca 72

<210> SEQ ID NO 11
<211> LENGTH: 24
<212> TYPE: PRT
<213> ORGANISM: Artificial sequence
<220> FEATURE:
<223> OTHER INFORMATION: Signal peptide from the capsid of JEV (JEVsp)

<400> SEQUENCE: 11

Met Gly Lys Arg Ser Ala Gly Ser Ile Met Trp Leu Ala Ser Leu Ala
1 5 10 15

Val Val Ile Ala Cys Ala Gly Ala
20

<210> SEQ ID NO 12
<211> LENGTH: 87
<212> TYPE: DNA
<213> ORGANISM: Artificial sequence
<220> FEATURE:
<223> OTHER INFORMATION: Native nucleotide sequence of signal peptide from the fusion protein of MV (MVsp)

<400> SEQUENCE: 12
atgtccatca tgggtctcaa ggtgaacgtc tctgccatat tcatggcagt actgttaact 60
ctccaaacac ccaccggtca aatccat 87

<210> SEQ ID NO 13
<211> LENGTH: 87
<212> TYPE: DNA
<213> ORGANISM: Artificial sequence
<220> FEATURE:
<223> OTHER INFORMATION: Codon-optimized nucleotide sequence of signal peptide from the fusion protein of MV (MVsp)

<400> SEQUENCE: 13
atgagcatca tgggcctgaa ggtgaacgtg tccgccatct tcatggccgt gctgctgacc 60
ctgcagacac caacaggcca gatccac 87

```
<210> SEQ ID NO 14
<211> LENGTH: 29
<212> TYPE: PRT
<213> ORGANISM: Artificial sequence
<220> FEATURE:
<223> OTHER INFORMATION: Signal peptide from the fusion protein of MV
      (MVsp)

<400> SEQUENCE: 14

Met Ser Ile Met Gly Leu Lys Val Asn Val Ser Ala Ile Phe Met Ala
1               5                   10                  15

Val Leu Leu Thr Leu Gln Thr Pro Thr Gly Gln Ile His
            20                  25


<210> SEQ ID NO 15
<211> LENGTH: 81
<212> TYPE: DNA
<213> ORGANISM: Artificial sequence
<220> FEATURE:
<223> OTHER INFORMATION: Native nucleotide sequence of modified signal
      peptide from the fusion protein of MV (MVsp)

<400> SEQUENCE: 15

atgtccatca tgggtctcaa ggtgaacgtc tctgccatat tcatggcagt actgttaact     60

ctccaaacac ccaccggtca a                                               81


<210> SEQ ID NO 16
<211> LENGTH: 81
<212> TYPE: DNA
<213> ORGANISM: Artificial sequence
<220> FEATURE:
<223> OTHER INFORMATION: Codon-optimized nucleotide sequence of modified
      signal peptide from the fusion protein of MV (MVsp)

<400> SEQUENCE: 16

atgagcatca tgggcctgaa ggtgaacgtg tccgccatct tcatggccgt gctgctgacc     60

ctgcagacac caacaggcca g                                               81


<210> SEQ ID NO 17
<211> LENGTH: 27
<212> TYPE: PRT
<213> ORGANISM: Artificial sequence
<220> FEATURE:
<223> OTHER INFORMATION: Modified signal peptide from the fusion protein
      of MV (MVsp)

<400> SEQUENCE: 17

Met Ser Ile Met Gly Leu Lys Val Asn Val Ser Ala Ile Phe Met Ala
1               5                   10                  15

Val Leu Leu Thr Leu Gln Thr Pro Thr Gly Gln
            20                  25


<210> SEQ ID NO 18
<211> LENGTH: 504
<212> TYPE: DNA
<213> ORGANISM: Artificial sequence
<220> FEATURE:
<223> OTHER INFORMATION: Native nucleotide sequence of precursor of
      membrane (prM) protein of ZIKV

<400> SEQUENCE: 18

gcggaggtca ctagacgtgg gagtgcatac tatatgtact tggacagaaa cgatgctggg     60

gaggccatat cttttccaac cacattgggg atgaataagt gttatataca gatcatggat    120
```

-continued

```
cttggacaca tgtgtgatgc caccatgagc tatgaatgcc ctatgctgga tgagggggtg    180

gaaccagatg acgtcgattg ttggtgcaac acgacgtcaa cttgggttgt gtacggaacc    240

tgccatcaca aaaaaggtga agcacggaga tctagaagag ctgtgacgct cccctcccat    300

tccactagga agctgcaaac gcggtcgcaa acctggttgg aatcaagaga atacacaaag    360

cacttgatta gagtcgaaaa ttggatattc aggaaccctg gcttcgcgtt agcagcagct    420

gccatcgctt ggcttttggg aagctcaacg agccaaaaag tcatatactt ggtcatgata    480

ctgctgattg ccccggcata cagc                                           504
```

<210> SEQ ID NO 19
<211> LENGTH: 505
<212> TYPE: DNA
<213> ORGANISM: Artificial sequence
<220> FEATURE:
<223> OTHER INFORMATION: Codon-optimized nucleotide sequence of precursor of membrane (prM) protein of ZIKV

<400> SEQUENCE: 19

```
gcagaggtga ccaggagagg aagcgcctac tatatgtacc tggacaggaa tgatgccggc     60

gaggccatct ccttcccaac cacactgggc atgaacaagt gctacatcca gatcatggac    120

ctgggccaca tgtgcgatgc caccatgtcc tatgagtgtc caatgctgga cgagggcgtg    180

gagcccgacg atgtggattg ctggtgtaat accacatcta catgggtggt gtacggcacc    240

tgtcaccaca agaagggaga ggcccggcgg agccggcggg ccgtgacact gccttcccac    300

tctaccagga agctgcagac acgcagccag acctggctgg agtccagaga gtataccaag    360

cacctgatca gggtggagaa ctggatcttt cgcaatccag gattcgcact ggcagcagca    420

gcaatcgcat ggctgctggg aagctccacc agccagaaag tgatctacct ggtcatgatc    480

ctgctgatcg ctcctgccta ttcta                                          505
```

<210> SEQ ID NO 20
<211> LENGTH: 168
<212> TYPE: PRT
<213> ORGANISM: Artificial sequence
<220> FEATURE:
<223> OTHER INFORMATION: Precursor of membrane (prM) protein of ZIKV

<400> SEQUENCE: 20

```
Ala Glu Val Thr Arg Arg Gly Ser Ala Tyr Tyr Met Tyr Leu Asp Arg
1               5                   10                  15

Asn Asp Ala Gly Glu Ala Ile Ser Phe Pro Thr Thr Leu Gly Met Asn
            20                  25                  30

Lys Cys Tyr Ile Gln Ile Met Asp Leu Gly His Met Cys Asp Ala Thr
        35                  40                  45

Met Ser Tyr Glu Cys Pro Met Leu Asp Glu Gly Val Glu Pro Asp Asp
    50                  55                  60

Val Asp Cys Trp Cys Asn Thr Thr Ser Thr Trp Val Val Tyr Gly Thr
65                  70                  75                  80

Cys His His Lys Lys Gly Glu Ala Arg Arg Ser Arg Arg Ala Val Thr
                85                  90                  95

Leu Pro Ser His Ser Thr Arg Lys Leu Gln Thr Arg Ser Gln Thr Trp
            100                 105                 110

Leu Glu Ser Arg Glu Tyr Thr Lys His Leu Ile Arg Val Glu Asn Trp
        115                 120                 125

Ile Phe Arg Asn Pro Gly Phe Ala Leu Ala Ala Ala Ala Ile Ala Trp
```

-continued

```
    130                 135                 140

Leu Leu Gly Ser Ser Thr Ser Gln Lys Val Ile Tyr Leu Val Met Ile
145                 150                 155                 160

Leu Leu Ile Ala Pro Ala Tyr Ser
                165
```

<210> SEQ ID NO 21
<211> LENGTH: 1512
<212> TYPE: DNA
<213> ORGANISM: Artificial sequence
<220> FEATURE:
<223> OTHER INFORMATION: Native nucleotide sequence of full-length E protein of ZIKV

<400> SEQUENCE: 21

```
atcaggtgca taggagtcag caatagggac tttgtggaag gtatgtcagg tgggacttgg     60

gttgatgttg tcttggaaca tggaggttgt gtcaccgtaa tggcacagga caaaccgact    120

gtcgacatag agctggttac aacaacagtc agcaacatgg cggaggtaag atcctactgc    180

tatgaggcat caatatcaga catggcttcg gacagccgct gcccaacaca aggtgaagcc    240

taccttgaca agcaatcaga cactcaatat gtctgcaaaa gaacgttagt ggacagaggc    300

tggggaaatg gatgtggact tttggcaaa gggagcctgg tgacatgcgc taagtttgca    360

tgctccaaga aaatgaccgg gaagagcatc cagccagaga atctggagta ccggataatg    420

ctgtcagttc atggctccca gcacagtggg atgatcgtta atgacacagg acatgaaact    480

gatgagaata gagcgaaggt tgagataacg cccaattcac caagagccga agccaccctg    540

gggggtttg gaagcctagg acttgattgt gaaccgagga caggccttga cttttcagat    600

ttgtattact tgactatgaa taacaagcac tggttggttc acaaggagtg gttccacgac    660

attccattac cttggcacgc tggggcagac accggaactc cacactggaa caacaaagaa    720

gcactggtag agttcaagga cgcacatgcc aaaaggcaaa ctgtcgtggt tctagggagt    780

caagaaggag cagttcacac ggcccttgct ggagctctgg aggctgagat ggatggtgca    840

aagggaaggc tgtcctctgg ccacttgaaa tgtcgcctga aaatggataa acttagattg    900

aagggcgtgt catactcctt gtgtaccgca gcgttcacat tcaccaagat cccggctgaa    960

acactgcacg ggacagtcac agtggaggta cagtacgcag ggacagatgg accttgcaag   1020

gttccagctc agatggcggt ggacatgcaa actctgaccc cagttgggag gttgataacc   1080

gctaaccccg taatcactga aagcactgag aactctaaga tgatgctgga acttgatcca   1140

ccatttgggg actcttacat tgtcatagga gtcggggaga agaagatcac ccaccactgg   1200

cacaggagtg gcagcaccat tggaaaagca tttgaagcca ctgtgagagg tgccaagaga   1260

atggcagtct tgggagacac agcctgggac tttggatcag ttggaggcgc tctcaactca   1320

ttgggcaagg gcatccatca aatttttgga gcagctttca aatcattgtt tggaggaatg   1380

tcctggttct cacaaattct cattggaacg ttgctgatgt ggttgggtct gaacacaaag   1440

aatggatcta tttcccttat gtgcttggcc ttagggggag tgttgatctt cttatccaca   1500

gccgtctctg ct                                                       1512
```

<210> SEQ ID NO 22
<211> LENGTH: 1511
<212> TYPE: DNA
<213> ORGANISM: Artificial sequence
<220> FEATURE:
<223> OTHER INFORMATION: Codon-optimized nucleotide sequence of full-length E protein of ZIKV

<400> SEQUENCE: 22

```
tccggtgcat cggcgtgagc aatagagact tcgtggaggg aatgtccgga ggaacctggg     60
tggatgtggt gctggagcac ggcggctgcg tgacagtgat ggcccaggac aagccaaccg    120
tggatatcga gctggtgacc acaaccgtgt ccaacatggc cgaggtgagg tcttactgct    180
atgaggccag catctccgac atggcctctg atagcaggtg tccaacccag ggagaggcat    240
acctggacaa gcagtccgat acacagtacg tgtgcaagcg gaccctggtg gacagaggct    300
ggggcaatgg ctgtggcctg tttggcaagg gctctctggt gacatgcgcc aagttcgcct    360
gtagcaagaa gatgaccggc aagtccatcc agccagagaa cctggagtac cggatcatgc    420
tgtctgtgca cggctcccag cactctggca tgatcgtgaa cgacacaggc cacgagacag    480
atgagaatcg ggccaaggtg gagatcacac ctaactctcc aagagccgag gccaccctgg    540
gaggatttgg ctctctgggc ctggactgcg agcctagaac aggcctggac ttctccgatc    600
tgtactatct gaccatgaac aataagcact ggctggtgca caaggagtgg tttcacgaca    660
tcccactgcc atggcacgca ggagcagata caggaacacc acactggaac aataaggagg    720
ccctggtgga gttcaaggat gcccacgcca agcggcagac agtggtggtg ctgggcagcc    780
aggagggagc agtgcacacc gccctggcag gcgccctgga ggcagagatg gacggagcta    840
agggcagact gtctagcggc cacctgaagt gcaggctgaa gatggataag ctgcgcctga    900
agggcgtgtc ctactctctg tgcacagccg ccttcacctt caccaagatc cctgccgaga    960
cactgcacgg cacagtgacc gtggaggtgc agtatgccgg cacagacgga ccctgtaagg   1020
tgcctgccca gatggccgtg gatatgcaga cactgacacc tgtgggcagg ctgatcaccg   1080
ccaatccagt gatcacagag tctaccgaga acagcaagat gatgctggag ctggacccac   1140
catttggcga tagctatatc gtgatcggcg tgggcgagaa gaagatcaca caccactggc   1200
accgcagcgg ctccacaatc ggcaaggcct ttgaggcaac cgtgcgcgga gcaaagagaa   1260
tggccgtgct gggcgacacc gcatgggatt tcggatctgt gggaggcgcc ctgaacagcc   1320
tgggcaaggg catccaccag atcttcggcg ccgcctttaa gtccctgttc ggcggcatga   1380
gctggttctc acagatcctg atcggcacac tgctgatgtg gctgggcctg aacaccaaga   1440
atggctctat cagcctgatg tgcctggccc tgggaggcgt gctgatcttc ctgtccaccg   1500
ccgtgtctgc c                                                        1511
```

<210> SEQ ID NO 23
<211> LENGTH: 504
<212> TYPE: PRT
<213> ORGANISM: Artificial sequence
<220> FEATURE:
<223> OTHER INFORMATION: Full-length E protein of ZIKV

<400> SEQUENCE: 23

```
Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80
```

-continued

```
Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu Phe Gly Gly Met Ser Trp Phe Ser
    450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
                485                 490                 495
```

Phe Leu Ser Thr Ala Val Ser Ala
500

<210> SEQ ID NO 24
<211> LENGTH: 1368
<212> TYPE: DNA
<213> ORGANISM: Artificial sequence
<220> FEATURE:
<223> OTHER INFORMATION: Native nucleotide sequence of E protein of ZIKV truncated at amino acid position x (Edx)

<400> SEQUENCE: 24
atcaggtgca taggagtcag caatagggac tttgtggaag gtatgtcagg tgggacttgg 60
gttgatgttg tcttggaaca tggaggttgt gtcaccgtaa tggcacagga caaaccgact 120
gtcgacatag agctggttac aacaacagtc agcaacatgg cggaggtaag atcctactgc 180
tatgaggcat caatatcaga catggcttcg gacagccgct gcccaacaca aggtgaagcc 240
taccttgaca agcaatcaga cactcaatat gtctgcaaaa gaacgttagt ggacagaggc 300
tggggaaatg gatgtggact ttttggcaaa gggagcctgg tgacatgcgc taagtttgca 360
tgctccaaga aaatgaccgg gaagagcatc cagccagaga atctggagta ccggataatg 420
ctgtcagttc atggctccca gcacagtggg atgatcgtta atgacacagg acatgaaact 480
gatgagaata gagcgaaggt tgagataacg cccaattcac caagagccga agccaccctg 540
gggggttttg gaagcctagg acttgattgt gaaccgagga caggccttga cttttcagat 600
ttgtattact tgactatgaa taacaagcac tggttggttc acaaggagtg gttccacgac 660
attccattac cttggcacgc tggggcagac accggaactc cacactggaa caacaaagaa 720
gcactggtag agttcaagga cgcacatgcc aaaaggcaaa ctgtcgtggt tctagggagt 780
caagaaggag cagttcacac ggcccttgct ggagctctgg aggctgagat ggatggtgca 840
aagggaaggc tgtcctctgg ccacttgaaa tgtcgcctga aaatggataa acttagattg 900
aagggcgtgt catactcctt gtgtaccgca gcgttcacat tcaccaagat cccggctgaa 960
acactgcacg ggacagtcac agtggaggta cagtacgcag ggacagatgg accttgcaag 1020
gttccagctc agatggcggt ggacatgcaa actctgaccc cagttgggag gttgataacc 1080
gctaaccccg taatcactga aagcactgag aactctaaga tgatgctgga acttgatcca 1140
ccatttgggg actcttacat tgtcatagga gtcggggaga agaagatcac ccaccactgg 1200
cacaggagtg gcagcaccat tggaaaagca tttgaagcca ctgtgagagg tgccaagaga 1260
atggcagtct tgggagacac agcctgggac tttggatcag ttggaggcgc tctcaactca 1320
ttgggcaagg gcatccatca aatttttgga gcagctttca aatcattg 1368

<210> SEQ ID NO 25
<211> LENGTH: 1367
<212> TYPE: DNA
<213> ORGANISM: Artificial sequence
<220> FEATURE:
<223> OTHER INFORMATION: Codon-optimized nucleotide sequence of E protein of ZIKV truncated at amino acid position x (Edx)

<400> SEQUENCE: 25
tccggtgcat cggcgtgagc aatagagact tcgtggaggg aatgtccgga ggaacctggg 60
tggatgtggt gctggagcac ggcggctgcg tgacagtgat ggcccaggac aagccaaccg 120
tggatatcga gctggtgacc acaaccgtgt ccaacatggc cgaggtgagg tcttactgct 180
atgaggccag catctccgac atggcctctg atagcaggtg tccaacccag ggagaggcat 240

```
acctggacaa gcagtccgat acacagtacg tgtgcaagcg gaccctggtg gacagaggct    300

ggggcaatgg ctgtggcctg tttggcaagg gctctctggt gacatgcgcc aagttcgcct    360

gtagcaagaa gatgaccggc aagtccatcc agccagagaa cctggagtac cggatcatgc    420

tgtctgtgca cggctcccag cactctggca tgatcgtgaa cgacacaggc cacgagacag    480

atgagaatcg ggccaaggtg gagatcacac ctaactctcc aagagccgag gccaccctgg    540

gaggatttgg ctctctgggc ctggactgcg agcctagaac aggcctggac ttctccgatc    600

tgtactatct gaccatgaac aataagcact ggctggtgca caaggagtgg tttcacgaca    660

tcccactgcc atggcacgca ggagcagata caggaacacc acactggaac aataaggagg    720

ccctggtgga gttcaaggat gcccacgcca agcggcagac agtggtggtg ctgggcagcc    780

aggagggagc agtgcacacc gccctggcag gcgccctgga ggcagagatg gacggagcta    840

agggcagact gtctagcggc cacctgaagt gcaggctgaa gatggataag ctgcgcctga    900

agggcgtgtc ctactctctg tgcacagccg ccttcacctt caccaagatc cctgccgaga    960

cactgcacgg cacagtgacc gtggaggtgc agtatgccgg cacagacgga ccctgtaagg   1020

tgcctgccca gatggccgtg gatatgcaga cactgacacc tgtgggcagg ctgatcaccg   1080

ccaatccagt gatcacagag tctaccgaga acagcaagat gatgctggag ctggacccac   1140

catttggcga tagctatatc gtgatcggcg tgggcgagaa gaagatcaca caccactggc   1200

accgcagcgg ctccacaatc ggcaaggcct ttgaggcaac cgtgcgcgga gcaaagagaa   1260

tggccgtgct gggcgacacc gcatgggatt tcggatctgt gggaggcgcc ctgaacagcc   1320

tgggcaaggg catccaccag atcttcggcg ccgcctttaa gtccctg                 1367
```

<210> SEQ ID NO 26
<211> LENGTH: 456
<212> TYPE: PRT
<213> ORGANISM: Artificial sequence
<220> FEATURE:
<223> OTHER INFORMATION: E protein of ZIKV truncated at amino acid position x (Edx)

<400> SEQUENCE: 26

```
Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160
```

-continued

```
Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
        435                 440                 445

Phe Gly Ala Ala Phe Lys Ser Leu
    450                 455


<210> SEQ ID NO 27
<211> LENGTH: 1335
<212> TYPE: DNA
<213> ORGANISM: Artificial sequence
<220> FEATURE:
<223> OTHER INFORMATION: Native nucleotide sequence of E protein of ZIKV
      truncated at amino acid position 411 (Ed411)

<400> SEQUENCE: 27

atcaggtgca taggagtcag caatagggac tttgtggaag gtatgtcagg tgggacttgg     60

gttgatgttg tcttggaaca tggaggttgt gtcaccgtaa tggcacagga caaaccgact    120

gtcgacatag agctggttac aacaacagtc agcaacatgg cggaggtaag atcctactgc    180

tatgaggcat caatatcaga catggcttcg gacagccgct gcccaacaca aggtgaagcc    240

taccttgaca agcaatcaga cactcaatat gtctgcaaaa gaacgttagt ggacagaggc    300

tggggaaatg gatgtggact tttggcaaa gggagcctgg tgacatgcgc taagtttgca    360

tgctccaaga aaatgaccgg gaagagcatc cagccagaga atctggagta ccggataatg    420

ctgtcagttc atggctccca gcacagtggg atgatcgtta atgacacagg acatgaaact    480
```

```
gatgagaata gagcgaaggt tgagataacg cccaattcac caagagccga agccaccctg    540
gggggttttg gaagcctagg acttgattgt gaaccgagga caggccttga cttttcagat    600
ttgtattact tgactatgaa taacaagcac tggttggttc acaaggagtg gttccacgac    660
attccattac cttggcacgc tggggcagac accggaactc cacactggaa caacaaagaa    720
gcactggtag agttcaagga cgcacatgcc aaaaggcaaa ctgtcgtggt tctagggagt    780
caagaaggag cagttcacac ggcccttgct ggagctctgg aggctgagat ggatggtgca    840
aagggaaggc tgtcctctgg ccacttgaaa tgtcgcctga aaatggataa acttagattg    900
aagggcgtgt catactcctt gtgtaccgca gcgttcacat tcaccaagat cccggctgaa    960
acactgcacg ggacagtcac agtggaggta cagtacgcag ggacagatgg accttgcaag   1020
gttccagctc agatggcggt ggacatgcaa actctgaccc cagttgggag gttgataacc   1080
gctaaccccg taatcactga aagcactgag aactctaaga tgatgctgga acttgatcca   1140
ccatttgggg actcttacat tgtcatagga gtcggggaga agaagatcac ccaccactgg   1200
cacaggagtg gcagcaccat tggaaaagca tttgaagcca ctgtgagagg tgccaagaga   1260
atggcagtct tgggagacac agcctgggac tttggatcag ttggaggcgc tctcaactca   1320
ttgggcaagg gcatc                                                     1335
```

<210> SEQ ID NO 28
<211> LENGTH: 1334
<212> TYPE: DNA
<213> ORGANISM: Artificial sequence
<220> FEATURE:
<223> OTHER INFORMATION: Codon-optimized nucleotide sequence of E protein of ZIKV truncated at amino acid position 411 (Ed411)

<400> SEQUENCE: 28

```
tccggtgcat cggcgtgagc aatagagact tcgtggaggg aatgtccgga ggaacctggg     60
tggatgtggt gctggagcac ggcggctgcg tgacagtgat ggcccaggac aagccaaccg    120
tggatatcga gctggtgacc acaaccgtgt ccaacatggc cgaggtgagg tcttactgct    180
atgaggccag catctccgac atggcctctg atagcaggtg tccaacccag ggagaggcat    240
acctggacaa gcagtccgat acacagtacg tgtgcaagcg gaccctggtg gacagaggct    300
ggggcaatgg ctgtggcctg tttggcaagg gctctctggt gacatgcgcc aagttcgcct    360
gtagcaagaa gatgaccggc aagtccatcc agccagagaa cctggagtac cggatcatgc    420
tgtctgtgca cggctcccag cactctggca tgatcgtgaa cgacacaggc cacgagacag    480
atgagaatcg ggccaaggtg gagatcacac ctaactctcc aagagccgag gccaccctgg    540
gaggatttgg ctctctgggc ctggactgcg agcctagaac aggcctggac ttctccgatc    600
tgtactatct gaccatgaac aataagcact ggctggtgca caaggagtgg tttcacgaca    660
tcccactgcc atggcacgca ggagcagata caggaacacc acactggaac aataaggagg    720
ccctggtgga gttcaaggat gcccacgcca agcggcagac agtggtggtg ctgggcagcc    780
aggagggagc agtgcacacc gccctggcag gcgccctgga ggcagagatg gacggagcta    840
agggcagact gtctagcggc cacctgaagt gcaggctgaa gatggataag ctgcgcctga    900
agggcgtgtc ctactctctg tgcacagccg ccttcacctt caccaagatc cctgccgaga    960
cactgcacgg cacagtgacc gtggaggtgc agtatgccgg cacagacgga ccctgtaagg   1020
tgcctgccca gatggccgtg gatatgcaga cactgacacc tgtgggcagg ctgatcaccg   1080
ccaatccagt gatcacagag tctaccgaga acagcaagat gatgctggag ctggacccac   1140
```

```
catttggcga tagctatatc gtgatcggcg tgggcgagaa gaagatcaca caccactggc   1200

accgcagcgg ctccacaatc ggcaaggcct ttgaggcaac cgtgcgcgga gcaaagagaa   1260

tggccgtgct gggcgacacc gcatgggatt tcggatctgt gggaggcgcc ctgaacagcc   1320

tgggcaaggg catc                                                     1334


<210> SEQ ID NO 29
<211> LENGTH: 445
<212> TYPE: PRT
<213> ORGANISM: Artificial sequence
<220> FEATURE:
<223> OTHER INFORMATION: E protein of ZIKV truncated at amino acid
      position 411 (Ed411)

<400> SEQUENCE: 29

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320
```

-continued

```
Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
                405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile
        435                 440                 445


<210> SEQ ID NO 30
<211> LENGTH: 1212
<212> TYPE: DNA
<213> ORGANISM: Artificial sequence
<220> FEATURE:
<223> OTHER INFORMATION: Native nucleotide sequence of E protein of ZIKV
      truncated at amino acid position 395 (Ed395)

<400> SEQUENCE: 30

atcaggtgca taggagtcag caatagggac tttgtggaag gtatgtcagg tgggacttgg      60

gttgatgttg tcttggaaca tggaggttgt gtcaccgtaa tggcacagga caaaccgact     120

gtcgacatag agctggttac aacaacagtc agcaacatgg cggaggtaag atcctactgc     180

tatgaggcat caatatcaga catggcttcg gacagccgct gcccaacaca aggtgaagcc     240

taccttgaca agcaatcaga cactcaatat gtctgcaaaa gaacgttagt ggacagaggc     300

tggggaaatg gatgtggact ttttggcaaa gggagcctgg tgacatgcgc taagtttgca     360

tgctccaaga aaatgaccgg gaagagcatc cagccagaga atctggagta ccggataatg     420

ctgtcagttc atggctccca gcacagtggg atgatcgtta atgacacagg acatgaaact     480

gatgagaata gagcgaaggt tgagataacg cccaattcac caagagccga agccaccctg     540

gggggttttg gaagcctagg acttgattgt gaaccgagga caggccttga cttttcagat     600

ttgtattact tgactatgaa taacaagcac tggttggttc acaaggagtg gttccacgac     660

attccattac cttggcacgc tggggcagac accggaactc cacactggaa caacaaagaa     720

gcactggtag agttcaagga cgcacatgcc aaaaggcaaa ctgtcgtggt tctagggagt     780

caagaaggag cagttcacac ggcccttgct ggagctctgg aggctgagat ggatggtgca     840

aagggaaggc tgtcctctgg ccacttgaaa tgtcgcctga aaatggataa acttagattg     900

aagggcgtgt catactcctt gtgtaccgca gcgttcacat tcaccaagat cccggctgaa     960

acactgcacg ggacagtcac agtggaggta cagtacgcag ggacagatgg accttgcaag    1020

gttccagctc agatggcggt ggacatgcaa actctgaccc cagttgggag gttgataacc    1080

gctaaccccg taatcactga aagcactgag aactctaaga tgatgctgga acttgatcca    1140

ccatttgggg actcttacat tgtcatagga gtcggggaga agaagatcac ccaccactgg    1200

cacaggagtg gc                                                        1212
```

```
<210> SEQ ID NO 31
<211> LENGTH: 1211
<212> TYPE: DNA
<213> ORGANISM: Artificial sequence
<220> FEATURE:
<223> OTHER INFORMATION: Codon-optimized nucleotide sequence of E
      protein of ZIKV truncated at amino acid position 395 (Ed395)

<400> SEQUENCE: 31

tccggtgcat cggcgtgagc aatagagact tcgtggaggg aatgtccgga ggaacctggg      60

tggatgtggt gctggagcac ggcggctgcg tgacagtgat ggcccaggac aagccaaccg     120

tggatatcga gctggtgacc acaaccgtgt ccaacatggc cgaggtgagg tcttactgct     180

atgaggccag catctccgac atggcctctg atagcaggtg tccaacccag ggagaggcat     240

acctggacaa gcagtccgat acacagtacg tgtgcaagcg gaccctggtg gacagaggct     300

ggggcaatgg ctgtggcctg tttggcaagg gctctctggt gacatgcgcc aagttcgcct     360

gtagcaagaa gatgaccggc aagtccatcc agccagagaa cctggagtac cggatcatgc     420

tgtctgtgca cggctcccag cactctggca tgatcgtgaa cgacacaggc cacgagacag     480

atgagaatcg ggccaaggtg gagatcacac ctaactctcc aagagccgag gccaccctgg     540

gaggatttgg ctctctgggc ctggactgcg agcctagaac aggcctggac ttctccgatc     600

tgtactatct gaccatgaac aataagcact ggctggtgca caaggagtgg tttcacgaca     660

tcccactgcc atggcacgca ggagcagata caggaacacc acactggaac aataaggagg     720

ccctggtgga gttcaaggat gcccacgcca agcggcagac agtggtggtg ctgggcagcc     780

aggagggagc agtgcacacc gccctggcag gcgccctgga ggcagagatg gacggagcta     840

agggcagact gtctagcggc cacctgaagt gcaggctgaa gatggataag ctgcgcctga     900

agggcgtgtc ctactctctg tgcacagccg ccttcacctt caccaagatc cctgccgaga     960

cactgcacgg cacagtgacc gtggaggtgc agtatgccgg cacagacgga ccctgtaagg    1020

tgcctgccca gatggccgtg gatatgcaga cactgacacc tgtgggcagg ctgatcaccg    1080

ccaatccagt gatcacagag tctaccgaga acagcaagat gatgctggag ctggacccac    1140

catttggcga tagctatatc gtgatcggcg tgggcgagaa gaagatcaca caccactggc    1200

accgcagcgg c                                                         1211


<210> SEQ ID NO 32
<211> LENGTH: 404
<212> TYPE: PRT
<213> ORGANISM: Artificial sequence
<220> FEATURE:
<223> OTHER INFORMATION: E protein of ZIKV truncated at amino acid
      position 395 (Ed395)

<400> SEQUENCE: 32

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
```

```
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300

Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
                325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
        355                 360                 365

Thr Glu Asn Ser Lys Met Met Leu Glu Leu Asp Pro Pro Phe Gly Asp
    370                 375                 380

Ser Tyr Ile Val Ile Gly Val Gly Glu Lys Lys Ile Thr His His Trp
385                 390                 395                 400

His Arg Ser Gly
```

<210> SEQ ID NO 33
<211> LENGTH: 156
<212> TYPE: DNA
<213> ORGANISM: Artificial sequence
<220> FEATURE:
<223> OTHER INFORMATION: Native nucleotide sequence of E stem region of ZIKV

<400> SEQUENCE: 33

```
agcaccattg gaaaagcatt tgaagccact gtgagaggtg ccaagagaat ggcagtcttg     60

ggagacacag cctgggactt tggatcagtt ggaggcgctc tcaactcatt gggcaagggc    120

atccatcaaa tttttggagc agctttcaaa tcattg                              156
```

<210> SEQ ID NO 34
<211> LENGTH: 156
<212> TYPE: DNA
<213> ORGANISM: Artificial sequence
<220> FEATURE:
<223> OTHER INFORMATION: Codon-optimized nucleotide sequence of E stem region of ZIKV

<400> SEQUENCE: 34

```
tccacaatcg gcaaggcctt tgaggcaacc gtgcgcggag caaagagaat ggccgtgctg     60

ggcgacaccg catgggattt cggatctgtg ggaggcgccc tgaacagcct gggcaagggc    120

atccaccaga tcttcggcgc cgcctttaag tccctg                             156
```

<210> SEQ ID NO 35
<211> LENGTH: 52
<212> TYPE: PRT
<213> ORGANISM: Artificial sequence
<220> FEATURE:
<223> OTHER INFORMATION: E stem region of ZIKV

<400> SEQUENCE: 35

```
Ser Thr Ile Gly Lys Ala Phe Glu Ala Thr Val Arg Gly Ala Lys Arg
1               5                   10                  15

Met Ala Val Leu Gly Asp Thr Ala Trp Asp Phe Gly Ser Val Gly Gly
            20                  25                  30

Ala Leu Asn Ser Leu Gly Lys Gly Ile His Gln Ile Phe Gly Ala Ala
        35                  40                  45

Phe Lys Ser Leu
    50
```

<210> SEQ ID NO 36
<211> LENGTH: 24
<212> TYPE: DNA
<213> ORGANISM: Artificial sequence
<220> FEATURE:
<223> OTHER INFORMATION: Native nucleotide sequence of intermediate domain between E stem and E anchor regions of ZIKV

<400> SEQUENCE: 36

```
tttggaggaa tgtcctggtt ctca                                           24
```

<210> SEQ ID NO 37
<211> LENGTH: 34
<212> TYPE: DNA
<213> ORGANISM: Artificial sequence
<220> FEATURE:
<223> OTHER INFORMATION: Codon-optimized nucleotide sequence of intermediate domain between E stem and E anchor regions of ZIKV

<400> SEQUENCE: 37

```
ttcggcggca tgagctggtt ctcacagatc ctga                                34
```

<210> SEQ ID NO 38
<211> LENGTH: 8
<212> TYPE: PRT
<213> ORGANISM: Artificial sequence
<220> FEATURE:
<223> OTHER INFORMATION: Intermediate domain between E stem and E anchor regions of ZIKV

<400> SEQUENCE: 38

```
Phe Gly Gly Met Ser Trp Phe Ser
1               5
```

<210> SEQ ID NO 39
<211> LENGTH: 120
<212> TYPE: DNA
<213> ORGANISM: Artificial sequence
<220> FEATURE:
<223> OTHER INFORMATION: Native nucleotide sequence of E anchor region of ZIKV

<400> SEQUENCE: 39
caaattctca ttggaacgtt gctgatgtgg ttgggtctga acacaaagaa tggatctatt 60
tcccttatgt gcttggcctt agggggagtg ttgatcttct tatccacagc cgtctctgct 120

<210> SEQ ID NO 40
<211> LENGTH: 110
<212> TYPE: DNA
<213> ORGANISM: Artificial sequence
<220> FEATURE:
<223> OTHER INFORMATION: Codon-optimized nucleotide sequence of E anchor region of ZIKV

<400> SEQUENCE: 40
tcggcacact gctgatgtgg ctgggcctga acaccaagaa tggctctatc agcctgatgt 60
gcctggccct gggaggcgtg ctgatcttcc tgtccaccgc cgtgtctgcc 110

<210> SEQ ID NO 41
<211> LENGTH: 40
<212> TYPE: PRT
<213> ORGANISM: Artificial sequence
<220> FEATURE:
<223> OTHER INFORMATION: E anchor region of ZIKV

<400> SEQUENCE: 41

Gln Ile Leu Ile Gly Thr Leu Leu Met Trp Leu Gly Leu Asn Thr Lys
1 5 10 15

Asn Gly Ser Ile Ser Leu Met Cys Leu Ala Leu Gly Gly Val Leu Ile
20 25 30

Phe Leu Ser Thr Ala Val Ser Ala
35 40

<210> SEQ ID NO 42
<211> LENGTH: 192
<212> TYPE: DNA
<213> ORGANISM: Artificial sequence
<220> FEATURE:
<223> OTHER INFORMATION: Native nucleotide sequence of transmembrane (TM) and intracytoplasmic tail of MV F protein

<400> SEQUENCE: 42
atgaaaggtt tatcgagcac tagcatagtc tacatcctga ttgcagtgtg tcttggaggg 60
ttgataggga tccccgcttt aatatgttgc tgcagggggc gttgtaacaa aaagggagaa 120
caagttggta tgtcaagacc aggcctaaag cctgatctta cgggaacatc aaaatcctat 180
gtaaggtcgc tc 192

<210> SEQ ID NO 43
<211> LENGTH: 192
<212> TYPE: DNA
<213> ORGANISM: Artificial sequence
<220> FEATURE:
<223> OTHER INFORMATION: Codon-optimized nucleotide sequence of transmembrane (TM) and intracytoplasmic tail of MV F protein

<400> SEQUENCE: 43
atgaagggcc tgtcctctac ctctatcgtg tacatcctga tcgccgtgtg cctgggaggc 60

```
ctgatcggaa tcccagccct gatctgctgt tgcagaggcc gctgcaacaa gaagggagag    120

caagtgggaa tgtctcggcc aggcctgaag ccagacctga caggcacctc caagtcttat    180

gtgagaagcc tg                                                         192
```

<210> SEQ ID NO 44
<211> LENGTH: 64
<212> TYPE: PRT
<213> ORGANISM: Artificial sequence
<220> FEATURE:
<223> OTHER INFORMATION: Transmembrane (TM) and intracytoplasmic tail of
      MV F protein

<400> SEQUENCE: 44

```
Met Lys Gly Leu Ser Ser Thr Ser Ile Val Tyr Ile Leu Ile Ala Val
1               5                   10                  15

Cys Leu Gly Gly Leu Ile Gly Ile Pro Ala Leu Ile Cys Cys Cys Arg
            20                  25                  30

Gly Arg Cys Asn Lys Lys Gly Glu Gln Val Gly Met Ser Arg Pro Gly
        35                  40                  45

Leu Lys Pro Asp Leu Thr Gly Thr Ser Lys Ser Tyr Val Arg Ser Leu
    50                  55                  60
```

<210> SEQ ID NO 45
<211> LENGTH: 2094
<212> TYPE: DNA
<213> ORGANISM: Artificial sequence
<220> FEATURE:
<223> OTHER INFORMATION: Native nucleotide sequence of Zikasp_ZikaprME protein (A1)

<400> SEQUENCE: 45

```
atggagaaga agagacgagg cgcagatact agtgtcggaa ttgttggcct cctgctgacc     60
acagctatgg cagcggaggt cactagacgt gggagtgcat actatatgta cttggacaga    120
aacgatgctg gggaggccat atcttttcca accacattgg ggatgaataa gtgttatata    180
cagatcatgg atcttggaca catgtgtgat gccaccatga gctatgaatg ccctatgctg    240
gatgaggggg tggaaccaga tgacgtcgat tgttggtgca acacgacgtc aacttgggtt    300
gtgtacggaa cctgccatca caaaaaaggt gaagcacgga gatctagaag agctgtgacg    360
ctcccctccc attccactag gaagctgcaa acgcggtcgc aaacctggtt ggaatcaaga    420
gaatacacaa agcacttgat tagagtcgaa aattggatat tcaggaaccc tggcttcgcg    480
ttagcagcag ctgccatcgc ttggcttttg ggaagctcaa cgagccaaaa agtcatatac    540
ttggtcatga tactgctgat tgccccggca tacagcatca ggtgcatagg agtcagcaat    600
agggactttg tggaaggtat gtcaggtggg acttgggttg atgttgtctt ggaacatgga    660
ggttgtgtca ccgtaatggc acaggacaaa ccgactgtcg acatagagct ggttacaaca    720
acagtcagca acatggcgga ggtaagatcc tactgctatg aggcatcaat atcagacatg    780
gcttcggaca gccgctgccc aacacaaggt gaagcctacc ttgacaagca atcagacact    840
caatatgtct gcaaaagaac gttagtggac agaggctggg gaaatggatg tggacttttt    900
ggcaaaggga gcctggtgac atgcgctaag tttgcatgct ccaagaaaat gaccgggaag    960
agcatccagc cagagaatct ggagtaccgg ataatgctgt cagttcatgg ctcccagcac   1020
agtgggatga tcgttaatga cacaggacat gaaactgatg agaatagagc gaaggttgag   1080
ataacgccca attcaccaag agccgaagcc accctggggg gttttggaag cctaggactt   1140
```

-continued

```
gattgtgaac cgaggacagg ccttgacttt tcagatttgt attacttgac tatgaataac   1200

aagcactggt tggttcacaa ggagtggttc cacgacattc cattaccttg gcacgctggg   1260

gcagacaccg gaactccaca ctggaacaac aaagaagcac tggtagagtt caaggacgca   1320

catgccaaaa ggcaaactgt cgtggttcta gggagtcaag aaggagcagt tcacacggcc   1380

cttgctggag ctctggaggc tgagatggat ggtgcaaagg gaaggctgtc ctctggccac   1440

ttgaaatgtc gcctgaaaat ggataaactt agattgaagg gcgtgtcata ctccttgtgt   1500

accgcagcgt tcacattcac caagatcccg gctgaaacac tgcacgggac agtcacagtg   1560

gaggtacagt acgcagggac agatggacct tgcaaggttc cagctcagat ggcggtggac   1620

atgcaaactc tgaccccagt tgggaggttg ataaccgcta accccgtaat cactgaaagc   1680

actgagaact ctaagatgat gctggaactt gatccaccat ttggggactc ttacattgtc   1740

ataggagtcg gggagaagaa gatcacccac cactggcaca ggagtggcag caccattgga   1800

aaagcatttg aagccactgt gagaggtgcc aagagaatgg cagtcttggg agacacagcc   1860

tgggactttg gatcagttgg aggcgctctc aactcattgg gcaagggcat ccatcaaatt   1920

tttggagcag ctttcaaatc attgtttgga ggaatgtcct ggttctcaca aattctcatt   1980

ggaacgttgc tgatgtggtt gggtctgaac acaaagaatg gatctatttc ccttatgtgc   2040

ttggccttag gggagtgttt gatcttctta tccacagccg tctctgcttg atga         2094
```

```
<210> SEQ ID NO 46
<211> LENGTH: 2094
<212> TYPE: DNA
<213> ORGANISM: Artificial sequence
<220> FEATURE:
<223> OTHER INFORMATION: Codon-optimized nucleotide sequence of
      Zikasp_ZikaprME protein (A1)

<400> SEQUENCE: 46

atggagaaga agcggagagg agcagacaca agcgtgggaa tcgtgggcct gctgctgacc     60

acagcaatgg cagcagaggt gaccaggaga ggaagcgcct actatatgta cctggacagg    120

aatgatgccg gcgaggccat ctccttccca accacactgg gcatgaacaa gtgctacatc    180

cagatcatgg acctgggcca catgtgcgat gccaccatgt cctatgagtg tccaatgctg    240

gacgagggcg tggagcccga cgatgtggat tgctggtgta ataccacatc tacatgggtg    300

gtgtacggca cctgtcacca caagaaggga gaggcccggc ggagccggcg ggccgtgaca    360

ctgccttccc actctaccag gaagctgcag acacgcagcc agacctggct ggagtccaga    420

gagtatacca agcacctgat cagggtggag aactggatct ttcgcaatcc aggattcgca    480

ctggcagcag cagcaatcgc atggctgctg ggaagctcca ccagccagaa agtgatctac    540

ctggtcatga tcctgctgat cgctcctgcc tattctatcc ggtgcatcgg cgtgagcaat    600

agagacttcg tggagggaat gtccggagga acctgggtgg atgtggtgct ggagcacggc    660

ggctgcgtga cagtgatggc ccaggacaag ccaaccgtgg atatcgagct ggtgaccaca    720

accgtgtcca acatggccga ggtgaggtct tactgctatg aggccagcat ctccgacatg    780

gcctctgata gcaggtgtcc aacccaggga gaggcatacc tggacaagca gtccgataca    840

cagtacgtgt gcaagcggac cctggtggac agaggctggg gcaatggctg tggcctgttt    900

ggcaagggct ctctggtgac atgcgccaag ttcgcctgta gcaagaagat gaccggcaag    960

tccatccagc cagagaacct ggagtaccgg atcatgctgt ctgtgcacgg ctcccagcac   1020

tctggcatga tcgtgaacga cacaggccac gagacagatg agaatcgggc caaggtggag   1080
```

```
atcacaccta actctccaag agccgaggcc accctgggag gatttggctc tctgggcctg   1140

gactgcgagc ctagaacagg cctggacttc tccgatctgt actatctgac catgaacaat   1200

aagcactggc tggtgcacaa ggagtggttt cacgacatcc cactgccatg gcacgcagga   1260

gcagatacag gaacaccaca ctggaacaat aaggaggccc tggtggagtt caaggatgcc   1320

cacgccaagc ggcagacagt ggtggtgctg ggcagccagg agggagcagt gcacaccgcc   1380

ctggcaggcg ccctggaggc agagatggac ggagctaagg gcagactgtc tagcggccac   1440

ctgaagtgca ggctgaagat ggataagctg cgcctgaagg gcgtgtccta ctctctgtgc   1500

acagccgcct tcaccttcac caagatccct gccgagacac tgcacggcac agtgaccgtg   1560

gaggtgcagt atgccggcac agacggaccc tgtaaggtgc ctgcccagat ggccgtggat   1620

atgcagacac tgacacctgt gggcaggctg atcaccgcca atccagtgat cacagagtct   1680

accgagaaca gcaagatgat gctggagctg gacccaccat ttggcgatag ctatatcgtg   1740

atcggcgtgg gcgagaagaa gatcacacac cactggcacc gcagcggctc cacaatcggc   1800

aaggcctttg aggcaaccgt gcgcggagca aagagaatgg ccgtgctggg cgacaccgca   1860

tgggatttcg gatctgtggg aggcgccctg aacagcctgg gcaagggcat ccaccagatc   1920

ttcggcgccg cctttaagtc cctgttcggc ggcatgagct ggttctcaca gatcctgatc   1980

ggcacactgc tgatgtggct gggcctgaac accaagaatg gctctatcag cctgatgtgc   2040

ctggccctgg gaggcgtgct gatcttcctg tccaccgccg tgtctgcctg atga         2094
```

<210> SEQ ID NO 47
<211> LENGTH: 696
<212> TYPE: PRT
<213> ORGANISM: Artificial sequence
<220> FEATURE:
<223> OTHER INFORMATION: Zikasp_ZikaprME protein (A1)

<400> SEQUENCE: 47

```
Met Glu Lys Lys Arg Arg Gly Ala Asp Thr Ser Val Gly Ile Val Gly
1               5                   10                  15

Leu Leu Leu Thr Thr Ala Met Ala Ala Glu Val Thr Arg Arg Gly Ser
            20                  25                  30

Ala Tyr Tyr Met Tyr Leu Asp Arg Asn Asp Ala Gly Glu Ala Ile Ser
        35                  40                  45

Phe Pro Thr Thr Leu Gly Met Asn Lys Cys Tyr Ile Gln Ile Met Asp
    50                  55                  60

Leu Gly His Met Cys Asp Ala Thr Met Ser Tyr Glu Cys Pro Met Leu
65                  70                  75                  80

Asp Glu Gly Val Glu Pro Asp Asp Val Asp Cys Trp Cys Asn Thr Thr
                85                  90                  95

Ser Thr Trp Val Val Tyr Gly Thr Cys His His Lys Lys Gly Glu Ala
            100                 105                 110

Arg Arg Ser Arg Arg Ala Val Thr Leu Pro Ser His Ser Thr Arg Lys
        115                 120                 125

Leu Gln Thr Arg Ser Gln Thr Trp Leu Glu Ser Arg Glu Tyr Thr Lys
    130                 135                 140

His Leu Ile Arg Val Glu Asn Trp Ile Phe Arg Asn Pro Gly Phe Ala
145                 150                 155                 160

Leu Ala Ala Ala Ala Ile Ala Trp Leu Leu Gly Ser Ser Thr Ser Gln
                165                 170                 175

Lys Val Ile Tyr Leu Val Met Ile Leu Leu Ile Ala Pro Ala Tyr Ser
            180                 185                 190
```

-continued

```
Ile Arg Cys Ile Gly Val Ser Asn Arg Asp Phe Val Glu Gly Met Ser
        195                 200                 205

Gly Gly Thr Trp Val Asp Val Val Leu Glu His Gly Gly Cys Val Thr
    210                 215                 220

Val Met Ala Gln Asp Lys Pro Thr Val Asp Ile Glu Leu Val Thr Thr
225                 230                 235                 240

Thr Val Ser Asn Met Ala Glu Val Arg Ser Tyr Cys Tyr Glu Ala Ser
                245                 250                 255

Ile Ser Asp Met Ala Ser Asp Ser Arg Cys Pro Thr Gln Gly Glu Ala
            260                 265                 270

Tyr Leu Asp Lys Gln Ser Asp Thr Gln Tyr Val Cys Lys Arg Thr Leu
        275                 280                 285

Val Asp Arg Gly Trp Gly Asn Gly Cys Gly Leu Phe Gly Lys Gly Ser
    290                 295                 300

Leu Val Thr Cys Ala Lys Phe Ala Cys Ser Lys Lys Met Thr Gly Lys
305                 310                 315                 320

Ser Ile Gln Pro Glu Asn Leu Glu Tyr Arg Ile Met Leu Ser Val His
                325                 330                 335

Gly Ser Gln His Ser Gly Met Ile Val Asn Asp Thr Gly His Glu Thr
            340                 345                 350

Asp Glu Asn Arg Ala Lys Val Glu Ile Thr Pro Asn Ser Pro Arg Ala
        355                 360                 365

Glu Ala Thr Leu Gly Gly Phe Gly Ser Leu Gly Leu Asp Cys Glu Pro
    370                 375                 380

Arg Thr Gly Leu Asp Phe Ser Asp Leu Tyr Tyr Leu Thr Met Asn Asn
385                 390                 395                 400

Lys His Trp Leu Val His Lys Glu Trp Phe His Asp Ile Pro Leu Pro
                405                 410                 415

Trp His Ala Gly Ala Asp Thr Gly Thr Pro His Trp Asn Asn Lys Glu
            420                 425                 430

Ala Leu Val Glu Phe Lys Asp Ala His Ala Lys Arg Gln Thr Val Val
        435                 440                 445

Val Leu Gly Ser Gln Glu Gly Ala Val His Thr Ala Leu Ala Gly Ala
    450                 455                 460

Leu Glu Ala Glu Met Asp Gly Ala Lys Gly Arg Leu Ser Ser Gly His
465                 470                 475                 480

Leu Lys Cys Arg Leu Lys Met Asp Lys Leu Arg Leu Lys Gly Val Ser
                485                 490                 495

Tyr Ser Leu Cys Thr Ala Ala Phe Thr Phe Thr Lys Ile Pro Ala Glu
            500                 505                 510

Thr Leu His Gly Thr Val Thr Val Glu Val Gln Tyr Ala Gly Thr Asp
        515                 520                 525

Gly Pro Cys Lys Val Pro Ala Gln Met Ala Val Asp Met Gln Thr Leu
    530                 535                 540

Thr Pro Val Gly Arg Leu Ile Thr Ala Asn Pro Val Ile Thr Glu Ser
545                 550                 555                 560

Thr Glu Asn Ser Lys Met Met Leu Glu Leu Asp Pro Pro Phe Gly Asp
                565                 570                 575

Ser Tyr Ile Val Ile Gly Val Gly Glu Lys Lys Ile Thr His His Trp
            580                 585                 590

His Arg Ser Gly Ser Thr Ile Gly Lys Ala Phe Glu Ala Thr Val Arg
        595                 600                 605
```

```
Gly Ala Lys Arg Met Ala Val Leu Gly Asp Thr Ala Trp Asp Phe Gly
    610                 615                 620

Ser Val Gly Gly Ala Leu Asn Ser Leu Gly Lys Gly Ile His Gln Ile
625                 630                 635                 640

Phe Gly Ala Ala Phe Lys Ser Leu Phe Gly Gly Met Ser Trp Phe Ser
                645                 650                 655

Gln Ile Leu Ile Gly Thr Leu Leu Met Trp Leu Gly Leu Asn Thr Lys
            660                 665                 670

Asn Gly Ser Ile Ser Leu Met Cys Leu Ala Leu Gly Gly Val Leu Ile
        675                 680                 685

Phe Leu Ser Thr Ala Val Ser Ala
    690                 695
```

<210> SEQ ID NO 48
<211> LENGTH: 1950
<212> TYPE: DNA
<213> ORGANISM: Artificial sequence
<220> FEATURE:
<223> OTHER INFORMATION: Native nucleotide sequence of Zikasp_Zika_prME_no_Anchor protein (A2)

<400> SEQUENCE: 48

```
atggagaaga agagacgagg cgcagatact agtgtcggaa ttgttggcct cctgctgacc     60

acagctatgg cagcggaggt cactagacgt gggagtgcat actatatgta cttggacaga    120

aacgatgctg gggaggccat atcttttcca accacattgg ggatgaataa gtgttatata    180

cagatcatgg atcttggaca catgtgtgat gccaccatga gctatgaatg ccctatgctg    240

gatgaggggg tggaaccaga tgacgtcgat tgttggtgca acacgacgtc aacttgggtt    300

gtgtacggaa cctgccatca caaaaaaggt gaagcacgga gatctagaag agctgtgacg    360

ctcccctccc attccactag gaagctgcaa acgcggtcgc aaacctggtt ggaatcaaga    420

gaatacacaa agcacttgat tagagtcgaa aattggatat tcaggaaccc tggcttcgcg    480

ttagcagcag ctgccatcgc ttggcttttg ggaagctcaa cgagccaaaa agtcatatac    540

ttggtcatga tactgctgat tgccccggca tacagcatca ggtgcatagg agtcagcaat    600

agggactttg tggaaggtat gtcaggtggg acttgggttg atgttgtctt ggaacatgga    660

ggttgtgtca ccgtaatggc acaggacaaa ccgactgtcg acatagagct ggttacaaca    720

acagtcagca acatggcgga ggtaagatcc tactgctatg aggcatcaat atcagacatg    780

gcttcggaca gccgctgccc aacacaaggt gaagcctacc ttgacaagca atcagacact    840

caatatgtct gcaaaagaac gttagtggac agaggctggg gaaatggatg tggacttttt    900

ggcaaaggga gcctggtgac atgcgctaag tttgcatgct ccaagaaaat gaccgggaag    960

agcatccagc cagagaatct ggagtaccgg ataatgctgt cagttcatgg ctcccagcac   1020

agtgggatga tcgttaatga cacaggacat gaaactgatg agaatagagc gaaggttgag   1080

ataacgccca attcaccaag agccgaagcc accctggggg gttttggaag cctaggactt   1140

gattgtgaac cgaggacagg ccttgacttt tcagatttgt attacttgac tatgaataac   1200

aagcactggt tggttcacaa ggagtggttc cacgacattc cattaccttg gcacgctggg   1260

gcagacaccg gaactccaca ctggaacaac aaagaagcac tggtagagtt caaggacgca   1320

catgccaaaa ggcaaactgt cgtggttcta gggagtcaag aaggagcagt tcacacggcc   1380

cttgctggag ctctggaggc tgagatggat ggtgcaaagg gaaggctgtc ctctggccac   1440

ttgaaatgtc gcctgaaaat ggataaactt agattgaagg gcgtgtcata ctccttgtgt   1500
```

```
accgcagcgt tcacattcac caagatcccg gctgaaacac tgcacgggac agtcacagtg   1560

gaggtacagt acgcagggac agatggacct tgcaaggttc cagctcagat ggcggtggac   1620

atgcaaactc tgaccccagt tgggaggttg ataaccgcta accccgtaat cactgaaagc   1680

actgagaact ctaagatgat gctggaactt gatccaccat ttggggactc ttacattgtc   1740

ataggagtcg gggagaagaa gatcacccac cactggcaca ggagtggcag caccattgga   1800

aaagcatttg aagccactgt gagaggtgcc aagagaatgg cagtcttggg agacacagcc   1860

tgggactttg gatcagttgg aggcgctctc aactcattgg gcaagggcat ccatcaaatt   1920

tttggagcag ctttcaaatc attgtgatga                                    1950
```

```
<210> SEQ ID NO 49
<211> LENGTH: 1950
<212> TYPE: DNA
<213> ORGANISM: Artificial sequence
<220> FEATURE:
<223> OTHER INFORMATION: Codon-optimized nucleotide sequence of
      Zikasp_Zika_prME_no_Anchor protein (A2)

<400> SEQUENCE: 49

atggagaaga agcggagagg agcagacaca agcgtgggaa tcgtgggcct gctgctgacc     60

acagcaatgg cagcagaggt gaccaggaga ggaagcgcct actatatgta cctggacagg    120

aatgatgccg gcgaggccat ctccttccca accacactgg gcatgaacaa gtgctacatc    180

cagatcatgg acctgggcca catgtgcgat gccaccatgt cctatgagtg tccaatgctg    240

gacgagggcg tggagcccga cgatgtggat tgctggtgta ataccacatc tacatgggtg    300

gtgtacggca cctgtcacca caagaaggga gaggcccggc ggagccggcg ggccgtgaca    360

ctgccttccc actctaccag gaagctgcag acacgcagcc agacctggct ggagtccaga    420

gagtatacca agcacctgat cagggtggag aactggatct ttcgcaatcc aggattcgca    480

ctggcagcag cagcaatcgc atggctgctg ggaagctcca ccagccagaa agtgatctac    540

ctggtcatga tcctgctgat cgctcctgcc tattctatcc ggtgcatcgg cgtgagcaat    600

agagacttcg tggagggaat gtccggagga acctgggtgg atgtggtgct ggagcacggc    660

ggctgcgtga cagtgatggc ccaggacaag ccaaccgtgg atatcgagct ggtgaccaca    720

accgtgtcca acatggccga ggtgaggtct tactgctatg aggccagcat ctccgacatg    780

gcctctgata gcaggtgtcc aacccaggga gaggcatacc tggacaagca gtccgataca    840

cagtacgtgt gcaagcggac cctggtggac agaggctggg gcaatggctg tggcctgttt    900

ggcaagggct ctctggtgac atgcgccaag ttcgcctgta gcaagaagat gaccggcaag    960

tccatccagc cagagaacct ggagtaccgg atcatgctgt ctgtgcacgg ctcccagcac   1020

tctggcatga tcgtgaacga cacaggccac gagacagatg agaatcgggc caaggtggag   1080

atcacaccta actctccaag agccgaggcc accctgggag gatttggctc tctgggcctg   1140

gactgcgagc ctagaacagg cctggacttc tccgatctgt actatctgac catgaacaat   1200

aagcactggc tggtgcacaa ggagtggttt cacgacatcc cactgccatg gcacgcagga   1260

gcagatacag gaacaccaca ctggaacaat aaggaggccc tggtggagtt caaggatgcc   1320

cacgccaagc ggcagacagt ggtggtgctg ggcagccagg agggagcagt gcacaccgcc   1380

ctggcaggcg ccctggaggc agagatggac ggagctaagg gcagactgtc tagcggccac   1440

ctgaagtgca ggctgaagat ggataagctg cgcctgaagg gcgtgtccta ctctctgtgc   1500

acagccgcct tcaccttcac caagatccct gccgagacac tgcacggcac agtgaccgtg   1560
```

```
gaggtgcagt atgccggcac agacggaccc tgtaaggtgc ctgcccagat ggccgtggat   1620

atgcagacac tgacacctgt gggcaggctg atcaccgcca atccagtgat cacagagtct   1680

accgagaaca gcaagatgat gctggagctg gacccaccat ttggcgatag ctatatcgtg   1740

atcggcgtgg gcgagaagaa gatcacacac cactggcacc gcagcggctc cacaatcggc   1800

aaggcctttg aggcaaccgt gcgcggagca aagagaatgg ccgtgctggg cgacaccgca   1860

tgggatttcg gatctgtggg aggcgccctg aacagcctgg gcaagggcat ccaccagatc   1920

ttcggcgccg cctttaagtc cctgtgatga                                    1950


<210> SEQ ID NO 50
<211> LENGTH: 648
<212> TYPE: PRT
<213> ORGANISM: Artificial sequence
<220> FEATURE:
<223> OTHER INFORMATION: Zikasp_Zika_prME_no_Anchor protein (A2)

<400> SEQUENCE: 50

Met Glu Lys Lys Arg Arg Gly Ala Asp Thr Ser Val Gly Ile Val Gly
1               5                   10                  15

Leu Leu Leu Thr Thr Ala Met Ala Ala Glu Val Thr Arg Arg Gly Ser
            20                  25                  30

Ala Tyr Tyr Met Tyr Leu Asp Arg Asn Asp Ala Gly Glu Ala Ile Ser
        35                  40                  45

Phe Pro Thr Thr Leu Gly Met Asn Lys Cys Tyr Ile Gln Ile Met Asp
    50                  55                  60

Leu Gly His Met Cys Asp Ala Thr Met Ser Tyr Glu Cys Pro Met Leu
65                  70                  75                  80

Asp Glu Gly Val Glu Pro Asp Asp Val Asp Cys Trp Cys Asn Thr Thr
                85                  90                  95

Ser Thr Trp Val Val Tyr Gly Thr Cys His His Lys Lys Gly Glu Ala
            100                 105                 110

Arg Arg Ser Arg Arg Ala Val Thr Leu Pro Ser His Ser Thr Arg Lys
        115                 120                 125

Leu Gln Thr Arg Ser Gln Thr Trp Leu Glu Ser Arg Glu Tyr Thr Lys
    130                 135                 140

His Leu Ile Arg Val Glu Asn Trp Ile Phe Arg Asn Pro Gly Phe Ala
145                 150                 155                 160

Leu Ala Ala Ala Ala Ile Ala Trp Leu Leu Gly Ser Ser Thr Ser Gln
                165                 170                 175

Lys Val Ile Tyr Leu Val Met Ile Leu Leu Ile Ala Pro Ala Tyr Ser
            180                 185                 190

Ile Arg Cys Ile Gly Val Ser Asn Arg Asp Phe Val Glu Gly Met Ser
        195                 200                 205

Gly Gly Thr Trp Val Asp Val Val Leu Glu His Gly Gly Cys Val Thr
    210                 215                 220

Val Met Ala Gln Asp Lys Pro Thr Val Asp Ile Glu Leu Val Thr Thr
225                 230                 235                 240

Thr Val Ser Asn Met Ala Glu Val Arg Ser Tyr Cys Tyr Glu Ala Ser
                245                 250                 255

Ile Ser Asp Met Ala Ser Asp Ser Arg Cys Pro Thr Gln Gly Glu Ala
            260                 265                 270

Tyr Leu Asp Lys Gln Ser Asp Thr Gln Tyr Val Cys Lys Arg Thr Leu
        275                 280                 285

Val Asp Arg Gly Trp Gly Asn Gly Cys Gly Leu Phe Gly Lys Gly Ser
```

```
    290                 295                 300

Leu Val Thr Cys Ala Lys Phe Ala Cys Ser Lys Lys Met Thr Gly Lys
305                 310                 315                 320

Ser Ile Gln Pro Glu Asn Leu Glu Tyr Arg Ile Met Leu Ser Val His
                325                 330                 335

Gly Ser Gln His Ser Gly Met Ile Val Asn Asp Thr Gly His Glu Thr
            340                 345                 350

Asp Glu Asn Arg Ala Lys Val Glu Ile Thr Pro Asn Ser Pro Arg Ala
        355                 360                 365

Glu Ala Thr Leu Gly Gly Phe Gly Ser Leu Gly Leu Asp Cys Glu Pro
    370                 375                 380

Arg Thr Gly Leu Asp Phe Ser Asp Leu Tyr Tyr Leu Thr Met Asn Asn
385                 390                 395                 400

Lys His Trp Leu Val His Lys Glu Trp Phe His Asp Ile Pro Leu Pro
                405                 410                 415

Trp His Ala Gly Ala Asp Thr Gly Thr Pro His Trp Asn Asn Lys Glu
            420                 425                 430

Ala Leu Val Glu Phe Lys Asp Ala His Ala Lys Arg Gln Thr Val Val
        435                 440                 445

Val Leu Gly Ser Gln Glu Gly Ala Val His Thr Ala Leu Ala Gly Ala
    450                 455                 460

Leu Glu Ala Glu Met Asp Gly Ala Lys Gly Arg Leu Ser Ser Gly His
465                 470                 475                 480

Leu Lys Cys Arg Leu Lys Met Asp Lys Leu Arg Leu Lys Gly Val Ser
                485                 490                 495

Tyr Ser Leu Cys Thr Ala Ala Phe Thr Phe Thr Lys Ile Pro Ala Glu
            500                 505                 510

Thr Leu His Gly Thr Val Thr Val Glu Val Gln Tyr Ala Gly Thr Asp
        515                 520                 525

Gly Pro Cys Lys Val Pro Ala Gln Met Ala Val Asp Met Gln Thr Leu
    530                 535                 540

Thr Pro Val Gly Arg Leu Ile Thr Ala Asn Pro Val Ile Thr Glu Ser
545                 550                 555                 560

Thr Glu Asn Ser Lys Met Met Leu Glu Leu Asp Pro Pro Phe Gly Asp
                565                 570                 575

Ser Tyr Ile Val Ile Gly Val Gly Glu Lys Lys Ile Thr His His Trp
            580                 585                 590

His Arg Ser Gly Ser Thr Ile Gly Lys Ala Phe Glu Ala Thr Val Arg
        595                 600                 605

Gly Ala Lys Arg Met Ala Val Leu Gly Asp Thr Ala Trp Asp Phe Gly
    610                 615                 620

Ser Val Gly Gly Ala Leu Asn Ser Leu Gly Lys Gly Ile His Gln Ile
625                 630                 635                 640

Phe Gly Ala Ala Phe Lys Ser Leu
                645
```

<210> SEQ ID NO 51
<211> LENGTH: 1914
<212> TYPE: DNA
<213> ORGANISM: Artificial sequence
<220> FEATURE:
<223> OTHER INFORMATION: Native nucleotide sequence of
      Zikasp_Zika_prME411 protein (A3)

<400> SEQUENCE: 51

-continued

```
atggagaaga agagacgagg cgcagatact agtgtcggaa ttgttggcct cctgctgacc     60

acagctatgg cagcggaggt cactagacgt gggagtgcat actatatgta cttggacaga    120

aacgatgctg gggaggccat atcttttcca accacattgg ggatgaataa gtgttatata    180

cagatcatgg atcttggaca catgtgtgat gccaccatga gctatgaatg ccctatgctg    240

gatgaggggg tggaaccaga tgacgtcgat tgttggtgca acacgacgtc aacttgggtt    300

gtgtacggaa cctgccatca caaaaaaggt gaagcacgga gatctagaag agctgtgacg    360

ctcccctccc attccactag gaagctgcaa acgcggtcgc aaacctggtt ggaatcaaga    420

gaatacacaa agcacttgat tagagtcgaa aattggatat tcaggaaccc tggcttcgcg    480

ttagcagcag ctgccatcgc ttggcttttg ggaagctcaa cgagccaaaa agtcatatac    540

ttggtcatga tactgctgat tgccccggca tacagcatca ggtgcatagg agtcagcaat    600

agggactttg tggaaggtat gtcaggtggg acttgggttg atgttgtctt ggaacatgga    660

ggttgtgtca ccgtaatggc acaggacaaa ccgactgtcg acatagagct ggttacaaca    720

acagtcagca acatggcgga ggtaagatcc tactgctatg aggcatcaat atcagacatg    780

gcttcggaca gccgctgccc aacacaaggt gaagcctacc ttgacaagca atcagacact    840

caatatgtct gcaaaagaac gttagtggac agaggctggg gaaatggatg tggacttttt    900

ggcaaaggga gcctggtgac atgcgctaag tttgcatgct ccaagaaaat gaccgggaag    960

agcatccagc cagagaatct ggagtaccgg ataatgctgt cagttcatgg ctcccagcac   1020

agtgggatga tcgttaatga cacaggacat gaaactgatg agaatagagc gaaggttgag   1080

ataacgccca attcaccaag agccgaagcc accctggggg gttttggaag cctaggactt   1140

gattgtgaac cgaggacagg ccttgacttt tcagatttgt attacttgac tatgaataac   1200

aagcactggt tggttcacaa ggagtggttc cacgacattc cattaccttg gcacgctggg   1260

gcagacaccg gaactccaca ctggaacaac aaagaagcac tggtagagtt caaggacgca   1320

catgccaaaa ggcaaactgt cgtggttcta gggagtcaag aaggagcagt tcacacggcc   1380

cttgctggag ctctggaggc tgagatggat ggtgcaaagg gaaggctgtc ctctggccac   1440

ttgaaatgtc gcctgaaaat ggataaactt agattgaagg gcgtgtcata ctccttgtgt   1500

accgcagcgt tcacattcac caagatcccg gctgaaacac tgcacgggac agtcacagtg   1560

gaggtacagt acgcagggac agatggacct tgcaaggttc cagctcagat ggcggtggac   1620

atgcaaactc tgaccccagt tgggaggttg ataaccgcta accccgtaat cactgaaagc   1680

actgagaact ctaagatgat gctggaactt gatccaccat ttggggactc ttacattgtc   1740

ataggagtcg gggagaagaa gatcacccac cactggcaca ggagtggcag caccattgga   1800

aaagcatttg aagccactgt gagaggtgcc aagagaatgg cagtcttggg agacacagcc   1860

tgggactttg gatcagttgg aggcgctctc aactcattgg gcaagggcat ctga         1914
```

<210> SEQ ID NO 52
<211> LENGTH: 1914
<212> TYPE: DNA
<213> ORGANISM: Artificial sequence
<220> FEATURE:
<223> OTHER INFORMATION: Codon-optimized nucleotide sequence of Zikasp_Zika_prME411 protein (A3)

<400> SEQUENCE: 52

```
atggagaaga agcggagagg agcagacaca agcgtgggaa tcgtgggcct gctgctgacc     60

acagcaatgg cagcagaggt gaccaggaga ggaagcgcct actatatgta cctggacagg    120
```

-continued

```
aatgatgccg gcgaggccat ctccttccca accacactgg gcatgaacaa gtgctacatc    180
cagatcatgg acctgggcca catgtgcgat gccaccatgt cctatgagtg tccaatgctg    240
gacgagggcg tggagcccga cgatgtggat tgctggtgta ataccacatc tacatgggtg    300
gtgtacggca cctgtcacca caagaaggga gaggcccggc ggagccggcg ggccgtgaca    360
ctgccttccc actctaccag gaagctgcag acacgcagcc agacctggct ggagtccaga    420
gagtatacca agcacctgat cagggtggag aactggatct ttcgcaatcc aggattcgca    480
ctggcagcag cagcaatcgc atggctgctg ggaagctcca ccagccagaa agtgatctac    540
ctggtcatga tcctgctgat cgctcctgcc tattctatcc ggtgcatcgg cgtgagcaat    600
agagacttcg tggagggaat gtccggagga acctgggtgg atgtggtgct ggagcacggc    660
ggctgcgtga cagtgatggc ccaggacaag ccaaccgtgg atatcgagct ggtgaccaca    720
accgtgtcca acatggccga ggtgaggtct tactgctatg aggccagcat ctccgacatg    780
gcctctgata gcaggtgtcc aacccaggga gaggcatacc tggacaagca gtccgataca    840
cagtacgtgt gcaagcggac cctggtggac agaggctggg gcaatggctg tggcctgttt    900
ggcaagggct ctctggtgac atgcgccaag ttcgcctgta gcaagaagat gaccggcaag    960
tccatccagc cagagaacct ggagtaccgg atcatgctgt ctgtgcacgg ctcccagcac   1020
tctggcatga tcgtgaacga cacaggccac gagacagatg agaatcgggc caaggtggag   1080
atcacaccta actctccaag agccgaggcc accctgggag gatttggctc tctgggcctg   1140
gactgcgagc ctagaacagg cctggacttc tccgatctgt actatctgac catgaacaat   1200
aagcactggc tggtgcacaa ggagtggttt cacgacatcc cactgccatg gcacgcagga   1260
gcagatacag gaacaccaca ctggaacaat aaggaggccc tggtggagtt caaggatgcc   1320
cacgccaagc ggcagacagt ggtggtgctg ggcagccagg agggagcagt gcacaccgcc   1380
ctggcaggcg ccctggaggc agagatggac ggagctaagg gcagactgtc tagcggccac   1440
ctgaagtgca ggctgaagat ggataagctg cgcctgaagg gcgtgtccta ctctctgtgc   1500
acagccgcct tcaccttcac caagatccct gccgagacac tgcacggcac agtgaccgtg   1560
gaggtgcagt atgccggcac agacggaccc tgtaaggtgc ctgcccagat ggccgtggat   1620
atgcagacac tgacacctgt gggcaggctg atcaccgcca atccagtgat cacagagtct   1680
accgagaaca gcaagatgat gctggagctg gacccaccat ttggcgatag ctatatcgtg   1740
atcggcgtgg gcgagaagaa gatcacacac cactggcacc gcagcggctc cacaatcggc   1800
aaggcctttg aggcaaccgt gcgcggagca aagagaatgg ccgtgctggg cgacaccgca   1860
tgggatttcg gatctgtggg aggcgccctg aacagcctgg gcaagggcat ctga         1914
```

<210> SEQ ID NO 53
<211> LENGTH: 637
<212> TYPE: PRT
<213> ORGANISM: Artificial sequence
<220> FEATURE:
<223> OTHER INFORMATION: Zikasp_Zika_prME411 protein (A3)

<400> SEQUENCE: 53

```
Met Glu Lys Lys Arg Arg Gly Ala Asp Thr Ser Val Gly Ile Val Gly
1               5                   10                  15

Leu Leu Leu Thr Thr Ala Met Ala Ala Glu Val Thr Arg Arg Gly Ser
            20                  25                  30

Ala Tyr Tyr Met Tyr Leu Asp Arg Asn Asp Ala Gly Glu Ala Ile Ser
        35                  40                  45
```

-continued

```
Phe Pro Thr Thr Leu Gly Met Asn Lys Cys Tyr Ile Gln Ile Met Asp
    50                  55                  60

Leu Gly His Met Cys Asp Ala Thr Met Ser Tyr Glu Cys Pro Met Leu
65                  70                  75                  80

Asp Glu Gly Val Glu Pro Asp Asp Val Asp Cys Trp Cys Asn Thr Thr
                85                  90                  95

Ser Thr Trp Val Val Tyr Gly Thr Cys His His Lys Lys Gly Glu Ala
            100                 105                 110

Arg Arg Ser Arg Arg Ala Val Thr Leu Pro Ser His Ser Thr Arg Lys
        115                 120                 125

Leu Gln Thr Arg Ser Gln Thr Trp Leu Glu Ser Arg Glu Tyr Thr Lys
    130                 135                 140

His Leu Ile Arg Val Glu Asn Trp Ile Phe Arg Asn Pro Gly Phe Ala
145                 150                 155                 160

Leu Ala Ala Ala Ala Ile Ala Trp Leu Leu Gly Ser Ser Thr Ser Gln
                165                 170                 175

Lys Val Ile Tyr Leu Val Met Ile Leu Leu Ile Ala Pro Ala Tyr Ser
            180                 185                 190

Ile Arg Cys Ile Gly Val Ser Asn Arg Asp Phe Val Glu Gly Met Ser
        195                 200                 205

Gly Gly Thr Trp Val Asp Val Val Leu Glu His Gly Gly Cys Val Thr
    210                 215                 220

Val Met Ala Gln Asp Lys Pro Thr Val Asp Ile Glu Leu Val Thr Thr
225                 230                 235                 240

Thr Val Ser Asn Met Ala Glu Val Arg Ser Tyr Cys Tyr Glu Ala Ser
                245                 250                 255

Ile Ser Asp Met Ala Ser Asp Ser Arg Cys Pro Thr Gln Gly Glu Ala
            260                 265                 270

Tyr Leu Asp Lys Gln Ser Asp Thr Gln Tyr Val Cys Lys Arg Thr Leu
        275                 280                 285

Val Asp Arg Gly Trp Gly Asn Gly Cys Gly Leu Phe Gly Lys Gly Ser
    290                 295                 300

Leu Val Thr Cys Ala Lys Phe Ala Cys Ser Lys Lys Met Thr Gly Lys
305                 310                 315                 320

Ser Ile Gln Pro Glu Asn Leu Glu Tyr Arg Ile Met Leu Ser Val His
                325                 330                 335

Gly Ser Gln His Ser Gly Met Ile Val Asn Asp Thr Gly His Glu Thr
            340                 345                 350

Asp Glu Asn Arg Ala Lys Val Glu Ile Thr Pro Asn Ser Pro Arg Ala
        355                 360                 365

Glu Ala Thr Leu Gly Gly Phe Gly Ser Leu Gly Leu Asp Cys Glu Pro
    370                 375                 380

Arg Thr Gly Leu Asp Phe Ser Asp Leu Tyr Tyr Leu Thr Met Asn Asn
385                 390                 395                 400

Lys His Trp Leu Val His Lys Glu Trp Phe His Asp Ile Pro Leu Pro
                405                 410                 415

Trp His Ala Gly Ala Asp Thr Gly Thr Pro His Trp Asn Asn Lys Glu
            420                 425                 430

Ala Leu Val Glu Phe Lys Asp Ala His Ala Lys Arg Gln Thr Val Val
        435                 440                 445

Val Leu Gly Ser Gln Glu Gly Ala Val His Thr Ala Leu Ala Gly Ala
    450                 455                 460

Leu Glu Ala Glu Met Asp Gly Ala Lys Gly Arg Leu Ser Ser Gly His
```

-continued

```
465                 470                 475                 480

Leu Lys Cys Arg Leu Lys Met Asp Lys Leu Arg Leu Lys Gly Val Ser
                485                 490                 495

Tyr Ser Leu Cys Thr Ala Ala Phe Thr Phe Thr Lys Ile Pro Ala Glu
            500                 505                 510

Thr Leu His Gly Thr Val Thr Val Glu Val Gln Tyr Ala Gly Thr Asp
        515                 520                 525

Gly Pro Cys Lys Val Pro Ala Gln Met Ala Val Asp Met Gln Thr Leu
    530                 535                 540

Thr Pro Val Gly Arg Leu Ile Thr Ala Asn Pro Val Ile Thr Glu Ser
545                 550                 555                 560

Thr Glu Asn Ser Lys Met Met Leu Glu Leu Asp Pro Pro Phe Gly Asp
                565                 570                 575

Ser Tyr Ile Val Ile Gly Val Gly Glu Lys Lys Ile Thr His His Trp
            580                 585                 590

His Arg Ser Gly Ser Thr Ile Gly Lys Ala Phe Glu Ala Thr Val Arg
        595                 600                 605

Gly Ala Lys Arg Met Ala Val Leu Gly Asp Thr Ala Trp Asp Phe Gly
    610                 615                 620

Ser Val Gly Gly Ala Leu Asn Ser Leu Gly Lys Gly Ile
625                 630                 635


<210> SEQ ID NO 54
<211> LENGTH: 1794
<212> TYPE: DNA
<213> ORGANISM: Artificial sequence
<220> FEATURE:
<223> OTHER INFORMATION: Native nucleotide sequence of
      Zikasp_Zika_prME395 protein (A4)

<400> SEQUENCE: 54

atggagaaga agagacgagg cgcagatact agtgtcggaa ttgttggcct cctgctgacc      60

acagctatgg cagcggaggt cactagacgt gggagtgcat actatatgta cttggacaga     120

aacgatgctg gggaggccat atcttttcca accacattgg ggatgaataa gtgttatata     180

cagatcatgg atcttggaca catgtgtgat gccaccatga gctatgaatg ccctatgctg     240

gatgaggggg tggaaccaga tgacgtcgat tgttggtgca acacgacgtc aacttgggtt     300

gtgtacggaa cctgccatca caaaaaaggt gaagcacgga gatctagaag agctgtgacg     360

ctcccctccc attccactag gaagctgcaa acgcggtcgc aaacctggtt ggaatcaaga     420

gaatacacaa agcacttgat tagagtcgaa aattggatat tcaggaaccc tggcttcgcg     480

ttagcagcag ctgccatcgc ttggcttttg ggaagctcaa cgagccaaaa agtcatatac     540

ttggtcatga tactgctgat tgccccggca tacagcatca ggtgcatagg agtcagcaat     600

agggactttg tggaaggtat gtcaggtggg acttgggttg atgttgtctt ggaacatgga     660

ggttgtgtca ccgtaatggc acaggacaaa ccgactgtcg acatagagct ggttacaaca     720

acagtcagca acatggcgga ggtaagatcc tactgctatg aggcatcaat atcagacatg     780

gcttcggaca gccgctgccc aacacaaggt gaagcctacc ttgacaagca atcagacact     840

caatatgtct gcaaaagaac gttagtggac agaggctggg gaaatggatg tggacttttt     900

ggcaaaggga gcctggtgac atgcgctaag tttgcatgct ccaagaaaat gaccgggaag     960

agcatccagc cagagaatct ggagtaccgg ataatgctgt cagttcatgg ctcccagcac    1020

agtgggatga tcgttaatga cacaggacat gaaactgatg agaatagagc gaaggttgag    1080
```

```
ataacgccca attcaccaag agccgaagcc accctggggg gttttggaag cctaggactt   1140

gattgtgaac cgaggacagg ccttgacttt tcagatttgt attacttgac tatgaataac   1200

aagcactggt tggttcacaa ggagtggttc cacgacattc cattaccttg gcacgctggg   1260

gcagacaccg gaactccaca ctggaacaac aaagaagcac tggtagagtt caaggacgca   1320

catgccaaaa ggcaaactgt cgtggttcta gggagtcaag aaggagcagt tcacacggcc   1380

cttgctggag ctctggaggc tgagatggat ggtgcaaagg gaaggctgtc ctctggccac   1440

ttgaaatgtc gcctgaaaat ggataaactt agattgaagg gcgtgtcata ctccttgtgt   1500

accgcagcgt tcacattcac caagatcccg gctgaaacac tgcacgggac agtcacagtg   1560

gaggtacagt acgcagggac agatggacct tgcaaggttc cagctcagat ggcggtggac   1620

atgcaaactc tgaccccagt tgggaggttg ataaccgcta accccgtaat cactgaaagc   1680

actgagaact ctaagatgat gctggaactt gatccaccat ttggggactc ttacattgtc   1740

ataggagtcg gggagaagaa gatcacccac cactggcaca ggagtggctg atga         1794
```

<210> SEQ ID NO 55
<211> LENGTH: 1794
<212> TYPE: DNA
<213> ORGANISM: Artificial sequence
<220> FEATURE:
<223> OTHER INFORMATION: Codon-optimized nucleotide sequence of Zikasp_Zika_prME395 protein (A4)

<400> SEQUENCE: 55

```
atggagaaga agcggagagg agcagacaca agcgtgggaa tcgtgggcct gctgctgacc     60

acagcaatgg cagcagaggt gaccaggaga ggaagcgcct actatatgta cctggacagg    120

aatgatgccg gcgaggccat ctccttccca accacactgg gcatgaacaa gtgctacatc    180

cagatcatgg acctgggcca catgtgcgat gccaccatgt cctatgagtg tccaatgctg    240

gacgagggcg tggagcccga cgatgtggat tgctggtgta ataccacatc tacatgggtg    300

gtgtacggca cctgtcacca caagaaggga gaggcccggc ggagccggcg ggccgtgaca    360

ctgccttccc actctaccag gaagctgcag acacgcagcc agacctggct ggagtccaga    420

gagtatacca agcacctgat cagggtggag aactggatct ttcgcaatcc aggattcgca    480

ctggcagcag cagcaatcgc atggctgctg ggaagctcca ccagccagaa agtgatctac    540

ctggtcatga tcctgctgat cgctcctgcc tattctatcc ggtgcatcgg cgtgagcaat    600

agagacttcg tggagggaat gtccggagga acctgggtgg atgtggtgct ggagcacggc    660

ggctgcgtga cagtgatggc ccaggacaag ccaaccgtgg atatcgagct ggtgaccaca    720

accgtgtcca acatggccga ggtgaggtct tactgctatg aggccagcat ctccgacatg    780

gcctctgata gcaggtgtcc aacccaggga gaggcatacc tggacaagca gtccgataca    840

cagtacgtgt gcaagcggac cctggtggac agaggctggg gcaatggctg tggcctgttt    900

ggcaagggct ctctggtgac atgcgccaag ttcgcctgta gcaagaagat gaccggcaag    960

tccatccagc cagagaacct ggagtaccgg atcatgctgt ctgtgcacgg ctcccagcac   1020

tctggcatga tcgtgaacga cacaggccac gagacagatg agaatcgggc caaggtggag   1080

atcacaccta actctccaag agccgaggcc accctgggag gatttggctc tctgggcctg   1140

gactgcgagc ctagaacagg cctggacttc tccgatctgt actatctgac catgaacaat   1200

aagcactggc tggtgcacaa ggagtggttt cacgacatcc cactgccatg gcacgcagga   1260

gcagatacag gaacaccaca ctggaacaat aaggaggccc tggtggagtt caaggatgcc   1320
```

```
cacgccaagc ggcagacagt ggtggtgctg ggcagccagg agggagcagt gcacaccgcc   1380

ctggcaggcg ccctggaggc agagatggac ggagctaagg gcagactgtc tagcggccac   1440

ctgaagtgca ggctgaagat ggataagctg cgcctgaagg gcgtgtccta ctctctgtgc   1500

acagccgcct tcaccttcac caagatccct gccgagacac tgcacggcac agtgaccgtg   1560

gaggtgcagt atgccggcac agacggaccc tgtaaggtgc ctgcccagat ggccgtggat   1620

atgcagacac tgacacctgt gggcaggctg atcaccgcca atccagtgat cacagagtct   1680

accgagaaca gcaagatgat gctggagctg gacccaccat ttggcgatag ctatatcgtg   1740

atcggcgtgg gcgagaagaa gatcacacac cactggcacc gcagcggctg atga         1794


<210> SEQ ID NO 56
<211> LENGTH: 596
<212> TYPE: PRT
<213> ORGANISM: Artificial sequence
<220> FEATURE:
<223> OTHER INFORMATION: Zikasp_Zika_prME395 protein (A4)

<400> SEQUENCE: 56

Met Glu Lys Lys Arg Arg Gly Ala Asp Thr Ser Val Gly Ile Val Gly
1               5                   10                  15

Leu Leu Leu Thr Thr Ala Met Ala Ala Glu Val Thr Arg Arg Gly Ser
            20                  25                  30

Ala Tyr Tyr Met Tyr Leu Asp Arg Asn Asp Ala Gly Glu Ala Ile Ser
        35                  40                  45

Phe Pro Thr Thr Leu Gly Met Asn Lys Cys Tyr Ile Gln Ile Met Asp
    50                  55                  60

Leu Gly His Met Cys Asp Ala Thr Met Ser Tyr Glu Cys Pro Met Leu
65                  70                  75                  80

Asp Glu Gly Val Glu Pro Asp Asp Val Asp Cys Trp Cys Asn Thr Thr
                85                  90                  95

Ser Thr Trp Val Val Tyr Gly Thr Cys His His Lys Lys Gly Glu Ala
            100                 105                 110

Arg Arg Ser Arg Arg Ala Val Thr Leu Pro Ser His Ser Thr Arg Lys
        115                 120                 125

Leu Gln Thr Arg Ser Gln Thr Trp Leu Glu Ser Arg Glu Tyr Thr Lys
    130                 135                 140

His Leu Ile Arg Val Glu Asn Trp Ile Phe Arg Asn Pro Gly Phe Ala
145                 150                 155                 160

Leu Ala Ala Ala Ala Ile Ala Trp Leu Leu Gly Ser Ser Thr Ser Gln
                165                 170                 175

Lys Val Ile Tyr Leu Val Met Ile Leu Leu Ile Ala Pro Ala Tyr Ser
            180                 185                 190

Ile Arg Cys Ile Gly Val Ser Asn Arg Asp Phe Val Glu Gly Met Ser
        195                 200                 205

Gly Gly Thr Trp Val Asp Val Val Leu Glu His Gly Gly Cys Val Thr
    210                 215                 220

Val Met Ala Gln Asp Lys Pro Thr Val Asp Ile Glu Leu Val Thr Thr
225                 230                 235                 240

Thr Val Ser Asn Met Ala Glu Val Arg Ser Tyr Cys Tyr Glu Ala Ser
                245                 250                 255

Ile Ser Asp Met Ala Ser Asp Ser Arg Cys Pro Thr Gln Gly Glu Ala
            260                 265                 270

Tyr Leu Asp Lys Gln Ser Asp Thr Gln Tyr Val Cys Lys Arg Thr Leu
        275                 280                 285
```

```
Val Asp Arg Gly Trp Gly Asn Gly Cys Gly Leu Phe Gly Lys Gly Ser
    290                 295                 300

Leu Val Thr Cys Ala Lys Phe Ala Cys Ser Lys Lys Met Thr Gly Lys
305                 310                 315                 320

Ser Ile Gln Pro Glu Asn Leu Glu Tyr Arg Ile Met Leu Ser Val His
                325                 330                 335

Gly Ser Gln His Ser Gly Met Ile Val Asn Asp Thr Gly His Glu Thr
            340                 345                 350

Asp Glu Asn Arg Ala Lys Val Glu Ile Thr Pro Asn Ser Pro Arg Ala
        355                 360                 365

Glu Ala Thr Leu Gly Gly Phe Gly Ser Leu Gly Leu Asp Cys Glu Pro
    370                 375                 380

Arg Thr Gly Leu Asp Phe Ser Asp Leu Tyr Tyr Leu Thr Met Asn Asn
385                 390                 395                 400

Lys His Trp Leu Val His Lys Glu Trp Phe His Asp Ile Pro Leu Pro
                405                 410                 415

Trp His Ala Gly Ala Asp Thr Gly Thr Pro His Trp Asn Asn Lys Glu
            420                 425                 430

Ala Leu Val Glu Phe Lys Asp Ala His Ala Lys Arg Gln Thr Val Val
        435                 440                 445

Val Leu Gly Ser Gln Glu Gly Ala Val His Thr Ala Leu Ala Gly Ala
    450                 455                 460

Leu Glu Ala Glu Met Asp Gly Ala Lys Gly Arg Leu Ser Ser Gly His
465                 470                 475                 480

Leu Lys Cys Arg Leu Lys Met Asp Lys Leu Arg Leu Lys Gly Val Ser
                485                 490                 495

Tyr Ser Leu Cys Thr Ala Ala Phe Thr Phe Thr Lys Ile Pro Ala Glu
            500                 505                 510

Thr Leu His Gly Thr Val Thr Val Glu Val Gln Tyr Ala Gly Thr Asp
        515                 520                 525

Gly Pro Cys Lys Val Pro Ala Gln Met Ala Val Asp Met Gln Thr Leu
    530                 535                 540

Thr Pro Val Gly Arg Leu Ile Thr Ala Asn Pro Val Ile Thr Glu Ser
545                 550                 555                 560

Thr Glu Asn Ser Lys Met Met Leu Glu Leu Asp Pro Pro Phe Gly Asp
                565                 570                 575

Ser Tyr Ile Val Ile Gly Val Gly Glu Lys Lys Ile Thr His His Trp
            580                 585                 590

His Arg Ser Gly
        595
```

<210> SEQ ID NO 57
<211> LENGTH: 1590
<212> TYPE: DNA
<213> ORGANISM: Artificial sequence
<220> FEATURE:
<223> OTHER INFORMATION: Native nucleotide sequence of Zikasp_ZikaE
protein (A5)

<400> SEQUENCE: 57

```
atggagaaga agagacgagg cgcagatact agtgtcggaa ttgttggcct cctgctgacc     60

acagctatgg caatcaggtg cataggagtc agcaataggg actttgtgga aggtatgtca    120

ggtgggactt gggttgatgt tgtcttggaa catggaggtt gtgtcaccgt aatggcacag    180

gacaaaccga ctgtcgacat agagctggtt acaacaacag tcagcaacat ggcggaggta    240
```

```
agatcctact gctatgaggc atcaatatca gacatggctt cggacagccg ctgcccaaca    300
caaggtgaag cctaccttga caagcaatca gacactcaat atgtctgcaa aagaacgtta    360
gtggacagag gctggggaaa tggatgtgga ctttttggca aagggagcct ggtgacatgc    420
gctaagtttg catgctccaa gaaaatgacc gggaagagca tccagccaga gaatctggag    480
taccggataa tgctgtcagt tcatggctcc cagcacagtg ggatgatcgt taatgacaca    540
ggacatgaaa ctgatgagaa tagagcgaag gttgagataa cgcccaattc accaagagcc    600
gaagccaccc tgggggtttt tggaagccta ggacttgatt gtgaaccgag gacaggcctt    660
gacttttcag atttgtatta cttgactatg aataacaagc actggttggt tcacaaggag    720
tggttccacg acattccatt accttggcac gctggggcag acaccggaac tccacactgg    780
aacaacaaag aagcactggt agagttcaag gacgcacatg ccaaaaggca aactgtcgtg    840
gttctaggga gtcaagaagg agcagttcac acggcccttg ctggagctct ggaggctgag    900
atggatggtg caaagggaag gctgtcctct ggccacttga aatgtcgcct gaaaatggat    960
aaacttagat tgaagggcgt gtcatactcc ttgtgtaccg cagcgttcac attcaccaag   1020
atcccggctg aaacactgca cgggacagtc acagtggagg tacagtacgc agggacagat   1080
ggaccttgca aggttccagc tcagatggcg gtggacatgc aaactctgac cccagttggg   1140
aggttgataa ccgctaaccc cgtaatcact gaaagcactg agaactctaa gatgatgctg   1200
gaacttgatc caccatttgg ggactcttac attgtcatag gagtcgggga gaagaagatc   1260
acccaccact ggcacaggag tggcagcacc attggaaaag catttgaagc cactgtgaga   1320
ggtgccaaga gaatggcagt cttgggagac acagcctggg actttggatc agttggaggc   1380
gctctcaact cattgggcaa gggcatccat caaatttttg gagcagcttt caaatcattg   1440
tttggaggaa tgtcctggtt ctcacaaatt ctcattggaa cgttgctgat gtggttgggt   1500
ctgaacacaa agaatggatc tatttccctt atgtgcttgg ccttaggggg agtgttgatc   1560
ttcttatcca cagccgtctc tgcttgatga                                    1590
```

<210> SEQ ID NO 58
<211> LENGTH: 1590
<212> TYPE: DNA
<213> ORGANISM: Artificial sequence
<220> FEATURE:
<223> OTHER INFORMATION: Codon-optimized nucleotide sequence of
Zikasp_ZikaE protein (A5)

<400> SEQUENCE: 58

```
atggagaaga agcggagagg agcagacaca agcgtgggaa tcgtgggcct gctgctgacc     60
acagcaatgg caatccggtg catcggcgtg agcaatagag acttcgtgga gggaatgtcc    120
ggaggaacct gggtggatgt ggtgctggag cacggcggct gcgtgacagt gatggcccag    180
gacaagccaa ccgtggatat cgagctggtg accacaaccg tgtccaacat ggccgaggtg    240
aggtcttact gctatgaggc cagcatctcc gacatggcct ctgatagcag gtgtccaacc    300
cagggagagg catacctgga caagcagtcc gatacacagt acgtgtgcaa gcggaccctg    360
gtggacagag gctggggcaa tggctgtggc ctgtttggca agggctctct ggtgacatgc    420
gccaagttcg cctgtagcaa gaagatgacc ggcaagtcca tccagccaga gaacctggag    480
taccggatca tgctgtctgt gcacggctcc cagcactctg gcatgatcgt gaacgacaca    540
ggccacgaga cagatgagaa tcgggccaag gtggagatca cacctaactc tccaagagcc    600
gaggccaccc tgggaggatt tggctctctg ggcctggact gcgagcctag aacaggcctg    660
```

```
gacttctccg atctgtacta tctgaccatg aacaataagc actggctggt gcacaaggag    720

tggtttcacg acatcccact gccatggcac gcaggagcag atacaggaac accacactgg    780

aacaataagg aggccctggt ggagttcaag gatgcccacg ccaagcggca gacagtggtg    840

gtgctgggca gccaggaggg agcagtgcac accgccctgg caggcgccct ggaggcagag    900

atggacggag ctaagggcag actgtctagc ggccacctga agtgcaggct gaagatggat    960

aagctgcgcc tgaagggcgt gtcctactct ctgtgcacag ccgccttcac cttcaccaag   1020

atccctgccg agacactgca cggcacagtg accgtggagg tgcagtatgc cggcacagac   1080

ggaccctgta aggtgcctgc ccagatggcc gtggatatgc agacactgac acctgtgggc   1140

aggctgatca ccgccaatcc agtgatcaca gagtctaccg agaacagcaa gatgatgctg   1200

gagctggacc caccatttgg cgatagctat atcgtgatcg gcgtgggcga gaagaagatc   1260

acacaccact ggcaccgcag cggctccaca atcggcaagg cctttgaggc aaccgtgcgc   1320

ggagcaaaga gaatggccgt gctgggcgac accgcatggg atttcggatc tgtgggaggc   1380

gccctgaaca gcctgggcaa gggcatccac cagatcttcg gcgccgcctt taagtccctg   1440

ttcggcggca tgagctggtt ctcacagatc ctgatcggca cactgctgat gtggctgggc   1500

ctgaacacca agaatggctc tatcagcctg atgtgcctgg ccctgggagg cgtgctgatc   1560

ttcctgtcca ccgccgtgtc tgcctgatga                                    1590
```

```
<210> SEQ ID NO 59
<211> LENGTH: 528
<212> TYPE: PRT
<213> ORGANISM: Artificial sequence
<220> FEATURE:
<223> OTHER INFORMATION: Zikasp_ZikaE protein (A5)

<400> SEQUENCE: 59

Met Glu Lys Lys Arg Arg Gly Ala Asp Thr Ser Val Gly Ile Val Gly
1               5                   10                  15

Leu Leu Leu Thr Thr Ala Met Ala Ile Arg Cys Ile Gly Val Ser Asn
            20                  25                  30

Arg Asp Phe Val Glu Gly Met Ser Gly Gly Thr Trp Val Asp Val Val
        35                  40                  45

Leu Glu His Gly Gly Cys Val Thr Val Met Ala Gln Asp Lys Pro Thr
    50                  55                  60

Val Asp Ile Glu Leu Val Thr Thr Thr Val Ser Asn Met Ala Glu Val
65                  70                  75                  80

Arg Ser Tyr Cys Tyr Glu Ala Ser Ile Ser Asp Met Ala Ser Asp Ser
                85                  90                  95

Arg Cys Pro Thr Gln Gly Glu Ala Tyr Leu Asp Lys Gln Ser Asp Thr
            100                 105                 110

Gln Tyr Val Cys Lys Arg Thr Leu Val Asp Arg Gly Trp Gly Asn Gly
        115                 120                 125

Cys Gly Leu Phe Gly Lys Gly Ser Leu Val Thr Cys Ala Lys Phe Ala
    130                 135                 140

Cys Ser Lys Lys Met Thr Gly Lys Ser Ile Gln Pro Glu Asn Leu Glu
145                 150                 155                 160

Tyr Arg Ile Met Leu Ser Val His Gly Ser Gln His Ser Gly Met Ile
                165                 170                 175

Val Asn Asp Thr Gly His Glu Thr Asp Glu Asn Arg Ala Lys Val Glu
            180                 185                 190
```

```
Ile Thr Pro Asn Ser Pro Arg Ala Glu Ala Thr Leu Gly Gly Phe Gly
        195                 200                 205

Ser Leu Gly Leu Asp Cys Glu Pro Arg Thr Gly Leu Asp Phe Ser Asp
    210                 215                 220

Leu Tyr Tyr Leu Thr Met Asn Asn Lys His Trp Leu Val His Lys Glu
225                 230                 235                 240

Trp Phe His Asp Ile Pro Leu Pro Trp His Ala Gly Ala Asp Thr Gly
                245                 250                 255

Thr Pro His Trp Asn Asn Lys Glu Ala Leu Val Glu Phe Lys Asp Ala
            260                 265                 270

His Ala Lys Arg Gln Thr Val Val Val Leu Gly Ser Gln Glu Gly Ala
        275                 280                 285

Val His Thr Ala Leu Ala Gly Ala Leu Glu Ala Glu Met Asp Gly Ala
    290                 295                 300

Lys Gly Arg Leu Ser Ser Gly His Leu Lys Cys Arg Leu Lys Met Asp
305                 310                 315                 320

Lys Leu Arg Leu Lys Gly Val Ser Tyr Ser Leu Cys Thr Ala Ala Phe
                325                 330                 335

Thr Phe Thr Lys Ile Pro Ala Glu Thr Leu His Gly Thr Val Thr Val
            340                 345                 350

Glu Val Gln Tyr Ala Gly Thr Asp Gly Pro Cys Lys Val Pro Ala Gln
        355                 360                 365

Met Ala Val Asp Met Gln Thr Leu Thr Pro Val Gly Arg Leu Ile Thr
    370                 375                 380

Ala Asn Pro Val Ile Thr Glu Ser Thr Glu Asn Ser Lys Met Met Leu
385                 390                 395                 400

Glu Leu Asp Pro Pro Phe Gly Asp Ser Tyr Ile Val Ile Gly Val Gly
                405                 410                 415

Glu Lys Lys Ile Thr His His Trp His Arg Ser Gly Ser Thr Ile Gly
            420                 425                 430

Lys Ala Phe Glu Ala Thr Val Arg Gly Ala Lys Arg Met Ala Val Leu
        435                 440                 445

Gly Asp Thr Ala Trp Asp Phe Gly Ser Val Gly Gly Ala Leu Asn Ser
    450                 455                 460

Leu Gly Lys Gly Ile His Gln Ile Phe Gly Ala Ala Phe Lys Ser Leu
465                 470                 475                 480

Phe Gly Gly Met Ser Trp Phe Ser Gln Ile Leu Ile Gly Thr Leu Leu
                485                 490                 495

Met Trp Leu Gly Leu Asn Thr Lys Asn Gly Ser Ile Ser Leu Met Cys
            500                 505                 510

Leu Ala Leu Gly Gly Val Leu Ile Phe Leu Ser Thr Ala Val Ser Ala
        515                 520                 525
```

<210> SEQ ID NO 60
<211> LENGTH: 1446
<212> TYPE: DNA
<213> ORGANISM: Artificial sequence
<220> FEATURE:
<223> OTHER INFORMATION: Native nucleotide sequence of
Zikasp_ZikaE_no_Anchor protein (A6)

<400> SEQUENCE: 60

```
atggagaaga agagacgagg cgcagatact agtgtcggaa ttgttggcct cctgctgacc     60

acagctatgg caatcaggtg cataggagtc agcaataggg actttgtgga aggtatgtca    120

ggtgggactt gggttgatgt tgtcttggaa catggaggtt gtgtcaccgt aatggcacag    180
```

gacaaaccga ctgtcgacat agagctggtt acaacaacag tcagcaacat ggcggaggta 240
agatcctact gctatgaggc atcaatatca gacatggctt cggacagccg ctgcccaaca 300
caaggtgaag cctaccttga caagcaatca gacactcaat atgtctgcaa aagaacgtta 360
gtggacagag gctggggaaa tggatgtgga ctttttggca aagggagcct ggtgacatgc 420
gctaagtttg catgctccaa gaaaatgacc gggaagagca tccagccaga gaatctggag 480
taccggataa tgctgtcagt tcatggctcc cagcacagtg ggatgatcgt taatgacaca 540
ggacatgaaa ctgatgagaa tagagcgaag gttgagataa cgcccaattc accaagagcc 600
gaagccaccc tgggggggttt tggaagccta ggacttgatt gtgaaccgag gacaggcctt 660
gacttttcag atttgtatta cttgactatg aataacaagc actggttggt tcacaaggag 720
tggttccacg acattccatt accttggcac gctggggcag acaccggaac tccacactgg 780
aacaacaaag aagcactggt agagttcaag gacgcacatg ccaaaaggca aactgtcgtg 840
gttctaggga gtcaagaagg agcagttcac acggcccttg ctggagctct ggaggctgag 900
atggatggtg caaagggaag gctgtcctct ggccacttga aatgtcgcct gaaaatggat 960
aaacttagat tgaagggcgt gtcatactcc ttgtgtaccg cagcgttcac attcaccaag 1020
atcccggctg aaacactgca cgggacagtc acagtggagg tacagtacgc agggacagat 1080
ggaccttgca aggttccagc tcagatggcg gtggacatgc aaactctgac cccagttggg 1140
aggttgataa ccgctaaccc cgtaatcact gaaagcactg agaactctaa gatgatgctg 1200
gaacttgatc caccatttgg ggactcttac attgtcatag gagtcgggga gaagaagatc 1260
acccaccact ggcacaggag tggcagcacc attggaaaag catttgaagc cactgtgaga 1320
ggtgccaaga gaatggcagt cttgggagac acagcctggg actttggatc agttggaggc 1380
gctctcaact cattgggcaa gggcatccat caaatttttg gagcagcttt caaatcattg 1440
tgatga 1446

<210> SEQ ID NO 61
<211> LENGTH: 1446
<212> TYPE: DNA
<213> ORGANISM: Artificial sequence
<220> FEATURE:
<223> OTHER INFORMATION: Codon-optimized nucleotide sequence of
Zikasp_ZikaE_no_Anchor protein (A6)

<400> SEQUENCE: 61
atggagaaga agcggagagg agcagacaca agcgtgggaa tcgtgggcct gctgctgacc 60
acagcaatgg caatccggtg catcggcgtg agcaatagag acttcgtgga gggaatgtcc 120
ggaggaacct gggtggatgt ggtgctggag cacggcggct gcgtgacagt gatggcccag 180
gacaagccaa ccgtggatat cgagctggtg accacaaccg tgtccaacat ggccgaggtg 240
aggtcttact gctatgaggc cagcatctcc gacatggcct ctgatagcag gtgtccaacc 300
cagggagagg catacctgga caagcagtcc gatacacagt acgtgtgcaa gcggaccctg 360
gtggacagag gctggggcaa tggctgtggc ctgtttggca agggctctct ggtgacatgc 420
gccaagttcg cctgtagcaa gaagatgacc ggcaagtcca tccagccaga gaacctggag 480
taccggatca tgctgtctgt gcacggctcc cagcactctg gcatgatcgt gaacgacaca 540
ggccacgaga cagatgagaa tcgggccaag gtggagatca cacctaactc tccaagagcc 600
gaggccaccc tgggaggatt tggctctctg ggcctggact gcgagcctag aacaggcctg 660
gacttctccg atctgtacta tctgaccatg aacaataagc actggctggt gcacaaggag 720

```
tggtttcacg acatcccact gccatggcac gcaggagcag atacaggaac accacactgg     780

aacaataagg aggccctggt ggagttcaag gatgcccacg ccaagcggca gacagtggtg     840

gtgctgggca gccaggaggg agcagtgcac accgccctgg caggcgccct ggaggcagag     900

atggacggag ctaagggcag actgtctagc ggccacctga agtgcaggct gaagatggat     960

aagctgcgcc tgaagggcgt gtcctactct ctgtgcacag ccgccttcac cttcaccaag    1020

atccctgccg agacactgca cggcacagtg accgtggagg tgcagtatgc cggcacagac    1080

ggaccctgta aggtgcctgc ccagatggcc gtggatatgc agacactgac acctgtgggc    1140

aggctgatca ccgccaatcc agtgatcaca gagtctaccg agaacagcaa gatgatgctg    1200

gagctggacc caccatttgg cgatagctat atcgtgatcg gcgtgggcga gaagaagatc    1260

acacaccact ggcaccgcag cggctccaca atcggcaagg cctttgaggc aaccgtgcgc    1320

ggagcaaaga gaatggccgt gctgggcgac accgcatggg atttcggatc tgtgggaggc    1380

gccctgaaca gcctgggcaa gggcatccac cagatcttcg gcgccgcctt taagtccctg    1440

tgatga                                                               1446
```

```
<210> SEQ ID NO 62
<211> LENGTH: 480
<212> TYPE: PRT
<213> ORGANISM: Artificial sequence
<220> FEATURE:
<223> OTHER INFORMATION: Zikasp_ZikaE_no_Anchor protein (A6)

<400> SEQUENCE: 62

Met Glu Lys Lys Arg Arg Gly Ala Asp Thr Ser Val Gly Ile Val Gly
1               5                   10                  15

Leu Leu Leu Thr Thr Ala Met Ala Ile Arg Cys Ile Gly Val Ser Asn
            20                  25                  30

Arg Asp Phe Val Glu Gly Met Ser Gly Gly Thr Trp Val Asp Val Val
        35                  40                  45

Leu Glu His Gly Gly Cys Val Thr Val Met Ala Gln Asp Lys Pro Thr
    50                  55                  60

Val Asp Ile Glu Leu Val Thr Thr Thr Val Ser Asn Met Ala Glu Val
65                  70                  75                  80

Arg Ser Tyr Cys Tyr Glu Ala Ser Ile Ser Asp Met Ala Ser Asp Ser
                85                  90                  95

Arg Cys Pro Thr Gln Gly Glu Ala Tyr Leu Asp Lys Gln Ser Asp Thr
            100                 105                 110

Gln Tyr Val Cys Lys Arg Thr Leu Val Asp Arg Gly Trp Gly Asn Gly
        115                 120                 125

Cys Gly Leu Phe Gly Lys Gly Ser Leu Val Thr Cys Ala Lys Phe Ala
    130                 135                 140

Cys Ser Lys Lys Met Thr Gly Lys Ser Ile Gln Pro Glu Asn Leu Glu
145                 150                 155                 160

Tyr Arg Ile Met Leu Ser Val His Gly Ser Gln His Ser Gly Met Ile
                165                 170                 175

Val Asn Asp Thr Gly His Glu Thr Asp Glu Asn Arg Ala Lys Val Glu
            180                 185                 190

Ile Thr Pro Asn Ser Pro Arg Ala Glu Ala Thr Leu Gly Gly Phe Gly
        195                 200                 205

Ser Leu Gly Leu Asp Cys Glu Pro Arg Thr Gly Leu Asp Phe Ser Asp
    210                 215                 220
```

-continued

```
Leu Tyr Tyr Leu Thr Met Asn Asn Lys His Trp Leu Val His Lys Glu
225                 230                 235                 240

Trp Phe His Asp Ile Pro Leu Pro Trp His Ala Gly Ala Asp Thr Gly
                245                 250                 255

Thr Pro His Trp Asn Asn Lys Glu Ala Leu Val Glu Phe Lys Asp Ala
            260                 265                 270

His Ala Lys Arg Gln Thr Val Val Val Leu Gly Ser Gln Glu Gly Ala
        275                 280                 285

Val His Thr Ala Leu Ala Gly Ala Leu Glu Ala Glu Met Asp Gly Ala
    290                 295                 300

Lys Gly Arg Leu Ser Ser Gly His Leu Lys Cys Arg Leu Lys Met Asp
305                 310                 315                 320

Lys Leu Arg Leu Lys Gly Val Ser Tyr Ser Leu Cys Thr Ala Ala Phe
                325                 330                 335

Thr Phe Thr Lys Ile Pro Ala Glu Thr Leu His Gly Thr Val Thr Val
            340                 345                 350

Glu Val Gln Tyr Ala Gly Thr Asp Gly Pro Cys Lys Val Pro Ala Gln
        355                 360                 365

Met Ala Val Asp Met Gln Thr Leu Thr Pro Val Gly Arg Leu Ile Thr
    370                 375                 380

Ala Asn Pro Val Ile Thr Glu Ser Thr Glu Asn Ser Lys Met Met Leu
385                 390                 395                 400

Glu Leu Asp Pro Pro Phe Gly Asp Ser Tyr Ile Val Ile Gly Val Gly
                405                 410                 415

Glu Lys Lys Ile Thr His His Trp His Arg Ser Gly Ser Thr Ile Gly
            420                 425                 430

Lys Ala Phe Glu Ala Thr Val Arg Gly Ala Lys Arg Met Ala Val Leu
        435                 440                 445

Gly Asp Thr Ala Trp Asp Phe Gly Ser Val Gly Gly Ala Leu Asn Ser
    450                 455                 460

Leu Gly Lys Gly Ile His Gln Ile Phe Gly Ala Ala Phe Lys Ser Leu
465                 470                 475                 480
```

<210> SEQ ID NO 63
<211> LENGTH: 1410
<212> TYPE: DNA
<213> ORGANISM: Artificial sequence
<220> FEATURE:
<223> OTHER INFORMATION: Native nucleotide sequence of Zikasp_ZikaE411 protein (A7)

<400> SEQUENCE: 63

```
atggagaaga agagacgagg cgcagatact agtgtcggaa ttgttggcct cctgctgacc      60

acagctatgg caatcaggtg cataggagtc agcaataggg actttgtgga aggtatgtca     120

ggtgggactt gggttgatgt tgtcttggaa catggaggtt gtgtcaccgt aatggcacag     180

gacaaaccga ctgtcgacat agagctggtt acaacaacag tcagcaacat ggcggaggta     240

agatcctact gctatgaggc atcaatatca gacatggctt cggacagccg ctgcccaaca     300

caaggtgaag cctaccttga caagcaatca gacactcaat atgtctgcaa aagaacgtta     360

gtggacagag gctggggaaa tggatgtgga ctttttggca aagggagcct ggtgacatgc     420

gctaagtttg catgctccaa gaaaaatgacc gggaagagca tccagccaga gaatctggag     480

taccggataa tgctgtcagt tcatggctcc cagcacagtg ggatgatcgt taatgacaca     540

ggacatgaaa ctgatgagaa tagagcgaag gttgagataa cgcccaattc accaagagcc     600
```

```
gaagccaccc tggggggttt tggaagccta ggacttgatt gtgaaccgag gacaggcctt    660

gacttttcag atttgtatta cttgactatg aataacaagc actggttggt tcacaaggag    720

tggttccacg acattccatt accttggcac gctggggcag acaccggaac tccacactgg    780

aacaacaaag aagcactggt agagttcaag gacgcacatg ccaaaaggca aactgtcgtg    840

gttctaggga gtcaagaagg agcagttcac acggcccttg ctggagctct ggaggctgag    900

atggatggtg caaagggaag gctgtcctct ggccacttga aatgtcgcct gaaaatggat    960

aaacttagat tgaagggcgt gtcatactcc ttgtgtaccg cagcgttcac attcaccaag   1020

atcccggctg aaacactgca cgggacagtc acagtggagg tacagtacgc agggacagat   1080

ggaccttgca aggttccagc tcagatggcg gtggacatgc aaactctgac cccagttggg   1140

aggttgataa ccgctaaccc cgtaatcact gaaagcactg agaactctaa gatgatgctg   1200

gaacttgatc caccatttgg ggactcttac attgtcatag gagtcgggga gaagaagatc   1260

acccaccact ggcacaggag tggcagcacc attggaaaag catttgaagc cactgtgaga   1320

ggtgccaaga gaatggcagt cttgggagac acagcctggg actttggatc agttggaggc   1380

gctctcaact cattgggcaa gggcatctga                                    1410
```

<210> SEQ ID NO 64
<211> LENGTH: 1410
<212> TYPE: DNA
<213> ORGANISM: Artificial sequence
<220> FEATURE:
<223> OTHER INFORMATION: Codon-optimized nucleotide sequence of Zikasp_ZikaE411 protein (A7)

<400> SEQUENCE: 64

```
atggagaaga agcggagagg agcagacaca agcgtgggaa tcgtgggcct gctgctgacc     60

acagcaatgg caatccggtg catcggcgtg agcaatagag acttcgtgga gggaatgtcc    120

ggaggaacct gggtggatgt ggtgctggag cacggcggct gcgtgacagt gatggcccag    180

gacaagccaa ccgtggatat cgagctggtg accacaaccg tgtccaacat ggccgaggtg    240

aggtcttact gctatgaggc cagcatctcc gacatggcct ctgatagcag gtgtccaacc    300

cagggagagg catacctgga caagcagtcc gatacacagt acgtgtgcaa gcggaccctg    360

gtggacagag gctggggcaa tggctgtggc ctgtttggca agggctctct ggtgacatgc    420

gccaagttcg cctgtagcaa gaagatgacc ggcaagtcca tccagccaga gaacctggag    480

taccggatca tgctgtctgt gcacggctcc cagcactctg gcatgatcgt gaacgacaca    540

ggccacgaga cagatgagaa tcgggccaag gtggagatca cacctaactc tccaagagcc    600

gaggccaccc tgggaggatt tggctctctg ggcctggact gcgagcctag aacaggcctg    660

gacttctccg atctgtacta tctgaccatg aacaataagc actggctggt gcacaaggag    720

tggtttcacg acatcccact gccatggcac gcaggagcag atacaggaac accacactgg    780

aacaataagg aggccctggt ggagttcaag gatgcccacg ccaagcggca gacagtggtg    840

gtgctgggca gccaggaggg agcagtgcac accgccctgg caggcgccct ggaggcagag    900

atggacggag ctaagggcag actgtctagc ggccacctga agtgcaggct gaagatggat    960

aagctgcgcc tgaagggcgt gtcctactct ctgtgcacag ccgccttcac cttcaccaag   1020

atccctgccg agacactgca cggcacagtg accgtggagg tgcagtatgc cggcacagac   1080

ggaccctgta aggtgcctgc ccagatggcc gtggatatgc agacactgac acctgtgggc   1140

aggctgatca ccgccaatcc agtgatcaca gagtctaccg agaacagcaa gatgatgctg   1200
```

```
gagctggacc caccatttgg cgatagctat atcgtgatcg gcgtgggcga gaagaagatc   1260

acacaccact ggcaccgcag cggctccaca atcggcaagg cctttgaggc aaccgtgcgc   1320

ggagcaaaga gaatggccgt gctgggcgac accgcatggg atttcggatc tgtgggaggc   1380

gccctgaaca gcctgggcaa gggcatctga                                    1410
```

<210> SEQ ID NO 65
<211> LENGTH: 469
<212> TYPE: PRT
<213> ORGANISM: Artificial sequence
<220> FEATURE:
<223> OTHER INFORMATION: Zikasp_ZikaE411 protein (A7)

<400> SEQUENCE: 65

```
Met Glu Lys Lys Arg Arg Gly Ala Asp Thr Ser Val Gly Ile Val Gly
1               5                   10                  15

Leu Leu Leu Thr Thr Ala Met Ala Ile Arg Cys Ile Gly Val Ser Asn
            20                  25                  30

Arg Asp Phe Val Glu Gly Met Ser Gly Gly Thr Trp Val Asp Val Val
        35                  40                  45

Leu Glu His Gly Gly Cys Val Thr Val Met Ala Gln Asp Lys Pro Thr
    50                  55                  60

Val Asp Ile Glu Leu Val Thr Thr Thr Val Ser Asn Met Ala Glu Val
65                  70                  75                  80

Arg Ser Tyr Cys Tyr Glu Ala Ser Ile Ser Asp Met Ala Ser Asp Ser
                85                  90                  95

Arg Cys Pro Thr Gln Gly Glu Ala Tyr Leu Asp Lys Gln Ser Asp Thr
            100                 105                 110

Gln Tyr Val Cys Lys Arg Thr Leu Val Asp Arg Gly Trp Gly Asn Gly
        115                 120                 125

Cys Gly Leu Phe Gly Lys Gly Ser Leu Val Thr Cys Ala Lys Phe Ala
    130                 135                 140

Cys Ser Lys Lys Met Thr Gly Lys Ser Ile Gln Pro Glu Asn Leu Glu
145                 150                 155                 160

Tyr Arg Ile Met Leu Ser Val His Gly Ser Gln His Ser Gly Met Ile
                165                 170                 175

Val Asn Asp Thr Gly His Glu Thr Asp Glu Asn Arg Ala Lys Val Glu
            180                 185                 190

Ile Thr Pro Asn Ser Pro Arg Ala Glu Ala Thr Leu Gly Gly Phe Gly
        195                 200                 205

Ser Leu Gly Leu Asp Cys Glu Pro Arg Thr Gly Leu Asp Phe Ser Asp
    210                 215                 220

Leu Tyr Tyr Leu Thr Met Asn Asn Lys His Trp Leu Val His Lys Glu
225                 230                 235                 240

Trp Phe His Asp Ile Pro Leu Pro Trp His Ala Gly Ala Asp Thr Gly
                245                 250                 255

Thr Pro His Trp Asn Asn Lys Glu Ala Leu Val Glu Phe Lys Asp Ala
            260                 265                 270

His Ala Lys Arg Gln Thr Val Val Val Leu Gly Ser Gln Glu Gly Ala
        275                 280                 285

Val His Thr Ala Leu Ala Gly Ala Leu Glu Ala Glu Met Asp Gly Ala
    290                 295                 300

Lys Gly Arg Leu Ser Ser Gly His Leu Lys Cys Arg Leu Lys Met Asp
305                 310                 315                 320

Lys Leu Arg Leu Lys Gly Val Ser Tyr Ser Leu Cys Thr Ala Ala Phe
```

```
                325                 330                 335

Thr Phe Thr Lys Ile Pro Ala Glu Thr Leu His Gly Thr Val Thr Val
            340                 345                 350

Glu Val Gln Tyr Ala Gly Thr Asp Gly Pro Cys Lys Val Pro Ala Gln
        355                 360                 365

Met Ala Val Asp Met Gln Thr Leu Thr Pro Val Gly Arg Leu Ile Thr
    370                 375                 380

Ala Asn Pro Val Ile Thr Glu Ser Thr Glu Asn Ser Lys Met Met Leu
385                 390                 395                 400

Glu Leu Asp Pro Pro Phe Gly Asp Ser Tyr Ile Val Ile Gly Val Gly
                405                 410                 415

Glu Lys Lys Ile Thr His His Trp His Arg Ser Gly Ser Thr Ile Gly
            420                 425                 430

Lys Ala Phe Glu Ala Thr Val Arg Gly Ala Lys Arg Met Ala Val Leu
        435                 440                 445

Gly Asp Thr Ala Trp Asp Phe Gly Ser Val Gly Gly Ala Leu Asn Ser
    450                 455                 460

Leu Gly Lys Gly Ile
465


<210> SEQ ID NO 66
<211> LENGTH: 1290
<212> TYPE: DNA
<213> ORGANISM: Artificial sequence
<220> FEATURE:
<223> OTHER INFORMATION: Native nucleotide sequence of Zikasp_ZikaE395
      protein (A8)

<400> SEQUENCE: 66

atggagaaga agagacgagg cgcagatact agtgtcggaa ttgttggcct cctgctgacc     60

acagctatgg caatcaggtg cataggagtc agcaataggg actttgtgga aggtatgtca    120

ggtgggactt gggttgatgt tgtcttggaa catggaggtt gtgtcaccgt aatggcacag    180

gacaaaccga ctgtcgacat agagctggtt acaacaacag tcagcaacat ggcggaggta    240

agatcctact gctatgaggc atcaatatca gacatggctt cggacagccg ctgcccaaca    300

caaggtgaag cctaccttga caagcaatca gacactcaat atgtctgcaa aagaacgtta    360

gtggacagag gctggggaaa tggatgtgga ctttttggca aagggagcct ggtgacatgc    420

gctaagtttg catgctccaa gaaaatgacc gggaagagca tccagccaga gaatctggag    480

taccggataa tgctgtcagt tcatggctcc cagcacagtg ggatgatcgt taatgacaca    540

ggacatgaaa ctgatgagaa tagagcgaag gttgagataa cgcccaattc accaagagcc    600

gaagccaccc tgggggggttt tggaagccta ggacttgatt gtgaaccgag gacaggcctt    660

gacttttcag atttgtatta cttgactatg aataacaagc actggttggt tcacaaggag    720

tggttccacg acattccatt accttggcac gctggggcag acaccggaac tccacactgg    780

aacaacaaag aagcactggt agagttcaag gacgcacatg ccaaaaggca aactgtcgtg    840

gttctaggga gtcaagaagg agcagttcac acggcccttg ctggagctct ggaggctgag    900

atggatggtg caaagggaag gctgtcctct ggccacttga aatgtcgcct gaaaatggat    960

aaacttagat tgaagggcgt gtcatactcc ttgtgtaccg cagcgttcac attcaccaag   1020

atcccggctg aaacactgca cgggacagtc acagtggagg tacagtacgc agggacagat   1080

ggaccttgca aggttccagc tcagatggcg gtggacatgc aaactctgac cccagttggg   1140

aggttgataa ccgctaaccc cgtaatcact gaaagcactg agaactctaa gatgatgctg   1200
```

gaacttgatc caccatttgg ggactcttac attgtcatag gagtcgggga gaagaagatc 1260
acccaccact ggcacaggag tggctgatga 1290

<210> SEQ ID NO 67
<211> LENGTH: 1290
<212> TYPE: DNA
<213> ORGANISM: Artificial sequence
<220> FEATURE:
<223> OTHER INFORMATION: Codon-optimized nucleotide sequence of
Zikasp_ZikaE395 protein (A8)

<400> SEQUENCE: 67
atggagaaga agcggagagg agcagacaca agcgtgggaa tcgtgggcct gctgctgacc 60
acagcaatgg caatccggtg catcggcgtg agcaatagag acttcgtgga gggaatgtcc 120
ggaggaacct gggtggatgt ggtgctggag cacggcggct gcgtgacagt gatggcccag 180
gacaagccaa ccgtggatat cgagctggtg accacaaccg tgtccaacat ggccgaggtg 240
aggtcttact gctatgaggc cagcatctcc gacatggcct ctgatagcag gtgtccaacc 300
cagggagagg catacctgga caagcagtcc gatacacagt acgtgtgcaa gcggaccctg 360
gtggacagag gctggggcaa tggctgtggc ctgtttggca agggctctct ggtgacatgc 420
gccaagttcg cctgtagcaa gaagatgacc ggcaagtcca tccagccaga gaacctggag 480
taccggatca tgctgtctgt gcacggctcc cagcactctg gcatgatcgt gaacgacaca 540
ggccacgaga cagatgagaa tcgggccaag gtggagatca cacctaactc tccaagagcc 600
gaggccaccc tgggaggatt tggctctctg ggcctggact gcgagcctag aacaggcctg 660
gacttctccg atctgtacta tctgaccatg aacaataagc actggctggt gcacaaggag 720
tggtttcacg acatcccact gccatggcac gcaggagcag atacaggaac accacactgg 780
aacaataagg aggccctggt ggagttcaag gatgcccacg ccaagcggca gacagtggtg 840
gtgctgggca gccaggaggg agcagtgcac accgccctgg caggcgccct ggaggcagag 900
atggacggag ctaagggcag actgtctagc ggccacctga agtgcaggct gaagatggat 960
aagctgcgcc tgaagggcgt gtcctactct ctgtgcacag ccgccttcac cttcaccaag 1020
atccctgccg agacactgca cggcacagtg accgtggagg tgcagtatgc cggcacagac 1080
ggaccctgta aggtgcctgc ccagatggcc gtggatatgc agacactgac acctgtgggc 1140
aggctgatca ccgccaatcc agtgatcaca gagtctaccg agaacagcaa gatgatgctg 1200
gagctggacc caccatttgg cgatagctat atcgtgatcg gcgtgggcga gaagaagatc 1260
acacaccact ggcaccgcag cggctgatga 1290

<210> SEQ ID NO 68
<211> LENGTH: 428
<212> TYPE: PRT
<213> ORGANISM: Artificial sequence
<220> FEATURE:
<223> OTHER INFORMATION: Zikasp_ZikaE395 protein (A8)

<400> SEQUENCE: 68

Met Glu Lys Lys Arg Arg Gly Ala Asp Thr Ser Val Gly Ile Val Gly
1 5 10 15

Leu Leu Leu Thr Thr Ala Met Ala Ile Arg Cys Ile Gly Val Ser Asn
20 25 30

Arg Asp Phe Val Glu Gly Met Ser Gly Gly Thr Trp Val Asp Val Val
35 40 45

```
Leu Glu His Gly Gly Cys Val Thr Val Met Ala Gln Asp Lys Pro Thr
    50                  55                  60

Val Asp Ile Glu Leu Val Thr Thr Thr Val Ser Asn Met Ala Glu Val
65                  70                  75                  80

Arg Ser Tyr Cys Tyr Glu Ala Ser Ile Ser Asp Met Ala Ser Asp Ser
                85                  90                  95

Arg Cys Pro Thr Gln Gly Glu Ala Tyr Leu Asp Lys Gln Ser Asp Thr
            100                 105                 110

Gln Tyr Val Cys Lys Arg Thr Leu Val Asp Arg Gly Trp Gly Asn Gly
        115                 120                 125

Cys Gly Leu Phe Gly Lys Gly Ser Leu Val Thr Cys Ala Lys Phe Ala
    130                 135                 140

Cys Ser Lys Lys Met Thr Gly Lys Ser Ile Gln Pro Glu Asn Leu Glu
145                 150                 155                 160

Tyr Arg Ile Met Leu Ser Val His Gly Ser Gln His Ser Gly Met Ile
                165                 170                 175

Val Asn Asp Thr Gly His Glu Thr Asp Glu Asn Arg Ala Lys Val Glu
            180                 185                 190

Ile Thr Pro Asn Ser Pro Arg Ala Glu Ala Thr Leu Gly Gly Phe Gly
        195                 200                 205

Ser Leu Gly Leu Asp Cys Glu Pro Arg Thr Gly Leu Asp Phe Ser Asp
    210                 215                 220

Leu Tyr Tyr Leu Thr Met Asn Asn Lys His Trp Leu Val His Lys Glu
225                 230                 235                 240

Trp Phe His Asp Ile Pro Leu Pro Trp His Ala Gly Ala Asp Thr Gly
                245                 250                 255

Thr Pro His Trp Asn Asn Lys Glu Ala Leu Val Glu Phe Lys Asp Ala
            260                 265                 270

His Ala Lys Arg Gln Thr Val Val Val Leu Gly Ser Gln Glu Gly Ala
        275                 280                 285

Val His Thr Ala Leu Ala Gly Ala Leu Glu Ala Glu Met Asp Gly Ala
    290                 295                 300

Lys Gly Arg Leu Ser Ser Gly His Leu Lys Cys Arg Leu Lys Met Asp
305                 310                 315                 320

Lys Leu Arg Leu Lys Gly Val Ser Tyr Ser Leu Cys Thr Ala Ala Phe
                325                 330                 335

Thr Phe Thr Lys Ile Pro Ala Glu Thr Leu His Gly Thr Val Thr Val
            340                 345                 350

Glu Val Gln Tyr Ala Gly Thr Asp Gly Pro Cys Lys Val Pro Ala Gln
        355                 360                 365

Met Ala Val Asp Met Gln Thr Leu Thr Pro Val Gly Arg Leu Ile Thr
    370                 375                 380

Ala Asn Pro Val Ile Thr Glu Ser Thr Glu Asn Ser Lys Met Met Leu
385                 390                 395                 400

Glu Leu Asp Pro Pro Phe Gly Asp Ser Tyr Ile Val Ile Gly Val Gly
                405                 410                 415

Glu Lys Lys Ile Thr His His Trp His Arg Ser Gly
            420                 425
```

<210> SEQ ID NO 69
<211> LENGTH: 1572
<212> TYPE: DNA
<213> ORGANISM: Artificial sequence
<220> FEATURE:
<223> OTHER INFORMATION: Native nucleotide sequence of Zikasp_ZikaE protein (A9)

<400> SEQUENCE: 69

```
atgcaaaaag tcatatactt ggtcatgata ctgctgattg ccccggcata cagcatcagg     60
tgcataggag tcagcaatag ggactttgtg gaaggtatgt caggtgggac ttgggttgat    120
gttgtcttgg aacatggagg ttgtgtcacc gtaatggcac aggacaaacc gactgtcgac    180
atagagctgg ttacaacaac agtcagcaac atggcggagg taagatccta ctgctatgag    240
gcatcaatat cagacatggc ttcggacagc cgctgcccaa cacaaggtga agcctacctt    300
gacaagcaat cagacactca atatgtctgc aaaagaacgt tagtggacag aggctgggga    360
aatggatgtg gactttttgg caaagggagc ctggtgacat gcgctaagtt tgcatgctcc    420
aagaaaatga ccgggaagag catccagcca gagaatctgg agtaccggat aatgctgtca    480
gttcatggct cccagcacag tgggatgatc gttaatgaca caggacatga aactgatgag    540
aatagagcga aggttgagat aacgcccaat tcaccaagag ccgaagccac cctgggggt    600
tttggaagcc taggacttga ttgtgaaccg aggacaggcc ttgacttttc agatttgtat    660
tacttgacta tgaataacaa gcactggttg gttcacaagg agtggttcca cgacattcca    720
ttaccttggc acgctggggc agacaccgga actccacact ggaacaacaa agaagcactg    780
gtagagttca aggacgcaca tgccaaaagg caaactgtcg tggttctagg gagtcaagaa    840
ggagcagttc acacggccct tgctggagct ctggaggctg agatggatgg tgcaaaggga    900
aggctgtcct ctggccactt gaaatgtcgc ctgaaaatgg ataaacttag attgaagggc    960
gtgtcatact ccttgtgtac cgcagcgttc acattcacca agatcccggc tgaaacactg   1020
cacgggacag tcacagtgga ggtacagtac gcagggacag atggaccttg caaggttcca   1080
gctcagatgg cggtggacat gcaaactctg accccagttg ggaggttgat aaccgctaac   1140
cccgtaatca ctgaaagcac tgagaactct aagatgatgc tggaacttga tccaccattt   1200
ggggactctt acattgtcat aggagtcggg gagaagaaga tcacccacca ctggcacagg   1260
agtggcagca ccattggaaa agcatttgaa gccactgtga gaggtgccaa gagaatggca   1320
gtcttgggag acacagcctg ggactttgga tcagttggag gcgctctcaa ctcattgggc   1380
aagggcatcc atcaaatttt tggagcagct ttcaaatcat tgtttggagg aatgtcctgg   1440
ttctcacaaa ttctcattgg aacgttgctg atgtggttgg gtctgaacac aaagaatgga   1500
tctatttccc ttatgtgctt ggccttaggg ggagtgttga tcttcttatc cacagccgtc   1560
tctgcttgat ga                                                       1572
```

<210> SEQ ID NO 70
<211> LENGTH: 1572
<212> TYPE: DNA
<213> ORGANISM: Artificial sequence
<220> FEATURE:
<223> OTHER INFORMATION: Codon-optimized nucleotide sequence of
Zikasp_ZikaE protein (A9)

<400> SEQUENCE: 70

```
atgcagaaag tgatctacct ggtcatgatc ctgctgatcg ctcctgccta ttctatccgg     60
tgcatcggcg tgagcaatag agacttcgtg gagggaatgt ccggaggaac ctgggtggat    120
gtggtgctgg agcacggcgg ctgcgtgaca gtgatggccc aggacaagcc aaccgtggat    180
atcgagctgg tgaccacaac cgtgtccaac atggccgagg tgaggtctta ctgctatgag    240
gccagcatct ccgacatggc ctctgatagc aggtgtccaa cccagggaga ggcatacctg    300
```

```
gacaagcagt ccgatacaca gtacgtgtgc aagcggaccc tggtggacag aggctggggc    360
aatggctgtg gcctgtttgg caagggctct ctggtgacat gcgccaagtt cgcctgtagc    420
aagaagatga ccggcaagtc catccagcca gagaacctgg agtaccggat catgctgtct    480
gtgcacggct cccagcactc tggcatgatc gtgaacgaca caggccacga gacagatgag    540
aatcgggcca aggtggagat cacacctaac tctccaagag ccgaggccac cctgggagga    600
tttggctctc tgggcctgga ctgcgagcct agaacaggcc tggacttctc cgatctgtac    660
tatctgacca tgaacaataa gcactggctg gtgcacaagg agtggtttca cgacatccca    720
ctgccatggc acgcaggagc agatacagga acaccacact ggaacaataa ggaggccctg    780
gtggagttca aggatgccca cgccaagcgg cagacagtgg tggtgctggg cagccaggag    840
ggagcagtgc acaccgccct ggcaggcgcc ctggaggcag agatggacgg agctaagggc    900
agactgtcta gcggccacct gaagtgcagg ctgaagatgg ataagctgcg cctgaagggc    960
gtgtcctact ctctgtgcac agccgccttc accttcacca agatccctgc cgagacactg   1020
cacggcacag tgaccgtgga ggtgcagtat gccggcacag acggaccctg taaggtgcct   1080
gcccagatgg ccgtggatat gcagacactg acacctgtgg gcaggctgat caccgccaat   1140
ccagtgatca cagagtctac cgagaacagc aagatgatgc tggagctgga cccaccattt   1200
ggcgatagct atatcgtgat cggcgtgggc gagaagaaga tcacacacca ctggcaccgc   1260
agcggctcca caatcggcaa ggcctttgag gcaaccgtgc gcggagcaaa gagaatggcc   1320
gtgctgggcg acaccgcatg ggatttcgga tctgtgggag gcgccctgaa cagcctgggc   1380
aagggcatcc accagatctt cggcgccgcc tttaagtccc tgttcggcgg catgagctgg   1440
ttctcacaga tcctgatcgg cacactgctg atgtggctgg gcctgaacac caagaatggc   1500
tctatcagcc tgatgtgcct ggccctggga ggcgtgctga tcttcctgtc caccgccgtg   1560
tctgcctgat ga                                                       1572
```

<210> SEQ ID NO 71
<211> LENGTH: 522
<212> TYPE: PRT
<213> ORGANISM: Artificial sequence
<220> FEATURE:
<223> OTHER INFORMATION: Zikasp_ZikaE protein (A9)

<400> SEQUENCE: 71

```
Met Gln Lys Val Ile Tyr Leu Val Met Ile Leu Leu Ile Ala Pro Ala
1               5                   10                  15

Tyr Ser Ile Arg Cys Ile Gly Val Ser Asn Arg Asp Phe Val Glu Gly
            20                  25                  30

Met Ser Gly Gly Thr Trp Val Asp Val Val Leu Glu His Gly Gly Cys
        35                  40                  45

Val Thr Val Met Ala Gln Asp Lys Pro Thr Val Asp Ile Glu Leu Val
    50                  55                  60

Thr Thr Thr Val Ser Asn Met Ala Glu Val Arg Ser Tyr Cys Tyr Glu
65                  70                  75                  80

Ala Ser Ile Ser Asp Met Ala Ser Asp Ser Arg Cys Pro Thr Gln Gly
                85                  90                  95

Glu Ala Tyr Leu Asp Lys Gln Ser Asp Thr Gln Tyr Val Cys Lys Arg
            100                 105                 110

Thr Leu Val Asp Arg Gly Trp Gly Asn Gly Cys Gly Leu Phe Gly Lys
        115                 120                 125

Gly Ser Leu Val Thr Cys Ala Lys Phe Ala Cys Ser Lys Lys Met Thr
```

```
    130                 135                 140

Gly Lys Ser Ile Gln Pro Glu Asn Leu Glu Tyr Arg Ile Met Leu Ser
145                 150                 155                 160

Val His Gly Ser Gln His Ser Gly Met Ile Val Asn Asp Thr Gly His
                165                 170                 175

Glu Thr Asp Glu Asn Arg Ala Lys Val Glu Ile Thr Pro Asn Ser Pro
            180                 185                 190

Arg Ala Glu Ala Thr Leu Gly Gly Phe Gly Ser Leu Gly Leu Asp Cys
        195                 200                 205

Glu Pro Arg Thr Gly Leu Asp Phe Ser Asp Leu Tyr Tyr Leu Thr Met
    210                 215                 220

Asn Asn Lys His Trp Leu Val His Lys Glu Trp Phe His Asp Ile Pro
225                 230                 235                 240

Leu Pro Trp His Ala Gly Ala Asp Thr Gly Thr Pro His Trp Asn Asn
                245                 250                 255

Lys Glu Ala Leu Val Glu Phe Lys Asp Ala His Ala Lys Arg Gln Thr
            260                 265                 270

Val Val Val Leu Gly Ser Gln Glu Gly Ala Val His Thr Ala Leu Ala
        275                 280                 285

Gly Ala Leu Glu Ala Glu Met Asp Gly Ala Lys Gly Arg Leu Ser Ser
    290                 295                 300

Gly His Leu Lys Cys Arg Leu Lys Met Asp Lys Leu Arg Leu Lys Gly
305                 310                 315                 320

Val Ser Tyr Ser Leu Cys Thr Ala Ala Phe Thr Phe Thr Lys Ile Pro
                325                 330                 335

Ala Glu Thr Leu His Gly Thr Val Thr Val Glu Val Gln Tyr Ala Gly
            340                 345                 350

Thr Asp Gly Pro Cys Lys Val Pro Ala Gln Met Ala Val Asp Met Gln
        355                 360                 365

Thr Leu Thr Pro Val Gly Arg Leu Ile Thr Ala Asn Pro Val Ile Thr
    370                 375                 380

Glu Ser Thr Glu Asn Ser Lys Met Met Leu Glu Leu Asp Pro Pro Phe
385                 390                 395                 400

Gly Asp Ser Tyr Ile Val Ile Gly Val Gly Glu Lys Lys Ile Thr His
                405                 410                 415

His Trp His Arg Ser Gly Ser Thr Ile Gly Lys Ala Phe Glu Ala Thr
            420                 425                 430

Val Arg Gly Ala Lys Arg Met Ala Val Leu Gly Asp Thr Ala Trp Asp
        435                 440                 445

Phe Gly Ser Val Gly Gly Ala Leu Asn Ser Leu Gly Lys Gly Ile His
    450                 455                 460

Gln Ile Phe Gly Ala Ala Phe Lys Ser Leu Phe Gly Gly Met Ser Trp
465                 470                 475                 480

Phe Ser Gln Ile Leu Ile Gly Thr Leu Leu Met Trp Leu Gly Leu Asn
                485                 490                 495

Thr Lys Asn Gly Ser Ile Ser Leu Met Cys Leu Ala Leu Gly Gly Val
            500                 505                 510

Leu Ile Phe Leu Ser Thr Ala Val Ser Ala
        515                 520
```

<210> SEQ ID NO 72
<211> LENGTH: 1428
<212> TYPE: DNA
<213> ORGANISM: Artificial sequence
<220> FEATURE:
<223> OTHER INFORMATION: Native nucleotide sequence of
Zikasp_ZikaE_no_anchor protein (A10)

<400> SEQUENCE: 72

```
atgcaaaaag tcatatactt ggtcatgata ctgctgattg ccccggcata cagcatcagg     60

tgcataggag tcagcaatag ggactttgtg gaaggtatgt caggtgggac ttgggttgat    120

gttgtcttgg aacatggagg ttgtgtcacc gtaatggcac aggacaaacc gactgtcgac    180

atagagctgg ttacaacaac agtcagcaac atggcggagg taagatccta ctgctatgag    240

gcatcaatat cagacatggc ttcggacagc cgctgcccaa cacaaggtga agcctacctt    300

gacaagcaat cagacactca atatgtctgc aaaagaacgt tagtggacag aggctgggga    360

aatggatgtg gactttttgg caaagggagc ctggtgacat gcgctaagtt tgcatgctcc    420

aagaaaatga ccgggaagag catccagcca gagaatctgg agtaccggat aatgctgtca    480

gttcatggct cccagcacag tgggatgatc gttaatgaca caggacatga aactgatgag    540

aatagagcga aggttgagat aacgcccaat tcaccaagag ccgaagccac cctgggggggt    600

tttggaagcc taggacttga ttgtgaaccg aggacaggcc ttgacttttc agatttgtat    660

tacttgacta tgaataacaa gcactggttg gttcacaagg agtggttcca cgacattcca    720

ttaccttggc acgctggggc agacaccgga actccacact ggaacaacaa agaagcactg    780

gtagagttca aggacgcaca tgccaaaagg caaactgtcg tggttctagg gagtcaagaa    840

ggagcagttc acacggccct tgctggagct ctggaggctg agatggatgg tgcaaaggga    900

aggctgtcct ctggccactt gaaatgtcgc ctgaaaatgg ataaacttag attgaagggc    960

gtgtcatact ccttgtgtac cgcagcgttc acattcacca agatcccggc tgaaacactg   1020

cacgggacag tcacagtgga ggtacagtac gcagggacag atggaccttg caaggttcca   1080

gctcagatgg cggtggacat gcaaactctg accccagttg ggaggttgat aaccgctaac   1140

cccgtaatca ctgaaagcac tgagaactct aagatgatgc tggaacttga tccaccattt   1200

ggggactctt acattgtcat aggagtcggg gagaagaaga tcacccacca ctggcacagg   1260

agtggcagca ccattggaaa agcatttgaa gccactgtga gaggtgccaa gagaatggca   1320

gtcttgggag acacagcctg ggactttgga tcagttggag gcgctctcaa ctcattgggc   1380

aagggcatcc atcaaatttt tggagcagct ttcaaatcat tgtgatga                1428
```

<210> SEQ ID NO 73
<211> LENGTH: 1428
<212> TYPE: DNA
<213> ORGANISM: Artificial sequence
<220> FEATURE:
<223> OTHER INFORMATION: Codon-optimized nucleotide sequence of
Zikasp_ZikaE_no_anchor protein (A10)

<400> SEQUENCE: 73

```
atgcagaaag tgatctacct ggtcatgatc ctgctgatcg ctcctgccta ttctatccgg     60

tgcatcggcg tgagcaatag agacttcgtg gagggaatgt ccggaggaac ctgggtggat    120

gtggtgctgg agcacggcgg ctgcgtgaca gtgatggccc aggacaagcc aaccgtggat    180

atcgagctgg tgaccacaac cgtgtccaac atggccgagg tgaggtctta ctgctatgag    240

gccagcatct ccgacatggc ctctgatagc aggtgtccaa cccagggaga ggcatacctg    300

gacaagcagt ccgatacaca gtacgtgtgc aagcggaccc tggtggacag aggctggggc    360

aatggctgtg gcctgtttgg caagggctct ctggtgacat gcgccaagtt cgcctgtagc    420
```

```
aagaagatga ccggcaagtc catccagcca gagaacctgg agtaccggat catgctgtct    480

gtgcacggct cccagcactc tggcatgatc gtgaacgaca caggccacga gacagatgag    540

aatcgggcca aggtggagat cacacctaac tctccaagag ccgaggccac cctgggagga    600

tttggctctc tgggcctgga ctgcgagcct agaacaggcc tggacttctc cgatctgtac    660

tatctgacca tgaacaataa gcactggctg gtgcacaagg agtggtttca cgacatccca    720

ctgccatggc acgcaggagc agatacagga acaccacact ggaacaataa ggaggccctg    780

gtggagttca aggatgccca cgccaagcgg cagacagtgg tggtgctggg cagccaggag    840

ggagcagtgc acaccgccct ggcaggcgcc ctggaggcag agatggacgg agctaagggc    900

agactgtcta gcggccacct gaagtgcagg ctgaagatgg ataagctgcg cctgaagggc    960

gtgtcctact ctctgtgcac agccgccttc accttcacca agatccctgc cgagacactg   1020

cacggcacag tgaccgtgga ggtgcagtat gccggcacag acggaccctg taaggtgcct   1080

gcccagatgg ccgtggatat gcagacactg acacctgtgg gcaggctgat caccgccaat   1140

ccagtgatca cagagtctac cgagaacagc aagatgatgc tggagctgga cccaccattt   1200

ggcgatagct atatcgtgat cggcgtgggc gagaagaaga tcacacacca ctggcaccgc   1260

agcggctcca caatcggcaa ggcctttgag gcaaccgtgc gcggagcaaa gagaatggcc   1320

gtgctgggcg acaccgcatg ggatttcgga tctgtgggag gcgccctgaa cagcctgggc   1380

aagggcatcc accagatctt cggcgccgcc tttaagtccc tgtgatga                1428
```

<210> SEQ ID NO 74
<211> LENGTH: 474
<212> TYPE: PRT
<213> ORGANISM: Artificial sequence
<220> FEATURE:
<223> OTHER INFORMATION: Zikasp_ZikaE_no_anchor protein (A10)

<400> SEQUENCE: 74

```
Met Gln Lys Val Ile Tyr Leu Val Met Ile Leu Leu Ile Ala Pro Ala
1               5                   10                  15

Tyr Ser Ile Arg Cys Ile Gly Val Ser Asn Arg Asp Phe Val Glu Gly
            20                  25                  30

Met Ser Gly Gly Thr Trp Val Asp Val Val Leu Glu His Gly Gly Cys
        35                  40                  45

Val Thr Val Met Ala Gln Asp Lys Pro Thr Val Asp Ile Glu Leu Val
    50                  55                  60

Thr Thr Thr Val Ser Asn Met Ala Glu Val Arg Ser Tyr Cys Tyr Glu
65                  70                  75                  80

Ala Ser Ile Ser Asp Met Ala Ser Asp Ser Arg Cys Pro Thr Gln Gly
                85                  90                  95

Glu Ala Tyr Leu Asp Lys Gln Ser Asp Thr Gln Tyr Val Cys Lys Arg
            100                 105                 110

Thr Leu Val Asp Arg Gly Trp Gly Asn Gly Cys Gly Leu Phe Gly Lys
        115                 120                 125

Gly Ser Leu Val Thr Cys Ala Lys Phe Ala Cys Ser Lys Lys Met Thr
    130                 135                 140

Gly Lys Ser Ile Gln Pro Glu Asn Leu Glu Tyr Arg Ile Met Leu Ser
145                 150                 155                 160

Val His Gly Ser Gln His Ser Gly Met Ile Val Asn Asp Thr Gly His
                165                 170                 175

Glu Thr Asp Glu Asn Arg Ala Lys Val Glu Ile Thr Pro Asn Ser Pro
            180                 185                 190
```

```
Arg Ala Glu Ala Thr Leu Gly Gly Phe Gly Ser Leu Gly Leu Asp Cys
        195                 200                 205

Glu Pro Arg Thr Gly Leu Asp Phe Ser Asp Leu Tyr Tyr Leu Thr Met
    210                 215                 220

Asn Asn Lys His Trp Leu Val His Lys Glu Trp Phe His Asp Ile Pro
225                 230                 235                 240

Leu Pro Trp His Ala Gly Ala Asp Thr Gly Thr Pro His Trp Asn Asn
                245                 250                 255

Lys Glu Ala Leu Val Glu Phe Lys Asp Ala His Ala Lys Arg Gln Thr
            260                 265                 270

Val Val Val Leu Gly Ser Gln Glu Gly Ala Val His Thr Ala Leu Ala
        275                 280                 285

Gly Ala Leu Glu Ala Glu Met Asp Gly Ala Lys Gly Arg Leu Ser Ser
    290                 295                 300

Gly His Leu Lys Cys Arg Leu Lys Met Asp Lys Leu Arg Leu Lys Gly
305                 310                 315                 320

Val Ser Tyr Ser Leu Cys Thr Ala Ala Phe Thr Phe Thr Lys Ile Pro
                325                 330                 335

Ala Glu Thr Leu His Gly Thr Val Thr Val Glu Val Gln Tyr Ala Gly
            340                 345                 350

Thr Asp Gly Pro Cys Lys Val Pro Ala Gln Met Ala Val Asp Met Gln
        355                 360                 365

Thr Leu Thr Pro Val Gly Arg Leu Ile Thr Ala Asn Pro Val Ile Thr
    370                 375                 380

Glu Ser Thr Glu Asn Ser Lys Met Met Leu Glu Leu Asp Pro Pro Phe
385                 390                 395                 400

Gly Asp Ser Tyr Ile Val Ile Gly Val Gly Glu Lys Lys Ile Thr His
                405                 410                 415

His Trp His Arg Ser Gly Ser Thr Ile Gly Lys Ala Phe Glu Ala Thr
            420                 425                 430

Val Arg Gly Ala Lys Arg Met Ala Val Leu Gly Asp Thr Ala Trp Asp
        435                 440                 445

Phe Gly Ser Val Gly Gly Ala Leu Asn Ser Leu Gly Lys Gly Ile His
    450                 455                 460

Gln Ile Phe Gly Ala Ala Phe Lys Ser Leu
465                 470
```

<210> SEQ ID NO 75
<211> LENGTH: 1392
<212> TYPE: DNA
<213> ORGANISM: Artificial sequence
<220> FEATURE:
<223> OTHER INFORMATION: Native nucleotide sequence of Zikasp_ZikaE411 protein (A11)

<400> SEQUENCE: 75

```
atgcaaaaag tcatatactt ggtcatgata ctgctgattg ccccggcata cagcatcagg     60

tgcataggag tcagcaatag ggactttgtg gaaggtatgt caggtgggac ttgggttgat    120

gttgtcttgg aacatggagg ttgtgtcacc gtaatggcac aggacaaacc gactgtcgac    180

atagagctgg ttacaacaac agtcagcaac atggcggagg taagatccta ctgctatgag    240

gcatcaatat cagacatggc ttcggacagc cgctgcccaa cacaaggtga agcctacctt    300

gacaagcaat cagacactca atatgtctgc aaaagaacgt tagtggacag aggctgggga    360

aatggatgtg gactttttgg caaagggagc ctggtgacat gcgctaagtt tgcatgctcc    420
```

aagaaaatga ccgggaagag catccagcca gagaatctgg agtaccggat aatgctgtca 480
gttcatggct cccagcacag tgggatgatc gttaatgaca caggacatga aactgatgag 540
aatagagcga aggttgagat aacgcccaat tcaccaagag ccgaagccac cctgggggt 600 tttggaagcc taggacttga ttgtgaaccg aggacaggcc ttgacttttc agatttgtat 660
tacttgacta tgaataacaa gcactggttg gttcacaagg agtggttcca cgacattcca 720
ttaccttggc acgctggggc agacaccgga actccacact ggaacaacaa agaagcactg 780
gtagagttca aggacgcaca tgccaaaagg caaactgtcg tggttctagg gagtcaagaa 840
ggagcagttc acacggccct tgctggagct ctggaggctg agatggatgg tgcaaaggga 900
aggctgtcct ctggccactt gaaatgtcgc ctgaaaatgg ataaacttag attgaagggc 960
gtgtcatact ccttgtgtac cgcagcgttc acattcacca agatcccggc tgaaacactg 1020
cacgggacag tcacagtgga ggtacagtac gcagggacag atggaccttg caaggttcca 1080
gctcagatgg cggtggacat gcaaactctg accccagttg ggaggttgat aaccgctaac 1140
cccgtaatca ctgaaagcac tgagaactct aagatgatgc tggaacttga tccaccattt 1200
ggggactctt acattgtcat aggagtcggg gagaagaaga tcacccacca ctggcacagg 1260
agtggcagca ccattggaaa agcatttgaa gccactgtga gaggtgccaa gagaatggca 1320
gtcttgggag acacagcctg ggactttgga tcagttggag gcgctctcaa ctcattgggc 1380
aagggcatct ga 1392

<210> SEQ ID NO 76
<211> LENGTH: 1392
<212> TYPE: DNA
<213> ORGANISM: Artificial sequence
<220> FEATURE:
<223> OTHER INFORMATION: Codon-optimized nucleotide sequence of
Zikasp_ZikaE411 protein (A11)

<400> SEQUENCE: 76
atgcagaaag tgatctacct ggtcatgatc ctgctgatcg ctcctgccta ttctatccgg 60
tgcatcggcg tgagcaatag agacttcgtg gagggaatgt ccggaggaac ctgggtggat 120
gtggtgctgg agcacggcgg ctgcgtgaca gtgatggccc aggacaagcc aaccgtggat 180
atcgagctgg tgaccacaac cgtgtccaac atggccgagg tgaggtctta ctgctatgag 240
gccagcatct ccgacatggc ctctgatagc aggtgtccaa cccagggaga ggcatacctg 300
gacaagcagt ccgatacaca gtacgtgtgc aagcggaccc tggtggacag aggctggggc 360
aatggctgtg gcctgtttgg caagggctct ctggtgacat gcgccaagtt cgcctgtagc 420
aagaagatga ccggcaagtc catccagcca gagaacctgg agtaccggat catgctgtct 480
gtgcacggct cccagcactc tggcatgatc gtgaacgaca caggccacga gacagatgag 540
aatcgggcca aggtggagat cacacctaac tctccaagag ccgaggccac cctgggagga 600
tttggctctc tgggcctgga ctgcgagcct agaacaggcc tggacttctc cgatctgtac 660
tatctgacca tgaacaataa gcactggctg gtgcacaagg agtggtttca cgacatccca 720
ctgccatggc acgcaggagc agatacagga acaccacact ggaacaataa ggaggccctg 780
gtggagttca aggatgccca cgccaagcgg cagacagtgg tggtgctggg cagccaggag 840
ggagcagtgc acaccgccct ggcaggcgcc ctggaggcag agatggacgg agctaagggc 900
agactgtcta gcggccacct gaagtgcagg ctgaagatgg ataagctgcg cctgaagggc 960
gtgtcctact ctctgtgcac agccgccttc accttcacca agatccctgc cgagacactg 1020

```
cacggcacag tgaccgtgga ggtgcagtat gccggcacag acggaccctg taaggtgcct   1080

gcccagatgg ccgtggatat gcagacactg acacctgtgg gcaggctgat caccgccaat   1140

ccagtgatca cagagtctac cgagaacagc aagatgatgc tggagctgga cccaccattt   1200

ggcgatagct atatcgtgat cggcgtgggc gagaagaaga tcacacacca ctggcaccgc   1260

agcggctcca caatcggcaa ggcctttgag gcaaccgtgc gcggagcaaa gagaatggcc   1320

gtgctgggcg acaccgcatg ggatttcgga tctgtgggag gcgccctgaa cagcctgggc   1380

aagggcatct ga                                                       1392
```

<210> SEQ ID NO 77
<211> LENGTH: 463
<212> TYPE: PRT
<213> ORGANISM: Artificial sequence
<220> FEATURE:
<223> OTHER INFORMATION: Zikasp_ZikaE411 protein (A11)

<400> SEQUENCE: 77

```
Met Gln Lys Val Ile Tyr Leu Val Met Ile Leu Leu Ile Ala Pro Ala
1               5                   10                  15

Tyr Ser Ile Arg Cys Ile Gly Val Ser Asn Arg Asp Phe Val Glu Gly
            20                  25                  30

Met Ser Gly Gly Thr Trp Val Asp Val Val Leu Glu His Gly Gly Cys
        35                  40                  45

Val Thr Val Met Ala Gln Asp Lys Pro Thr Val Asp Ile Glu Leu Val
    50                  55                  60

Thr Thr Thr Val Ser Asn Met Ala Glu Val Arg Ser Tyr Cys Tyr Glu
65                  70                  75                  80

Ala Ser Ile Ser Asp Met Ala Ser Asp Ser Arg Cys Pro Thr Gln Gly
                85                  90                  95

Glu Ala Tyr Leu Asp Lys Gln Ser Asp Thr Gln Tyr Val Cys Lys Arg
            100                 105                 110

Thr Leu Val Asp Arg Gly Trp Gly Asn Gly Cys Gly Leu Phe Gly Lys
        115                 120                 125

Gly Ser Leu Val Thr Cys Ala Lys Phe Ala Cys Ser Lys Lys Met Thr
    130                 135                 140

Gly Lys Ser Ile Gln Pro Glu Asn Leu Glu Tyr Arg Ile Met Leu Ser
145                 150                 155                 160

Val His Gly Ser Gln His Ser Gly Met Ile Val Asn Asp Thr Gly His
                165                 170                 175

Glu Thr Asp Glu Asn Arg Ala Lys Val Glu Ile Thr Pro Asn Ser Pro
            180                 185                 190

Arg Ala Glu Ala Thr Leu Gly Gly Phe Gly Ser Leu Gly Leu Asp Cys
        195                 200                 205

Glu Pro Arg Thr Gly Leu Asp Phe Ser Asp Leu Tyr Tyr Leu Thr Met
    210                 215                 220

Asn Asn Lys His Trp Leu Val His Lys Glu Trp Phe His Asp Ile Pro
225                 230                 235                 240

Leu Pro Trp His Ala Gly Ala Asp Thr Gly Thr Pro His Trp Asn Asn
                245                 250                 255

Lys Glu Ala Leu Val Glu Phe Lys Asp Ala His Ala Lys Arg Gln Thr
            260                 265                 270

Val Val Val Leu Gly Ser Gln Glu Gly Ala Val His Thr Ala Leu Ala
        275                 280                 285
```

```
Gly Ala Leu Glu Ala Glu Met Asp Gly Ala Lys Gly Arg Leu Ser Ser
    290                 295                 300

Gly His Leu Lys Cys Arg Leu Lys Met Asp Lys Leu Arg Leu Lys Gly
305                 310                 315                 320

Val Ser Tyr Ser Leu Cys Thr Ala Ala Phe Thr Phe Thr Lys Ile Pro
                325                 330                 335

Ala Glu Thr Leu His Gly Thr Val Thr Val Glu Val Gln Tyr Ala Gly
            340                 345                 350

Thr Asp Gly Pro Cys Lys Val Pro Ala Gln Met Ala Val Asp Met Gln
        355                 360                 365

Thr Leu Thr Pro Val Gly Arg Leu Ile Thr Ala Asn Pro Val Ile Thr
    370                 375                 380

Glu Ser Thr Glu Asn Ser Lys Met Met Leu Glu Leu Asp Pro Pro Phe
385                 390                 395                 400

Gly Asp Ser Tyr Ile Val Ile Gly Val Gly Glu Lys Lys Ile Thr His
                405                 410                 415

His Trp His Arg Ser Gly Ser Thr Ile Gly Lys Ala Phe Glu Ala Thr
            420                 425                 430

Val Arg Gly Ala Lys Arg Met Ala Val Leu Gly Asp Thr Ala Trp Asp
        435                 440                 445

Phe Gly Ser Val Gly Gly Ala Leu Asn Ser Leu Gly Lys Gly Ile
    450                 455                 460


<210> SEQ ID NO 78
<211> LENGTH: 1266
<212> TYPE: DNA
<213> ORGANISM: Artificial sequence
<220> FEATURE:
<223> OTHER INFORMATION: Native nucleotide sequence of Zikasp_ZikaE395
      protein (A12)

<400> SEQUENCE: 78

atgcaaaaag tcatatactt ggtcatgata ctgctgattg ccccggcata cagcatcagg     60

tgcataggag tcagcaatag ggactttgtg gaaggtatgt caggtgggac ttgggttgat    120

gttgtcttgg aacatggagg ttgtgtcacc gtaatggcac aggacaaacc gactgtcgac    180

atagagctgg ttacaacaac agtcagcaac atggcggagg taagatccta ctgctatgag    240

gcatcaatat cagacatggc ttcggacagc cgctgcccaa cacaaggtga agcctacctt    300

gacaagcaat cagacactca atatgtctgc aaaagaacgt tagtggacag aggctgggga    360

aatggatgtg gactttttgg caaagggagc ctggtgacat gcgctaagtt tgcatgctcc    420

aagaaaatga ccgggaagag catccagcca gagaatctgg agtaccggat aatgctgtca    480

gttcatggct cccagcacag tgggatgatc gttaatgaca caggacatga aactgatgag    540

aatagagcga aggttgagat aacgcccaat tcaccaagag ccgaagccac cctgggggt     600

tttggaagcc taggacttga ttgtgaaccg aggacaggcc ttgacttttc agatttgtat    660

tacttgacta tgaataacaa gcactggttg gttcacaagg agtggttcca cgacattcca    720

ttaccttggc acgctggggc agacaccgga actccacact ggaacaacaa agaagcactg    780

gtagagttca aggacgcaca tgccaaaagg caaactgtcg tggttctagg gagtcaagaa    840

ggagcagttc acacggccct tgctggagct ctggaggctg agatggatgg tgcaaaggga    900

aggctgtcct ctggccactt gaaatgtcgc ctgaaaatgg ataaacttag attgaagggc    960

gtgtcatact ccttgtgtac cgcagcgttc acattcacca agatcccggc tgaaacactg   1020

cacgggacag tcacagtgga ggtacagtac gcagggacag atggaccttg caaggttcca   1080
```

gctcagatgg cggtggacat gcaaactctg accccagttg ggaggttgat aaccgctaac 1140
cccgtaatca ctgaaagcac tgagaactct aagatgatgc tggaacttga tccaccattt 1200
ggggactctt acattgtcat aggagtcggg gagaagaaga tcacccacca ctggcacagg 1260
agtggc 1266

<210> SEQ ID NO 79
<211> LENGTH: 1272
<212> TYPE: DNA
<213> ORGANISM: Artificial sequence
<220> FEATURE:
<223> OTHER INFORMATION: Codon-optimized nucleotide sequence of
Zikasp_ZikaE395 protein (A12)

<400> SEQUENCE: 79
atgcagaaag tgatctacct ggtcatgatc ctgctgatcg ctcctgccta ttctatccgg 60
tgcatcggcg tgagcaatag agacttcgtg gagggaatgt ccggaggaac ctgggtggat 120
gtggtgctgg agcacggcgg ctgcgtgaca gtgatggccc aggacaagcc aaccgtggat 180
atcgagctgg tgaccacaac cgtgtccaac atggccgagg tgaggtctta ctgctatgag 240
gccagcatct ccgacatggc ctctgatagc aggtgtccaa cccagggaga ggcatacctg 300
gacaagcagt ccgatacaca gtacgtgtgc aagcggaccc tggtggacag aggctggggc 360
aatggctgtg gcctgtttgg caagggctct ctggtgacat gcgccaagtt cgcctgtagc 420
aagaagatga ccggcaagtc catccagcca gagaacctgg agtaccggat catgctgtct 480
gtgcacggct cccagcactc tggcatgatc gtgaacgaca caggccacga gacagatgag 540
aatcgggcca aggtggagat cacacctaac tctccaagag ccgaggccac cctgggagga 600
tttggctctc tgggcctgga ctgcgagcct agaacaggcc tggacttctc cgatctgtac 660
tatctgacca tgaacaataa gcactggctg gtgcacaagg agtggtttca cgacatccca 720
ctgccatggc acgcaggagc agatacagga acaccacact ggaacaataa ggaggccctg 780
gtggagttca aggatgccca cgccaagcgg cagacagtgg tggtgctggg cagccaggag 840
ggagcagtgc acaccgccct ggcaggcgcc ctggaggcag agatggacgg agctaagggc 900
agactgtcta gcggccacct gaagtgcagg ctgaagatgg ataagctgcg cctgaagggc 960
gtgtcctact ctctgtgcac agccgccttc accttcacca agatccctgc cgagacactg 1020
cacggcacag tgaccgtgga ggtgcagtat gccggcacag acggaccctg taaggtgcct 1080
gcccagatgg ccgtggatat gcagacactg acacctgtgg gcaggctgat caccgccaat 1140
ccagtgatca cagagtctac cgagaacagc aagatgatgc tggagctgga cccaccattt 1200
ggcgatagct atatcgtgat cggcgtgggc gagaagaaga tcacacacca ctggcaccgc 1260
agcggctgat ga 1272

<210> SEQ ID NO 80
<211> LENGTH: 422
<212> TYPE: PRT
<213> ORGANISM: Artificial sequence
<220> FEATURE:
<223> OTHER INFORMATION: Zikasp_ZikaE395 protein (A12)

<400> SEQUENCE: 80

Met Gln Lys Val Ile Tyr Leu Val Met Ile Leu Leu Ile Ala Pro Ala
1 5 10 15

Tyr Ser Ile Arg Cys Ile Gly Val Ser Asn Arg Asp Phe Val Glu Gly
20 25 30

```
Met Ser Gly Gly Thr Trp Val Asp Val Val Leu Glu His Gly Gly Cys
        35                  40                  45

Val Thr Val Met Ala Gln Asp Lys Pro Thr Val Asp Ile Glu Leu Val
    50                  55                  60

Thr Thr Thr Val Ser Asn Met Ala Glu Val Arg Ser Tyr Cys Tyr Glu
65                  70                  75                  80

Ala Ser Ile Ser Asp Met Ala Ser Asp Ser Arg Cys Pro Thr Gln Gly
                85                  90                  95

Glu Ala Tyr Leu Asp Lys Gln Ser Asp Thr Gln Tyr Val Cys Lys Arg
            100                 105                 110

Thr Leu Val Asp Arg Gly Trp Gly Asn Gly Cys Gly Leu Phe Gly Lys
        115                 120                 125

Gly Ser Leu Val Thr Cys Ala Lys Phe Ala Cys Ser Lys Lys Met Thr
    130                 135                 140

Gly Lys Ser Ile Gln Pro Glu Asn Leu Glu Tyr Arg Ile Met Leu Ser
145                 150                 155                 160

Val His Gly Ser Gln His Ser Gly Met Ile Val Asn Asp Thr Gly His
                165                 170                 175

Glu Thr Asp Glu Asn Arg Ala Lys Val Glu Ile Thr Pro Asn Ser Pro
            180                 185                 190

Arg Ala Glu Ala Thr Leu Gly Gly Phe Gly Ser Leu Gly Leu Asp Cys
        195                 200                 205

Glu Pro Arg Thr Gly Leu Asp Phe Ser Asp Leu Tyr Tyr Leu Thr Met
    210                 215                 220

Asn Asn Lys His Trp Leu Val His Lys Glu Trp Phe His Asp Ile Pro
225                 230                 235                 240

Leu Pro Trp His Ala Gly Ala Asp Thr Gly Thr Pro His Trp Asn Asn
                245                 250                 255

Lys Glu Ala Leu Val Glu Phe Lys Asp Ala His Ala Lys Arg Gln Thr
            260                 265                 270

Val Val Val Leu Gly Ser Gln Glu Gly Ala Val His Thr Ala Leu Ala
        275                 280                 285

Gly Ala Leu Glu Ala Glu Met Asp Gly Ala Lys Gly Arg Leu Ser Ser
    290                 295                 300

Gly His Leu Lys Cys Arg Leu Lys Met Asp Lys Leu Arg Leu Lys Gly
305                 310                 315                 320

Val Ser Tyr Ser Leu Cys Thr Ala Ala Phe Thr Phe Thr Lys Ile Pro
                325                 330                 335

Ala Glu Thr Leu His Gly Thr Val Thr Val Glu Val Gln Tyr Ala Gly
            340                 345                 350

Thr Asp Gly Pro Cys Lys Val Pro Ala Gln Met Ala Val Asp Met Gln
        355                 360                 365

Thr Leu Thr Pro Val Gly Arg Leu Ile Thr Ala Asn Pro Val Ile Thr
    370                 375                 380

Glu Ser Thr Glu Asn Ser Lys Met Met Leu Glu Leu Asp Pro Pro Phe
385                 390                 395                 400

Gly Asp Ser Tyr Ile Val Ile Gly Val Gly Glu Lys Lys Ile Thr His
                405                 410                 415

His Trp His Arg Ser Gly
            420
```

<210> SEQ ID NO 81
<211> LENGTH: 2094

<212> TYPE: DNA
<213> ORGANISM: Artificial sequence
<220> FEATURE:
<223> OTHER INFORMATION: Native nucleotide sequence of JEVsp_ZikaprME
protein (B1)

<400> SEQUENCE: 81
atgggcaaac gatcagccgg ctcaatcatg tggctcgcga gcttggcagt tgtcatagct 60
tgtgcaggag ccgcggaggt cactagacgt gggagtgcat actatatgta cttggacaga 120
aacgatgctg gggaggccat atcttttcca accacattgg ggatgaataa gtgttatata 180
cagatcatgg atcttggaca catgtgtgat gccaccatga gctatgaatg ccctatgctg 240
gatgaggggg tggaaccaga tgacgtcgat tgttggtgca acacgacgtc aacttgggtt 300
gtgtacggaa cctgccatca caaaaaaggt gaagcacgga gatctagaag agctgtgacg 360
ctcccctccc attccactag gaagctgcaa acgcggtcgc aaacctggtt ggaatcaaga 420
gaatacacaa agcacttgat tagagtcgaa aattggatat tcaggaaccc tggcttcgcg 480
ttagcagcag ctgccatcgc ttggcttttg ggaagctcaa cgagccaaaa agtcatatac 540
ttggtcatga tactgctgat tgccccggca tacagcatca ggtgcatagg agtcagcaat 600
agggactttg tggaaggtat gtcaggtggg acttgggttg atgttgtctt ggaacatgga 660
ggttgtgtca ccgtaatggc acaggacaaa ccgactgtcg acatagagct ggttacaaca 720
acagtcagca acatggcgga ggtaagatcc tactgctatg aggcatcaat atcagacatg 780
gcttcggaca gccgctgccc aacacaaggt gaagcctacc ttgacaagca atcagacact 840
caatatgtct gcaaaagaac gttagtggac agaggctggg gaaatggatg tggacttttt 900
ggcaaaggga gcctggtgac atgcgctaag tttgcatgct ccaagaaaat gaccgggaag 960
agcatccagc cagagaatct ggagtaccgg ataatgctgt cagttcatgg ctcccagcac 1020
agtgggatga tcgttaatga cacaggacat gaaactgatg agaatagagc gaaggttgag 1080
ataacgccca attcaccaag agccgaagcc accctggggg gttttggaag cctaggactt 1140
gattgtgaac cgaggacagg ccttgacttt tcagatttgt attacttgac tatgaataac 1200
aagcactggt tggttcacaa ggagtggttc cacgacattc cattaccttg gcacgctggg 1260
gcagacaccg gaactccaca ctggaacaac aaagaagcac tggtagagtt caaggacgca 1320
catgccaaaa ggcaaactgt cgtggttcta gggagtcaag aaggagcagt tcacacggcc 1380
cttgctggag ctctggaggc tgagatggat ggtgcaaagg gaaggctgtc ctctggccac 1440
ttgaaatgtc gcctgaaaat ggataaactt agattgaagg gcgtgtcata ctccttgtgt 1500
accgcagcgt tcacattcac caagatcccg gctgaaacac tgcacgggac agtcacagtg 1560
gaggtacagt acgcagggac agatggacct tgcaaggttc cagctcagat ggcggtggac 1620
atgcaaactc tgaccccagt tgggaggttg ataaccgcta accccgtaat cactgaaagc 1680
actgagaact ctaagatgat gctggaactt gatccaccat ttggggactc ttacattgtc 1740
ataggagtcg gggagaagaa gatcacccac cactggcaca ggagtggcag caccattgga 1800
aaagcatttg aagccactgt gagaggtgcc aagagaatgg cagtcttggg agacacagcc 1860
tgggactttg gatcagttgg aggcgctctc aactcattgg gcaagggcat ccatcaaatt 1920
tttggagcag ctttcaaatc attgtttgga ggaatgtcct ggttctcaca aattctcatt 1980
ggaacgttgc tgatgtggtt gggtctgaac acaaagaatg gatctatttc ccttatgtgc 2040
ttggccttag gggagtgttt gatcttctta tccacagccg tctctgcttg atga 2094

<210> SEQ ID NO 82
<211> LENGTH: 2094
<212> TYPE: DNA
<213> ORGANISM: Artificial sequence
<220> FEATURE:
<223> OTHER INFORMATION: Codon-optimized nucleotide sequence of
JEVsp_ZikaprME protein (B1)

<400> SEQUENCE: 82

```
atgggcaaga ggtccgcagg gagcattatg tggctggcat ctctggcagt cgtcatcgct     60

tgtgcaggag cagcagaggt gaccaggaga ggaagcgcct actatatgta cctggacagg    120

aatgatgccg gcgaggccat ctccttccca accacactgg gcatgaacaa gtgctacatc    180

cagatcatgg acctgggcca catgtgcgat gccaccatgt cctatgagtg tccaatgctg    240

gacgagggcg tggagcccga cgatgtggat tgctggtgta ataccacatc tacatgggtg    300

gtgtacggca cctgtcacca caagaaggga gaggcccggc ggagccggcg ggccgtgaca    360

ctgccttccc actctaccag gaagctgcag acacgcagcc agacctggct ggagtccaga    420

gagtatacca agcacctgat cagggtggag aactggatct ttcgcaatcc aggattcgca    480

ctggcagcag cagcaatcgc atggctgctg ggaagctcca ccagccagaa agtgatctac    540

ctggtcatga tcctgctgat cgctcctgcc tattctatcc ggtgcatcgg cgtgagcaat    600

agagacttcg tggagggaat gtccggagga acctgggtgg atgtggtgct ggagcacggc    660

ggctgcgtga cagtgatggc ccaggacaag ccaaccgtgg atatcgagct ggtgaccaca    720

accgtgtcca acatggccga ggtgaggtct tactgctatg aggccagcat ctccgacatg    780

gcctctgata gcaggtgtcc aacccaggga gaggcatacc tggacaagca gtccgataca    840

cagtacgtgt gcaagcggac cctggtggac agaggctggg gcaatggctg tggcctgttt    900

ggcaagggct ctctggtgac atgcgccaag ttcgcctgta gcaagaagat gaccggcaag    960

tccatccagc cagagaacct ggagtaccgg atcatgctgt ctgtgcacgg ctcccagcac   1020

tctggcatga tcgtgaacga cacaggccac gagacagatg agaatcgggc caaggtggag   1080

atcacaccta actctccaag agccgaggcc accctgggag gatttggctc tctgggcctg   1140

gactgcgagc ctagaacagg cctggacttc tccgatctgt actatctgac catgaacaat   1200

aagcactggc tggtgcacaa ggagtggttt cacgacatcc cactgccatg gcacgcagga   1260

gcagatacag gaacaccaca ctggaacaat aaggaggccc tggtggagtt caaggatgcc   1320

cacgccaagc ggcagacagt ggtggtgctg ggcagccagg agggagcagt gcacaccgcc   1380

ctggcaggcg ccctggaggc agagatggac ggagctaagg gcagactgtc tagcggccac   1440

ctgaagtgca ggctgaagat ggataagctg cgcctgaagg gcgtgtccta ctctctgtgc   1500

acagccgcct tcaccttcac caagatccct gccgagacac tgcacggcac agtgaccgtg   1560

gaggtgcagt atgccggcac agacggaccc tgtaaggtgc ctgcccagat ggccgtggat   1620

atgcagacac tgacacctgt gggcaggctg atcaccgcca atccagtgat cacagagtct   1680

accgagaaca gcaagatgat gctggagctg gacccaccat ttggcgatag ctatatcgtg   1740

atcggcgtgg gcgagaagaa gatcacacac cactggcacc gcagcggctc cacaatcggc   1800

aaggcctttg aggcaaccgt gcgcggagca aagagaatgg ccgtgctggg cgacaccgca   1860

tgggatttcg gatctgtggg aggcgccctg aacagcctgg gcaagggcat ccaccagatc   1920

ttcggcgccg cctttaagtc cctgttcggc ggcatgagct ggttctcaca gatcctgatc   1980

ggcacactgc tgatgtggct gggcctgaac accaagaatg gctctatcag cctgatgtgc   2040

ctggccctgg gaggcgtgct gatcttcctg tccaccgccg tgtctgcctg atga         2094
```

<210> SEQ ID NO 83
<211> LENGTH: 696
<212> TYPE: PRT
<213> ORGANISM: Artificial sequence
<220> FEATURE:
<223> OTHER INFORMATION: JEVsp_ZikaprME protein (B1)

<400> SEQUENCE: 83

```
Met Gly Lys Arg Ser Ala Gly Ser Ile Met Trp Leu Ala Ser Leu Ala
1               5                   10                  15

Val Val Ile Ala Cys Ala Gly Ala Ala Glu Val Thr Arg Arg Gly Ser
            20                  25                  30

Ala Tyr Tyr Met Tyr Leu Asp Arg Asn Asp Ala Gly Glu Ala Ile Ser
        35                  40                  45

Phe Pro Thr Thr Leu Gly Met Asn Lys Cys Tyr Ile Gln Ile Met Asp
    50                  55                  60

Leu Gly His Met Cys Asp Ala Thr Met Ser Tyr Glu Cys Pro Met Leu
65                  70                  75                  80

Asp Glu Gly Val Glu Pro Asp Asp Val Asp Cys Trp Cys Asn Thr Thr
                85                  90                  95

Ser Thr Trp Val Val Tyr Gly Thr Cys His His Lys Lys Gly Glu Ala
            100                 105                 110

Arg Arg Ser Arg Arg Ala Val Thr Leu Pro Ser His Ser Thr Arg Lys
        115                 120                 125

Leu Gln Thr Arg Ser Gln Thr Trp Leu Glu Ser Arg Glu Tyr Thr Lys
    130                 135                 140

His Leu Ile Arg Val Glu Asn Trp Ile Phe Arg Asn Pro Gly Phe Ala
145                 150                 155                 160

Leu Ala Ala Ala Ala Ile Ala Trp Leu Leu Gly Ser Ser Thr Ser Gln
                165                 170                 175

Lys Val Ile Tyr Leu Val Met Ile Leu Leu Ile Ala Pro Ala Tyr Ser
            180                 185                 190

Ile Arg Cys Ile Gly Val Ser Asn Arg Asp Phe Val Glu Gly Met Ser
        195                 200                 205

Gly Gly Thr Trp Val Asp Val Val Leu Glu His Gly Gly Cys Val Thr
    210                 215                 220

Val Met Ala Gln Asp Lys Pro Thr Val Asp Ile Glu Leu Val Thr Thr
225                 230                 235                 240

Thr Val Ser Asn Met Ala Glu Val Arg Ser Tyr Cys Tyr Glu Ala Ser
                245                 250                 255

Ile Ser Asp Met Ala Ser Asp Ser Arg Cys Pro Thr Gln Gly Glu Ala
            260                 265                 270

Tyr Leu Asp Lys Gln Ser Asp Thr Gln Tyr Val Cys Lys Arg Thr Leu
        275                 280                 285

Val Asp Arg Gly Trp Gly Asn Gly Cys Gly Leu Phe Gly Lys Gly Ser
    290                 295                 300

Leu Val Thr Cys Ala Lys Phe Ala Cys Ser Lys Lys Met Thr Gly Lys
305                 310                 315                 320

Ser Ile Gln Pro Glu Asn Leu Glu Tyr Arg Ile Met Leu Ser Val His
                325                 330                 335

Gly Ser Gln His Ser Gly Met Ile Val Asn Asp Thr Gly His Glu Thr
            340                 345                 350

Asp Glu Asn Arg Ala Lys Val Glu Ile Thr Pro Asn Ser Pro Arg Ala
        355                 360                 365
```

```
Glu Ala Thr Leu Gly Gly Phe Gly Ser Leu Gly Leu Asp Cys Glu Pro
    370                 375                 380

Arg Thr Gly Leu Asp Phe Ser Asp Leu Tyr Tyr Leu Thr Met Asn Asn
385                 390                 395                 400

Lys His Trp Leu Val His Lys Glu Trp Phe His Asp Ile Pro Leu Pro
                405                 410                 415

Trp His Ala Gly Ala Asp Thr Gly Thr Pro His Trp Asn Asn Lys Glu
            420                 425                 430

Ala Leu Val Glu Phe Lys Asp Ala His Ala Lys Arg Gln Thr Val Val
        435                 440                 445

Val Leu Gly Ser Gln Glu Gly Ala Val His Thr Ala Leu Ala Gly Ala
    450                 455                 460

Leu Glu Ala Glu Met Asp Gly Ala Lys Gly Arg Leu Ser Ser Gly His
465                 470                 475                 480

Leu Lys Cys Arg Leu Lys Met Asp Lys Leu Arg Leu Lys Gly Val Ser
                485                 490                 495

Tyr Ser Leu Cys Thr Ala Ala Phe Thr Phe Thr Lys Ile Pro Ala Glu
            500                 505                 510

Thr Leu His Gly Thr Val Thr Val Glu Val Gln Tyr Ala Gly Thr Asp
        515                 520                 525

Gly Pro Cys Lys Val Pro Ala Gln Met Ala Val Asp Met Gln Thr Leu
    530                 535                 540

Thr Pro Val Gly Arg Leu Ile Thr Ala Asn Pro Val Ile Thr Glu Ser
545                 550                 555                 560

Thr Glu Asn Ser Lys Met Met Leu Glu Leu Asp Pro Pro Phe Gly Asp
                565                 570                 575

Ser Tyr Ile Val Ile Gly Val Gly Glu Lys Lys Ile Thr His His Trp
            580                 585                 590

His Arg Ser Gly Ser Thr Ile Gly Lys Ala Phe Glu Ala Thr Val Arg
        595                 600                 605

Gly Ala Lys Arg Met Ala Val Leu Gly Asp Thr Ala Trp Asp Phe Gly
    610                 615                 620

Ser Val Gly Gly Ala Leu Asn Ser Leu Gly Lys Gly Ile His Gln Ile
625                 630                 635                 640

Phe Gly Ala Ala Phe Lys Ser Leu Phe Gly Gly Met Ser Trp Phe Ser
                645                 650                 655

Gln Ile Leu Ile Gly Thr Leu Leu Met Trp Leu Gly Leu Asn Thr Lys
            660                 665                 670

Asn Gly Ser Ile Ser Leu Met Cys Leu Ala Leu Gly Gly Val Leu Ile
        675                 680                 685

Phe Leu Ser Thr Ala Val Ser Ala
    690                 695
```

<210> SEQ ID NO 84
<211> LENGTH: 1950
<212> TYPE: DNA
<213> ORGANISM: Artificial sequence
<220> FEATURE:
<223> OTHER INFORMATION: Native nucleotide sequence of JEVsp_Zika_prME_no_Anchor protein (B2)

<400> SEQUENCE: 84

```
atgggcaaac gatcagccgg ctcaatcatg tggctcgcga gcttggcagt tgtcatagct      60

tgtgcaggag ccgcggaggt cactagacgt gggagtgcat actatatgta cttggacaga     120
```

-continued

```
aacgatgctg gggaggccat atcttttcca accacattgg ggatgaataa gtgttatata    180

cagatcatgg atcttggaca catgtgtgat gccaccatga gctatgaatg ccctatgctg    240

gatgaggggg tggaaccaga tgacgtcgat tgttggtgca acacgacgtc aacttgggtt    300

gtgtacggaa cctgccatca caaaaaaggt gaagcacgga gatctagaag agctgtgacg    360

ctcccctccc attccactag gaagctgcaa acgcggtcgc aaacctggtt ggaatcaaga    420

gaatacacaa agcacttgat tagagtcgaa aattggatat tcaggaaccc tggcttcgcg    480

ttagcagcag ctgccatcgc ttggcttttg ggaagctcaa cgagccaaaa agtcatatac    540

ttggtcatga tactgctgat tgccccggca tacagcatca ggtgcatagg agtcagcaat    600

agggactttg tggaaggtat gtcaggtggg acttgggttg atgttgtctt ggaacatgga    660

ggttgtgtca ccgtaatggc acaggacaaa ccgactgtcg acatagagct ggttacaaca    720

acagtcagca acatggcgga ggtaagatcc tactgctatg aggcatcaat atcagacatg    780

gcttcggaca gccgctgccc aacacaaggt gaagcctacc ttgacaagca atcagacact    840

caatatgtct gcaaaagaac gttagtggac agaggctggg gaaatggatg tggacttttt    900

ggcaaaggga gcctggtgac atgcgctaag tttgcatgct ccaagaaaat gaccgggaag    960

agcatccagc cagagaatct ggagtaccgg ataatgctgt cagttcatgg ctcccagcac   1020

agtgggatga tcgttaatga cacaggacat gaaactgatg agaatagagc gaaggttgag   1080

ataacgccca attcaccaag agccgaagcc accctggggg gttttggaag cctaggactt   1140

gattgtgaac cgaggacagg ccttgacttt tcagatttgt attacttgac tatgaataac   1200

aagcactggt tggttcacaa ggagtggttc cacgacattc cattaccttg gcacgctggg   1260

gcagacaccg gaactccaca ctggaacaac aaagaagcac tggtagagtt caaggacgca   1320

catgccaaaa ggcaaactgt cgtggttcta gggagtcaag aaggagcagt tcacacggcc   1380

cttgctggag ctctggaggc tgagatggat ggtgcaaagg gaaggctgtc ctctggccac   1440

ttgaaatgtc gcctgaaaat ggataaactt agattgaagg gcgtgtcata ctccttgtgt   1500

accgcagcgt tcacattcac caagatcccg gctgaaacac tgcacgggac agtcacagtg   1560

gaggtacagt acgcagggac agatggacct tgcaaggttc cagctcagat ggcggtggac   1620

atgcaaactc tgaccccagt tgggaggttg ataaccgcta accccgtaat cactgaaagc   1680

actgagaact ctaagatgat gctggaactt gatccaccat ttggggactc ttacattgtc   1740

ataggagtcg gggagaagaa gatcacccac cactggcaca ggagtggcag caccattgga   1800

aaagcatttg aagccactgt gagaggtgcc aagagaatgg cagtcttggg agacacagcc   1860

tgggactttg gatcagttgg aggcgctctc aactcattgg gcaagggcat ccatcaaatt   1920

tttggagcag ctttcaaatc attgtgatga                                    1950
```

<210> SEQ ID NO 85
<211> LENGTH: 1950
<212> TYPE: DNA
<213> ORGANISM: Artificial sequence
<220> FEATURE:
<223> OTHER INFORMATION: Codon-optimized nucleotide sequence of JEVsp_Zika_prME_no_Anchor protein (B2)

<400> SEQUENCE: 85

```
atgggcaaga ggtccgcagg gagcattatg tggctggcat ctctggcagt cgtcatcgct     60

tgtgcaggag cagcagaggt gaccaggaga ggaagcgcct actatatgta cctggacagg    120

aatgatgccg gcgaggccat ctccttccca accacactgg gcatgaacaa gtgctacatc    180
```

```
cagatcatgg acctgggcca catgtgcgat gccaccatgt cctatgagtg tccaatgctg    240
gacgagggcg tggagcccga cgatgtggat tgctggtgta ataccacatc tacatgggtg    300
gtgtacggca cctgtcacca caagaaggga gaggcccggc ggagccggcg ggccgtgaca    360
ctgccttccc actctaccag gaagctgcag acacgcagcc agacctggct ggagtccaga    420
gagtatacca agcacctgat cagggtggag aactggatct ttcgcaatcc aggattcgca    480
ctggcagcag cagcaatcgc atggctgctg ggaagctcca ccagccagaa agtgatctac    540
ctggtcatga tcctgctgat cgctcctgcc tattctatcc ggtgcatcgg cgtgagcaat    600
agagacttcg tggagggaat gtccggagga acctgggtgg atgtggtgct ggagcacggc    660
ggctgcgtga cagtgatggc ccaggacaag ccaaccgtgg atatcgagct ggtgaccaca    720
accgtgtcca acatggccga ggtgaggtct tactgctatg aggccagcat ctccgacatg    780
gcctctgata gcaggtgtcc aacccaggga gaggcatacc tggacaagca gtccgataca    840
cagtacgtgt gcaagcggac cctggtggac agaggctggg gcaatggctg tggcctgttt    900
ggcaagggct ctctggtgac atgcgccaag ttcgcctgta gcaagaagat gaccggcaag    960
tccatccagc cagagaacct ggagtaccgg atcatgctgt ctgtgcacgg ctcccagcac   1020
tctggcatga tcgtgaacga cacaggccac gagacagatg agaatcgggc caaggtggag   1080
atcacaccta actctccaag agccgaggcc accctgggag gatttggctc tctgggcctg   1140
gactgcgagc ctagaacagg cctggacttc tccgatctgt actatctgac catgaacaat   1200
aagcactggc tggtgcacaa ggagtggttt cacgacatcc cactgccatg gcacgcagga   1260
gcagatacag gaacaccaca ctggaacaat aaggaggccc tggtggagtt caaggatgcc   1320
cacgccaagc ggcagacagt ggtggtgctg ggcagccagg agggagcagt gcacaccgcc   1380
ctggcaggcg ccctggaggc agagatggac ggagctaagg gcagactgtc tagcggccac   1440
ctgaagtgca ggctgaagat ggataagctg cgcctgaagg gcgtgtccta ctctctgtgc   1500
acagccgcct tcaccttcac caagatccct gccgagacac tgcacggcac agtgaccgtg   1560
gaggtgcagt atgccggcac agacggaccc tgtaaggtgc ctgcccagat ggccgtggat   1620
atgcagacac tgacacctgt gggcaggctg atcaccgcca atccagtgat cacagagtct   1680
accgagaaca gcaagatgat gctggagctg gacccaccat ttggcgatag ctatatcgtg   1740
atcggcgtgg gcgagaagaa gatcacacac cactggcacc gcagcggctc cacaatcggc   1800
aaggcctttg aggcaaccgt gcgcggagca aagagaatgg ccgtgctggg cgacaccgca   1860
tgggatttcg gatctgtggg aggcgccctg aacagcctgg gcaagggcat ccaccagatc   1920
ttcggcgccg cctttaagtc cctgtgatga                                    1950
```

<210> SEQ ID NO 86
<211> LENGTH: 648
<212> TYPE: PRT
<213> ORGANISM: Artificial sequence
<220> FEATURE:
<223> OTHER INFORMATION: JEVsp_Zika_prME_no_Anchor protein (B2)

<400> SEQUENCE: 86

```
Met Gly Lys Arg Ser Ala Gly Ser Ile Met Trp Leu Ala Ser Leu Ala
1               5                   10                  15

Val Val Ile Ala Cys Ala Gly Ala Ala Glu Val Thr Arg Arg Gly Ser
            20                  25                  30

Ala Tyr Tyr Met Tyr Leu Asp Arg Asn Asp Ala Gly Glu Ala Ile Ser
        35                  40                  45
```

```
Phe Pro Thr Thr Leu Gly Met Asn Lys Cys Tyr Ile Gln Ile Met Asp
    50                  55                  60

Leu Gly His Met Cys Asp Ala Thr Met Ser Tyr Glu Cys Pro Met Leu
65                  70                  75                  80

Asp Glu Gly Val Glu Pro Asp Asp Val Asp Cys Trp Cys Asn Thr Thr
                85                  90                  95

Ser Thr Trp Val Val Tyr Gly Thr Cys His His Lys Lys Gly Glu Ala
            100                 105                 110

Arg Arg Ser Arg Arg Ala Val Thr Leu Pro Ser His Ser Thr Arg Lys
        115                 120                 125

Leu Gln Thr Arg Ser Gln Thr Trp Leu Glu Ser Arg Glu Tyr Thr Lys
    130                 135                 140

His Leu Ile Arg Val Glu Asn Trp Ile Phe Arg Asn Pro Gly Phe Ala
145                 150                 155                 160

Leu Ala Ala Ala Ala Ile Ala Trp Leu Leu Gly Ser Ser Thr Ser Gln
                165                 170                 175

Lys Val Ile Tyr Leu Val Met Ile Leu Leu Ile Ala Pro Ala Tyr Ser
            180                 185                 190

Ile Arg Cys Ile Gly Val Ser Asn Arg Asp Phe Val Glu Gly Met Ser
        195                 200                 205

Gly Gly Thr Trp Val Asp Val Val Leu Glu His Gly Gly Cys Val Thr
    210                 215                 220

Val Met Ala Gln Asp Lys Pro Thr Val Asp Ile Glu Leu Val Thr Thr
225                 230                 235                 240

Thr Val Ser Asn Met Ala Glu Val Arg Ser Tyr Cys Tyr Glu Ala Ser
                245                 250                 255

Ile Ser Asp Met Ala Ser Asp Ser Arg Cys Pro Thr Gln Gly Glu Ala
            260                 265                 270

Tyr Leu Asp Lys Gln Ser Asp Thr Gln Tyr Val Cys Lys Arg Thr Leu
        275                 280                 285

Val Asp Arg Gly Trp Gly Asn Gly Cys Gly Leu Phe Gly Lys Gly Ser
    290                 295                 300

Leu Val Thr Cys Ala Lys Phe Ala Cys Ser Lys Lys Met Thr Gly Lys
305                 310                 315                 320

Ser Ile Gln Pro Glu Asn Leu Glu Tyr Arg Ile Met Leu Ser Val His
                325                 330                 335

Gly Ser Gln His Ser Gly Met Ile Val Asn Asp Thr Gly His Glu Thr
            340                 345                 350

Asp Glu Asn Arg Ala Lys Val Glu Ile Thr Pro Asn Ser Pro Arg Ala
        355                 360                 365

Glu Ala Thr Leu Gly Gly Phe Gly Ser Leu Gly Leu Asp Cys Glu Pro
    370                 375                 380

Arg Thr Gly Leu Asp Phe Ser Asp Leu Tyr Tyr Leu Thr Met Asn Asn
385                 390                 395                 400

Lys His Trp Leu Val His Lys Glu Trp Phe His Asp Ile Pro Leu Pro
                405                 410                 415

Trp His Ala Gly Ala Asp Thr Gly Thr Pro His Trp Asn Asn Lys Glu
            420                 425                 430

Ala Leu Val Glu Phe Lys Asp Ala His Ala Lys Arg Gln Thr Val Val
        435                 440                 445

Val Leu Gly Ser Gln Glu Gly Ala Val His Thr Ala Leu Ala Gly Ala
    450                 455                 460

Leu Glu Ala Glu Met Asp Gly Ala Lys Gly Arg Leu Ser Ser Gly His
```

-continued 465 470 475 480

Leu Lys Cys Arg Leu Lys Met Asp Lys Leu Arg Leu Lys Gly Val Ser
485 490 495

Tyr Ser Leu Cys Thr Ala Ala Phe Thr Phe Thr Lys Ile Pro Ala Glu
500 505 510

Thr Leu His Gly Thr Val Thr Val Glu Val Gln Tyr Ala Gly Thr Asp
515 520 525

Gly Pro Cys Lys Val Pro Ala Gln Met Ala Val Asp Met Gln Thr Leu
530 535 540

Thr Pro Val Gly Arg Leu Ile Thr Ala Asn Pro Val Ile Thr Glu Ser
545 550 555 560

Thr Glu Asn Ser Lys Met Met Leu Glu Leu Asp Pro Pro Phe Gly Asp
565 570 575

Ser Tyr Ile Val Ile Gly Val Gly Glu Lys Lys Ile Thr His His Trp
580 585 590

His Arg Ser Gly Ser Thr Ile Gly Lys Ala Phe Glu Ala Thr Val Arg
595 600 605

Gly Ala Lys Arg Met Ala Val Leu Gly Asp Thr Ala Trp Asp Phe Gly
610 615 620

Ser Val Gly Gly Ala Leu Asn Ser Leu Gly Lys Gly Ile His Gln Ile
625 630 635 640

Phe Gly Ala Ala Phe Lys Ser Leu
645

<210> SEQ ID NO 87
<211> LENGTH: 1914
<212> TYPE: DNA
<213> ORGANISM: Artificial sequence
<220> FEATURE:
<223> OTHER INFORMATION: Native nucleotide sequence of
JEVsp_Zika_prME411 protein (B3)

<400> SEQUENCE: 87
atgggcaaac gatcagccgg ctcaatcatg tggctcgcga gcttggcagt tgtcatagct 60
tgtgcaggag ccgcggaggt cactagacgt gggagtgcat actatatgta cttggacaga 120
aacgatgctg gggaggccat atcttttcca accacattgg ggatgaataa gtgttatata 180
cagatcatgg atcttggaca catgtgtgat gccaccatga gctatgaatg ccctatgctg 240
gatgaggggg tggaaccaga tgacgtcgat tgttggtgca acacgacgtc aacttgggtt 300
gtgtacggaa cctgccatca caaaaaaggt gaagcacgga gatctagaag agctgtgacg 360
ctcccctccc attccactag gaagctgcaa acgcggtcgc aaacctggtt ggaatcaaga 420
gaatacacaa agcacttgat tagagtcgaa aattggatat tcaggaaccc tggcttcgcg 480
ttagcagcag ctgccatcgc ttggcttttg ggaagctcaa cgagccaaaa agtcatatac 540
ttggtcatga tactgctgat tgccccggca tacagcatca ggtgcatagg agtcagcaat 600
agggactttg tggaaggtat gtcaggtggg acttgggttg atgttgtctt ggaacatgga 660
ggttgtgtca ccgtaatggc acaggacaaa ccgactgtcg acatagagct ggttacaaca 720
acagtcagca acatggcgga ggtaagatcc tactgctatg aggcatcaat atcagacatg 780
gcttcggaca gccgctgccc aacacaaggt gaagcctacc ttgacaagca atcagacact 840
caatatgtct gcaaaagaac gttagtggac agaggctggg gaaatggatg tggacttttt 900
ggcaaaggga gcctggtgac atgcgctaag tttgcatgct ccaagaaaat gaccgggaag 960
agcatccagc cagagaatct ggagtaccgg ataatgctgt cagttcatgg ctcccagcac 1020

```
agtgggatga tcgttaatga cacaggacat gaaactgatg agaatagagc gaaggttgag   1080

ataacgccca attcaccaag agccgaagcc accctggggg gttttggaag cctaggactt   1140

gattgtgaac cgaggacagg ccttgacttt tcagatttgt attacttgac tatgaataac   1200

aagcactggt tggttcacaa ggagtggttc cacgacattc cattaccttg gcacgctggg   1260

gcagacaccg gaactccaca ctggaacaac aaagaagcac tggtagagtt caaggacgca   1320

catgccaaaa ggcaaactgt cgtggttcta gggagtcaag aaggagcagt tcacacggcc   1380

cttgctggag ctctggaggc tgagatggat ggtgcaaagg gaaggctgtc ctctggccac   1440

ttgaaatgtc gcctgaaaat ggataaactt agattgaagg gcgtgtcata ctccttgtgt   1500

accgcagcgt tcacattcac caagatcccg gctgaaacac tgcacgggac agtcacagtg   1560

gaggtacagt acgcagggac agatggacct tgcaaggttc cagctcagat ggcggtggac   1620

atgcaaactc tgaccccagt tgggaggttg ataaccgcta accccgtaat cactgaaagc   1680

actgagaact ctaagatgat gctggaactt gatccaccat ttggggactc ttacattgtc   1740

ataggagtcg gggagaagaa gatcacccac cactggcaca ggagtggcag caccattgga   1800

aaagcatttg aagccactgt gagaggtgcc aagagaatgg cagtcttggg agacacagcc   1860

tgggactttg gatcagttgg aggcgctctc aactcattgg gcaagggcat ctga         1914
```

<210> SEQ ID NO 88
<211> LENGTH: 1914
<212> TYPE: DNA
<213> ORGANISM: Artificial sequence
<220> FEATURE:
<223> OTHER INFORMATION: Codon-optimized nucleotide sequence of JEVsp_Zika_prME411 protein (B3)

<400> SEQUENCE: 88

```
atgggcaaga ggtccgcagg gagcattatg tggctggcat ctctggcagt cgtcatcgct     60

tgtgcaggag cagcagaggt gaccaggaga ggaagcgcct actatatgta cctggacagg    120

aatgatgccg gcgaggccat ctccttccca accacactgg gcatgaacaa gtgctacatc    180

cagatcatgg acctgggcca catgtgcgat gccaccatgt cctatgagtg tccaatgctg    240

gacgagggcg tggagcccga cgatgtggat tgctggtgta ataccacatc tacatgggtg    300

gtgtacggca cctgtcacca caagaaggga gaggcccggc ggagccggcg ggccgtgaca    360

ctgccttccc actctaccag gaagctgcag acacgcagcc agacctggct ggagtccaga    420

gagtatacca agcacctgat cagggtggag aactggatct ttcgcaatcc aggattcgca    480

ctggcagcag cagcaatcgc atggctgctg ggaagctcca ccagccagaa agtgatctac    540

ctggtcatga tcctgctgat cgctcctgcc tattctatcc ggtgcatcgg cgtgagcaat    600

agagacttcg tggagggaat gtccggagga acctgggtgg atgtggtgct ggagcacggc    660

ggctgcgtga cagtgatggc ccaggacaag ccaaccgtgg atatcgagct ggtgaccaca    720

accgtgtcca acatggccga ggtgaggtct tactgctatg aggccagcat ctccgacatg    780

gcctctgata gcaggtgtcc aacccaggga gaggcatacc tggacaagca gtccgataca    840

cagtacgtgt gcaagcggac cctggtggac agaggctggg gcaatggctg tggcctgttt    900

ggcaagggct ctctggtgac atgcgccaag ttcgcctgta gcaagaagat gaccggcaag    960

tccatccagc cagagaacct ggagtaccgg atcatgctgt ctgtgcacgg ctcccagcac   1020

tctggcatga tcgtgaacga cacaggccac gagacagatg agaatcgggc caaggtggag   1080

atcacaccta actctccaag agccgaggcc accctgggag gatttggctc tctgggcctg   1140
```

gactgcgagc ctagaacagg cctggacttc tccgatctgt actatctgac catgaacaat 1200
aagcactggc tggtgcacaa ggagtggttt cacgacatcc cactgccatg gcacgcagga 1260
gcagatacag gaacaccaca ctggaacaat aaggaggccc tggtggagtt caaggatgcc 1320
cacgccaagc ggcagacagt ggtggtgctg ggcagccagg agggagcagt gcacaccgcc 1380
ctggcaggcg ccctggaggc agagatggac ggagctaagg gcagactgtc tagcggccac 1440
ctgaagtgca ggctgaagat ggataagctg cgcctgaagg gcgtgtccta ctctctgtgc 1500
acagccgcct tcaccttcac caagatccct gccgagacac tgcacggcac agtgaccgtg 1560
gaggtgcagt atgccggcac agacggaccc tgtaaggtgc ctgcccagat ggccgtggat 1620
atgcagacac tgacacctgt gggcaggctg atcaccgcca atccagtgat cacagagtct 1680
accgagaaca gcaagatgat gctggagctg gacccaccat ttggcgatag ctatatcgtg 1740
atcggcgtgg gcgagaagaa gatcacacac cactggcacc gcagcggctc cacaatcggc 1800
aaggcctttg aggcaaccgt gcgcggagca aagagaatgg ccgtgctggg cgacaccgca 1860
tgggatttcg gatctgtggg aggcgccctg aacagcctgg gcaagggcat ctga 1914

<210> SEQ ID NO 89
<211> LENGTH: 637
<212> TYPE: PRT
<213> ORGANISM: Artificial sequence
<220> FEATURE:
<223> OTHER INFORMATION: JEVsp_Zika_prME411 protein (B3)

<400> SEQUENCE: 89

Met Gly Lys Arg Ser Ala Gly Ser Ile Met Trp Leu Ala Ser Leu Ala
1 5 10 15

Val Val Ile Ala Cys Ala Gly Ala Ala Glu Val Thr Arg Arg Gly Ser
20 25 30

Ala Tyr Tyr Met Tyr Leu Asp Arg Asn Asp Ala Gly Glu Ala Ile Ser
35 40 45

Phe Pro Thr Thr Leu Gly Met Asn Lys Cys Tyr Ile Gln Ile Met Asp
50 55 60

Leu Gly His Met Cys Asp Ala Thr Met Ser Tyr Glu Cys Pro Met Leu
65 70 75 80

Asp Glu Gly Val Glu Pro Asp Asp Val Asp Cys Trp Cys Asn Thr Thr
85 90 95

Ser Thr Trp Val Val Tyr Gly Thr Cys His His Lys Lys Gly Glu Ala
100 105 110

Arg Arg Ser Arg Arg Ala Val Thr Leu Pro Ser His Ser Thr Arg Lys
115 120 125

Leu Gln Thr Arg Ser Gln Thr Trp Leu Glu Ser Arg Glu Tyr Thr Lys
130 135 140

His Leu Ile Arg Val Glu Asn Trp Ile Phe Arg Asn Pro Gly Phe Ala
145 150 155 160

Leu Ala Ala Ala Ala Ile Ala Trp Leu Leu Gly Ser Ser Thr Ser Gln
165 170 175

Lys Val Ile Tyr Leu Val Met Ile Leu Leu Ile Ala Pro Ala Tyr Ser
180 185 190

Ile Arg Cys Ile Gly Val Ser Asn Arg Asp Phe Val Glu Gly Met Ser
195 200 205

Gly Gly Thr Trp Val Asp Val Val Leu Glu His Gly Gly Cys Val Thr
210 215 220

```
Val Met Ala Gln Asp Lys Pro Thr Val Asp Ile Glu Leu Val Thr Thr
225                 230                 235                 240

Thr Val Ser Asn Met Ala Glu Val Arg Ser Tyr Cys Tyr Glu Ala Ser
                245                 250                 255

Ile Ser Asp Met Ala Ser Asp Ser Arg Cys Pro Thr Gln Gly Glu Ala
            260                 265                 270

Tyr Leu Asp Lys Gln Ser Asp Thr Gln Tyr Val Cys Lys Arg Thr Leu
        275                 280                 285

Val Asp Arg Gly Trp Gly Asn Gly Cys Gly Leu Phe Gly Lys Gly Ser
    290                 295                 300

Leu Val Thr Cys Ala Lys Phe Ala Cys Ser Lys Lys Met Thr Gly Lys
305                 310                 315                 320

Ser Ile Gln Pro Glu Asn Leu Glu Tyr Arg Ile Met Leu Ser Val His
                325                 330                 335

Gly Ser Gln His Ser Gly Met Ile Val Asn Asp Thr Gly His Glu Thr
            340                 345                 350

Asp Glu Asn Arg Ala Lys Val Glu Ile Thr Pro Asn Ser Pro Arg Ala
        355                 360                 365

Glu Ala Thr Leu Gly Gly Phe Gly Ser Leu Gly Leu Asp Cys Glu Pro
    370                 375                 380

Arg Thr Gly Leu Asp Phe Ser Asp Leu Tyr Tyr Leu Thr Met Asn Asn
385                 390                 395                 400

Lys His Trp Leu Val His Lys Glu Trp Phe His Asp Ile Pro Leu Pro
                405                 410                 415

Trp His Ala Gly Ala Asp Thr Gly Thr Pro His Trp Asn Asn Lys Glu
            420                 425                 430

Ala Leu Val Glu Phe Lys Asp Ala His Ala Lys Arg Gln Thr Val Val
        435                 440                 445

Val Leu Gly Ser Gln Glu Gly Ala Val His Thr Ala Leu Ala Gly Ala
    450                 455                 460

Leu Glu Ala Glu Met Asp Gly Ala Lys Gly Arg Leu Ser Ser Gly His
465                 470                 475                 480

Leu Lys Cys Arg Leu Lys Met Asp Lys Leu Arg Leu Lys Gly Val Ser
                485                 490                 495

Tyr Ser Leu Cys Thr Ala Ala Phe Thr Phe Thr Lys Ile Pro Ala Glu
            500                 505                 510

Thr Leu His Gly Thr Val Thr Val Glu Val Gln Tyr Ala Gly Thr Asp
        515                 520                 525

Gly Pro Cys Lys Val Pro Ala Gln Met Ala Val Asp Met Gln Thr Leu
    530                 535                 540

Thr Pro Val Gly Arg Leu Ile Thr Ala Asn Pro Val Ile Thr Glu Ser
545                 550                 555                 560

Thr Glu Asn Ser Lys Met Met Leu Glu Leu Asp Pro Pro Phe Gly Asp
                565                 570                 575

Ser Tyr Ile Val Ile Gly Val Gly Glu Lys Lys Ile Thr His His Trp
            580                 585                 590

His Arg Ser Gly Ser Thr Ile Gly Lys Ala Phe Glu Ala Thr Val Arg
        595                 600                 605

Gly Ala Lys Arg Met Ala Val Leu Gly Asp Thr Ala Trp Asp Phe Gly
    610                 615                 620

Ser Val Gly Gly Ala Leu Asn Ser Leu Gly Lys Gly Ile
625                 630                 635
```

<210> SEQ ID NO 90
<211> LENGTH: 1794
<212> TYPE: DNA
<213> ORGANISM: Artificial sequence
<220> FEATURE:
<223> OTHER INFORMATION: Native nucleotide sequence of
JEVsp_Zika_prME395 protein (B4)

<400> SEQUENCE: 90

```
atgggcaaac gatcagccgg ctcaatcatg tggctcgcga gcttggcagt tgtcatagct     60

tgtgcaggag ccgcggaggt cactagacgt gggagtgcat actatatgta cttggacaga    120

aacgatgctg gggaggccat atcttttcca accacattgg ggatgaataa gtgttatata    180

cagatcatgg atcttggaca catgtgtgat gccaccatga gctatgaatg ccctatgctg    240

gatgaggggg tggaaccaga tgacgtcgat tgttggtgca acacgacgtc aacttgggtt    300

gtgtacggaa cctgccatca caaaaaaggt gaagcacgga gatctagaag agctgtgacg    360

ctcccctccc attccactag gaagctgcaa acgcggtcgc aaacctggtt ggaatcaaga    420

gaatacacaa agcacttgat tagagtcgaa aattggatat tcaggaaccc tggcttcgcg    480

ttagcagcag ctgccatcgc ttggcttttg ggaagctcaa cgagccaaaa agtcatatac    540

ttggtcatga tactgctgat tgccccggca tacagcatca ggtgcatagg agtcagcaat    600

agggactttg tggaaggtat gtcaggtggg acttgggttg atgttgtctt ggaacatgga    660

ggttgtgtca ccgtaatggc acaggacaaa ccgactgtcg acatagagct ggttacaaca    720

acagtcagca acatggcgga ggtaagatcc tactgctatg aggcatcaat atcagacatg    780

gcttcggaca gccgctgccc aacacaaggt gaagcctacc ttgacaagca atcagacact    840

caatatgtct gcaaaagaac gttagtggac agaggctggg gaaatggatg tggacttttt    900

ggcaaaggga gcctggtgac atgcgctaag tttgcatgct ccaagaaaat gaccgggaag    960

agcatccagc cagagaatct ggagtaccgg ataatgctgt cagttcatgg ctcccagcac   1020

agtgggatga tcgttaatga cacaggacat gaaactgatg agaatagagc gaaggttgag   1080

ataacgccca attcaccaag agccgaagcc accctggggg gttttggaag cctaggactt   1140

gattgtgaac cgaggacagg ccttgacttt tcagatttgt attacttgac tatgaataac   1200

aagcactggt tggttcacaa ggagtggttc cacgacattc cattaccttg gcacgctggg   1260

gcagacaccg gaactccaca ctggaacaac aaagaagcac tggtagagtt caaggacgca   1320

catgccaaaa ggcaaactgt cgtggttcta gggagtcaag aaggagcagt tcacacggcc   1380

cttgctggag ctctggaggc tgagatggat ggtgcaaagg gaaggctgtc ctctggccac   1440

ttgaaatgtc gcctgaaaat ggataaactt agattgaagg gcgtgtcata ctccttgtgt   1500

accgcagcgt tcacattcac caagatcccg gctgaaacac tgcacgggac agtcacagtg   1560

gaggtacagt acgcagggac agatggacct tgcaaggttc cagctcagat ggcggtggac   1620

atgcaaactc tgaccccagt tgggaggttg ataaccgcta accccgtaat cactgaaagc   1680

actgagaact ctaagatgat gctggaactt gatccaccat ttggggactc ttacattgtc   1740

ataggagtcg gggagaagaa gatcacccac cactggcaca ggagtggctg atga         1794
```

<210> SEQ ID NO 91
<211> LENGTH: 1794
<212> TYPE: DNA
<213> ORGANISM: Artificial sequence
<220> FEATURE:
<223> OTHER INFORMATION: Codon-optimized nucleotide sequence of
JEVsp_Zika_prME395 protein (B4)

<400> SEQUENCE: 91
atgggcaaga ggtccgcagg gagcattatg tggctggcat ctctggcagt cgtcatcgct 60
tgtgcaggag cagcagaggt gaccaggaga ggaagcgcct actatatgta cctggacagg 120
aatgatgccg gcgaggccat ctccttccca accacactgg gcatgaacaa gtgctacatc 180
cagatcatgg acctgggcca catgtgcgat gccaccatgt cctatgagtg tccaatgctg 240
gacgagggcg tggagcccga cgatgtggat tgctggtgta ataccacatc tacatgggtg 300
gtgtacggca cctgtcacca caagaaggga gaggcccggc ggagccggcg ggccgtgaca 360
ctgccttccc actctaccag gaagctgcag acacgcagcc agacctggct ggagtccaga 420
gagtatacca agcacctgat cagggtggag aactggatct ttcgcaatcc aggattcgca 480
ctggcagcag cagcaatcgc atggctgctg ggaagctcca ccagccagaa agtgatctac 540
ctggtcatga tcctgctgat cgctcctgcc tattctatcc ggtgcatcgg cgtgagcaat 600
agagacttcg tggagggaat gtccggagga acctgggtgg atgtggtgct ggagcacggc 660
ggctgcgtga cagtgatggc ccaggacaag ccaaccgtgg atatcgagct ggtgaccaca 720
accgtgtcca acatggccga ggtgaggtct tactgctatg aggccagcat ctccgacatg 780
gcctctgata gcaggtgtcc aacccaggga gaggcatacc tggacaagca gtccgataca 840
cagtacgtgt gcaagcggac cctggtggac agaggctggg gcaatggctg tggcctgttt 900
ggcaagggct ctctggtgac atgcgccaag ttcgcctgta gcaagaagat gaccggcaag 960
tccatccagc cagagaacct ggagtaccgg atcatgctgt ctgtgcacgg ctcccagcac 1020
tctggcatga tcgtgaacga cacaggccac gagacagatg agaatcgggc caaggtggag 1080
atcacaccta actctccaag agccgaggcc accctgggag gatttggctc tctgggcctg 1140
gactgcgagc ctagaacagg cctggacttc tccgatctgt actatctgac catgaacaat 1200
aagcactggc tggtgcacaa ggagtggttt cacgacatcc cactgccatg gcacgcagga 1260
gcagatacag gaacaccaca ctggaacaat aaggaggccc tggtggagtt caaggatgcc 1320
cacgccaagc ggcagacagt ggtggtgctg ggcagccagg agggagcagt gcacaccgcc 1380
ctggcaggcg ccctggaggc agagatggac ggagctaagg gcagactgtc tagcggccac 1440
ctgaagtgca ggctgaagat ggataagctg cgcctgaagg gcgtgtccta ctctctgtgc 1500
acagccgcct tcaccttcac caagatccct gccgagacac tgcacggcac agtgaccgtg 1560
gaggtgcagt atgccggcac agacggaccc tgtaaggtgc ctgcccagat ggccgtggat 1620
atgcagacac tgacacctgt gggcaggctg atcaccgcca atccagtgat cacagagtct 1680
accgagaaca gcaagatgat gctggagctg gacccaccat ttggcgatag ctatatcgtg 1740
atcggcgtgg gcgagaagaa gatcacacac cactggcacc gcagcggctg atga 1794

<210> SEQ ID NO 92
<211> LENGTH: 596
<212> TYPE: PRT
<213> ORGANISM: Artificial sequence
<220> FEATURE:
<223> OTHER INFORMATION: JEVsp_Zika_prME395 protein (B4)

<400> SEQUENCE: 92

Met Gly Lys Arg Ser Ala Gly Ser Ile Met Trp Leu Ala Ser Leu Ala
1 5 10 15

Val Val Ile Ala Cys Ala Gly Ala Ala Glu Val Thr Arg Arg Gly Ser
20 25 30

Ala Tyr Tyr Met Tyr Leu Asp Arg Asn Asp Ala Gly Glu Ala Ile Ser

```
        35                  40                  45

Phe Pro Thr Thr Leu Gly Met Asn Lys Cys Tyr Ile Gln Ile Met Asp
    50                  55                  60

Leu Gly His Met Cys Asp Ala Thr Met Ser Tyr Glu Cys Pro Met Leu
65                  70                  75                  80

Asp Glu Gly Val Glu Pro Asp Asp Val Asp Cys Trp Cys Asn Thr Thr
                85                  90                  95

Ser Thr Trp Val Val Tyr Gly Thr Cys His His Lys Lys Gly Glu Ala
            100                 105                 110

Arg Arg Ser Arg Arg Ala Val Thr Leu Pro Ser His Ser Thr Arg Lys
        115                 120                 125

Leu Gln Thr Arg Ser Gln Thr Trp Leu Glu Ser Arg Glu Tyr Thr Lys
    130                 135                 140

His Leu Ile Arg Val Glu Asn Trp Ile Phe Arg Asn Pro Gly Phe Ala
145                 150                 155                 160

Leu Ala Ala Ala Ala Ile Ala Trp Leu Leu Gly Ser Ser Thr Ser Gln
                165                 170                 175

Lys Val Ile Tyr Leu Val Met Ile Leu Leu Ile Ala Pro Ala Tyr Ser
            180                 185                 190

Ile Arg Cys Ile Gly Val Ser Asn Arg Asp Phe Val Glu Gly Met Ser
        195                 200                 205

Gly Gly Thr Trp Val Asp Val Val Leu Glu His Gly Gly Cys Val Thr
    210                 215                 220

Val Met Ala Gln Asp Lys Pro Thr Val Asp Ile Glu Leu Val Thr Thr
225                 230                 235                 240

Thr Val Ser Asn Met Ala Glu Val Arg Ser Tyr Cys Tyr Glu Ala Ser
                245                 250                 255

Ile Ser Asp Met Ala Ser Asp Ser Arg Cys Pro Thr Gln Gly Glu Ala
            260                 265                 270

Tyr Leu Asp Lys Gln Ser Asp Thr Gln Tyr Val Cys Lys Arg Thr Leu
        275                 280                 285

Val Asp Arg Gly Trp Gly Asn Gly Cys Gly Leu Phe Gly Lys Gly Ser
    290                 295                 300

Leu Val Thr Cys Ala Lys Phe Ala Cys Ser Lys Lys Met Thr Gly Lys
305                 310                 315                 320

Ser Ile Gln Pro Glu Asn Leu Glu Tyr Arg Ile Met Leu Ser Val His
                325                 330                 335

Gly Ser Gln His Ser Gly Met Ile Val Asn Asp Thr Gly His Glu Thr
            340                 345                 350

Asp Glu Asn Arg Ala Lys Val Glu Ile Thr Pro Asn Ser Pro Arg Ala
        355                 360                 365

Glu Ala Thr Leu Gly Gly Phe Gly Ser Leu Gly Leu Asp Cys Glu Pro
    370                 375                 380

Arg Thr Gly Leu Asp Phe Ser Asp Leu Tyr Tyr Leu Thr Met Asn Asn
385                 390                 395                 400

Lys His Trp Leu Val His Lys Glu Trp Phe His Asp Ile Pro Leu Pro
                405                 410                 415

Trp His Ala Gly Ala Asp Thr Gly Thr Pro His Trp Asn Asn Lys Glu
            420                 425                 430

Ala Leu Val Glu Phe Lys Asp Ala His Ala Lys Arg Gln Thr Val Val
        435                 440                 445

Val Leu Gly Ser Gln Glu Gly Ala Val His Thr Ala Leu Ala Gly Ala
    450                 455                 460
```

```
Leu Glu Ala Glu Met Asp Gly Ala Lys Gly Arg Leu Ser Ser Gly His
465                 470                 475                 480

Leu Lys Cys Arg Leu Lys Met Asp Lys Leu Arg Leu Lys Gly Val Ser
                485                 490                 495

Tyr Ser Leu Cys Thr Ala Ala Phe Thr Phe Thr Lys Ile Pro Ala Glu
            500                 505                 510

Thr Leu His Gly Thr Val Thr Val Glu Val Gln Tyr Ala Gly Thr Asp
        515                 520                 525

Gly Pro Cys Lys Val Pro Ala Gln Met Ala Val Asp Met Gln Thr Leu
    530                 535                 540

Thr Pro Val Gly Arg Leu Ile Thr Ala Asn Pro Val Ile Thr Glu Ser
545                 550                 555                 560

Thr Glu Asn Ser Lys Met Met Leu Glu Leu Asp Pro Pro Phe Gly Asp
                565                 570                 575

Ser Tyr Ile Val Ile Gly Val Gly Glu Lys Lys Ile Thr His His Trp
            580                 585                 590

His Arg Ser Gly
        595
```

<210> SEQ ID NO 93
<211> LENGTH: 1590
<212> TYPE: DNA
<213> ORGANISM: Artificial sequence
<220> FEATURE:
<223> OTHER INFORMATION: Native nucleotide sequence of JEVsp_ZikaE protein (B5)

<400> SEQUENCE: 93

```
atgggcaaac gatcagccgg ctcaatcatg tggctcgcga gcttggcagt tgtcatagct     60

tgtgcaggag ccatcaggtg cataggagtc agcaataggg actttgtgga aggtatgtca    120

ggtgggactt gggttgatgt tgtcttggaa catggaggtt gtgtcaccgt aatggcacag    180

gacaaaccga ctgtcgacat agagctggtt acaacaacag tcagcaacat ggcggaggta    240

agatcctact gctatgaggc atcaatatca gacatggctt cggacagccg ctgcccaaca    300

caaggtgaag cctaccttga caagcaatca gacactcaat atgtctgcaa aagaacgtta    360

gtggacagag gctggggaaa tggatgtgga ctttttggca aagggagcct ggtgacatgc    420

gctaagtttg catgctccaa gaaaatgacc gggaagagca tccagccaga gaatctggag    480

taccggataa tgctgtcagt tcatggctcc cagcacagtg ggatgatcgt taatgacaca    540

ggacatgaaa ctgatgagaa tagagcgaag gttgagataa cgcccaattc accaagagcc    600

gaagccaccc tgggggggttt tggaagccta ggacttgatt gtgaaccgag gacaggcctt    660

gacttttcag atttgtatta cttgactatg aataacaagc actggttggt tcacaaggag    720

tggttccacg acattccatt accttggcac gctggggcag acaccggaac tccacactgg    780

aacaacaaag aagcactggt agagttcaag gacgcacatg ccaaaaggca aactgtcgtg    840

gttctaggga gtcaagaagg agcagttcac acggcccttg ctggagctct ggaggctgag    900

atggatggtg caaagggaag gctgtcctct ggccacttga aatgtcgcct gaaaatggat    960

aaacttagat tgaagggcgt gtcatactcc ttgtgtaccg cagcgttcac attcaccaag   1020

atcccggctg aaacactgca cgggacagtc acagtggagg tacagtacgc agggacagat   1080

ggaccttgca aggttccagc tcagatggcg gtggacatgc aaactctgac cccagttggg   1140

aggttgataa ccgctaaccc cgtaatcact gaaagcactg agaactctaa gatgatgctg   1200
```

gaacttgatc caccatttgg ggactcttac attgtcatag gagtcgggga gaagaagatc 1260
acccaccact ggcacaggag tggcagcacc attggaaaag catttgaagc cactgtgaga 1320
ggtgccaaga gaatggcagt cttgggagac acagcctggg actttggatc agttggaggc 1380
gctctcaact cattgggcaa gggcatccat caaatttttg gagcagcttt caaatcattg 1440
tttggaggaa tgtcctggtt ctcacaaatt ctcattggaa cgttgctgat gtggttgggt 1500
ctgaacacaa agaatggatc tatttccctt atgtgcttgg ccttaggggg agtgttgatc 1560
ttcttatcca cagccgtctc tgcttgatga 1590

<210> SEQ ID NO 94
<211> LENGTH: 1590
<212> TYPE: DNA
<213> ORGANISM: Artificial sequence
<220> FEATURE:
<223> OTHER INFORMATION: Codon-optimized nucleotide sequence of JEVsp_ZikaE protein (B5)

<400> SEQUENCE: 94
atgggcaaga ggtccgcagg gagcattatg tggctggcat ctctggcagt cgtcatcgct 60
tgtgcaggag caatccggtg catcggcgtg agcaatagag acttcgtgga gggaatgtcc 120
ggaggaacct gggtggatgt ggtgctggag cacggcggct gcgtgacagt gatggcccag 180
gacaagccaa ccgtggatat cgagctggtg accacaaccg tgtccaacat ggccgaggtg 240
aggtcttact gctatgaggc cagcatctcc gacatggcct ctgatagcag gtgtccaacc 300
cagggagagg catacctgga caagcagtcc gatacacagt acgtgtgcaa gcggaccctg 360
gtggacagag gctggggcaa tggctgtggc ctgtttggca agggctctct ggtgacatgc 420
gccaagttcg cctgtagcaa gaagatgacc ggcaagtcca tccagccaga gaacctggag 480
taccggatca tgctgtctgt gcacggctcc cagcactctg gcatgatcgt gaacgacaca 540
ggccacgaga cagatgagaa tcgggccaag gtggagatca cacctaactc tccaagagcc 600
gaggccaccc tgggaggatt tggctctctg ggcctggact gcgagcctag aacaggcctg 660
gacttctccg atctgtacta tctgaccatg aacaataagc actggctggt gcacaaggag 720
tggtttcacg acatcccact gccatggcac gcaggagcag atacaggaac accacactgg 780
aacaataagg aggccctggt ggagttcaag gatgcccacg ccaagcggca gacagtggtg 840
gtgctgggca gccaggaggg agcagtgcac accgccctgg caggcgccct ggaggcagag 900
atggacggag ctaagggcag actgtctagc ggccacctga agtgcaggct gaagatggat 960
aagctgcgcc tgaagggcgt gtcctactct ctgtgcacag ccgccttcac cttcaccaag 1020
atccctgccg agacactgca cggcacagtg accgtggagg tgcagtatgc cggcacagac 1080
ggaccctgta aggtgcctgc ccagatggcc gtggatatgc agacactgac acctgtgggc 1140
aggctgatca ccgccaatcc agtgatcaca gagtctaccg agaacagcaa gatgatgctg 1200
gagctggacc caccatttgg cgatagctat atcgtgatcg gcgtgggcga gaagaagatc 1260
acacaccact ggcaccgcag cggctccaca atcggcaagg cctttgaggc aaccgtgcgc 1320
ggagcaaaga gaatggccgt gctgggcgac accgcatggg atttcggatc tgtgggaggc 1380
gccctgaaca gcctgggcaa gggcatccac cagatcttcg gcgccgcctt taagtccctg 1440
ttcggcggca tgagctggtt ctcacagatc ctgatcggca cactgctgat gtggctgggc 1500
ctgaacacca agaatggctc tatcagcctg atgtgcctgg ccctgggagg cgtgctgatc 1560
ttcctgtcca ccgccgtgtc tgcctgatga 1590

<210> SEQ ID NO 95
<211> LENGTH: 528
<212> TYPE: PRT
<213> ORGANISM: Artificial sequence
<220> FEATURE:
<223> OTHER INFORMATION: JEVsp_ZikaE protein (B5)

<400> SEQUENCE: 95

```
Met Gly Lys Arg Ser Ala Gly Ser Ile Met Trp Leu Ala Ser Leu Ala
1               5                   10                  15

Val Val Ile Ala Cys Ala Gly Ala Ile Arg Cys Ile Gly Val Ser Asn
            20                  25                  30

Arg Asp Phe Val Glu Gly Met Ser Gly Gly Thr Trp Val Asp Val Val
        35                  40                  45

Leu Glu His Gly Gly Cys Val Thr Val Met Ala Gln Asp Lys Pro Thr
    50                  55                  60

Val Asp Ile Glu Leu Val Thr Thr Thr Val Ser Asn Met Ala Glu Val
65                  70                  75                  80

Arg Ser Tyr Cys Tyr Glu Ala Ser Ile Ser Asp Met Ala Ser Asp Ser
                85                  90                  95

Arg Cys Pro Thr Gln Gly Glu Ala Tyr Leu Asp Lys Gln Ser Asp Thr
            100                 105                 110

Gln Tyr Val Cys Lys Arg Thr Leu Val Asp Arg Gly Trp Gly Asn Gly
        115                 120                 125

Cys Gly Leu Phe Gly Lys Gly Ser Leu Val Thr Cys Ala Lys Phe Ala
    130                 135                 140

Cys Ser Lys Lys Met Thr Gly Lys Ser Ile Gln Pro Glu Asn Leu Glu
145                 150                 155                 160

Tyr Arg Ile Met Leu Ser Val His Gly Ser Gln His Ser Gly Met Ile
                165                 170                 175

Val Asn Asp Thr Gly His Glu Thr Asp Glu Asn Arg Ala Lys Val Glu
            180                 185                 190

Ile Thr Pro Asn Ser Pro Arg Ala Glu Ala Thr Leu Gly Gly Phe Gly
        195                 200                 205

Ser Leu Gly Leu Asp Cys Glu Pro Arg Thr Gly Leu Asp Phe Ser Asp
    210                 215                 220

Leu Tyr Tyr Leu Thr Met Asn Asn Lys His Trp Leu Val His Lys Glu
225                 230                 235                 240

Trp Phe His Asp Ile Pro Leu Pro Trp His Ala Gly Ala Asp Thr Gly
                245                 250                 255

Thr Pro His Trp Asn Asn Lys Glu Ala Leu Val Glu Phe Lys Asp Ala
            260                 265                 270

His Ala Lys Arg Gln Thr Val Val Val Leu Gly Ser Gln Glu Gly Ala
        275                 280                 285

Val His Thr Ala Leu Ala Gly Ala Leu Glu Ala Glu Met Asp Gly Ala
    290                 295                 300

Lys Gly Arg Leu Ser Ser Gly His Leu Lys Cys Arg Leu Lys Met Asp
305                 310                 315                 320

Lys Leu Arg Leu Lys Gly Val Ser Tyr Ser Leu Cys Thr Ala Ala Phe
                325                 330                 335

Thr Phe Thr Lys Ile Pro Ala Glu Thr Leu His Gly Thr Val Thr Val
            340                 345                 350

Glu Val Gln Tyr Ala Gly Thr Asp Gly Pro Cys Lys Val Pro Ala Gln
        355                 360                 365
```

-continued

```
Met Ala Val Asp Met Gln Thr Leu Thr Pro Val Gly Arg Leu Ile Thr
    370                 375                 380

Ala Asn Pro Val Ile Thr Glu Ser Thr Glu Asn Ser Lys Met Met Leu
385                 390                 395                 400

Glu Leu Asp Pro Pro Phe Gly Asp Ser Tyr Ile Val Ile Gly Val Gly
                405                 410                 415

Glu Lys Lys Ile Thr His His Trp His Arg Ser Gly Ser Thr Ile Gly
            420                 425                 430

Lys Ala Phe Glu Ala Thr Val Arg Gly Ala Lys Arg Met Ala Val Leu
        435                 440                 445

Gly Asp Thr Ala Trp Asp Phe Gly Ser Val Gly Gly Ala Leu Asn Ser
    450                 455                 460

Leu Gly Lys Gly Ile His Gln Ile Phe Gly Ala Ala Phe Lys Ser Leu
465                 470                 475                 480

Phe Gly Gly Met Ser Trp Phe Ser Gln Ile Leu Ile Gly Thr Leu Leu
                485                 490                 495

Met Trp Leu Gly Leu Asn Thr Lys Asn Gly Ser Ile Ser Leu Met Cys
            500                 505                 510

Leu Ala Leu Gly Gly Val Leu Ile Phe Leu Ser Thr Ala Val Ser Ala
        515                 520                 525
```

<210> SEQ ID NO 96
<211> LENGTH: 1446
<212> TYPE: DNA
<213> ORGANISM: Artificial sequence
<220> FEATURE:
<223> OTHER INFORMATION: Native nucleotide sequence of
      JEVsp_ZikaE_no_Anchor protein (B6)

<400> SEQUENCE: 96

```
atgggcaaac gatcagccgg ctcaatcatg tggctcgcga gcttggcagt tgtcatagct     60

tgtgcaggag ccatcaggtg cataggagtc agcaataggg actttgtgga aggtatgtca    120

ggtgggactt gggttgatgt tgtcttggaa catggaggtt gtgtcaccgt aatggcacag    180

gacaaaccga ctgtcgacat agagctggtt acaacaacag tcagcaacat ggcggaggta    240

agatcctact gctatgaggc atcaatatca gacatggctt cggacagccg ctgcccaaca    300

caaggtgaag cctaccttga caagcaatca gacactcaat atgtctgcaa aagaacgtta    360

gtggacagag gctggggaaa tggatgtgga ctttttggca aagggagcct ggtgacatgc    420

gctaagtttg catgctccaa gaaaatgacc gggaagagca tccagccaga gaatctggag    480

taccggataa tgctgtcagt tcatggctcc cagcacagtg ggatgatcgt taatgacaca    540

ggacatgaaa ctgatgagaa tagagcgaag gttgagataa cgcccaattc accaagagcc    600

gaagccaccc tggggggttt tggaagccta ggacttgatt gtgaaccgag gacaggcctt    660

gacttttcag atttgtatta cttgactatg aataacaagc actggttggt tcacaaggag    720

tggttccacg acattccatt accttggcac gctggggcag acaccggaac tccacactgg    780

aacaacaaag aagcactggt agagttcaag gacgcacatg ccaaaaggca aactgtcgtg    840

gttctaggga gtcaagaagg agcagttcac acggcccttg ctggagctct ggaggctgag    900

atggatggtg caaagggaag gctgtcctct ggccacttga aatgtcgcct gaaaatggat    960

aaacttagat tgaagggcgt gtcatactcc ttgtgtaccg cagcgttcac attcaccaag   1020

atcccggctg aaacactgca cgggacagtc acagtggagg tacagtacgc agggacagat   1080

ggaccttgca aggttccagc tcagatggcg gtggacatgc aaactctgac cccagttggg   1140
```

aggttgataa ccgctaaccc cgtaatcact gaaagcactg agaactctaa gatgatgctg 1200
gaacttgatc caccatttgg ggactcttac attgtcatag gagtcgggga gaagaagatc 1260
acccaccact ggcacaggag tggcagcacc attggaaaag catttgaagc cactgtgaga 1320
ggtgccaaga gaatggcagt cttgggagac acagcctggg actttggatc agttggaggc 1380
gctctcaact cattgggcaa gggcatccat caaatttttg gagcagcttt caaatcattg 1440
tgatga 1446

<210> SEQ ID NO 97
<211> LENGTH: 1446
<212> TYPE: DNA
<213> ORGANISM: Artificial sequence
<220> FEATURE:
<223> OTHER INFORMATION: Codon-optimized nucleotide sequence of JEVsp_ZikaE_no_Anchor protein (B6)

<400> SEQUENCE: 97
atgggcaaga ggtccgcagg gagcattatg tggctggcat ctctggcagt cgtcatcgct 60
tgtgcaggag caatccggtg catcggcgtg agcaatagag acttcgtgga gggaatgtcc 120
ggaggaacct gggtggatgt ggtgctggag cacggcggct gcgtgacagt gatggcccag 180
gacaagccaa ccgtggatat cgagctggtg accacaaccg tgtccaacat ggccgaggtg 240
aggtcttact gctatgaggc cagcatctcc gacatggcct ctgatagcag gtgtccaacc 300
cagggagagg catacctgga caagcagtcc gatacacagt acgtgtgcaa gcggaccctg 360
gtggacagag gctggggcaa tggctgtggc ctgtttggca agggctctct ggtgacatgc 420
gccaagttcg cctgtagcaa gaagatgacc ggcaagtcca tccagccaga gaacctggag 480
taccggatca tgctgtctgt gcacggctcc cagcactctg gcatgatcgt gaacgacaca 540
ggccacgaga cagatgagaa tcgggccaag gtggagatca cacctaactc tccaagagcc 600
gaggccaccc tgggaggatt tggctctctg ggcctggact gcgagcctag aacaggcctg 660
gacttctccg atctgtacta tctgaccatg aacaataagc actggctggt gcacaaggag 720
tggtttcacg acatcccact gccatggcac gcaggagcag atacaggaac accacactgg 780
aacaataagg aggccctggt ggagttcaag gatgcccacg ccaagcggca gacagtggtg 840
gtgctgggca gccaggaggg agcagtgcac accgccctgg caggcgccct ggaggcagag 900
atggacggag ctaagggcag actgtctagc ggccacctga agtgcaggct gaagatggat 960
aagctgcgcc tgaagggcgt gtcctactct ctgtgcacag ccgccttcac cttcaccaag 1020
atccctgccg agacactgca cggcacagtg accgtggagg tgcagtatgc cggcacagac 1080
ggaccctgta aggtgcctgc ccagatggcc gtggatatgc agacactgac acctgtgggc 1140
aggctgatca ccgccaatcc agtgatcaca gagtctaccg agaacagcaa gatgatgctg 1200
gagctggacc caccatttgg cgatagctat atcgtgatcg gcgtgggcga gaagaagatc 1260
acacaccact ggcaccgcag cggctccaca atcggcaagg cctttgaggc aaccgtgcgc 1320
ggagcaaaga gaatggccgt gctgggcgac accgcatggg atttcggatc tgtgggaggc 1380
gccctgaaca gcctgggcaa gggcatccac cagatcttcg gcgccgcctt taagtccctg 1440
tgatga 1446

<210> SEQ ID NO 98
<211> LENGTH: 480
<212> TYPE: PRT
<213> ORGANISM: Artificial sequence
<220> FEATURE:

<223> OTHER INFORMATION: JEVsp_ZikaE_no_Anchor protein (B6)

<400> SEQUENCE: 98

```
Met Gly Lys Arg Ser Ala Gly Ser Ile Met Trp Leu Ala Ser Leu Ala
1               5                   10                  15

Val Val Ile Ala Cys Ala Gly Ala Ile Arg Cys Ile Gly Val Ser Asn
            20                  25                  30

Arg Asp Phe Val Glu Gly Met Ser Gly Gly Thr Trp Val Asp Val Val
        35                  40                  45

Leu Glu His Gly Gly Cys Val Thr Val Met Ala Gln Asp Lys Pro Thr
    50                  55                  60

Val Asp Ile Glu Leu Val Thr Thr Thr Val Ser Asn Met Ala Glu Val
65                  70                  75                  80

Arg Ser Tyr Cys Tyr Glu Ala Ser Ile Ser Asp Met Ala Ser Asp Ser
                85                  90                  95

Arg Cys Pro Thr Gln Gly Glu Ala Tyr Leu Asp Lys Gln Ser Asp Thr
            100                 105                 110

Gln Tyr Val Cys Lys Arg Thr Leu Val Asp Arg Gly Trp Gly Asn Gly
        115                 120                 125

Cys Gly Leu Phe Gly Lys Gly Ser Leu Val Thr Cys Ala Lys Phe Ala
    130                 135                 140

Cys Ser Lys Lys Met Thr Gly Lys Ser Ile Gln Pro Glu Asn Leu Glu
145                 150                 155                 160

Tyr Arg Ile Met Leu Ser Val His Gly Ser Gln His Ser Gly Met Ile
                165                 170                 175

Val Asn Asp Thr Gly His Glu Thr Asp Glu Asn Arg Ala Lys Val Glu
            180                 185                 190

Ile Thr Pro Asn Ser Pro Arg Ala Glu Ala Thr Leu Gly Gly Phe Gly
        195                 200                 205

Ser Leu Gly Leu Asp Cys Glu Pro Arg Thr Gly Leu Asp Phe Ser Asp
    210                 215                 220

Leu Tyr Tyr Leu Thr Met Asn Asn Lys His Trp Leu Val His Lys Glu
225                 230                 235                 240

Trp Phe His Asp Ile Pro Leu Pro Trp His Ala Gly Ala Asp Thr Gly
                245                 250                 255

Thr Pro His Trp Asn Asn Lys Glu Ala Leu Val Glu Phe Lys Asp Ala
            260                 265                 270

His Ala Lys Arg Gln Thr Val Val Val Leu Gly Ser Gln Glu Gly Ala
        275                 280                 285

Val His Thr Ala Leu Ala Gly Ala Leu Glu Ala Glu Met Asp Gly Ala
    290                 295                 300

Lys Gly Arg Leu Ser Ser Gly His Leu Lys Cys Arg Leu Lys Met Asp
305                 310                 315                 320

Lys Leu Arg Leu Lys Gly Val Ser Tyr Ser Leu Cys Thr Ala Ala Phe
                325                 330                 335

Thr Phe Thr Lys Ile Pro Ala Glu Thr Leu His Gly Thr Val Thr Val
            340                 345                 350

Glu Val Gln Tyr Ala Gly Thr Asp Gly Pro Cys Lys Val Pro Ala Gln
        355                 360                 365

Met Ala Val Asp Met Gln Thr Leu Thr Pro Val Gly Arg Leu Ile Thr
    370                 375                 380

Ala Asn Pro Val Ile Thr Glu Ser Thr Glu Asn Ser Lys Met Met Leu
385                 390                 395                 400
```

-continued

```
Glu Leu Asp Pro Pro Phe Gly Asp Ser Tyr Ile Val Ile Gly Val Gly
                405                 410                 415

Glu Lys Lys Ile Thr His His Trp His Arg Ser Gly Ser Thr Ile Gly
            420                 425                 430

Lys Ala Phe Glu Ala Thr Val Arg Gly Ala Lys Arg Met Ala Val Leu
        435                 440                 445

Gly Asp Thr Ala Trp Asp Phe Gly Ser Val Gly Gly Ala Leu Asn Ser
    450                 455                 460

Leu Gly Lys Gly Ile His Gln Ile Phe Gly Ala Ala Phe Lys Ser Leu
465                 470                 475                 480


<210> SEQ ID NO 99
<211> LENGTH: 1410
<212> TYPE: DNA
<213> ORGANISM: Artificial sequence
<220> FEATURE:
<223> OTHER INFORMATION: Native nucleotide sequence of JEVsp_ZikaE411
      protein (B7)

<400> SEQUENCE: 99

atgggcaaac gatcagccgg ctcaatcatg tggctcgcga gcttggcagt tgtcatagct     60

tgtgcaggag ccatcaggtg cataggagtc agcaataggg actttgtgga aggtatgtca    120

ggtgggactt gggttgatgt tgtcttggaa catggaggtt gtgtcaccgt aatggcacag    180

gacaaaccga ctgtcgacat agagctggtt acaacaacag tcagcaacat ggcggaggta    240

agatcctact gctatgaggc atcaatatca gacatggctt cggacagccg ctgcccaaca    300

caaggtgaag cctaccttga caagcaatca gacactcaat atgtctgcaa aagaacgtta    360

gtggacagag gctggggaaa tggatgtgga ctttttggca aagggagcct ggtgacatgc    420

gctaagtttg catgctccaa gaaaatgacc gggaagagca tccagccaga gaatctggag    480

taccggataa tgctgtcagt tcatggctcc cagcacagtg ggatgatcgt taatgacaca    540

ggacatgaaa ctgatgagaa tagagcgaag gttgagataa cgcccaattc accaagagcc    600

gaagccaccc tgggggggttt tggaagccta ggacttgatt gtgaaccgag gacaggcctt    660

gacttttcag atttgtatta cttgactatg aataacaagc actggttggt tcacaaggag    720

tggttccacg acattccatt accttggcac gctggggcag acaccggaac tccacactgg    780

aacaacaaag aagcactggt agagttcaag gacgcacatg ccaaaaggca aactgtcgtg    840

gttctaggga gtcaagaagg agcagttcac acggcccttg ctggagctct ggaggctgag    900

atggatggtg caaagggaag gctgtcctct ggccacttga aatgtcgcct gaaaatggat    960

aaacttagat tgaagggcgt gtcatactcc ttgtgtaccg cagcgttcac attcaccaag   1020

atcccggctg aaacactgca cgggacagtc acagtggagg tacagtacgc agggacagat   1080

ggaccttgca aggttccagc tcagatggcg gtggacatgc aaactctgac cccagttggg   1140

aggttgataa ccgctaaccc cgtaatcact gaaagcactg agaactctaa gatgatgctg   1200

gaacttgatc caccatttgg ggactcttac attgtcatag gagtcgggga gaagaagatc   1260

acccaccact ggcacaggag tggcagcacc attggaaaag catttgaagc cactgtgaga   1320

ggtgccaaga gaatggcagt cttgggagac acagcctggg actttggatc agttggaggc   1380

gctctcaact cattgggcaa gggcatctga                                     1410


<210> SEQ ID NO 100
<211> LENGTH: 1410
<212> TYPE: DNA
<213> ORGANISM: Artificial sequence
```

<220> FEATURE:
<223> OTHER INFORMATION: Codon-optimized nucleotide sequence of
JEVsp_ZikaE411 protein (B7)

<400> SEQUENCE: 100
atgggcaaga ggtccgcagg gagcattatg tggctggcat ctctggcagt cgtcatcgct 60
tgtgcaggag caatccggtg catcggcgtg agcaatagag acttcgtgga gggaatgtcc 120
ggaggaacct gggtggatgt ggtgctggag cacggcggct gcgtgacagt gatggcccag 180
gacaagccaa ccgtggatat cgagctggtg accacaaccg tgtccaacat ggccgaggtg 240
aggtcttact gctatgaggc cagcatctcc gacatggcct ctgatagcag gtgtccaacc 300
cagggagagg catacctgga caagcagtcc gatacacagt acgtgtgcaa gcggaccctg 360
gtggacagag gctggggcaa tggctgtggc ctgtttggca agggctctct ggtgacatgc 420
gccaagttcg cctgtagcaa gaagatgacc ggcaagtcca tccagccaga gaacctggag 480
taccggatca tgctgtctgt gcacggctcc cagcactctg gcatgatcgt gaacgacaca 540
ggccacgaga cagatgagaa tcgggccaag gtggagatca cacctaactc tccaagagcc 600
gaggccaccc tgggaggatt tggctctctg ggcctggact gcgagcctag aacaggcctg 660
gacttctccg atctgtacta tctgaccatg aacaataagc actggctggt gcacaaggag 720
tggtttcacg acatccccact gccatggcac gcaggagcag atacaggaac accacactgg 780
aacaataagg aggccctggt ggagttcaag gatgcccacg ccaagcggca gacagtggtg 840
gtgctgggca gccaggaggg agcagtgcac accgccctgg caggcgccct ggaggcagag 900
atggacggag ctaagggcag actgtctagc ggccacctga agtgcaggct gaagatggat 960
aagctgcgcc tgaagggcgt gtcctactct ctgtgcacag ccgccttcac cttcaccaag 1020
atccctgccg agacactgca cggcacagtg accgtggagg tgcagtatgc cggcacagac 1080
ggaccctgta aggtgcctgc ccagatggcc gtggatatgc agacactgac acctgtgggc 1140
aggctgatca ccgccaatcc agtgatcaca gagtctaccg agaacagcaa gatgatgctg 1200
gagctggacc caccatttgg cgatagctat atcgtgatcg gcgtgggcga gaagaagatc 1260
acacaccact ggcaccgcag cggctccaca atcggcaagg cctttgaggc aaccgtgcgc 1320
ggagcaaaga gaatggccgt gctgggcgac accgcatggg atttcggatc tgtgggaggc 1380
gccctgaaca gcctgggcaa gggcatctga 1410

<210> SEQ ID NO 101
<211> LENGTH: 469
<212> TYPE: PRT
<213> ORGANISM: Artificial sequence
<220> FEATURE:
<223> OTHER INFORMATION: JEVsp_ZikaE411 protein (B7)

<400> SEQUENCE: 101

Met Gly Lys Arg Ser Ala Gly Ser Ile Met Trp Leu Ala Ser Leu Ala
1 5 10 15

Val Val Ile Ala Cys Ala Gly Ala Ile Arg Cys Ile Gly Val Ser Asn
20 25 30

Arg Asp Phe Val Glu Gly Met Ser Gly Gly Thr Trp Val Asp Val Val
35 40 45

Leu Glu His Gly Gly Cys Val Thr Val Met Ala Gln Asp Lys Pro Thr
50 55 60

Val Asp Ile Glu Leu Val Thr Thr Thr Val Ser Asn Met Ala Glu Val
65 70 75 80

```
Arg Ser Tyr Cys Tyr Glu Ala Ser Ile Ser Asp Met Ala Ser Asp Ser
                85                  90                  95

Arg Cys Pro Thr Gln Gly Glu Ala Tyr Leu Asp Lys Gln Ser Asp Thr
            100                 105                 110

Gln Tyr Val Cys Lys Arg Thr Leu Val Asp Arg Gly Trp Gly Asn Gly
        115                 120                 125

Cys Gly Leu Phe Gly Lys Gly Ser Leu Val Thr Cys Ala Lys Phe Ala
    130                 135                 140

Cys Ser Lys Lys Met Thr Gly Lys Ser Ile Gln Pro Glu Asn Leu Glu
145                 150                 155                 160

Tyr Arg Ile Met Leu Ser Val His Gly Ser Gln His Ser Gly Met Ile
                165                 170                 175

Val Asn Asp Thr Gly His Glu Thr Asp Glu Asn Arg Ala Lys Val Glu
            180                 185                 190

Ile Thr Pro Asn Ser Pro Arg Ala Glu Ala Thr Leu Gly Gly Phe Gly
        195                 200                 205

Ser Leu Gly Leu Asp Cys Glu Pro Arg Thr Gly Leu Asp Phe Ser Asp
    210                 215                 220

Leu Tyr Tyr Leu Thr Met Asn Asn Lys His Trp Leu Val His Lys Glu
225                 230                 235                 240

Trp Phe His Asp Ile Pro Leu Pro Trp His Ala Gly Ala Asp Thr Gly
                245                 250                 255

Thr Pro His Trp Asn Asn Lys Glu Ala Leu Val Glu Phe Lys Asp Ala
            260                 265                 270

His Ala Lys Arg Gln Thr Val Val Val Leu Gly Ser Gln Glu Gly Ala
        275                 280                 285

Val His Thr Ala Leu Ala Gly Ala Leu Glu Ala Glu Met Asp Gly Ala
    290                 295                 300

Lys Gly Arg Leu Ser Ser Gly His Leu Lys Cys Arg Leu Lys Met Asp
305                 310                 315                 320

Lys Leu Arg Leu Lys Gly Val Ser Tyr Ser Leu Cys Thr Ala Ala Phe
                325                 330                 335

Thr Phe Thr Lys Ile Pro Ala Glu Thr Leu His Gly Thr Val Thr Val
            340                 345                 350

Glu Val Gln Tyr Ala Gly Thr Asp Gly Pro Cys Lys Val Pro Ala Gln
        355                 360                 365

Met Ala Val Asp Met Gln Thr Leu Thr Pro Val Gly Arg Leu Ile Thr
    370                 375                 380

Ala Asn Pro Val Ile Thr Glu Ser Thr Glu Asn Ser Lys Met Met Leu
385                 390                 395                 400

Glu Leu Asp Pro Pro Phe Gly Asp Ser Tyr Ile Val Ile Gly Val Gly
                405                 410                 415

Glu Lys Lys Ile Thr His His Trp His Arg Ser Gly Ser Thr Ile Gly
            420                 425                 430

Lys Ala Phe Glu Ala Thr Val Arg Gly Ala Lys Arg Met Ala Val Leu
        435                 440                 445

Gly Asp Thr Ala Trp Asp Phe Gly Ser Val Gly Gly Ala Leu Asn Ser
    450                 455                 460

Leu Gly Lys Gly Ile
465
```

<210> SEQ ID NO 102
<211> LENGTH: 1290
<212> TYPE: DNA

<213> ORGANISM: Artificial sequence
<220> FEATURE:
<223> OTHER INFORMATION: Native nucleotide sequence of JEVsp_ZikaE395
protein (B8)

<400> SEQUENCE: 102
atgggcaaac gatcagccgg ctcaatcatg tggctcgcga gcttggcagt tgtcatagct 60
tgtgcaggag ccatcaggtg cataggagtc agcaataggg actttgtgga aggtatgtca 120
ggtgggactt gggttgatgt tgtcttggaa catggaggtt gtgtcaccgt aatggcacag 180
gacaaaccga ctgtcgacat agagctggtt acaacaacag tcagcaacat ggcggaggta 240
agatcctact gctatgaggc atcaatatca gacatggctt cggacagccg ctgcccaaca 300
caaggtgaag cctaccttga caagcaatca gacactcaat atgtctgcaa aagaacgtta 360
gtggacagag gctggggaaa tggatgtgga ctttttggca aagggagcct ggtgacatgc 420
gctaagtttg catgctccaa gaaaatgacc gggaagagca tccagccaga gaatctggag 480
taccggataa tgctgtcagt tcatggctcc cagcacagtg ggatgatcgt taatgacaca 540
ggacatgaaa ctgatgagaa tagagcgaag gttgagataa cgcccaattc accaagagcc 600
gaagccaccc tgggggggttt tggaagccta ggacttgatt gtgaaccgag gacaggcctt 660
gacttttcag atttgtatta cttgactatg aataacaagc actggttggt tcacaaggag 720
tggttccacg acattccatt accttggcac gctggggcag acaccggaac tccacactgg 780
aacaacaaag aagcactggt agagttcaag gacgcacatg ccaaaaggca aactgtcgtg 840
gttctaggga gtcaagaagg agcagttcac acggcccttg ctggagctct ggaggctgag 900
atggatggtg caaagggaag gctgtcctct ggccacttga aatgtcgcct gaaaatggat 960
aaacttagat tgaagggcgt gtcatactcc ttgtgtaccg cagcgttcac attcaccaag 1020
atcccggctg aaacactgca cgggacagtc acagtggagg tacagtacgc agggacagat 1080
ggaccttgca aggttccagc tcagatggcg gtggacatgc aaactctgac cccagttggg 1140
aggttgataa ccgctaaccc cgtaatcact gaaagcactg agaactctaa gatgatgctg 1200
gaacttgatc caccatttgg ggactcttac attgtcatag gagtcgggga gaagaagatc 1260
acccaccact ggcacaggag tggctgatga 1290

<210> SEQ ID NO 103
<211> LENGTH: 1290
<212> TYPE: DNA
<213> ORGANISM: Artificial sequence
<220> FEATURE:
<223> OTHER INFORMATION: Codon-optimized nucleotide sequence of
JEVsp_ZikaE395 protein (B8)

<400> SEQUENCE: 103
atgggcaaga ggtccgcagg gagcattatg tggctggcat ctctggcagt cgtcatcgct 60
tgtgcaggag caatccggtg catcggcgtg agcaatagag acttcgtgga gggaatgtcc 120
ggaggaacct gggtggatgt ggtgctggag cacggcggct gcgtgacagt gatggcccag 180
gacaagccaa ccgtggatat cgagctggtg accacaaccg tgtccaacat ggccgaggtg 240
aggtcttact gctatgaggc cagcatctcc gacatggcct ctgatagcag gtgtccaacc 300
cagggagagg catacctgga caagcagtcc gatacacagt acgtgtgcaa gcggaccctg 360
gtggacagag gctggggcaa tggctgtggc ctgtttggca agggctctct ggtgacatgc 420
gccaagttcg cctgtagcaa gaagatgacc ggcaagtcca tccagccaga gaacctggag 480
taccggatca tgctgtctgt gcacggctcc cagcactctg gcatgatcgt gaacgacaca 540

```
ggccacgaga cagatgagaa tcgggccaag gtggagatca cacctaactc tccaagagcc    600

gaggccaccc tgggaggatt tggctctctg ggcctggact gcgagcctag aacaggcctg    660

gacttctccg atctgtacta tctgaccatg aacaataagc actggctggt gcacaaggag    720

tggtttcacg acatccccact gccatggcac gcaggagcag atacaggaac accacactgg    780

aacaataagg aggccctggt ggagttcaag gatgcccacg ccaagcggca gacagtggtg    840

gtgctgggca gccaggaggg agcagtgcac accgccctgg caggcgccct ggaggcagag    900

atggacggag ctaagggcag actgtctagc ggccacctga agtgcaggct gaagatggat    960

aagctgcgcc tgaagggcgt gtcctactct ctgtgcacag ccgccttcac cttcaccaag   1020

atccctgccg agacactgca cggcacagtg accgtggagg tgcagtatgc cggcacagac   1080

ggaccctgta aggtgcctgc ccagatggcc gtggatatgc agacactgac acctgtgggc   1140

aggctgatca ccgccaatcc agtgatcaca gagtctaccg agaacagcaa gatgatgctg   1200

gagctggacc caccatttgg cgatagctat atcgtgatcg gcgtgggcga gaagaagatc   1260

acacaccact ggcaccgcag cggctgatga                                     1290
```

<210> SEQ ID NO 104
<211> LENGTH: 428
<212> TYPE: PRT
<213> ORGANISM: Artificial sequence
<220> FEATURE:
<223> OTHER INFORMATION: JEVsp_ZikaE395 protein (B8)

<400> SEQUENCE: 104

```
Met Gly Lys Arg Ser Ala Gly Ser Ile Met Trp Leu Ala Ser Leu Ala
1               5                   10                  15

Val Val Ile Ala Cys Ala Gly Ala Ile Arg Cys Ile Gly Val Ser Asn
            20                  25                  30

Arg Asp Phe Val Glu Gly Met Ser Gly Gly Thr Trp Val Asp Val Val
        35                  40                  45

Leu Glu His Gly Gly Cys Val Thr Val Met Ala Gln Asp Lys Pro Thr
    50                  55                  60

Val Asp Ile Glu Leu Val Thr Thr Thr Val Ser Asn Met Ala Glu Val
65                  70                  75                  80

Arg Ser Tyr Cys Tyr Glu Ala Ser Ile Ser Asp Met Ala Ser Asp Ser
                85                  90                  95

Arg Cys Pro Thr Gln Gly Glu Ala Tyr Leu Asp Lys Gln Ser Asp Thr
            100                 105                 110

Gln Tyr Val Cys Lys Arg Thr Leu Val Asp Arg Gly Trp Gly Asn Gly
        115                 120                 125

Cys Gly Leu Phe Gly Lys Gly Ser Leu Val Thr Cys Ala Lys Phe Ala
    130                 135                 140

Cys Ser Lys Lys Met Thr Gly Lys Ser Ile Gln Pro Glu Asn Leu Glu
145                 150                 155                 160

Tyr Arg Ile Met Leu Ser Val His Gly Ser Gln His Ser Gly Met Ile
                165                 170                 175

Val Asn Asp Thr Gly His Glu Thr Asp Glu Asn Arg Ala Lys Val Glu
            180                 185                 190

Ile Thr Pro Asn Ser Pro Arg Ala Glu Ala Thr Leu Gly Gly Phe Gly
        195                 200                 205

Ser Leu Gly Leu Asp Cys Glu Pro Arg Thr Gly Leu Asp Phe Ser Asp
    210                 215                 220
```

-continued

```
Leu Tyr Tyr Leu Thr Met Asn Asn Lys His Trp Leu Val His Lys Glu
225                 230                 235                 240

Trp Phe His Asp Ile Pro Leu Pro Trp His Ala Gly Ala Asp Thr Gly
                245                 250                 255

Thr Pro His Trp Asn Asn Lys Glu Ala Leu Val Glu Phe Lys Asp Ala
            260                 265                 270

His Ala Lys Arg Gln Thr Val Val Val Leu Gly Ser Gln Glu Gly Ala
        275                 280                 285

Val His Thr Ala Leu Ala Gly Ala Leu Glu Ala Glu Met Asp Gly Ala
    290                 295                 300

Lys Gly Arg Leu Ser Ser Gly His Leu Lys Cys Arg Leu Lys Met Asp
305                 310                 315                 320

Lys Leu Arg Leu Lys Gly Val Ser Tyr Ser Leu Cys Thr Ala Ala Phe
                325                 330                 335

Thr Phe Thr Lys Ile Pro Ala Glu Thr Leu His Gly Thr Val Thr Val
            340                 345                 350

Glu Val Gln Tyr Ala Gly Thr Asp Gly Pro Cys Lys Val Pro Ala Gln
        355                 360                 365

Met Ala Val Asp Met Gln Thr Leu Thr Pro Val Gly Arg Leu Ile Thr
    370                 375                 380

Ala Asn Pro Val Ile Thr Glu Ser Thr Glu Asn Ser Lys Met Met Leu
385                 390                 395                 400

Glu Leu Asp Pro Pro Phe Gly Asp Ser Tyr Ile Val Ile Gly Val Gly
                405                 410                 415

Glu Lys Lys Ile Thr His His Trp His Arg Ser Gly
            420                 425
```

<210> SEQ ID NO 105
<211> LENGTH: 2106
<212> TYPE: DNA
<213> ORGANISM: Artificial sequence
<220> FEATURE:
<223> OTHER INFORMATION: Native nucleotide sequence of MVsp_ZikaprME (C1)

<400> SEQUENCE: 105

```
atgtccatca tgggtctcaa ggtgaacgtc tctgccatat tcatggcagt actgttaact     60

ctccaaacac ccaccggtca aatccatgcg gaggtcacta gacgtgggag tgcatactat    120

atgtacttgg acagaaacga tgctggggag gccatatctt ttccaaccac attggggatg    180

aataagtgtt atatacagat catggatctt ggacacatgt gtgatgccac catgagctat    240

gaatgcccta tgctggatga gggggtggaa ccagatgacg tcgattgttg gtgcaacacg    300

acgtcaactt gggttgtgta cggaacctgc catcacaaaa aaggtgaagc acggagatct    360

agaagagctg tgacgctccc ctcccattcc actaggaagc tgcaaacgcg gtcgcaaacc    420

tggttggaat caagagaata cacaaagcac ttgattagag tcgaaaattg gatattcagg    480

aaccctggct tcgcgttagc agcagctgcc atcgcttggc ttttgggaag ctcaacgagc    540

caaaaagtca tatacttggt catgatactg ctgattgccc cggcatacag catcaggtgc    600

ataggagtca gcaataggga ctttgtggaa ggtatgtcag gtgggacttg ggttgatgtt    660

gtcttggaac atggaggttg tgtcaccgta atggcacagg acaaaccgac tgtcgacata    720

gagctggtta caacaacagt cagcaacatg gcggaggtaa gatcctactg ctatgaggca    780

tcaatatcag acatggcttc ggacagccgc tgcccaacac aaggtgaagc ctaccttgac    840

aagcaatcag acactcaata tgtctgcaaa agaacgttag tggacagagg ctggggaaat    900
```

ggatgtggac tttttggcaa agggagcctg gtgacatgcg ctaagtttgc atgctccaag 960
aaaatgaccg ggaagagcat ccagccagag aatctggagt accggataat gctgtcagtt 1020
catggctccc agcacagtgg gatgatcgtt aatgacacag gacatgaaac tgatgagaat 1080
agagcgaagg ttgagataac gcccaattca ccaagagccg aagccaccct ggggggtttt 1140
ggaagcctag gacttgattg tgaaccgagg acaggccttg acttttcaga tttgtattac 1200
ttgactatga ataacaagca ctggttggtt cacaaggagt ggttccacga cattccatta 1260
ccttggcacg ctggggcaga caccggaact ccacactgga acaacaaaga agcactggta 1320
gagttcaagg acgcacatgc caaaaggcaa actgtcgtgg ttctagggag tcaagaagga 1380
gcagttcaca cggcccttgc tggagctctg gaggctgaga tggatggtgc aaagggaagg 1440
ctgtcctctg gccacttgaa atgtcgcctg aaaatggata aacttagatt gaagggcgtg 1500
tcatactcct tgtgtaccgc agcgttcaca ttcaccaaga tcccggctga aacactgcac 1560
gggacagtca cagtggaggt acagtacgca gggacagatg gaccttgcaa ggttccagct 1620
cagatggcgg tggacatgca aactctgacc ccagttggga ggttgataac cgctaacccc 1680
gtaatcactg aaagcactga gaactctaag atgatgctgg aacttgatcc accatttggg 1740
gactcttaca ttgtcatagg agtcggggag aagaagatca cccaccactg gcacaggagt 1800
ggcagcacca ttggaaaagc atttgaagcc actgtgagag gtgccaagag aatggcagtc 1860
ttgggagaca cagcctggga ctttggatca gttggaggcg ctctcaactc attgggcaag 1920
ggcatccatc aaatttttgg agcagctttc aaatcattgt ttggaggaat gtcctggttc 1980
tcacaaattc tcattggaac gttgctgatg tggttgggtc tgaacacaaa gaatggatct 2040
atttccctta tgtgcttggc cttaggggga gtgttgatct tcttatccac agccgtctct 2100
gcttga 2106

<210> SEQ ID NO 106
<211> LENGTH: 2106
<212> TYPE: DNA
<213> ORGANISM: Artificial sequence
<220> FEATURE:
<223> OTHER INFORMATION: Codon-optimized nucleotide sequence of MVsp_ZikaprME (C1)

<400> SEQUENCE: 106
atgagcatca tgggcctgaa ggtgaacgtg tccgccatct tcatggccgt gctgctgacc 60
ctgcagacac caacaggcca gatccacgca gaggtgacca ggagaggaag cgcctactat 120
atgtacctgg acaggaatga tgccggcgag gccatctcct tcccaaccac actgggcatg 180
aacaagtgct acatccagat catggacctg ggccacatgt gcgatgccac catgtcctat 240
gagtgtccaa tgctggacga gggcgtggag cccgacgatg tggattgctg gtgtaatacc 300
acatctacat gggtggtgta cggcacctgt caccacaaga agggagaggc ccggcggagc 360
cggcgggccg tgacactgcc ttcccactct accaggaagc tgcagacacg cagccagacc 420
tggctggagt ccagagagta taccaagcac ctgatcaggg tggagaactg gatctttcgc 480
aatccaggat tcgcactggc agcagcagca atcgcatggc tgctgggaag ctccaccagc 540
cagaaagtga tctacctggt catgatcctg ctgatcgctc ctgcctattc tatccggtgc 600
atcggcgtga gcaatagaga cttcgtggag ggaatgtccg gaggaacctg ggtggatgtg 660
gtgctggagc acggcggctg cgtgacagtg atggcccagg acaagccaac cgtggatatc 720
gagctggtga ccacaaccgt gtccaacatg gccgaggtga ggtcttactg ctatgaggcc 780
agcatctccg acatggcctc tgatagcagg tgtccaaccc agggagaggc atacctggac 840
aagcagtccg atacacagta cgtgtgcaag cggaccctgg tggacagagg ctggggcaat 900
ggctgtggcc tgtttggcaa gggctctctg gtgacatgcg ccaagttcgc ctgtagcaag 960
aagatgaccg gcaagtccat ccagccagag aacctggagt accggatcat gctgtctgtg 1020
cacggctccc agcactctgg catgatcgtg aacgacacag gccacgagac agatgagaat 1080
cgggccaagg tggagatcac acctaactct ccaagagccg aggccaccct gggaggattt 1140
ggctctctgg gcctggactg cgagcctaga acaggcctgg acttctccga tctgtactat 1200
ctgaccatga acaataagca ctggctggtg cacaaggagt ggtttcacga catcccactg 1260
ccatggcacg caggagcaga tacaggaaca ccacactgga acaataagga ggccctggtg 1320
gagttcaagg atgcccacgc caagcggcag acagtggtgg tgctgggcag ccaggaggga 1380
gcagtgcaca ccgccctggc aggcgccctg gaggcagaga tggacggagc taagggcaga 1440
ctgtctagcg gccacctgaa gtgcaggctg aagatggata agctgcgcct gaagggcgtg 1500
tcctactctc tgtgcacagc cgccttcacc ttcaccaaga tccctgccga gacactgcac 1560
ggcacagtga ccgtggaggt gcagtatgcc ggcacagacg gaccctgtaa ggtgcctgcc 1620
cagatggccg tggatatgca gacactgaca cctgtgggca ggctgatcac cgccaatcca 1680
gtgatcacag agtctaccga gaacagcaag atgatgctgg agctggaccc accatttggc 1740
gatagctata tcgtgatcgg cgtgggcgag aagaagatca cacaccactg gcaccgcagc 1800
ggctccacaa tcggcaaggc ctttgaggca accgtgcgcg gagcaaagag aatggccgtg 1860
ctgggcgaca ccgcatggga tttcggatct gtgggaggcg ccctgaacag cctgggcaag 1920
ggcatccacc agatcttcgg cgccgccttt aagtccctgt tcggcggcat gagctggttc 1980
tcacagatcc tgatcggcac actgctgatg tggctgggcc tgaacaccaa gaatggctct 2040
atcagcctga tgtgcctggc cctgggaggc gtgctgatct tcctgtccac cgccgtgtct 2100
gcctga 2106

<210> SEQ ID NO 107
<211> LENGTH: 701
<212> TYPE: PRT
<213> ORGANISM: Artificial sequence
<220> FEATURE:
<223> OTHER INFORMATION: MVsp_ZikaprME (C1)

<400> SEQUENCE: 107

Met Ser Ile Met Gly Leu Lys Val Asn Val Ser Ala Ile Phe Met Ala
1 5 10 15

Val Leu Leu Thr Leu Gln Thr Pro Thr Gly Gln Ile His Ala Glu Val
20 25 30

Thr Arg Arg Gly Ser Ala Tyr Tyr Met Tyr Leu Asp Arg Asn Asp Ala
35 40 45

Gly Glu Ala Ile Ser Phe Pro Thr Thr Leu Gly Met Asn Lys Cys Tyr
50 55 60

Ile Gln Ile Met Asp Leu Gly His Met Cys Asp Ala Thr Met Ser Tyr
65 70 75 80

Glu Cys Pro Met Leu Asp Glu Gly Val Glu Pro Asp Asp Val Asp Cys
85 90 95

Trp Cys Asn Thr Thr Ser Thr Trp Val Val Tyr Gly Thr Cys His His
100 105 110

Lys Lys Gly Glu Ala Arg Arg Ser Arg Arg Ala Val Thr Leu Pro Ser

```
        115                 120                 125

His Ser Thr Arg Lys Leu Gln Thr Arg Ser Gln Thr Trp Leu Glu Ser
    130                 135                 140

Arg Glu Tyr Thr Lys His Leu Ile Arg Val Glu Asn Trp Ile Phe Arg
145                 150                 155                 160

Asn Pro Gly Phe Ala Leu Ala Ala Ala Ala Ile Ala Trp Leu Leu Gly
                165                 170                 175

Ser Ser Thr Ser Gln Lys Val Ile Tyr Leu Val Met Ile Leu Leu Ile
            180                 185                 190

Ala Pro Ala Tyr Ser Ile Arg Cys Ile Gly Val Ser Asn Arg Asp Phe
        195                 200                 205

Val Glu Gly Met Ser Gly Gly Thr Trp Val Asp Val Val Leu Glu His
    210                 215                 220

Gly Gly Cys Val Thr Val Met Ala Gln Asp Lys Pro Thr Val Asp Ile
225                 230                 235                 240

Glu Leu Val Thr Thr Thr Val Ser Asn Met Ala Glu Val Arg Ser Tyr
                245                 250                 255

Cys Tyr Glu Ala Ser Ile Ser Asp Met Ala Ser Asp Ser Arg Cys Pro
            260                 265                 270

Thr Gln Gly Glu Ala Tyr Leu Asp Lys Gln Ser Asp Thr Gln Tyr Val
        275                 280                 285

Cys Lys Arg Thr Leu Val Asp Arg Gly Trp Gly Asn Gly Cys Gly Leu
    290                 295                 300

Phe Gly Lys Gly Ser Leu Val Thr Cys Ala Lys Phe Ala Cys Ser Lys
305                 310                 315                 320

Lys Met Thr Gly Lys Ser Ile Gln Pro Glu Asn Leu Glu Tyr Arg Ile
                325                 330                 335

Met Leu Ser Val His Gly Ser Gln His Ser Gly Met Ile Val Asn Asp
            340                 345                 350

Thr Gly His Glu Thr Asp Glu Asn Arg Ala Lys Val Glu Ile Thr Pro
        355                 360                 365

Asn Ser Pro Arg Ala Glu Ala Thr Leu Gly Gly Phe Gly Ser Leu Gly
    370                 375                 380

Leu Asp Cys Glu Pro Arg Thr Gly Leu Asp Phe Ser Asp Leu Tyr Tyr
385                 390                 395                 400

Leu Thr Met Asn Asn Lys His Trp Leu Val His Lys Glu Trp Phe His
                405                 410                 415

Asp Ile Pro Leu Pro Trp His Ala Gly Ala Asp Thr Gly Thr Pro His
            420                 425                 430

Trp Asn Asn Lys Glu Ala Leu Val Glu Phe Lys Asp Ala His Ala Lys
        435                 440                 445

Arg Gln Thr Val Val Val Leu Gly Ser Gln Glu Gly Ala Val His Thr
    450                 455                 460

Ala Leu Ala Gly Ala Leu Glu Ala Glu Met Asp Gly Ala Lys Gly Arg
465                 470                 475                 480

Leu Ser Ser Gly His Leu Lys Cys Arg Leu Lys Met Asp Lys Leu Arg
                485                 490                 495

Leu Lys Gly Val Ser Tyr Ser Leu Cys Thr Ala Ala Phe Thr Phe Thr
            500                 505                 510

Lys Ile Pro Ala Glu Thr Leu His Gly Thr Val Thr Val Glu Val Gln
        515                 520                 525

Tyr Ala Gly Thr Asp Gly Pro Cys Lys Val Pro Ala Gln Met Ala Val
    530                 535                 540
```

```
Asp Met Gln Thr Leu Thr Pro Val Gly Arg Leu Ile Thr Ala Asn Pro
545                 550                 555                 560

Val Ile Thr Glu Ser Thr Glu Asn Ser Lys Met Met Leu Glu Leu Asp
                565                 570                 575

Pro Pro Phe Gly Asp Ser Tyr Ile Val Ile Gly Val Gly Glu Lys Lys
            580                 585                 590

Ile Thr His His Trp His Arg Ser Gly Ser Thr Ile Gly Lys Ala Phe
        595                 600                 605

Glu Ala Thr Val Arg Gly Ala Lys Arg Met Ala Val Leu Gly Asp Thr
    610                 615                 620

Ala Trp Asp Phe Gly Ser Val Gly Gly Ala Leu Asn Ser Leu Gly Lys
625                 630                 635                 640

Gly Ile His Gln Ile Phe Gly Ala Ala Phe Lys Ser Leu Phe Gly Gly
                645                 650                 655

Met Ser Trp Phe Ser Gln Ile Leu Ile Gly Thr Leu Leu Met Trp Leu
            660                 665                 670

Gly Leu Asn Thr Lys Asn Gly Ser Ile Ser Leu Met Cys Leu Ala Leu
        675                 680                 685

Gly Gly Val Leu Ile Phe Leu Ser Thr Ala Val Ser Ala
    690                 695                 700
```

<210> SEQ ID NO 108
<211> LENGTH: 1962
<212> TYPE: DNA
<213> ORGANISM: Artificial sequence
<220> FEATURE:
<223> OTHER INFORMATION: Native nucleotide sequence of
MVsp_Zika_prME_no_anchor (C2)

<400> SEQUENCE: 108

```
atgtccatca tgggtctcaa ggtgaacgtc tctgccatat tcatggcagt actgttaact     60

ctccaaacac ccaccggtca aatccatgcg gaggtcacta gacgtgggag tgcatactat    120

atgtacttgg acagaaacga tgctggggag gccatatctt ttccaaccac attggggatg    180

aataagtgtt atatacagat catggatctt ggacacatgt gtgatgccac catgagctat    240

gaatgcccta tgctggatga gggggtggaa ccagatgacg tcgattgttg gtgcaacacg    300

acgtcaactt gggttgtgta cggaacctgc catcacaaaa aaggtgaagc acggagatct    360

agaagagctg tgacgctccc ctcccattcc actaggaagc tgcaaacgcg gtcgcaaacc    420

tggttggaat caagagaata cacaaagcac ttgattagag tcgaaaattg gatattcagg    480

aaccctggct tcgcgttagc agcagctgcc atcgcttggc ttttgggaag ctcaacgagc    540

caaaaagtca tatacttggt catgatactg ctgattgccc cggcatacag catcaggtgc    600

ataggagtca gcaataggga ctttgtggaa ggtatgtcag gtgggacttg ggttgatgtt    660

gtcttggaac atggaggttg tgtcaccgta atggcacagg acaaaccgac tgtcgacata    720

gagctggtta caacaacagt cagcaacatg gcggaggtaa gatcctactg ctatgaggca    780

tcaatatcag acatggcttc ggacagccgc tgcccaacac aaggtgaagc ctaccttgac    840

aagcaatcag acactcaata tgtctgcaaa agaacgttag tggacagagg ctggggaaat    900

ggatgtggac tttttggcaa agggagcctg gtgacatgcg ctaagtttgc atgctccaag    960

aaaatgaccg ggaagagcat ccagccagag aatctggagt accggataat gctgtcagtt   1020

catggctccc agcacagtgg gatgatcgtt aatgacacag gacatgaaac tgatgagaat   1080

agagcgaagg ttgagataac gcccaattca ccaagagccg aagccaccct gggggggtttt   1140
```

```
ggaagcctag gacttgattg tgaaccgagg acaggccttg acttttcaga tttgtattac   1200

ttgactatga ataacaagca ctggttggtt cacaaggagt ggttccacga cattccatta   1260

ccttggcacg ctggggcaga caccggaact ccacactgga acaacaaaga agcactggta   1320

gagttcaagg acgcacatgc caaaaggcaa actgtcgtgg ttctagggag tcaagaagga   1380

gcagttcaca cggcccttgc tggagctctg gaggctgaga tggatggtgc aaagggaagg   1440

ctgtcctctg gccacttgaa atgtcgcctg aaaatggata aacttagatt gaagggcgtg   1500

tcatactcct tgtgtaccgc agcgttcaca ttcaccaaga tcccggctga aacactgcac   1560

gggacagtca cagtggaggt acagtacgca gggacagatg gaccttgcaa ggttccagct   1620

cagatggcgg tggacatgca aactctgacc ccagttggga ggttgataac cgctaacccc   1680

gtaatcactg aaagcactga gaactctaag atgatgctgg aacttgatcc accatttggg   1740

gactcttaca ttgtcatagg agtcggggag aagaagatca cccaccactg gcacaggagt   1800

ggcagcacca ttggaaaagc atttgaagcc actgtgagag gtgccaagag aatggcagtc   1860

ttgggagaca cagcctggga ctttggatca gttggaggcg ctctcaactc attgggcaag   1920

ggcatccatc aaatttttgg agcagctttc aaatcattgt ga                      1962
```

<210> SEQ ID NO 109
<211> LENGTH: 1962
<212> TYPE: DNA
<213> ORGANISM: Artificial sequence
<220> FEATURE:
<223> OTHER INFORMATION: Codon-optimized nucleotide sequence of MVsp_Zika_prME_no_anchor (C2)

<400> SEQUENCE: 109

```
atgagcatca tgggcctgaa ggtgaacgtg tccgccatct tcatggccgt gctgctgacc     60

ctgcagacac caacaggcca gatccacgca gaggtgacca ggagaggaag cgcctactat    120

atgtacctgg acaggaatga tgccggcgag gccatctcct tcccaaccac actgggcatg    180

aacaagtgct acatccagat catggacctg ggccacatgt gcgatgccac catgtcctat    240

gagtgtccaa tgctggacga gggcgtggag cccgacgatg tggattgctg gtgtaatacc    300

acatctacat gggtggtgta cggcacctgt caccacaaga agggagaggc ccggcggagc    360

cggcgggccg tgacactgcc ttcccactct accaggaagc tgcagacacg cagccagacc    420

tggctggagt ccagagagta taccaagcac ctgatcaggg tggagaactg gatctttcgc    480

aatccaggat tcgcactggc agcagcagca atcgcatggc tgctgggaag ctccaccagc    540

cagaaagtga tctacctggt catgatcctg ctgatcgctc ctgcctattc tatccggtgc    600

atcggcgtga gcaatagaga cttcgtggag ggaatgtccg gaggaacctg ggtggatgtg    660

gtgctggagc acggcggctg cgtgacagtg atggcccagg acaagccaac cgtggatatc    720

gagctggtga ccacaaccgt gtccaacatg gccgaggtga ggtcttactg ctatgaggcc    780

agcatctccg acatggcctc tgatagcagg tgtccaaccc agggagaggc atacctggac    840

aagcagtccg atacacagta cgtgtgcaag cggaccctgg tggacagagg ctggggcaat    900

ggctgtggcc tgtttggcaa gggctctctg gtgacatgcg ccaagttcgc ctgtagcaag    960

aagatgaccg gcaagtccat ccagccagag aacctggagt accggatcat gctgtctgtg   1020

cacggctccc agcactctgg catgatcgtg aacgacacag gccacgagac agatgagaat   1080

cgggccaagg tggagatcac acctaactct ccaagagccg aggccaccct gggaggattt   1140

ggctctctgg gcctggactg cgagcctaga acaggcctgg acttctccga tctgtactat   1200
```

ctgaccatga acaataagca ctggctggtg cacaaggagt ggtttcacga catcccactg 1260
ccatggcacg caggagcaga tacaggaaca ccacactgga acaataagga ggccctggtg 1320
gagttcaagg atgcccacgc caagcggcag acagtggtgg tgctgggcag ccaggaggga 1380
gcagtgcaca ccgccctggc aggcgccctg gaggcagaga tggacggagc taagggcaga 1440
ctgtctagcg gccacctgaa gtgcaggctg aagatggata agctgcgcct gaagggcgtg 1500
tcctactctc tgtgcacagc cgccttcacc ttcaccaaga tccctgccga gacactgcac 1560
ggcacagtga ccgtggaggt gcagtatgcc ggcacagacg gaccctgtaa ggtgcctgcc 1620
cagatggccg tggatatgca gacactgaca cctgtgggca ggctgatcac cgccaatcca 1680
gtgatcacag agtctaccga gaacagcaag atgatgctgg agctggaccc accatttggc 1740
gatagctata tcgtgatcgg cgtgggcgag aagaagatca cacaccactg gcaccgcagc 1800
ggctccacaa tcggcaaggc ctttgaggca accgtgcgcg gagcaaagag aatggccgtg 1860
ctgggcgaca ccgcatggga tttcggatct gtgggaggcg ccctgaacag cctgggcaag 1920
ggcatccacc agatcttcgg cgccgccttt aagtccctgt ga 1962

<210> SEQ ID NO 110
<211> LENGTH: 653
<212> TYPE: PRT
<213> ORGANISM: Artificial sequence
<220> FEATURE:
<223> OTHER INFORMATION: MVsp_Zika_prME_no_anchor (C2)

<400> SEQUENCE: 110

Met Ser Ile Met Gly Leu Lys Val Asn Val Ser Ala Ile Phe Met Ala
1 5 10 15

Val Leu Leu Thr Leu Gln Thr Pro Thr Gly Gln Ile His Ala Glu Val
20 25 30

Thr Arg Arg Gly Ser Ala Tyr Tyr Met Tyr Leu Asp Arg Asn Asp Ala
35 40 45

Gly Glu Ala Ile Ser Phe Pro Thr Thr Leu Gly Met Asn Lys Cys Tyr
50 55 60

Ile Gln Ile Met Asp Leu Gly His Met Cys Asp Ala Thr Met Ser Tyr
65 70 75 80

Glu Cys Pro Met Leu Asp Glu Gly Val Glu Pro Asp Asp Val Asp Cys
85 90 95

Trp Cys Asn Thr Thr Ser Thr Trp Val Val Tyr Gly Thr Cys His His
100 105 110

Lys Lys Gly Glu Ala Arg Arg Ser Arg Arg Ala Val Thr Leu Pro Ser
115 120 125

His Ser Thr Arg Lys Leu Gln Thr Arg Ser Gln Thr Trp Leu Glu Ser
130 135 140

Arg Glu Tyr Thr Lys His Leu Ile Arg Val Glu Asn Trp Ile Phe Arg
145 150 155 160

Asn Pro Gly Phe Ala Leu Ala Ala Ala Ala Ile Ala Trp Leu Leu Gly
165 170 175

Ser Ser Thr Ser Gln Lys Val Ile Tyr Leu Val Met Ile Leu Leu Ile
180 185 190

Ala Pro Ala Tyr Ser Ile Arg Cys Ile Gly Val Ser Asn Arg Asp Phe
195 200 205

Val Glu Gly Met Ser Gly Gly Thr Trp Val Asp Val Val Leu Glu His
210 215 220

-continued

```
Gly Gly Cys Val Thr Val Met Ala Gln Asp Lys Pro Thr Val Asp Ile
225                 230                 235                 240

Glu Leu Val Thr Thr Thr Val Ser Asn Met Ala Glu Val Arg Ser Tyr
                245                 250                 255

Cys Tyr Glu Ala Ser Ile Ser Asp Met Ala Ser Asp Ser Arg Cys Pro
            260                 265                 270

Thr Gln Gly Glu Ala Tyr Leu Asp Lys Gln Ser Asp Thr Gln Tyr Val
        275                 280                 285

Cys Lys Arg Thr Leu Val Asp Arg Gly Trp Gly Asn Gly Cys Gly Leu
    290                 295                 300

Phe Gly Lys Gly Ser Leu Val Thr Cys Ala Lys Phe Ala Cys Ser Lys
305                 310                 315                 320

Lys Met Thr Gly Lys Ser Ile Gln Pro Glu Asn Leu Glu Tyr Arg Ile
                325                 330                 335

Met Leu Ser Val His Gly Ser Gln His Ser Gly Met Ile Val Asn Asp
            340                 345                 350

Thr Gly His Glu Thr Asp Glu Asn Arg Ala Lys Val Glu Ile Thr Pro
        355                 360                 365

Asn Ser Pro Arg Ala Glu Ala Thr Leu Gly Gly Phe Gly Ser Leu Gly
    370                 375                 380

Leu Asp Cys Glu Pro Arg Thr Gly Leu Asp Phe Ser Asp Leu Tyr Tyr
385                 390                 395                 400

Leu Thr Met Asn Asn Lys His Trp Leu Val His Lys Glu Trp Phe His
                405                 410                 415

Asp Ile Pro Leu Pro Trp His Ala Gly Ala Asp Thr Gly Thr Pro His
            420                 425                 430

Trp Asn Asn Lys Glu Ala Leu Val Glu Phe Lys Asp Ala His Ala Lys
        435                 440                 445

Arg Gln Thr Val Val Val Leu Gly Ser Gln Glu Gly Ala Val His Thr
    450                 455                 460

Ala Leu Ala Gly Ala Leu Glu Ala Glu Met Asp Gly Ala Lys Gly Arg
465                 470                 475                 480

Leu Ser Ser Gly His Leu Lys Cys Arg Leu Lys Met Asp Lys Leu Arg
                485                 490                 495

Leu Lys Gly Val Ser Tyr Ser Leu Cys Thr Ala Ala Phe Thr Phe Thr
            500                 505                 510

Lys Ile Pro Ala Glu Thr Leu His Gly Thr Val Thr Val Glu Val Gln
        515                 520                 525

Tyr Ala Gly Thr Asp Gly Pro Cys Lys Val Pro Ala Gln Met Ala Val
    530                 535                 540

Asp Met Gln Thr Leu Thr Pro Val Gly Arg Leu Ile Thr Ala Asn Pro
545                 550                 555                 560

Val Ile Thr Glu Ser Thr Glu Asn Ser Lys Met Met Leu Glu Leu Asp
                565                 570                 575

Pro Pro Phe Gly Asp Ser Tyr Ile Val Ile Gly Val Gly Glu Lys Lys
            580                 585                 590

Ile Thr His His Trp His Arg Ser Gly Ser Thr Ile Gly Lys Ala Phe
        595                 600                 605

Glu Ala Thr Val Arg Gly Ala Lys Arg Met Ala Val Leu Gly Asp Thr
    610                 615                 620

Ala Trp Asp Phe Gly Ser Val Gly Gly Ala Leu Asn Ser Leu Gly Lys
625                 630                 635                 640

Gly Ile His Gln Ile Phe Gly Ala Ala Phe Lys Ser Leu
```

645 650

<210> SEQ ID NO 111
<211> LENGTH: 1932
<212> TYPE: DNA
<213> ORGANISM: Artificial sequence
<220> FEATURE:
<223> OTHER INFORMATION: Native nucleotide sequence of MVsp_Zika_prME411
(C3)

<400> SEQUENCE: 111
atgtccatca tgggtctcaa ggtgaacgtc tctgccatat tcatggcagt actgttaact 60
ctccaaacac ccaccggtca aatccatgcg gaggtcacta gacgtgggag tgcatactat 120
atgtacttgg acagaaacga tgctggggag gccatatctt ttccaaccac attggggatg 180
aataagtgtt atatacagat catggatctt ggacacatgt gtgatgccac catgagctat 240
gaatgcccta tgctggatga gggggtggaa ccagatgacg tcgattgttg gtgcaacacg 300
acgtcaactt gggttgtgta cggaacctgc catcacaaaa aaggtgaagc acggagatct 360
agaagagctg tgacgctccc ctcccattcc actaggaagc tgcaaacgcg gtcgcaaacc 420
tggttggaat caagagaata cacaaagcac ttgattagag tcgaaaattg gatattcagg 480
aaccctggct tcgcgttagc agcagctgcc atcgcttggc ttttgggaag ctcaacgagc 540
caaaaagtca tatacttggt catgatactg ctgattgccc cggcatacag catcaggtgc 600
ataggagtca gcaataggga ctttgtggaa ggtatgtcag gtgggacttg ggttgatgtt 660
gtcttggaac atggaggttg tgtcaccgta atggcacagg acaaaccgac tgtcgacata 720
gagctggtta caacaacagt cagcaacatg gcggaggtaa gatcctactg ctatgaggca 780
tcaatatcag acatggcttc ggacagccgc tgcccaacac aaggtgaagc ctaccttgac 840
aagcaatcag acactcaata tgtctgcaaa agaacgttag tggacagagg ctggggaaat 900
ggatgtggac tttttggcaa agggagcctg gtgacatgcg ctaagtttgc atgctccaag 960
aaaatgaccg ggaagagcat ccagccagag aatctggagt accggataat gctgtcagtt 1020
catggctccc agcacagtgg gatgatcgtt aatgacacag gacatgaaac tgatgagaat 1080
agagcgaagg ttgagataac gcccaattca ccaagagccg aagccaccct ggggggtttt 1140
ggaagcctag gacttgattg tgaaccgagg acaggccttg acttttcaga tttgtattac 1200
ttgactatga ataacaagca ctggttggtt cacaaggagt ggttccacga cattccatta 1260
ccttggcacg ctggggcaga caccggaact ccacactgga acaacaaaga agcactggta 1320
gagttcaagg acgcacatgc caaaaggcaa actgtcgtgg ttctagggag tcaagaagga 1380
gcagttcaca cggcccttgc tggagctctg gaggctgaga tggatggtgc aaagggaagg 1440
ctgtcctctg gccacttgaa atgtcgcctg aaaatggata aacttagatt gaagggcgtg 1500
tcatactcct tgtgtaccgc agcgttcaca ttcaccaaga tcccggctga aacactgcac 1560
gggacagtca cagtggaggt acagtacgca gggacagatg gaccttgcaa ggttccagct 1620
cagatggcgg tggacatgca aactctgacc ccagttggga ggttgataac cgctaacccc 1680
gtaatcactg aaagcactga gaactctaag atgatgctgg aacttgatcc accatttggg 1740
gactcttaca ttgtcatagg agtcggggag aagaagatca cccaccactg gcacaggagt 1800
ggcagcacca ttggaaaagc atttgaagcc actgtgagag gtgccaagag aatggcagtc 1860
ttgggagaca cagcctggga ctttggatca gttggaggcg ctctcaactc attgggcaag 1920
ggcatctgat ga 1932

<210> SEQ ID NO 112
<211> LENGTH: 1932
<212> TYPE: DNA
<213> ORGANISM: Artificial sequence
<220> FEATURE:
<223> OTHER INFORMATION: Codon-optimized nucleotide sequence of MVsp_Zika_prME411 (C3)

<400> SEQUENCE: 112

```
atgagcatca tgggcctgaa ggtgaacgtg tccgccatct tcatggccgt gctgctgacc     60
ctgcagacac caacaggcca gatccacgca gaggtgacca ggagaggaag cgcctactat    120
atgtacctgg acaggaatga tgccggcgag gccatctcct tcccaaccac actgggcatg    180
aacaagtgct acatccagat catggacctg ggccacatgt gcgatgccac catgtcctat    240
gagtgtccaa tgctggacga gggcgtggag cccgacgatg tggattgctg gtgtaatacc    300
acatctacat gggtggtgta cggcacctgt caccacaaga agggagaggc ccggcggagc    360
cggcgggccg tgacactgcc ttcccactct accaggaagc tgcagacacg cagccagacc    420
tggctggagt ccagagagta taccaagcac ctgatcaggg tggagaactg gatctttcgc    480
aatccaggat tcgcactggc agcagcagca atcgcatggc tgctgggaag ctccaccagc    540
cagaaagtga tctacctggt catgatcctg ctgatcgctc ctgcctattc tatccggtgc    600
atcggcgtga gcaatagaga cttcgtggag ggaatgtccg gaggaacctg ggtggatgtg    660
gtgctggagc acggcggctg cgtgacagtg atggcccagg acaagccaac cgtggatatc    720
gagctggtga ccacaaccgt gtccaacatg gccgaggtga ggtcttactg ctatgaggcc    780
agcatctccg acatggcctc tgatagcagg tgtccaaccc agggagaggc atacctggac    840
aagcagtccg atacacagta cgtgtgcaag cggaccctgg tggacagagg ctggggcaat    900
ggctgtggcc tgtttggcaa gggctctctg gtgacatgcg ccaagttcgc ctgtagcaag    960
aagatgaccg gcaagtccat ccagccagag aacctggagt accggatcat gctgtctgtg   1020
cacggctccc agcactctgg catgatcgtg aacgacacag gccacgagac agatgagaat   1080
cgggccaagg tggagatcac acctaactct ccaagagccg aggccaccct gggaggattt   1140
ggctctctgg gcctggactg cgagcctaga acaggcctgg acttctccga tctgtactat   1200
ctgaccatga acaataagca ctggctggtg cacaaggagt ggtttcacga catcccactg   1260
ccatggcacg caggagcaga tacaggaaca ccacactgga acaataagga ggccctggtg   1320
gagttcaagg atgcccacgc caagcggcag acagtggtgg tgctgggcag ccaggaggga   1380
gcagtgcaca ccgccctggc aggcgccctg gaggcagaga tggacggagc taagggcaga   1440
ctgtctagcg gccacctgaa gtgcaggctg aagatggata agctgcgcct gaagggcgtg   1500
tcctactctc tgtgcacagc cgccttcacc ttcaccaaga tccctgccga gacactgcac   1560
ggcacagtga ccgtggaggt gcagtatgcc ggcacagacg gaccctgtaa ggtgcctgcc   1620
cagatggccg tggatatgca gacactgaca cctgtgggca ggctgatcac cgccaatcca   1680
gtgatcacag agtctaccga gaacagcaag atgatgctgg agctggaccc accatttggc   1740
gatagctata tcgtgatcgg cgtgggcgag aagaagatca cacaccactg gcaccgcagc   1800
ggctccacaa tcggcaaggc ctttgaggca accgtgcgcg gagcaaagag aatggccgtg   1860
ctgggcgaca ccgcatggga tttcggatct gtgggaggcg ccctgaacag cctgggcaag   1920
ggcatctgat ga                                                       1932
```

<210> SEQ ID NO 113

<211> LENGTH: 642
<212> TYPE: PRT
<213> ORGANISM: Artificial sequence
<220> FEATURE:
<223> OTHER INFORMATION: MVsp_Zika_prME411 (C3)

<400> SEQUENCE: 113

Met Ser Ile Met Gly Leu Lys Val Asn Val Ser Ala Ile Phe Met Ala
1 5 10 15

Val Leu Leu Thr Leu Gln Thr Pro Thr Gly Gln Ile His Ala Glu Val
20 25 30

Thr Arg Arg Gly Ser Ala Tyr Tyr Met Tyr Leu Asp Arg Asn Asp Ala
35 40 45

Gly Glu Ala Ile Ser Phe Pro Thr Thr Leu Gly Met Asn Lys Cys Tyr
50 55 60

Ile Gln Ile Met Asp Leu Gly His Met Cys Asp Ala Thr Met Ser Tyr
65 70 75 80

Glu Cys Pro Met Leu Asp Glu Gly Val Glu Pro Asp Asp Val Asp Cys
85 90 95

Trp Cys Asn Thr Thr Ser Thr Trp Val Val Tyr Gly Thr Cys His His
100 105 110

Lys Lys Gly Glu Ala Arg Arg Ser Arg Arg Ala Val Thr Leu Pro Ser
115 120 125

His Ser Thr Arg Lys Leu Gln Thr Arg Ser Gln Thr Trp Leu Glu Ser
130 135 140

Arg Glu Tyr Thr Lys His Leu Ile Arg Val Glu Asn Trp Ile Phe Arg
145 150 155 160

Asn Pro Gly Phe Ala Leu Ala Ala Ala Ala Ile Ala Trp Leu Leu Gly
165 170 175

Ser Ser Thr Ser Gln Lys Val Ile Tyr Leu Val Met Ile Leu Leu Ile
180 185 190

Ala Pro Ala Tyr Ser Ile Arg Cys Ile Gly Val Ser Asn Arg Asp Phe
195 200 205

Val Glu Gly Met Ser Gly Gly Thr Trp Val Asp Val Val Leu Glu His
210 215 220

Gly Gly Cys Val Thr Val Met Ala Gln Asp Lys Pro Thr Val Asp Ile
225 230 235 240

Glu Leu Val Thr Thr Thr Val Ser Asn Met Ala Glu Val Arg Ser Tyr
245 250 255

Cys Tyr Glu Ala Ser Ile Ser Asp Met Ala Ser Asp Ser Arg Cys Pro
260 265 270

Thr Gln Gly Glu Ala Tyr Leu Asp Lys Gln Ser Asp Thr Gln Tyr Val
275 280 285

Cys Lys Arg Thr Leu Val Asp Arg Gly Trp Gly Asn Gly Cys Gly Leu
290 295 300

Phe Gly Lys Gly Ser Leu Val Thr Cys Ala Lys Phe Ala Cys Ser Lys
305 310 315 320

Lys Met Thr Gly Lys Ser Ile Gln Pro Glu Asn Leu Glu Tyr Arg Ile
325 330 335

Met Leu Ser Val His Gly Ser Gln His Ser Gly Met Ile Val Asn Asp
340 345 350

Thr Gly His Glu Thr Asp Glu Asn Arg Ala Lys Val Glu Ile Thr Pro
355 360 365

Asn Ser Pro Arg Ala Glu Ala Thr Leu Gly Gly Phe Gly Ser Leu Gly
370 375 380

```
Leu Asp Cys Glu Pro Arg Thr Gly Leu Asp Phe Ser Asp Leu Tyr Tyr
385                 390                 395                 400

Leu Thr Met Asn Asn Lys His Trp Leu Val His Lys Glu Trp Phe His
                405                 410                 415

Asp Ile Pro Leu Pro Trp His Ala Gly Ala Asp Thr Gly Thr Pro His
            420                 425                 430

Trp Asn Asn Lys Glu Ala Leu Val Glu Phe Lys Asp Ala His Ala Lys
        435                 440                 445

Arg Gln Thr Val Val Val Leu Gly Ser Gln Glu Gly Ala Val His Thr
    450                 455                 460

Ala Leu Ala Gly Ala Leu Glu Ala Glu Met Asp Gly Ala Lys Gly Arg
465                 470                 475                 480

Leu Ser Ser Gly His Leu Lys Cys Arg Leu Lys Met Asp Lys Leu Arg
                485                 490                 495

Leu Lys Gly Val Ser Tyr Ser Leu Cys Thr Ala Ala Phe Thr Phe Thr
            500                 505                 510

Lys Ile Pro Ala Glu Thr Leu His Gly Thr Val Thr Val Glu Val Gln
        515                 520                 525

Tyr Ala Gly Thr Asp Gly Pro Cys Lys Val Pro Ala Gln Met Ala Val
    530                 535                 540

Asp Met Gln Thr Leu Thr Pro Val Gly Arg Leu Ile Thr Ala Asn Pro
545                 550                 555                 560

Val Ile Thr Glu Ser Thr Glu Asn Ser Lys Met Met Leu Glu Leu Asp
                565                 570                 575

Pro Pro Phe Gly Asp Ser Tyr Ile Val Ile Gly Val Gly Glu Lys Lys
            580                 585                 590

Ile Thr His His Trp His Arg Ser Gly Ser Thr Ile Gly Lys Ala Phe
        595                 600                 605

Glu Ala Thr Val Arg Gly Ala Lys Arg Met Ala Val Leu Gly Asp Thr
    610                 615                 620

Ala Trp Asp Phe Gly Ser Val Gly Gly Ala Leu Asn Ser Leu Gly Lys
625                 630                 635                 640

Gly Ile
```

<210> SEQ ID NO 114
<211> LENGTH: 1806
<212> TYPE: DNA
<213> ORGANISM: Artificial sequence
<220> FEATURE:
<223> OTHER INFORMATION: Native nucleotide sequence of MVsp_Zika_prME395 (C4)

<400> SEQUENCE: 114

```
atgtccatca tgggtctcaa ggtgaacgtc tctgccatat tcatggcagt actgttaact     60

ctccaaacac ccaccggtca aatccatgcg gaggtcacta gacgtgggag tgcatactat    120

atgtacttgg acagaaacga tgctggggag gccatatctt ttccaaccac attggggatg    180

aataagtgtt atatacagat catggatctt ggacacatgt gtgatgccac catgagctat    240

gaatgcccta tgctggatga gggggtggaa ccagatgacg tcgattgttg gtgcaacacg    300

acgtcaactt gggttgtgta cggaacctgc catcacaaaa aaggtgaagc acggagatct    360

agaagagctg tgacgctccc ctcccattcc actaggaagc tgcaaacgcg gtcgcaaacc    420

tggttggaat caagagaata cacaaagcac ttgattagag tcgaaaattg gatattcagg    480

aaccctggct tcgcgttagc agcagctgcc atcgcttggc ttttgggaag ctcaacgagc    540
```

caaaaagtca tatacttggt catgatactg ctgattgccc cggcatacag catcaggtgc 600
ataggagtca gcaataggga ctttgtggaa ggtatgtcag gtgggacttg ggttgatgtt 660
gtcttggaac atggaggttg tgtcaccgta atggcacagg acaaaccgac tgtcgacata 720
gagctggtta caacaacagt cagcaacatg gcggaggtaa gatcctactg ctatgaggca 780
tcaatatcag acatggcttc ggacagccgc tgcccaacac aaggtgaagc ctaccttgac 840
aagcaatcag acactcaata tgtctgcaaa agaacgttag tggacagagg ctggggaaat 900
ggatgtggac tttttggcaa agggagcctg gtgacatgcg ctaagtttgc atgctccaag 960
aaaatgaccg ggaagagcat ccagccagag aatctggagt accggataat gctgtcagtt 1020
catggctccc agcacagtgg gatgatcgtt aatgacacag gacatgaaac tgatgagaat 1080
agagcgaagg ttgagataac gcccaattca ccaagagccg aagccaccct ggggggtttt 1140
ggaagcctag gacttgattg tgaaccgagg acaggccttg acttttcaga tttgtattac 1200
ttgactatga ataacaagca ctggttggtt cacaaggagt ggttccacga cattccatta 1260
ccttggcacg ctggggcaga caccggaact ccacactgga acaacaaaga agcactggta 1320
gagttcaagg acgcacatgc caaaaggcaa actgtcgtgg ttctagggag tcaagaagga 1380
gcagttcaca cggcccttgc tggagctctg gaggctgaga tggatggtgc aaagggaagg 1440
ctgtcctctg gccacttgaa atgtcgcctg aaaatggata aacttagatt gaagggcgtg 1500
tcatactcct tgtgtaccgc agcgttcaca ttcaccaaga tcccggctga aacactgcac 1560
gggacagtca cagtggaggt acagtacgca gggacagatg gaccttgcaa ggttccagct 1620
cagatggcgg tggacatgca aactctgacc ccagttggga ggttgataac cgctaacccc 1680
gtaatcactg aaagcactga gaactctaag atgatgctgg aacttgatcc accatttggg 1740
gactcttaca ttgtcatagg agtcggggag aagaagatca cccaccactg gcacaggagt 1800
ggctga 1806

<210> SEQ ID NO 115
<211> LENGTH: 1806
<212> TYPE: DNA
<213> ORGANISM: Artificial sequence
<220> FEATURE:
<223> OTHER INFORMATION: Codon-optimized nucleotide sequence of MVsp_Zika_prME395 (C4)

<400> SEQUENCE: 115
atgagcatca tgggcctgaa ggtgaacgtg tccgccatct tcatggccgt gctgctgacc 60
ctgcagacac caacaggcca gatccacgca gaggtgacca ggagaggaag cgcctactat 120
atgtacctgg acaggaatga tgccggcgag gccatctcct tcccaaccac actgggcatg 180
aacaagtgct acatccagat catggacctg ggccacatgt gcgatgccac catgtcctat 240
gagtgtccaa tgctggacga gggcgtggag cccgacgatg tggattgctg gtgtaatacc 300
acatctacat gggtggtgta cggcacctgt caccacaaga agggagaggc ccggcggagc 360
cggcgggccg tgacactgcc ttcccactct accaggaagc tgcagacacg cagccagacc 420
tggctggagt ccagagagta taccaagcac ctgatcaggg tggagaactg gatctttcgc 480
aatccaggat tcgcactggc agcagcagca atcgcatggc tgctgggaag ctccaccagc 540
cagaaagtga tctacctggt catgatcctg ctgatcgctc ctgcctattc tatccggtgc 600
atcggcgtga gcaatagaga cttcgtggag ggaatgtccg gaggaacctg ggtggatgtg 660
gtgctggagc acggcggctg cgtgacagtg atggcccagg acaagccaac cgtggatatc 720

```
gagctggtga ccacaaccgt gtccaacatg gccgaggtga ggtcttactg ctatgaggcc    780

agcatctccg acatggcctc tgatagcagg tgtccaaccc agggagaggc atacctggac    840

aagcagtccg atacacagta cgtgtgcaag cggaccctgg tggacagagg ctggggcaat    900

ggctgtggcc tgtttggcaa gggctctctg gtgacatgcg ccaagttcgc ctgtagcaag    960

aagatgaccg gcaagtccat ccagccagag aacctggagt accggatcat gctgtctgtg   1020

cacggctccc agcactctgg catgatcgtg aacgacacag gccacgagac agatgagaat   1080

cgggccaagg tggagatcac acctaactct ccaagagccg aggccaccct gggaggattt   1140

ggctctctgg gcctggactg cgagcctaga acaggcctgg acttctccga tctgtactat   1200

ctgaccatga acaataagca ctggctggtg cacaaggagt ggtttcacga catcccactg   1260

ccatggcacg caggagcaga tacaggaaca ccacactgga acaataagga ggccctggtg   1320

gagttcaagg atgcccacgc caagcggcag acagtggtgg tgctgggcag ccaggaggga   1380

gcagtgcaca ccgccctggc aggcgccctg gaggcagaga tggacggagc taagggcaga   1440

ctgtctagcg gccacctgaa gtgcaggctg aagatggata agctgcgcct gaagggcgtg   1500

tcctactctc tgtgcacagc cgccttcacc ttcaccaaga tccctgccga gacactgcac   1560

ggcacagtga ccgtggaggt gcagtatgcc ggcacagacg gaccctgtaa ggtgcctgcc   1620

cagatggccg tggatatgca gacactgaca cctgtgggca ggctgatcac cgccaatcca   1680

gtgatcacag agtctaccga gaacagcaag atgatgctgg agctggaccc accatttggc   1740

gatagctata tcgtgatcgg cgtgggcgag aagaagatca cacaccactg gcaccgcagc   1800

ggctga                                                              1806
```

<210> SEQ ID NO 116
<211> LENGTH: 601
<212> TYPE: PRT
<213> ORGANISM: Artificial sequence
<220> FEATURE:
<223> OTHER INFORMATION: MVsp_Zika_prME395 (C4)

<400> SEQUENCE: 116

```
Met Ser Ile Met Gly Leu Lys Val Asn Val Ser Ala Ile Phe Met Ala
1               5                   10                  15

Val Leu Leu Thr Leu Gln Thr Pro Thr Gly Gln Ile His Ala Glu Val
            20                  25                  30

Thr Arg Arg Gly Ser Ala Tyr Tyr Met Tyr Leu Asp Arg Asn Asp Ala
        35                  40                  45

Gly Glu Ala Ile Ser Phe Pro Thr Thr Leu Gly Met Asn Lys Cys Tyr
    50                  55                  60

Ile Gln Ile Met Asp Leu Gly His Met Cys Asp Ala Thr Met Ser Tyr
65                  70                  75                  80

Glu Cys Pro Met Leu Asp Glu Gly Val Glu Pro Asp Asp Val Asp Cys
                85                  90                  95

Trp Cys Asn Thr Thr Ser Thr Trp Val Val Tyr Gly Thr Cys His His
            100                 105                 110

Lys Lys Gly Glu Ala Arg Arg Ser Arg Arg Ala Val Thr Leu Pro Ser
        115                 120                 125

His Ser Thr Arg Lys Leu Gln Thr Arg Ser Gln Thr Trp Leu Glu Ser
    130                 135                 140

Arg Glu Tyr Thr Lys His Leu Ile Arg Val Glu Asn Trp Ile Phe Arg
145                 150                 155                 160
```

```
Asn Pro Gly Phe Ala Leu Ala Ala Ala Ala Ile Ala Trp Leu Leu Gly
                165                 170                 175

Ser Ser Thr Ser Gln Lys Val Ile Tyr Leu Val Met Ile Leu Leu Ile
            180                 185                 190

Ala Pro Ala Tyr Ser Ile Arg Cys Ile Gly Val Ser Asn Arg Asp Phe
        195                 200                 205

Val Glu Gly Met Ser Gly Gly Thr Trp Val Asp Val Val Leu Glu His
    210                 215                 220

Gly Gly Cys Val Thr Val Met Ala Gln Asp Lys Pro Thr Val Asp Ile
225                 230                 235                 240

Glu Leu Val Thr Thr Thr Val Ser Asn Met Ala Glu Val Arg Ser Tyr
                245                 250                 255

Cys Tyr Glu Ala Ser Ile Ser Asp Met Ala Ser Asp Ser Arg Cys Pro
            260                 265                 270

Thr Gln Gly Glu Ala Tyr Leu Asp Lys Gln Ser Asp Thr Gln Tyr Val
        275                 280                 285

Cys Lys Arg Thr Leu Val Asp Arg Gly Trp Gly Asn Gly Cys Gly Leu
    290                 295                 300

Phe Gly Lys Gly Ser Leu Val Thr Cys Ala Lys Phe Ala Cys Ser Lys
305                 310                 315                 320

Lys Met Thr Gly Lys Ser Ile Gln Pro Glu Asn Leu Glu Tyr Arg Ile
                325                 330                 335

Met Leu Ser Val His Gly Ser Gln His Ser Gly Met Ile Val Asn Asp
            340                 345                 350

Thr Gly His Glu Thr Asp Glu Asn Arg Ala Lys Val Glu Ile Thr Pro
        355                 360                 365

Asn Ser Pro Arg Ala Glu Ala Thr Leu Gly Gly Phe Gly Ser Leu Gly
    370                 375                 380

Leu Asp Cys Glu Pro Arg Thr Gly Leu Asp Phe Ser Asp Leu Tyr Tyr
385                 390                 395                 400

Leu Thr Met Asn Asn Lys His Trp Leu Val His Lys Glu Trp Phe His
                405                 410                 415

Asp Ile Pro Leu Pro Trp His Ala Gly Ala Asp Thr Gly Thr Pro His
            420                 425                 430

Trp Asn Asn Lys Glu Ala Leu Val Glu Phe Lys Asp Ala His Ala Lys
        435                 440                 445

Arg Gln Thr Val Val Val Leu Gly Ser Gln Glu Gly Ala Val His Thr
    450                 455                 460

Ala Leu Ala Gly Ala Leu Glu Ala Glu Met Asp Gly Ala Lys Gly Arg
465                 470                 475                 480

Leu Ser Ser Gly His Leu Lys Cys Arg Leu Lys Met Asp Lys Leu Arg
                485                 490                 495

Leu Lys Gly Val Ser Tyr Ser Leu Cys Thr Ala Ala Phe Thr Phe Thr
            500                 505                 510

Lys Ile Pro Ala Glu Thr Leu His Gly Thr Val Thr Val Glu Val Gln
        515                 520                 525

Tyr Ala Gly Thr Asp Gly Pro Cys Lys Val Pro Ala Gln Met Ala Val
    530                 535                 540

Asp Met Gln Thr Leu Thr Pro Val Gly Arg Leu Ile Thr Ala Asn Pro
545                 550                 555                 560

Val Ile Thr Glu Ser Thr Glu Asn Ser Lys Met Met Leu Glu Leu Asp
                565                 570                 575

Pro Pro Phe Gly Asp Ser Tyr Ile Val Ile Gly Val Gly Glu Lys Lys
```

580 585 590

Ile Thr His His Trp His Arg Ser Gly
595 600

<210> SEQ ID NO 117
<211> LENGTH: 1602
<212> TYPE: DNA
<213> ORGANISM: Artificial sequence
<220> FEATURE:
<223> OTHER INFORMATION: Native nucleotide sequence of MVsp_ZikaE (C5)

<400> SEQUENCE: 117
atgtccatca tgggtctcaa ggtgaacgtc tctgccatat tcatggcagt actgttaact 60
ctccaaacac ccaccggtca aatccatatc aggtgcatag gagtcagcaa tagggacttt 120
gtggaaggta tgtcaggtgg gacttgggtt gatgttgtct tggaacatgg aggttgtgtc 180
accgtaatgg cacaggacaa accgactgtc gacatagagc tggttacaac aacagtcagc 240
aacatggcgg aggtaagatc ctactgctat gaggcatcaa tatcagacat ggcttcggac 300
agccgctgcc caacacaagg tgaagcctac cttgacaagc aatcagacac tcaatatgtc 360
tgcaaaagaa cgttagtgga cagaggctgg ggaaatggat gtggactttt tggcaaaggg 420
agcctggtga catgcgctaa gtttgcatgc tccaagaaaa tgaccgggaa gagcatccag 480
ccagagaatc tggagtaccg gataatgctg tcagttcatg gctcccagca cagtgggatg 540
atcgttaatg acacaggaca tgaaactgat gagaatagag cgaaggttga gataacgccc 600
aattcaccaa gagccgaagc caccctgggg ggttttggaa gcctaggact tgattgtgaa 660
ccgaggacag gccttgactt ttcagatttg tattacttga ctatgaataa caagcactgg 720
ttggttcaca aggagtggtt ccacgacatt ccattacctt ggcacgctgg ggcagacacc 780
ggaactccac actggaacaa caaagaagca ctggtagagt tcaaggacgc acatgccaaa 840
aggcaaactg tcgtggttct agggagtcaa gaaggagcag ttcacacggc ccttgctgga 900
gctctggagg ctgagatgga tggtgcaaag ggaaggctgt cctctggcca cttgaaatgt 960
cgcctgaaaa tggataaact tagattgaag ggcgtgtcat actccttgtg taccgcagcg 1020
ttcacattca ccaagatccc ggctgaaaca ctgcacggga cagtcacagt ggaggtacag 1080
tacgcaggga cagatggacc ttgcaaggtt ccagctcaga tggcggtgga catgcaaact 1140
ctgaccccag ttgggaggtt gataaccgct aaccccgtaa tcactgaaag cactgagaac 1200
tctaagatga tgctggaact tgatccacca tttggggact cttacattgt cataggagtc 1260
ggggagaaga agatcaccca ccactggcac aggagtggca gcaccattgg aaaagcattt 1320
gaagccactg tgagaggtgc caagagaatg gcagtcttgg gagacacagc ctgggacttt 1380
ggatcagttg gaggcgctct caactcattg ggcaagggca tccatcaaat ttttggagca 1440
gctttcaaat cattgtttgg aggaatgtcc tggttctcac aaattctcat tggaacgttg 1500
ctgatgtggt tgggtctgaa cacaaagaat ggatctattt cccttatgtg cttggcctta 1560
gggggagtgt tgatcttctt atccacagcc gtctctgctt ga 1602

<210> SEQ ID NO 118
<211> LENGTH: 1602
<212> TYPE: DNA
<213> ORGANISM: Artificial sequence
<220> FEATURE:
<223> OTHER INFORMATION: Codon-optimized nucleotide sequence of
MVsp_ZikaE (C5)

<400> SEQUENCE: 118

```
atgagcatca tgggcctgaa ggtgaacgtg tccgccatct tcatggccgt gctgctgacc     60

ctgcagacac caacaggcca gatccacatc cggtgcatcg gcgtgagcaa tagagacttc    120

gtggagggaa tgtccggagg aacctgggtg gatgtggtgc tggagcacgg cggctgcgtg    180

acagtgatgg cccaggacaa gccaaccgtg gatatcgagc tggtgaccac aaccgtgtcc    240

aacatggccg aggtgaggtc ttactgctat gaggccagca tctccgacat ggcctctgat    300

agcaggtgtc caacccaggg agaggcatac ctggacaagc agtccgatac acagtacgtg    360

tgcaagcgga ccctggtgga cagaggctgg ggcaatggct gtggcctgtt tggcaagggc    420

tctctggtga catgcgccaa gttcgcctgt agcaagaaga tgaccggcaa gtccatccag    480

ccagagaacc tggagtaccg gatcatgctg tctgtgcacg gctcccagca ctctggcatg    540

atcgtgaacg acacaggcca cgagacagat gagaatcggg ccaaggtgga gatcacacct    600

aactctccaa gagccgaggc caccctggga ggatttggct ctctgggcct ggactgcgag    660

cctagaacag gcctggactt ctccgatctg tactatctga ccatgaacaa taagcactgg    720

ctggtgcaca aggagtggtt tcacgacatc ccactgccat ggcacgcagg agcagataca    780

ggaacaccac actggaacaa taaggaggcc ctggtggagt tcaaggatgc ccacgccaag    840

cggcagacag tggtggtgct gggcagccag gagggagcag tgcacaccgc cctggcaggc    900

gccctggagg cagagatgga cggagctaag ggcagactgt ctagcggcca cctgaagtgc    960

aggctgaaga tggataagct gcgcctgaag ggcgtgtcct actctctgtg cacagccgcc   1020

ttcaccttca ccaagatccc tgccgagaca ctgcacggca cagtgaccgt ggaggtgcag   1080

tatgccggca cagacggacc ctgtaaggtg cctgcccaga tggccgtgga tatgcagaca   1140

ctgacacctg tgggcaggct gatcaccgcc aatccagtga tcacagagtc taccgagaac   1200

agcaagatga tgctggagct ggacccacca tttggcgata gctatatcgt gatcggcgtg   1260

ggcgagaaga agatcacaca ccactggcac cgcagcggct ccacaatcgg caaggccttt   1320

gaggcaaccg tgcgcggagc aaagagaatg gccgtgctgg gcgacaccgc atgggatttc   1380

ggatctgtgg gaggcgccct gaacagcctg ggcaagggca tccaccagat cttcggcgcc   1440

gcctttaagt ccctgttcgg cggcatgagc tggttctcac agatcctgat cggcacactg   1500

ctgatgtggc tgggcctgaa caccaagaat ggctctatca gcctgatgtg cctggccctg   1560

ggaggcgtgc tgatcttcct gtccaccgcc gtgtctgcct ga                      1602
```

<210> SEQ ID NO 119
<211> LENGTH: 533
<212> TYPE: PRT
<213> ORGANISM: Artificial sequence
<220> FEATURE:
<223> OTHER INFORMATION: MVsp_ZikaE (C5)

<400> SEQUENCE: 119

```
Met Ser Ile Met Gly Leu Lys Val Asn Val Ser Ala Ile Phe Met Ala
1               5                   10                  15

Val Leu Leu Thr Leu Gln Thr Pro Thr Gly Gln Ile His Ile Arg Cys
            20                  25                  30

Ile Gly Val Ser Asn Arg Asp Phe Val Glu Gly Met Ser Gly Gly Thr
        35                  40                  45

Trp Val Asp Val Val Leu Glu His Gly Gly Cys Val Thr Val Met Ala
    50                  55                  60

Gln Asp Lys Pro Thr Val Asp Ile Glu Leu Val Thr Thr Thr Val Ser
65                  70                  75                  80
```

```
Asn Met Ala Glu Val Arg Ser Tyr Cys Tyr Glu Ala Ser Ile Ser Asp
                85                  90                  95

Met Ala Ser Asp Ser Arg Cys Pro Thr Gln Gly Glu Ala Tyr Leu Asp
            100                 105                 110

Lys Gln Ser Asp Thr Gln Tyr Val Cys Lys Arg Thr Leu Val Asp Arg
        115                 120                 125

Gly Trp Gly Asn Gly Cys Gly Leu Phe Gly Lys Gly Ser Leu Val Thr
    130                 135                 140

Cys Ala Lys Phe Ala Cys Ser Lys Lys Met Thr Gly Lys Ser Ile Gln
145                 150                 155                 160

Pro Glu Asn Leu Glu Tyr Arg Ile Met Leu Ser Val His Gly Ser Gln
                165                 170                 175

His Ser Gly Met Ile Val Asn Asp Thr Gly His Glu Thr Asp Glu Asn
            180                 185                 190

Arg Ala Lys Val Glu Ile Thr Pro Asn Ser Pro Arg Ala Glu Ala Thr
        195                 200                 205

Leu Gly Gly Phe Gly Ser Leu Gly Leu Asp Cys Glu Pro Arg Thr Gly
    210                 215                 220

Leu Asp Phe Ser Asp Leu Tyr Tyr Leu Thr Met Asn Asn Lys His Trp
225                 230                 235                 240

Leu Val His Lys Glu Trp Phe His Asp Ile Pro Leu Pro Trp His Ala
                245                 250                 255

Gly Ala Asp Thr Gly Thr Pro His Trp Asn Asn Lys Glu Ala Leu Val
            260                 265                 270

Glu Phe Lys Asp Ala His Ala Lys Arg Gln Thr Val Val Val Leu Gly
        275                 280                 285

Ser Gln Glu Gly Ala Val His Thr Ala Leu Ala Gly Ala Leu Glu Ala
    290                 295                 300

Glu Met Asp Gly Ala Lys Gly Arg Leu Ser Ser Gly His Leu Lys Cys
305                 310                 315                 320

Arg Leu Lys Met Asp Lys Leu Arg Leu Lys Gly Val Ser Tyr Ser Leu
                325                 330                 335

Cys Thr Ala Ala Phe Thr Phe Thr Lys Ile Pro Ala Glu Thr Leu His
            340                 345                 350

Gly Thr Val Thr Val Glu Val Gln Tyr Ala Gly Thr Asp Gly Pro Cys
        355                 360                 365

Lys Val Pro Ala Gln Met Ala Val Asp Met Gln Thr Leu Thr Pro Val
    370                 375                 380

Gly Arg Leu Ile Thr Ala Asn Pro Val Ile Thr Glu Ser Thr Glu Asn
385                 390                 395                 400

Ser Lys Met Met Leu Glu Leu Asp Pro Pro Phe Gly Asp Ser Tyr Ile
                405                 410                 415

Val Ile Gly Val Gly Glu Lys Lys Ile Thr His His Trp His Arg Ser
            420                 425                 430

Gly Ser Thr Ile Gly Lys Ala Phe Glu Ala Thr Val Arg Gly Ala Lys
        435                 440                 445

Arg Met Ala Val Leu Gly Asp Thr Ala Trp Asp Phe Gly Ser Val Gly
    450                 455                 460

Gly Ala Leu Asn Ser Leu Gly Lys Gly Ile His Gln Ile Phe Gly Ala
465                 470                 475                 480

Ala Phe Lys Ser Leu Phe Gly Gly Met Ser Trp Phe Ser Gln Ile Leu
                485                 490                 495
```

Ile Gly Thr Leu Leu Met Trp Leu Gly Leu Asn Thr Lys Asn Gly Ser
500 505 510

Ile Ser Leu Met Cys Leu Ala Leu Gly Gly Val Leu Ile Phe Leu Ser
515 520 525

Thr Ala Val Ser Ala
530

<210> SEQ ID NO 120
<211> LENGTH: 1458
<212> TYPE: DNA
<213> ORGANISM: Artificial sequence
<220> FEATURE:
<223> OTHER INFORMATION: Native nucleotide sequence of MVsp_ZikaE_no_anchor (C6)

<400> SEQUENCE: 120
atgtccatca tgggtctcaa ggtgaacgtc tctgccatat tcatggcagt actgttaact 60
ctccaaacac ccaccggtca aatccatatc aggtgcatag gagtcagcaa tagggacttt 120
gtggaaggta tgtcaggtgg gacttgggtt gatgttgtct tggaacatgg aggttgtgtc 180
accgtaatgg cacaggacaa accgactgtc gacatagagc tggttacaac aacagtcagc 240
aacatggcgg aggtaagatc ctactgctat gaggcatcaa tatcagacat ggcttcggac 300
agccgctgcc caacacaagg tgaagcctac cttgacaagc aatcagacac tcaatatgtc 360
tgcaaaagaa cgttagtgga cagaggctgg ggaaatggat gtggactttt tggcaaaggg 420
agcctggtga catgcgctaa gtttgcatgc tccaagaaaa tgaccgggaa gagcatccag 480
ccagagaatc tggagtaccg gataatgctg tcagttcatg gctcccagca cagtgggatg 540
atcgttaatg acacaggaca tgaaactgat gagaatagag cgaaggttga gataacgccc 600
aattcaccaa gagccgaagc caccctgggg ggttttggaa gcctaggact tgattgtgaa 660
ccgaggacag gccttgactt ttcagatttg tattacttga ctatgaataa caagcactgg 720
ttggttcaca aggagtggtt ccacgacatt ccattacctt ggcacgctgg ggcagacacc 780
ggaactccac actggaacaa caaagaagca ctggtagagt tcaaggacgc acatgccaaa 840
aggcaaactg tcgtggttct agggagtcaa gaaggagcag ttcacacggc ccttgctgga 900
gctctggagg ctgagatgga tggtgcaaag ggaaggctgt cctctggcca cttgaaatgt 960
cgcctgaaaa tggataaact tagattgaag ggcgtgtcat actccttgtg taccgcagcg 1020
ttcacattca ccaagatccc ggctgaaaca ctgcacggga cagtcacagt ggaggtacag 1080
tacgcaggga cagatggacc ttgcaaggtt ccagctcaga tggcggtgga catgcaaact 1140
ctgaccccag ttgggaggtt gataaccgct aaccccgtaa tcactgaaag cactgagaac 1200
tctaagatga tgctggaact tgatccacca tttggggact cttacattgt cataggagtc 1260
ggggagaaga agatcaccca ccactggcac aggagtggca gcaccattgg aaaagcattt 1320
gaagccactg tgagaggtgc caagagaatg gcagtcttgg gagacacagc ctgggacttt 1380
ggatcagttg gaggcgctct caactcattg ggcaagggca tccatcaaat ttttggagca 1440
gctttcaaat cattgtga 1458

<210> SEQ ID NO 121
<211> LENGTH: 1458
<212> TYPE: DNA
<213> ORGANISM: Artificial sequence
<220> FEATURE:
<223> OTHER INFORMATION: Codon-optimized nucleotide sequence of MVsp_ZikaE_no_anchor (C6)

<400> SEQUENCE: 121
atgagcatca tgggcctgaa ggtgaacgtg tccgccatct tcatggccgt gctgctgacc 60
ctgcagacac caacaggcca gatccacatc cggtgcatcg gcgtgagcaa tagagacttc 120
gtggagggaa tgtccggagg aacctgggtg gatgtggtgc tggagcacgg cggctgcgtg 180
acagtgatgg cccaggacaa gccaaccgtg gatatcgagc tggtgaccac aaccgtgtcc 240
aacatggccg aggtgaggtc ttactgctat gaggccagca tctccgacat ggcctctgat 300
agcaggtgtc caacccaggg agaggcatac ctggacaagc agtccgatac acagtacgtg 360
tgcaagcgga ccctggtgga cagaggctgg ggcaatggct gtggcctgtt tggcaagggc 420
tctctggtga catgcgccaa gttcgcctgt agcaagaaga tgaccggcaa gtccatccag 480
ccagagaacc tggagtaccg gatcatgctg tctgtgcacg gctcccagca ctctggcatg 540
atcgtgaacg acacaggcca cgagacagat gagaatcggg ccaaggtgga gatcacacct 600
aactctccaa gagccgaggc caccctggga ggatttggct ctctgggcct ggactgcgag 660
cctagaacag gcctggactt ctccgatctg tactatctga ccatgaacaa taagcactgg 720
ctggtgcaca aggagtggtt tcacgacatc ccactgccat ggcacgcagg agcagataca 780
ggaacaccac actggaacaa taaggaggcc ctggtggagt tcaaggatgc ccacgccaag 840
cggcagacag tggtggtgct gggcagccag gagggagcag tgcacaccgc cctggcaggc 900
gccctggagg cagagatgga cggagctaag ggcagactgt ctagcggcca cctgaagtgc 960
aggctgaaga tggataagct gcgcctgaag ggcgtgtcct actctctgtg cacagccgcc 1020
ttcaccttca ccaagatccc tgccgagaca ctgcacggca cagtgaccgt ggaggtgcag 1080
tatgccggca cagacggacc ctgtaaggtg cctgcccaga tggccgtgga tatgcagaca 1140
ctgacacctg tgggcaggct gatcaccgcc aatccagtga tcacagagtc taccgagaac 1200
agcaagatga tgctggagct ggacccacca tttggcgata gctatatcgt gatcggcgtg 1260
ggcgagaaga agatcacaca ccactggcac cgcagcggct ccacaatcgg caaggccttt 1320
gaggcaaccg tgcgcggagc aaagagaatg gccgtgctgg gcgacaccgc atgggatttc 1380
ggatctgtgg gaggcgccct gaacagcctg ggcaagggca tccaccagat cttcggcgcc 1440
gcctttaagt ccctgtga 1458

<210> SEQ ID NO 122
<211> LENGTH: 485
<212> TYPE: PRT
<213> ORGANISM: Artificial sequence
<220> FEATURE:
<223> OTHER INFORMATION: MVsp_ZikaE_no_anchor (C6)

<400> SEQUENCE: 122

Met Ser Ile Met Gly Leu Lys Val Asn Val Ser Ala Ile Phe Met Ala
1               5                   10                  15

Val Leu Leu Thr Leu Gln Thr Pro Thr Gly Gln Ile His Ile Arg Cys
            20                  25                  30

Ile Gly Val Ser Asn Arg Asp Phe Val Glu Gly Met Ser Gly Gly Thr
        35                  40                  45

Trp Val Asp Val Val Leu Glu His Gly Gly Cys Val Thr Val Met Ala
    50                  55                  60

Gln Asp Lys Pro Thr Val Asp Ile Glu Leu Val Thr Thr Thr Val Ser
65                  70                  75                  80

Asn Met Ala Glu Val Arg Ser Tyr Cys Tyr Glu Ala Ser Ile Ser Asp
                85                  90                  95

```
Met Ala Ser Asp Ser Arg Cys Pro Thr Gln Gly Glu Ala Tyr Leu Asp
            100                 105                 110

Lys Gln Ser Asp Thr Gln Tyr Val Cys Lys Arg Thr Leu Val Asp Arg
        115                 120                 125

Gly Trp Gly Asn Gly Cys Gly Leu Phe Gly Lys Gly Ser Leu Val Thr
    130                 135                 140

Cys Ala Lys Phe Ala Cys Ser Lys Lys Met Thr Gly Lys Ser Ile Gln
145                 150                 155                 160

Pro Glu Asn Leu Glu Tyr Arg Ile Met Leu Ser Val His Gly Ser Gln
                165                 170                 175

His Ser Gly Met Ile Val Asn Asp Thr Gly His Glu Thr Asp Glu Asn
            180                 185                 190

Arg Ala Lys Val Glu Ile Thr Pro Asn Ser Pro Arg Ala Glu Ala Thr
        195                 200                 205

Leu Gly Gly Phe Gly Ser Leu Gly Leu Asp Cys Glu Pro Arg Thr Gly
    210                 215                 220

Leu Asp Phe Ser Asp Leu Tyr Tyr Leu Thr Met Asn Asn Lys His Trp
225                 230                 235                 240

Leu Val His Lys Glu Trp Phe His Asp Ile Pro Leu Pro Trp His Ala
                245                 250                 255

Gly Ala Asp Thr Gly Thr Pro His Trp Asn Asn Lys Glu Ala Leu Val
            260                 265                 270

Glu Phe Lys Asp Ala His Ala Lys Arg Gln Thr Val Val Val Leu Gly
        275                 280                 285

Ser Gln Glu Gly Ala Val His Thr Ala Leu Ala Gly Ala Leu Glu Ala
    290                 295                 300

Glu Met Asp Gly Ala Lys Gly Arg Leu Ser Ser Gly His Leu Lys Cys
305                 310                 315                 320

Arg Leu Lys Met Asp Lys Leu Arg Leu Lys Gly Val Ser Tyr Ser Leu
                325                 330                 335

Cys Thr Ala Ala Phe Thr Phe Thr Lys Ile Pro Ala Glu Thr Leu His
            340                 345                 350

Gly Thr Val Thr Val Glu Val Gln Tyr Ala Gly Thr Asp Gly Pro Cys
        355                 360                 365

Lys Val Pro Ala Gln Met Ala Val Asp Met Gln Thr Leu Thr Pro Val
    370                 375                 380

Gly Arg Leu Ile Thr Ala Asn Pro Val Ile Thr Glu Ser Thr Glu Asn
385                 390                 395                 400

Ser Lys Met Met Leu Glu Leu Asp Pro Pro Phe Gly Asp Ser Tyr Ile
                405                 410                 415

Val Ile Gly Val Gly Glu Lys Lys Ile Thr His His Trp His Arg Ser
            420                 425                 430

Gly Ser Thr Ile Gly Lys Ala Phe Glu Ala Thr Val Arg Gly Ala Lys
        435                 440                 445

Arg Met Ala Val Leu Gly Asp Thr Ala Trp Asp Phe Gly Ser Val Gly
    450                 455                 460

Gly Ala Leu Asn Ser Leu Gly Lys Gly Ile His Gln Ile Phe Gly Ala
465                 470                 475                 480

Ala Phe Lys Ser Leu
                485
```

<210> SEQ ID NO 123
<211> LENGTH: 1428

<212> TYPE: DNA
<213> ORGANISM: Artificial sequence
<220> FEATURE:
<223> OTHER INFORMATION: Native nucleotide sequence of MVsp_ZikaE411 (C7)

<400> SEQUENCE: 123
atgtccatca tgggtctcaa ggtgaacgtc tctgccatat tcatggcagt actgttaact 60
ctccaaacac ccaccggtca aatccatatc aggtgcatag gagtcagcaa tagggacttt 120
gtggaaggta tgtcaggtgg gacttgggtt gatgttgtct tggaacatgg aggttgtgtc 180
accgtaatgg cacaggacaa accgactgtc gacatagagc tggttacaac aacagtcagc 240
aacatggcgg aggtaagatc ctactgctat gaggcatcaa tatcagacat ggcttcggac 300
agccgctgcc caacacaagg tgaagcctac cttgacaagc aatcagacac tcaatatgtc 360
tgcaaaagaa cgttagtgga cagaggctgg ggaaatggat gtggactttt tggcaaaggg 420
agcctggtga catgcgctaa gtttgcatgc tccaagaaaa tgaccgggaa gagcatccag 480
ccagagaatc tggagtaccg gataatgctg tcagttcatg gctcccagca cagtgggatg 540
atcgttaatg acacaggaca tgaaactgat gagaatagag cgaaggttga gataacgccc 600
aattcaccaa gagccgaagc caccctgggg ggttttggaa gcctaggact tgattgtgaa 660
ccgaggacag gccttgactt ttcagatttg tattacttga ctatgaataa caagcactgg 720
ttggttcaca aggagtggtt ccacgacatt ccattacctt ggcacgctgg ggcagacacc 780
ggaactccac actggaacaa caaagaagca ctggtagagt tcaaggacgc acatgccaaa 840
aggcaaactg tcgtggttct agggagtcaa gaaggagcag ttcacacggc ccttgctgga 900
gctctggagg ctgagatgga tggtgcaaag ggaaggctgt cctctggcca cttgaaatgt 960
cgcctgaaaa tggataaact tagattgaag ggcgtgtcat actccttgtg taccgcagcg 1020
ttcacattca ccaagatccc ggctgaaaca ctgcacggga cagtcacagt ggaggtacag 1080
tacgcaggga cagatggacc ttgcaaggtt ccagctcaga tggcggtgga catgcaaact 1140
ctgaccccag ttgggaggtt gataaccgct aaccccgtaa tcactgaaag cactgagaac 1200
tctaagatga tgctggaact tgatccacca tttggggact cttacattgt cataggagtc 1260
ggggagaaga agatcaccca ccactggcac aggagtggca gcaccattgg aaaagcattt 1320
gaagccactg tgagaggtgc caagagaatg gcagtcttgg gagacacagc ctgggacttt 1380
ggatcagttg gaggcgctct caactcattg ggcaagggca tctgatga 1428

<210> SEQ ID NO 124
<211> LENGTH: 1428
<212> TYPE: DNA
<213> ORGANISM: Artificial sequence
<220> FEATURE:
<223> OTHER INFORMATION: Codon-optimized nucleotide sequence of MVsp_ZikaE411 (C7)

<400> SEQUENCE: 124
atgagcatca tgggcctgaa ggtgaacgtg tccgccatct tcatggccgt gctgctgacc 60
ctgcagacac caacaggcca gatccacatc cggtgcatcg gcgtgagcaa tagagacttc 120
gtggagggaa tgtccggagg aacctgggtg gatgtggtgc tggagcacgg cggctgcgtg 180
acagtgatgg cccaggacaa gccaaccgtg gatatcgagc tggtgaccac aaccgtgtcc 240
aacatggccg aggtgaggtc ttactgctat gaggccagca tctccgacat ggcctctgat 300
agcaggtgtc caacccaggg agaggcatac ctggacaagc agtccgatac acagtacgtg 360

-continued

```
tgcaagcgga ccctggtgga cagaggctgg ggcaatggct gtggcctgtt tggcaagggc    420

tctctggtga catgcgccaa gttcgcctgt agcaagaaga tgaccggcaa gtccatccag    480

ccagagaacc tggagtaccg gatcatgctg tctgtgcacg gctcccagca ctctggcatg    540

atcgtgaacg acacaggcca cgagacagat gagaatcggg ccaaggtgga gatcacacct    600

aactctccaa gagccgaggc caccctggga ggatttggct ctctgggcct ggactgcgag    660

cctagaacag gcctggactt ctccgatctg tactatctga ccatgaacaa taagcactgg    720

ctggtgcaca aggagtggtt tcacgacatc ccactgccat ggcacgcagg agcagataca    780

ggaacaccac actggaacaa taaggaggcc ctggtggagt tcaaggatgc ccacgccaag    840

cggcagacag tggtggtgct gggcagccag gagggagcag tgcacaccgc cctggcaggc    900

gccctggagg cagagatgga cggagctaag ggcagactgt ctagcggcca cctgaagtgc    960

aggctgaaga tggataagct gcgcctgaag ggcgtgtcct actctctgtg cacagccgcc   1020

ttcaccttca ccaagatccc tgccgagaca ctgcacggca cagtgaccgt ggaggtgcag   1080

tatgccggca cagacggacc ctgtaaggtg cctgcccaga tggccgtgga tatgcagaca   1140

ctgacacctg tgggcaggct gatcaccgcc aatccagtga tcacagagtc taccgagaac   1200

agcaagatga tgctggagct ggacccacca tttggcgata gctatatcgt gatcggcgtg   1260

ggcgagaaga agatcacaca ccactggcac cgcagcggct ccacaatcgg caaggccttt   1320

gaggcaaccg tgcgcggagc aaagagaatg gccgtgctgg gcgacaccgc atgggatttc   1380

ggatctgtgg gaggcgccct gaacagcctg ggcaagggca tctgatga                1428


<210> SEQ ID NO 125
<211> LENGTH: 474
<212> TYPE: PRT
<213> ORGANISM: Artificial sequence
<220> FEATURE:
<223> OTHER INFORMATION: MVsp_ZikaE411 (C7)

<400> SEQUENCE: 125

Met Ser Ile Met Gly Leu Lys Val Asn Val Ser Ala Ile Phe Met Ala
1               5                   10                  15

Val Leu Leu Thr Leu Gln Thr Pro Thr Gly Gln Ile His Ile Arg Cys
            20                  25                  30

Ile Gly Val Ser Asn Arg Asp Phe Val Glu Gly Met Ser Gly Gly Thr
        35                  40                  45

Trp Val Asp Val Val Leu Glu His Gly Gly Cys Val Thr Val Met Ala
    50                  55                  60

Gln Asp Lys Pro Thr Val Asp Ile Glu Leu Val Thr Thr Thr Val Ser
65                  70                  75                  80

Asn Met Ala Glu Val Arg Ser Tyr Cys Tyr Glu Ala Ser Ile Ser Asp
                85                  90                  95

Met Ala Ser Asp Ser Arg Cys Pro Thr Gln Gly Glu Ala Tyr Leu Asp
            100                 105                 110

Lys Gln Ser Asp Thr Gln Tyr Val Cys Lys Arg Thr Leu Val Asp Arg
        115                 120                 125

Gly Trp Gly Asn Gly Cys Gly Leu Phe Gly Lys Gly Ser Leu Val Thr
    130                 135                 140

Cys Ala Lys Phe Ala Cys Ser Lys Lys Met Thr Gly Lys Ser Ile Gln
145                 150                 155                 160

Pro Glu Asn Leu Glu Tyr Arg Ile Met Leu Ser Val His Gly Ser Gln
                165                 170                 175
```

```
His Ser Gly Met Ile Val Asn Asp Thr Gly His Glu Thr Asp Glu Asn
            180                 185                 190

Arg Ala Lys Val Glu Ile Thr Pro Asn Ser Pro Arg Ala Glu Ala Thr
        195                 200                 205

Leu Gly Gly Phe Gly Ser Leu Gly Leu Asp Cys Glu Pro Arg Thr Gly
    210                 215                 220

Leu Asp Phe Ser Asp Leu Tyr Tyr Leu Thr Met Asn Asn Lys His Trp
225                 230                 235                 240

Leu Val His Lys Glu Trp Phe His Asp Ile Pro Leu Pro Trp His Ala
                245                 250                 255

Gly Ala Asp Thr Gly Thr Pro His Trp Asn Asn Lys Glu Ala Leu Val
            260                 265                 270

Glu Phe Lys Asp Ala His Ala Lys Arg Gln Thr Val Val Val Leu Gly
        275                 280                 285

Ser Gln Glu Gly Ala Val His Thr Ala Leu Ala Gly Ala Leu Glu Ala
    290                 295                 300

Glu Met Asp Gly Ala Lys Gly Arg Leu Ser Ser Gly His Leu Lys Cys
305                 310                 315                 320

Arg Leu Lys Met Asp Lys Leu Arg Leu Lys Gly Val Ser Tyr Ser Leu
                325                 330                 335

Cys Thr Ala Ala Phe Thr Phe Thr Lys Ile Pro Ala Glu Thr Leu His
            340                 345                 350

Gly Thr Val Thr Val Glu Val Gln Tyr Ala Gly Thr Asp Gly Pro Cys
        355                 360                 365

Lys Val Pro Ala Gln Met Ala Val Asp Met Gln Thr Leu Thr Pro Val
    370                 375                 380

Gly Arg Leu Ile Thr Ala Asn Pro Val Ile Thr Glu Ser Thr Glu Asn
385                 390                 395                 400

Ser Lys Met Met Leu Glu Leu Asp Pro Pro Phe Gly Asp Ser Tyr Ile
                405                 410                 415

Val Ile Gly Val Gly Glu Lys Lys Ile Thr His His Trp His Arg Ser
            420                 425                 430

Gly Ser Thr Ile Gly Lys Ala Phe Glu Ala Thr Val Arg Gly Ala Lys
        435                 440                 445

Arg Met Ala Val Leu Gly Asp Thr Ala Trp Asp Phe Gly Ser Val Gly
    450                 455                 460

Gly Ala Leu Asn Ser Leu Gly Lys Gly Ile
465                 470
```

<210> SEQ ID NO 126
<211> LENGTH: 1302
<212> TYPE: DNA
<213> ORGANISM: Artificial sequence
<220> FEATURE:
<223> OTHER INFORMATION: Native nucleotide sequence of MVsp_ZikaE395 (C8)

<400> SEQUENCE: 126

```
atgtccatca tgggtctcaa ggtgaacgtc tctgccatat tcatggcagt actgttaact      60

ctccaaacac ccaccggtca aatccatatc aggtgcatag gagtcagcaa tagggacttt     120

gtggaaggta tgtcaggtgg gacttgggtt gatgttgtct tggaacatgg aggttgtgtc     180

accgtaatgg cacaggacaa accgactgtc gacatagagc tggttacaac aacagtcagc     240

aacatggcgg aggtaagatc ctactgctat gaggcatcaa tatcagacat ggcttcggac     300

agccgctgcc caacacaagg tgaagcctac cttgacaagc aatcagacac tcaatatgtc     360
```

```
tgcaaaagaa cgttagtgga cagaggctgg ggaaatggat gtggactttt tggcaaaggg    420

agcctggtga catgcgctaa gtttgcatgc tccaagaaaa tgaccgggaa gagcatccag    480

ccagagaatc tggagtaccg gataatgctg tcagttcatg gctcccagca cagtgggatg    540

atcgttaatg acacaggaca tgaaactgat gagaatagag cgaaggttga gataacgccc    600

aattcaccaa gagccgaagc caccctgggg ggttttggaa gcctaggact tgattgtgaa    660

ccgaggacag gccttgactt ttcagatttg tattacttga ctatgaataa caagcactgg    720

ttggttcaca aggagtggtt ccacgacatt ccattacctt ggcacgctgg ggcagacacc    780

ggaactccac actggaacaa caaagaagca ctggtagagt tcaaggacgc acatgccaaa    840

aggcaaactg tcgtggttct agggagtcaa gaaggagcag ttcacacggc ccttgctgga    900

gctctggagg ctgagatgga tggtgcaaag ggaaggctgt cctctggcca cttgaaatgt    960

cgcctgaaaa tggataaact tagattgaag ggcgtgtcat actccttgtg taccgcagcg   1020

ttcacattca ccaagatccc ggctgaaaca ctgcacggga cagtcacagt ggaggtacag   1080

tacgcaggga cagatggacc ttgcaaggtt ccagctcaga tggcggtgga catgcaaact   1140

ctgaccccag ttgggaggtt gataaccgct aaccccgtaa tcactgaaag cactgagaac   1200

tctaagatga tgctggaact tgatccacca tttggggact cttacattgt cataggagtc   1260

ggggagaaga agatcaccca ccactggcac aggagtggct ga                      1302
```

<210> SEQ ID NO 127
<211> LENGTH: 1302
<212> TYPE: DNA
<213> ORGANISM: Artificial sequence
<220> FEATURE:
<223> OTHER INFORMATION: Codon-optimized nucleotide sequence of MVsp_ZikaE395 (C8)

<400> SEQUENCE: 127

```
atgagcatca tgggcctgaa ggtgaacgtg tccgccatct tcatggccgt gctgctgacc     60

ctgcagacac caacaggcca gatccacatc cggtgcatcg gcgtgagcaa tagagacttc    120

gtggagggaa tgtccggagg aacctgggtg gatgtggtgc tggagcacgg cggctgcgtg    180

acagtgatgg cccaggacaa gccaaccgtg gatatcgagc tggtgaccac aaccgtgtcc    240

aacatggccg aggtgaggtc ttactgctat gaggccagca tctccgacat ggcctctgat    300

agcaggtgtc caacccaggg agaggcatac ctggacaagc agtccgatac acagtacgtg    360

tgcaagcgga ccctggtgga cagaggctgg ggcaatggct gtggcctgtt tggcaagggc    420

tctctggtga catgcgccaa gttcgcctgt agcaagaaga tgaccggcaa gtccatccag    480

ccagagaacc tggagtaccg gatcatgctg tctgtgcacg gctcccagca ctctggcatg    540

atcgtgaacg acacaggcca cgagacagat gagaatcggg ccaaggtgga gatcacacct    600

aactctccaa gagccgaggc caccctggga ggatttggct ctctgggcct ggactgcgag    660

cctagaacag gcctggactt ctccgatctg tactatctga ccatgaacaa taagcactgg    720

ctggtgcaca aggagtggtt tcacgacatc ccactgccat ggcacgcagg agcagataca    780

ggaacaccac actggaacaa taaggaggcc ctggtggagt tcaaggatgc ccacgccaag    840

cggcagacag tggtggtgct gggcagccag gagggagcag tgcacaccgc cctggcaggc    900

gccctggagg cagagatgga cggagctaag ggcagactgt ctagcggcca cctgaagtgc    960

aggctgaaga tggataagct gcgcctgaag ggcgtgtcct actctctgtg cacagccgcc   1020

ttcaccttca ccaagatccc tgccgagaca ctgcacggca cagtgaccgt ggaggtgcag   1080
```

```
tatgccggca cagacggacc ctgtaaggtg cctgcccaga tggccgtgga tatgcagaca   1140

ctgacacctg tgggcaggct gatcaccgcc aatccagtga tcacagagtc taccgagaac   1200

agcaagatga tgctggagct ggacccacca tttggcgata gctatatcgt gatcggcgtg   1260

ggcgagaaga agatcacaca ccactggcac cgcagcggct ga                      1302


<210> SEQ ID NO 128
<211> LENGTH: 433
<212> TYPE: PRT
<213> ORGANISM: Artificial sequence
<220> FEATURE:
<223> OTHER INFORMATION: MVsp_ZikaE395 (C8)

<400> SEQUENCE: 128

Met Ser Ile Met Gly Leu Lys Val Asn Val Ser Ala Ile Phe Met Ala
1               5                   10                  15

Val Leu Leu Thr Leu Gln Thr Pro Thr Gly Gln Ile His Ile Arg Cys
            20                  25                  30

Ile Gly Val Ser Asn Arg Asp Phe Val Glu Gly Met Ser Gly Gly Thr
        35                  40                  45

Trp Val Asp Val Val Leu Glu His Gly Gly Cys Val Thr Val Met Ala
    50                  55                  60

Gln Asp Lys Pro Thr Val Asp Ile Glu Leu Val Thr Thr Thr Val Ser
65                  70                  75                  80

Asn Met Ala Glu Val Arg Ser Tyr Cys Tyr Glu Ala Ser Ile Ser Asp
                85                  90                  95

Met Ala Ser Asp Ser Arg Cys Pro Thr Gln Gly Glu Ala Tyr Leu Asp
            100                 105                 110

Lys Gln Ser Asp Thr Gln Tyr Val Cys Lys Arg Thr Leu Val Asp Arg
        115                 120                 125

Gly Trp Gly Asn Gly Cys Gly Leu Phe Gly Lys Gly Ser Leu Val Thr
    130                 135                 140

Cys Ala Lys Phe Ala Cys Ser Lys Lys Met Thr Gly Lys Ser Ile Gln
145                 150                 155                 160

Pro Glu Asn Leu Glu Tyr Arg Ile Met Leu Ser Val His Gly Ser Gln
                165                 170                 175

His Ser Gly Met Ile Val Asn Asp Thr Gly His Glu Thr Asp Glu Asn
            180                 185                 190

Arg Ala Lys Val Glu Ile Thr Pro Asn Ser Pro Arg Ala Glu Ala Thr
        195                 200                 205

Leu Gly Gly Phe Gly Ser Leu Gly Leu Asp Cys Glu Pro Arg Thr Gly
    210                 215                 220

Leu Asp Phe Ser Asp Leu Tyr Tyr Leu Thr Met Asn Asn Lys His Trp
225                 230                 235                 240

Leu Val His Lys Glu Trp Phe His Asp Ile Pro Leu Pro Trp His Ala
                245                 250                 255

Gly Ala Asp Thr Gly Thr Pro His Trp Asn Asn Lys Glu Ala Leu Val
            260                 265                 270

Glu Phe Lys Asp Ala His Ala Lys Arg Gln Thr Val Val Val Leu Gly
        275                 280                 285

Ser Gln Glu Gly Ala Val His Thr Ala Leu Ala Gly Ala Leu Glu Ala
    290                 295                 300

Glu Met Asp Gly Ala Lys Gly Arg Leu Ser Ser Gly His Leu Lys Cys
305                 310                 315                 320
```

```
Arg Leu Lys Met Asp Lys Leu Arg Leu Lys Gly Val Ser Tyr Ser Leu
                325                 330                 335

Cys Thr Ala Ala Phe Thr Phe Thr Lys Ile Pro Ala Glu Thr Leu His
            340                 345                 350

Gly Thr Val Thr Val Glu Val Gln Tyr Ala Gly Thr Asp Gly Pro Cys
        355                 360                 365

Lys Val Pro Ala Gln Met Ala Val Asp Met Gln Thr Leu Thr Pro Val
    370                 375                 380

Gly Arg Leu Ile Thr Ala Asn Pro Val Ile Thr Glu Ser Thr Glu Asn
385                 390                 395                 400

Ser Lys Met Met Leu Glu Leu Asp Pro Pro Phe Gly Asp Ser Tyr Ile
                405                 410                 415

Val Ile Gly Val Gly Glu Lys Lys Ile Thr His His Trp His Arg Ser
            420                 425                 430

Gly
```

<210> SEQ ID NO 129
<211> LENGTH: 2178
<212> TYPE: DNA
<213> ORGANISM: Artificial sequence
<220> FEATURE:
<223> OTHER INFORMATION: Native nucleotide sequence of
      MVsp_ZikaprME_MVTMintracyto (C9)

<400> SEQUENCE: 129

```
atgtccatca tgggtctcaa ggtgaacgtc tctgccatat tcatggcagt actgttaact     60

ctccaaacac ccaccggtca aatccatgcg gaggtcacta gacgtgggag tgcatactat    120

atgtacttgg acagaaacga tgctggggag gccatatctt ttccaaccac attggggatg    180

aataagtgtt atatacagat catggatctt ggacacatgt gtgatgccac catgagctat    240

gaatgcccta tgctggatga gggggtggaa ccagatgacg tcgattgttg gtgcaacacg    300

acgtcaactt gggttgtgta cggaacctgc catcacaaaa aaggtgaagc acggagatct    360

agaagagctg tgacgctccc ctcccattcc actaggaagc tgcaaacgcg gtcgcaaacc    420

tggttggaat caagagaata cacaaagcac ttgattagag tcgaaaattg gatattcagg    480

aaccctggct tcgcgttagc agcagctgcc atcgcttggc ttttgggaag ctcaacgagc    540

caaaaagtca tatacttggt catgatactg ctgattgccc cggcatacag catcaggtgc    600

ataggagtca gcaataggga ctttgtggaa ggtatgtcag gtgggacttg ggttgatgtt    660

gtcttggaac atggaggttg tgtcaccgta atggcacagg acaaaccgac tgtcgacata    720

gagctggtta caacaacagt cagcaacatg gcggaggtaa gatcctactg ctatgaggca    780

tcaatatcag acatggcttc ggacagccgc tgcccaacac aaggtgaagc ctaccttgac    840

aagcaatcag acactcaata tgtctgcaaa agaacgttag tggacagagg ctggggaaat    900

ggatgtggac tttttggcaa agggagcctg gtgacatgcg ctaagtttgc atgctccaag    960

aaaatgaccg ggaagagcat ccagccagag aatctggagt accggataat gctgtcagtt   1020

catggctccc agcacagtgg gatgatcgtt aatgacacag gacatgaaac tgatgagaat   1080

agagcgaagg ttgagataac gcccaattca ccaagagccg aagccaccct gggggggtttt   1140

ggaagcctag gacttgattg tgaaccgagg acaggccttg acttttcaga tttgtattac   1200

ttgactatga ataacaagca ctggttggtt cacaaggagt ggttccacga cattccatta   1260

ccttggcacg ctggggcaga caccggaact ccacactgga acaacaaaga agcactggta   1320

gagttcaagg acgcacatgc caaaaggcaa actgtcgtgg ttctagggag tcaagaagga   1380
```

gcagttcaca cggcccttgc tggagctctg gaggctgaga tggatggtgc aaagggaagg 1440
ctgtcctctg gccacttgaa atgtcgcctg aaaatggata aacttagatt gaagggcgtg 1500
tcatactcct tgtgtaccgc agcgttcaca ttcaccaaga tcccggctga aacactgcac 1560
gggacagtca cagtggaggt acagtacgca gggacagatg gaccttgcaa ggttccagct 1620
cagatggcgg tggacatgca aactctgacc ccagttggga ggttgataac cgctaacccc 1680
gtaatcactg aaagcactga gaactctaag atgatgctgg aacttgatcc accatttggg 1740
gactcttaca ttgtcatagg agtcggggag aagaagatca cccaccactg gcacaggagt 1800
ggcagcacca ttggaaaagc atttgaagcc actgtgagag gtgccaagag aatggcagtc 1860
ttgggagaca cagcctggga ctttggatca gttggaggcg ctctcaactc attgggcaag 1920
ggcatccatc aaatttttgg agcagctttc aaatcattgt ttggaggaat gtcctggttc 1980
tcaatgaaag gtttatcgag cactagcata gtctacatcc tgattgcagt gtgtcttgga 2040
gggttgatag ggatccccgc tttaatatgt tgctgcaggg ggcgttgtaa caaaaaggga 2100
gaacaagttg gtatgtcaag accaggccta aagcctgatc ttacgggaac atcaaaatcc 2160
tatgtaaggt cgctctga 2178

<210> SEQ ID NO 130
<211> LENGTH: 2178
<212> TYPE: DNA
<213> ORGANISM: Artificial sequence
<220> FEATURE:
<223> OTHER INFORMATION: Codon-optimized nucleotide sequence of
MVsp_ZikaprME_MVTMintracyto (C9)

<400> SEQUENCE: 130
atgagcatca tgggcctgaa ggtgaacgtg tccgccatct tcatggccgt gctgctgacc 60
ctgcagacac caacaggcca gatccacgca gaggtgacca ggagaggaag cgcctactat 120
atgtacctgg acaggaatga tgccggcgag gccatctcct tcccaaccac actgggcatg 180
aacaagtgct acatccagat catggacctg ggccacatgt gcgatgccac catgtcctat 240
gagtgtccaa tgctggacga gggcgtggag cccgacgatg tggattgctg gtgtaatacc 300
acatctacat gggtggtgta cggcacctgt caccacaaga agggagaggc ccggcggagc 360
cggcgggccg tgacactgcc ttcccactct accaggaagc tgcagacacg cagccagacc 420
tggctggagt ccagagagta taccaagcac ctgatcaggg tggagaactg gatctttcgc 480
aatccaggat tcgcactggc agcagcagca atcgcatggc tgctgggaag ctccaccagc 540
cagaaagtga tctacctggt catgatcctg ctgatcgctc ctgcctattc tatccggtgc 600
atcggcgtga gcaatagaga cttcgtggag ggaatgtccg gaggaacctg ggtggatgtg 660
gtgctggagc acggcggctg cgtgacagtg atggcccagg acaagccaac cgtggatatc 720
gagctggtga ccacaaccgt gtccaacatg gccgaggtga ggtcttactg ctatgaggcc 780
agcatctccg acatggcctc tgatagcagg tgtccaaccc agggagaggc atacctggac 840
aagcagtccg atacacagta cgtgtgcaag cggaccctgg tggacagagg ctggggcaat 900
ggctgtggcc tgtttggcaa gggctctctg gtgacatgcg ccaagttcgc ctgtagcaag 960
aagatgaccg gcaagtccat ccagccagag aacctggagt accggatcat gctgtctgtg 1020
cacggctccc agcactctgg catgatcgtg aacgacacag gccacgagac agatgagaat 1080
cgggccaagg tggagatcac acctaactct ccaagagccg aggccaccct gggaggattt 1140
ggctctctgg gcctggactg cgagcctaga acaggcctgg acttctccga tctgtactat 1200

```
ctgaccatga acaataagca ctggctggtg cacaaggagt ggtttcacga catcccactg   1260

ccatggcacg caggagcaga tacaggaaca ccacactgga acaataagga ggccctggtg   1320

gagttcaagg atgcccacgc caagcggcag acagtggtgg tgctgggcag ccaggaggga   1380

gcagtgcaca ccgccctggc aggcgccctg gaggcagaga tggacggagc taagggcaga   1440

ctgtctagcg gccacctgaa gtgcaggctg aagatggata agctgcgcct gaagggcgtg   1500

tcctactctc tgtgcacagc cgccttcacc ttcaccaaga tccctgccga gacactgcac   1560

ggcacagtga ccgtggaggt gcagtatgcc ggcacagacg gaccctgtaa ggtgcctgcc   1620

cagatggccg tggatatgca gacactgaca cctgtgggca ggctgatcac cgccaatcca   1680

gtgatcacag agtctaccga gaacagcaag atgatgctgg agctggaccc accatttggc   1740

gatagctata tcgtgatcgg cgtgggcgag aagaagatca cacaccactg gcaccgcagc   1800

ggctccacaa tcggcaaggc ctttgaggca accgtgcgcg gagcaaagag aatggccgtg   1860

ctgggcgaca ccgcatggga tttcggatct gtgggaggcg ccctgaacag cctgggcaag   1920

ggcatccacc agatcttcgg cgccgccttt aagtccctgt tcggcggcat gagctggttc   1980

tcaatgaagg gcctgtcctc tacctctatc gtgtacatcc tgatcgccgt gtgcctggga   2040

ggcctgatcg gaatcccagc cctgatctgc tgttgcagag gccgctgcaa caagaaggga   2100

gagcaagtgg gaatgtctcg gccaggcctg aagccagacc tgacaggcac ctccaagtct   2160

tatgtgagaa gcctgtga                                                 2178
```

```
<210> SEQ ID NO 131
<211> LENGTH: 725
<212> TYPE: PRT
<213> ORGANISM: Artificial sequence
<220> FEATURE:
<223> OTHER INFORMATION: MVsp_ZikaprME_MVTMintracyto (C9)

<400> SEQUENCE: 131

Met Ser Ile Met Gly Leu Lys Val Asn Val Ser Ala Ile Phe Met Ala
1               5                   10                  15

Val Leu Leu Thr Leu Gln Thr Pro Thr Gly Gln Ile His Ala Glu Val
            20                  25                  30

Thr Arg Arg Gly Ser Ala Tyr Tyr Met Tyr Leu Asp Arg Asn Asp Ala
        35                  40                  45

Gly Glu Ala Ile Ser Phe Pro Thr Thr Leu Gly Met Asn Lys Cys Tyr
    50                  55                  60

Ile Gln Ile Met Asp Leu Gly His Met Cys Asp Ala Thr Met Ser Tyr
65                  70                  75                  80

Glu Cys Pro Met Leu Asp Glu Gly Val Glu Pro Asp Asp Val Asp Cys
                85                  90                  95

Trp Cys Asn Thr Thr Ser Thr Trp Val Val Tyr Gly Thr Cys His His
            100                 105                 110

Lys Lys Gly Glu Ala Arg Arg Ser Arg Arg Ala Val Thr Leu Pro Ser
        115                 120                 125

His Ser Thr Arg Lys Leu Gln Thr Arg Ser Gln Thr Trp Leu Glu Ser
    130                 135                 140

Arg Glu Tyr Thr Lys His Leu Ile Arg Val Glu Asn Trp Ile Phe Arg
145                 150                 155                 160

Asn Pro Gly Phe Ala Leu Ala Ala Ala Ala Ile Ala Trp Leu Leu Gly
                165                 170                 175

Ser Ser Thr Ser Gln Lys Val Ile Tyr Leu Val Met Ile Leu Leu Ile
```

```
            180                 185                 190

Ala Pro Ala Tyr Ser Ile Arg Cys Ile Gly Val Ser Asn Arg Asp Phe
        195                 200                 205

Val Glu Gly Met Ser Gly Gly Thr Trp Val Asp Val Val Leu Glu His
    210                 215                 220

Gly Gly Cys Val Thr Val Met Ala Gln Asp Lys Pro Thr Val Asp Ile
225                 230                 235                 240

Glu Leu Val Thr Thr Thr Val Ser Asn Met Ala Glu Val Arg Ser Tyr
                245                 250                 255

Cys Tyr Glu Ala Ser Ile Ser Asp Met Ala Ser Asp Ser Arg Cys Pro
            260                 265                 270

Thr Gln Gly Glu Ala Tyr Leu Asp Lys Gln Ser Asp Thr Gln Tyr Val
        275                 280                 285

Cys Lys Arg Thr Leu Val Asp Arg Gly Trp Gly Asn Gly Cys Gly Leu
    290                 295                 300

Phe Gly Lys Gly Ser Leu Val Thr Cys Ala Lys Phe Ala Cys Ser Lys
305                 310                 315                 320

Lys Met Thr Gly Lys Ser Ile Gln Pro Glu Asn Leu Glu Tyr Arg Ile
                325                 330                 335

Met Leu Ser Val His Gly Ser Gln His Ser Gly Met Ile Val Asn Asp
            340                 345                 350

Thr Gly His Glu Thr Asp Glu Asn Arg Ala Lys Val Glu Ile Thr Pro
        355                 360                 365

Asn Ser Pro Arg Ala Glu Ala Thr Leu Gly Gly Phe Gly Ser Leu Gly
    370                 375                 380

Leu Asp Cys Glu Pro Arg Thr Gly Leu Asp Phe Ser Asp Leu Tyr Tyr
385                 390                 395                 400

Leu Thr Met Asn Asn Lys His Trp Leu Val His Lys Glu Trp Phe His
                405                 410                 415

Asp Ile Pro Leu Pro Trp His Ala Gly Ala Asp Thr Gly Thr Pro His
            420                 425                 430

Trp Asn Asn Lys Glu Ala Leu Val Glu Phe Lys Asp Ala His Ala Lys
        435                 440                 445

Arg Gln Thr Val Val Val Leu Gly Ser Gln Glu Gly Ala Val His Thr
    450                 455                 460

Ala Leu Ala Gly Ala Leu Glu Ala Glu Met Asp Gly Ala Lys Gly Arg
465                 470                 475                 480

Leu Ser Ser Gly His Leu Lys Cys Arg Leu Lys Met Asp Lys Leu Arg
                485                 490                 495

Leu Lys Gly Val Ser Tyr Ser Leu Cys Thr Ala Ala Phe Thr Phe Thr
            500                 505                 510

Lys Ile Pro Ala Glu Thr Leu His Gly Thr Val Thr Val Glu Val Gln
        515                 520                 525

Tyr Ala Gly Thr Asp Gly Pro Cys Lys Val Pro Ala Gln Met Ala Val
    530                 535                 540

Asp Met Gln Thr Leu Thr Pro Val Gly Arg Leu Ile Thr Ala Asn Pro
545                 550                 555                 560

Val Ile Thr Glu Ser Thr Glu Asn Ser Lys Met Met Leu Glu Leu Asp
                565                 570                 575

Pro Pro Phe Gly Asp Ser Tyr Ile Val Ile Gly Val Gly Glu Lys Lys
            580                 585                 590

Ile Thr His His Trp His Arg Ser Gly Ser Thr Ile Gly Lys Ala Phe
        595                 600                 605
```

```
Glu Ala Thr Val Arg Gly Ala Lys Arg Met Ala Val Leu Gly Asp Thr
    610                 615                 620

Ala Trp Asp Phe Gly Ser Val Gly Gly Ala Leu Asn Ser Leu Gly Lys
625                 630                 635                 640

Gly Ile His Gln Ile Phe Gly Ala Ala Phe Lys Ser Leu Phe Gly Gly
                645                 650                 655

Met Ser Trp Phe Ser Met Lys Gly Leu Ser Ser Thr Ser Ile Val Tyr
            660                 665                 670

Ile Leu Ile Ala Val Cys Leu Gly Gly Leu Ile Gly Ile Pro Ala Leu
        675                 680                 685

Ile Cys Cys Cys Arg Gly Arg Cys Asn Lys Lys Gly Glu Gln Val Gly
    690                 695                 700

Met Ser Arg Pro Gly Leu Lys Pro Asp Leu Thr Gly Thr Ser Lys Ser
705                 710                 715                 720

Tyr Val Arg Ser Leu
                725
```

<210> SEQ ID NO 132
<211> LENGTH: 1674
<212> TYPE: DNA
<213> ORGANISM: Artificial sequence
<220> FEATURE:
<223> OTHER INFORMATION: Native nucleotide sequence of MVsp_Zika_MVTMintracytoE (C10)

<400> SEQUENCE: 132

```
atgtccatca tgggtctcaa ggtgaacgtc tctgccatat tcatggcagt actgttaact     60

ctccaaacac ccaccggtca aatccatatc aggtgcatag gagtcagcaa tagggacttt    120

gtggaaggta tgtcaggtgg gacttgggtt gatgttgtct tggaacatgg aggttgtgtc    180

accgtaatgg cacaggacaa accgactgtc gacatagagc tggttacaac aacagtcagc    240

aacatggcgg aggtaagatc ctactgctat gaggcatcaa tatcagacat ggcttcggac    300

agccgctgcc caacacaagg tgaagcctac cttgacaagc aatcagacac tcaatatgtc    360

tgcaaaagaa cgttagtgga cagaggctgg ggaaatggat gtggactttt tggcaaaggg    420

agcctggtga catgcgctaa gtttgcatgc tccaagaaaa tgaccgggaa gagcatccag    480

ccagagaatc tggagtaccg gataatgctg tcagttcatg gctcccagca cagtgggatg    540

atcgttaatg acacaggaca tgaaactgat gagaatagag cgaaggttga gataacgccc    600

aattcaccaa gagccgaagc caccctgggg ggttttggaa gcctaggact tgattgtgaa    660

ccgaggacag gccttgactt ttcagatttg tattacttga ctatgaataa caagcactgg    720

ttggttcaca aggagtggtt ccacgacatt ccattacctt ggcacgctgg ggcagacacc    780

ggaactccac actggaacaa caaagaagca ctggtagagt tcaaggacgc acatgccaaa    840

aggcaaactg tcgtggttct agggagtcaa gaaggagcag ttcacacggc ccttgctgga    900

gctctggagg ctgagatgga tggtgcaaag ggaaggctgt cctctggcca cttgaaatgt    960

cgcctgaaaa tggataaact tagattgaag ggcgtgtcat actccttgtg taccgcagcg   1020

ttcacattca ccaagatccc ggctgaaaca ctgcacggga cagtcacagt ggaggtacag   1080

tacgcaggga cagatggacc ttgcaaggtt ccagctcaga tggcggtgga catgcaaact   1140

ctgaccccag ttgggaggtt gataaccgct aaccccgtaa tcactgaaag cactgagaac   1200

tctaagatga tgctggaact tgatccacca tttggggact cttacattgt cataggagtc   1260

ggggagaaga agatcaccca ccactggcac aggagtggca gcaccattgg aaaagcattt   1320
```

gaagccactg tgagaggtgc caagagaatg gcagtcttgg gagacacagc ctgggacttt 1380
ggatcagttg gaggcgctct caactcattg ggcaagggca tccatcaaat tttggagca 1440 gctttcaaat cattgtttgg aggaatgtcc tggttctcaa tgaaaggttt atcgagcact 1500
agcatagtct acatcctgat tgcagtgtgt cttggagggt tgatagggat ccccgcttta 1560
atatgttgct gcagggggcg ttgtaacaaa aagggagaac aagttggtat gtcaagacca 1620
ggcctaaagc ctgatcttac gggaacatca aaatcctatg taaggtcgct ctga 1674

<210> SEQ ID NO 133
<211> LENGTH: 1674
<212> TYPE: DNA
<213> ORGANISM: Artificial sequence
<220> FEATURE:
<223> OTHER INFORMATION: Codon-optimized nucleotide sequence of MVsp_Zika_MVTMintracytoE (C10)

<400> SEQUENCE: 133
atgagcatca tgggcctgaa ggtgaacgtg tccgccatct tcatggccgt gctgctgacc 60
ctgcagacac caacaggcca gatccacatc cggtgcatcg gcgtgagcaa tagagacttc 120
gtggagggaa tgtccggagg aacctgggtg gatgtggtgc tggagcacgg cggctgcgtg 180
acagtgatgg cccaggacaa gccaaccgtg gatatcgagc tggtgaccac aaccgtgtcc 240
aacatggccg aggtgaggtc ttactgctat gaggccagca tctccgacat ggcctctgat 300
agcaggtgtc caacccaggg agaggcatac ctggacaagc agtccgatac acagtacgtg 360
tgcaagcgga ccctggtgga cagaggctgg ggcaatggct gtggcctgtt tggcaagggc 420
tctctggtga catgcgccaa gttcgcctgt agcaagaaga tgaccggcaa gtccatccag 480
ccagagaacc tggagtaccg gatcatgctg tctgtgcacg gctcccagca ctctggcatg 540
atcgtgaacg acacaggcca cgagacagat gagaatcggg ccaaggtgga gatcacacct 600
aactctccaa gagccgaggc caccctggga ggatttggct ctctgggcct ggactgcgag 660
cctagaacag gcctggactt ctccgatctg tactatctga ccatgaacaa taagcactgg 720
ctggtgcaca aggagtggtt tcacgacatc ccactgccat ggcacgcagg agcagataca 780
ggaacaccac actggaacaa taaggaggcc ctggtggagt tcaaggatgc ccacgccaag 840
cggcagacag tggtggtgct gggcagccag gagggagcag tgcacaccgc cctggcaggc 900
gccctggagg cagagatgga cggagctaag ggcagactgt ctagcggcca cctgaagtgc 960
aggctgaaga tggataagct gcgcctgaag ggcgtgtcct actctctgtg cacagccgcc 1020
ttcaccttca ccaagatccc tgccgagaca ctgcacggca cagtgaccgt ggaggtgcag 1080
tatgccggca cagacggacc ctgtaaggtg cctgcccaga tggccgtgga tatgcagaca 1140
ctgacacctg tgggcaggct gatcaccgcc aatccagtga tcacagagtc taccgagaac 1200
agcaagatga tgctggagct ggacccacca tttggcgata gctatatcgt gatcggcgtg 1260
ggcgagaaga agatcacaca ccactggcac cgcagcggct ccacaatcgg caaggccttt 1320
gaggcaaccg tgcgcggagc aaagagaatg gccgtgctgg gcgacaccgc atgggatttc 1380
ggatctgtgg gaggcgccct gaacagcctg ggcaagggca tccaccagat cttcggcgcc 1440
gcctttaagt ccctgttcgg cggcatgagc tggttctcaa tgaagggcct gtcctctacc 1500
tctatcgtgt acatcctgat cgccgtgtgc ctgggaggcc tgatcggaat cccagccctg 1560
atctgctgtt gcagaggccg ctgcaacaag aagggagagc aagtgggaat gtctcggcca 1620
ggcctgaagc cagacctgac aggcacctcc aagtcttatg tgagaagcct gtga 1674

<210> SEQ ID NO 134
<211> LENGTH: 557
<212> TYPE: PRT
<213> ORGANISM: Artificial sequence
<220> FEATURE:
<223> OTHER INFORMATION: MVsp_Zika_MVTMintracytoE (C10)

<400> SEQUENCE: 134

```
Met Ser Ile Met Gly Leu Lys Val Asn Val Ser Ala Ile Phe Met Ala
1               5                   10                  15

Val Leu Leu Thr Leu Gln Thr Pro Thr Gly Gln Ile His Ile Arg Cys
            20                  25                  30

Ile Gly Val Ser Asn Arg Asp Phe Val Glu Gly Met Ser Gly Gly Thr
        35                  40                  45

Trp Val Asp Val Val Leu Glu His Gly Gly Cys Val Thr Val Met Ala
    50                  55                  60

Gln Asp Lys Pro Thr Val Asp Ile Glu Leu Val Thr Thr Thr Val Ser
65                  70                  75                  80

Asn Met Ala Glu Val Arg Ser Tyr Cys Tyr Glu Ala Ser Ile Ser Asp
                85                  90                  95

Met Ala Ser Asp Ser Arg Cys Pro Thr Gln Gly Glu Ala Tyr Leu Asp
            100                 105                 110

Lys Gln Ser Asp Thr Gln Tyr Val Cys Lys Arg Thr Leu Val Asp Arg
        115                 120                 125

Gly Trp Gly Asn Gly Cys Gly Leu Phe Gly Lys Gly Ser Leu Val Thr
    130                 135                 140

Cys Ala Lys Phe Ala Cys Ser Lys Lys Met Thr Gly Lys Ser Ile Gln
145                 150                 155                 160

Pro Glu Asn Leu Glu Tyr Arg Ile Met Leu Ser Val His Gly Ser Gln
                165                 170                 175

His Ser Gly Met Ile Val Asn Asp Thr Gly His Glu Thr Asp Glu Asn
            180                 185                 190

Arg Ala Lys Val Glu Ile Thr Pro Asn Ser Pro Arg Ala Glu Ala Thr
        195                 200                 205

Leu Gly Gly Phe Gly Ser Leu Gly Leu Asp Cys Glu Pro Arg Thr Gly
    210                 215                 220

Leu Asp Phe Ser Asp Leu Tyr Tyr Leu Thr Met Asn Asn Lys His Trp
225                 230                 235                 240

Leu Val His Lys Glu Trp Phe His Asp Ile Pro Leu Pro Trp His Ala
                245                 250                 255

Gly Ala Asp Thr Gly Thr Pro His Trp Asn Asn Lys Glu Ala Leu Val
            260                 265                 270

Glu Phe Lys Asp Ala His Ala Lys Arg Gln Thr Val Val Val Leu Gly
        275                 280                 285

Ser Gln Glu Gly Ala Val His Thr Ala Leu Ala Gly Ala Leu Glu Ala
    290                 295                 300

Glu Met Asp Gly Ala Lys Gly Arg Leu Ser Ser Gly His Leu Lys Cys
305                 310                 315                 320

Arg Leu Lys Met Asp Lys Leu Arg Leu Lys Gly Val Ser Tyr Ser Leu
                325                 330                 335

Cys Thr Ala Ala Phe Thr Phe Thr Lys Ile Pro Ala Glu Thr Leu His
            340                 345                 350

Gly Thr Val Thr Val Glu Val Gln Tyr Ala Gly Thr Asp Gly Pro Cys
        355                 360                 365
```

```
Lys Val Pro Ala Gln Met Ala Val Asp Met Gln Thr Leu Thr Pro Val
    370                 375                 380

Gly Arg Leu Ile Thr Ala Asn Pro Val Ile Thr Glu Ser Thr Glu Asn
385                 390                 395                 400

Ser Lys Met Met Leu Glu Leu Asp Pro Pro Phe Gly Asp Ser Tyr Ile
                405                 410                 415

Val Ile Gly Val Gly Glu Lys Lys Ile Thr His His Trp His Arg Ser
            420                 425                 430

Gly Ser Thr Ile Gly Lys Ala Phe Glu Ala Thr Val Arg Gly Ala Lys
        435                 440                 445

Arg Met Ala Val Leu Gly Asp Thr Ala Trp Asp Phe Gly Ser Val Gly
    450                 455                 460

Gly Ala Leu Asn Ser Leu Gly Lys Gly Ile His Gln Ile Phe Gly Ala
465                 470                 475                 480

Ala Phe Lys Ser Leu Phe Gly Gly Met Ser Trp Phe Ser Met Lys Gly
                485                 490                 495

Leu Ser Ser Thr Ser Ile Val Tyr Ile Leu Ile Ala Val Cys Leu Gly
            500                 505                 510

Gly Leu Ile Gly Ile Pro Ala Leu Ile Cys Cys Cys Arg Gly Arg Cys
        515                 520                 525

Asn Lys Lys Gly Glu Gln Val Gly Met Ser Arg Pro Gly Leu Lys Pro
    530                 535                 540

Asp Leu Thr Gly Thr Ser Lys Ser Tyr Val Arg Ser Leu
545                 550                 555


<210> SEQ ID NO 135
<211> LENGTH: 2100
<212> TYPE: DNA
<213> ORGANISM: Artificial sequence
<220> FEATURE:
<223> OTHER INFORMATION: Native nucleotide sequence of MVsp_ZikaprME
      (D1)

<400> SEQUENCE: 135

atgtccatca tgggtctcaa ggtgaacgtc tctgccatat tcatggcagt actgttaact      60

ctccaaacac ccaccggtca agcggaggtc actagacgtg ggagtgcata ctatatgtac     120

ttggacagaa acgatgctgg ggaggccata tcttttccaa ccacattggg gatgaataag     180

tgttatatac agatcatgga tcttggacac atgtgtgatg ccaccatgag ctatgaatgc     240

cctatgctgg atgagggggt ggaaccagat gacgtcgatt gttggtgcaa cacgacgtca     300

acttgggttg tgtacggaac ctgccatcac aaaaaaggtg aagcacggag atctagaaga     360

gctgtgacgc tcccctccca ttccactagg aagctgcaaa cgcggtcgca aacctggttg     420

gaatcaagag aatacacaaa gcacttgatt agagtcgaaa attggatatt caggaaccct     480

ggcttcgcgt tagcagcagc tgccatcgct tggcttttgg gaagctcaac gagccaaaaa     540

gtcatatact tggtcatgat actgctgatt gccccggcat acagcatcag gtgcatagga     600

gtcagcaata gggactttgt ggaaggtatg tcaggtggga cttgggttga tgttgtcttg     660

gaacatggag gttgtgtcac cgtaatggca caggacaaac cgactgtcga catagagctg     720

gttacaacaa cagtcagcaa catggcggag gtaagatcct actgctatga ggcatcaata     780

tcagacatgg cttcggacag ccgctgccca acacaaggtg aagcctacct tgacaagcaa     840

tcagacactc aatatgtctg caaaagaacg ttagtggaca gaggctgggg aaatggatgt     900

ggactttttg gcaaagggag cctggtgaca tgcgctaagt ttgcatgctc caagaaaatg     960
```

-continued

```
accgggaaga gcatccagcc agagaatctg gagtaccgga taatgctgtc agttcatggc   1020

tcccagcaca gtgggatgat cgttaatgac acaggacatg aaactgatga gaatagagcg   1080

aaggttgaga taacgcccaa ttcaccaaga gccgaagcca ccctgggggg ttttggaagc   1140

ctaggacttg attgtgaacc gaggacaggc cttgactttt cagatttgta ttacttgact   1200

atgaataaca agcactggtt ggttcacaag gagtggttcc acgacattcc attaccttgg   1260

cacgctgggg cagacaccgg aactccacac tggaacaaca aagaagcact ggtagagttc   1320

aaggacgcac atgccaaaag gcaaactgtc gtggttctag ggagtcaaga aggagcagtt   1380

cacacggccc ttgctggagc tctggaggct gagatggatg gtgcaaaggg aaggctgtcc   1440

tctggccact tgaaatgtcg cctgaaaatg gataaactta gattgaaggg cgtgtcatac   1500

tccttgtgta ccgcagcgtt cacattcacc aagatcccgg ctgaaacact gcacgggaca   1560

gtcacagtgg aggtacagta cgcagggaca gatggacctt gcaaggttcc agctcagatg   1620

gcggtggaca tgcaaactct gaccccagtt gggaggttga taaccgctaa ccccgtaatc   1680

actgaaagca ctgagaactc taagatgatg ctggaacttg atccaccatt tggggactct   1740

tacattgtca taggagtcgg ggagaagaag atcacccacc actggcacag gagtggcagc   1800

accattggaa aagcatttga agccactgtg agaggtgcca agagaatggc agtcttggga   1860

gacacagcct gggactttgg atcagttgga ggcgctctca actcattggg caagggcatc   1920

catcaaattt ttggagcagc tttcaaatca ttgtttggag gaatgtcctg gttctcacaa   1980

attctcattg gaacgttgct gatgtggttg ggtctgaaca caaagaatgg atctatttcc   2040

cttatgtgct tggccttagg gggagtgttg atcttcttat ccacagccgt ctctgcttga   2100
```

<210> SEQ ID NO 136
<211> LENGTH: 2100
<212> TYPE: DNA
<213> ORGANISM: Artificial sequence
<220> FEATURE:
<223> OTHER INFORMATION: Codon-optimized nucleotide sequence of MVsp_ZikaprME (D1)

<400> SEQUENCE: 136

```
atgagcatca tgggcctgaa ggtgaacgtg tccgccatct tcatggccgt gctgctgacc     60

ctgcagacac caacaggcca ggcagaggtg accaggagag gaagcgccta ctatatgtac    120

ctggacagga atgatgccgg cgaggccatc tccttcccaa ccacactggg catgaacaag    180

tgctacatcc agatcatgga cctgggccac atgtgcgatg ccaccatgtc ctatgagtgt    240

ccaatgctgg acgagggcgt ggagcccgac gatgtggatt gctggtgtaa taccacatct    300

acatgggtgg tgtacggcac ctgtcaccac aagaagggag aggcccggcg gagccggcgg    360

gccgtgacac tgccttccca ctctaccagg aagctgcaga cacgcagcca gacctggctg    420

gagtccagag agtataccaa gcacctgatc agggtggaga actggatctt tcgcaatcca    480

ggattcgcac tggcagcagc agcaatcgca tggctgctgg gaagctccac cagccagaaa    540

gtgatctacc tggtcatgat cctgctgatc gctcctgcct attctatccg gtgcatcggc    600

gtgagcaata gagacttcgt ggagggaatg tccggaggaa cctgggtgga tgtggtgctg    660

gagcacggcg gctgcgtgac agtgatggcc caggacaagc caaccgtgga tatcgagctg    720

gtgaccacaa ccgtgtccaa catggccgag gtgaggtctt actgctatga ggccagcatc    780

tccgacatgg cctctgatag caggtgtcca acccagggag aggcatacct ggacaagcag    840

tccgatacac agtacgtgtg caagcggacc ctggtggaca gaggctgggg caatggctgt    900
```

```
ggcctgtttg gcaagggctc tctggtgaca tgcgccaagt tcgcctgtag caagaagatg    960

accggcaagt ccatccagcc agagaacctg gagtaccgga tcatgctgtc tgtgcacggc   1020

tcccagcact ctggcatgat cgtgaacgac acaggccacg agacagatga gaatcgggcc   1080

aaggtggaga tcacacctaa ctctccaaga gccgaggcca ccctgggagg atttggctct   1140

ctgggcctgg actgcgagcc tagaacaggc ctggacttct ccgatctgta ctatctgacc   1200

atgaacaata agcactggct ggtgcacaag gagtggtttc acgacatccc actgccatgg   1260

cacgcaggag cagatacagg aacaccacac tggaacaata aggaggccct ggtggagttc   1320

aaggatgccc acgccaagcg gcagacagtg gtggtgctgg gcagccagga gggagcagtg   1380

cacaccgccc tggcaggcgc cctggaggca gagatggacg gagctaaggg cagactgtct   1440

agcggccacc tgaagtgcag gctgaagatg gataagctgc gcctgaaggg cgtgtcctac   1500

tctctgtgca cagccgcctt caccttcacc aagatccctg ccgagacact gcacggcaca   1560

gtgaccgtgg aggtgcagta tgccggcaca gacggaccct gtaaggtgcc tgcccagatg   1620

gccgtggata tgcagacact gacacctgtg ggcaggctga tcaccgccaa tccagtgatc   1680

acagagtcta ccgagaacag caagatgatg ctggagctgg acccaccatt tggcgatagc   1740

tatatcgtga tcggcgtggg cgagaagaag atcacacacc actggcaccg cagcggctcc   1800

acaatcggca aggcctttga ggcaaccgtg cgcggagcaa agagaatggc cgtgctgggc   1860

gacaccgcat gggatttcgg atctgtggga ggcgccctga acagcctggg caagggcatc   1920

caccagatct tcggcgccgc ctttaagtcc ctgttcggcg gcatgagctg gttctcacag   1980

atcctgatcg gcacactgct gatgtggctg ggcctgaaca ccaagaatgg ctctatcagc   2040

ctgatgtgcc tggccctggg aggcgtgctg atcttcctgt ccaccgccgt gtctgcctga   2100
```

<210> SEQ ID NO 137
<211> LENGTH: 699
<212> TYPE: PRT
<213> ORGANISM: Artificial sequence
<220> FEATURE:
<223> OTHER INFORMATION: MVsp_ZikaprME (D1)

<400> SEQUENCE: 137

```
Met Ser Ile Met Gly Leu Lys Val Asn Val Ser Ala Ile Phe Met Ala
1               5                   10                  15

Val Leu Leu Thr Leu Gln Thr Pro Thr Gly Gln Ala Glu Val Thr Arg
            20                  25                  30

Arg Gly Ser Ala Tyr Tyr Met Tyr Leu Asp Arg Asn Asp Ala Gly Glu
        35                  40                  45

Ala Ile Ser Phe Pro Thr Thr Leu Gly Met Asn Lys Cys Tyr Ile Gln
    50                  55                  60

Ile Met Asp Leu Gly His Met Cys Asp Ala Thr Met Ser Tyr Glu Cys
65                  70                  75                  80

Pro Met Leu Asp Glu Gly Val Glu Pro Asp Asp Val Asp Cys Trp Cys
                85                  90                  95

Asn Thr Thr Ser Thr Trp Val Val Tyr Gly Thr Cys His His Lys Lys
            100                 105                 110

Gly Glu Ala Arg Arg Ser Arg Arg Ala Val Thr Leu Pro Ser His Ser
        115                 120                 125

Thr Arg Lys Leu Gln Thr Arg Ser Gln Thr Trp Leu Glu Ser Arg Glu
    130                 135                 140

Tyr Thr Lys His Leu Ile Arg Val Glu Asn Trp Ile Phe Arg Asn Pro
```

```
145                 150                 155                 160

Gly Phe Ala Leu Ala Ala Ala Ala Ile Ala Trp Leu Leu Gly Ser Ser
                165                 170                 175

Thr Ser Gln Lys Val Ile Tyr Leu Val Met Ile Leu Leu Ile Ala Pro
            180                 185                 190

Ala Tyr Ser Ile Arg Cys Ile Gly Val Ser Asn Arg Asp Phe Val Glu
        195                 200                 205

Gly Met Ser Gly Gly Thr Trp Val Asp Val Val Leu Glu His Gly Gly
    210                 215                 220

Cys Val Thr Val Met Ala Gln Asp Lys Pro Thr Val Asp Ile Glu Leu
225                 230                 235                 240

Val Thr Thr Thr Val Ser Asn Met Ala Glu Val Arg Ser Tyr Cys Tyr
                245                 250                 255

Glu Ala Ser Ile Ser Asp Met Ala Ser Asp Ser Arg Cys Pro Thr Gln
            260                 265                 270

Gly Glu Ala Tyr Leu Asp Lys Gln Ser Asp Thr Gln Tyr Val Cys Lys
        275                 280                 285

Arg Thr Leu Val Asp Arg Gly Trp Gly Asn Gly Cys Gly Leu Phe Gly
    290                 295                 300

Lys Gly Ser Leu Val Thr Cys Ala Lys Phe Ala Cys Ser Lys Lys Met
305                 310                 315                 320

Thr Gly Lys Ser Ile Gln Pro Glu Asn Leu Glu Tyr Arg Ile Met Leu
                325                 330                 335

Ser Val His Gly Ser Gln His Ser Gly Met Ile Val Asn Asp Thr Gly
            340                 345                 350

His Glu Thr Asp Glu Asn Arg Ala Lys Val Glu Ile Thr Pro Asn Ser
        355                 360                 365

Pro Arg Ala Glu Ala Thr Leu Gly Gly Phe Gly Ser Leu Gly Leu Asp
    370                 375                 380

Cys Glu Pro Arg Thr Gly Leu Asp Phe Ser Asp Leu Tyr Tyr Leu Thr
385                 390                 395                 400

Met Asn Asn Lys His Trp Leu Val His Lys Glu Trp Phe His Asp Ile
                405                 410                 415

Pro Leu Pro Trp His Ala Gly Ala Asp Thr Gly Thr Pro His Trp Asn
            420                 425                 430

Asn Lys Glu Ala Leu Val Glu Phe Lys Asp Ala His Ala Lys Arg Gln
        435                 440                 445

Thr Val Val Val Leu Gly Ser Gln Glu Gly Ala Val His Thr Ala Leu
    450                 455                 460

Ala Gly Ala Leu Glu Ala Glu Met Asp Gly Ala Lys Gly Arg Leu Ser
465                 470                 475                 480

Ser Gly His Leu Lys Cys Arg Leu Lys Met Asp Lys Leu Arg Leu Lys
                485                 490                 495

Gly Val Ser Tyr Ser Leu Cys Thr Ala Ala Phe Thr Phe Thr Lys Ile
            500                 505                 510

Pro Ala Glu Thr Leu His Gly Thr Val Thr Val Glu Val Gln Tyr Ala
        515                 520                 525

Gly Thr Asp Gly Pro Cys Lys Val Pro Ala Gln Met Ala Val Asp Met
    530                 535                 540

Gln Thr Leu Thr Pro Val Gly Arg Leu Ile Thr Ala Asn Pro Val Ile
545                 550                 555                 560

Thr Glu Ser Thr Glu Asn Ser Lys Met Met Leu Glu Leu Asp Pro Pro
                565                 570                 575
```

```
Phe Gly Asp Ser Tyr Ile Val Ile Gly Val Gly Glu Lys Lys Ile Thr
            580                 585                 590

His His Trp His Arg Ser Gly Ser Thr Ile Gly Lys Ala Phe Glu Ala
        595                 600                 605

Thr Val Arg Gly Ala Lys Arg Met Ala Val Leu Gly Asp Thr Ala Trp
    610                 615                 620

Asp Phe Gly Ser Val Gly Gly Ala Leu Asn Ser Leu Gly Lys Gly Ile
625                 630                 635                 640

His Gln Ile Phe Gly Ala Ala Phe Lys Ser Leu Phe Gly Gly Met Ser
                645                 650                 655

Trp Phe Ser Gln Ile Leu Ile Gly Thr Leu Leu Met Trp Leu Gly Leu
            660                 665                 670

Asn Thr Lys Asn Gly Ser Ile Ser Leu Met Cys Leu Ala Leu Gly Gly
        675                 680                 685

Val Leu Ile Phe Leu Ser Thr Ala Val Ser Ala
    690                 695


<210> SEQ ID NO 138
<211> LENGTH: 1956
<212> TYPE: DNA
<213> ORGANISM: Artificial sequence
<220> FEATURE:
<223> OTHER INFORMATION: Native nucleotide sequence of
      MVsp_Zika_prME_no_anchor (D2)

<400> SEQUENCE: 138

atgtccatca tgggtctcaa ggtgaacgtc tctgccatat tcatggcagt actgttaact     60

ctccaaacac ccaccggtca agcggaggtc actagacgtg ggagtgcata ctatatgtac    120

ttggacagaa acgatgctgg ggaggccata tcttttccaa ccacattggg gatgaataag    180

tgttatatac agatcatgga tcttggacac atgtgtgatg ccaccatgag ctatgaatgc    240

cctatgctgg atgagggggt ggaaccagat gacgtcgatt gttggtgcaa cacgacgtca    300

acttgggttg tgtacggaac ctgccatcac aaaaaaggtg aagcacggag atctagaaga    360

gctgtgacgc tcccctccca ttccactagg aagctgcaaa cgcggtcgca aacctggttg    420

gaatcaagag aatacacaaa gcacttgatt agagtcgaaa attggatatt caggaaccct    480

ggcttcgcgt tagcagcagc tgccatcgct tggcttttgg gaagctcaac gagccaaaaa    540

gtcatatact tggtcatgat actgctgatt gccccggcat acagcatcag gtgcatagga    600

gtcagcaata gggactttgt ggaaggtatg tcaggtggga cttgggttga tgttgtcttg    660

gaacatggag gttgtgtcac cgtaatggca caggacaaac cgactgtcga catagagctg    720

gttacaacaa cagtcagcaa catggcggag gtaagatcct actgctatga ggcatcaata    780

tcagacatgg cttcggacag ccgctgccca acacaaggtg aagcctacct tgacaagcaa    840

tcagacactc aatatgtctg caaaagaacg ttagtggaca gaggctgggg aaatggatgt    900

ggactttttg gcaaagggag cctggtgaca tgcgctaagt ttgcatgctc caagaaaatg    960

accgggaaga gcatccagcc agagaatctg gagtaccgga taatgctgtc agttcatggc   1020

tcccagcaca gtgggatgat cgttaatgac acaggacatg aaactgatga gaatagagcg   1080

aaggttgaga taacgcccaa ttcaccaaga gccgaagcca ccctgggggg ttttggaagc   1140

ctaggacttg attgtgaacc gaggacaggc cttgactttt cagatttgta ttacttgact   1200

atgaataaca agcactggtt ggttcacaag gagtggttcc acgacattcc attaccttgg   1260

cacgctgggg cagacaccgg aactccacac tggaacaaca aagaagcact ggtagagttc   1320
```

aaggacgcac atgccaaaag gcaaactgtc gtggttctag ggagtcaaga aggagcagtt 1380
cacacggccc ttgctggagc tctggaggct gagatggatg gtgcaaaggg aaggctgtcc 1440
tctggccact tgaaatgtcg cctgaaaatg gataaactta gattgaaggg cgtgtcatac 1500
tccttgtgta ccgcagcgtt cacattcacc aagatcccgg ctgaaacact gcacgggaca 1560
gtcacagtgg aggtacagta cgcagggaca gatggacctt gcaaggttcc agctcagatg 1620
gcggtggaca tgcaaactct gaccccagtt gggaggttga taaccgctaa ccccgtaatc 1680
actgaaagca ctgagaactc taagatgatg ctggaacttg atccaccatt tggggactct 1740
tacattgtca taggagtcgg ggagaagaag atcacccacc actggcacag gagtggcagc 1800
accattggaa aagcatttga agccactgtg agaggtgcca agagaatggc agtcttggga 1860
gacacagcct gggactttgg atcagttgga ggcgctctca actcattggg caagggcatc 1920
catcaaattt ttggagcagc tttcaaatca ttgtga 1956

<210> SEQ ID NO 139
<211> LENGTH: 1956
<212> TYPE: DNA
<213> ORGANISM: Artificial sequence
<220> FEATURE:
<223> OTHER INFORMATION: Codon-optimized nucleotide sequence of
MVsp_Zika_prME_no_anchor (D2)

<400> SEQUENCE: 139
atgagcatca tgggcctgaa ggtgaacgtg tccgccatct tcatggccgt gctgctgacc 60
ctgcagacac caacaggcca ggcagaggtg accaggagag gaagcgccta ctatatgtac 120
ctggacagga atgatgccgg cgaggccatc tccttcccaa ccacactggg catgaacaag 180
tgctacatcc agatcatgga cctgggccac atgtgcgatg ccaccatgtc ctatgagtgt 240
ccaatgctgg acgagggcgt ggagcccgac gatgtggatt gctggtgtaa taccacatct 300
acatgggtgg tgtacggcac ctgtcaccac aagaagggag aggcccggcg gagccggcgg 360
gccgtgacac tgccttccca ctctaccagg aagctgcaga cacgcagcca gacctggctg 420
gagtccagag agtataccaa gcacctgatc agggtggaga actggatctt tcgcaatcca 480
ggattcgcac tggcagcagc agcaatcgca tggctgctgg gaagctccac cagccagaaa 540
gtgatctacc tggtcatgat cctgctgatc gctcctgcct attctatccg gtgcatcggc 600
gtgagcaata gagacttcgt ggagggaatg tccggaggaa cctgggtgga tgtggtgctg 660
gagcacggcg gctgcgtgac agtgatggcc caggacaagc caaccgtgga tatcgagctg 720
gtgaccacaa ccgtgtccaa catggccgag gtgaggtctt actgctatga ggccagcatc 780
tccgacatgg cctctgatag caggtgtcca acccagggag aggcatacct ggacaagcag 840
tccgatacac agtacgtgtg caagcggacc ctggtggaca gaggctgggg caatggctgt 900
ggcctgtttg gcaagggctc tctggtgaca tgcgccaagt tcgcctgtag caagaagatg 960
accggcaagt ccatccagcc agagaacctg gagtaccgga tcatgctgtc tgtgcacggc 1020
tcccagcact ctggcatgat cgtgaacgac acaggccacg agacagatga gaatcgggcc 1080
aaggtggaga tcacacctaa ctctccaaga gccgaggcca ccctgggagg atttggctct 1140
ctgggcctgg actgcgagcc tagaacaggc ctggacttct ccgatctgta ctatctgacc 1200
atgaacaata agcactggct ggtgcacaag gagtggtttc acgacatccc actgccatgg 1260
cacgcaggag cagatacagg aacaccacac tggaacaata aggaggccct ggtggagttc 1320
aaggatgccc acgccaagcg gcagacagtg gtggtgctgg gcagccagga gggagcagtg 1380

```
cacaccgccc tggcaggcgc cctggaggca gagatggacg gagctaaggg cagactgtct   1440

agcggccacc tgaagtgcag gctgaagatg gataagctgc gcctgaaggg cgtgtcctac   1500

tctctgtgca cagccgcctt caccttcacc aagatccctg ccgagacact gcacggcaca   1560

gtgaccgtgg aggtgcagta tgccggcaca gacggaccct gtaaggtgcc tgcccagatg   1620

gccgtggata tgcagacact gacacctgtg ggcaggctga tcaccgccaa tccagtgatc   1680

acagagtcta ccgagaacag caagatgatg ctggagctgg acccaccatt tggcgatagc   1740

tatatcgtga tcggcgtggg cgagaagaag atcacacacc actggcaccg cagcggctcc   1800

acaatcggca aggcctttga ggcaaccgtg cgcggagcaa agagaatggc cgtgctgggc   1860

gacaccgcat gggatttcgg atctgtggga ggcgccctga acagcctggg caagggcatc   1920

caccagatct tcggcgccgc ctttaagtcc ctgtga                              1956
```

<210> SEQ ID NO 140
<211> LENGTH: 651
<212> TYPE: PRT
<213> ORGANISM: Artificial sequence
<220> FEATURE:
<223> OTHER INFORMATION: MVsp_Zika_prME_no_anchor (D2)

<400> SEQUENCE: 140

```
Met Ser Ile Met Gly Leu Lys Val Asn Val Ser Ala Ile Phe Met Ala
1               5                   10                  15

Val Leu Leu Thr Leu Gln Thr Pro Thr Gly Gln Ala Glu Val Thr Arg
            20                  25                  30

Arg Gly Ser Ala Tyr Tyr Met Tyr Leu Asp Arg Asn Asp Ala Gly Glu
        35                  40                  45

Ala Ile Ser Phe Pro Thr Thr Leu Gly Met Asn Lys Cys Tyr Ile Gln
    50                  55                  60

Ile Met Asp Leu Gly His Met Cys Asp Ala Thr Met Ser Tyr Glu Cys
65                  70                  75                  80

Pro Met Leu Asp Glu Gly Val Glu Pro Asp Asp Val Asp Cys Trp Cys
                85                  90                  95

Asn Thr Thr Ser Thr Trp Val Val Tyr Gly Thr Cys His His Lys Lys
            100                 105                 110

Gly Glu Ala Arg Arg Ser Arg Arg Ala Val Thr Leu Pro Ser His Ser
        115                 120                 125

Thr Arg Lys Leu Gln Thr Arg Ser Gln Thr Trp Leu Glu Ser Arg Glu
    130                 135                 140

Tyr Thr Lys His Leu Ile Arg Val Glu Asn Trp Ile Phe Arg Asn Pro
145                 150                 155                 160

Gly Phe Ala Leu Ala Ala Ala Ala Ile Ala Trp Leu Leu Gly Ser Ser
                165                 170                 175

Thr Ser Gln Lys Val Ile Tyr Leu Val Met Ile Leu Leu Ile Ala Pro
            180                 185                 190

Ala Tyr Ser Ile Arg Cys Ile Gly Val Ser Asn Arg Asp Phe Val Glu
        195                 200                 205

Gly Met Ser Gly Gly Thr Trp Val Asp Val Val Leu Glu His Gly Gly
    210                 215                 220

Cys Val Thr Val Met Ala Gln Asp Lys Pro Thr Val Asp Ile Glu Leu
225                 230                 235                 240

Val Thr Thr Thr Val Ser Asn Met Ala Glu Val Arg Ser Tyr Cys Tyr
                245                 250                 255
```

```
Glu Ala Ser Ile Ser Asp Met Ala Ser Asp Ser Arg Cys Pro Thr Gln
            260                 265                 270

Gly Glu Ala Tyr Leu Asp Lys Gln Ser Asp Thr Gln Tyr Val Cys Lys
        275                 280                 285

Arg Thr Leu Val Asp Arg Gly Trp Gly Asn Gly Cys Gly Leu Phe Gly
    290                 295                 300

Lys Gly Ser Leu Val Thr Cys Ala Lys Phe Ala Cys Ser Lys Lys Met
305                 310                 315                 320

Thr Gly Lys Ser Ile Gln Pro Glu Asn Leu Glu Tyr Arg Ile Met Leu
                325                 330                 335

Ser Val His Gly Ser Gln His Ser Gly Met Ile Val Asn Asp Thr Gly
            340                 345                 350

His Glu Thr Asp Glu Asn Arg Ala Lys Val Glu Ile Thr Pro Asn Ser
        355                 360                 365

Pro Arg Ala Glu Ala Thr Leu Gly Gly Phe Gly Ser Leu Gly Leu Asp
    370                 375                 380

Cys Glu Pro Arg Thr Gly Leu Asp Phe Ser Asp Leu Tyr Tyr Leu Thr
385                 390                 395                 400

Met Asn Asn Lys His Trp Leu Val His Lys Glu Trp Phe His Asp Ile
                405                 410                 415

Pro Leu Pro Trp His Ala Gly Ala Asp Thr Gly Thr Pro His Trp Asn
            420                 425                 430

Asn Lys Glu Ala Leu Val Glu Phe Lys Asp Ala His Ala Lys Arg Gln
        435                 440                 445

Thr Val Val Val Leu Gly Ser Gln Glu Gly Ala Val His Thr Ala Leu
    450                 455                 460

Ala Gly Ala Leu Glu Ala Glu Met Asp Gly Ala Lys Gly Arg Leu Ser
465                 470                 475                 480

Ser Gly His Leu Lys Cys Arg Leu Lys Met Asp Lys Leu Arg Leu Lys
                485                 490                 495

Gly Val Ser Tyr Ser Leu Cys Thr Ala Ala Phe Thr Phe Thr Lys Ile
            500                 505                 510

Pro Ala Glu Thr Leu His Gly Thr Val Thr Val Glu Val Gln Tyr Ala
        515                 520                 525

Gly Thr Asp Gly Pro Cys Lys Val Pro Ala Gln Met Ala Val Asp Met
    530                 535                 540

Gln Thr Leu Thr Pro Val Gly Arg Leu Ile Thr Ala Asn Pro Val Ile
545                 550                 555                 560

Thr Glu Ser Thr Glu Asn Ser Lys Met Met Leu Glu Leu Asp Pro Pro
                565                 570                 575

Phe Gly Asp Ser Tyr Ile Val Ile Gly Val Gly Glu Lys Lys Ile Thr
            580                 585                 590

His His Trp His Arg Ser Gly Ser Thr Ile Gly Lys Ala Phe Glu Ala
        595                 600                 605

Thr Val Arg Gly Ala Lys Arg Met Ala Val Leu Gly Asp Thr Ala Trp
    610                 615                 620

Asp Phe Gly Ser Val Gly Gly Ala Leu Asn Ser Leu Gly Lys Gly Ile
625                 630                 635                 640

His Gln Ile Phe Gly Ala Ala Phe Lys Ser Leu
                645                 650
```

<210> SEQ ID NO 141
<211> LENGTH: 1926
<212> TYPE: DNA

<213> ORGANISM: Artificial sequence
<220> FEATURE:
<223> OTHER INFORMATION: Native nucleotide sequence of MVsp_Zika_prME411
(D3)

<400> SEQUENCE: 141

```
atgtccatca tgggtctcaa ggtgaacgtc tctgccatat tcatggcagt actgttaact     60
ctccaaacac ccaccggtca agcggaggtc actagacgtg ggagtgcata ctatatgtac    120
ttggacagaa acgatgctgg ggaggccata tcttttccaa ccacattggg gatgaataag    180
tgttatatac agatcatgga tcttggacac atgtgtgatg ccaccatgag ctatgaatgc    240
cctatgctgg atgagggggt ggaaccagat gacgtcgatt gttggtgcaa cacgacgtca    300
acttgggttg tgtacggaac ctgccatcac aaaaaaggtg aagcacggag atctagaaga    360
gctgtgacgc tcccctccca ttccactagg aagctgcaaa cgcggtcgca aacctggttg    420
gaatcaagag aatacacaaa gcacttgatt agagtcgaaa attggatatt caggaaccct    480
ggcttcgcgt tagcagcagc tgccatcgct tggcttttgg gaagctcaac gagccaaaaa    540
gtcatatact tggtcatgat actgctgatt gccccggcat acagcatcag gtgcatagga    600
gtcagcaata gggactttgt ggaaggtatg tcaggtggga cttgggttga tgttgtcttg    660
gaacatggag gttgtgtcac cgtaatggca caggacaaac cgactgtcga catagagctg    720
gttacaacaa cagtcagcaa catggcggag gtaagatcct actgctatga ggcatcaata    780
tcagacatgg cttcggacag ccgctgccca acacaaggtg aagcctacct tgacaagcaa    840
tcagacactc aatatgtctg caaaagaacg ttagtggaca gaggctgggg aaatggatgt    900
ggactttttg gcaaagggag cctggtgaca tgcgctaagt ttgcatgctc caagaaaatg    960
accgggaaga gcatccagcc agagaatctg gagtaccgga taatgctgtc agttcatggc   1020
tcccagcaca gtgggatgat cgttaatgac acaggacatg aaactgatga gaatagagcg   1080
aaggttgaga taacgcccaa ttcaccaaga gccgaagcca ccctgggggg ttttggaagc   1140
ctaggacttg attgtgaacc gaggacaggc cttgactttt cagatttgta ttacttgact   1200
atgaataaca agcactggtt ggttcacaag gagtggttcc acgacattcc attaccttgg   1260
cacgctgggg cagacaccgg aactccacac tggaacaaca aagaagcact ggtagagttc   1320
aaggacgcac atgccaaaag gcaaactgtc gtggttctag ggagtcaaga aggagcagtt   1380
cacacggccc ttgctggagc tctggaggct gagatggatg gtgcaaaggg aaggctgtcc   1440
tctggccact tgaaatgtcg cctgaaaatg gataaactta gattgaaggg cgtgtcatac   1500
tccttgtgta ccgcagcgtt cacattcacc aagatcccgg ctgaaacact gcacgggaca   1560
gtcacagtgg aggtacagta cgcagggaca gatggacctt gcaaggttcc agctcagatg   1620
gcggtggaca tgcaaactct gaccccagtt gggaggttga taaccgctaa ccccgtaatc   1680
actgaaagca ctgagaactc taagatgatg ctggaacttg atccaccatt tggggactct   1740
tacattgtca taggagtcgg ggagaagaag atcacccacc actggcacag gagtggcagc   1800
accattggaa aagcatttga agccactgtg agaggtgcca agagaatggc agtcttggga   1860
gacacagcct gggactttgg atcagttgga ggcgctctca actcattggg caagggcatc   1920
tgatga                                                               1926
```

<210> SEQ ID NO 142
<211> LENGTH: 1926
<212> TYPE: DNA
<213> ORGANISM: Artificial sequence
<220> FEATURE:

<223> OTHER INFORMATION: Codon-optimized nucleotide sequence of
MVsp_Zika_prME411 (D3)

<400> SEQUENCE: 142

```
atgagcatca tgggcctgaa ggtgaacgtg tccgccatct tcatggccgt gctgctgacc     60
ctgcagacac caacaggcca ggcagaggtg accaggagag gaagcgccta ctatatgtac    120
ctggacagga atgatgccgg cgaggccatc tccttcccaa ccacactggg catgaacaag    180
tgctacatcc agatcatgga cctgggccac atgtgcgatg ccaccatgtc ctatgagtgt    240
ccaatgctgg acgagggcgt ggagcccgac gatgtggatt gctggtgtaa taccacatct    300
acatgggtgg tgtacggcac ctgtcaccac aagaagggag aggcccggcg gagccggcgg    360
gccgtgacac tgccttccca ctctaccagg aagctgcaga cacgcagcca gacctggctg    420
gagtccagag agtataccaa gcacctgatc agggtggaga actggatctt tcgcaatcca    480
ggattcgcac tggcagcagc agcaatcgca tggctgctgg gaagctccac cagccagaaa    540
gtgatctacc tggtcatgat cctgctgatc gctcctgcct attctatccg gtgcatcggc    600
gtgagcaata gagacttcgt ggagggaatg tccggaggaa cctgggtgga tgtggtgctg    660
gagcacggcg gctgcgtgac agtgatggcc caggacaagc caaccgtgga tatcgagctg    720
gtgaccacaa ccgtgtccaa catggccgag gtgaggtctt actgctatga ggccagcatc    780
tccgacatgg cctctgatag caggtgtcca acccagggag aggcatacct ggacaagcag    840
tccgatacac agtacgtgtg caagcggacc ctggtggaca gaggctgggg caatggctgt    900
ggcctgtttg gcaagggctc tctggtgaca tgcgccaagt tcgcctgtag caagaagatg    960
accggcaagt ccatccagcc agagaacctg gagtaccgga tcatgctgtc tgtgcacggc   1020
tcccagcact ctggcatgat cgtgaacgac acaggccacg agacagatga gaatcgggcc   1080
aaggtggaga tcacacctaa ctctccaaga gccgaggcca ccctgggagg atttggctct   1140
ctgggcctgg actgcgagcc tagaacaggc ctggacttct ccgatctgta ctatctgacc   1200
atgaacaata agcactggct ggtgcacaag gagtggtttc acgacatccc actgccatgg   1260
cacgcaggag cagatacagg aacaccacac tggaacaata aggaggccct ggtggagttc   1320
aaggatgccc acgccaagcg gcagacagtg gtggtgctgg gcagccagga gggagcagtg   1380
cacaccgccc tggcaggcgc cctggaggca gagatggacg gagctaaggg cagactgtct   1440
agcggccacc tgaagtgcag gctgaagatg gataagctgc gcctgaaggg cgtgtcctac   1500
tctctgtgca cagccgcctt caccttcacc aagatccctg ccgagacact gcacggcaca   1560
gtgaccgtgg aggtgcagta tgccggcaca gacggaccct gtaaggtgcc tgcccagatg   1620
gccgtggata tgcagacact gacacctgtg ggcaggctga tcaccgccaa tccagtgatc   1680
acagagtcta ccgagaacag caagatgatg ctggagctgg acccaccatt tggcgatagc   1740
tatatcgtga tcggcgtggg cgagaagaag atcacacacc actggcaccg cagcggctcc   1800
acaatcggca aggcctttga ggcaaccgtg cgcggagcaa agagaatggc cgtgctgggc   1860
gacaccgcat gggatttcgg atctgtggga ggcgccctga acagcctggg caagggcatc   1920
tgatga                                                              1926
```

<210> SEQ ID NO 143
<211> LENGTH: 640
<212> TYPE: PRT
<213> ORGANISM: Artificial sequence
<220> FEATURE:
<223> OTHER INFORMATION: MVsp_Zika_prME411 (D3)

<400> SEQUENCE: 143

Met Ser Ile Met Gly Leu Lys Val Asn Val Ser Ala Ile Phe Met Ala
1               5                   10                  15

Val Leu Leu Thr Leu Gln Thr Pro Thr Gly Gln Ala Glu Val Thr Arg
            20                  25                  30

Arg Gly Ser Ala Tyr Tyr Met Tyr Leu Asp Arg Asn Asp Ala Gly Glu
        35                  40                  45

Ala Ile Ser Phe Pro Thr Thr Leu Gly Met Asn Lys Cys Tyr Ile Gln
    50                  55                  60

Ile Met Asp Leu Gly His Met Cys Asp Ala Thr Met Ser Tyr Glu Cys
65                  70                  75                  80

Pro Met Leu Asp Glu Gly Val Glu Pro Asp Asp Val Asp Cys Trp Cys
                85                  90                  95

Asn Thr Thr Ser Thr Trp Val Val Tyr Gly Thr Cys His His Lys Lys
            100                 105                 110

Gly Glu Ala Arg Arg Ser Arg Arg Ala Val Thr Leu Pro Ser His Ser
        115                 120                 125

Thr Arg Lys Leu Gln Thr Arg Ser Gln Thr Trp Leu Glu Ser Arg Glu
    130                 135                 140

Tyr Thr Lys His Leu Ile Arg Val Glu Asn Trp Ile Phe Arg Asn Pro
145                 150                 155                 160

Gly Phe Ala Leu Ala Ala Ala Ala Ile Ala Trp Leu Leu Gly Ser Ser
                165                 170                 175

Thr Ser Gln Lys Val Ile Tyr Leu Val Met Ile Leu Leu Ile Ala Pro
            180                 185                 190

Ala Tyr Ser Ile Arg Cys Ile Gly Val Ser Asn Arg Asp Phe Val Glu
        195                 200                 205

Gly Met Ser Gly Gly Thr Trp Val Asp Val Val Leu Glu His Gly Gly
    210                 215                 220

Cys Val Thr Val Met Ala Gln Asp Lys Pro Thr Val Asp Ile Glu Leu
225                 230                 235                 240

Val Thr Thr Thr Val Ser Asn Met Ala Glu Val Arg Ser Tyr Cys Tyr
                245                 250                 255

Glu Ala Ser Ile Ser Asp Met Ala Ser Asp Ser Arg Cys Pro Thr Gln
            260                 265                 270

Gly Glu Ala Tyr Leu Asp Lys Gln Ser Asp Thr Gln Tyr Val Cys Lys
        275                 280                 285

Arg Thr Leu Val Asp Arg Gly Trp Gly Asn Gly Cys Gly Leu Phe Gly
    290                 295                 300

Lys Gly Ser Leu Val Thr Cys Ala Lys Phe Ala Cys Ser Lys Lys Met
305                 310                 315                 320

Thr Gly Lys Ser Ile Gln Pro Glu Asn Leu Glu Tyr Arg Ile Met Leu
                325                 330                 335

Ser Val His Gly Ser Gln His Ser Gly Met Ile Val Asn Asp Thr Gly
            340                 345                 350

His Glu Thr Asp Glu Asn Arg Ala Lys Val Glu Ile Thr Pro Asn Ser
        355                 360                 365

Pro Arg Ala Glu Ala Thr Leu Gly Gly Phe Gly Ser Leu Gly Leu Asp
    370                 375                 380

Cys Glu Pro Arg Thr Gly Leu Asp Phe Ser Asp Leu Tyr Tyr Leu Thr
385                 390                 395                 400

Met Asn Asn Lys His Trp Leu Val His Lys Glu Trp Phe His Asp Ile
                405                 410                 415

Pro Leu Pro Trp His Ala Gly Ala Asp Thr Gly Thr Pro His Trp Asn
420 425 430

Asn Lys Glu Ala Leu Val Glu Phe Lys Asp Ala His Ala Lys Arg Gln
435 440 445

Thr Val Val Val Leu Gly Ser Gln Glu Gly Ala Val His Thr Ala Leu
450 455 460

Ala Gly Ala Leu Glu Ala Glu Met Asp Gly Ala Lys Gly Arg Leu Ser
465 470 475 480

Ser Gly His Leu Lys Cys Arg Leu Lys Met Asp Lys Leu Arg Leu Lys
485 490 495

Gly Val Ser Tyr Ser Leu Cys Thr Ala Ala Phe Thr Phe Thr Lys Ile
500 505 510

Pro Ala Glu Thr Leu His Gly Thr Val Thr Val Glu Val Gln Tyr Ala
515 520 525

Gly Thr Asp Gly Pro Cys Lys Val Pro Ala Gln Met Ala Val Asp Met
530 535 540

Gln Thr Leu Thr Pro Val Gly Arg Leu Ile Thr Ala Asn Pro Val Ile
545 550 555 560

Thr Glu Ser Thr Glu Asn Ser Lys Met Met Leu Glu Leu Asp Pro Pro
565 570 575

Phe Gly Asp Ser Tyr Ile Val Ile Gly Val Gly Glu Lys Lys Ile Thr
580 585 590

His His Trp His Arg Ser Gly Ser Thr Ile Gly Lys Ala Phe Glu Ala
595 600 605

Thr Val Arg Gly Ala Lys Arg Met Ala Val Leu Gly Asp Thr Ala Trp
610 615 620

Asp Phe Gly Ser Val Gly Gly Ala Leu Asn Ser Leu Gly Lys Gly Ile
625 630 635 640

<210> SEQ ID NO 144
<211> LENGTH: 1800
<212> TYPE: DNA
<213> ORGANISM: Artificial sequence
<220> FEATURE:
<223> OTHER INFORMATION: Native nucleotide sequence of MVsp_Zika_prME395 (D4)

<400> SEQUENCE: 144
atgtccatca tgggtctcaa ggtgaacgtc tctgccatat tcatggcagt actgttaact 60
ctccaaacac ccaccggtca agcggaggtc actagacgtg ggagtgcata ctatatgtac 120
ttggacagaa acgatgctgg ggaggccata tcttttccaa ccacattggg gatgaataag 180
tgttatatac agatcatgga tcttggacac atgtgtgatg ccaccatgag ctatgaatgc 240
cctatgctgg atgagggggt ggaaccagat gacgtcgatt gttggtgcaa cacgacgtca 300
acttgggttg tgtacggaac ctgccatcac aaaaaaggtg aagcacggag atctagaaga 360
gctgtgacgc tcccctccca ttccactagg aagctgcaaa cgcggtcgca aacctggttg 420
gaatcaagag aatacacaaa gcacttgatt agagtcgaaa attggatatt caggaaccct 480
ggcttcgcgt tagcagcagc tgccatcgct tggcttttgg gaagctcaac gagccaaaaa 540
gtcatatact tggtcatgat actgctgatt gccccggcat acagcatcag gtgcatagga 600
gtcagcaata gggactttgt ggaaggtatg tcaggtggga cttgggttga tgttgtcttg 660
gaacatggag gttgtgtcac cgtaatggca caggacaaac cgactgtcga catagagctg 720
gttacaacaa cagtcagcaa catggcggag gtaagatcct actgctatga ggcatcaata 780
tcagacatgg cttcggacag ccgctgccca acacaaggtg aagcctacct tgacaagcaa 840
tcagacactc aatatgtctg caaaagaacg ttagtggaca gaggctgggg aaatggatgt 900
ggactttttg gcaaagggag cctggtgaca tgcgctaagt ttgcatgctc caagaaaatg 960
accgggaaga gcatccagcc agagaatctg gagtaccgga taatgctgtc agttcatggc 1020
tcccagcaca gtgggatgat cgttaatgac acaggacatg aaactgatga gaatagagcg 1080
aaggttgaga taacgcccaa ttcaccaaga gccgaagcca ccctgggggg ttttggaagc 1140
ctaggacttg attgtgaacc gaggacaggc cttgactttt cagatttgta ttacttgact 1200
atgaataaca agcactggtt ggttcacaag gagtggttcc acgacattcc attaccttgg 1260
cacgctgggg cagacaccgg aactccacac tggaacaaca aagaagcact ggtagagttc 1320
aaggacgcac atgccaaaag gcaaactgtc gtggttctag ggagtcaaga aggagcagtt 1380
cacacggccc ttgctggagc tctggaggct gagatggatg gtgcaaaggg aaggctgtcc 1440
tctggccact tgaaatgtcg cctgaaaatg gataaactta gattgaaggg cgtgtcatac 1500
tccttgtgta ccgcagcgtt cacattcacc aagatcccgg ctgaaacact gcacgggaca 1560
gtcacagtgg aggtacagta cgcagggaca gatggacctt gcaaggttcc agctcagatg 1620
gcggtggaca tgcaaactct gaccccagtt gggaggttga taaccgctaa ccccgtaatc 1680
actgaaagca ctgagaactc taagatgatg ctggaacttg atccaccatt tggggactct 1740
tacattgtca taggagtcgg ggagaagaag atcacccacc actggcacag gagtggctga 1800

<210> SEQ ID NO 145
<211> LENGTH: 1800
<212> TYPE: DNA
<213> ORGANISM: Artificial sequence
<220> FEATURE:
<223> OTHER INFORMATION: Codon-optimized nucleotide sequence of
MVsp_Zika_prME395 (D4)

<400> SEQUENCE: 145
atgagcatca tgggcctgaa ggtgaacgtg tccgccatct tcatggccgt gctgctgacc 60
ctgcagacac caacaggcca ggcagaggtg accaggagag gaagcgccta ctatatgtac 120
ctggacagga atgatgccgg cgaggccatc tccttcccaa ccacactggg catgaacaag 180
tgctacatcc agatcatgga cctgggccac atgtgcgatg ccaccatgtc ctatgagtgt 240
ccaatgctgg acgagggcgt ggagcccgac gatgtggatt gctggtgtaa taccacatct 300
acatgggtgg tgtacggcac ctgtcaccac aagaagggag aggcccggcg gagccggcgg 360
gccgtgacac tgccttccca ctctaccagg aagctgcaga cacgcagcca gacctggctg 420
gagtccagag agtataccaa gcacctgatc agggtggaga actggatctt tcgcaatcca 480
ggattcgcac tggcagcagc agcaatcgca tggctgctgg gaagctccac cagccagaaa 540
gtgatctacc tggtcatgat cctgctgatc gctcctgcct attctatccg gtgcatcggc 600
gtgagcaata gagacttcgt ggagggaatg tccggaggaa cctgggtgga tgtggtgctg 660
gagcacggcg gctgcgtgac agtgatggcc caggacaagc caaccgtgga tatcgagctg 720
gtgaccacaa ccgtgtccaa catggccgag gtgaggtctt actgctatga ggccagcatc 780
tccgacatgg cctctgatag caggtgtcca acccagggag aggcatacct ggacaagcag 840
tccgatacac agtacgtgtg caagcggacc ctggtggaca gaggctgggg caatggctgt 900
ggcctgtttg gcaagggctc tctggtgaca tgcgccaagt tcgcctgtag caagaagatg 960
accggcaagt ccatccagcc agagaacctg gagtaccgga tcatgctgtc tgtgcacggc 1020

```
tcccagcact ctggcatgat cgtgaacgac acaggccacg agacagatga gaatcgggcc   1080

aaggtggaga tcacacctaa ctctccaaga gccgaggcca ccctgggagg atttggctct   1140

ctgggcctgg actgcgagcc tagaacaggc ctggacttct ccgatctgta ctatctgacc   1200

atgaacaata agcactggct ggtgcacaag gagtggtttc acgacatccc actgccatgg   1260

cacgcaggag cagatacagg aacaccacac tggaacaata aggaggccct ggtggagttc   1320

aaggatgccc acgccaagcg gcagacagtg gtggtgctgg gcagccagga gggagcagtg   1380

cacaccgccc tggcaggcgc cctggaggca gagatggacg gagctaaggg cagactgtct   1440

agcggccacc tgaagtgcag gctgaagatg gataagctgc gcctgaaggg cgtgtcctac   1500

tctctgtgca cagccgcctt caccttcacc aagatccctg ccgagacact gcacggcaca   1560

gtgaccgtgg aggtgcagta tgccggcaca gacggaccct gtaaggtgcc tgcccagatg   1620

gccgtggata tgcagacact gacacctgtg ggcaggctga tcaccgccaa tccagtgatc   1680

acagagtcta ccgagaacag caagatgatg ctggagctgg acccaccatt tggcgatagc   1740

tatatcgtga tcggcgtggg cgagaagaag atcacacacc actggcaccg cagcggctga   1800
```

```
<210> SEQ ID NO 146
<211> LENGTH: 599
<212> TYPE: PRT
<213> ORGANISM: Artificial sequence
<220> FEATURE:
<223> OTHER INFORMATION: MVsp_Zika_prME395 (D4)

<400> SEQUENCE: 146

Met Ser Ile Met Gly Leu Lys Val Asn Val Ser Ala Ile Phe Met Ala
1               5                   10                  15

Val Leu Leu Thr Leu Gln Thr Pro Thr Gly Gln Ala Glu Val Thr Arg
            20                  25                  30

Arg Gly Ser Ala Tyr Tyr Met Tyr Leu Asp Arg Asn Asp Ala Gly Glu
        35                  40                  45

Ala Ile Ser Phe Pro Thr Thr Leu Gly Met Asn Lys Cys Tyr Ile Gln
    50                  55                  60

Ile Met Asp Leu Gly His Met Cys Asp Ala Thr Met Ser Tyr Glu Cys
65                  70                  75                  80

Pro Met Leu Asp Glu Gly Val Glu Pro Asp Asp Val Asp Cys Trp Cys
                85                  90                  95

Asn Thr Thr Ser Thr Trp Val Val Tyr Gly Thr Cys His His Lys Lys
            100                 105                 110

Gly Glu Ala Arg Arg Ser Arg Arg Ala Val Thr Leu Pro Ser His Ser
        115                 120                 125

Thr Arg Lys Leu Gln Thr Arg Ser Gln Thr Trp Leu Glu Ser Arg Glu
    130                 135                 140

Tyr Thr Lys His Leu Ile Arg Val Glu Asn Trp Ile Phe Arg Asn Pro
145                 150                 155                 160

Gly Phe Ala Leu Ala Ala Ala Ala Ile Ala Trp Leu Leu Gly Ser Ser
                165                 170                 175

Thr Ser Gln Lys Val Ile Tyr Leu Val Met Ile Leu Leu Ile Ala Pro
            180                 185                 190

Ala Tyr Ser Ile Arg Cys Ile Gly Val Ser Asn Arg Asp Phe Val Glu
        195                 200                 205

Gly Met Ser Gly Gly Thr Trp Val Asp Val Val Leu Glu His Gly Gly
    210                 215                 220
```

```
Cys Val Thr Val Met Ala Gln Asp Lys Pro Thr Val Asp Ile Glu Leu
225                 230                 235                 240

Val Thr Thr Thr Val Ser Asn Met Ala Glu Val Arg Ser Tyr Cys Tyr
                245                 250                 255

Glu Ala Ser Ile Ser Asp Met Ala Ser Asp Ser Arg Cys Pro Thr Gln
            260                 265                 270

Gly Glu Ala Tyr Leu Asp Lys Gln Ser Asp Thr Gln Tyr Val Cys Lys
        275                 280                 285

Arg Thr Leu Val Asp Arg Gly Trp Gly Asn Gly Cys Gly Leu Phe Gly
    290                 295                 300

Lys Gly Ser Leu Val Thr Cys Ala Lys Phe Ala Cys Ser Lys Lys Met
305                 310                 315                 320

Thr Gly Lys Ser Ile Gln Pro Glu Asn Leu Glu Tyr Arg Ile Met Leu
                325                 330                 335

Ser Val His Gly Ser Gln His Ser Gly Met Ile Val Asn Asp Thr Gly
            340                 345                 350

His Glu Thr Asp Glu Asn Arg Ala Lys Val Glu Ile Thr Pro Asn Ser
        355                 360                 365

Pro Arg Ala Glu Ala Thr Leu Gly Gly Phe Gly Ser Leu Gly Leu Asp
    370                 375                 380

Cys Glu Pro Arg Thr Gly Leu Asp Phe Ser Asp Leu Tyr Tyr Leu Thr
385                 390                 395                 400

Met Asn Asn Lys His Trp Leu Val His Lys Glu Trp Phe His Asp Ile
                405                 410                 415

Pro Leu Pro Trp His Ala Gly Ala Asp Thr Gly Thr Pro His Trp Asn
            420                 425                 430

Asn Lys Glu Ala Leu Val Glu Phe Lys Asp Ala His Ala Lys Arg Gln
        435                 440                 445

Thr Val Val Val Leu Gly Ser Gln Glu Gly Ala Val His Thr Ala Leu
    450                 455                 460

Ala Gly Ala Leu Glu Ala Glu Met Asp Gly Ala Lys Gly Arg Leu Ser
465                 470                 475                 480

Ser Gly His Leu Lys Cys Arg Leu Lys Met Asp Lys Leu Arg Leu Lys
                485                 490                 495

Gly Val Ser Tyr Ser Leu Cys Thr Ala Ala Phe Thr Phe Thr Lys Ile
            500                 505                 510

Pro Ala Glu Thr Leu His Gly Thr Val Thr Val Glu Val Gln Tyr Ala
        515                 520                 525

Gly Thr Asp Gly Pro Cys Lys Val Pro Ala Gln Met Ala Val Asp Met
    530                 535                 540

Gln Thr Leu Thr Pro Val Gly Arg Leu Ile Thr Ala Asn Pro Val Ile
545                 550                 555                 560

Thr Glu Ser Thr Glu Asn Ser Lys Met Met Leu Glu Leu Asp Pro Pro
                565                 570                 575

Phe Gly Asp Ser Tyr Ile Val Ile Gly Val Gly Glu Lys Lys Ile Thr
            580                 585                 590

His His Trp His Arg Ser Gly
        595
```

<210> SEQ ID NO 147
<211> LENGTH: 1596
<212> TYPE: DNA
<213> ORGANISM: Artificial sequence
<220> FEATURE:
<223> OTHER INFORMATION: Native nucleotide sequence of MVsp_ZikaE (D5)

<400> SEQUENCE: 147
atgtccatca tgggtctcaa ggtgaacgtc tctgccatat tcatggcagt actgttaact 60
ctccaaacac ccaccggtca aatcaggtgc ataggagtca gcaataggga ctttgtggaa 120
ggtatgtcag gtgggacttg ggttgatgtt gtcttggaac atggaggttg tgtcaccgta 180
atggcacagg acaaaccgac tgtcgacata gagctggtta caacaacagt cagcaacatg 240
gcggaggtaa gatcctactg ctatgaggca tcaatatcag acatggcttc ggacagccgc 300
tgcccaacac aaggtgaagc ctaccttgac aagcaatcag acactcaata tgtctgcaaa 360
agaacgttag tggacagagg ctggggaaat ggatgtggac tttttggcaa agggagcctg 420
gtgacatgcg ctaagtttgc atgctccaag aaaatgaccg ggaagagcat ccagccagag 480
aatctggagt accggataat gctgtcagtt catggctccc agcacagtgg gatgatcgtt 540
aatgacacag gacatgaaac tgatgagaat agagcgaagg ttgagataac gcccaattca 600
ccaagagccg aagccaccct gggggggtttt ggaagcctag gacttgattg tgaaccgagg 660
acaggccttg acttttcaga tttgtattac ttgactatga ataacaagca ctggttggtt 720
cacaaggagt ggttccacga cattccatta ccttggcacg ctggggcaga caccggaact 780
ccacactgga acaacaaaga agcactggta gagttcaagg acgcacatgc caaaaggcaa 840
actgtcgtgg ttctagggag tcaagaagga gcagttcaca cggcccttgc tggagctctg 900
gaggctgaga tggatggtgc aaagggaagg ctgtcctctg gccacttgaa atgtcgcctg 960
aaaatggata aacttagatt gaagggcgtg tcatactcct tgtgtaccgc agcgttcaca 1020
ttcaccaaga tcccggctga aacactgcac gggacagtca cagtggaggt acagtacgca 1080
gggacagatg gaccttgcaa ggttccagct cagatggcgg tggacatgca aactctgacc 1140
ccagttggga ggttgataac cgctaacccc gtaatcactg aaagcactga gaactctaag 1200
atgatgctgg aacttgatcc accatttggg gactcttaca ttgtcatagg agtcggggag 1260
aagaagatca cccaccactg gcacaggagt ggcagcacca ttggaaaagc atttgaagcc 1320
actgtgagag gtgccaagag aatggcagtc ttgggagaca cagcctggga ctttggatca 1380
gttggaggcg ctctcaactc attgggcaag ggcatccatc aaatttttgg agcagctttc 1440
aaatcattgt ttggaggaat gtcctggttc tcacaaattc tcattggaac gttgctgatg 1500
tggttgggtc tgaacacaaa gaatggatct atttccctta tgtgcttggc cttaggggga 1560
gtgttgatct tcttatccac agccgtctct gcttga 1596

<210> SEQ ID NO 148
<211> LENGTH: 1596
<212> TYPE: DNA
<213> ORGANISM: Artificial sequence
<220> FEATURE:
<223> OTHER INFORMATION: Codon-optimized nucleotide sequence of MVsp_ZikaE (D5)

<400> SEQUENCE: 148
atgagcatca tgggcctgaa ggtgaacgtg tccgccatct tcatggccgt gctgctgacc 60
ctgcagacac caacaggcca gatccggtgc atcggcgtga gcaatagaga cttcgtggag 120
ggaatgtccg gaggaacctg ggtggatgtg gtgctggagc acggcggctg cgtgacagtg 180
atggcccagg acaagccaac cgtggatatc gagctggtga ccacaaccgt gtccaacatg 240
gccgaggtga ggtcttactg ctatgaggcc agcatctccg acatggcctc tgatagcagg 300
tgtccaaccc agggagaggc atacctggac aagcagtccg atacacagta cgtgtgcaag 360

```
cggaccctgg tggacagagg ctggggcaat ggctgtggcc tgtttggcaa gggctctctg    420

gtgacatgcg ccaagttcgc ctgtagcaag aagatgaccg gcaagtccat ccagccagag    480

aacctggagt accggatcat gctgtctgtg cacggctccc agcactctgg catgatcgtg    540

aacgacacag gccacgagac agatgagaat cgggccaagg tggagatcac acctaactct    600

ccaagagccg aggccaccct gggaggattt ggctctctgg gcctggactg cgagcctaga    660

acaggcctgg acttctccga tctgtactat ctgaccatga acaataagca ctggctggtg    720

cacaaggagt ggtttcacga catcccactg ccatggcacg caggagcaga tacaggaaca    780

ccacactgga acaataagga ggccctggtg gagttcaagg atgcccacgc caagcggcag    840

acagtggtgg tgctgggcag ccaggaggga gcagtgcaca ccgccctggc aggcgccctg    900

gaggcagaga tggacggagc taagggcaga ctgtctagcg gccacctgaa gtgcaggctg    960

aagatggata agctgcgcct gaagggcgtg tcctactctc tgtgcacagc cgccttcacc   1020

ttcaccaaga tccctgccga gacactgcac ggcacagtga ccgtggaggt gcagtatgcc   1080

ggcacagacg gaccctgtaa ggtgcctgcc cagatggccg tggatatgca gacactgaca   1140

cctgtgggca ggctgatcac cgccaatcca gtgatcacag agtctaccga gaacagcaag   1200

atgatgctgg agctggaccc accatttggc gatagctata tcgtgatcgg cgtgggcgag   1260

aagaagatca cacaccactg gcaccgcagc ggctccacaa tcggcaaggc ctttgaggca   1320

accgtgcgcg gagcaaagag aatggccgtg ctgggcgaca ccgcatggga tttcggatct   1380

gtgggaggcg ccctgaacag cctgggcaag ggcatccacc agatcttcgg cgccgccttt   1440

aagtccctgt tcggcggcat gagctggttc tcacagatcc tgatcggcac actgctgatg   1500

tggctgggcc tgaacaccaa gaatggctct atcagcctga tgtgcctggc cctgggaggc   1560

gtgctgatct tcctgtccac cgccgtgtct gcctga                             1596
```

<210> SEQ ID NO 149
<211> LENGTH: 531
<212> TYPE: PRT
<213> ORGANISM: Artificial sequence
<220> FEATURE:
<223> OTHER INFORMATION: MVsp_ZikaE (D5)

<400> SEQUENCE: 149

```
Met Ser Ile Met Gly Leu Lys Val Asn Val Ser Ala Ile Phe Met Ala
1               5                   10                  15

Val Leu Leu Thr Leu Gln Thr Pro Thr Gly Gln Ile Arg Cys Ile Gly
            20                  25                  30

Val Ser Asn Arg Asp Phe Val Glu Gly Met Ser Gly Gly Thr Trp Val
        35                  40                  45

Asp Val Val Leu Glu His Gly Gly Cys Val Thr Val Met Ala Gln Asp
    50                  55                  60

Lys Pro Thr Val Asp Ile Glu Leu Val Thr Thr Thr Val Ser Asn Met
65                  70                  75                  80

Ala Glu Val Arg Ser Tyr Cys Tyr Glu Ala Ser Ile Ser Asp Met Ala
                85                  90                  95

Ser Asp Ser Arg Cys Pro Thr Gln Gly Glu Ala Tyr Leu Asp Lys Gln
            100                 105                 110

Ser Asp Thr Gln Tyr Val Cys Lys Arg Thr Leu Val Asp Arg Gly Trp
        115                 120                 125

Gly Asn Gly Cys Gly Leu Phe Gly Lys Gly Ser Leu Val Thr Cys Ala
    130                 135                 140
```

Lys Phe Ala Cys Ser Lys Lys Met Thr Gly Lys Ser Ile Gln Pro Glu
145 150 155 160

Asn Leu Glu Tyr Arg Ile Met Leu Ser Val His Gly Ser Gln His Ser
165 170 175

Gly Met Ile Val Asn Asp Thr Gly His Glu Thr Asp Glu Asn Arg Ala
180 185 190

Lys Val Glu Ile Thr Pro Asn Ser Pro Arg Ala Glu Ala Thr Leu Gly
195 200 205

Gly Phe Gly Ser Leu Gly Leu Asp Cys Glu Pro Arg Thr Gly Leu Asp
210 215 220

Phe Ser Asp Leu Tyr Tyr Leu Thr Met Asn Asn Lys His Trp Leu Val
225 230 235 240

His Lys Glu Trp Phe His Asp Ile Pro Leu Pro Trp His Ala Gly Ala
245 250 255

Asp Thr Gly Thr Pro His Trp Asn Asn Lys Glu Ala Leu Val Glu Phe
260 265 270

Lys Asp Ala His Ala Lys Arg Gln Thr Val Val Val Leu Gly Ser Gln
275 280 285

Glu Gly Ala Val His Thr Ala Leu Ala Gly Ala Leu Glu Ala Glu Met
290 295 300

Asp Gly Ala Lys Gly Arg Leu Ser Ser Gly His Leu Lys Cys Arg Leu
305 310 315 320

Lys Met Asp Lys Leu Arg Leu Lys Gly Val Ser Tyr Ser Leu Cys Thr
325 330 335

Ala Ala Phe Thr Phe Thr Lys Ile Pro Ala Glu Thr Leu His Gly Thr
340 345 350

Val Thr Val Glu Val Gln Tyr Ala Gly Thr Asp Gly Pro Cys Lys Val
355 360 365

Pro Ala Gln Met Ala Val Asp Met Gln Thr Leu Thr Pro Val Gly Arg
370 375 380

Leu Ile Thr Ala Asn Pro Val Ile Thr Glu Ser Thr Glu Asn Ser Lys
385 390 395 400

Met Met Leu Glu Leu Asp Pro Pro Phe Gly Asp Ser Tyr Ile Val Ile
405 410 415

Gly Val Gly Glu Lys Lys Ile Thr His His Trp His Arg Ser Gly Ser
420 425 430

Thr Ile Gly Lys Ala Phe Glu Ala Thr Val Arg Gly Ala Lys Arg Met
435 440 445

Ala Val Leu Gly Asp Thr Ala Trp Asp Phe Gly Ser Val Gly Gly Ala
450 455 460

Leu Asn Ser Leu Gly Lys Gly Ile His Gln Ile Phe Gly Ala Ala Phe
465 470 475 480

Lys Ser Leu Phe Gly Gly Met Ser Trp Phe Ser Gln Ile Leu Ile Gly
485 490 495

Thr Leu Leu Met Trp Leu Gly Leu Asn Thr Lys Asn Gly Ser Ile Ser
500 505 510

Leu Met Cys Leu Ala Leu Gly Gly Val Leu Ile Phe Leu Ser Thr Ala
515 520 525

Val Ser Ala
530

<210> SEQ ID NO 150
<211> LENGTH: 1452

```
<212> TYPE: DNA
<213> ORGANISM: Artificial sequence
<220> FEATURE:
<223> OTHER INFORMATION: Native nucleotide sequence of
      MVsp_ZikaE_no_anchor (D6)

<400> SEQUENCE: 150

atgtccatca tgggtctcaa ggtgaacgtc tctgccatat tcatggcagt actgttaact     60

ctccaaacac ccaccggtca aatcaggtgc ataggagtca gcaataggga ctttgtggaa    120

ggtatgtcag gtgggacttg ggttgatgtt gtcttggaac atggaggttg tgtcaccgta    180

atggcacagg acaaaccgac tgtcgacata gagctggtta caacaacagt cagcaacatg    240

gcggaggtaa gatcctactg ctatgaggca tcaatatcag acatggcttc ggacagccgc    300

tgcccaacac aaggtgaagc ctaccttgac aagcaatcag acactcaata tgtctgcaaa    360

agaacgttag tggacagagg ctggggaaat ggatgtggac tttttggcaa agggagcctg    420

gtgacatgcg ctaagtttgc atgctccaag aaaatgaccg ggaagagcat ccagccagag    480

aatctggagt accggataat gctgtcagtt catggctccc agcacagtgg gatgatcgtt    540

aatgacacag gacatgaaac tgatgagaat agagcgaagg ttgagataac gcccaattca    600

ccaagagccg aagccaccct gggggggtttt ggaagcctag gacttgattg tgaaccgagg    660

acaggccttg acttttcaga tttgtattac ttgactatga ataacaagca ctggttggtt    720

cacaaggagt ggttccacga cattccatta ccttggcacg ctggggcaga caccggaact    780

ccacactgga acaacaaaga agcactggta gagttcaagg acgcacatgc caaaaggcaa    840

actgtcgtgg ttctagggag tcaagaagga gcagttcaca cggcccttgc tggagctctg    900

gaggctgaga tggatggtgc aaagggaagg ctgtcctctg gccacttgaa atgtcgcctg    960

aaaatggata aacttagatt gaagggcgtg tcatactcct tgtgtaccgc agcgttcaca   1020

ttcaccaaga tcccggctga aacactgcac gggacagtca cagtggaggt acagtacgca   1080

gggacagatg gaccttgcaa ggttccagct cagatggcgg tggacatgca aactctgacc   1140

ccagttggga ggttgataac cgctaacccc gtaatcactg aaagcactga gaactctaag   1200

atgatgctgg aacttgatcc accatttggg gactcttaca ttgtcatagg agtcggggag   1260

aagaagatca cccaccactg gcacaggagt ggcagcacca ttggaaaagc atttgaagcc   1320

actgtgagag gtgccaagag aatggcagtc ttgggagaca cagcctggga ctttggatca   1380

gttggaggcg ctctcaactc attgggcaag ggcatccatc aaatttttgg agcagctttc   1440

aaatcattgt ga                                                       1452


<210> SEQ ID NO 151
<211> LENGTH: 1452
<212> TYPE: DNA
<213> ORGANISM: Artificial sequence
<220> FEATURE:
<223> OTHER INFORMATION: Codon-optimized nucleotide sequence of
      MVsp_ZikaE_no_anchor (D6)

<400> SEQUENCE: 151

atgagcatca tgggcctgaa ggtgaacgtg tccgccatct tcatggccgt gctgctgacc     60

ctgcagacac caacaggcca gatccggtgc atcggcgtga gcaatagaga cttcgtggag    120

ggaatgtccg gaggaacctg ggtggatgtg gtgctggagc acggcggctg cgtgacagtg    180

atggcccagg acaagccaac cgtggatatc gagctggtga ccacaaccgt gtccaacatg    240

gccgaggtga ggtcttactg ctatgaggcc agcatctccg acatggcctc tgatagcagg    300
```

-continued

```
tgtccaaccc agggagaggc atacctggac aagcagtccg atacacagta cgtgtgcaag    360

cggaccctgg tggacagagg ctggggcaat ggctgtggcc tgtttggcaa gggctctctg    420

gtgacatgcg ccaagttcgc ctgtagcaag aagatgaccg gcaagtccat ccagccagag    480

aacctggagt accggatcat gctgtctgtg cacggctccc agcactctgg catgatcgtg    540

aacgacacag gccacgagac agatgagaat cgggccaagg tggagatcac acctaactct    600

ccaagagccg aggccaccct gggaggattt ggctctctgg gcctggactg cgagcctaga    660

acaggcctgg acttctccga tctgtactat ctgaccatga acaataagca ctggctggtg    720

cacaaggagt ggtttcacga catcccactg ccatggcacg caggagcaga tacaggaaca    780

ccacactgga acaataagga ggccctggtg gagttcaagg atgcccacgc caagcggcag    840

acagtggtgg tgctgggcag ccaggaggga gcagtgcaca ccgccctggc aggcgccctg    900

gaggcagaga tggacggagc taagggcaga ctgtctagcg gccacctgaa gtgcaggctg    960

aagatggata agctgcgcct gaagggcgtg tcctactctc tgtgcacagc cgccttcacc   1020

ttcaccaaga tccctgccga gacactgcac ggcacagtga ccgtggaggt gcagtatgcc   1080

ggcacagacg gaccctgtaa ggtgcctgcc cagatggccg tggatatgca gacactgaca   1140

cctgtgggca ggctgatcac cgccaatcca gtgatcacag agtctaccga gaacagcaag   1200

atgatgctgg agctggaccc accatttggc gatagctata tcgtgatcgg cgtgggcgag   1260

aagaagatca cacaccactg gcaccgcagc ggctccacaa tcggcaaggc ctttgaggca   1320

accgtgcgcg gagcaaagag aatggccgtg ctgggcgaca ccgcatggga tttcggatct   1380

gtgggaggcg ccctgaacag cctgggcaag ggcatccacc agatcttcgg cgccgccttt   1440

aagtccctgt ga                                                       1452
```

<210> SEQ ID NO 152
<211> LENGTH: 483
<212> TYPE: PRT
<213> ORGANISM: Artificial sequence
<220> FEATURE:
<223> OTHER INFORMATION: MVsp_ZikaE_no_anchor (D6)

<400> SEQUENCE: 152

```
Met Ser Ile Met Gly Leu Lys Val Asn Val Ser Ala Ile Phe Met Ala
1               5                   10                  15

Val Leu Leu Thr Leu Gln Thr Pro Thr Gly Gln Ile Arg Cys Ile Gly
            20                  25                  30

Val Ser Asn Arg Asp Phe Val Glu Gly Met Ser Gly Gly Thr Trp Val
        35                  40                  45

Asp Val Val Leu Glu His Gly Gly Cys Val Thr Val Met Ala Gln Asp
    50                  55                  60

Lys Pro Thr Val Asp Ile Glu Leu Val Thr Thr Thr Val Ser Asn Met
65                  70                  75                  80

Ala Glu Val Arg Ser Tyr Cys Tyr Glu Ala Ser Ile Ser Asp Met Ala
                85                  90                  95

Ser Asp Ser Arg Cys Pro Thr Gln Gly Glu Ala Tyr Leu Asp Lys Gln
            100                 105                 110

Ser Asp Thr Gln Tyr Val Cys Lys Arg Thr Leu Val Asp Arg Gly Trp
        115                 120                 125

Gly Asn Gly Cys Gly Leu Phe Gly Lys Gly Ser Leu Val Thr Cys Ala
    130                 135                 140

Lys Phe Ala Cys Ser Lys Lys Met Thr Gly Lys Ser Ile Gln Pro Glu
145                 150                 155                 160
```

Asn Leu Glu Tyr Arg Ile Met Leu Ser Val His Gly Ser Gln His Ser
165 170 175

Gly Met Ile Val Asn Asp Thr Gly His Glu Thr Asp Glu Asn Arg Ala
180 185 190

Lys Val Glu Ile Thr Pro Asn Ser Pro Arg Ala Glu Ala Thr Leu Gly
195 200 205

Gly Phe Gly Ser Leu Gly Leu Asp Cys Glu Pro Arg Thr Gly Leu Asp
210 215 220

Phe Ser Asp Leu Tyr Tyr Leu Thr Met Asn Asn Lys His Trp Leu Val
225 230 235 240

His Lys Glu Trp Phe His Asp Ile Pro Leu Pro Trp His Ala Gly Ala
245 250 255

Asp Thr Gly Thr Pro His Trp Asn Asn Lys Glu Ala Leu Val Glu Phe
260 265 270

Lys Asp Ala His Ala Lys Arg Gln Thr Val Val Val Leu Gly Ser Gln
275 280 285

Glu Gly Ala Val His Thr Ala Leu Ala Gly Ala Leu Glu Ala Glu Met
290 295 300

Asp Gly Ala Lys Gly Arg Leu Ser Ser Gly His Leu Lys Cys Arg Leu
305 310 315 320

Lys Met Asp Lys Leu Arg Leu Lys Gly Val Ser Tyr Ser Leu Cys Thr
325 330 335

Ala Ala Phe Thr Phe Thr Lys Ile Pro Ala Glu Thr Leu His Gly Thr
340 345 350

Val Thr Val Glu Val Gln Tyr Ala Gly Thr Asp Gly Pro Cys Lys Val
355 360 365

Pro Ala Gln Met Ala Val Asp Met Gln Thr Leu Thr Pro Val Gly Arg
370 375 380

Leu Ile Thr Ala Asn Pro Val Ile Thr Glu Ser Thr Glu Asn Ser Lys
385 390 395 400

Met Met Leu Glu Leu Asp Pro Pro Phe Gly Asp Ser Tyr Ile Val Ile
405 410 415

Gly Val Gly Glu Lys Lys Ile Thr His His Trp His Arg Ser Gly Ser
420 425 430

Thr Ile Gly Lys Ala Phe Glu Ala Thr Val Arg Gly Ala Lys Arg Met
435 440 445

Ala Val Leu Gly Asp Thr Ala Trp Asp Phe Gly Ser Val Gly Gly Ala
450 455 460

Leu Asn Ser Leu Gly Lys Gly Ile His Gln Ile Phe Gly Ala Ala Phe
465 470 475 480

Lys Ser Leu

<210> SEQ ID NO 153
<211> LENGTH: 1422
<212> TYPE: DNA
<213> ORGANISM: Artificial sequence
<220> FEATURE:
<223> OTHER INFORMATION: Native nucleotide sequence of MVsp_ZikaE411 (D7)

<400> SEQUENCE: 153
atgtccatca tgggtctcaa ggtgaacgtc tctgccatat tcatggcagt actgttaact 60
ctccaaacac ccaccggtca aatcaggtgc ataggagtca gcaataggga ctttgtggaa 120
ggtatgtcag gtgggacttg ggttgatgtt gtcttggaac atggaggttg tgtcaccgta 180

```
atggcacagg acaaaccgac tgtcgacata gagctggtta caacaacagt cagcaacatg    240
gcggaggtaa gatcctactg ctatgaggca tcaatatcag acatggcttc ggacagccgc    300
tgcccaacac aaggtgaagc ctaccttgac aagcaatcag acactcaata tgtctgcaaa    360
agaacgttag tggacagagg ctggggaaat ggatgtggac tttttggcaa agggagcctg    420
gtgacatgcg ctaagtttgc atgctccaag aaaatgaccg ggaagagcat ccagccagag    480
aatctggagt accggataat gctgtcagtt catggctccc agcacagtgg gatgatcgtt    540
aatgacacag gacatgaaac tgatgagaat agagcgaagg ttgagataac gcccaattca    600
ccaagagccg aagccaccct gggggggtttt ggaagcctag gacttgattg tgaaccgagg    660
acaggccttg acttttcaga tttgtattac ttgactatga ataacaagca ctggttggtt    720
cacaaggagt ggttccacga cattccatta ccttggcacg ctggggcaga caccggaact    780
ccacactgga acaacaaaga agcactggta gagttcaagg acgcacatgc caaaaggcaa    840
actgtcgtgg ttctagggag tcaagaagga gcagttcaca cggcccttgc tggagctctg    900
gaggctgaga tggatggtgc aaagggaagg ctgtcctctg gccacttgaa atgtcgcctg    960
aaaatggata aacttagatt gaagggcgtg tcatactcct tgtgtaccgc agcgttcaca   1020
ttcaccaaga tcccggctga aacactgcac gggacagtca cagtggaggt acagtacgca   1080
gggacagatg gaccttgcaa ggttccagct cagatggcgg tggacatgca aactctgacc   1140
ccagttggga ggttgataac cgctaacccc gtaatcactg aaagcactga gaactctaag   1200
atgatgctgg aacttgatcc accatttggg gactcttaca ttgtcatagg agtcggggag   1260
aagaagatca cccaccactg gcacaggagt ggcagcacca ttggaaaagc atttgaagcc   1320
actgtgagag gtgccaagag aatggcagtc ttgggagaca cagcctggga ctttggatca   1380
gttggaggcg ctctcaactc attgggcaag ggcatctgat ga                      1422
```

<210> SEQ ID NO 154
<211> LENGTH: 1422
<212> TYPE: DNA
<213> ORGANISM: Artificial sequence
<220> FEATURE:
<223> OTHER INFORMATION: Codon-optimized nucleotide sequence of
MVsp_ZikaE411 (D7)

<400> SEQUENCE: 154

```
atgagcatca tgggcctgaa ggtgaacgtg tccgccatct tcatggccgt gctgctgacc     60
ctgcagacac caacaggcca gatccggtgc atcggcgtga gcaatagaga cttcgtggag    120
ggaatgtccg gaggaacctg ggtggatgtg gtgctggagc acggcggctg cgtgacagtg    180
atggcccagg acaagccaac cgtggatatc gagctggtga ccacaaccgt gtccaacatg    240
gccgaggtga ggtcttactg ctatgaggcc agcatctccg acatggcctc tgatagcagg    300
tgtccaaccc agggagaggc atacctggac aagcagtccg atacacagta cgtgtgcaag    360
cggaccctgg tggacagagg ctggggcaat ggctgtggcc tgtttggcaa gggctctctg    420
gtgacatgcg ccaagttcgc ctgtagcaag aagatgaccg gcaagtccat ccagccagag    480
aacctggagt accggatcat gctgtctgtg cacggctccc agcactctgg catgatcgtg    540
aacgacacag gccacgagac agatgagaat cgggccaagg tggagatcac acctaactct    600
ccaagagccg aggccaccct gggaggattt ggctctctgg gcctggactg cgagcctaga    660
acaggcctgg acttctccga tctgtactat ctgaccatga acaataagca ctggctggtg    720
cacaaggagt ggtttcacga catcccactg ccatggcacg caggagcaga tacaggaaca    780
```

```
ccacactgga acaataagga ggccctggtg gagttcaagg atgcccacgc caagcggcag    840

acagtggtgg tgctgggcag ccaggaggga gcagtgcaca ccgccctggc aggcgccctg    900

gaggcagaga tggacggagc taagggcaga ctgtctagcg gccacctgaa gtgcaggctg    960

aagatggata agctgcgcct gaagggcgtg tcctactctc tgtgcacagc cgccttcacc   1020

ttcaccaaga tccctgccga gacactgcac ggcacagtga ccgtggaggt gcagtatgcc   1080

ggcacagacg gaccctgtaa ggtgcctgcc cagatggccg tggatatgca gacactgaca   1140

cctgtgggca ggctgatcac cgccaatcca gtgatcacag agtctaccga gaacagcaag   1200

atgatgctgg agctggaccc accatttggc gatagctata tcgtgatcgg cgtgggcgag   1260

aagaagatca cacaccactg gcaccgcagc ggctccacaa tcggcaaggc ctttgaggca   1320

accgtgcgcg gagcaaagag aatggccgtg ctgggcgaca ccgcatggga tttcggatct   1380

gtgggaggcg ccctgaacag cctgggcaag ggcatctgat ga                      1422
```

<210> SEQ ID NO 155
<211> LENGTH: 472
<212> TYPE: PRT
<213> ORGANISM: Artificial sequence
<220> FEATURE:
<223> OTHER INFORMATION: MVsp_ZikaE411 (D7)

<400> SEQUENCE: 155

```
Met Ser Ile Met Gly Leu Lys Val Asn Val Ser Ala Ile Phe Met Ala
1               5                   10                  15

Val Leu Leu Thr Leu Gln Thr Pro Thr Gly Gln Ile Arg Cys Ile Gly
            20                  25                  30

Val Ser Asn Arg Asp Phe Val Glu Gly Met Ser Gly Gly Thr Trp Val
        35                  40                  45

Asp Val Val Leu Glu His Gly Gly Cys Val Thr Val Met Ala Gln Asp
    50                  55                  60

Lys Pro Thr Val Asp Ile Glu Leu Val Thr Thr Thr Val Ser Asn Met
65                  70                  75                  80

Ala Glu Val Arg Ser Tyr Cys Tyr Glu Ala Ser Ile Ser Asp Met Ala
                85                  90                  95

Ser Asp Ser Arg Cys Pro Thr Gln Gly Glu Ala Tyr Leu Asp Lys Gln
            100                 105                 110

Ser Asp Thr Gln Tyr Val Cys Lys Arg Thr Leu Val Asp Arg Gly Trp
        115                 120                 125

Gly Asn Gly Cys Gly Leu Phe Gly Lys Gly Ser Leu Val Thr Cys Ala
    130                 135                 140

Lys Phe Ala Cys Ser Lys Lys Met Thr Gly Lys Ser Ile Gln Pro Glu
145                 150                 155                 160

Asn Leu Glu Tyr Arg Ile Met Leu Ser Val His Gly Ser Gln His Ser
                165                 170                 175

Gly Met Ile Val Asn Asp Thr Gly His Glu Thr Asp Glu Asn Arg Ala
            180                 185                 190

Lys Val Glu Ile Thr Pro Asn Ser Pro Arg Ala Glu Ala Thr Leu Gly
        195                 200                 205

Gly Phe Gly Ser Leu Gly Leu Asp Cys Glu Pro Arg Thr Gly Leu Asp
    210                 215                 220

Phe Ser Asp Leu Tyr Tyr Leu Thr Met Asn Asn Lys His Trp Leu Val
225                 230                 235                 240

His Lys Glu Trp Phe His Asp Ile Pro Leu Pro Trp His Ala Gly Ala
```

```
                245                 250                 255

Asp Thr Gly Thr Pro His Trp Asn Asn Lys Glu Ala Leu Val Glu Phe
            260                 265                 270

Lys Asp Ala His Ala Lys Arg Gln Thr Val Val Val Leu Gly Ser Gln
        275                 280                 285

Glu Gly Ala Val His Thr Ala Leu Ala Gly Ala Leu Glu Ala Glu Met
    290                 295                 300

Asp Gly Ala Lys Gly Arg Leu Ser Ser Gly His Leu Lys Cys Arg Leu
305                 310                 315                 320

Lys Met Asp Lys Leu Arg Leu Lys Gly Val Ser Tyr Ser Leu Cys Thr
                325                 330                 335

Ala Ala Phe Thr Phe Thr Lys Ile Pro Ala Glu Thr Leu His Gly Thr
            340                 345                 350

Val Thr Val Glu Val Gln Tyr Ala Gly Thr Asp Gly Pro Cys Lys Val
        355                 360                 365

Pro Ala Gln Met Ala Val Asp Met Gln Thr Leu Thr Pro Val Gly Arg
    370                 375                 380

Leu Ile Thr Ala Asn Pro Val Ile Thr Glu Ser Thr Glu Asn Ser Lys
385                 390                 395                 400

Met Met Leu Glu Leu Asp Pro Pro Phe Gly Asp Ser Tyr Ile Val Ile
                405                 410                 415

Gly Val Gly Glu Lys Lys Ile Thr His His Trp His Arg Ser Gly Ser
            420                 425                 430

Thr Ile Gly Lys Ala Phe Glu Ala Thr Val Arg Gly Ala Lys Arg Met
        435                 440                 445

Ala Val Leu Gly Asp Thr Ala Trp Asp Phe Gly Ser Val Gly Gly Ala
    450                 455                 460

Leu Asn Ser Leu Gly Lys Gly Ile
465                 470


<210> SEQ ID NO 156
<211> LENGTH: 1296
<212> TYPE: DNA
<213> ORGANISM: Artificial sequence
<220> FEATURE:
<223> OTHER INFORMATION: Native nucleotide sequence of MVsp_ZikaE395
      (D8)

<400> SEQUENCE: 156

atgtccatca tgggtctcaa ggtgaacgtc tctgccatat tcatggcagt actgttaact      60

ctccaaacac ccaccggtca aatcaggtgc ataggagtca gcaataggga ctttgtggaa     120

ggtatgtcag gtgggacttg ggttgatgtt gtcttggaac atggaggttg tgtcaccgta     180

atggcacagg acaaaccgac tgtcgacata gagctggtta caacaacagt cagcaacatg     240

gcggaggtaa gatcctactg ctatgaggca tcaatatcag acatggcttc ggacagccgc     300

tgcccaacac aaggtgaagc ctaccttgac aagcaatcag acactcaata tgtctgcaaa     360

agaacgttag tggacagagg ctggggaaat ggatgtggac tttttggcaa agggagcctg     420

gtgacatgcg ctaagtttgc atgctccaag aaaatgaccg ggaagagcat ccagccagag     480

aatctggagt accggataat gctgtcagtt catggctccc agcacagtgg gatgatcgtt     540

aatgacacag gacatgaaac tgatgagaat agagcgaagg ttgagataac gcccaattca     600

ccaagagccg aagccaccct gggggtttt ggaagcctag gacttgattg tgaaccgagg     660

acaggccttg acttttcaga tttgtattac ttgactatga ataacaagca ctggttggtt     720
```

```
cacaaggagt ggttccacga cattccatta ccttggcacg ctggggcaga caccggaact    780

ccacactgga acaacaaaga agcactggta gagttcaagg acgcacatgc caaaaggcaa    840

actgtcgtgg ttctagggag tcaagaagga gcagttcaca cggcccttgc tggagctctg    900

gaggctgaga tggatggtgc aaagggaagg ctgtcctctg gccacttgaa atgtcgcctg    960

aaaatggata aacttagatt gaagggcgtg tcatactcct tgtgtaccgc agcgttcaca   1020

ttcaccaaga tcccggctga aacactgcac gggacagtca cagtggaggt acagtacgca   1080

gggacagatg gaccttgcaa ggttccagct cagatggcgg tggacatgca aactctgacc   1140

ccagttggga ggttgataac cgctaacccc gtaatcactg aaagcactga gaactctaag   1200

atgatgctgg aacttgatcc accatttggg gactcttaca ttgtcatagg agtcggggag   1260

aagaagatca cccaccactg gcacaggagt ggctga                             1296
```

```
<210> SEQ ID NO 157
<211> LENGTH: 1296
<212> TYPE: DNA
<213> ORGANISM: Artificial sequence
<220> FEATURE:
<223> OTHER INFORMATION: Codon-optimized nucleotide sequence of
      MVsp_ZikaE395 (D8)

<400> SEQUENCE: 157

atgagcatca tgggcctgaa ggtgaacgtg tccgccatct tcatggccgt gctgctgacc     60

ctgcagacac caacaggcca gatccggtgc atcggcgtga gcaatagaga cttcgtggag    120

ggaatgtccg gaggaacctg ggtggatgtg gtgctggagc acggcggctg cgtgacagtg    180

atggcccagg acaagccaac cgtggatatc gagctggtga ccacaaccgt gtccaacatg    240

gccgaggtga ggtcttactg ctatgaggcc agcatctccg acatggcctc tgatagcagg    300

tgtccaaccc agggagaggc atacctggac aagcagtccg atacacagta cgtgtgcaag    360

cggaccctgg tggacagagg ctggggcaat ggctgtggcc tgtttggcaa gggctctctg    420

gtgacatgcg ccaagttcgc ctgtagcaag aagatgaccg gcaagtccat ccagccagag    480

aacctggagt accggatcat gctgtctgtg cacggctccc agcactctgg catgatcgtg    540

aacgacacag gccacgagac agatgagaat cgggccaagg tggagatcac acctaactct    600

ccaagagccg aggccaccct gggaggattt ggctctctgg gcctggactg cgagcctaga    660

acaggcctgg acttctccga tctgtactat ctgaccatga acaataagca ctggctggtg    720

cacaaggagt ggtttcacga catcccactg ccatggcacg caggagcaga tacaggaaca    780

ccacactgga acaataagga ggccctggtg gagttcaagg atgcccacgc caagcggcag    840

acagtggtgg tgctgggcag ccaggaggga gcagtgcaca ccgccctggc aggcgccctg    900

gaggcagaga tggacggagc taagggcaga ctgtctagcg gccacctgaa gtgcaggctg    960

aagatggata agctgcgcct gaagggcgtg tcctactctc tgtgcacagc cgccttcacc   1020

ttcaccaaga tccctgccga gacactgcac ggcacagtga ccgtggaggt gcagtatgcc   1080

ggcacagacg gaccctgtaa ggtgcctgcc cagatggccg tggatatgca gacactgaca   1140

cctgtgggca ggctgatcac cgccaatcca gtgatcacag agtctaccga gaacagcaag   1200

atgatgctgg agctggaccc accatttggc gatagctata tcgtgatcgg cgtgggcgag   1260

aagaagatca cacaccactg gcaccgcagc ggctga                             1296
```

```
<210> SEQ ID NO 158
<211> LENGTH: 431
<212> TYPE: PRT
```

```
<213> ORGANISM: Artificial sequence
<220> FEATURE:
<223> OTHER INFORMATION: MVsp_ZikaE395 (D8)

<400> SEQUENCE: 158

Met Ser Ile Met Gly Leu Lys Val Asn Val Ser Ala Ile Phe Met Ala
1               5                   10                  15

Val Leu Leu Thr Leu Gln Thr Pro Thr Gly Gln Ile Arg Cys Ile Gly
            20                  25                  30

Val Ser Asn Arg Asp Phe Val Glu Gly Met Ser Gly Gly Thr Trp Val
        35                  40                  45

Asp Val Val Leu Glu His Gly Gly Cys Val Thr Val Met Ala Gln Asp
    50                  55                  60

Lys Pro Thr Val Asp Ile Glu Leu Val Thr Thr Thr Val Ser Asn Met
65                  70                  75                  80

Ala Glu Val Arg Ser Tyr Cys Tyr Glu Ala Ser Ile Ser Asp Met Ala
                85                  90                  95

Ser Asp Ser Arg Cys Pro Thr Gln Gly Glu Ala Tyr Leu Asp Lys Gln
            100                 105                 110

Ser Asp Thr Gln Tyr Val Cys Lys Arg Thr Leu Val Asp Arg Gly Trp
        115                 120                 125

Gly Asn Gly Cys Gly Leu Phe Gly Lys Gly Ser Leu Val Thr Cys Ala
    130                 135                 140

Lys Phe Ala Cys Ser Lys Lys Met Thr Gly Lys Ser Ile Gln Pro Glu
145                 150                 155                 160

Asn Leu Glu Tyr Arg Ile Met Leu Ser Val His Gly Ser Gln His Ser
                165                 170                 175

Gly Met Ile Val Asn Asp Thr Gly His Glu Thr Asp Glu Asn Arg Ala
            180                 185                 190

Lys Val Glu Ile Thr Pro Asn Ser Pro Arg Ala Glu Ala Thr Leu Gly
        195                 200                 205

Gly Phe Gly Ser Leu Gly Leu Asp Cys Glu Pro Arg Thr Gly Leu Asp
    210                 215                 220

Phe Ser Asp Leu Tyr Tyr Leu Thr Met Asn Asn Lys His Trp Leu Val
225                 230                 235                 240

His Lys Glu Trp Phe His Asp Ile Pro Leu Pro Trp His Ala Gly Ala
                245                 250                 255

Asp Thr Gly Thr Pro His Trp Asn Asn Lys Glu Ala Leu Val Glu Phe
            260                 265                 270

Lys Asp Ala His Ala Lys Arg Gln Thr Val Val Val Leu Gly Ser Gln
        275                 280                 285

Glu Gly Ala Val His Thr Ala Leu Ala Gly Ala Leu Glu Ala Glu Met
    290                 295                 300

Asp Gly Ala Lys Gly Arg Leu Ser Ser Gly His Leu Lys Cys Arg Leu
305                 310                 315                 320

Lys Met Asp Lys Leu Arg Leu Lys Gly Val Ser Tyr Ser Leu Cys Thr
                325                 330                 335

Ala Ala Phe Thr Phe Thr Lys Ile Pro Ala Glu Thr Leu His Gly Thr
            340                 345                 350

Val Thr Val Glu Val Gln Tyr Ala Gly Thr Asp Gly Pro Cys Lys Val
        355                 360                 365

Pro Ala Gln Met Ala Val Asp Met Gln Thr Leu Thr Pro Val Gly Arg
    370                 375                 380

Leu Ile Thr Ala Asn Pro Val Ile Thr Glu Ser Thr Glu Asn Ser Lys
```

```
385                 390                 395                 400

Met Met Leu Glu Leu Asp Pro Pro Phe Gly Asp Ser Tyr Ile Val Ile
                405                 410                 415

Gly Val Gly Glu Lys Lys Ile Thr His His Trp His Arg Ser Gly
            420                 425                 430


<210> SEQ ID NO 159
<211> LENGTH: 2172
<212> TYPE: DNA
<213> ORGANISM: Artificial sequence
<220> FEATURE:
<223> OTHER INFORMATION: Native nucleotide sequence of
      MVsp_ZikaprME_MVTMintracyto (D9)

<400> SEQUENCE: 159

atgtccatca tgggtctcaa ggtgaacgtc tctgccatat tcatggcagt actgttaact     60

ctccaaacac ccaccggtca agcggaggtc actagacgtg ggagtgcata ctatatgtac    120

ttggacagaa acgatgctgg ggaggccata tcttttccaa ccacattggg gatgaataag    180

tgttatatac agatcatgga tcttggacac atgtgtgatg ccaccatgag ctatgaatgc    240

cctatgctgg atgagggggt ggaaccagat gacgtcgatt gttggtgcaa cacgacgtca    300

acttgggttg tgtacggaac ctgccatcac aaaaaaggtg aagcacggag atctagaaga    360

gctgtgacgc tcccctccca ttccactagg aagctgcaaa cgcggtcgca aacctggttg    420

gaatcaagag aatacacaaa gcacttgatt agagtcgaaa attggatatt caggaaccct    480

ggcttcgcgt tagcagcagc tgccatcgct tggcttttgg gaagctcaac gagccaaaaa    540

gtcatatact tggtcatgat actgctgatt gccccggcat acagcatcag gtgcatagga    600

gtcagcaata gggactttgt ggaaggtatg tcaggtggga cttgggttga tgttgtcttg    660

gaacatggag gttgtgtcac cgtaatggca caggacaaac cgactgtcga catagagctg    720

gttacaacaa cagtcagcaa catggcggag gtaagatcct actgctatga ggcatcaata    780

tcagacatgg cttcggacag ccgctgccca acacaaggtg aagcctacct tgacaagcaa    840

tcagacactc aatatgtctg caaaagaacg ttagtggaca gaggctgggg aaatggatgt    900

ggactttttg gcaaagggag cctggtgaca tgcgctaagt ttgcatgctc caagaaaatg    960

accgggaaga gcatccagcc agagaatctg gagtaccgga taatgctgtc agttcatggc   1020

tcccagcaca gtgggatgat cgttaatgac acaggacatg aaactgatga gaatagagcg   1080

aaggttgaga taacgcccaa ttcaccaaga gccgaagcca ccctgggggg ttttggaagc   1140

ctaggacttg attgtgaacc gaggacaggc cttgactttt cagatttgta ttacttgact   1200

atgaataaca agcactggtt ggttcacaag gagtggttcc acgacattcc attaccttgg   1260

cacgctgggg cagacaccgg aactccacac tggaacaaca aagaagcact ggtagagttc   1320

aaggacgcac atgccaaaag gcaaactgtc gtggttctag ggagtcaaga aggagcagtt   1380

cacacggccc ttgctggagc tctggaggct gagatggatg gtgcaaaggg aaggctgtcc   1440

tctggccact tgaaatgtcg cctgaaaatg gataaactta gattgaaggg cgtgtcatac   1500

tccttgtgta ccgcagcgtt cacattcacc aagatcccgg ctgaaacact gcacgggaca   1560

gtcacagtgg aggtacagta cgcagggaca gatggacctt gcaaggttcc agctcagatg   1620

gcggtggaca tgcaaactct gaccccagtt gggaggttga taaccgctaa ccccgtaatc   1680

actgaaagca ctgagaactc taagatgatg ctggaacttg atccaccatt tggggactct   1740

tacattgtca taggagtcgg ggagaagaag atcacccacc actggcacag gagtggcagc   1800
```

accattggaa aagcatttga agccactgtg agaggtgcca agagaatggc agtcttggga 1860
gacacagcct gggactttgg atcagttgga ggcgctctca actcattggg caagggcatc 1920
catcaaattt ttggagcagc tttcaaatca ttgtttggag gaatgtcctg gttctcaatg 1980
aaaggtttat cgagcactag catagtctac atcctgattg cagtgtgtct tggagggttg 2040
atagggatcc ccgctttaat atgttgctgc agggggcgtt gtaacaaaaa gggagaacaa 2100
gttggtatgt caagaccagg cctaaagcct gatcttacgg gaacatcaaa atcctatgta 2160
aggtcgctct ga 2172

<210> SEQ ID NO 160
<211> LENGTH: 2172
<212> TYPE: DNA
<213> ORGANISM: Artificial sequence
<220> FEATURE:
<223> OTHER INFORMATION: Codon-optimized nucleotide sequence of
MVsp_ZikaprME_MVTMintracyto (D9)

<400> SEQUENCE: 160
atgagcatca tgggcctgaa ggtgaacgtg tccgccatct tcatggccgt gctgctgacc 60
ctgcagacac caacaggcca ggcagaggtg accaggagag gaagcgccta ctatatgtac 120
ctggacagga atgatgccgg cgaggccatc tccttcccaa ccacactggg catgaacaag 180
tgctacatcc agatcatgga cctgggccac atgtgcgatg ccaccatgtc ctatgagtgt 240
ccaatgctgg acgagggcgt ggagcccgac gatgtggatt gctggtgtaa taccacatct 300
acatgggtgg tgtacggcac ctgtcaccac aagaagggag aggcccggcg gagccggcgg 360
gccgtgacac tgccttccca ctctaccagg aagctgcaga cacgcagcca gacctggctg 420
gagtccagag agtataccaa gcacctgatc agggtggaga actggatctt tcgcaatcca 480
ggattcgcac tggcagcagc agcaatcgca tggctgctgg gaagctccac cagccagaaa 540
gtgatctacc tggtcatgat cctgctgatc gctcctgcct attctatccg gtgcatcggc 600
gtgagcaata gagacttcgt ggagggaatg tccggaggaa cctgggtgga tgtggtgctg 660
gagcacggcg gctgcgtgac agtgatggcc caggacaagc caaccgtgga tatcgagctg 720
gtgaccacaa ccgtgtccaa catggccgag gtgaggtctt actgctatga ggccagcatc 780
tccgacatgg cctctgatag caggtgtcca acccagggag aggcatacct ggacaagcag 840
tccgatacac agtacgtgtg caagcggacc ctggtggaca gaggctgggg caatggctgt 900
ggcctgtttg gcaagggctc tctggtgaca tgcgccaagt tcgcctgtag caagaagatg 960
accggcaagt ccatccagcc agagaacctg gagtaccgga tcatgctgtc tgtgcacggc 1020
tcccagcact ctggcatgat cgtgaacgac acaggccacg agacagatga gaatcgggcc 1080
aaggtggaga tcacacctaa ctctccaaga gccgaggcca ccctgggagg atttggctct 1140
ctgggcctgg actgcgagcc tagaacaggc ctggacttct ccgatctgta ctatctgacc 1200
atgaacaata agcactggct ggtgcacaag gagtggtttc acgacatccc actgccatgg 1260
cacgcaggag cagatacagg aacaccacac tggaacaata aggaggccct ggtggagttc 1320
aaggatgccc acgccaagcg gcagacagtg gtggtgctgg gcagccagga gggagcagtg 1380
cacaccgccc tggcaggcgc cctggaggca gagatggacg gagctaaggg cagactgtct 1440
agcggccacc tgaagtgcag gctgaagatg gataagctgc gcctgaaggg cgtgtcctac 1500
tctctgtgca cagccgcctt caccttcacc aagatccctg ccgagacact gcacggcaca 1560
gtgaccgtgg aggtgcagta tgccggcaca gacggaccct gtaaggtgcc tgcccagatg 1620

```
gccgtggata tgcagacact gacacctgtg ggcaggctga tcaccgccaa tccagtgatc   1680

acagagtcta ccgagaacag caagatgatg ctggagctgg acccaccatt tggcgatagc   1740

tatatcgtga tcggcgtggg cgagaagaag atcacacacc actggcaccg cagcggctcc   1800

acaatcggca aggcctttga ggcaaccgtg cgcggagcaa agagaatggc cgtgctgggc   1860

gacaccgcat gggatttcgg atctgtggga ggcgccctga acagcctggg caagggcatc   1920

caccagatct tcggcgccgc ctttaagtcc ctgttcggcg gcatgagctg gttctcaatg   1980

aagggcctgt cctctacctc tatcgtgtac atcctgatcg ccgtgtgcct gggaggcctg   2040

atcggaatcc cagccctgat ctgctgttgc agaggccgct gcaacaagaa gggagagcaa   2100

gtgggaatgt ctcggccagg cctgaagcca gacctgacag gcacctccaa gtcttatgtg   2160

agaagcctgt ga                                                       2172


<210> SEQ ID NO 161
<211> LENGTH: 723
<212> TYPE: PRT
<213> ORGANISM: Artificial sequence
<220> FEATURE:
<223> OTHER INFORMATION: MVsp_ZikaprME_MVTMintracyto (D9)

<400> SEQUENCE: 161

Met Ser Ile Met Gly Leu Lys Val Asn Val Ser Ala Ile Phe Met Ala
1               5                   10                  15

Val Leu Leu Thr Leu Gln Thr Pro Thr Gly Gln Ala Glu Val Thr Arg
            20                  25                  30

Arg Gly Ser Ala Tyr Tyr Met Tyr Leu Asp Arg Asn Asp Ala Gly Glu
        35                  40                  45

Ala Ile Ser Phe Pro Thr Thr Leu Gly Met Asn Lys Cys Tyr Ile Gln
    50                  55                  60

Ile Met Asp Leu Gly His Met Cys Asp Ala Thr Met Ser Tyr Glu Cys
65                  70                  75                  80

Pro Met Leu Asp Glu Gly Val Glu Pro Asp Asp Val Asp Cys Trp Cys
                85                  90                  95

Asn Thr Thr Ser Thr Trp Val Val Tyr Gly Thr Cys His His Lys Lys
            100                 105                 110

Gly Glu Ala Arg Arg Ser Arg Arg Ala Val Thr Leu Pro Ser His Ser
        115                 120                 125

Thr Arg Lys Leu Gln Thr Arg Ser Gln Thr Trp Leu Glu Ser Arg Glu
    130                 135                 140

Tyr Thr Lys His Leu Ile Arg Val Glu Asn Trp Ile Phe Arg Asn Pro
145                 150                 155                 160

Gly Phe Ala Leu Ala Ala Ala Ala Ile Ala Trp Leu Leu Gly Ser Ser
                165                 170                 175

Thr Ser Gln Lys Val Ile Tyr Leu Val Met Ile Leu Leu Ile Ala Pro
            180                 185                 190

Ala Tyr Ser Ile Arg Cys Ile Gly Val Ser Asn Arg Asp Phe Val Glu
        195                 200                 205

Gly Met Ser Gly Gly Thr Trp Val Asp Val Val Leu Glu His Gly Gly
    210                 215                 220

Cys Val Thr Val Met Ala Gln Asp Lys Pro Thr Val Asp Ile Glu Leu
225                 230                 235                 240

Val Thr Thr Thr Val Ser Asn Met Ala Glu Val Arg Ser Tyr Cys Tyr
                245                 250                 255

Glu Ala Ser Ile Ser Asp Met Ala Ser Asp Ser Arg Cys Pro Thr Gln
```

```
            260                 265                 270

Gly Glu Ala Tyr Leu Asp Lys Gln Ser Asp Thr Gln Tyr Val Cys Lys
        275                 280                 285

Arg Thr Leu Val Asp Arg Gly Trp Gly Asn Gly Cys Gly Leu Phe Gly
    290                 295                 300

Lys Gly Ser Leu Val Thr Cys Ala Lys Phe Ala Cys Ser Lys Lys Met
305                 310                 315                 320

Thr Gly Lys Ser Ile Gln Pro Glu Asn Leu Glu Tyr Arg Ile Met Leu
                325                 330                 335

Ser Val His Gly Ser Gln His Ser Gly Met Ile Val Asn Asp Thr Gly
            340                 345                 350

His Glu Thr Asp Glu Asn Arg Ala Lys Val Glu Ile Thr Pro Asn Ser
        355                 360                 365

Pro Arg Ala Glu Ala Thr Leu Gly Gly Phe Gly Ser Leu Gly Leu Asp
    370                 375                 380

Cys Glu Pro Arg Thr Gly Leu Asp Phe Ser Asp Leu Tyr Tyr Leu Thr
385                 390                 395                 400

Met Asn Asn Lys His Trp Leu Val His Lys Glu Trp Phe His Asp Ile
                405                 410                 415

Pro Leu Pro Trp His Ala Gly Ala Asp Thr Gly Thr Pro His Trp Asn
            420                 425                 430

Asn Lys Glu Ala Leu Val Glu Phe Lys Asp Ala His Ala Lys Arg Gln
        435                 440                 445

Thr Val Val Val Leu Gly Ser Gln Glu Gly Ala Val His Thr Ala Leu
    450                 455                 460

Ala Gly Ala Leu Glu Ala Glu Met Asp Gly Ala Lys Gly Arg Leu Ser
465                 470                 475                 480

Ser Gly His Leu Lys Cys Arg Leu Lys Met Asp Lys Leu Arg Leu Lys
                485                 490                 495

Gly Val Ser Tyr Ser Leu Cys Thr Ala Ala Phe Thr Phe Thr Lys Ile
            500                 505                 510

Pro Ala Glu Thr Leu His Gly Thr Val Thr Val Glu Val Gln Tyr Ala
        515                 520                 525

Gly Thr Asp Gly Pro Cys Lys Val Pro Ala Gln Met Ala Val Asp Met
    530                 535                 540

Gln Thr Leu Thr Pro Val Gly Arg Leu Ile Thr Ala Asn Pro Val Ile
545                 550                 555                 560

Thr Glu Ser Thr Glu Asn Ser Lys Met Met Leu Glu Leu Asp Pro Pro
                565                 570                 575

Phe Gly Asp Ser Tyr Ile Val Ile Gly Val Gly Glu Lys Lys Ile Thr
            580                 585                 590

His His Trp His Arg Ser Gly Ser Thr Ile Gly Lys Ala Phe Glu Ala
        595                 600                 605

Thr Val Arg Gly Ala Lys Arg Met Ala Val Leu Gly Asp Thr Ala Trp
    610                 615                 620

Asp Phe Gly Ser Val Gly Gly Ala Leu Asn Ser Leu Gly Lys Gly Ile
625                 630                 635                 640

His Gln Ile Phe Gly Ala Ala Phe Lys Ser Leu Phe Gly Gly Met Ser
                645                 650                 655

Trp Phe Ser Met Lys Gly Leu Ser Ser Thr Ser Ile Val Tyr Ile Leu
            660                 665                 670

Ile Ala Val Cys Leu Gly Gly Leu Ile Gly Ile Pro Ala Leu Ile Cys
        675                 680                 685
```

Cys Cys Arg Gly Arg Cys Asn Lys Lys Gly Glu Gln Val Gly Met Ser
    690                 695                 700

Arg Pro Gly Leu Lys Pro Asp Leu Thr Gly Thr Ser Lys Ser Tyr Val
705                 710                 715                 720

Arg Ser Leu

<210> SEQ ID NO 162
<211> LENGTH: 1668
<212> TYPE: DNA
<213> ORGANISM: Artificial sequence
<220> FEATURE:
<223> OTHER INFORMATION: Native nucleotide sequence of
      MVsp_Zika_MVTMintracytoE (D10)

<400> SEQUENCE: 162
atgtccatca tgggtctcaa ggtgaacgtc tctgccatat tcatggcagt actgttaact 60
ctccaaacac ccaccggtca aatcaggtgc ataggagtca gcaataggga ctttgtggaa 120
ggtatgtcag gtgggacttg ggttgatgtt gtcttggaac atggaggttg tgtcaccgta 180
atggcacagg acaaaccgac tgtcgacata gagctggtta caacaacagt cagcaacatg 240
gcggaggtaa gatcctactg ctatgaggca tcaatatcag acatggcttc ggacagccgc 300
tgcccaacac aaggtgaagc ctaccttgac aagcaatcag acactcaata tgtctgcaaa 360
agaacgttag tggacagagg ctggggaaat ggatgtggac tttttggcaa agggagcctg 420
gtgacatgcg ctaagtttgc atgctccaag aaaatgaccg ggaagagcat ccagccagag 480
aatctggagt accggataat gctgtcagtt catggctccc agcacagtgg gatgatcgtt 540
aatgacacag gacatgaaac tgatgagaat agagcgaagg ttgagataac gcccaattca 600
ccaagagccg aagccaccct gggggtttt ggaagcctag gacttgattg tgaaccgagg 660
acaggccttg acttttcaga tttgtattac ttgactatga ataacaagca ctggttggtt 720
cacaaggagt ggttccacga cattccatta ccttggcacg ctggggcaga caccggaact 780
ccacactgga acaacaaaga agcactggta gagttcaagg acgcacatgc caaaaggcaa 840
actgtcgtgg ttctagggag tcaagaagga gcagttcaca cggcccttgc tggagctctg 900
gaggctgaga tggatggtgc aaagggaagg ctgtcctctg gccacttgaa atgtcgcctg 960
aaaatggata aacttagatt gaagggcgtg tcatactcct tgtgtaccgc agcgttcaca 1020
ttcaccaaga tcccggctga aacactgcac gggacagtca cagtggaggt acagtacgca 1080
gggacagatg gaccttgcaa ggttccagct cagatggcgg tggacatgca aactctgacc 1140
ccagttggga ggttgataac cgctaacccc gtaatcactg aaagcactga gaactctaag 1200
atgatgctgg aacttgatcc accatttggg gactcttaca ttgtcatagg agtcggggag 1260
aagaagatca cccaccactg gcacaggagt ggcagcacca ttggaaaagc atttgaagcc 1320
actgtgagag gtgccaagag aatggcagtc ttgggagaca cagcctggga ctttggatca 1380
gttggaggcg ctctcaactc attgggcaag ggcatccatc aaatttttgg agcagctttc 1440
aaatcattgt ttggaggaat gtcctggttc tcaatgaaag gtttatcgag cactagcata 1500
gtctacatcc tgattgcagt gtgtcttgga gggttgatag ggatccccgc tttaatatgt 1560
tgctgcaggg ggcgttgtaa caaaaaggga gaacaagttg gtatgtcaag accaggccta 1620
aagcctgatc ttacgggaac atcaaaatcc tatgtaaggt cgctctga 1668

<210> SEQ ID NO 163
<211> LENGTH: 1668

<212> TYPE: DNA
<213> ORGANISM: Artificial sequence
<220> FEATURE:
<223> OTHER INFORMATION: Codon-optimized nucleotide sequence of MVsp_Zika_MVTMintracytoE (D10)

<400> SEQUENCE: 163

```
atgagcatca tgggcctgaa ggtgaacgtg tccgccatct tcatggccgt gctgctgacc     60
ctgcagacac caacaggcca gatccggtgc atcggcgtga gcaatagaga cttcgtggag    120
ggaatgtccg gaggaacctg ggtggatgtg gtgctggagc acggcggctg cgtgacagtg    180
atggcccagg acaagccaac cgtggatatc gagctggtga ccacaaccgt gtccaacatg    240
gccgaggtga ggtcttactg ctatgaggcc agcatctccg acatggcctc tgatagcagg    300
tgtccaaccc agggagaggc atacctggac aagcagtccg atacacagta cgtgtgcaag    360
cggaccctgg tggacagagg ctggggcaat ggctgtggcc tgtttggcaa gggctctctg    420
gtgacatgcg ccaagttcgc ctgtagcaag aagatgaccg gcaagtccat ccagccagag    480
aacctggagt accggatcat gctgtctgtg cacggctccc agcactctgg catgatcgtg    540
aacgacacag gccacgagac agatgagaat cgggccaagg tggagatcac acctaactct    600
ccaagagccg aggccaccct gggaggattt ggctctctgg gcctggactg cgagcctaga    660
acaggcctgg acttctccga tctgtactat ctgaccatga acaataagca ctggctggtg    720
cacaaggagt ggtttcacga catcccactg ccatggcacg caggagcaga tacaggaaca    780
ccacactgga acaataagga ggccctggtg gagttcaagg atgcccacgc caagcggcag    840
acagtggtgg tgctgggcag ccaggaggga gcagtgcaca ccgccctggc aggcgccctg    900
gaggcagaga tggacggagc taagggcaga ctgtctagcg gccacctgaa gtgcaggctg    960
aagatggata agctgcgcct gaagggcgtg tcctactctc tgtgcacagc cgccttcacc   1020
ttcaccaaga tccctgccga gacactgcac ggcacagtga ccgtggaggt gcagtatgcc   1080
ggcacagacg gaccctgtaa ggtgcctgcc cagatggccg tggatatgca gacactgaca   1140
cctgtgggca ggctgatcac cgccaatcca gtgatcacag agtctaccga gaacagcaag   1200
atgatgctgg agctggaccc accatttggc gatagctata tcgtgatcgg cgtgggcgag   1260
aagaagatca cacaccactg gcaccgcagc ggctccacaa tcggcaaggc ctttgaggca   1320
accgtgcgcg gagcaaagag aatggccgtg ctgggcgaca ccgcatggga tttcggatct   1380
gtgggaggcg ccctgaacag cctgggcaag ggcatccacc agatcttcgg cgccgccttt   1440
aagtccctgt tcggcggcat gagctggttc tcaatgaagg gcctgtcctc tacctctatc   1500
gtgtacatcc tgatcgccgt gtgcctggga ggcctgatcg gaatcccagc cctgatctgc   1560
tgttgcagag gccgctgcaa caagaaggga gagcaagtgg gaatgtctcg gccaggcctg   1620
aagccagacc tgacaggcac ctccaagtct tatgtgagaa gcctgtga                1668
```

<210> SEQ ID NO 164
<211> LENGTH: 555
<212> TYPE: PRT
<213> ORGANISM: Artificial sequence
<220> FEATURE:
<223> OTHER INFORMATION: MVsp_Zika_MVTMintracytoE (D10)

<400> SEQUENCE: 164

```
Met Ser Ile Met Gly Leu Lys Val Asn Val Ser Ala Ile Phe Met Ala
1               5                   10                  15

Val Leu Leu Thr Leu Gln Thr Pro Thr Gly Gln Ile Arg Cys Ile Gly
            20                  25                  30
```

```
Val Ser Asn Arg Asp Phe Val Glu Gly Met Ser Gly Gly Thr Trp Val
        35                  40                  45

Asp Val Val Leu Glu His Gly Gly Cys Val Thr Val Met Ala Gln Asp
    50                  55                  60

Lys Pro Thr Val Asp Ile Glu Leu Val Thr Thr Thr Val Ser Asn Met
65                  70                  75                  80

Ala Glu Val Arg Ser Tyr Cys Tyr Glu Ala Ser Ile Ser Asp Met Ala
                85                  90                  95

Ser Asp Ser Arg Cys Pro Thr Gln Gly Glu Ala Tyr Leu Asp Lys Gln
            100                 105                 110

Ser Asp Thr Gln Tyr Val Cys Lys Arg Thr Leu Val Asp Arg Gly Trp
        115                 120                 125

Gly Asn Gly Cys Gly Leu Phe Gly Lys Gly Ser Leu Val Thr Cys Ala
    130                 135                 140

Lys Phe Ala Cys Ser Lys Lys Met Thr Gly Lys Ser Ile Gln Pro Glu
145                 150                 155                 160

Asn Leu Glu Tyr Arg Ile Met Leu Ser Val His Gly Ser Gln His Ser
                165                 170                 175

Gly Met Ile Val Asn Asp Thr Gly His Glu Thr Asp Glu Asn Arg Ala
            180                 185                 190

Lys Val Glu Ile Thr Pro Asn Ser Pro Arg Ala Glu Ala Thr Leu Gly
        195                 200                 205

Gly Phe Gly Ser Leu Gly Leu Asp Cys Glu Pro Arg Thr Gly Leu Asp
    210                 215                 220

Phe Ser Asp Leu Tyr Tyr Leu Thr Met Asn Asn Lys His Trp Leu Val
225                 230                 235                 240

His Lys Glu Trp Phe His Asp Ile Pro Leu Pro Trp His Ala Gly Ala
                245                 250                 255

Asp Thr Gly Thr Pro His Trp Asn Asn Lys Glu Ala Leu Val Glu Phe
            260                 265                 270

Lys Asp Ala His Ala Lys Arg Gln Thr Val Val Val Leu Gly Ser Gln
        275                 280                 285

Glu Gly Ala Val His Thr Ala Leu Ala Gly Ala Leu Glu Ala Glu Met
    290                 295                 300

Asp Gly Ala Lys Gly Arg Leu Ser Ser Gly His Leu Lys Cys Arg Leu
305                 310                 315                 320

Lys Met Asp Lys Leu Arg Leu Lys Gly Val Ser Tyr Ser Leu Cys Thr
                325                 330                 335

Ala Ala Phe Thr Phe Thr Lys Ile Pro Ala Glu Thr Leu His Gly Thr
            340                 345                 350

Val Thr Val Glu Val Gln Tyr Ala Gly Thr Asp Gly Pro Cys Lys Val
        355                 360                 365

Pro Ala Gln Met Ala Val Asp Met Gln Thr Leu Thr Pro Val Gly Arg
    370                 375                 380

Leu Ile Thr Ala Asn Pro Val Ile Thr Glu Ser Thr Glu Asn Ser Lys
385                 390                 395                 400

Met Met Leu Glu Leu Asp Pro Pro Phe Gly Asp Ser Tyr Ile Val Ile
                405                 410                 415

Gly Val Gly Glu Lys Lys Ile Thr His His Trp His Arg Ser Gly Ser
            420                 425                 430

Thr Ile Gly Lys Ala Phe Glu Ala Thr Val Arg Gly Ala Lys Arg Met
        435                 440                 445
```

```
Ala Val Leu Gly Asp Thr Ala Trp Asp Phe Gly Ser Val Gly Gly Ala
    450                 455                 460

Leu Asn Ser Leu Gly Lys Gly Ile His Gln Ile Phe Gly Ala Ala Phe
465                 470                 475                 480

Lys Ser Leu Phe Gly Gly Met Ser Trp Phe Ser Met Lys Gly Leu Ser
                485                 490                 495

Ser Thr Ser Ile Val Tyr Ile Leu Ile Ala Val Cys Leu Gly Gly Leu
            500                 505                 510

Ile Gly Ile Pro Ala Leu Ile Cys Cys Cys Arg Gly Arg Cys Asn Lys
        515                 520                 525

Lys Gly Glu Gln Val Gly Met Ser Arg Pro Gly Leu Lys Pro Asp Leu
    530                 535                 540

Thr Gly Thr Ser Lys Ser Tyr Val Arg Ser Leu
545                 550                 555


<210> SEQ ID NO 165
<211> LENGTH: 21169
<212> TYPE: DNA
<213> ORGANISM: Artificial sequence
<220> FEATURE:
<223> OTHER INFORMATION: pTM2-MVSchw_A1_Zikasp_ZikaprME
<220> FEATURE:
<221> NAME/KEY: misc_feature
<222> LOCATION: (9)..(28)
<223> OTHER INFORMATION: T7 promoter
<220> FEATURE:
<221> NAME/KEY: misc_feature
<222> LOCATION: (83)..(189)
<223> OTHER INFORMATION: MV Leader and N promoter
<220> FEATURE:
<221> NAME/KEY: misc_feature
<222> LOCATION: (190)..(1767)
<223> OTHER INFORMATION: MV N ORF
<220> FEATURE:
<221> NAME/KEY: misc_feature
<222> LOCATION: (1889)..(3414)
<223> OTHER INFORMATION: MV P ORF
<220> FEATURE:
<221> NAME/KEY: misc_feature
<222> LOCATION: (3532)..(5625)
<223> OTHER INFORMATION: A1. Zikasp_ZikaprME
<220> FEATURE:
<221> NAME/KEY: misc_feature
<222> LOCATION: (5722)..(6729)
<223> OTHER INFORMATION: MV M ORF
<220> FEATURE:
<221> NAME/KEY: misc_feature
<222> LOCATION: (7733)..(9394)
<223> OTHER INFORMATION: MV F ORF
<220> FEATURE:
<221> NAME/KEY: misc_feature
<222> LOCATION: (9555)..(11408)
<223> OTHER INFORMATION: MV H ORF
<220> FEATURE:
<221> NAME/KEY: misc_feature
<222> LOCATION: (11518)..(18069)
<223> OTHER INFORMATION: MV L ORF
<220> FEATURE:
<221> NAME/KEY: misc_feature
<222> LOCATION: (18179)..(18262)
<223> OTHER INFORMATION: HDV ribozyme
<220> FEATURE:
<221> NAME/KEY: misc_feature
<222> LOCATION: (18263)..(18404)
<223> OTHER INFORMATION: T7 terminator
<220> FEATURE:
<221> NAME/KEY: misc_feature
<222> LOCATION: (18438)..(18457)
<223> OTHER INFORMATION: T3
<220> FEATURE:
<221> NAME/KEY: misc_feature
<222> LOCATION: (18475)..(18495)
```

<223> OTHER INFORMATION: M13-rev
<220> FEATURE:
<221> NAME/KEY: misc_feature
<222> LOCATION: (18501)..(18523)
<223> OTHER INFORMATION: LacO
<220> FEATURE:
<221> NAME/KEY: misc_feature
<222> LOCATION: (18863)..(19491)
<223> OTHER INFORMATION: ColE1 origin
<220> FEATURE:
<221> NAME/KEY: misc_feature
<222> LOCATION: (19643)..(20302)
<223> OTHER INFORMATION: AmpR
<220> FEATURE:
<221> NAME/KEY: misc_feature
<222> LOCATION: (20542)..(20570)
<223> OTHER INFORMATION: Amp prom
<220> FEATURE:
<221> NAME/KEY: misc_feature
<222> LOCATION: (20632)..(21087)
<223> OTHER INFORMATION: M13 origin
<220> FEATURE:
<221> NAME/KEY: misc_feature
<222> LOCATION: (20642)..(21082)
<223> OTHER INFORMATION: F1 ori
<220> FEATURE:
<221> NAME/KEY: misc_feature
<222> LOCATION: (21089)..(21157)
<223> OTHER INFORMATION: LacZ alpha

<400> SEQUENCE: 165
gcggccgcta atacgactca ctatagggcc aactttgttt ggtctgatga gtccgtgagg 60
acgaaacccg gagtcccggg tcaccaaaca aagttgggta aggatagttc aatcaatgat 120
catcttctag tgcacttagg attcaagatc ctattatcag ggacaagagc aggattaggg 180
atatccgaga tggccacact tttaaggagc ttagcattgt tcaaaagaaa caaggacaaa 240
ccacccatta catcaggatc cggtggagcc atcagaggaa tcaaacacat tattatagta 300
ccaatccctg gagattcctc aattaccact cgatccagac ttctggaccg gttggtgagg 360
ttaattggaa acccggatgt gagcgggccc aaactaacag gggcactaat aggtatatta 420
tccttatttg tggagtctcc aggtcaattg attcagagga tcaccgatga ccctgacgtt 480
agcataaggc tgttagaggt tgtccagagt gaccagtcac aatctggcct taccttcgca 540
tcaagaggta ccaacatgga ggatgaggcg gaccaatact tttcacatga tgatccaatt 600
agtagtgatc aatccaggtt cggatggttc gggaacaagg aaatctcaga tattgaagtg 660
caagaccctg agggattcaa catgattctg ggtaccatcc tagcccaaat ttgggtcttg 720
ctcgcaaagg cggttacggc cccagacacg gcagctgatt cggagctaag aaggtggata 780
aagtacaccc aacaaagaag ggtagttggt gaatttagat tggagagaaa atggttggat 840
gtggtgagga acaggattgc cgaggacctc tccttacgcc gattcatggt cgctctaatc 900
ctggatatca agagaacacc cggaaacaaa cccaggattg ctgaaatgat atgtgacatt 960
gatacatata tcgtagaggc aggattagcc agttttatcc tgactattaa gtttgggata 1020
gaaactatgt atcctgctct tggactgcat gaatttgctg gtgagttatc cacacttgag 1080
tccttgatga acctttacca gcaaatgggg gaaactgcac cctacatggt aatcctggag 1140
aactcaattc agaacaagtt cagtgcagga tcatacccte tgctctggag ctatgccatg 1200
ggagtaggag tggaacttga aaactccatg ggaggtttga actttggccg atcttacttt 1260
gatccagcat attttagatt agggcaagag atggtaagga ggtcagctgg aaaggtcagt 1320
tccacattgg catctgaact cggtatcact gccgaggatg caaggcttgt ttcagagatt 1380
gcaatgcata ctactgagga caagatcagt agagcggttg gacccagaca agcccaagta 1440

```
tcatttctac acggtgatca aagtgagaat gagctaccga gattgggggg caaggaagat   1500
aggagggtca aacagagtcg aggagaagcc agggagagct acagagaaac cgggcccagc   1560
agagcaagtg atgcgagagc tgcccatctt ccaaccggca caccccctaga cattgacact   1620
gcaacggagt ccagccaaga tccgcaggac agtcgaaggt cagctgacgc cctgcttagg   1680
ctgcaagcca tggcaggaat ctcggaagaa caaggctcag acacggacac ccctatagtg   1740
tacaatgaca gaaatcttct agactaggtg cgagaggccg agggccagaa caacatccgc   1800
ctaccatcca tcattgttat aaaaaactta ggaaccaggt ccacacagcc gccagcccat   1860
caaccatcca ctcccacgat tggagccaat ggcagaagag caggcacgcc atgtcaaaaa   1920
cggactggaa tgcatccggg ctctcaaggc cgagcccatc ggctcactgg ccatcgagga   1980
agctatggca gcatggtcag aaatatcaga caacccagga caggagcgag ccacctgcag   2040
ggaagagaag gcaggcagtt cgggtctcag caaaccatgc ctctcagcaa ttggatcaac   2100
tgaaggcggt gcacctcgca tccgcggtca gggacctgga gagagcgatg acgacgctga   2160
aactttggga atccccccaa gaaatctcca ggcatcaagc actgggttac agtgttatta   2220
cgtttatgat cacagcggtg aagcggttaa gggaatccaa gatgctgact ctatcatggt   2280
tcaatcaggc cttgatggtg atagcaccct ctcaggagga gacaatgaat ctgaaaacag   2340
cgatgtggat attggcgaac ctgataccga gggatatgct atcactgacc ggggatctgc   2400
tcccatctct atggggttca gggcttctga tgttgaaact gcagaaggag gggagatcca   2460
cgagctcctg agactccaat ccagaggcaa caactttccg aagcttggga aaactctcaa   2520
tgttcctccg cccccggacc ccggtagggc cagcacttcc gggacaccca ttaaaaaggg   2580
cacagacgcg agattagcct catttggaac ggagatcgcg tctttattga caggtggtgc   2640
aacccaatgt gctcgaaagt caccctcgga accatcaggg ccaggtgcac ctgcggggaa   2700
tgtccccgag tgtgtgagca atgccgcact gatacaggag tggacacccg aatctggtac   2760
cacaatctcc ccgagatccc agaataatga agaaggggga gactattatg atgatgagct   2820
gttctctgat gtccaagata ttaaaacagc cttggccaaa atacacgagg ataatcagaa   2880
gataatctcc aagctagaat cactgctgtt attgaaggga gaagttgagt caattaagaa   2940
gcagatcaac aggcaaaata tcagcatatc caccctggaa ggacacctct caagcatcat   3000
gatcgccatt cctggacttg ggaaggatcc caacgacccc actgcagatg tcgaaatcaa   3060
tcccgacttg aaacccatca taggcagaga ttcaggccga gcactggccg aagttctcaa   3120
gaaacccgtt gccagccgac aactccaagg aatgacaaat ggacggacca gttccagagg   3180
acagctgctg aaggaatttc agctaaagcc gatcgggaaa aagatgagct cagccgtcgg   3240
gtttgttcct gacaccggcc ctgcatcacg cagtgtaatc cgctccatta taaaatccag   3300
ccggctagag gaggatcgga agcgttacct gatgactctc cttgatgata tcaaaggagc   3360
caatgatctt gccaagttcc accagatgct gatgaagata ataatgaagt agctacagct   3420
caacttacct gccaacccca tgccagtcga cccaactagc ctaccctcca tcattgttat   3480
aaaaaactta ggaaccaggt ccacacagcc gccagcccat caacgcgtac gatggagaag   3540
aagcggagag gagcagacac aagcgtggga atcgtgggcc tgctgctgac cacagcaatg   3600
gcagcagagg tgaccaggag aggaagcgcc tactatatgt acctggacag gaatgatgcc   3660
ggcgaggcca tctccttccc aaccacactg ggcatgaaca agtgctacat ccagatcatg   3720
gacctgggcc acatgtgcga tgccaccatg tcctatgagt gtccaatgct ggacgagggc   3780
```

-continued gtggagcccg acgatgtgga ttgctggtgt aataccacat ctacatgggt ggtgtacggc 3840
acctgtcacc acaagaaggg agaggcccgg cggagccggc gggccgtgac actgccttcc 3900
cactctacca ggaagctgca gacacgcagc cagacctggc tggagtccag agagtatacc 3960
aagcacctga tcagggtgga gaactggatc tttcgcaatc caggattcgc actggcagca 4020
gcagcaatcg catggctgct gggaagctcc accagccaga aagtgatcta cctggtcatg 4080
atcctgctga tcgctcctgc ctattctatc cggtgcatcg gcgtgagcaa tagagacttc 4140
gtggagggaa tgtccggagg aacctgggtg gatgtggtgc tggagcacgg cggctgcgtg 4200
acagtgatgg cccaggacaa gccaaccgtg gatatcgagc tggtgaccac aaccgtgtcc 4260
aacatggccg aggtgaggtc ttactgctat gaggccagca tctccgacat ggcctctgat 4320
agcaggtgtc caacccaggg agaggcatac ctggacaagc agtccgatac acagtacgtg 4380
tgcaagcgga ccctggtgga cagaggctgg ggcaatggct gtggcctgtt tggcaagggc 4440
tctctggtga catgcgccaa gttcgcctgt agcaagaaga tgaccggcaa gtccatccag 4500
ccagagaacc tggagtaccg gatcatgctg tctgtgcacg gctcccagca ctctggcatg 4560
atcgtgaacg acacaggcca cgagacagat gagaatcggg ccaaggtgga gatcacacct 4620
aactctccaa gagccgaggc caccctggga ggatttggct ctctgggcct ggactgcgag 4680
cctagaacag gcctggactt ctccgatctg tactatctga ccatgaacaa taagcactgg 4740
ctggtgcaca aggagtggtt tcacgacatc ccactgccat ggcacgcagg agcagataca 4800
ggaacaccac actggaacaa taaggaggcc ctggtggagt tcaaggatgc ccacgccaag 4860
cggcagacag tggtggtgct gggcagccag gagggagcag tgcacaccgc cctggcaggc 4920
gccctggagg cagagatgga cggagctaag ggcagactgt ctagcggcca cctgaagtgc 4980
aggctgaaga tggataagct gcgcctgaag ggcgtgtcct actctctgtg cacagccgcc 5040
ttcaccttca ccaagatccc tgccgagaca ctgcacggca cagtgaccgt ggaggtgcag 5100
tatgccggca cagacggacc ctgtaaggtg cctgcccaga tggccgtgga tatgcagaca 5160
ctgacacctg tgggcaggct gatcaccgcc aatccagtga tcacagagtc taccgagaac 5220
agcaagatga tgctggagct ggacccacca tttggcgata gctatatcgt gatcggcgtg 5280
ggcgagaaga agatcacaca ccactggcac cgcagcggct ccacaatcgg caaggccttt 5340
gaggcaaccg tgcgcggagc aaagagaatg gccgtgctgg gcgacaccgc atgggatttc 5400
ggatctgtgg gaggcgccct gaacagcctg ggcaagggca tccaccagat cttcggcgcc 5460
gcctttaagt ccctgttcgg cggcatgagc tggttctcac agatcctgat cggcacactg 5520
ctgatgtggc tgggcctgaa caccaagaat ggctctatca gcctgatgtg cctggccctg 5580
ggaggcgtgc tgatcttcct gtccaccgcc gtgtctgcct gatgagcgcg cagcgcttag 5640
acgtctcgcg atcgatacta gtacaaccta aatccattat aaaaaactta ggagcaaagt 5700
gattgcctcc caaggtccac aatgacagag acctacgact tcgacaagtc ggcatgggac 5760
atcaaagggt cgatcgctcc gatacaaccc accacctaca gtgatggcag gctggtgccc 5820
caggtcagag tcatagatcc tggtctaggc gacaggaagg atgaatgctt tatgtacatg 5880
tttctgctgg gggttgttga ggacagcgat tccctagggc ctccaatcgg gcgagcattt 5940
gggttcctgc ccttaggtgt tggcagatcc acagcaaagc ccgaaaaact cctcaaagag 6000
gccactgagc ttgacatagt tgttagacgt acagcagggc tcaatgaaaa actggtgttc 6060
tacaacaaca ccccactaac tctcctcaca ccttggagaa aggtcctaac aacagggagt 6120
gtcttcaacg caaaccaagt gtgcaatgcg gttaatctga taccgctcga taccccgcag 6180
aggttccgtg ttgtttatat gagcatcacc cgtctttcgg ataacgggta ttacaccgtt 6240
cctagaagaa tgctggaatt cagatcggtc aatgcagtgg ccttcaacct gctggtgacc 6300
cttaggattg acaaggcgat aggccctggg aagatcatcg acaatacaga gcaacttcct 6360
gaggcaacat ttatggtcca catcgggaac ttcaggagaa agaagagtga agtctactct 6420
gccgattatt gcaaaatgaa aatcgaaaag atgggcctgg tttttgcact tggtgggata 6480
gggggcacca gtcttcacat tagaagcaca ggcaaaatga gcaagactct ccatgcacaa 6540
ctcgggttca agaagacctt atgttacccg ctgatggata tcaatgaaga ccttaatcga 6600
ttactctgga ggagcagatg caagatagta agaatccagg cagttttgca gccatcagtt 6660
cctcaagaat tccgcattta cgacgacgtg atcataaatg atgaccaagg actattcaaa 6720
gttctgtaga ccgtagtgcc cagcaatgcc cgaaaacgac ccccctcaca atgacagcca 6780
gaaggcccgg acaaaaaagc cccctccgaa agactccacg gaccaagcga gaggccagcc 6840
agcagccgac ggcaagcgcg aacaccaggc ggccccagca cagaacagcc ctgacacaag 6900
gccaccacca gccaccccaa tctgcatcct cctcgtggga cccccgagga ccaaccccca 6960
aggctgcccc cgatccaaac caccaaccgc atccccacca cccccgggaa agaaaccccc 7020
agcaattgga aggcccctcc ccctcttcct caacacaaga actccacaac cgaaccgcac 7080
aagcgaccga ggtgacccaa ccgcaggcat ccgactccct agacagatcc tctctccccg 7140
gcaaactaaa caaaacttag ggccaaggaa catacacacc caacagaacc cagaccccgg 7200
cccacggcgc cgcgccccca acccccgaca accagaggga gcccccaacc aatcccgccg 7260
gctcccccgg tgcccacagg cagggacacc aacccccgaa cagacccagc acccaaccat 7320
cgacaatcca agacgggggg gcccccccaa aaaaaggccc ccaggggccg acagccagca 7380
ccgcgaggaa gcccacccac cccacacacg accacggcaa ccaaaccaga acccagacca 7440
ccctgggcca ccagctccca gactcggcca tcaccccgca gaaaggaaag gccacaaccc 7500
gcgcacccca gccccgatcc ggcggggagc cacccaaccc gaaccagcac ccaagagcga 7560
tccccgaagg acccccgaac cgcaaaggac atcagtatcc cacagcctct ccaagtcccc 7620
cggtctcctc ctcttctcga agggaccaaa agatcaatcc accacacccg acgacactca 7680
actccccacc cctaaaggag acaccgggaa tcccagaatc aagactcatc caatgtccat 7740
catgggtctc aaggtgaacg tctctgccat attcatggca gtactgttaa ctctccaaac 7800
acccaccggt caaatccatt ggggcaatct ctctaagata ggggtggtag gaataggaag 7860
tgcaagctac aaagttatga ctcgttccag ccatcaatca ttagtcataa aattaatgcc 7920
caatataact ctcctcaata actgcacgag ggtagagatt gcagaataca ggagactact 7980
gagaacagtt ttggaaccaa ttagagatgc acttaatgca atgacccaga atataagacc 8040
ggttcagagt gtagcttcaa gtaggagaca caagagattt gcgggagtag tcctggcagg 8100
tgcggcccta ggcgttgcca cagctgctca gataacagcc ggcattgcac ttcaccagtc 8160
catgctgaac tctcaagcca tcgacaatct gagagcgagc ctggaaacta ctaatcaggc 8220
aattgagaca atcagacaag cagggcagga gatgatattg gctgttcagg gtgtccaaga 8280
ctacatcaat aatgagctga taccgtctat gaaccaacta tcttgtgatt taatcggcca 8340
gaagctcggg ctcaaattgc tcagatacta tacagaaatc ctgtcattat ttggccccag 8400
tttacgggac cccatatctg cggagatatc tatccaggct ttgagctatg cgcttggagg 8460
agacatcaat aaggtgttag aaaagctcgg atacagtgga ggtgatttac tgggcatctt 8520

```
agagagcgga ggaataaagg cccggataac tcacgtcgac acagagtcct acttcattgt   8580
cctcagtata gcctatccga cgctgtccga gattaagggg gtgattgtcc accggctaga   8640
gggggtctcg tacaacatag gctctcaaga gtggtatacc actgtgccca agtatgttgc   8700
aacccaaggg taccttatct cgaattttga tgagtcatcg tgtactttca tgccagaggg   8760
gactgtgtgc agccaaaatg ccttgtaccc gatgagtcct ctgctccaag aatgcctccg   8820
ggggtacacc aagtcctgtg ctcgtacact cgtatccggg tcttttggga accggttcat   8880
tttatcacaa gggaacctaa tagccaattg tgcatcaatc ctttgcaagt gttacacaac   8940
aggaacgatc attaatcaag accctgacaa gatcctaaca tacattgctg ccgatcactg   9000
cccggtagtc gaggtgaacg gcgtgaccat ccaagtcggg agcaggaggt atccagacgc   9060
tgtgtacttg cacagaattg acctcggtcc tcccatatca ttggagaggt tggacgtagg   9120
gacaaatctg gggaatgcaa ttgctaagtt ggaggatgcc aaggaattgt tggagtcatc   9180
ggaccagata ttgaggagta tgaaaggttt atcgagcact agcatagtct acatcctgat   9240
tgcagtgtgt cttggagggt tgatagggat ccccgcttta atatgttgct gcagggggcg   9300
ttgtaacaaa aagggagaac aagttggtat gtcaagacca ggcctaaagc ctgatcttac   9360
gggaacatca aaatcctatg taaggtcgct ctgatcctct acaactcttg aaacacaaat   9420
gtcccacaag tctcctcttc gtcatcaagc aaccaccgca cccagcatca agcccacctg   9480
aaattatctc cggcttccct ctggccgaac aatatcggta gttaatcaaa acttagggtg   9540
caagatcatc cacaatgtca ccacaacgag accggataaa tgccttctac aaagataacc   9600
cccatcccaa gggaagtagg atagtcatta acagagaaca tcttatgatt gatagacctt   9660
atgttttgct ggctgttctg tttgtcatgt ttctgagctt gatcgggttg ctagccattg   9720
caggcattag acttcatcgg gcagccatct acaccgcaga gatccataaa agcctcagca   9780
ccaatctaga tgtaactaac tcaatcgagc atcaggtcaa ggacgtgctg acaccactct   9840
tcaaaatcat cggtgatgaa gtgggcctga ggacacctca gagattcact gacctagtga   9900
aattaatctc tgacaagatt aaattcctta atccggatag ggagtacgac ttcagagatc   9960
tcacttggtg tatcaacccg ccagagagaa tcaaattgga ttatgatcaa tactgtgcag  10020
atgtggctgc tgaagagctc atgaatgcat tggtgaactc aactctactg gagaccagaa  10080
caaccaatca gttcctagct gtctcaaagg gaaactgctc agggcccact acaatcagag  10140
gtcaattctc aaacatgtcg ctgtccctgt tagacttgta tttaggtcga ggttacaatg  10200
tgtcatctat agtcactatg acatcccagg gaatgtatgg gggaacttac ctagtggaaa  10260
agcctaatct gagcagcaaa aggtcagagt tgtcacaact gagcatgtac cgagtgtttg  10320
aagtaggtgt tatcagaaat ccgggtttgg gggctccggt gttccatatg acaaactatc  10380
ttgagcaacc agtcagtaat gatctcagca actgtatggt ggctttgggg gagctcaaac  10440
tcgcagccct ttgtcacggg gaagattcta tcacaattcc ctatcaggga tcagggaaag  10500
gtgtcagctt ccagctcgtc aagctaggtg tctggaaatc ccccaaccgac atgcaatcct  10560
gggtcccctt atcaacggat gatccagtga tagacaggct ttacctctca tctcacagag  10620
gtgttatcgc tgacaatcaa gcaaaatggg ctgtcccgac aacacgaaca gatgacaagt  10680
tgcgaatgga gacatgcttc caacaggcgt gtaagggtaa aatccaagca ctctgcgaga  10740
atcccgagtg ggcaccattg aaggataaca ggattccttc atacggggtc ttgtctgttg  10800
atctgagtct gacagttgag cttaaaatca aaattgcttc gggattcggg ccattgatca  10860
cacacggttc agggatggac ctatacaaat ccaaccacaa caatgtgtat tggctgacta  10920
```

```
tcccgccaat gaagaaccta gccttaggtg taatcaacac attggagtgg ataccgagat  10980
tcaaggttag tccctacctc ttcactgtcc caattaagga agcaggcgaa gactgccatg  11040
ccccaacata cctacctgcg gaggtggatg gtgatgtcaa actcagttcc aatctggtga  11100
ttctacctgg tcaagatctc caatatgttt tggcaaccta cgatacttcc agggttgaac  11160
atgctgtggt ttattacgtt tacagcccaa gccgctcatt ttcttacttt tatccttttta  11220
ggttgcctat aaagggggtc cccatcgaat tacaagtgga atgcttcaca tgggaccaaa  11280
aactctggtg ccgtcacttc tgtgtgcttg cggactcaga atctggtgga catatcactc  11340
actctgggat ggtgggcatg ggagtcagct gcacagtcac ccgggaagat ggaaccaatc  11400
gcagataggg ctgctagtga accaatcaca tgatgtcacc cagacatcag gcatacccac  11460
tagtgtgaaa tagacatcag aattaagaaa aacgtagggt ccaagtggtt ccccgttatg  11520
gactcgctat ctgtcaacca gatcttatac cctgaagttc acctagatag cccgatagtt  11580
accaataaga tagtagccat cctggagtat gctcgagtcc ctcacgctta cagcctggag  11640
gaccctacac tgtgtcagaa catcaagcac cgcctaaaaa acggattttc caaccaaatg  11700
attataaaca atgtggaagt tggaatgtc atcaagtcca agcttaggag ttatccggcc  11760
cactctcata ttccatatcc aaattgtaat caggatttat ttaacataga agacaaagag  11820
tcaacgagga agatccgtga actcctcaaa aaggggaatt cgctgtactc caaagtcagt  11880
gataaggttt tccaatgctt aagggacact aactcacggc ttggcctagg ctccgaattg  11940
agggaggaca tcaaggagaa agttattaac ttgggagttt acatgcacag ctcccagtgg  12000
tttgagccct ttctgttttg gtttacagtc aagactgaga tgaggtcagt gattaaatca  12060
caaacccata cttgccatag gaggagacac acacctgtat tcttcactgg tagttcagtt  12120
gagttgctaa tctctcgtga ccttgttgct ataatcagta aagagtctca acatgtatat  12180
tacctgacat ttgaactggt tttgatgtat tgtgatgtca tagaggggag gttaatgaca  12240
gagaccgcta tgactattga tgctaggtat acagagcttc taggaagagt cagatacatg  12300
tggaaactga tagatggttt cttccctgca ctcgggaatc caacttatca aattgtagcc  12360
atgctggagc ctctttcact tgcttacctg cagctgaggg atataacagt agaactcaga  12420
ggtgctttcc ttaaccactg ctttactgaa atacatgatg ttcttgacca aaacgggttt  12480
tctgatgaag gtacttatca tgagttaact gaagctctag attacatttt cataactgat  12540
gacatacatc tgacagggga gattttctca tttttcagaa gtttcggcca ccccagactt  12600
gaagcagtaa cggctgctga aaatgttagg aaatacatga atcagcctaa agtcattgtg  12660
tatgagactc tgatgaaagg tcatgccata ttttgtggaa tcataatcaa cggctatcgt  12720
gacaggcacg gaggcagttg gccaccgctg accctccccc tgcatgctgc agacacaatc  12780
cggaatgctc aagcttcagg tgaagggtta acacatgagc agtgcgttga taactggaaa  12840
tcttttgctg gagtgaaatt tggctgcttt atgcctctta gcctggatag tgatctgaca  12900
atgtacctaa aggacaaggc acttgctgct ctccaaaggg aatgggattc agtttacccg  12960
aaagagttcc tgcgttacga ccctcccaag ggaaccgggt cacggaggct tgtagatgtt  13020
ttccttaatg attcgagctt tgacccatat gatgtgataa tgtatgttgt aagtggagct  13080
tacctccatg accctgagtt caacctgtct tacagcctga aagaaaagga gatcaaggaa  13140
acaggtagac tttttgctaa aatgacttac aaaatgaggg catgccaagt gattgctgaa  13200
aatctaatct caaacgggat tggcaaatat tttaaggaca atgggatggc caaggatgag  13260
```

-continued

```
cacgatttga ctaaggcact ccacactcta gctgtctcag gagtccccaa agatctcaaa  13320
gaaagtcaca ggggggggcc agtcttaaaa acctactccc gaagcccagt ccacacaagt  13380
accaggaacg tgagagcagc aaaagggttt atagggttcc ctcaagtaat tcggcaggac  13440
caagacactg atcatccgga gaatatggaa gcttacgaga cagtcagtgc atttatcacg  13500
actgatctca agaagtactg ccttaattgg agatatgaga ccatcagctt gtttgcacag  13560
aggctaaatg agatttacgg attgccctca tttttccagt ggctgcataa gaggcttgag  13620
acctctgtcc tgtatgtaag tgaccctcat tgcccccccg accttgacgc ccatatcccg  13680
ttatataaag tccccaatga tcaaatcttc attaagtacc ctatgggagg tatagaaggg  13740
tattgtcaga agctgtggac catcagcacc attccctatc tatacctggc tgcttatgag  13800
agcggagtaa ggattgcttc gttagtgcaa ggggacaatc agaccatagc cgtaacaaaa  13860
agggtaccca gcacatggcc ctacaacctt aagaaacggg aagctgctag agtaactaga  13920
gattactttg taattcttag gcaaaggcta catgatattg gccatcacct caaggcaaat  13980
gagacaattg tttcatcaca ttttttttgtc tattcaaaag gaatatatta tgatgggcta  14040
cttgtgtccc aatcactcaa gagcatcgca agatgtgtat tctggtcaga gactatagtt  14100
gatgaaacaa gggcagcatg cagtaatatt gctacaacaa tggctaaaag catcgagaga  14160
ggttatgacc gttaccttgc atattccctg aacgtcctaa aagtgataca gcaaattctg  14220
atctctcttg gcttcacaat caattcaacc atgacccggg atgtagtcat acccctcctc  14280
acaaacaacg acctcttaat aaggatggca ctgttgcccg ctcctattgg ggggatgaat  14340
tatctgaata tgagcaggct gtttgtcaga aacatcggtg atccagtaac atcatcaatt  14400
gctgatctca agagaatgat tctcgcctca ctaatgcctg aagagaccct ccatcaagta  14460
atgacacaac aaccggggga ctcttcattc ctagactggg ctagcgaccc ttactcagca  14520
aatcttgtat gtgtccagag catcactaga ctcctcaaga acataactgc aaggtttgtc  14580
ctgatccata gtccaaaccc aatgttaaaa ggattattcc atgatgacag taaagaagag  14640
gacgagggac tggcggcatt cctcatggac aggcatatta tagtacctag ggcagctcat  14700
gaaatcctgg atcatagtgt cacaggggca agagagtcta ttgcaggcat gctggatacc  14760
acaaaaggct tgattcgagc cagcatgagg aagggggggt taacctctcg agtgataacc  14820
agattgtcca attatgacta tgaacaattc agagcaggga tggtgctatt gacaggaaga  14880
aagagaaatg tcctcattga caaagagtca tgttcagtgc agctggcgag agctctaaga  14940
agccatatgt gggcgaggct agctcgagga cggcctattt acggccttga ggtccctgat  15000
gtactagaat ctatgcgagg ccaccttatt cggcgtcatg agacatgtgt catctgcgag  15060
tgtggatcag tcaactacgg atggtttttt gtcccctcgg gttgccaact ggatgatatt  15120
gacaaggaaa catcatcctt gagagtccca tatattggtt ctaccactga tgagagaaca  15180
gacatgaagc ttgccttcgt aagagcccca agtcgatcct tgcgatctgc tgttagaata  15240
gcaacagtgt actcatgggc ttacggtgat gatgatagct cttggaacga agcctggttg  15300
ttggctaggc aaagggccaa tgtgagcctg gaggagctaa gggtgatcac tcccatctca  15360
acttcgacta atttagcgca taggttgagg gatcgtagca ctcaagtgaa atactcaggt  15420
acatcccttg tccgagtggc gaggtatacc acaatctcca acgacaatct ctcatttgtc  15480
atatcagata agaaggttga tactaacttt atataccaac aaggaatgct tctagggttg  15540
ggtgttttag aaacattgtt tcgactcgag aaagataccg gatcatctaa cacggtatta  15600
catcttcacg tcgaaacaga ttgttgcgtg atcccgatga tagatcatcc caggataccc  15660
```

agctcccgca agctagagct gagggcagag ctatgtacca acccattgat atatgataat 15720
gcacctttaa ttgacagaga tgcaacaagg ctatacaccc agagccatag gaggcacctt 15780
gtggaatttg ttacatggtc cacaccccaa ctatatcaca ttttagctaa gtccacagca 15840
ctatctatga ttgacctggt aacaaaattt gagaaggacc atatgaatga aatttcagct 15900
ctcatagggg atgacgatat caatagtttc ataactgagt ttctgctcat agagccaaga 15960
ttattcacta tctacttggg ccagtgtgcg gccatcaatt gggcatttga tgtacattat 16020
catagaccat cagggaaata tcagatgggt gagctgttgt catcgttcct ttctagaatg 16080
agcaaaggag tgtttaaggt gcttgtcaat gctctaagcc acccaaagat ctacaagaaa 16140
ttctggcatt gtggtattat agagcctatc catggtcctt cacttgatgc tcaaaacttg 16200
cacacaactg tgtgcaacat ggtttacaca tgctatatga cctacctcga cctgttgttg 16260
aatgaagagt tagaagagtt cacatttctc ttgtgtgaaa gcgacgagga tgtagtaccg 16320
gacagattcg acaacatcca ggcaaaacac ttatgtgttc tggcagattt gtactgtcaa 16380
ccagggacct gcccaccaat tcgaggtcta agaccggtag agaaatgtgc agttctaacc 16440
gaccatatca aggcagaggc tatgttatct ccagcaggat cttcgtggaa cataaatcca 16500
attattgtag accattactc atgctctctg acttatctcc ggcgaggatc gatcaaacag 16560
ataagattga gagttgatcc aggattcatt ttcgacgccc tcgctgaggt aaatgtcagt 16620
cagccaaaga tcggcagcaa caacatctca aatatgagca tcaaggcttt cagaccccca 16680
cacgatgatg ttgcaaaatt gctcaaagat atcaacacaa gcaagcacaa tcttcccatt 16740
tcagggggca atctcgccaa ttatgaaatc catgctttcc gcagaatcgg gttgaactca 16800
tctgcttgct acaaagctgt tgagatatca acattaatta ggagatgcct tgagccaggg 16860
gaggacggct tgttcttggg tgagggatcg ggttctatgt tgatcactta taaagagata 16920
cttaaactaa acaagtgctt ctataatagt ggggtttccg ccaattctag atctggtcaa 16980
agggaattag caccctatcc ctccgaagtt ggccttgtcg aacacagaat gggagtaggt 17040
aatattgtca aagtgctctt taacgggagg cccgaagtca cgtgggtagg cagtgtagat 17100
tgcttcaatt tcatagttag taatatccct acctctagtg tggggtttat ccattcagat 17160
atagagacct tgcctgacaa agatactata gagaagctag aggaattggc agccatctta 17220
tcgatggctc tgctcctggg caaaatagga tcaatactgg tgattaagct tatgcctttc 17280
agcggggatt ttgttcaggg atttataagt tatgtagggt ctcattatag agaagtgaac 17340
cttgtatacc ctagatacag caacttcatc tctactgaat cttatttggt tatgacagat 17400
ctcaaggcta accggctaat gaatcctgaa aagattaagc agcagataat tgaatcatct 17460
gtgaggactt cacctggact tataggtcac atcctatcca ttaagcaact aagctgcata 17520
caagcaattg tgggagacgc agttagtaga ggtgatatca atcctactct gaaaaaactt 17580
acacctatag agcaggtgct gatcaattgc gggttggcaa ttaacggacc taagctgtgc 17640
aaagaattga tccaccatga tgttgcctca gggcaagatg gattgcttaa ttctatactc 17700
atcctctaca gggagttggc aagattcaaa gacaaccaaa gaagtcaaca agggatgttc 17760
cacgcttacc ccgtattggt aagtagcagg caacgagaac ttatatctag gatcacccgc 17820
aaattctggg ggcacattct tctttactcc gggaacaaaa agttgataaa taagtttatc 17880
cagaatctca agtccggcta tctgatacta gacttacacc agaatatctt cgttaagaat 17940
ctatccaagt cagagaaaca gattattatg acggggggtt tgaaacgtga gtgggttttt 18000
aaggtaacag tcaaggagac caaagaatgg tataagttag tcggatacag tgccctgatt 18060
aaggactaat tggttgaact ccggaaccct aatcctgccc taggtggtta ggcattattt 18120
gcaatatatt aaagaaaact ttgaaaatac gaagtttcta ttcccagctt tgtctggtgg 18180
ccggcatggt cccagcctcc tcgctggcgc cggctgggca acattccgag gggaccgtcc 18240
cctcggtaat ggcgaatggg acgcggccga tccggctgct aacaaagccc gaaaggaagc 18300
tgagttggct gctgccaccg ctgagcaata actagcataa ccccttgggg cctctaaacg 18360
ggtcttgagg ggttttttgc tgaaaggagg aactatatcc ggatgcggcc gcgggcccta 18420
tggtacccag cttttgttcc ctttagtgag ggttaattcc gagcttggcg taatcatggt 18480
catagctgtt tcctgtgtga aattgttatc cgctcacaat tccacacaac ataggagccg 18540
gaagcataaa gtgtaaagcc tggggtgcct aatgagtgag gtaactcaca ttaattgcgt 18600
tgcgctcact gcccgctttc cagtcgggaa acctgtcgtg ccagctgcat taatgaatcg 18660
gccaacgcgc ggggagaggc ggtttgcgta ttgggcgctc ttccgcttcc tcgctcactg 18720
actcgctgcg ctcggtcgtt cggctgcggc gagcggtatc agctcactca aaggcggtaa 18780
tacggttatc cacagaatca ggggataacg caggaaagaa catgtgagca aaaggccagc 18840
aaaaggccag gaaccgtaaa aaggccgcgt tgctggcgtt tttccatagg ctcggccccc 18900
ctgacgagca tcacaaaaat cgacgctcaa gtcagaggtg gcgaaacccg acaggactat 18960
aaagatacca ggcgttcccc cctggaagct ccctcgtgcg ctctcctgtt ccgaccctgc 19020
cgcttaccgg atacctgtcc gcctttctcc cttcgggaag cgtggcgctt tctcaatgct 19080
cacgctgtag gtatctcagt tcggtgtagg tcgttcgctc caagctgggc tgtgtgcacg 19140
aaccccccgt tcagcccgac cgctgcgcct tatccggtaa ctatcgtctt gagtccaacc 19200
cggtaagaca cgacttatcg ccactggcag cagccactgg taacaggatt agcagagcga 19260
ggtatgtagg cggtgctaca gagttcttga agtggtggcc taactacggc tacactagaa 19320
ggacagtatt tggtatctgc gctctgctga agccagttac cttcggaaaa agagttggta 19380
gctcttgatc cggcaaacaa accaccgctg gtagcggtgg tttttttgtt tgcaagcagc 19440
agattacgcg cagaaaaaaa ggatctcaag aagatccttt gatcttttct acggggtctg 19500
acgctcagtg gaacgaaaac tcacgttaag ggattttggt catgagatta tcaaaaagga 19560
tcttcaccta gatcctttta aattaaaaat gaagttttaa atcaatctaa agtatatatg 19620
agtaaacttg gtctgacagt taccaatgct taatcagtga ggcacctatc tcagcgatct 19680
gtctatttcg ttcatccata gttgcctgac tgcccgtcgt gtagataact acgatacggg 19740
agggcttacc atctggcccc agtgctgcaa tgataccgcg agacccacgc tcaccggctc 19800
cagatttatc agcaataaac cagccagccg gaagggccga gcgcagaagt ggtcctgcaa 19860
ctttatccgc ctccatccag tctattaatt gttgccggga agctagagta agtagttcgc 19920
cagttaatag tttgcgcaac gttgttgcca ttgctacagg catcgtggtg tcacgctcgt 19980
cgtttggtat ggcttcattc agctccggtt cccaacgatc aaggcgagtt acatgatccc 20040
ccatgttgtg aaaaaaagcg gttagctcct tcggtcctcc gatcgttgtc agaagtaagt 20100
tggccgcagt gttatcactc atgcttatgg cagcactgca taattctctt actgtcatgc 20160
catccgtaag atgcttttct gtgactggtg agtactcaac caagtcattc tgagaatagt 20220
gtatgcggcg accgagttgc tcttgcccgg cgtcaatacg ggataatacc gcgccacata 20280
gcagaacttt aaaagtgctc atcattggaa aacgttcttc ggggcgaaaa ctctcaagga 20340
tcttaccgct gttgagatcc agttcgatgt aacccactcg tgcacccaac tgatcttcag 20400

```
catcttttac tttcaccagc gtttctgggt gagcaaaaac aggaaggcaa aatgccgcaa  20460

aaaagggaat aagggcgaca cggaaatgtt gaatactcat actcttcctt tttcaatatt  20520

attgaagcat ttatcagggt tattgtctca tgagcggata catatttgaa tgtatttaga  20580

aaaataaaca aataggggtt ccgcgcacat ttccccgaaa agtgccacct gaaattgtaa  20640

acgttaatat tttgttaaaa ttcgcgttaa atttttgtta aatcagctca ttttttaacc  20700

aataggccga aatcggcaaa atcccttata aatcaaaaga atagaccgag atagggttga  20760

gtgttgttcc agtttggaac aagagtccac tattaaagaa cgtggactcc aacgtcaaag  20820

ggcgaaaaac cgtctatcag ggcgatggcc cactacgtga accatcaccc taatcaagtt  20880

ttttggggtc gaggtgccgt aaagcactaa atcggaaccc taaagggagc ccccgattta  20940

gagcttgacg gggaaagccg gcgaacgtgg cgagaaagga agggaagaaa gcgaaaggag  21000

cgggcgctag ggcgctggca agtgtagcgg tcacgctgcg cgtaaccacc acacccgccg  21060

cgcttaatgc gccgctacag ggcgcgtccc attcgccatt caggctgcgc aactgttggg  21120

aagggcgatc ggtgcgggcc tcttcgctat tacgccagcc accgcggtg             21169
```

<210> SEQ ID NO 166
<211> LENGTH: 20839
<212> TYPE: DNA
<213> ORGANISM: Artificial sequence
<220> FEATURE:
<223> OTHER INFORMATION: pTM2-MVSchw_insert 4 (native sequence)

<400> SEQUENCE: 166

```
gcggccgcta atacgactca ctatagggcc aactttgttt ggtctgatga gtccgtgagg     60

acgaaacccg gagtcccggg tcaccaaaca aagttgggta aggatagttc aatcaatgat    120

catcttctag tgcacttagg attcaagatc ctattatcag ggacaagagc aggattaggg    180

atatccgaga tggccacact tttaaggagc ttagcattgt tcaaaagaaa caaggacaaa    240

ccacccatta catcaggatc cggtggagcc atcagaggaa tcaaacacat tattatagta    300

ccaatccctg gagattcctc aattaccact cgatccagac ttctggaccg gttggtgagg    360

ttaattggaa acccggatgt gagcgggccc aaactaacag gggcactaat aggtatatta    420

tccttatttg tggagtctcc aggtcaattg attcagagga tcaccgatga ccctgacgtt    480

agcataaggc tgttagaggt tgtccagagt gaccagtcac aatctggcct taccttcgca    540

tcaagaggta ccaacatgga ggatgaggcg gaccaatact tttcacatga tgatccaatt    600

agtagtgatc aatccaggtt cggatggttc gggaacaagg aaatctcaga tattgaagtg    660

caagaccctg agggattcaa catgattctg ggtaccatcc tagcccaaat ttgggtcttg    720

ctcgcaaagg cggttacggc cccagacacg gcagctgatt cggagctaag aaggtggata    780

aagtacaccc aacaaagaag ggtagttggt gaatttagat tggagagaaa atggttggat    840

gtggtgagga acaggattgc cgaggacctc tccttacgcc gattcatggt cgctctaatc    900

ctggatatca agagaacacc cggaaacaaa cccaggattg ctgaaatgat atgtgacatt    960

gatacatata tcgtagaggc aggattagcc agttttatcc tgactattaa gtttgggata   1020

gaaactatgt atcctgctct tggactgcat gaatttgctg gtgagttatc cacacttgag   1080

tccttgatga acctttacca gcaaatgggg gaaactgcac cctacatggt aatcctggag   1140

aactcaattc agaacaagtt cagtgcagga tcatacccte tgctctggag ctatgccatg   1200

ggagtaggag tggaacttga aaactccatg ggaggtttga actttggccg atcttacttt   1260
```

-continued gatccagcat attttagatt agggcaagag atggtaagga ggtcagctgg aaaggtcagt 1320
tccacattgg catctgaact cggtatcact gccgaggatg caaggcttgt ttcagagatt 1380
gcaatgcata ctactgagga caagatcagt agagcggttg gacccagaca agcccaagta 1440
tcatttctac acggtgatca aagtgagaat gagctaccga gattgggggg caaggaagat 1500
aggagggtca aacagagtcg aggagaagcc agggagagct acagagaaac cgggcccagc 1560
agagcaagtg atgcgagagc tgcccatctt ccaaccggca caccccctaga cattgacact 1620 gcaacggagt ccagccaaga tccgcaggac agtcgaaggt cagctgacgc cctgcttagg 1680
ctgcaagcca tggcaggaat ctcggaagaa caaggctcag acacggacac ccctatagtg 1740
tacaatgaca gaaatcttct agactaggtg cgagaggccg agggccagaa caacatccgc 1800
ctaccatcca tcattgttat aaaaaactta ggaaccaggt ccacacagcc gccagcccat 1860
caaccatcca ctcccacgat tggagccaat ggcagaagag caggcacgcc atgtcaaaaa 1920
cggactggaa tgcatccggg ctctcaaggc cgagcccatc ggctcactgg ccatcgagga 1980
agctatggca gcatggtcag aaatatcaga caacccagga caggagcgag ccacctgcag 2040
ggaagagaag gcaggcagtt cgggtctcag caaaccatgc ctctcagcaa ttggatcaac 2100
tgaaggcggt gcacctcgca tccgcggtca gggacctgga gagagcgatg acgacgctga 2160
aactttggga atccccccaa gaaatctcca ggcatcaagc actgggttac agtgttatta 2220
cgtttatgat cacagcggtg aagcggttaa gggaatccaa gatgctgact ctatcatggt 2280
tcaatcaggc cttgatggtg atagcaccct ctcaggagga gacaatgaat ctgaaaacag 2340
cgatgtggat attggcgaac ctgataccga gggatatgct atcactgacc ggggatctgc 2400
tcccatctct atggggttca gggcttctga tgttgaaact gcagaaggag gggagatcca 2460
cgagctcctg agactccaat ccagaggcaa caactttccg aagcttggga aaactctcaa 2520
tgttcctccg cccccggacc ccggtagggc cagcacttcc gggacaccca ttaaaaaggg 2580
cacagacgcg agattagcct catttggaac ggagatcgcg tctttattga caggtggtgc 2640
aacccaatgt gctcgaaagt caccctcgga accatcaggg ccaggtgcac ctgcggggaa 2700
tgtccccgag tgtgtgagca atgccgcact gatacaggag tggacacccg aatctggtac 2760
cacaatctcc ccgagatccc agaataatga agaaggggga gactattatg atgatgagct 2820
gttctctgat gtccaagata ttaaaacagc cttggccaaa atacacgagg ataatcagaa 2880
gataatctcc aagctagaat cactgctgtt attgaaggga gaagttgagt caattaagaa 2940
gcagatcaac aggcaaaata tcagcatatc caccctggaa ggacacctct caagcatcat 3000
gatcgccatt cctggacttg ggaaggatcc caacgacccc actgcagatg tcgaaatcaa 3060
tcccgacttg aaacccatca taggcagaga ttcaggccga gcactggccg aagttctcaa 3120
gaaacccgtt gccagccgac aactccaagg aatgacaaat ggacggacca gttccagagg 3180
acagctgctg aaggaatttc agctaaagcc gatcgggaaa aagatgagct cagccgtcgg 3240
gtttgttcct gacaccggcc ctgcatcacg cagtgtaatc cgctccatta taaaatccag 3300
ccggctagag gaggatcgga agcgttacct gatgactctc cttgatgata tcaaaggagc 3360
caatgatctt gccaagttcc accagatgct gatgaagata ataatgaagt agctacagct 3420
caacttacct gccaacccca tgccagtcga cccaactagc ctaccctcca tcattgttat 3480
aaaaaactta ggaaccaggt ccacacagcc gccagcccat caacgcgtac gatgggtgtc 3540
ggaattgttg gcctcctgct gaccacagct atggcagcgg aggtcactag acgtgggagt 3600
gcatactata tgtacttgga cagaaacgac gctggggagg ccatatcttt tccaaccaca 3660

```
ttggggatga ataagtgtta tatacagatc atggatcttg gacacatgtg tgatgccacc   3720
atgagctatg aatgccctat gctggatgag gggtggaac cagatgacgt cgattgttgg   3780
tgcaacacga cgtcaacttg ggttgtgtac ggaacctgcc atcacaaaaa aggtgaagca   3840
cggagatcta gaagagctgt gacgctcccc tcccattcca ctaggaagct gcaaacgcgg   3900
tcgcaaacct ggttggaatc aagagaatac acaaagcact tgattagagt cgaaaattgg   3960
atattcagga accctggctt cgcgttagca gcagctgcca tcgcttggct tttgggaagc   4020
tcaacgagcc aaaaagtcat atacttggtc atgatactgc tgattgcccc ggcatacagc   4080
atcaggtgca taggagtcag caatagggac tttgtggaag gtatgtcagg tgggacttgg   4140
gttgatgttg tcttggaaca tggaggttgt gtcaccgtaa tggcacagga caaaccgact   4200
gtcgacatag agctggttac aacaacagtc agcaacatgg cggaggtaag atcctactgc   4260
tatgaggcat caatatcgga catggcttcg gacagccgct gcccaacaca aggtgaagcc   4320
taccttgaca agcaatcaga cactcaatat gtctgcaaaa gaacgttagt ggacagaggc   4380
tggggaaatg gatgtggact tttggcaaa gggagcctgg tgacatgcgc taagtttgca   4440
tgctccaaga aaatgaccgg gaagagcatc cagccagaga atctggagta ccggataatg   4500
ctgtcagttc atggctccca gcacagtggg atgatcgtta atgacacagg acatgaaact   4560
gatgagaata gagcgaaggt tgagataacg cccaattcac caagagccga agccaccctg   4620
gggggttttg gaagcctagg acttgattgt gaaccgagga caggccttga cttttcagat   4680
ttgtattact tgactatgaa taacaagcac tggttggttc acaaggagtg gttccacgac   4740
attccattac cttggcacgc tggggcagac accggaactc cacactggaa caacaaagaa   4800
gcactggtag agttcaagga cgcacatgcc aaaaggcaaa ctgtcgtggt tctagggagt   4860
caagaaggag cagttcacac ggcccttgct ggagctctgg aggctgagat ggatggtgca   4920
aagggaaggc tgtcctctgg ccacttgaaa tgtcgcctga aaatggataa acttagattg   4980
aagggcgtgt catactcctt gtgtaccgca gcgttcacat tcaccaagat cccggctgaa   5040
acactgcacg ggacagtcac agtggaggta cagtacgcag ggacagatgg accttgcaag   5100
gttccagctc agatggcggt ggacatgcaa actctgaccc cagttgggag gttgataacc   5160
gctaaccccg taatcactga aagcactgag aactctaaga tgatgctgga acttgatcca   5220
ccatttgggg actcttacat tgtcatagga gtcggggaga agaagatcac ccaccactgg   5280
cacaggagtg gctaagcgcg cagcgcttag acgtctcgcg atcgatacta gtacaaccta   5340
aatccattat aaaaaactta ggagcaaagt gattgcctcc caaggtccac aatgacagag   5400
acctacgact tcgacaagtc ggcatgggac atcaaagggt cgatcgctcc gatacaaccc   5460
accacctaca gtgatggcag gctggtgccc caggtcagag tcatagatcc tggtctaggc   5520
gacaggaagg atgaatgctt tatgtacatg tttctgctgg gggttgttga ggacagcgat   5580
tccctagggc ctccaatcgg gcgagcattt gggttcctgc ccttaggtgt tggcagatcc   5640
acagcaaagc ccgaaaaact cctcaaagag gccactgagc ttgacatagt tgttagacgt   5700
acagcagggc tcaatgaaaa actggtgttc tacaacaaca ccccactaac tctcctcaca   5760
ccttggagaa aggtcctaac aacagggagt gtcttcaacg caaaccaagt gtgcaatgcg   5820
gttaatctga taccgctcga taccccgcag aggttccgtg ttgtttatat gagcatcacc   5880
cgtctttcgg ataacgggta ttacaccgtt cctagaagaa tgctggaatt cagatcggtc   5940
aatgcagtgg ccttcaacct gctggtgacc cttaggattg acaaggcgat aggccctggg   6000
```

-continued aagatcatcg acaatacaga gcaacttcct gaggcaacat ttatggtcca catcgggaac 6060
ttcaggagaa agaagagtga agtctactct gccgattatt gcaaaatgaa aatcgaaaag 6120
atgggcctgg tttttgcact tggtgggata gggggcacca gtcttcacat tagaagcaca 6180
ggcaaaatga gcaagactct ccatgcacaa ctcgggttca agaagacctt atgttacccg 6240
ctgatggata tcaatgaaga ccttaatcga ttactctgga ggagcagatg caagatagta 6300
agaatccagg cagttttgca gccatcagtt cctcaagaat tccgcattta cgacgacgtg 6360
atcataaatg atgaccaagg actattcaaa gttctgtaga ccgtagtgcc cagcaatgcc 6420
cgaaaacgac ccccctcaca atgacagcca gaaggcccgg acaaaaaagc cccctccgaa 6480
agactccacg gaccaagcga gaggccagcc agcagccgac ggcaagcgcg aacaccaggc 6540
ggccccagca cagaacagcc ctgacacaag gccaccacca gccaccccaa tctgcatcct 6600
cctcgtggga cccccgagga ccaaccccca aggctgcccc cgatccaaac caccaaccgc 6660
atccccacca cccccgggaa agaaaccccc agcaattgga aggcccctcc ccctcttcct 6720
caacacaaga actccacaac cgaaccgcac aagcgaccga ggtgacccaa ccgcaggcat 6780
ccgactccct agacagatcc tctctccccg gcaaactaaa caaaacttag ggccaaggaa 6840
catacacacc caacagaacc cagaccccgg cccacggcgc cgcgccccca acccccgaca 6900
accagaggga gcccccaacc aatcccgccg gctcccccgg tgcccacagg cagggacacc 6960
aacccccgaa cagacccagc acccaaccat cgacaatcca agacgggggg gcccccccaa 7020
aaaaaggccc ccaggggccg acagccagca ccgcgaggaa gcccacccac cccacacacg 7080
accacggcaa ccaaaccaga acccagacca ccctgggcca ccagctccca gactcggcca 7140
tcaccccgca gaaaggaaag gccacaaccc gcgcaccccca gccccgatcc ggcggggagc 7200
cacccaaccc gaaccagcac ccaagagcga tccccgaagg acccccgaac cgcaaaggac 7260
atcagtatcc cacagcctct ccaagtcccc cggtctcctc ctcttctcga agggaccaaa 7320
agatcaatcc accacacccg acgacactca actccccacc cctaaaggag acaccgggaa 7380
tcccagaatc aagactcatc caatgtccat catgggtctc aaggtgaacg tctctgccat 7440
attcatggca gtactgttaa ctctccaaac acccaccggt caaatccatt ggggcaatct 7500
ctctaagata ggggtggtag gaataggaag tgcaagctac aaagttatga ctcgttccag 7560
ccatcaatca ttagtcataa aattaatgcc caatataact ctcctcaata actgcacgag 7620
ggtagagatt gcagaataca ggagactact gagaacagtt ttggaaccaa ttagagatgc 7680
acttaatgca atgacccaga atataagacc ggttcagagt gtagcttcaa gtaggagaca 7740
caagagattt gcgggagtag tcctggcagg tgcggcccta ggcgttgcca cagctgctca 7800
gataacagcc ggcattgcac ttcaccagtc catgctgaac tctcaagcca tcgacaatct 7860
gagagcgagc ctggaaacta ctaatcaggc aattgagaca atcagacaag cagggcagga 7920
gatgatattg gctgttcagg gtgtccaaga ctacatcaat aatgagctga taccgtctat 7980
gaaccaacta tcttgtgatt taatcggcca gaagctcggg ctcaaattgc tcagatacta 8040
tacagaaatc ctgtcattat ttggccccag tttacgggac cccatatctg cggagatatc 8100
tatccaggct ttgagctatg cgcttggagg agacatcaat aaggtgttag aaaagctcgg 8160
atacagtgga ggtgatttac tgggcatctt agagagcgga ggaataaagg cccggataac 8220
tcacgtcgac acagagtcct acttcattgt cctcagtata gcctatccga cgctgtccga 8280
gattaagggg gtgattgtcc accggctaga gggggtctcg tacaacatag gctctcaaga 8340
gtggtatacc actgtgccca agtatgttgc aacccaaggg taccttatct cgaattttga 8400

```
tgagtcatcg tgtactttca tgccagaggg gactgtgtgc agccaaaatg ccttgtaccc   8460
gatgagtcct ctgctccaag aatgcctccg gggtacacc aagtcctgtg ctcgtacact    8520
cgtatccggg tcttttggga accggttcat tttatcacaa gggaacctaa tagccaattg   8580
tgcatcaatc ctttgcaagt gttacacaac aggaacgatc attaatcaag accctgacaa   8640
gatcctaaca tacattgctg ccgatcactg cccggtagtc gaggtgaacg gcgtgaccat   8700
ccaagtcggg agcaggaggt atccagacgc tgtgtacttg cacagaattg acctcggtcc   8760
tcccatatca ttggagaggt tggacgtagg gacaaatctg gggaatgcaa ttgctaagtt   8820
ggaggatgcc aaggaattgt tggagtcatc ggaccagata ttgaggagta tgaaaggttt   8880
atcgagcact agcatagtct acatcctgat tgcagtgtgt cttggagggt tgatagggat   8940
ccccgcttta atatgttgct gcagggggcg ttgtaacaaa aagggagaac aagttggtat   9000
gtcaagacca ggcctaaagc ctgatcttac gggaacatca aaatcctatg taaggtcgct   9060
ctgatcctct acaactcttg aaacacaaat gtcccacaag tctcctcttc gtcatcaagc   9120
aaccaccgca cccagcatca agcccacctg aaattatctc cggcttccct ctggccgaac   9180
aatatcggta gttaatcaaa acttagggtg caagatcatc cacaatgtca ccacaacgag   9240
accggataaa tgccttctac aaagataacc cccatcccaa gggaagtagg atagtcatta   9300
acagagaaca tcttatgatt gatagacctt atgttttgct ggctgttctg tttgtcatgt   9360
ttctgagctt gatcgggttg ctagccattg caggcattag acttcatcgg gcagccatct   9420
acaccgcaga gatccataaa agcctcagca ccaatctaga tgtaactaac tcaatcgagc   9480
atcaggtcaa ggacgtgctg acaccactct tcaaaatcat cggtgatgaa gtgggcctga   9540
ggacacctca gagattcact gacctagtga aattaatctc tgacaagatt aaattcctta   9600
atccggatag ggagtacgac ttcagagatc tcacttggtg tatcaacccg ccagagagaa   9660
tcaaattgga ttatgatcaa tactgtgcag atgtggctgc tgaagagctc atgaatgcat   9720
tggtgaactc aactctactg gagaccagaa caaccaatca gttcctagct gtctcaaagg   9780
gaaactgctc agggcccact acaatcagag gtcaattctc aaacatgtcg ctgtccctgt   9840
tagacttgta tttaggtcga ggttacaatg tgtcatctat agtcactatg acatcccagg   9900
gaatgtatgg gggaacttac ctagtggaaa agcctaatct gagcagcaaa aggtcagagt   9960
tgtcacaact gagcatgtac cgagtgtttg aagtaggtgt tatcagaaat ccgggtttgg  10020
gggctccggt gttccatatg acaaactatc ttgagcaacc agtcagtaat gatctcagca  10080
actgtatggt ggctttgggg gagctcaaac tcgcagccct ttgtcacggg gaagattcta  10140
tcacaattcc ctatcaggga tcagggaaag gtgtcagctt ccagctcgtc aagctaggtg  10200
tctggaaatc ccccaaccgac atgcaatcct gggtcccctt atcaacggat gatccagtga  10260
tagacaggct ttacctctca tctcacagag gtgttatcgc tgacaatcaa gcaaaatggg  10320
ctgtcccgac aacacgaaca gatgacaagt tgcgaatgga gacatgcttc caacaggcgt  10380
gtaagggtaa aatccaagca ctctgcgaga atcccgagtg ggcaccattg aaggataaca  10440
ggattccttc atacggggtc ttgtctgttg atctgagtct gacagttgag cttaaaatca  10500
aaattgcttc gggattcggg ccattgatca cacacggttc agggatggac ctatacaaat  10560
ccaaccacaa caatgtgtat tggctgacta tcccgccaat gaagaaccta gccttaggtg  10620
taatcaacac attggagtgg ataccgagat tcaaggttag tccctacctc ttcactgtcc  10680
caattaagga agcaggcgaa gactgccatg ccccaacata cctacctgcg gaggtggatg  10740
```

-continued

```
gtgatgtcaa actcagttcc aatctggtga ttctacctgg tcaagatctc caatatgttt  10800
tggcaaccta cgatacttcc agggttgaac atgctgtggt ttattacgtt tacagcccaa  10860
gccgctcatt ttcttacttt tatcctttta ggttgcctat aaagggggtc cccatcgaat  10920
tacaagtgga atgcttcaca tgggaccaaa aactctggtg ccgtcacttc tgtgtgcttg  10980
cggactcaga atctggtgga catatcactc actctgggat ggtgggcatg ggagtcagct  11040
gcacagtcac ccgggaagat ggaaccaatc gcagataggg ctgctagtga accaatcaca  11100
tgatgtcacc cagacatcag gcatacccac tagtgtgaaa tagacatcag aattaagaaa  11160
aacgtagggt ccaagtggtt ccccgttatg gactcgctat ctgtcaacca gatcttatac  11220
cctgaagttc acctagatag cccgatagtt accaataaga tagtagccat cctggagtat  11280
gctcgagtcc ctcacgctta cagcctggag gaccctacac tgtgtcagaa catcaagcac  11340
cgcctaaaaa acggattttc caaccaaatg attataaaca atgtggaagt tgggaatgtc  11400
atcaagtcca agcttaggag ttatccggcc cactctcata ttccatatcc aaattgtaat  11460
caggatttat ttaacataga agacaaagag tcaacgagga agatccgtga actcctcaaa  11520
aaggggaatt cgctgtactc caaagtcagt gataaggttt tccaatgctt aagggacact  11580
aactcacggc ttggcctagg ctccgaattg agggaggaca tcaaggagaa agttattaac  11640
ttgggagttt acatgcacag ctcccagtgg tttgagccct ttctgttttg gtttacagtc  11700
aagactgaga tgaggtcagt gattaaatca caaacccata cttgccatag gaggagacac  11760
acacctgtat tcttcactgg tagttcagtt gagttgctaa tctctcgtga ccttgttgct  11820
ataatcagta aagagtctca acatgtatat tacctgacat ttgaactggt tttgatgtat  11880
tgtgatgtca tagaggggag gttaatgaca gagaccgcta tgactattga tgctaggtat  11940
acagagcttc taggaagagt cagatacatg tggaaactga tagatggttt cttccctgca  12000
ctcgggaatc caacttatca aattgtagcc atgctggagc ctctttcact tgcttacctg  12060
cagctgaggg atataacagt agaactcaga ggtgctttcc ttaaccactg ctttactgaa  12120
atacatgatg ttcttgacca aaacgggttt tctgatgaag gtacttatca tgagttaact  12180
gaagctctag attacatttt cataactgat gacatacatc tgacagggga gatttctca  12240
tttttcagaa gtttcggcca ccccagactt gaagcagtaa cggctgctga aaatgttagg  12300
aaatacatga atcagcctaa agtcattgtg tatgagactc tgatgaaagg tcatgccata  12360
ttttgtggaa tcataatcaa cggctatcgt gacaggcacg gaggcagttg gccaccgctg  12420
accctccccc tgcatgctgc agacacaatc cggaatgctc aagcttcagg tgaagggtta  12480
acacatgagc agtgcgttga taactggaaa tcttttgctg gagtgaaatt tggctgcttt  12540
atgcctctta gcctggatag tgatctgaca atgtacctaa aggacaaggc acttgctgct  12600
ctccaaaggg aatgggattc agtttacccg aaagagttcc tgcgttacga ccctcccaag  12660
ggaaccgggt cacggaggct tgtagatgtt ttccttaatg attcgagctt tgacccatat  12720
gatgtgataa tgtatgttgt aagtggagct tacctccatg accctgagtt caacctgtct  12780
tacagcctga aagaaaagga gatcaaggaa acaggtagac tttttgctaa aatgacttac  12840
aaaatgaggg catgccaagt gattgctgaa aatctaatct caaacgggat tggcaaatat  12900
tttaaggaca atgggatggc caaggatgag cacgatttga ctaaggcact ccacactcta  12960
gctgtctcag gagtccccaa agatctcaaa gaaagtcaca gggggggggcc agtcttaaaa  13020
acctactccc gaagcccagt ccacacaagt accaggaacg tgagagcagc aaaagggttt  13080
atagggttcc ctcaagtaat tcggcaggac caagacactg atcatccgga gaatatggaa  13140
```

gcttacgaga cagtcagtgc atttatcacg actgatctca agaagtactg ccttaattgg 13200
agatatgaga ccatcagctt gtttgcacag aggctaaatg agatttacgg attgccctca 13260
tttttccagt ggctgcataa gaggcttgag acctctgtcc tgtatgtaag tgaccctcat 13320
tgcccccccg accttgacgc ccatatcccg ttatataaag tccccaatga tcaaatcttc 13380
attaagtacc ctatgggagg tatagaaggg tattgtcaga agctgtggac catcagcacc 13440
attccctatc tatacctggc tgcttatgag agcggagtaa ggattgcttc gttagtgcaa 13500
ggggacaatc agaccatagc cgtaacaaaa agggtaccca gcacatggcc ctacaacctt 13560
aagaaacggg aagctgctag agtaactaga gattactttg taattcttag gcaaaggcta 13620
catgatattg gccatcacct caaggcaaat gagacaattg tttcatcaca ttttttgtc 13680
tattcaaaag gaatatatta tgatgggcta cttgtgtccc aatcactcaa gagcatcgca 13740
agatgtgtat tctggtcaga gactatagtt gatgaaacaa gggcagcatg cagtaatatt 13800
gctacaacaa tggctaaaag catcgagaga ggttatgacc gttaccttgc atattccctg 13860
aacgtcctaa aagtgataca gcaaattctg atctctcttg gcttcacaat caattcaacc 13920
atgacccggg atgtagtcat acccctcctc acaaacaacg acctcttaat aaggatggca 13980
ctgttgcccg ctcctattgg ggggatgaat tatctgaata tgagcaggct gtttgtcaga 14040
aacatcggtg atccagtaac atcatcaatt gctgatctca agagaatgat tctcgcctca 14100
ctaatgcctg aagagaccct ccatcaagta atgacacaac aaccggggga ctcttcattc 14160
ctagactggg ctagcgaccc ttactcagca aatcttgtat gtgtccagag catcactaga 14220
ctcctcaaga acataactgc aaggtttgtc ctgatccata gtccaaaccc aatgttaaaa 14280
ggattattcc atgatgacag taaagaagag gacgagggac tggcggcatt cctcatggac 14340
aggcatatta tagtacctag ggcagctcat gaaatcctgg atcatagtgt cacaggggca 14400
agagagtcta ttgcaggcat gctggatacc acaaaaggct tgattcgagc cagcatgagg 14460
aaggggggt taacctctcg agtgataacc agattgtcca attatgacta tgaacaattc 14520
agagcaggga tggtgctatt gacaggaaga aagagaaatg tcctcattga caaagagtca 14580
tgttcagtgc agctggcgag agctctaaga agccatatgt gggcgaggct agctcgagga 14640
cggcctattt acggccttga ggtccctgat gtactagaat ctatgcgagg ccaccttatt 14700
cggcgtcatg agacatgtgt catctgcgag tgtggatcag tcaactacgg atggtttttt 14760
gtcccctcgg gttgccaact ggatgatatt gacaaggaaa catcatcctt gagagtccca 14820
tatattggtt ctaccactga tgagagaaca gacatgaagc ttgccttcgt aagagcccca 14880
agtcgatcct tgcgatctgc tgttagaata gcaacagtgt actcatgggc ttacggtgat 14940
gatgatagct cttggaacga agcctggttg ttggctaggc aaagggccaa tgtgagcctg 15000
gaggagctaa gggtgatcac tcccatctca acttcgacta atttagcgca taggttgagg 15060
gatcgtagca ctcaagtgaa atactcaggt acatcccttg tccgagtggc gaggtatacc 15120
acaatctcca acgacaatct ctcatttgtc atatcagata agaaggttga tactaacttt 15180
atataccaac aaggaatgct tctagggttg ggtgttttag aaacattgtt tcgactcgag 15240
aaagataccg gatcatctaa cacggtatta catcttcacg tcgaaacaga ttgttgcgtg 15300
atcccgatga tagatcatcc caggataccc agctcccgca agctagagct gagggcagag 15360
ctatgtacca acccattgat atatgataat gcacctttaa ttgacagaga tgcaacaagg 15420
ctatacaccc agagccatag gaggcacctt gtggaatttg ttacatggtc cacaccccaa 15480
ctatatcaca ttttagctaa gtccacagca ctatctatga ttgacctggt aacaaaattt 15540
gagaaggacc atatgaatga aatttcagct ctcatagggg atgacgatat caatagtttc 15600
ataactgagt ttctgctcat agagccaaga ttattcacta tctacttggg ccagtgtgcg 15660
gccatcaatt gggcatttga tgtacattat catagaccat cagggaaata tcagatgggt 15720
gagctgttgt catcgttcct ttctagaatg agcaaaggag tgtttaaggt gcttgtcaat 15780
gctctaagcc acccaaagat ctacaagaaa ttctggcatt gtggtattat agagcctatc 15840
catggtcctt cacttgatgc tcaaaacttg cacacaactg tgtgcaacat ggtttacaca 15900
tgctatatga cctacctcga cctgttgttg aatgaagagt tagaagagtt cacatttctc 15960
ttgtgtgaaa gcgacgagga tgtagtaccg gacagattcg acaacatcca ggcaaaacac 16020
ttatgtgttc tggcagattt gtactgtcaa ccagggacct gcccaccaat tcgaggtcta 16080
agaccggtag agaaatgtgc agttctaacc gaccatatca aggcagaggc tatgttatct 16140
ccagcaggat cttcgtggaa cataaatcca attattgtag accattactc atgctctctg 16200
acttatctcc ggcgaggatc gatcaaacag ataagattga gagttgatcc aggattcatt 16260
ttcgacgccc tcgctgaggt aaatgtcagt cagccaaaga tcggcagcaa caacatctca 16320
aatatgagca tcaaggcttt cagaccccca cacgatgatg ttgcaaaatt gctcaaagat 16380
atcaacacaa gcaagcacaa tcttcccatt tcagggggca atctcgccaa ttatgaaatc 16440
catgctttcc gcagaatcgg gttgaactca tctgcttgct acaaagctgt tgagatatca 16500
acattaatta ggagatgcct tgagccaggg gaggacggct tgttcttggg tgagggatcg 16560
ggttctatgt tgatcactta taaagagata cttaaactaa acaagtgctt ctataatagt 16620
ggggtttccg ccaattctag atctggtcaa agggaattag caccctatcc ctccgaagtt 16680
ggccttgtcg aacacagaat gggagtaggt aatattgtca aagtgctctt taacgggagg 16740
cccgaagtca cgtgggtagg cagtgtagat tgcttcaatt tcatagttag taatatccct 16800
acctctagtg tggggtttat ccattcagat atagagacct tgcctgacaa agatactata 16860
gagaagctag aggaattggc agccatctta tcgatggctc tgctcctggg caaaatagga 16920
tcaatactgg tgattaagct tatgcctttc agcggggatt ttgttcaggg atttataagt 16980
tatgtagggt ctcattatag agaagtgaac cttgtatacc ctagatacag caacttcatc 17040
tctactgaat cttatttggt tatgacagat ctcaaggcta accggctaat gaatcctgaa 17100
aagattaagc agcagataat tgaatcatct gtgaggactt cacctggact tataggtcac 17160
atcctatcca ttaagcaact aagctgcata caagcaattg tgggagacgc agttagtaga 17220
ggtgatatca atcctactct gaaaaaactt acacctatag agcaggtgct gatcaattgc 17280
gggttggcaa ttaacggacc taagctgtgc aaagaattga tccaccatga tgttgcctca 17340
gggcaagatg gattgcttaa ttctatactc atcctctaca gggagttggc aagattcaaa 17400
gacaaccaaa gaagtcaaca agggatgttc cacgcttacc ccgtattggt aagtagcagg 17460
caacgagaac ttatatctag gatcacccgc aaattctggg ggcacattct tctttactcc 17520
gggaacaaaa agttgataaa taagtttatc cagaatctca agtccggcta tctgatacta 17580
gacttacacc agaatatctt cgttaagaat ctatccaagt cagagaaaca gattattatg 17640 acgggggggtt tgaaacgtga gtgggttttt aaggtaacag tcaaggagac caaagaatgg 17700
tataagttag tcggatacag tgccctgatt aaggactaat tggttgaact ccggaaccct 17760
aatcctgccc taggtggtta ggcattattt gcaatatatt aaagaaaact ttgaaaatac 17820
gaagtttcta ttcccagctt tgtctggtgg ccggcatggt cccagcctcc tcgctggcgc 17880
cggctgggca acattccgag gggaccgtcc cctcggtaat ggcgaatggg acgcggccga 17940
tccggctgct aacaaagccc gaaaggaagc tgagttggct gctgccaccg ctgagcaata 18000
actagcataa ccccttgggg cctctaaacg ggtcttgagg ggttttttgc tgaaaggagg 18060
aactatatcc ggatgcggcc gcgggcccta tggtacccag cttttgttcc ctttagtgag 18120
ggttaattcc gagcttggcg taatcatggt catagctgtt tcctgtgtga aattgttatc 18180
cgctcacaat tccacacaac ataggagccg gaagcataaa gtgtaaagcc tggggtgcct 18240
aatgagtgag gtaactcaca ttaattgcgt tgcgctcact gcccgctttc cagtcgggaa 18300
acctgtcgtg ccagctgcat taatgaatcg gccaacgcgc ggggagaggc ggtttgcgta 18360
ttgggcgctc ttccgcttcc tcgctcactg actcgctgcg ctcggtcgtt cggctgcggc 18420
gagcggtatc agctcactca aaggcggtaa tacggttatc cacagaatca ggggataacg 18480
caggaaagaa catgtgagca aaaggccagc aaaaggccag gaaccgtaaa aaggccgcgt 18540
tgctggcgtt tttccatagg ctcggccccc ctgacgagca tcacaaaaat cgacgctcaa 18600
gtcagaggtg gcgaaacccg acaggactat aaagatacca ggcgttcccc cctggaagct 18660
ccctcgtgcg ctctcctgtt ccgaccctgc cgcttaccgg atacctgtcc gcctttctcc 18720
cttcgggaag cgtggcgctt tctcaatgct cacgctgtag gtatctcagt tcggtgtagg 18780
tcgttcgctc caagctgggc tgtgtgcacg aaccccccgt tcagcccgac cgctgcgcct 18840
tatccggtaa ctatcgtctt gagtccaacc cggtaagaca cgacttatcg ccactggcag 18900
cagccactgg taacaggatt agcagagcga ggtatgtagg cggtgctaca gagttcttga 18960
agtggtggcc taactacggc tacactagaa ggacagtatt tggtatctgc gctctgctga 19020
agccagttac cttcggaaaa agagttggta gctcttgatc cggcaaacaa accaccgctg 19080
gtagcggtgg tttttttgtt tgcaagcagc agattacgcg cagaaaaaaa ggatctcaag 19140
aagatccttt gatcttttct acggggtctg acgctcagtg gaacgaaaac tcacgttaag 19200
ggattttggt catgagatta tcaaaaagga tcttcaccta gatcctttta aattaaaaat 19260
gaagttttaa atcaatctaa agtatatatg agtaaacttg gtctgacagt taccaatgct 19320
taatcagtga ggcacctatc tcagcgatct gtctatttcg ttcatccata gttgcctgac 19380
tgcccgtcgt gtagataact acgatacggg agggcttacc atctggcccc agtgctgcaa 19440
tgataccgcg agacccacgc tcaccggctc cagatttatc agcaataaac cagccagccg 19500
gaagggccga gcgcagaagt ggtcctgcaa ctttatccgc ctccatccag tctattaatt 19560
gttgccggga agctagagta agtagttcgc cagttaatag tttgcgcaac gttgttgcca 19620
ttgctacagg catcgtggtg tcacgctcgt cgtttggtat ggcttcattc agctccggtt 19680
cccaacgatc aaggcgagtt acatgatccc ccatgttgtg aaaaaaagcg gttagctcct 19740
tcggtcctcc gatcgttgtc agaagtaagt tggccgcagt gttatcactc atgcttatgg 19800
cagcactgca taattctctt actgtcatgc catccgtaag atgcttttct gtgactggtg 19860
agtactcaac caagtcattc tgagaatagt gtatgcggcg accgagttgc tcttgcccgg 19920
cgtcaatacg ggataatacc gcgccacata gcagaacttt aaaagtgctc atcattggaa 19980
aacgttcttc ggggcgaaaa ctctcaagga tcttaccgct gttgagatcc agttcgatgt 20040
aacccactcg tgcacccaac tgatcttcag catcttttac tttcaccagc gtttctgggt 20100
gagcaaaaac aggaaggcaa aatgccgcaa aaaagggaat aagggcgaca cggaaatgtt 20160
gaatactcat actcttcctt tttcaatatt attgaagcat ttatcagggt tattgtctca 20220
tgagcggata catatttgaa tgtatttaga aaaataaaca aataggggtt ccgcgcacat 20280
ttccccgaaa agtgccacct gaaattgtaa acgttaatat tttgttaaaa ttcgcgttaa 20340
atttttgtta aatcagctca ttttttaacc aataggccga aatcggcaaa atcccttata 20400
aatcaaaaga atagaccgag atagggttga gtgttgttcc agtttggaac aagagtccac 20460
tattaaagaa cgtggactcc aacgtcaaag ggcgaaaaac cgtctatcag ggcgatggcc 20520
cactacgtga accatcaccc taatcaagtt ttttggggtc gaggtgccgt aaagcactaa 20580
atcggaaccc taaagggagc ccccgattta gagcttgacg gggaaagccg gcgaacgtgg 20640
cgagaaagga agggaagaaa gcgaaaggag cgggcgctag ggcgctggca agtgtagcgg 20700
tcacgctgcg cgtaaccacc acacccgccg cgcttaatgc gccgctacag ggcgcgtccc 20760
attcgccatt caggctgcgc aactgttggg aagggcgatc ggtgcgggcc tcttcgctat 20820
tacgccagcc accgcggtg 20839

<210> SEQ ID NO 167
<211> LENGTH: 20467
<212> TYPE: DNA
<213> ORGANISM: Artificial sequence
<220> FEATURE:
<223> OTHER INFORMATION: pTM2-MVSchw_ insert 5 (native sequence)

<400> SEQUENCE: 167
gcggccgcta atacgactca ctatagggcc aactttgttt ggtctgatga gtccgtgagg 60
acgaaacccg gagtcccggg tcaccaaaca aagttgggta aggatagttc aatcaatgat 120
catcttctag tgcacttagg attcaagatc ctattatcag ggacaagagc aggattaggg 180
atatccgaga tggccacact tttaaggagc ttagcattgt tcaaaagaaa caaggacaaa 240
ccacccatta catcaggatc cggtggagcc atcagaggaa tcaaacacat tattatagta 300
ccaatccctg gagattcctc aattaccact cgatccagac ttctggaccg gttggtgagg 360
ttaattggaa acccggatgt gagcgggccc aaactaacag gggcactaat aggtatatta 420
tccttatttg tggagtctcc aggtcaattg attcagagga tcaccgatga ccctgacgtt 480
agcataaggc tgttagaggt tgtccagagt gaccagtcac aatctggcct taccttcgca 540
tcaagaggta ccaacatgga ggatgaggcg gaccaatact tttcacatga tgatccaatt 600
agtagtgatc aatccaggtt cggatggttc gggaacaagg aaatctcaga tattgaagtg 660
caagaccctg agggattcaa catgattctg ggtaccatcc tagcccaaat ttgggtcttg 720
ctcgcaaagg cggttacggc cccagacacg gcagctgatt cggagctaag aaggtggata 780
aagtacaccc aacaaagaag ggtagttggt gaatttagat tggagagaaa atggttggat 840
gtggtgagga acaggattgc cgaggacctc tccttacgcc gattcatggt cgctctaatc 900
ctggatatca agagaacacc cggaaacaaa cccaggattg ctgaaatgat atgtgacatt 960
gatacatata tcgtagaggc aggattagcc agttttatcc tgactattaa gtttgggata 1020
gaaactatgt atcctgctct tggactgcat gaatttgctg gtgagttatc cacacttgag 1080
tccttgatga acctttacca gcaaatgggg gaaactgcac cctacatggt aatcctggag 1140
aactcaattc agaacaagtt cagtgcagga tcataccctc tgctctggag ctatgccatg 1200
ggagtaggag tggaacttga aaactccatg ggaggtttga actttggccg atcttacttt 1260
gatccagcat attttagatt agggcaagag atggtaagga ggtcagctgg aaaggtcagt 1320
tccacattgg catctgaact cggtatcact gccgaggatg caaggcttgt ttcagagatt 1380
gcaatgcata ctactgagga caagatcagt agagcggttg gacccagaca agcccaagta 1440

```
tcatttctac acggtgatca aagtgagaat gagctaccga gattgggggg caaggaagat   1500
aggagggtca aacagagtcg aggagaagcc agggagagct acagagaaac cgggcccagc   1560
agagcaagtg atgcgagagc tgcccatctt ccaaccggca caccccctaga cattgacact   1620
gcaacggagt ccagccaaga tccgcaggac agtcgaaggt cagctgacgc cctgcttagg   1680
ctgcaagcca tggcaggaat ctcggaagaa caaggctcag acacggacac ccctatagtg   1740
tacaatgaca gaaatcttct agactaggtg cgagaggccg agggccagaa caacatccgc   1800
ctaccatcca tcattgttat aaaaaactta ggaaccaggt ccacacagcc gccagcccat   1860
caaccatcca ctcccacgat tggagccaat ggcagaagag caggcacgcc atgtcaaaaa   1920
cggactggaa tgcatccggg ctctcaaggc cgagcccatc ggctcactgg ccatcgagga   1980
agctatggca gcatggtcag aaatatcaga caacccagga caggagcgag ccacctgcag   2040
ggaagagaag gcaggcagtt cgggtctcag caaaccatgc ctctcagcaa ttggatcaac   2100
tgaaggcggt gcacctcgca tccgcggtca gggacctgga gagagcgatg acgacgctga   2160
aactttggga atccccccaa gaaatctcca ggcatcaagc actgggttac agtgttatta   2220
cgtttatgat cacagcggtg aagcggttaa gggaatccaa gatgctgact ctatcatggt   2280
tcaatcaggc cttgatggtg atagcaccct ctcaggagga gacaatgaat ctgaaaacag   2340
cgatgtggat attggcgaac ctgataccga gggatatgct atcactgacc ggggatctgc   2400
tcccatctct atggggttca gggcttctga tgttgaaact gcagaaggag gggagatcca   2460
cgagctcctg agactccaat ccagaggcaa caactttccg aagcttggga aaactctcaa   2520
tgttcctccg cccccggacc ccggtagggc cagcacttcc gggacaccca ttaaaaaggg   2580
cacagacgcg agattagcct catttggaac ggagatcgcg tctttattga caggtggtgc   2640
aacccaatgt gctcgaaagt caccctcgga accatcaggg ccaggtgcac ctgcggggaa   2700
tgtccccgag tgtgtgagca atgccgcact gatacaggag tggacacccg aatctggtac   2760
cacaatctcc ccgagatccc agaataatga agaaggggga gactattatg atgatgagct   2820
gttctctgat gtccaagata ttaaaacagc cttggccaaa atacacgagg ataatcagaa   2880
gataatctcc aagctagaat cactgctgtt attgaaggga gaagttgagt caattaagaa   2940
gcagatcaac aggcaaaata tcagcatatc caccctggaa ggacacctct caagcatcat   3000
gatcgccatt cctggacttg ggaaggatcc caacgacccc actgcagatg tcgaaatcaa   3060
tcccgacttg aaacccatca taggcagaga ttcaggccga gcactggccg aagttctcaa   3120
gaaacccgtt gccagccgac aactccaagg aatgacaaat ggacggacca gttccagagg   3180
acagctgctg aaggaatttc agctaaagcc gatcgggaaa aagatgagct cagccgtcgg   3240
gtttgttcct gacaccggcc ctgcatcacg cagtgtaatc cgctccatta taaaatccag   3300
ccggctagag gaggatcgga agcgttacct gatgactctc cttgatgata tcaaaggagc   3360
caatgatctt gccaagttcc accagatgct gatgaagata ataatgaagt agctacagct   3420
caacttacct gccaacccca tgccagtcga cccaactagc ctaccctcca tcattgttat   3480
aaaaaactta ggaaccaggt ccacacagcc gccagcccat caacgcgtac gatggaagtc   3540
atatacttgg tcatgatact gctgattgcc ccggcataca gcatcaggtg cataggagtc   3600
agcaataggg actttgtgga aggtatgtca ggtgggactt gggttgatgt tgtcttggaa   3660
catggaggtt gtgtcaccgt aatggcacag gacaaaccga ctgtcgacat agagctggtt   3720
acaacaacag tcagcaacat ggcggaggta agatcctact gctatgaggc atcaatatcg   3780
```

-continued gacatggctt cggacagccg ctgcccaaca caaggtgaag cctaccttga caagcaatca 3840
gacactcaat atgtctgcaa aagaacgtta gtggacagag gctggggaaa tggatgtgga 3900
ctttttggca aagggagcct ggtgacatgc gctaagtttg catgctccaa gaaaatgacc 3960
gggaagagca tccagccaga gaatctggag taccggataa tgctgtcagt tcatggctcc 4020
cagcacagtg ggatgatcgt taatgacaca ggacatgaaa ctgatgagaa tagagcgaag 4080
gttgagataa cgcccaattc accaagagcc gaagccaccc tggggggttt tggaagccta 4140
ggacttgatt gtgaaccgag gacaggcctt gacttttcag atttgtatta cttgactatg 4200
aataacaagc actggttggt tcacaaggag tggttccacg acattccatt accttggcac 4260
gctggggcag acaccggaac tccacactgg aacaacaaag aagcactggt agagttcaag 4320
gacgcacatg ccaaaaggca aactgtcgtg gttctaggga gtcaagaagg agcagttcac 4380
acggcccttg ctggagctct ggaggctgag atggatggtg caaagggaag gctgtcctct 4440
ggccacttga aatgtcgcct gaaaatggat aaacttagat tgaagggcgt gtcatactcc 4500
ttgtgtaccg cagcgttcac attcaccaag atcccggctg aaacactgca cgggacagtc 4560
acagtggagg tacagtacgc agggacagat ggaccttgca aggttccagc tcagatggcg 4620
gtggacatgc aaactctgac cccagttggg aggttgataa ccgctaaccc cgtaatcact 4680
gaaagcactg agaactctaa gatgatgctg gaacttgatc caccatttgg ggactcttac 4740
attgtcatag gagtcgggga gaagaagatc acccaccact ggcacaggag tggcagcacc 4800
attggaaaag catttgaagc cactgtgaga ggtgccaaga gaatggcagt cttgggagac 4860
acagcctggg actttggatc agttggaggc gctctcaact cattgggcaa gggcatctaa 4920
taagcgcgca gcgcttagac gtctcgcgat cgatactagt acaacctaaa tccattataa 4980
aaaacttagg agcaaagtga ttgcctccca aggtccacaa tgacagagac ctacgacttc 5040
gacaagtcgg catgggacat caaagggtcg atcgctccga tacaacccac cacctacagt 5100
gatggcaggc tggtgcccca ggtcagagtc atagatcctg gtctaggcga caggaaggat 5160
gaatgcttta tgtacatgtt tctgctgggg gttgttgagg acagcgattc cctagggcct 5220
ccaatcgggc gagcatttgg gttcctgccc ttaggtgttg gcagatccac agcaaagccc 5280
gaaaaactcc tcaaagaggc cactgagctt gacatagttg ttagacgtac agcagggctc 5340
aatgaaaaac tggtgttcta caacaacacc ccactaactc tcctcacacc ttggagaaag 5400
gtcctaacaa cagggagtgt cttcaacgca aaccaagtgt gcaatgcggt taatctgata 5460
ccgctcgata ccccgcagag gttccgtgtt gtttatatga gcatcacccg tctttcggat 5520
aacgggtatt acaccgttcc tagaagaatg ctggaattca gatcggtcaa tgcagtggcc 5580
ttcaacctgc tggtgaccct taggattgac aaggcgatag gccctgggaa gatcatcgac 5640
aatacagagc aacttcctga ggcaacattt atggtccaca tcgggaactt caggagaaag 5700
aagagtgaag tctactctgc cgattattgc aaaatgaaaa tcgaaaagat gggcctggtt 5760
tttgcacttg gtgggatagg gggcaccagt cttcacatta gaagcacagg caaaatgagc 5820
aagactctcc atgcacaact cgggttcaag aagaccttat gttacccgct gatggatatc 5880
aatgaagacc ttaatcgatt actctggagg agcagatgca agatagtaag aatccaggca 5940
gttttgcagc catcagttcc tcaagaattc cgcatttacg acgacgtgat cataaatgat 6000
gaccaaggac tattcaaagt tctgtagacc gtagtgccca gcaatgcccg aaaacgaccc 6060
ccctcacaat gacagccaga aggcccggac aaaaaagccc cctccgaaag actccacgga 6120
ccaagcgaga ggccagccag cagccgacgg caagcgcgaa caccaggcgg ccccagcaca 6180

```
gaacagccct gacacaaggc caccaccagc caccccaatc tgcatcctcc tcgtgggacc   6240
cccgaggacc aacccccaag gctgccccg atccaaacca ccaaccgcat ccccaccacc   6300
cccgggaaag aaaccccag caattggaag gcccctcccc ctcttcctca acacaagaac   6360
tccacaaccg aaccgcacaa gcgaccgagg tgacccaacc gcaggcatcc gactccctag   6420
acagatcctc tctccccggc aaactaaaca aaacttaggg ccaaggaaca tacacaccca   6480
acagaaccca gaccccggcc cacggcgccg cgcccccaac ccccgacaac cagagggagc   6540
ccccaaccaa tcccgccggc tcccccggtg cccacaggca gggacaccaa cccccgaaca   6600
gacccagcac ccaaccatcg acaatccaag acgggggggc ccccccaaaa aaaggccccc   6660
aggggccgac agccagcacc gcgaggaagc ccacccaccc cacacacgac cacggcaacc   6720
aaaccagaac ccagaccacc ctgggccacc agctcccaga ctcggccatc accccgcaga   6780
aaggaaaggc cacaacccgc gcaccccagc cccgatccgg cggggagcca cccaacccga   6840
accagcaccc aagagcgatc cccgaaggac ccccgaaccg caaaggacat cagtatccca   6900
cagcctctcc aagtccccg gtctcctcct cttctcgaag ggaccaaaag atcaatccac   6960
cacacccgac gacactcaac tccccacccc taaaggagac accgggaatc ccagaatcaa   7020
gactcatcca atgtccatca tgggtctcaa ggtgaacgtc tctgccatat tcatggcagt   7080
actgttaact ctccaaacac ccaccggtca aatccattgg ggcaatctct ctaagatagg   7140
ggtggtagga ataggaagtg caagctacaa agttatgact cgttccagcc atcaatcatt   7200
agtcataaaa ttaatgccca atataactct cctcaataac tgcacgaggg tagagattgc   7260
agaatacagg agactactga gaacagtttt ggaaccaatt agagatgcac ttaatgcaat   7320
gacccagaat ataagaccgg ttcagagtgt agcttcaagt aggagacaca agagatttgc   7380
gggagtagtc ctggcaggtg cggccctagg cgttgccaca gctgctcaga taacagccgg   7440
cattgcactt caccagtcca tgctgaactc tcaagccatc gacaatctga gagcgagcct   7500
ggaaactact aatcaggcaa ttgagacaat cagacaagca gggcaggaga tgatattggc   7560
tgttcagggt gtccaagact acatcaataa tgagctgata ccgtctatga accaactatc   7620
ttgtgattta atcggccaga agctcgggct caaattgctc agatactata cagaaatcct   7680
gtcattattt ggccccagtt tacgggaccc catatctgcg gagatatcta tccaggcttt   7740
gagctatgcg cttggaggag acatcaataa ggtgttagaa aagctcggat acagtggagg   7800
tgatttactg ggcatcttag agagcggagg aataaaggcc cggataactc acgtcgacac   7860
agagtcctac ttcattgtcc tcagtatagc ctatccgacg ctgtccgaga ttaagggggt   7920
gattgtccac cggctagagg gggtctcgta caacataggc tctcaagagt ggtataccac   7980
tgtgcccaag tatgttgcaa cccaagggta ccttatctcg aattttgatg agtcatcgtg   8040
tactttcatg ccagagggga ctgtgtgcag ccaaaatgcc ttgtacccga tgagtcctct   8100
gctccaagaa tgcctccggg ggtacaccaa gtcctgtgct cgtacactcg tatccgggtc   8160
ttttgggaac cggttcattt tatcacaagg gaacctaata gccaattgtg catcaatcct   8220
ttgcaagtgt tacacaacag gaacgatcat taatcaagac cctgacaaga tcctaacata   8280
cattgctgcc gatcactgcc cggtagtcga ggtgaacggc gtgaccatcc aagtcgggag   8340
caggaggtat ccagacgctg tgtacttgca cagaattgac ctcggtcctc ccatatcatt   8400
ggagaggttg gacgtaggga caaatctggg gaatgcaatt gctaagttgg aggatgccaa   8460
ggaattgttg gagtcatcgg accagatatt gaggagtatg aaaggtttat cgagcactag   8520
```

catagtctac atcctgattg cagtgtgtct tggagggttg atagggatcc ccgctttaat 8580
atgttgctgc agggggcgtt gtaacaaaaa gggagaacaa gttggtatgt caagaccagg 8640
cctaaagcct gatcttacgg gaacatcaaa atcctatgta aggtcgctct gatcctctac 8700
aactcttgaa acacaaatgt cccacaagtc tcctcttcgt catcaagcaa ccaccgcacc 8760
cagcatcaag cccacctgaa attatctccg gcttccctct ggccgaacaa tatcggtagt 8820
taatcaaaac ttagggtgca agatcatcca caatgtcacc acaacgagac cggataaatg 8880
ccttctacaa agataacccc catcccaagg gaagtaggat agtcattaac agagaacatc 8940
ttatgattga tagaccttat gttttgctgg ctgttctgtt tgtcatgttt ctgagcttga 9000
tcgggttgct agccattgca ggcattagac ttcatcgggc agccatctac accgcagaga 9060
tccataaaag cctcagcacc aatctagatg taactaactc aatcgagcat caggtcaagg 9120
acgtgctgac accactcttc aaaatcatcg gtgatgaagt gggcctgagg acacctcaga 9180
gattcactga cctagtgaaa ttaatctctg acaagattaa attccttaat ccggataggg 9240
agtacgactt cagagatctc acttggtgta tcaacccgcc agagagaatc aaattggatt 9300
atgatcaata ctgtgcagat gtggctgctg aagagctcat gaatgcattg gtgaactcaa 9360
ctctactgga gaccagaaca accaatcagt tcctagctgt ctcaaaggga aactgctcag 9420
ggcccactac aatcagaggt caattctcaa acatgtcgct gtccctgtta gacttgtatt 9480
taggtcgagg ttacaatgtg tcatctatag tcactatgac atcccaggga atgtatgggg 9540
gaacttacct agtggaaaag cctaatctga gcagcaaaag gtcagagttg tcacaactga 9600
gcatgtaccg agtgtttgaa gtaggtgtta tcagaaatcc gggtttgggg gctccggtgt 9660
tccatatgac aaactatctt gagcaaccag tcagtaatga tctcagcaac tgtatggtgg 9720
ctttggggga gctcaaactc gcagcccttt gtcacgggga agattctatc acaattccct 9780
atcagggatc agggaaaggt gtcagcttcc agctcgtcaa gctaggtgtc tggaaatccc 9840
caaccgacat gcaatcctgg gtccccttat caacggatga tccagtgata gacaggcttt 9900
acctctcatc tcacagaggt gttatcgctg acaatcaagc aaaatgggct gtcccgacaa 9960
cacgaacaga tgacaagttg cgaatggaga catgcttcca acaggcgtgt aagggtaaaa 10020
tccaagcact ctgcgagaat cccgagtggg caccattgaa ggataacagg attccttcat 10080
acggggtctt gtctgttgat ctgagtctga cagttgagct taaaatcaaa attgcttcgg 10140
gattcgggcc attgatcaca cacggttcag ggatggacct atacaaatcc aaccacaaca 10200
atgtgtattg gctgactatc ccgccaatga agaacctagc cttaggtgta atcaacacat 10260
tggagtggat accgagattc aaggttagtc cctacctctt cactgtccca attaaggaag 10320
caggcgaaga ctgccatgcc ccaacatacc tacctgcgga ggtggatggt gatgtcaaac 10380
tcagttccaa tctggtgatt ctacctggtc aagatctcca atatgttttg gcaacctacg 10440
atacttccag ggttgaacat gctgtggttt attacgttta cagcccaagc cgctcatttt 10500
cttactttta tccttttagg ttgcctataa agggggtccc catcgaatta caagtggaat 10560
gcttcacatg ggaccaaaaa ctctggtgcc gtcacttctg tgtgcttgcg gactcagaat 10620
ctggtggaca tatcactcac tctgggatgg tgggcatggg agtcagctgc acagtcaccc 10680
gggaagatgg aaccaatcgc agatagggct gctagtgaac caatcacatg atgtcaccca 10740
gacatcaggc atacccacta gtgtgaaata gacatcagaa ttaagaaaaa cgtagggtcc 10800
aagtggttcc ccgttatgga ctcgctatct gtcaaccaga tcttataccc tgaagttcac 10860
ctagatagcc cgatagttac caataagata gtagccatcc tggagtatgc tcgagtccct 10920
cacgcttaca gcctggagga ccctacactg tgtcagaaca tcaagcaccg cctaaaaaac 10980
ggattttcca accaaatgat tataaacaat gtggaagttg ggaatgtcat caagtccaag 11040
cttaggagtt atccggccca ctctcatatt ccatatccaa attgtaatca ggatttattt 11100
aacatagaag acaaagagtc aacgaggaag atccgtgaac tcctcaaaaa ggggaattcg 11160
ctgtactcca aagtcagtga taaggttttc caatgcttaa gggacactaa ctcacggctt 11220
ggcctaggct ccgaattgag ggaggacatc aaggagaaag ttattaactt gggagtttac 11280
atgcacagct cccagtggtt tgagcccttt ctgttttggt ttacagtcaa gactgagatg 11340
aggtcagtga ttaaatcaca aacccatact tgccatagga ggagacacac acctgtattc 11400
ttcactggta gttcagttga gttgctaatc tctcgtgacc ttgttgctat aatcagtaaa 11460
gagtctcaac atgtatatta cctgacattt gaactggttt tgatgtattg tgatgtcata 11520
gaggggaggt taatgacaga gaccgctatg actattgatg ctaggtatac agagcttcta 11580
ggaagagtca gatacatgtg gaaactgata gatggtttct tccctgcact cgggaatcca 11640
acttatcaaa ttgtagccat gctggagcct ctttcacttg cttacctgca gctgagggat 11700
ataacagtag aactcagagg tgctttcctt aaccactgct ttactgaaat acatgatgtt 11760
cttgaccaaa acgggttttc tgatgaaggt acttatcatg agttaactga agctctagat 11820
tacattttca taactgatga catacatctg acaggggaga ttttctcatt tttcagaagt 11880
ttcggccacc ccagacttga agcagtaacg gctgctgaaa atgttaggaa atacatgaat 11940
cagcctaaag tcattgtgta tgagactctg atgaaaggtc atgccatatt ttgtggaatc 12000
ataatcaacg gctatcgtga caggcacgga ggcagttggc caccgctgac cctccccctg 12060
catgctgcag acacaatccg gaatgctcaa gcttcaggtg aagggttaac acatgagcag 12120
tgcgttgata actggaaatc ttttgctgga gtgaaatttg gctgctttat gcctcttagc 12180
ctggatagtg atctgacaat gtacctaaag gacaaggcac ttgctgctct ccaaagggaa 12240
tgggattcag tttacccgaa agagttcctg cgttacgacc ctcccaaggg aaccgggtca 12300
cggaggcttg tagatgtttt ccttaatgat tcgagctttg acccatatga tgtgataatg 12360
tatgttgtaa gtggagctta cctccatgac cctgagttca acctgtctta cagcctgaaa 12420
gaaaaggaga tcaaggaaac aggtagactt tttgctaaaa tgacttacaa aatgagggca 12480
tgccaagtga ttgctgaaaa tctaatctca aacgggattg gcaaatattt taaggacaat 12540
gggatggcca aggatgagca cgatttgact aaggcactcc acactctagc tgtctcagga 12600
gtccccaaag atctcaaaga aagtcacagg ggggggccag tcttaaaaac ctactcccga 12660
agcccagtcc acacaagtac caggaacgtg agagcagcaa aagggtttat agggttccct 12720
caagtaattc ggcaggacca agacactgat catccggaga atatggaagc ttacgagaca 12780
gtcagtgcat ttatcacgac tgatctcaag aagtactgcc ttaattggag atatgagacc 12840
atcagcttgt ttgcacagag gctaaatgag atttacggat tgccctcatt tttccagtgg 12900
ctgcataaga ggcttgagac ctctgtcctg tatgtaagtg accctcattg cccccccgac 12960
cttgacgccc atatcccgtt atataaagtc cccaatgatc aaatcttcat taagtaccct 13020
atgggaggta tagaagggta ttgtcagaag ctgtggacca tcagcaccat tccctatcta 13080
tacctggctg cttatgagag cggagtaagg attgcttcgt tagtgcaagg ggacaatcag 13140
accatagccg taacaaaaag ggtacccagc acatggccct acaaccttaa gaaacgggaa 13200
gctgctagag taactagaga ttactttgta attcttaggc aaaggctaca tgatattggc 13260

-continued

```
catcacctca aggcaaatga gacaattgtt tcatcacatt tttttgtcta ttcaaaagga  13320
atatattatg atgggctact tgtgtcccaa tcactcaaga gcatcgcaag atgtgtattc  13380
tggtcagaga ctatagttga tgaaacaagg gcagcatgca gtaatattgc tacaacaatg  13440
gctaaaagca tcgagagagg ttatgaccgt taccttgcat attccctgaa cgtcctaaaa  13500
gtgatacagc aaattctgat ctctcttggc ttcacaatca attcaaccat gacccgggat  13560
gtagtcatac ccctcctcac aaacaacgac ctcttaataa ggatggcact gttgcccgct  13620
cctattgggg ggatgaatta tctgaatatg agcaggctgt ttgtcagaaa catcggtgat  13680
ccagtaacat catcaattgc tgatctcaag agaatgattc tcgcctcact aatgcctgaa  13740
gagaccctcc atcaagtaat gacacaacaa ccgggggact cttcattcct agactgggct  13800
agcgaccctt actcagcaaa tcttgtatgt gtccagagca tcactagact cctcaagaac  13860
ataactgcaa ggtttgtcct gatccatagt ccaaacccaa tgttaaaagg attattccat  13920
gatgacagta aagaagagga cgagggactg gcggcattcc tcatggacag gcatattata  13980
gtacctaggg cagctcatga aatcctggat catagtgtca caggggcaag agagtctatt  14040
gcaggcatgc tggataccac aaaaggcttg attcgagcca gcatgaggaa ggggggggtta  14100
acctctcgag tgataaccag attgtccaat tatgactatg aacaattcag agcagggatg  14160
gtgctattga caggaagaaa gagaaatgtc ctcattgaca aagagtcatg ttcagtgcag  14220
ctggcgagag ctctaagaag ccatatgtgg gcgaggctag ctcgaggacg gcctatttac  14280
ggccttgagg tccctgatgt actagaatct atgcgaggcc accttattcg gcgtcatgag  14340
acatgtgtca tctgcgagtg tggatcagtc aactacggat ggtttttttgt cccctcgggt  14400
tgccaactgg atgatattga caaggaaaca tcatccttga gagtcccata tattggttct  14460
accactgatg agagaacaga catgaagctt gccttcgtaa gagccccaag tcgatccttg  14520
cgatctgctg ttagaatagc aacagtgtac tcatgggctt acggtgatga tgatagctct  14580
tggaacgaag cctggttgtt ggctaggcaa agggccaatg tgagcctgga ggagctaagg  14640
gtgatcactc ccatctcaac ttcgactaat ttagcgcata ggttgaggga tcgtagcact  14700
caagtgaaat actcaggtac atcccttgtc cgagtggcga ggtataccac aatctccaac  14760
gacaatctct catttgtcat atcagataag aaggttgata ctaactttat ataccaacaa  14820
ggaatgcttc tagggttggg tgttttagaa acattgtttc gactcgagaa agataccgga  14880
tcatctaaca cggtattaca tcttcacgtc gaaacagatt gttgcgtgat cccgatgata  14940
gatcatccca ggatacccag ctcccgcaag ctagagctga gggcagagct atgtaccaac  15000
ccattgatat atgataatgc acctttaatt gacagagatg caacaaggct atacacccag  15060
agccatagga ggcaccttgt ggaatttgtt acatggtcca caccccaact atatcacatt  15120
ttagctaagt ccacagcact atctatgatt gacctggtaa caaaatttga gaaggaccat  15180
atgaatgaaa tttcagctct catagggggat gacgatatca atagtttcat aactgagttt  15240
ctgctcatag agccaagatt attcactatc tacttgggcc agtgtgcggc catcaattgg  15300
gcatttgatg tacattatca tagaccatca gggaaatatc agatgggtga gctgttgtca  15360
tcgttccttt ctagaatgag caaaggagtg tttaaggtgc ttgtcaatgc tctaagccac  15420
ccaaagatct acaagaaatt ctggcattgt ggtattatag agcctatcca tggtccttca  15480
cttgatgctc aaaacttgca cacaactgtg tgcaacatgg tttacacatg ctatatgacc  15540
tacctcgacc tgttgttgaa tgaagagtta gaagagttca catttctctt gtgtgaaagc  15600
gacgaggatg tagtaccgga cagattcgac aacatccagg caaaacactt atgtgttctg  15660
```

```
gcagatttgt actgtcaacc agggacctgc ccaccaattc gaggtctaag accggtagag  15720
aaatgtgcag ttctaaccga ccatatcaag gcagaggcta tgttatctcc agcaggatct  15780
tcgtggaaca taaatccaat tattgtagac cattactcat gctctctgac ttatctccgg  15840
cgaggatcga tcaaacagat aagattgaga gttgatccag gattcatttt cgacgccctc  15900
gctgaggtaa atgtcagtca gccaaagatc ggcagcaaca acatctcaaa tatgagcatc  15960
aaggctttca gacccccaca cgatgatgtt gcaaaattgc tcaaagatat caacacaagc  16020
aagcacaatc ttcccatttc aggggcaat ctcgccaatt atgaaatcca tgctttccgc  16080
agaatcgggt tgaactcatc tgcttgctac aaagctgttg agatatcaac attaattagg  16140
agatgccttg agccagggga ggacggcttg ttcttgggtg agggatcggg ttctatgttg  16200
atcacttata aagagatact taaactaaac aagtgcttct ataatagtgg ggtttccgcc  16260
aattctagat ctggtcaaag ggaattagca ccctatccct ccgaagttgg ccttgtcgaa  16320
cacagaatgg gagtaggtaa tattgtcaaa gtgctcttta acgggaggcc cgaagtcacg  16380
tgggtaggca gtgtagattg cttcaatttc atagttagta atatccctac ctctagtgtg  16440
gggtttatcc attcagatat agagaccttg cctgacaaag atactataga gaagctagag  16500
gaattggcag ccatcttatc gatggctctg ctcctgggca aaataggatc aatactggtg  16560
attaagctta tgcctttcag cggggatttt gttcagggat ttataagtta tgtagggtct  16620
cattatagag aagtgaacct tgtataccct agatacagca acttcatctc tactgaatct  16680
tatttggtta tgacagatct caaggctaac cggctaatga atcctgaaaa gattaagcag  16740
cagataattg aatcatctgt gaggacttca cctggactta taggtcacat cctatccatt  16800
aagcaactaa gctgcataca agcaattgtg ggagacgcag ttagtagagg tgatatcaat  16860
cctactctga aaaaacttac acctatagag caggtgctga tcaattgcgg gttggcaatt  16920
aacggaccta agctgtgcaa agaattgatc caccatgatg ttgcctcagg gcaagatgga  16980
ttgcttaatt ctatactcat cctctacagg gagttggcaa gattcaaaga caaccaaaga  17040
agtcaacaag ggatgttcca cgcttacccc gtattggtaa gtagcaggca acgagaactt  17100
atatctagga tcacccgcaa attctggggg cacattcttc tttactccgg gaacaaaaag  17160
ttgataaata agtttatcca gaatctcaag tccggctatc tgatactaga cttacaccag  17220
aatatcttcg ttaagaatct atccaagtca gagaaacaga ttattatgac ggggggtttg  17280
aaacgtgagt gggtttttaa ggtaacagtc aaggagacca aagaatggta taagttagtc  17340
ggatacagtg ccctgattaa ggactaattg gttgaactcc ggaaccctaa tcctgcccta  17400
ggtggttagg cattatttgc aatatattaa agaaaacttt gaaaatacga agtttctatt  17460
cccagctttg tctggtggcc ggcatggtcc cagcctcctc gctggcgccg gctgggcaac  17520
attccgaggg gaccgtcccc tcggtaatgg cgaatgggac gcggccgatc cggctgctaa  17580
caaagcccga aaggaagctg agttggctgc tgccaccgct gagcaataac tagcataacc  17640
ccttggggcc tctaaacggg tcttgagggg ttttttgctg aaaggaggaa ctatatccgg  17700
atgcggccgc gggccctatg gtacccagct tttgttccct ttagtgaggg ttaattccga  17760
gcttggcgta atcatggtca tagctgtttc ctgtgtgaaa ttgttatccg ctcacaattc  17820
cacacaacat aggagccgga agcataaagt gtaaagcctg gggtgcctaa tgagtgaggt  17880
aactcacatt aattgcgttg cgctcactgc ccgctttcca gtcgggaaac ctgtcgtgcc  17940
agctgcatta atgaatcggc caacgcgcgg ggagaggcgg tttgcgtatt gggcgctctt  18000
```

ccgcttcctc gctcactgac tcgctgcgct cggtcgttcg gctgcggcga gcggtatcag 18060
ctcactcaaa ggcggtaata cggttatcca cagaatcagg ggataacgca ggaaagaaca 18120
tgtgagcaaa aggccagcaa aaggccagga accgtaaaaa ggccgcgttg ctggcgtttt 18180
tccataggct ccgcccccct gacgagcatc acaaaaatcg acgctcaagt cagaggtggc 18240
gaaacccgac aggactataa agataccagg cgtttccccc tggaagctcc ctcgtgcgct 18300
ctcctgttcc gaccctgccg cttaccggat acctgtccgc ctttctccct tcgggaagcg 18360
tggcgctttc tcaatgctca cgctgtaggt atctcagttc ggtgtaggtc gttcgctcca 18420
agctgggctg tgtgcacgaa ccccccgttc agcccgaccg ctgcgcctta tccggtaact 18480
atcgtcttga gtccaacccg gtaagacacg acttatcgcc actggcagca gccactggta 18540
acaggattag cagagcgagg tatgtaggcg gtgctacaga gttcttgaag tggtggccta 18600
actacggcta cactagaagg acagtatttg gtatctgcgc tctgctgaag ccagttacct 18660
tcggaaaaag agttggtagc tcttgatccg gcaaacaaac caccgctggt agcggtggtt 18720
tttttgtttg caagcagcag attacgcgca gaaaaaaagg atctcaagaa gatcctttga 18780
tcttttctac ggggtctgac gctcagtgga acgaaaactc acgttaaggg attttggtca 18840
tgagattatc aaaaaggatc ttcacctaga tccttttaaa ttaaaaatga agttttaaat 18900
caatctaaag tatatatgag taaacttggt ctgacagtta ccaatgctta atcagtgagg 18960
cacctatctc agcgatctgt ctatttcgtt catccatagt tgcctgactg cccgtcgtgt 19020
agataactac gatacgggag ggcttaccat ctggccccag tgctgcaatg ataccgcgag 19080
acccacgctc accggctcca gatttatcag caataaacca gccagccgga agggccgagc 19140
gcagaagtgg tcctgcaact ttatccgcct ccatccagtc tattaattgt tgccgggaag 19200
ctagagtaag tagttcgcca gttaatagtt tgcgcaacgt tgttgccatt gctacaggca 19260
tcgtggtgtc acgctcgtcg tttggtatgg cttcattcag ctccggttcc caacgatcaa 19320
ggcgagttac atgatccccc atgttgtgaa aaaaagcggt tagctccttc ggtcctccga 19380
tcgttgtcag aagtaagttg gccgcagtgt tatcactcat gcttatggca gcactgcata 19440
attctcttac tgtcatgcca tccgtaagat gcttttctgt gactggtgag tactcaacca 19500
agtcattctg agaatagtgt atgcggcgac cgagttgctc ttgcccggcg tcaatacggg 19560
ataataccgc gccacatagc agaactttaa aagtgctcat cattggaaaa cgttcttcgg 19620
ggcgaaaact ctcaaggatc ttaccgctgt tgagatccag ttcgatgtaa cccactcgtg 19680
cacccaactg atcttcagca tcttttactt tcaccagcgt ttctgggtga gcaaaaacag 19740
gaaggcaaaa tgccgcaaaa aagggaataa gggcgacacg gaaatgttga atactcatac 19800
tcttcctttt tcaatattat tgaagcattt atcagggtta ttgtctcatg agcggataca 19860
tatttgaatg tatttagaaa aataaacaaa taggggttcc gcgcacattt ccccgaaaag 19920
tgccacctga aattgtaaac gttaatattt tgttaaaatt cgcgttaaat ttttgttaaa 19980
tcagctcatt ttttaaccaa taggccgaaa tcggcaaaat cccttataaa tcaaaagaat 20040
agaccgagat agggttgagt gttgttccag tttggaacaa gagtccacta ttaaagaacg 20100
tggactccaa cgtcaaaggg cgaaaaaccg tctatcaggg cgatggccca ctacgtgaac 20160
catcacccta atcaagtttt ttggggtcga ggtgccgtaa agcactaaat cggaacccta 20220
aagggagccc ccgatttaga gcttgacggg gaaagccggc gaacgtggcg agaaaggaag 20280
ggaagaaagc gaaaggagcg ggcgctaggg cgctggcaag tgtagcggtc acgctgcgcg 20340
taaccaccac acccgccgcg cttaatgcgc cgctacaggg cgcgtcccat tcgccattca 20400
ggctgcgcaa ctgttgggaa gggcgatcgg tgcgggcctc ttcgctatta cgccagccac 20460
cgcggtg 20467

<210> SEQ ID NO 168
<211> LENGTH: 1764
<212> TYPE: DNA
<213> ORGANISM: Artificial sequence
<220> FEATURE:
<223> OTHER INFORMATION: Native nucleotide sequence of insert 4

<400> SEQUENCE: 168
atgggtgtcg gaattgttgg cctcctgctg accacagcta tggcagcgga ggtcactaga 60
cgtgggagtg catactatat gtacttggac agaaacgacg ctggggaggc catatctttt 120
ccaaccacat tggggatgaa taagtgttat atacagatca tggatcttgg acacatgtgt 180
gatgccacca tgagctatga atgccctatg ctggatgagg gggtggaacc agatgacgtc 240
gattgttggt gcaacacgac gtcaacttgg gttgtgtacg gaacctgcca tcacaaaaaa 300
ggtgaagcac ggagatctag aagagctgtg acgctcccct cccattccac taggaagctg 360
caaacgcggt cgcaaacctg gttggaatca agagaataca caaagcactt gattagagtc 420
gaaaattgga tattcaggaa ccctggcttc gcgttagcag cagctgccat cgcttggctt 480
ttgggaagct caacgagcca aaaagtcata tacttggtca tgatactgct gattgccccg 540
gcatacagca tcaggtgcat aggagtcagc aatagggact ttgtggaagg tatgtcaggt 600
gggacttggg ttgatgttgt cttggaacat ggaggttgtg tcaccgtaat ggcacaggac 660
aaaccgactg tcgacataga gctggttaca acaacagtca gcaacatggc ggaggtaaga 720
tcctactgct atgaggcatc aatatcggac atggcttcgg acagccgctg cccaacacaa 780
ggtgaagcct accttgacaa gcaatcagac actcaatatg tctgcaaaag aacgttagtg 840
gacagaggct ggggaaatgg atgtggactt tttggcaaag ggagcctggt gacatgcgct 900
aagtttgcat gctccaagaa aatgaccggg aagagcatcc agccagagaa tctggagtac 960
cggataatgc tgtcagttca tggctcccag cacagtggga tgatcgttaa tgacacagga 1020
catgaaactg atgagaatag agcgaaggtt gagataacgc ccaattcacc aagagccgaa 1080
gccaccctgg ggggttttgg aagcctagga cttgattgtg aaccgaggac aggccttgac 1140
ttttcagatt tgtattactt gactatgaat aacaagcact ggttggttca caaggagtgg 1200
ttccacgaca ttccattacc ttggcacgct ggggcagaca ccggaactcc acactggaac 1260
aacaaagaag cactggtaga gttcaaggac gcacatgcca aaaggcaaac tgtcgtggtt 1320
ctagggagtc aagaaggagc agttcacacg gcccttgctg gagctctgga ggctgagatg 1380
gatggtgcaa agggaaggct gtcctctggc cacttgaaat gtcgcctgaa aatggataaa 1440
cttagattga agggcgtgtc atactccttg tgtaccgcag cgttcacatt caccaagatc 1500
ccggctgaaa cactgcacgg gacagtcaca gtggaggtac agtacgcagg gacagatgga 1560
ccttgcaagg ttccagctca gatggcggtg gacatgcaaa ctctgacccc agttgggagg 1620
ttgataaccg ctaaccccgt aatcactgaa agcactgaga actctaagat gatgctggaa 1680
cttgatccac catttgggga ctcttacatt gtcataggag tcggggagaa gaagatcacc 1740
caccactggc acaggagtgg ctaa 1764

<210> SEQ ID NO 169
<211> LENGTH: 587
<212> TYPE: PRT

<213> ORGANISM: Artificial sequence
<220> FEATURE:
<223> OTHER INFORMATION: Insert 4

<400> SEQUENCE: 169

```
Met Gly Val Gly Ile Val Gly Leu Leu Leu Thr Thr Ala Met Ala Ala
1               5                   10                  15

Glu Val Thr Arg Arg Gly Ser Ala Tyr Tyr Met Tyr Leu Asp Arg Asn
            20                  25                  30

Asp Ala Gly Glu Ala Ile Ser Phe Pro Thr Thr Leu Gly Met Asn Lys
        35                  40                  45

Cys Tyr Ile Gln Ile Met Asp Leu Gly His Met Cys Asp Ala Thr Met
    50                  55                  60

Ser Tyr Glu Cys Pro Met Leu Asp Glu Gly Val Glu Pro Asp Asp Val
65                  70                  75                  80

Asp Cys Trp Cys Asn Thr Thr Ser Thr Trp Val Val Tyr Gly Thr Cys
                85                  90                  95

His His Lys Lys Gly Glu Ala Arg Arg Ser Arg Arg Ala Val Thr Leu
            100                 105                 110

Pro Ser His Ser Thr Arg Lys Leu Gln Thr Arg Ser Gln Thr Trp Leu
        115                 120                 125

Glu Ser Arg Glu Tyr Thr Lys His Leu Ile Arg Val Glu Asn Trp Ile
    130                 135                 140

Phe Arg Asn Pro Gly Phe Ala Leu Ala Ala Ala Ala Ile Ala Trp Leu
145                 150                 155                 160

Leu Gly Ser Ser Thr Ser Gln Lys Val Ile Tyr Leu Val Met Ile Leu
                165                 170                 175

Leu Ile Ala Pro Ala Tyr Ser Ile Arg Cys Ile Gly Val Ser Asn Arg
            180                 185                 190

Asp Phe Val Glu Gly Met Ser Gly Gly Thr Trp Val Asp Val Val Leu
        195                 200                 205

Glu His Gly Gly Cys Val Thr Val Met Ala Gln Asp Lys Pro Thr Val
    210                 215                 220

Asp Ile Glu Leu Val Thr Thr Thr Val Ser Asn Met Ala Glu Val Arg
225                 230                 235                 240

Ser Tyr Cys Tyr Glu Ala Ser Ile Ser Asp Met Ala Ser Asp Ser Arg
                245                 250                 255

Cys Pro Thr Gln Gly Glu Ala Tyr Leu Asp Lys Gln Ser Asp Thr Gln
            260                 265                 270

Tyr Val Cys Lys Arg Thr Leu Val Asp Arg Gly Trp Gly Asn Gly Cys
        275                 280                 285

Gly Leu Phe Gly Lys Gly Ser Leu Val Thr Cys Ala Lys Phe Ala Cys
    290                 295                 300

Ser Lys Lys Met Thr Gly Lys Ser Ile Gln Pro Glu Asn Leu Glu Tyr
305                 310                 315                 320

Arg Ile Met Leu Ser Val His Gly Ser Gln His Ser Gly Met Ile Val
                325                 330                 335

Asn Asp Thr Gly His Glu Thr Asp Glu Asn Arg Ala Lys Val Glu Ile
            340                 345                 350

Thr Pro Asn Ser Pro Arg Ala Glu Ala Thr Leu Gly Gly Phe Gly Ser
        355                 360                 365

Leu Gly Leu Asp Cys Glu Pro Arg Thr Gly Leu Asp Phe Ser Asp Leu
    370                 375                 380

Tyr Tyr Leu Thr Met Asn Asn Lys His Trp Leu Val His Lys Glu Trp
```

-continued 385 390 395 400

Phe His Asp Ile Pro Leu Pro Trp His Ala Gly Ala Asp Thr Gly Thr
405 410 415

Pro His Trp Asn Asn Lys Glu Ala Leu Val Glu Phe Lys Asp Ala His
420 425 430

Ala Lys Arg Gln Thr Val Val Val Leu Gly Ser Gln Glu Gly Ala Val
435 440 445

His Thr Ala Leu Ala Gly Ala Leu Glu Ala Glu Met Asp Gly Ala Lys
450 455 460

Gly Arg Leu Ser Ser Gly His Leu Lys Cys Arg Leu Lys Met Asp Lys
465 470 475 480

Leu Arg Leu Lys Gly Val Ser Tyr Ser Leu Cys Thr Ala Ala Phe Thr
485 490 495

Phe Thr Lys Ile Pro Ala Glu Thr Leu His Gly Thr Val Thr Val Glu
500 505 510

Val Gln Tyr Ala Gly Thr Asp Gly Pro Cys Lys Val Pro Ala Gln Met
515 520 525

Ala Val Asp Met Gln Thr Leu Thr Pro Val Gly Arg Leu Ile Thr Ala
530 535 540

Asn Pro Val Ile Thr Glu Ser Thr Glu Asn Ser Lys Met Met Leu Glu
545 550 555 560

Leu Asp Pro Pro Phe Gly Asp Ser Tyr Ile Val Ile Gly Val Gly Glu
565 570 575

Lys Lys Ile Thr His His Trp His Arg Ser Gly
580 585

<210> SEQ ID NO 170
<211> LENGTH: 1392
<212> TYPE: DNA
<213> ORGANISM: Artificial sequence
<220> FEATURE:
<223> OTHER INFORMATION: Native nucleotide sequence of insert 5

<400> SEQUENCE: 170
atggaagtca tatacttggt catgatactg ctgattgccc cggcatacag catcaggtgc 60
ataggagtca gcaataggga ctttgtggaa ggtatgtcag gtgggacttg ggttgatgtt 120
gtcttggaac atggaggttg tgtcaccgta atggcacagg acaaaccgac tgtcgacata 180
gagctggtta caacaacagt cagcaacatg gcggaggtaa gatcctactg ctatgaggca 240
tcaatatcgg acatggcttc ggacagccgc tgcccaacac aaggtgaagc ctaccttgac 300
aagcaatcag acactcaata tgtctgcaaa agaacgttag tggacagagg ctggggaaat 360
ggatgtggac tttttggcaa agggagcctg gtgacatgcg ctaagtttgc atgctccaag 420
aaaatgaccg ggaagagcat ccagccagag aatctggagt accggataat gctgtcagtt 480
catggctccc agcacagtgg gatgatcgtt aatgacacag gacatgaaac tgatgagaat 540
agagcgaagg ttgagataac gcccaattca ccaagagccg aagccaccct gggggggtttt 600 ggaagcctag gacttgattg tgaaccgagg acaggccttg acttttcaga tttgtattac 660
ttgactatga ataacaagca ctggttggtt cacaaggagt ggttccacga cattccatta 720
ccttggcacg ctggggcaga caccggaact ccacactgga acaacaaaga agcactggta 780
gagttcaagg acgcacatgc caaaaggcaa actgtcgtgg ttctagggag tcaagaagga 840
gcagttcaca cggcccttgc tggagctctg gaggctgaga tggatggtgc aaagggaagg 900
ctgtcctctg gccacttgaa atgtcgcctg aaaatggata aacttagatt gaagggcgtg 960

```
tcatactcct tgtgtaccgc agcgttcaca ttcaccaaga tcccggctga aacactgcac   1020

gggacagtca cagtggaggt acagtacgca gggacagatg gaccttgcaa ggttccagct   1080

cagatggcgg tggacatgca aactctgacc ccagttggga ggttgataac cgctaacccc   1140

gtaatcactg aaagcactga gaactctaag atgatgctgg aacttgatcc accatttggg   1200

gactcttaca ttgtcatagg agtcggggag aagaagatca cccaccactg gcacaggagt   1260

ggcagcacca ttggaaaagc atttgaagcc actgtgagag gtgccaagag aatggcagtc   1320

ttgggagaca cagcctggga ctttggatca gttggaggcg ctctcaactc attgggcaag   1380

ggcatctaat aa                                                         1392


<210> SEQ ID NO 171
<211> LENGTH: 462
<212> TYPE: PRT
<213> ORGANISM: Artificial sequence
<220> FEATURE:
<223> OTHER INFORMATION: Insert 5

<400> SEQUENCE: 171

Met Glu Val Ile Tyr Leu Val Met Ile Leu Leu Ile Ala Pro Ala Tyr
1               5                   10                  15

Ser Ile Arg Cys Ile Gly Val Ser Asn Arg Asp Phe Val Glu Gly Met
            20                  25                  30

Ser Gly Gly Thr Trp Val Asp Val Val Leu Glu His Gly Gly Cys Val
        35                  40                  45

Thr Val Met Ala Gln Asp Lys Pro Thr Val Asp Ile Glu Leu Val Thr
    50                  55                  60

Thr Thr Val Ser Asn Met Ala Glu Val Arg Ser Tyr Cys Tyr Glu Ala
65                  70                  75                  80

Ser Ile Ser Asp Met Ala Ser Asp Ser Arg Cys Pro Thr Gln Gly Glu
                85                  90                  95

Ala Tyr Leu Asp Lys Gln Ser Asp Thr Gln Tyr Val Cys Lys Arg Thr
            100                 105                 110

Leu Val Asp Arg Gly Trp Gly Asn Gly Cys Gly Leu Phe Gly Lys Gly
        115                 120                 125

Ser Leu Val Thr Cys Ala Lys Phe Ala Cys Ser Lys Lys Met Thr Gly
    130                 135                 140

Lys Ser Ile Gln Pro Glu Asn Leu Glu Tyr Arg Ile Met Leu Ser Val
145                 150                 155                 160

His Gly Ser Gln His Ser Gly Met Ile Val Asn Asp Thr Gly His Glu
                165                 170                 175

Thr Asp Glu Asn Arg Ala Lys Val Glu Ile Thr Pro Asn Ser Pro Arg
            180                 185                 190

Ala Glu Ala Thr Leu Gly Gly Phe Gly Ser Leu Gly Leu Asp Cys Glu
        195                 200                 205

Pro Arg Thr Gly Leu Asp Phe Ser Asp Leu Tyr Tyr Leu Thr Met Asn
    210                 215                 220

Asn Lys His Trp Leu Val His Lys Glu Trp Phe His Asp Ile Pro Leu
225                 230                 235                 240

Pro Trp His Ala Gly Ala Asp Thr Gly Thr Pro His Trp Asn Asn Lys
                245                 250                 255

Glu Ala Leu Val Glu Phe Lys Asp Ala His Ala Lys Arg Gln Thr Val
            260                 265                 270

Val Val Leu Gly Ser Gln Glu Gly Ala Val His Thr Ala Leu Ala Gly
```

-continued

```
        275                 280                 285

Ala Leu Glu Ala Glu Met Asp Gly Ala Lys Gly Arg Leu Ser Ser Gly
    290                 295                 300

His Leu Lys Cys Arg Leu Lys Met Asp Lys Leu Arg Leu Lys Gly Val
305                 310                 315                 320

Ser Tyr Ser Leu Cys Thr Ala Ala Phe Thr Phe Thr Lys Ile Pro Ala
                325                 330                 335

Glu Thr Leu His Gly Thr Val Thr Val Glu Val Gln Tyr Ala Gly Thr
            340                 345                 350

Asp Gly Pro Cys Lys Val Pro Ala Gln Met Ala Val Asp Met Gln Thr
        355                 360                 365

Leu Thr Pro Val Gly Arg Leu Ile Thr Ala Asn Pro Val Ile Thr Glu
    370                 375                 380

Ser Thr Glu Asn Ser Lys Met Met Leu Glu Leu Asp Pro Pro Phe Gly
385                 390                 395                 400

Asp Ser Tyr Ile Val Ile Gly Val Gly Glu Lys Lys Ile Thr His His
                405                 410                 415

Trp His Arg Ser Gly Ser Thr Ile Gly Lys Ala Phe Glu Ala Thr Val
            420                 425                 430

Arg Gly Ala Lys Arg Met Ala Val Leu Gly Asp Thr Ala Trp Asp Phe
        435                 440                 445

Gly Ser Val Gly Gly Ala Leu Asn Ser Leu Gly Lys Gly Ile
    450                 455                 460
```